United States Patent
Blaquiere et al.

(10) Patent No.: US 9,175,009 B2
(45) Date of Patent: *Nov. 3, 2015

(54) BENZOXEPIN PI3K INHIBITOR COMPOUNDS AND METHODS OF USE

(71) Applicant: Genentech, Inc., South San Francisco, CA (US)

(72) Inventors: Nicole Blaquiere, San Francisco, CA (US); Steven Do, San Jose, CA (US); Danette Dudley, Pacifica, CA (US); Adrian Folkes, Berkshire (GB); Richard Goldsmith, Belmont, CA (US); Robert Heald, Harlow (GB); Timothy Heffron, Burlingame, CA (US); Aleksandr Kolesnikov, San Francisco, CA (US); Chudi Ndubaku, San Francisco, CA (US); Alan G. Olivero, Half Moon Bay, CA (US); Stephen Price, Harlow (GB); Steven Staben, San Francisco, CA (US); BinQing Wei, Belmont, CA (US)

(73) Assignee: GENENTECH, INC., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/565,669

(22) Filed: Dec. 10, 2014

(65) Prior Publication Data

US 2015/0094347 A1  Apr. 2, 2015

Related U.S. Application Data

(63) Continuation of application No. 14/162,520, filed on Jan. 23, 2014, now Pat. No. 8,952,043, which is a continuation of application No. 13/568,707, filed on Aug. 7, 2012, now Pat. No. 8,673,952, which is a continuation of application No. 12/890,810, filed on Sep. 27, 2010, now Pat. No. 8,263,633.

(60) Provisional application No. 61/246,386, filed on Sep. 28, 2009.

(51) Int. Cl.
*A61K 31/41* (2006.01)
*C07D 249/14* (2006.01)
(Continued)

(52) U.S. Cl.
CPC ............ *C07D 495/04* (2013.01); *A61K 31/381* (2013.01); *A61K 31/41* (2013.01); *A61K 31/4196* (2013.01); *A61K 31/429* (2013.01); *A61K 31/4245* (2013.01); *A61K 31/4365* (2013.01); *A61K 31/4439* (2013.01); *A61K 31/454* (2013.01); *A61K 31/4545* (2013.01);
(Continued)

(58) Field of Classification Search
CPC ............................ A61K 31/41; C07D 249/14
See application file for complete search history.

(56) References Cited

U.S. PATENT DOCUMENTS

| 4,797,414 A | 1/1989 | Rimbault |
| 5,314,889 A | 5/1994 | Boigegrain et al. |

(Continued)

FOREIGN PATENT DOCUMENTS

| WO | 01/64675 A1 | 9/2001 |
| WO | 2008/019139 A2 | 2/2008 |

(Continued)

OTHER PUBLICATIONS

Voskoglou-Nomikos et al., Clinical Cancer Research, vol. 9, 4227-4239.*

(Continued)

*Primary Examiner* — Rebecca Anderson
(74) *Attorney, Agent, or Firm* — Alex Andrus; Genentech, Inc.

(57) ABSTRACT

Benzoxepin compounds of Formula I, and including stereoisomers, geometric isomers, tautomers, solvates, metabolites and pharmaceutically acceptable salts thereof, wherein: $Z^1$ is $CR^1$ or N; $Z^2$ is $CR^2$ or N; $Z^3$ is $CR^3$ or N; $Z^4$ is $CR^4$ or N; and where (i) $X^1$ is N and $X^2$ is S, (ii) $X^1$ is S and $X^2$ is N, (iii) $X^1$ is $CR^7$ and $X^2$ is S, (iv) $X^1$ is S and $X^2$ is $CR^7$; (v) $X^1$ is $NR^8$ and $X^2$ is N, (vi) $X^1$ is N and $X^2$ is $NR^8$, (vii) $X^1$ is $CR^7$ and $X^2$ is O, (viii) $X^1$ is O and $X^2$ is $CR^7$, (ix) $X^1$ is $CR^7$ and $X^2$ is $C(R^7)_2$, (x) $X^1$ is $C(R^7)_2$ and $X^2$ is $CR^7$; (xi) $X^1$ is N and $X^2$ is O, or (xii) $X^1$ is O and $X^2$ is N, are useful for inhibiting lipid kinases including p110 alpha and other isoforms of PI3K, and for treating disorders such as cancer mediated by lipid kinases. Methods of using compounds of Formula I for in vitro, in situ, and in vivo diagnosis, prevention or treatment of such disorders in mammalian cells, or associated pathological conditions, are disclosed.

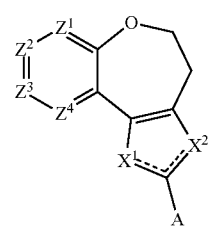

5 Claims, 13 Drawing Sheets

(51) Int. Cl.

| | | |
|---|---|---|
| *C07D 495/04* | (2006.01) | |
| *A61K 31/381* | (2006.01) | |
| *A61K 31/4245* | (2006.01) | |
| *A61K 31/429* | (2006.01) | |
| *A61K 31/4365* | (2006.01) | |
| *A61K 31/4439* | (2006.01) | |
| *A61K 31/454* | (2006.01) | |
| *A61K 31/496* | (2006.01) | |
| *A61K 31/5377* | (2006.01) | |
| *C07D 495/14* | (2006.01) | |
| *C07D 513/04* | (2006.01) | |
| *C07D 513/14* | (2006.01) | |
| *A61K 31/4196* | (2006.01) | |
| *A61K 31/4545* | (2006.01) | |
| *A61K 31/4985* | (2006.01) | |
| *A61K 31/506* | (2006.01) | |
| *A61K 31/541* | (2006.01) | |
| *A61K 31/551* | (2006.01) | |
| *A61K 45/06* | (2006.01) | |

(52) U.S. Cl.
CPC ............ *A61K 31/496* (2013.01); *A61K 31/4985* (2013.01); *A61K 31/506* (2013.01); *A61K 31/5377* (2013.01); *A61K 31/541* (2013.01); *A61K 31/551* (2013.01); *A61K 45/06* (2013.01); *C07D 249/14* (2013.01); *C07D 495/14* (2013.01); *C07D 513/04* (2013.01); *C07D 513/14* (2013.01)

(56) References Cited

U.S. PATENT DOCUMENTS

| | | | |
|---|---|---|---|
| 5,612,356 | A | 3/1997 | Yoshimura et al. |
| 5,985,799 | A | 11/1999 | Tseng |
| 6,187,801 | B1 | 2/2001 | Jaehne et al. |
| 6,251,922 | B1 | 6/2001 | Jaehne et al. |
| 6,329,407 | B1 | 12/2001 | Jaehne et al. |
| 6,476,059 | B1 | 11/2002 | Jaehne et al. |
| 7,273,880 | B2 | 9/2007 | Marzabadi et al. |
| 8,952,043 | B2 * | 2/2015 | Blaquiere et al. ............. 514/383 |
| 2004/0082602 | A1 | 4/2004 | Hagen et al. |
| 2004/0198791 | A1 | 10/2004 | Sato et al. |
| 2005/0239767 | A1 | 10/2005 | Chan et al. |
| 2005/0277630 | A1 | 12/2005 | Chupak et al. |
| 2006/0100254 | A1 | 5/2006 | Betzemeier et al. |
| 2006/0106013 | A1 | 5/2006 | Breitfelder et al. |
| 2008/0132513 | A1 | 6/2008 | Che et al. |
| 2009/0247567 | A1 | 10/2009 | Do et al. |

FOREIGN PATENT DOCUMENTS

| | | |
|---|---|---|
| WO | PCT/US 2009/038795 | 2/2009 |
| WO | 2011/036280 A1 | 3/2011 |

OTHER PUBLICATIONS ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
(FDA mulls drug to slow late-stage Alzheimer's [online], [retrieved on Sep. 23, 2003], 'Retrieved from the Internet, URL;http://www.cnn.com/2003/HEALTH/conditions/09/24/alzheimers.drug.ap/index.html>').
Banaszak et al. et al., "New and efficient RCM in pyridinic series: snythesis of 2H-dihydropyrano- or 2,3H-dihydrooxepino[3,2-b]pyridines" Tetrahedron Lett 47(35):6235-6238 ( 2006).
Cecil Textbook of Medicine, 20th edition 2:1992-1996 (1996).
Cecil Textbook of Medicine, 20th edition 2:2050-2057 (1996).
Heindel et al., "Salicylidene-thiolactone rearrangement. A direct synthesis of 4H-2-arylthieno[3,2-c][1]Benzopyran-4-ones" J Org Chem 42(8):1465-1466 ( 1977).
Huff, Joel R., "HIV protease: a novel chemotherapeutic target for AIDS" Journal of Medicinal Chemistry 34(8):2305-2314 (Aug. 1991).
Katsura et al., "Anti-Helicobacter pylori Agents. 4. 2-(substituted guanidine)-4-phenylthiazoles and some structurally rigid derivatives" J Med Chem 43(17):3315-3321 ( 2000).
Lala et al., "Role of nitric oxide in tumor progression: Lessons from experimental tumors" Cancer and Metastasis Reviews 17(1):91-106 (1998).
Majumdar et al., "Regioselective synthesis of thieno[3,2-c][1]benzopyran-4-ones by thio-Claisen rearrangement" Monatsh Chem 135(8):1001-1007 ( 2004).
Navarro et al., "Synthesis of 1H-[1]Benzopyrano[4,3-b]pyrrole and 4H-thieeno[3,2-c]Benzopyran derivatives, functionalisation by aromatic electrophilic substitution" Heterocycles 55(12):2369-2386 ( 2001).
Potts et al., "Carbon-carbon bond formation via intramolecular cycloadditions: Use of the thiocarbonyl ylide dipole in anhydro-4-hydroxythiazolium hydroxides" J Org Chem 54:1077-1088 ( 1989).
Potts et al., "Intramolecular 1,3-dipolar cycloadditions with thiocarbonyl ylides" J Chem Soc Chem Commun 7:561-3 ( 1986).
Reiter et al., "Pyrimidine benzamide-based thrombopoietin receptor agonists" Bioorganic & Medicinal Chemistry Letters 17(19):5447-5454 (2007).
Rueeger et al., "Discovery and SAR of potent, orally available and brain-penetrable 5,6-dihydro-4H-3-thio-1-aza-benzo[e]azulen derivatives as neuropeptide Y Y5 receptor antagonists" Bioorganic Medicinal Chem Letters 14(10):2451-2457 ( 2004).
Trieu et al., "Condensation of (beta-chlorovinyl)carbonyl compounds with alpha-mercaptocarboxylic acids (translated from German)" Zeitschrift Fuer Chemie (translated from German), 13(2):57-8 ( 1973).

* cited by examiner

R = Me, iPr

BENZOXEPIN PI3K INHIBITOR COMPOUNDS AND METHODS OF USE

CROSS REFERENCE TO RELATED APPLICATIONS

This non-provisional application filed under 37 CFR §1.53(b) is a continuation of U.S. Ser. No. 14/162,520 filed on 23 Jan. 2014, which is a continuation of U.S. Ser. No. 13/568,707, now U.S. Pat. No. 8,673,952, filed on 7 Aug. 2012, which is a continuation of U.S. Ser. No. 12/890,810, now U.S. Pat. No. 8,263,633, filed on 27 Sep. 2010, and also claims the benefit under 35 USC §119(e) of U.S. Provisional Application Ser. No. 61/246,386 filed on 28 Sep. 2009, each of which is incorporated by reference in its entirety.

FIELD OF THE INVENTION

The invention relates generally to compounds with anti-cancer activity and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110 α (alpha) (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield Md. (2004) Encyclopedia of Biological Chemistry (Lennarz W J, Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Folkes et al (2008) J. Med. Chem. 51:5522-5532; Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; U.S. Pat. No. 6,703,414; WO 97/15658; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070), including p110 alpha binding activity (US 2008/0207611; US 2008/0039459; US 2008/0076768; WO 2008/073785; WO 2008/070740).

SUMMARY OF THE INVENTION

The invention relates generally to benzoxepin compounds of Formula I with anti-cancer activity, and more specifically with PI3 kinase inhibitory activity. Certain hyperproliferative disorders are characterized by the modulation of PI3 kinase function, e.g. by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the benzoxepin compounds of Formula I for in vitro, in situ, and in vivo diagnosis or treatment of mammalian cells, organisms, or associated pathological conditions.

Formula I compounds include:

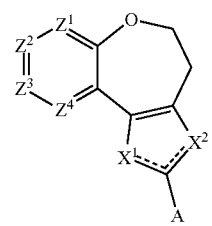

and stereoisomers, geometric isomers, tautomers, or pharmaceutically acceptable salts thereof, wherein: $Z^1$ is $CR^1$ or N; $Z^2$ is $CR^2$ or N; $Z^3$ is $CR^3$ or N; $Z^4$ is $CR^4$ or N; and where (i) $X^1$ is N and $X^2$ is S, (ii) $X^1$ is S and $X^2$ is N, (iii) $X^1$ is $CR^7$ and $X^2$ is S, (iv) $X^1$ is S and $X^2$ is $CR^7$; (v) $X^1$ is $NR^8$ and $X^2$ is N, (vi) $X^1$ is N and $X^2$ is $NR^8$, (vii) $X^1$ is $CR^7$ and $X^2$ is O, (viii) $X^1$ is O and $X^2$ is $CR^7$, (ix) $X^1$ is $CR^7$ and $X^2$ is $C(R^7)_2$, or (x) $X^1$ is $C(R^7)_2$ and $X^2$ is $CR^7$. The various substituents are as defined herein.

Another aspect of the invention provides a pharmaceutical composition comprising a benzoxepin compound of Formula I and a pharmaceutically acceptable carrier. The pharmaceutical composition may further comprise one or more additional therapeutic agent.

Another aspect of the invention provides methods of inhibiting PI3 kinase activity, comprising contacting a PI3 kinase with an effective inhibitory amount of a compound of Formula I.

Another aspect of the invention provides methods of preventing or treating a hyperproliferative disease or disorder modulated by PI3 kinases, comprising administering to a mammal in need of such treatment an effective amount of a compound of Formula I. Examples of such hyperproliferative disease or disorder include, but are not limited to, cancer.

Another aspect of the invention provides methods of preventing or treating a hyperproliferative disorder, comprising administering to a mammal in need of such treatment an effective amount of a compound of Formula I, alone or in combination with one or more additional compounds having anti-hyperproliferative properties.

In a further aspect the present invention provides a method of using a compound of this invention to treat a hyperproliferative disease or condition modulated by PI3 kinase in a mammal.

An additional aspect of the invention is the use of a compound of this invention for treating cancer modulated by PI3 kinase in a mammal.

Another aspect of the invention includes kits comprising a compound of Formula I, a container, and optionally a package insert or label indicating a treatment.

Another aspect of the invention includes methods of preparing, methods of separating, and methods of purifying compounds of Formula I.

Another aspect of the invention includes novel intermediates useful for preparing Formula I compounds.

DETAILED DESCRIPTION OF EXEMPLARY EMBODIMENTS

Figure 1:
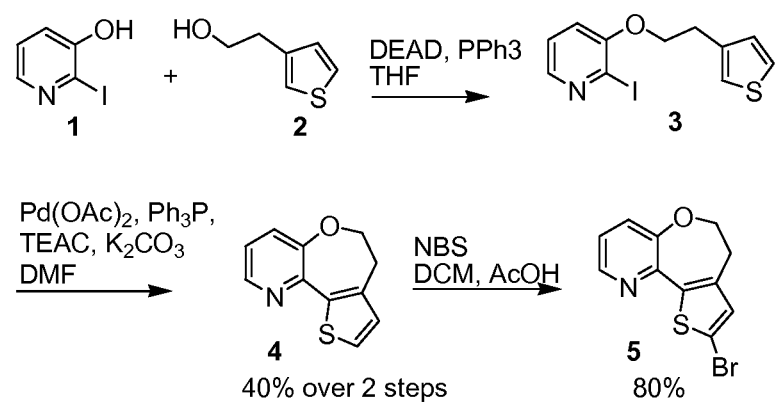
FIG. 1 shows a synthetic route to 2-Bromo-4,5-dihydro-6-oxa-1-thia-10-aza-benzo[e]azulene 5.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, sp² double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, sp$^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH=CH—), allyl (—CH$_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally. Examples include, but are not limited to, ethynylene (—C≡C—), propynylene (propargylene, —CH$_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, e.g., as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted The terms "heterocycle", "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), e.g.: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabiciclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, e.g., 2-hydroxypyridinyl), imidazolyl, imidazopyridinyl, pyrimidinyl (including, e.g., 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCINO), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, e.g., tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, e.g., 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, e.g., PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, e.g., ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result e.g. from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. E.g., proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion.

The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, e.g., treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, e.g., treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof Benzoxepin Compounds The present invention provides benzoxepin compounds, and pharmaceutical formulations thereof, which are potentially useful in the treatment of diseases, conditions and/or disorders modulated by PI3 kinases. More specifically, the present invention provides compounds of Formula I:

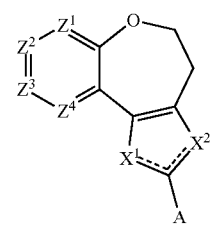

I and stereoisomers, geometric isomers, tautomers, or pharmaceutically acceptable salts thereof, wherein:

$Z^1$ is $CR^1$ or N;
$Z^2$ is $CR^2$ or N;
$Z^3$ is $CR^3$ or N;
$Z^4$ is $CR^4$ or N;
where (i) $X^1$ is N and $X^2$ is S, (ii) $X^1$ is S and $X^2$ is N, (iii) $X^1$ is $CR^7$ and $X^2$ is S, (iv) $X^1$ is S and $X^2$ is $CR^7$; (v) $X^1$ is $NR^8$ and $X^2$ is N, (vi) $X^1$ is N and $X^2$ is $NR^8$, (vii) $X^1$ is $CR^7$ and $X^2$ is O, (viii) $X^1$ is O and $X^2$ is $CR^7$, (ix) $X^1$ is $CR^7$ and $X^2$ is $C(R^7)_2$, (x) $X^1$ is $C(R^7)_2$ and $X^2$ is $CR^7$; (xi) $X^1$ is N and $X^2$ is O, or (xii) $X^1$ is O and $X^2$ is N;

$R^1$ is selected from H, F, Cl, Br, I, —CN, —$CF_3$, —$NO_2$, and $C_1$-$C_4$ alkyl;

$R^2$, $R^3$, $R^4$, and $R^7$ are independently selected from:

H, F, Cl, Br, I, —CN, —$COR^{10}$, —$CO_2R^{10}$, —C(=O)N($R^{10}$)$OR^{11}$, —C(=$NR^{10}$)$NR^{10}R^{11}$, —C(=O)$NR^{10}R^{11}$, —$NO_2$, —$NR^{10}R^{11}$, —$NR^{12}$C(=O)$R^{10}$, —$NR^{12}$C(=O)$OR^{11}$, —$NR^{12}$C(=O)$NR^{10}R^{11}$, —$NR^{12}$C(=O)($C_1$-$C_{12}$ alkylene)$NR^{10}R^{11}$, —$NR^{12}$($C_1$-$C_{12}$ alkylene)$NR^{10}R^{11}$, —$NR^{12}$($C_1$-$C_{12}$ alkylene)$OR^{10}$, —$NR^{12}$($C_1$-$C_{12}$ alkylene)C(=O)$NR^{10}R^{11}$, —$OR^{10}$, —$S(O)_2R^{10}$,
—C(=O)$NR^{10}$($C_1$-$C_{12}$ alkylene)$NR^{10}R^{11}$,
—C(=O)$NR^{10}$($C_1$-$C_{12}$ alkylene)$NR^{10}$C(=O)$OR^{11}$,
—C(=O)$NR^{10}$($C_1$-$C_{12}$ alkylene)$NR^{10}$C(=O)$R^{11}$,
—C(=O)$NR^{10}$($C_1$-$C_{12}$ alkylene)$R^{10}$,
$C_1$-$C_{12}$ alkyl,
$C_2$-$C_8$ alkenyl,
$C_2$-$C_8$ alkynyl,
$C_3$-$C_{12}$ carbocyclyl,
$C_2$-$C_{20}$ heterocyclyl,
$C_6$-$C_{20}$ aryl,
$C_1$-$C_{20}$ heteroaryl,
—($C_3$-$C_{12}$ carbocyclyl)-($C_1$-$C_{12}$ alkyl),
—($C_2$-$C_{20}$ heterocyclyl)-($C_1$-$C_{12}$ alkyl),
—($C_6$-$C_{20}$ aryl)-($C_1$-$C_{12}$ alkyl),
—($C_1$-$C_{20}$ heteroaryl)-($C_1$-$C_{12}$ alkyl),
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl),
—($C_1$-$C_{12}$ alkylene)-($C_1$-$C_{20}$ heteroaryl),
—($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)C(=O)$OR^{10}$,
—($C_1$-$C_{12}$ alkylene)-$NR^{10}R^{11}$,
—($C_1$-$C_{12}$ alkylene)$NR^{12}$C(=O)$R^{10}$,
—($C_1$-$C_{12}$ alkylene)$OR^{10}$,
—($C_1$-$C_{12}$ alkylene)-$NR^{10}$—($C_1$-$C_{12}$ alkylene)-($C_1$-$C_{20}$ heteroaryl),
—($C_1$-$C_{12}$ alkylene)-$NR^{10}$—($C_1$-$C_{12}$ alkylene)-($C_1$-$C_{20}$ heterocyclyl),
—($C_1$-$C_{12}$ alkylene)-$NR^{10}$—($C_1$-$C_{12}$ alkylene)-NHC(=O)—($C_1$-$C_{20}$ heteroaryl),
—($C_1$-$C_{12}$ alkylene)-($C_2$-$C_{20}$ heterocyclyl)-$NR^{10}R^{11}$, and
—($C_1$-$C_{12}$ alkylene)-($C_2$-$C_{20}$ heterocyclyl)-($C_1$-$C_{12}$ alkyl)-$NR^{10}R^{11}$, where alkyl, alkenyl, alkynyl, alkylene, carbocyclyl, heterocyclyl, aryl, and heteroaryl are optionally substituted with one or more groups independently selected from F, Cl, Br, I, $R^{10}$, —$SR^{10}$, —$S(O)_2R^{10}$, —$S(O)_2NR^{10}R^{11}$, —$NR^{10}R^{11}$, —$NR^{12}$C(O)$R^{10}$, —$CO_2R^{10}$, —C(O)$R^{10}$, —$CONR^{10}R^{11}$, oxo, and —$OR^{10}$;

A is selected from —C(=O)$NR^5R^6$, —$NR^5R^6$, $C_6$-$C_{20}$ aryl, $C_2$-$C_{20}$ heterocyclyl and $C_1$-$C_{20}$ heteroaryl wherein aryl, heterocyclyl and heteroaryl are optionally substituted with one or more groups independently selected from F, Cl, Br, I, —CN, —$COR^{10}$, —$CO_2R^{10}$, —C(=O)N($R^{10}$)$OR^{11}$, —C(=$NR^{10}$)$NR^{10}R^{11}$, —C(=O)$NR^{10}R^{11}$, —$NO_2$, —$NR^{10}R^{11}$, —$NR^{12}$C(=O)$R^{10}$, —$NR^{12}$C(=O)$OR^{11}$, —$NR^{12}$C(=O)$NR^{10}R^{11}$, —$NR^{12}$C(=O)($C_1$-$C_{12}$ alkylene)$NR^{10}R^{11}$, —$NR^{12}$($C_1$-$C_{12}$ alkylene)$NR^{10}R^{11}$, —$NR^{12}$($C_1$-$C_{12}$ alkylene)$OR^{10}$, —$NR^{12}$($C_1$-$C_{12}$ alkylene)C(=O)$NR^{10}R^{11}$, —$OR^{10}$, —$S(O)^2R^{10}$,
—C(=O)$NR^{10}$($C_1$-$C_{12}$ alkylene)$NR^{10}R^{11}$,
—C(=O)$NR^{10}$($C_1$-$C_{12}$ alkylene)$NR^{10}$C(=O)$OR^{11}$,
—C(=O)$NR^{10}$($C_1$-$C_{12}$ alkylene)$NR^{10}$C(=O)$R^{11}$,
—C(=O)$NR^{10}$($C_1$-$C_{12}$ alkylene)$R^{10}$,
$C_1$-$C_{12}$ alkyl,
$C_2$-$C_8$ alkenyl,
$C_2$-$C_8$ alkynyl,
$C_3$-$C_{12}$ carbocyclyl,
$C_2$-$C_{20}$ heterocyclyl,
$C_6$-$C_{20}$ aryl,
$C_1$-$C_{20}$ heteroaryl,
—($C_3$-$C_{12}$ carbocyclyl)-($C_1$-$C_{12}$ alkyl),
—($C_2$-$C_{20}$ heterocyclyl)-($C_1$-$C_{12}$ alkyl),
—($C_6$-$C_{20}$ aryl)-($C_1$-$C_{12}$ alkyl),
—($C_1$-$C_{20}$ heteroaryl)-($C_1$-$C_{12}$ alkyl),
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl),
—($C_1$-$C_{12}$ alkylene)-($C_1$-$C_{20}$ heteroaryl),
—($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)C(=O)$OR^{10}$,
—($C_1$-$C_{12}$ alkylene)-$NR^{10}R^{11}$,
—($C_1$-$C_{12}$ alkylene)$NR^{12}$C(=O)$R^{10}$,
—($C_1$-$C_{12}$ alkylene)$OR^{10}$,
—($C_1$-$C_{12}$ alkylene)-$NR^{10}$—($C_1$-$C_{12}$ alkylene)-($C_1$-$C_{20}$ heteroaryl),
—($C_1$-$C_{12}$ alkylene)-$NR^{10}$—($C_1$-$C_{12}$ alkylene)-($C_1$-$C_{20}$ heterocyclyl),
—($C_1$-$C_{12}$ alkylene)-$NR^{10}$—($C_1$-$C_{12}$ alkylene)-NHC(=O)—($C_1$-$C_{20}$ heteroaryl),
—($C_1$-$C_{12}$ alkylene)-($C_2$-$C_{20}$ heterocyclyl)-$NR^{10}R^{11}$, and
—($C_1$-$C_{12}$ alkylene)-($C_2$-$C_{20}$ heterocyclyl)-($C_1$-$C_{12}$ alkyl)-$NR^{10}R^{11}$, where alkyl, alkenyl, alkynyl, alkylene, carbocyclyl, heterocyclyl, aryl, and heteroaryl are optionally substituted with one or more groups independently selected from F, Cl, Br, I, $R^{10}$, —$SR^{10}$, —$S(O)_2R^{10}$, —$NR^{10}R^{11}$, —$NR^{12}$C(O)$R^{10}$, —$CO_2R^{10}$, —C(O)$R^{10}$, —$CONR^{10}R^{11}$, and —$OR^{10}$;

$R^5$ is selected from H, and $C_1$-$C_{12}$ alkyl, optionally substituted with one or more groups independently selected from F, Cl, Br, I, —CN, —$CO_2H$, —$CONH_2$, —$CONHCH_3$, —$NH_2$, —$NO_2$, —$N(CH_3)_2$, —$NHCOCH_3$, —$NHS(O)_2CH_3$, —OH, —$OCH_3$, —$OCH_2CH_3$, —$S(O)_2NH_2$, and —$S(O)_2CH_3$;

$R^6$ is selected from $C_1$-$C_{12}$ alkyl, $C_3$-$C_{12}$ carbocyclyl, $C_2$-$C_{20}$ heterocyclyl, $C_1$-$C_{20}$ heteroaryl, and $C_6$-$C_{20}$ aryl, each optionally substituted with one or more groups independently selected from F, Cl, Br, I, —CH$_3$, —CH$_2$OH, —CH$_2$C$_6$H$_5$, —CN, —CF$_3$, —CO$_2$H, —C(O)CH$_3$, —NH$_2$, —NO$_2$, —N(CH$_3$)$_2$, —NHCOCH$_3$, —NHS(O)$_2$CH$_3$, —OH, oxo, —OCH$_3$, —OCH$_2$CH$_3$, —S(O)$_2$NH$_2$, —S(O)$_2$CH$_3$, —C(=O)NR$^{10}$(C$_1$-C$_{12}$ alkylene)NR$^{10}$R$^{11}$, phenyl, pyridinyl, tetrahydro-furan-2-yl, 2,3-dihydro-benzofuran-2-yl, 1-isopropyl-pyrrolidin-3-ylmethyl, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, —CH=CHR$^{13}$, and —C(=O)NR$^{10}$R$^{11}$;

or $R^5$ and $R^6$ together with the nitrogen atom to which they are attached form $C_2$-$C_{20}$ heterocyclyl or $C_1$-$C_{20}$ heteroaryl optionally substituted with one or more groups selected from F, Cl, Br, I, CH$_3$, C(CH$_3$)$_3$, —CH$_2$OH, —CH$_2$CH$_2$OH, —CH$_2$C$_6$H$_5$, pyridin-2-yl, 6-methyl-pyridin-2-yl, pyridin-4-yl, pyridin-3-yl, pyrimidin-2-yl, pyrazin-2-yl, tetrahydro-furan-carbonyl, 2-methoxy-phenyl, benzoyl, cyclopropylmethyl, (tetra-furan-2-yl)methyl, 2,6-dimethyl-morpholin-4-yl, 4-methyl-piperazine-carbonyl, pyrrolidine-1-carbonyl, cyclopropanecarbonyl, 2,4-difluoro-phenyl, pyridin-2-ylmethyl, morpholin-4-yl, —CN, —CF$_3$, —CO$_2$H, —CONH$_2$, —CONHCH$_3$, —CON(CH$_3$)$_2$, —COCF$_3$, —COCH$_3$, —COCH(CH$_3$)$_2$, —NO$_2$, —NHCH$_3$, —N(CH$_3$)$_2$, —N(CH$_2$CH$_3$)$_2$, —NHCOCH$_3$, —NCH$_3$COCH$_3$, —NHS(O)$_2$CH$_3$, —OH, —OCH$_3$, —OCH$_2$CH$_3$, —CH$_2$OCH$_3$, —CH$_2$CH$_2$OCH$_3$, —CH$_2$S(O)$_2$NHCH$_3$, —CH$_2$S(O)$_2$CH$_2$CH$_3$, —S(O)$_2$NHCH$_3$, —S(O)$_2$CH$_2$CH$_3$, —S(O)$_2$NH$_2$, —S(O)$_2$N(CH$_3$)$_2$ and —S(O)$_2$CH$_3$;

$R^8$ is selected from H and $C_1$-$C_4$ alkyl;

$R^{10}$, $R^{11}$ and $R^{12}$ are independently selected from H, $C_1$-$C_{12}$ alkyl, —(C$_1$-C$_{12}$ alkylene)-(C$_2$-C$_{20}$ heterocyclyl), —(C$_1$-C$_{12}$ alkylene)-(C$_6$-C$_{20}$ aryl), —(C$_1$-C$_{12}$ alkylene)-(C$_3$-C$_{12}$ carbocyclyl), $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, each of which are optionally substituted with one or more groups independently selected from F, Cl, Br, I, —CH$_3$, —CH$_2$CH$_3$, —CH(CH$_3$)$_2$, —CH$_2$OH, —CH$_2$OCH$_3$, —CH$_2$CH$_2$OH, —C(CH$_3$)$_2$OH, —CH$_2$C(CH$_3$)$_2$OH, —CH$_2$CH(CH$_3$)OH, —CH$_2$CO$_2$H, —CH$_2$CO$_2$CH$_3$, —CH$_2$NH$_2$, —(CH$_2$)$_2$N(CH$_3$)$_2$, —CH$_2$C$_6$H$_5$, —CN, —CF$_3$, —CO$_2$H, —C(O)CH$_3$, —C(O)CH(OH)CH$_3$, —CO$_2$CH$_3$, —CONH$_2$, —CONHCH$_3$, —CON(CH$_3$)$_2$, —C(CH$_3$)$_2$CONH$_2$, —NH$_2$, —NO$_2$, —N(CH$_3$)$_2$, —N(CH$_3$)C(CH$_3$)$_2$CONH$_2$, —N(CH$_3$)CH$_2$CH$_2$S(O)$_2$CH$_3$, —NHCOCH$_3$, —NHS(O)$_2$CH$_3$, =O (oxo), —OH, —OCH$_3$, —OCH$_2$CH$_3$, —OCH$_2$CH$_2$OH, —OP(O)(OH)$_2$, —SCH$_3$, —S(O)$_2$CH$_3$, —S(O)$_2$NH$_2$, —S(O)$_2$N(CH$_3$)$_2$, —CH$_2$S(O)$_2$NHCH$_3$, —CH$_2$S(O)$_2$CH$_2$CH$_3$, —S(O)$_2$NHCH$_3$, —S(O)$_2$CH$_2$CH$_3$, pyrrolidin-1-yl, 2-oxopyrrolidin-1-yl, cyclopropyl, cyclopentyl, oxetanyl, 4-methylpiperazin-1-yl, and 4-morpholinyl;

or $R^{10}$ and $R^{11}$ together with the nitrogen atom to which they are attached form a $C_2$-$C_{20}$ heterocyclyl ring or $C_1$-$C_{20}$ heteroaryl each of which are optionally substituted with one or more groups independently selected from F, Cl, Br, I, —CH$_3$, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NH-COCH$_3$, —NHS(O)$_2$CH$_3$, —OH, oxo, —OCH$_3$, —OCH$_2$CH$_3$, —S(O)$_2$NH$_2$, —S(O)$_2$CH$_3$, —CH(CH$_3$)$_2$, —CH$_2$CF$_3$, —CH$_2$CH$_2$OH and —C(CH$_3$)$_2$OH; and $R^{13}$ is selected from H, F, Cl, Br, I, —CH$_3$, —CH$_2$CH$_3$, —CN, —CF$_3$, —CH$_2$N(CH$_3$)$_2$, —CH$_2$OH, —CO$_2$H, —CONH$_2$, —CON(CH$_3$)$_2$, —NO$_2$, and —S(O)$_2$CH$_3$.

Exemplary embodiments include Formulas Ii and Iii

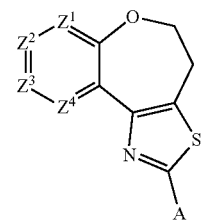

Ii

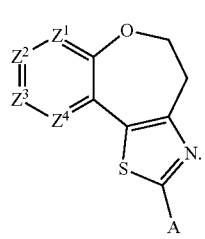

Iii

Exemplary embodiments include Formulas Iiii and Iiv

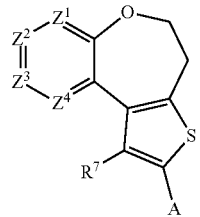

Iiii

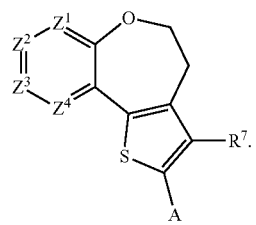

Iiv

Exemplary embodiments include Formulas Iv and Ivi

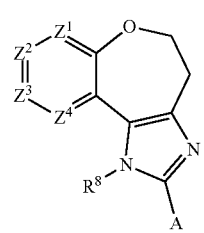

Iv

-continued

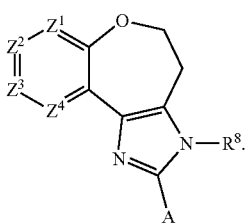
Ivi

Exemplary embodiments include Formulas Ivii and Iviii

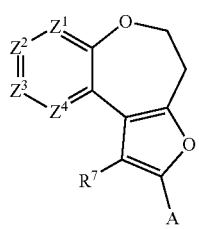
Ivii

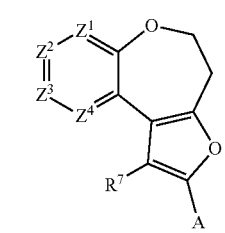
Iviii

Exemplary embodiments include Formulas Iix and Ix:

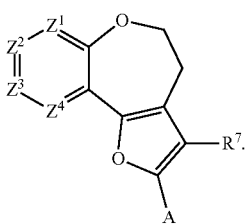
Iix

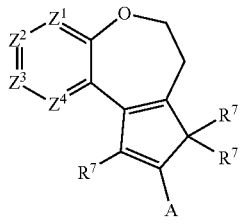
Ix

Exemplary embodiments include Formulas Ixi and Ixii:

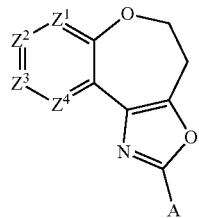
Ixi

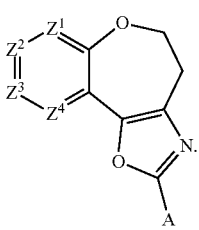
Ixii

Exemplary embodiments of Formula I compounds include wherein $Z^1$ is $CR^1$; $Z^2$ is $CR^2$; $Z^3$ is $CR^3$; and $Z^4$ is $CR^4$.

Exemplary embodiments of Formula I compounds include wherein $Z^1$ is N; $Z^2$ is $CR^2$; $Z^3$ is $CR^3$; and $Z^4$ is $CR^4$.

Exemplary embodiments of Formula I compounds include wherein $Z^1$ is $CR^1$; $Z^2$ is N; $Z^3$ is $CR^3$; and $Z^4$ is $CR^4$.

Exemplary embodiments of Formula I compounds include wherein $Z^1$ is $CR^1$; $Z^2$ is $CR^2$; $Z^3$ is N; and $Z^4$ is $CR^4$.

Exemplary embodiments of Formula I compounds include wherein $Z^1$ is $CR^1$; $Z^2$ is $CR^2$; $Z^3$ is $CR^3$; and $Z^4$ is N.

Exemplary embodiments include wherein A is —C(=O)NR$^5$R$^6$.

Exemplary embodiments include wherein $R^5$ is $CH_3$.

Exemplary embodiments include wherein $R^6$ is phenyl substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, —S(O)$_2$CH$_3$, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, and —CH=CHR$^{13}$.

Exemplary embodiments include wherein $R^5$ and $R^6$ together with the nitrogen atom to which they are attached form morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, or indolinyl.

Exemplary embodiments include wherein A is C$_2$-C$_{20}$ heterocyclyl or C$_1$-C$_{20}$ heteroaryl substituted with —CH$_2$OH, —CH$_2$CO$_2$H, —CH(CH$_3$)CH$_2$OCH$_3$, —CH$_3$, —CH(CH$_3$)$_2$, —CH$_2$CH(CH$_3$)$_2$, —CH$_2$CF$_3$, —C(=O)CH$_3$, —C(=O)NHCH$_3$, —C(=O)N(CH$_3$)$_2$, —CO$_2$H, —CO$_2$CH$_3$, —CH$_2$CO$_2$CH$_3$, —NH$_2$, —NHC(=O)CH$_3$, —OH, —OCH$_3$, —S(O)$_2$CH$_3$, 1-methylpiperid-4-yl, 4-methylpiperazin-1-yl, 4-morpholinyl, (4-methylpiperazin-1yl)carboxamide, —CH$_2$(1H-1,2,4-triazol-5-yl), cyclopropyl, cyclopropylmethyl, or cyclobutyl.

Exemplary embodiments include wherein A is a C$_1$-C$_{20}$ heteroaryl selected from pyridyl, isoxazolyl, imidazolyl, pyrazolyl, pyrrolyl, thiazolyl, pyridazinyl, pyrimidinyl, pyrazinyl, oxazolyl, oxadiazolyl, 1,3,4-oxadiazol-2(3H)-one, furanyl, thienyl, 1,2,3-triazolyl, 1,2,4-triazolyl, 1,2,4- triazol-5(4H)-one, 4,5-dihydro-1,2,4-triazin-6(1H)-one, tetrazolyl, pyrrolo[2,3-b]pyridinyl, indazolyl, 3,4-dihydroquinolinyl, and benzo[d]thiazole.

Exemplary embodiments include wherein A is selected from the structures:

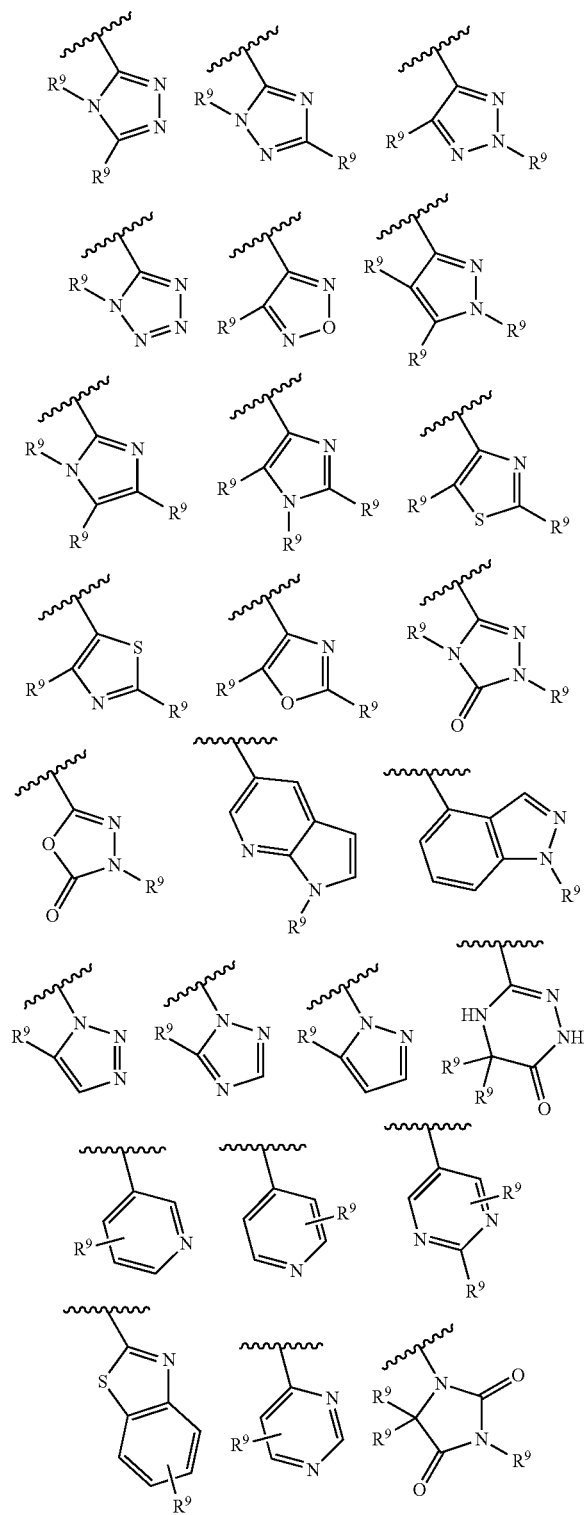

where $R^9$ is independently selected from H, F, Cl, Br, I, —CH₃, —CH₂CH₃, —CH(CH₃)₂, —CH₂CH(CH₃)₂, —CH₂OH, —CH₂CO₂H, —CH(CH₃)CH₂OCH₃, —CN, —CF₃, —CH₂CF₃, —CH₂NH₂, —CH₂CH₂NH₂, —C(═O)CH₃, —CH₂C(═O)NHCH₃, —C(═O)NHCH₃, —CO₂H, —CH₂CO₂CH₃, —NH₂, —OH, —OCH₃, —SCH₃, —S(O)₂CH₃, 1-methylpiperid-4-yl, 4-methylpiperazin-1-yl, 4-morpholinyl, morpholin-4-yl-ethyl, benzyl, and phenyl, where benzyl and phenyl are optionally substituted with one or more groups selected from F, Cl, Br, I, —CH₂OH, —CH₂CO₂H, —CN, —CH₂NH₂, —CH₃, —C(═O)CH₃, —C(═O)NHCH₃, —CO₂H, —CH₂CO₂CH₃, —NH₂, —OCH₃, —S(O)₂CH₃, 1-methylpiperid-4-yl, 4-methylpiperazin-1-yl, and 4-morpholinyl; and where the wavy line indicates the site of attachment.

Exemplary embodiments include wherein A is selected from the structures:

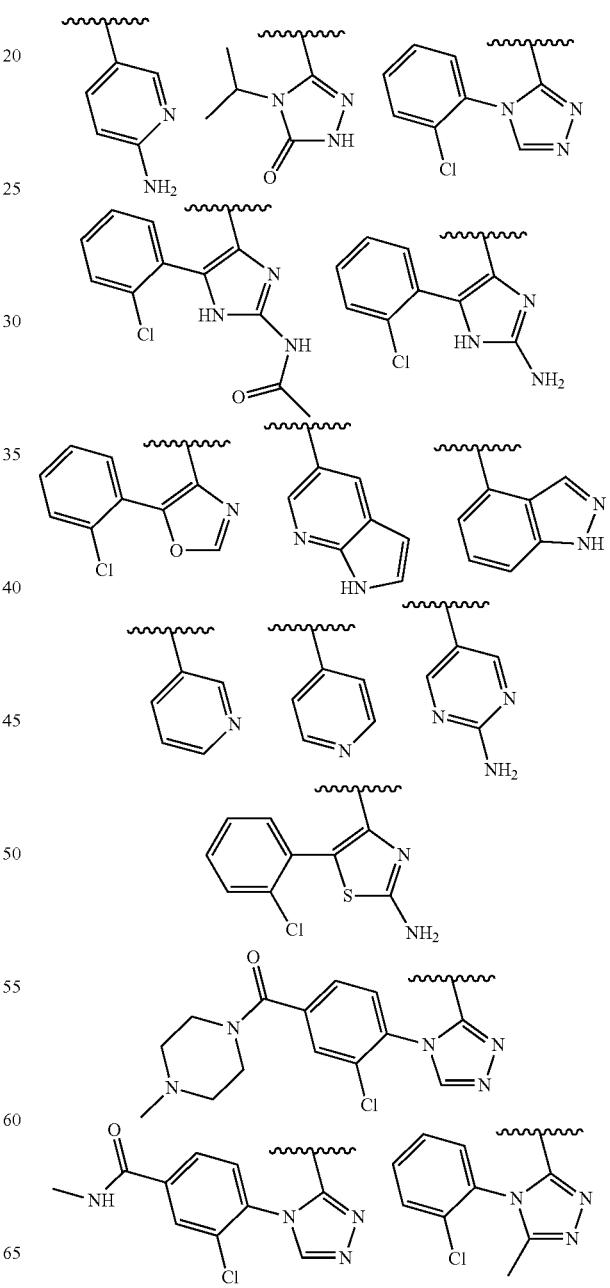

-continued

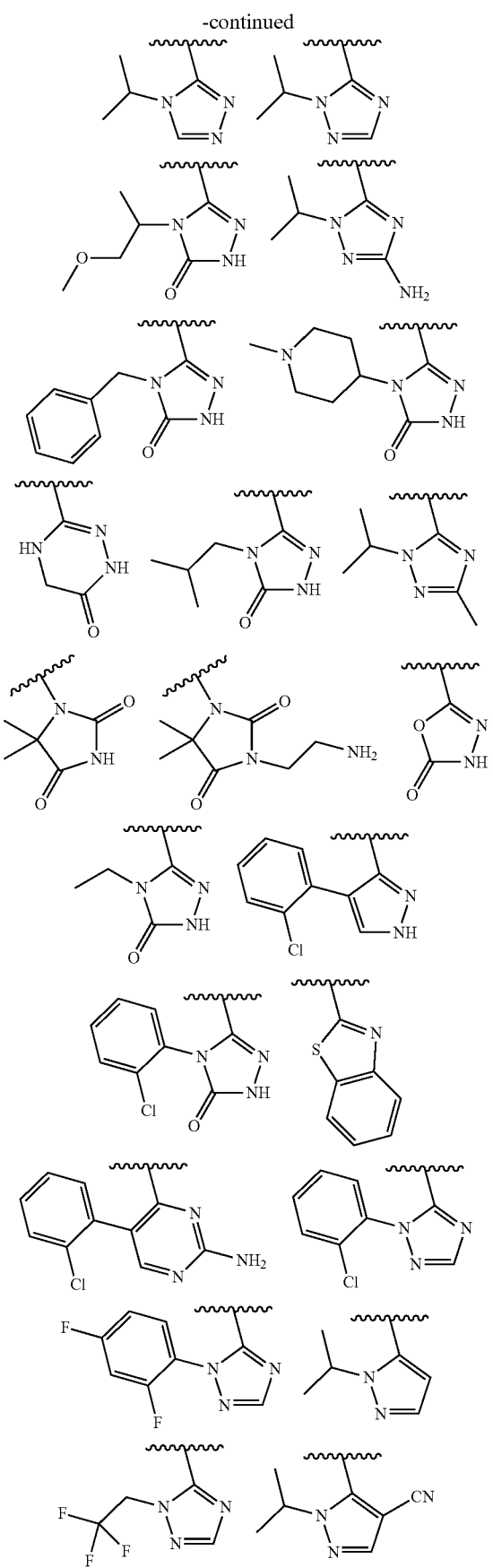

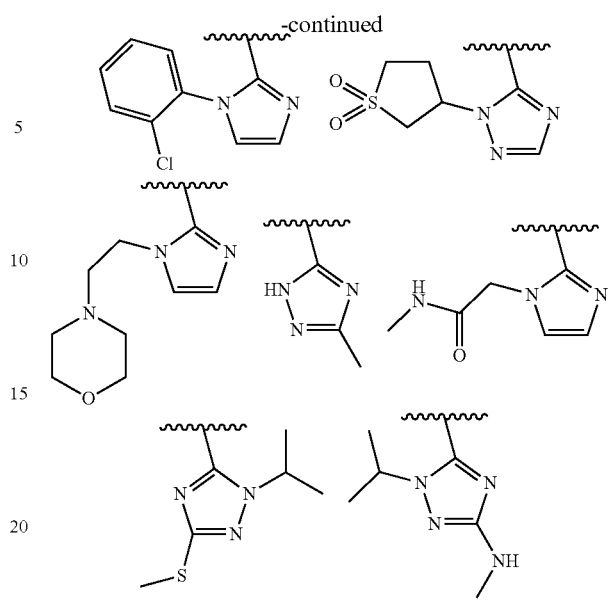

where the wavy line indicates the site of attachment.

Biological Evaluation

Determination of the PI3 kinase activity of a Formula I compound is possible by a number of direct and indirect detection methods. Certain exemplary compounds described herein were assayed for their p110α (alpha), and other isoform, PI3K binding activity (Example 601) and in vitro activity against tumor cells (Example 602). Certain exemplary compounds of the invention had PI3K binding activity $IC_{50}$ values less than 10 nM. Certain compounds of the invention had tumor cell-based activity $IC_{50}$ values less than 100 nM.

The cytotoxic or cytostatic activity of Formula I exemplary compounds was measured by: establishing a proliferating mammalian tumor cell line in a cell culture medium, adding a Formula I compound, culturing the cells for a period from about 6 hours to about 5 days; and measuring cell viability (Example 602). Cell-based in vitro assays were used to measure viability, i.e. proliferation ($IC_{50}$), cytotoxicity ($EC_{50}$), and induction of apoptosis (caspase activation).

The in vitro potency of Formula I exemplary compounds was measured by the cell proliferation assay, CellTiter-Glo® Luminescent Cell Viability Assay, commercially available from Promega Corp., Madison, Wis. (Example 602). This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) Anti Cancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative effects of Formula I exemplary compounds were measured by the CellTiter-Glo® Assay (Example 602) against several tumor cell lines. Potency $EC_{50}$ values were established for the tested compounds. The range of in vitro cell potency activities was about 100 nM to about 10 μM. Certain tested compounds had $EC_{50}$ values of less than 1 micromolar (1 μM) in stopping proliferation of certain tumor cell lines.

Certain ADME properties were measured for certain exemplary compounds by assays including: Caco-2 Permeability (Example 603), Hepatocyte Clearance (Example 604), Cytochrome P450 Inhibition (Example 605), Cytochrome P450 Induction (Example 606), Plasma Protein Binding (Example 607), and hERG channel blockage (Example 608).

Certain exemplary compounds were tested for efficacy by a dose escalation studies by administration in tumor xenograft Taconic nude mouse models (Example 609). The breast cancer cell line MDA-MB-361.1 mouse model was administered certain exemplary Formula I compounds along with Vehicle (MCT, negative control). The tumor growth delay was measured when dosed orally daily for 21 days at 50 and 100 mg/kg. Body weight change over the course of treatment was measured as an indicator of safety. Treatment of the MDA-MB-361.1 mouse model with certain exemplary Formula I compounds caused tumor growth stasis, inhibition, or regression when dosed orally daily for 21 days.

Exemplary Formula I compounds Nos. 101-512 in Table 1 and Nos. 513-548 in Table 2, were made, characterized, and tested for inhibition of PI3K alpha ($IC_{50}$ p110 alpha less than 1 micromolar, μM) and selectivity according to the methods of this invention, and have the following structures and corresponding names (ChemDraw Ultra, Version 9.0.1, CambridgeSoft Corp., Cambridge Mass.). E.g., compound 101 had an $IC_{50}$ of 0.031 micromole; compound 102 had an $IC_{50}$ of 0.0051 micromole; compound 103 had an $IC_{50}$ of 0.0018 micromole; compound 106 had an $IC_{50}$ of 0.0057 micromole; compound 109 had an $IC_{50}$ of 0.0013 micromole; compound 127 had an $IC_{50}$ of 0.00005 micromole; compound 147 had an $IC_{50}$ of 0.021 micromole; compound 151 had an $IC_{50}$ of 0.00020 micromole; and compound 153 had an $IC_{50}$ of 0.058 micromole.

TABLE 1

| No. | Structure | Name |
|---|---|---|
| 101 | 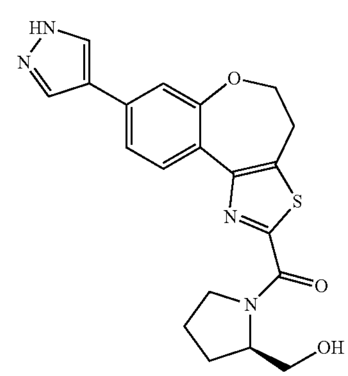 [SMILES: O=C(c1nc2c(s1)CCOc1cc(-c3cn[nH]c3)ccc1-2)N1CCC[C@@H]1CO] | ((R)-2-Hydroxymethyl-pyrrolidin-1-yl)-[8-(1H-pyrazol-4-yl)-4,5-dihydro-6-oxa-3-thia-1-aza-benzo[e]azulen-2-yl]-methanone |
| 102 | 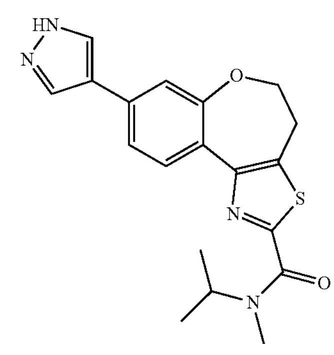 [SMILES: CC(C)N(C)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid isopropyl-methyl-amide |

TABLE 1-continued

| No. | Structure | Name |
|---|---|---|
| 103 | 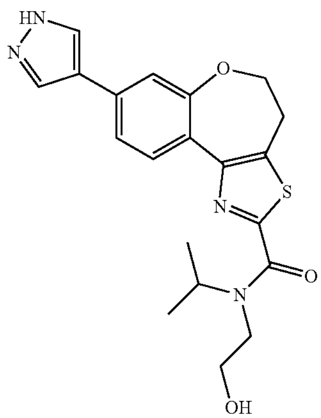 [SMILES: CC(C)N(CCO)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid (2-hydroxy-ethyl)-isopropyl-amide |
| 104 | 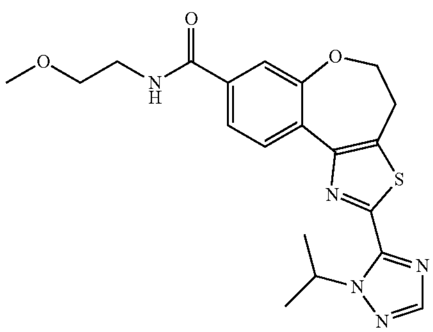 [SMILES: COCCNC(=O)c1ccc2c(c1)OCCc1sc(-c3ncnn3C(C)C)nc1-2] | 2-(2-Isopropyl-2H-[1,2,4]triazol-3-yl)-4,5-dihydro-6-oxa-3-thia-1-aza-benzo[e]azulene-8-carboxylic acid (2-methoxy-ethyl)-amide |
| 105 | 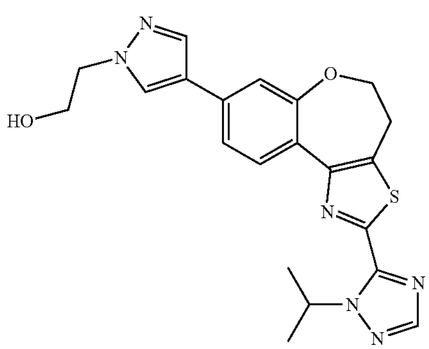 [SMILES: CC(C)n1ncnc1-c1nc2c(s1)CCOc1cc(-c3cnn(CCO)c3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-ethanol |
| 106 | 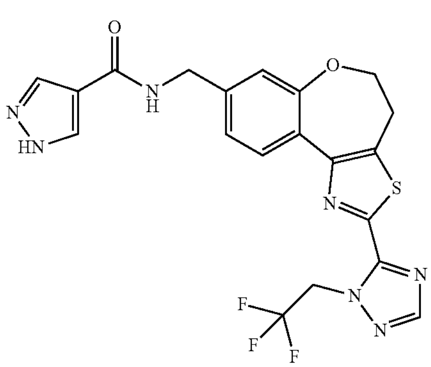 [SMILES: O=C(NCc1ccc2c(c1)OCCc1sc(-c3ncnn3CC(F)(F)F)nc1-2)c1cn[nH]c1] | 1H-Pyrazole-4-carboxylic acid {2-[2-(2,2,2-trifluoro-ethyl)-2H-[1,2,4]triazol-3-yl]-4,5-dihydro-6-oxa-3-thia-1-aza-benzo[e]azulen-8-ylmethyl}-amide |

TABLE 1-continued

| No. | Structure | Name |
|---|---|---|
| 107 | 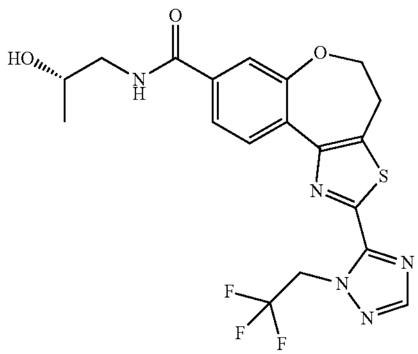 [SMILES: C[C@H](O)CNC(=O)c1ccc2c(c1)OCCc1sc(-c3ncnn3CC(F)(F)F)nc1-2] | 2-[2-(2,2,2-Trifluoro-ethyl)-2H-[1,2,4]triazol-3-yl]-4,5-dihydro-6-oxa-3-thia-1-aza-benzo[e]azulene-8-carboxyl acid ((S)-2-hydroxy-propyl)-amide |
| 108 | 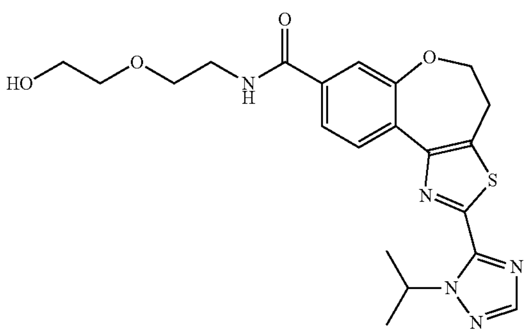 [SMILES: CC(C)n1ncnc1-c1nc2c(s1)CCOc1cc(C(=O)NCCOCCO)ccc1-2] | 2-(2-Isopropyl-2H-[1,2,4]triazol-3-yl)-4,5-dihydro-6-oxa-3-thia-1-aza-benzo[e]azulene-8-carboxylic acid[2-(2-hydroxy-ethoxy)-ethyl]-amide |
| 109 | 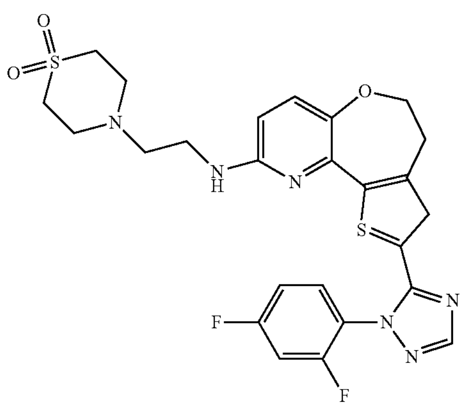 | {2-[2-(2,4-Difluoro-phenyl)-2H-[1,2,4]triazol-3-yl]-4,5-dihydro-6-oxa-l-thia-10-aza-benzo[e]azulen-9-yl}-[2-(1,1-dioxo-1S-thiomorpholin-4-yl)-ethyl]-amine |
| 110 | 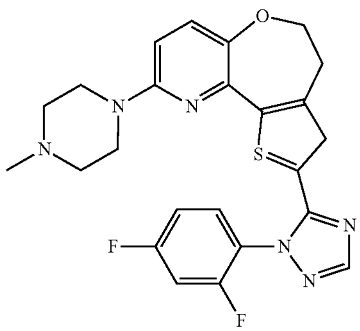 | 2-[2-(2,4-Difluoro-phenyl)-2H-[1,2,4]triazol-3-yl]-9-(4-methyl-piperazin-1-yl)-4,5-dihydro-6-oxa-1-thia-10-aza-benzo[c]azulene |

TABLE 1-continued

| No. | Structure | Name |
|---|---|---|
| 111 | 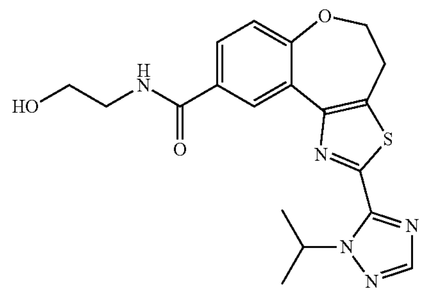 [SMILES: CC(C)n1ncnc1-c1nc2c(s1)CCOc1ccc(C(=O)NCCO)cc1-2] | 2-(2-Isopropyl-2H-[1,2,4]triazol-3-yl)-4,5-dihydro-6-oxa-3-thia-1-aza-benzo[e]azulene-9-carboxylic acid (2-hydroxy-ethyl)-amide |
| 112 | 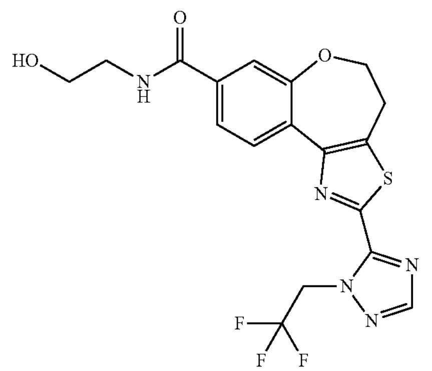 [SMILES: O=C(NCCO)c1ccc2c(c1)OCCc1sc(-c3ncnn3CC(F)(F)F)nc1-2] | 2-[2-(2,2,2-Trifluoro-ethyl)-2H-[1,2,4]triazol-3-yl]-4,5-dihydro-6-oxa-3-thia-1-aza-benzo[e]azulene-8-carboxylic acid (2-hydroxy-ethyl)-amide |
| 113 | 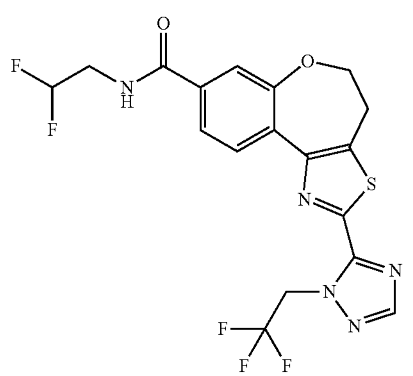 [SMILES: O=C(NCC(F)F)c1ccc2c(c1)OCCc1sc(-c3ncnn3CC(F)(F)F)nc1-2] | 2-[2-(2,2,2-Trifluoro-ethyl)-2H-[1,2,4]triazol-3-yl]-4,5-dihydro-6-oxa-3-thia-1-aza-benzo[e]azulene-8-carboxylic acid (2,2-difluoro-ethyl)-amide |
| 114 | 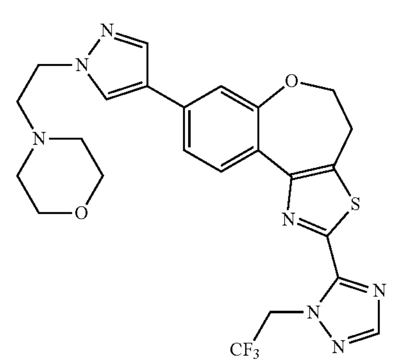 [SMILES: FC(F)(F)Cn1ncnc1-c1nc2c(s1)CCOc1cc(-c3cnn(CCN4CCOCC4)c3)ccc1-2] | 8-[1-(2-Morpholin-4-yl-ethyl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene |

TABLE 1-continued

| No. | Structure | Name |
|---|---|---|
| 115 | 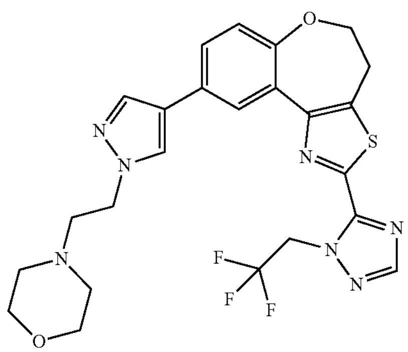 [SMILES: FC(F)(F)Cn1ncnc1-c1nc2c(s1)CCOc1ccc(-c3cnn(CCN4CCOCC4)c3)cc1-2] | 9-[1-(2-Morpholin-4-yl-ethyl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene |
| 116 | 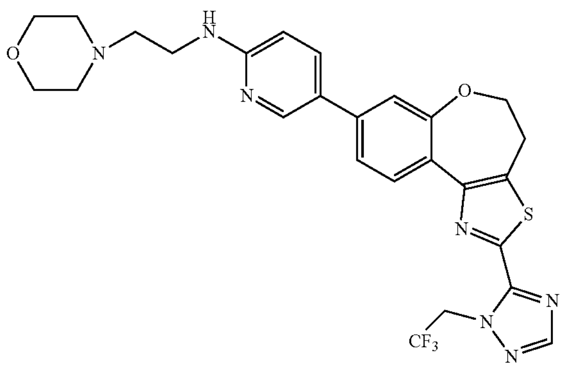 [SMILES: FC(F)(F)Cn1ncnc1-c1nc2c(s1)CCOc1cc(-c3ccc(NCCN4CCOCC4)nc3)ccc1-2] | (2-Morpholin-4-yl-ethyl)-(5-{2-[2-(2,2,2-trifluoro-ethyl)-2H-[1,2,4]triazol-3-yl]-4,5-dihydro-6-oxa-3-thia-1-aza-benzo[e]azulen-8-yl}-pyridin-2-yl)-amine |
| 117 | 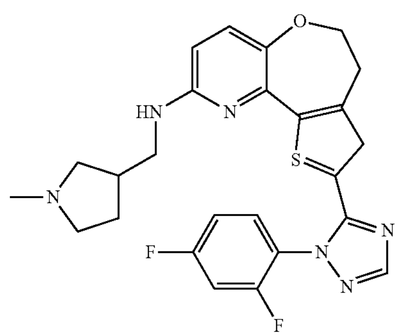 | {2-[2-(2,4-Difluoro-phenyl)-2H-[1,2,4]triazol-3-yl]-4,5-dihydro-6-oxa-1-thia-10-aza-benzo[e]azulen-9-yl}-(1-methyl-pyrrolidin-3-ylmethyl)-amine |
| 118 | 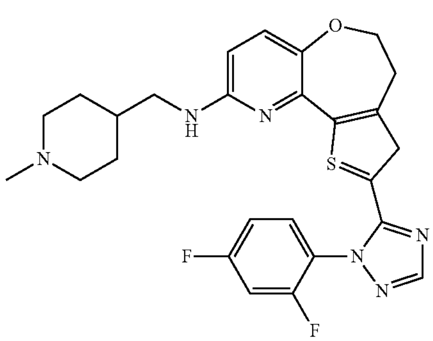 | {2-[2-(2,4-Difluoro-phenyl)-2H-[1,2,4]triazol-3-yl]-4,5-dihydro-6-oxa-1-thia-10-aza-benzo[e]azulen-9-yl}-(1-methyl-piperidin-4-ylmethyl)-amine |

TABLE 1-continued

| No. | Structure | Name |
| --- | --- | --- |
| 119 | 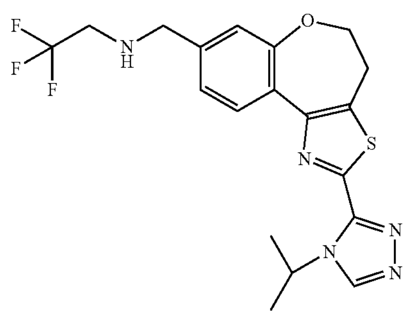 [SMILES: CC(C)n1cnnc1-c1nc2c(s1)CCOc1cc(CNCC(F)(F)F)ccc1-2] | [2-(4-Isopropyl-4H-[1,2,4]triazol-3-4,5-dihydro-6-oxa-3-thia-1-aza-benzo[e]azulen-8-ylmethyl]-(2,2,2-trifluoro-ethyl)-amine |
| 120 | 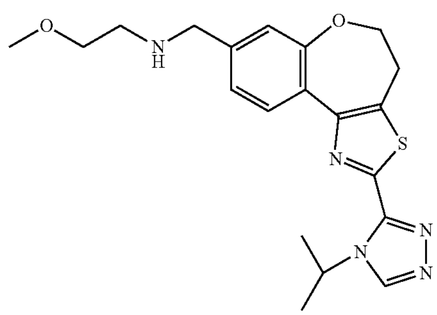 [SMILES: COCCNCc1ccc2c(c1)OCCc1sc(-c3nncn3C(C)C)nc1-2] | [2-(4-Isopropyl-4H-[1,2,4]triazol-3-yl)-4,5-dihydro-6-oxa-3-thia-1-aza-benzo[e]azulen-8-ylmethyl]-(2-methoxy-ethyl)-amine |
| 121 | 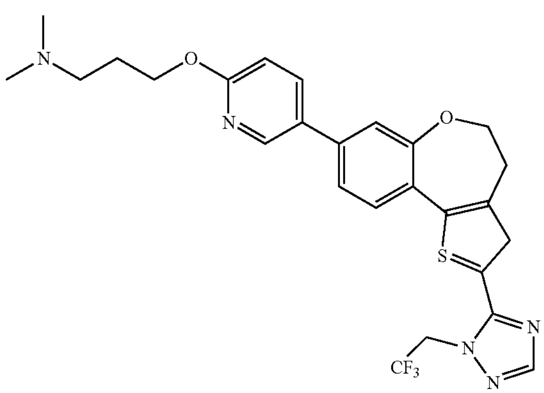 | Dimethyl-[3-(5-{2-[2-(2,2,2-trifluoro-ethyl)-2H-[1,2,4]triazol-3-yl]-4,5-dihydro-6-oxa-3-thia-1-aza-benzo[e]azulen-8-yl}-pyridin-2-yloxy)-propyl]-amine |
| 122 | 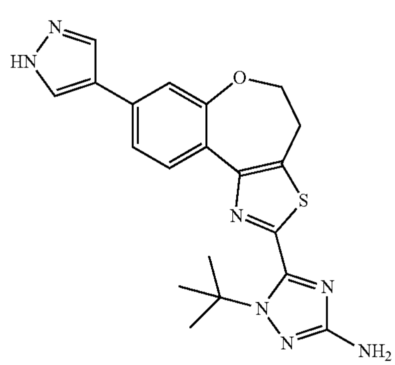 [SMILES: CC(C)(C)n1nc(N)nc1-c1nc2c(s1)CCOc1cc(-c3cn[nH]c3)ccc1-2] | 1-tert-Butyl-5-[8-(1H-pyrazol-4-yl)-4,5-dihydro-6-oxa-3-thia-1-aza-benzo[e]azulen-2-yl]-1H-[1,2,4]triazol-3-ylamine |

TABLE 1-continued

| No. | Structure | Name |
|---|---|---|
| 123 | 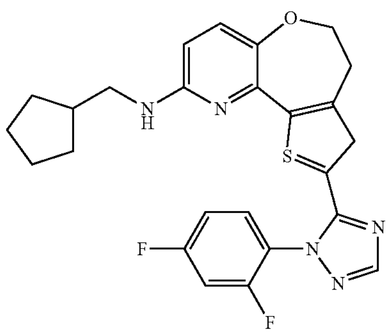 | Cyclopentylmethyl-{2-[2-(2,4-difluoro-phenyl)-2H-[1,2,4]triazol-3-yl]-4,5-dihydro-6-oxa-1-thia-10-aza-benzo[e]azulen-9-yl}-amine |
| 124 | 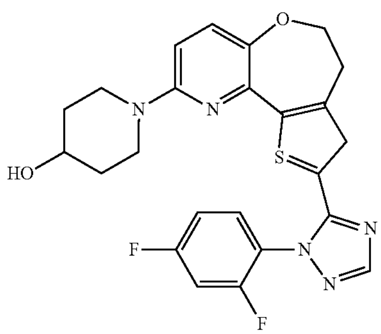 | 1-{2-[2-(2,4-Difluoro-phenyl)-2H-[1,2,4]triazol-3-yl]-4,5-dihydro-6-oxa-1-thia-10-aza-benzo[e]azulen-9-yl}-piperidin-4-ol |
| 125 | 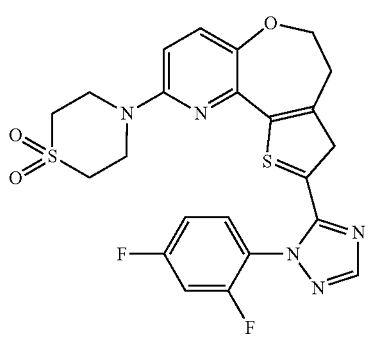 | 2-[2-(2,4-Difluoro-phenyl)-2H-[1,2,4]triazol-3-yl]-9-(1,1-dioxo-S-thiomorpholin-4-yl)-4,5-dihydro-6-oxa-1-thia-10-aza-benzo[e]azulene |
| 126 | 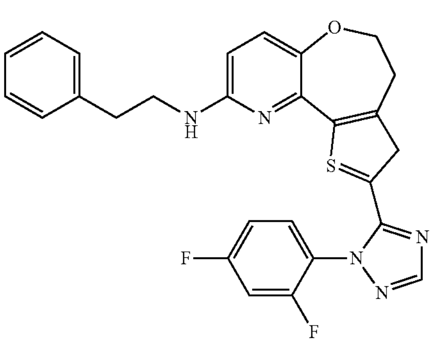 | {2-[2-(2,4-Difluoro-phenyl)-2H-[1,2,4]triazol-3-yl]-4,5-dihydro-6-oxa-1-thia-10-aza-benzo[e]azulen-9-yl}-phenethyl-amine |

TABLE 1-continued

| No. | Structure | Name |
|---|---|---|
| 127 | 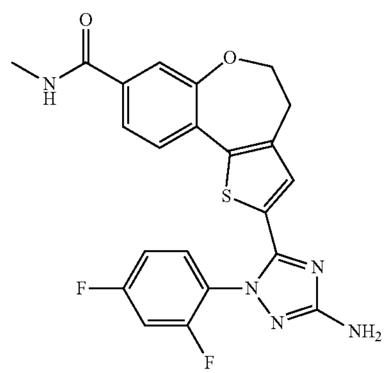 [SMILES: CNC(=O)c1ccc2c(c1)OCCc1cc(-c3nc(N)nn3-c3ccc(F)cc3F)sc1-2] | 2-(3-amino-1-(2,4-difluorophenyl)-1H-1,2,4-triazol-5-yl)-N-methyl-4,5-dihydrobenzo[b]thieno[2,3-d]oxepine-8-carboxamide |
| 128 | 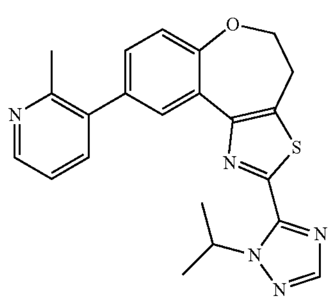 [SMILES: Cc1ncccc1-c1ccc2c(c1)-c1nc(-c3ncnn3C(C)C)sc1CCO2] | 2-(2-Isopropyl-2H-[1,2,4]triazol-3-yl)-9-(2-methyl-pyridin-3-yl)-4,5-dihydro-6-oxa-3-thia-1-aza-benzo[e]azulene |
| 129 | 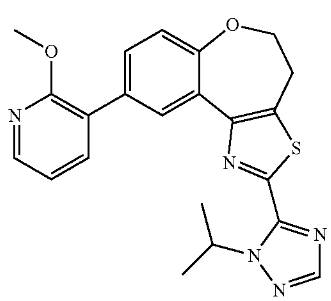 [SMILES: COc1ncccc1-c1ccc2c(c1)-c1nc(-c3ncnn3C(C)C)sc1CCO2] | 2-(2-Isopropyl-2H-[1,2,4]triazol-3-yl)-9-(2-methoxy-pyridin-3-yl)-4,5-dihydro-6-oxa-3-thia-1-aza-benzo[e]azulene |
| 130 | 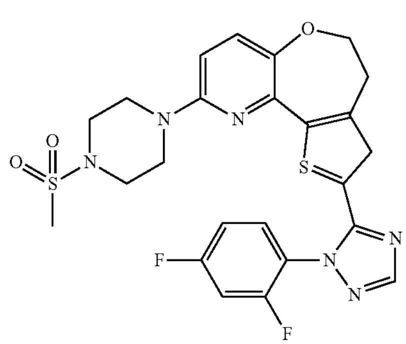 | 2-[2-(2,4-Difluoro-phenyl)-2H-[1,2,4]triazol-3-yl]-9-(4-methanesulfonyl-piperazin-1-yl)-4,5-dihydro-6-oxa-1-thia-10-aza-benzo[e]azulene |

TABLE 1-continued

| No. | Structure | Name |
|---|---|---|
| 131 | 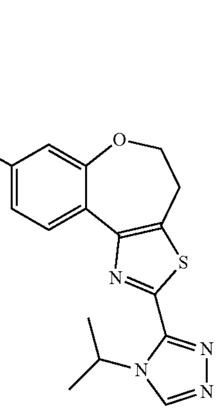 | 2-{[2-(4-Isopropyl-4H-[1,2,4]triazol-3-yl)-4,5-dihydro-6-oxa-3-thia-1-aza-benzo[e]azulen-8-ylmethyl]-amino}-ethanol |
| 132 | 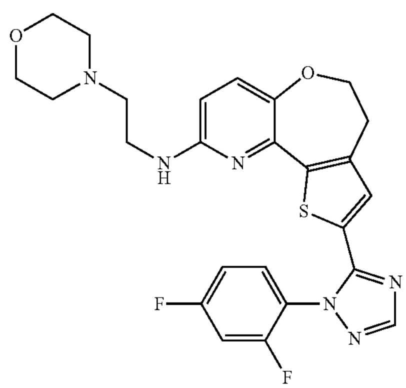 [SMILES: Fc1ccc(-n2ncnc2-c2cc3c(s2)-c2nc(NCCN4CCOCC4)ccc2OCC3)c(F)c1] | {2-[2-(2,4-Difluoro-phenyl)-2H-[1,2,4]triazol-3-yl]-4,5-dihydro-6-oxa-1-thia-10-aza-benzo[e]azulen-9-yl}-(2-morpholin-4-yl-ethyl)-amine |
| 133 | 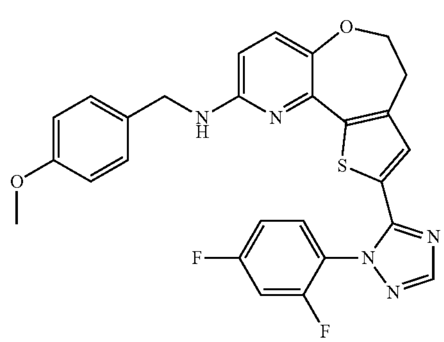 [SMILES: COc1ccc(CNc2ccc3c(n2)-c2sc(-c4ncnn4-c4ccc(F)cc4F)cc2CCO3)cc1] | {2-[2-(2,4-Difluoro-phenyl)-2H-[1,2,4]triazol-3-yl]-4,5-dihydro-6-oxa-1-thia-10-aza-benzo[e]azulen-9-yl}-(4-methoxy-benzyl)-amine |
| 134 | 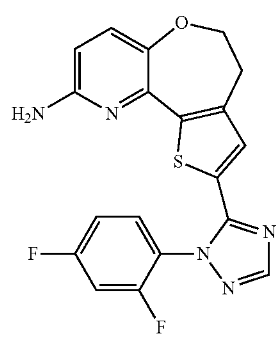 [SMILES: Nc1ccc2c(n1)-c1sc(-c3ncnn3-c3ccc(F)cc3F)cc1CCO2] | 2-[2-(2,4-Difluoro-phenyl)-2H-[1,2,4]triazol-3-yl]-4,5-dihydro-6-oxa-1-thia-10-aza-benzo[e]azulen-9-ylamine |

TABLE 1-continued

| No. | Structure | Name |
|---|---|---|
| 135 | 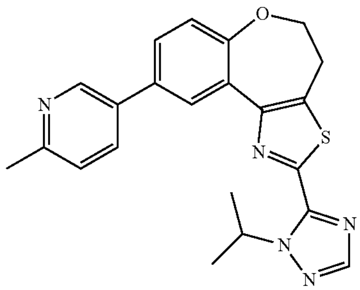 [SMILES: Cc1ccc(-c2ccc3c(c2)-c2nc(-c4ncnn4C(C)C)sc2CCO3)cn1] | 2-(2-Isopropyl-2H-[1,2,4]triazol-3-yl)-9-(6-methyl-pyridin-3-yl)-4,5-dihydro-6-oxa-3-thia-1-aza-benzo[e]azulene |
| 136 | 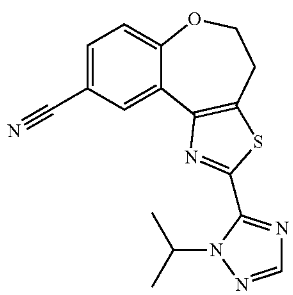 [SMILES: CC(C)n1ncnc1-c1nc2c(s1)CCOc1ccc(C#N)cc1-2] | 2-(2-Isopropyl-2H-[1,2,4]triazol-3-yl)-4,5-dihydro-6-oxa-3-thia-1-aza-benzo[e]azulene-9-carbonitrile |
| 137 | 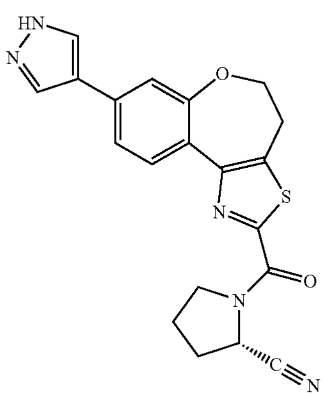 [SMILES: N#C[C@@H]1CCCN1C(=O)c1nc2c(s1)CCOc1cc(-c3cn[nH]c3)ccc1-2] | (S)-1-[8-(1H-Pyrazol-4-yl)-4,5-dihydro-6-oxa-3-thia-1-aza-benzo[e]azulene-2-carbonyl]-pyrrolidine-2-carbonitrile |
| 138 | 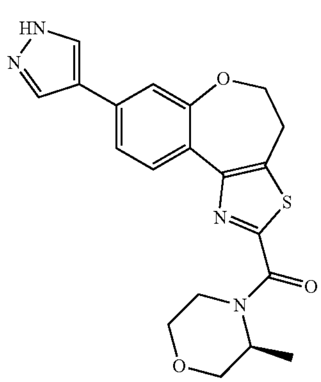 [SMILES: C[C@H]1COCCN1C(=O)c1nc2c(s1)CCOc1cc(-c3cn[nH]c3)ccc1-2] | ((S)-3-Methyl-morpholin-4-yl)-[8-(1H-pyrazol-4-yl)-4,5-dihydro-6-oxa-3-thia-1-aza-benzo[e]azulen-2-yl]-methanone |

TABLE 1-continued

| No. | Structure | Name |
|---|---|---|
| 139 | 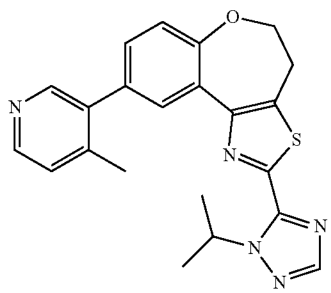 [SMILES: Cc1ccncc1-c1ccc2c(c1)-c1nc(-c3ncnn3C(C)C)sc1CCO2] | 2-(2-Isopropyl-2H-[1,2,4]triazol-3-yl)-9-(4-methyl-pyridin-3-yl)-4,5-dihydro-6-oxa-3-thia-1-aza-benzo[e]azulene |
| 140 | 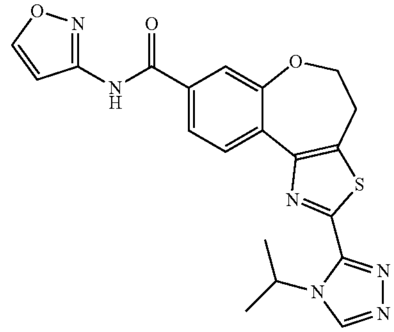 [SMILES: CC(C)n1cnnc1-c1nc2c(s1)CCOc1cc(C(=O)Nc3ccon3)ccc1-2] | 2-(4-Isopropyl-4H-[1,2,4]triazol-3-yl)-4,5-dihydro-6-oxa-3-thia-1-aza-benzo[e]azulene-8-carboxylic acid isoxazol-3-ylamide |
| 141 | 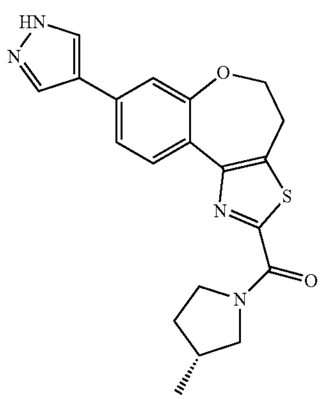 [SMILES: C[C@@H]1CCN(C(=O)c2nc3c(s2)CCOc2cc(-c4cn[nH]c4)ccc2-3)C1] | ((R)-3-Methyl-pyrrolidin-1-yl)-[8-(1H-pyrazol-4-yl)-4,5-dihydro-6-oxa-3-thia-1-aza-benzo[e]azulen-2-yl]-methanone |
| 142 | 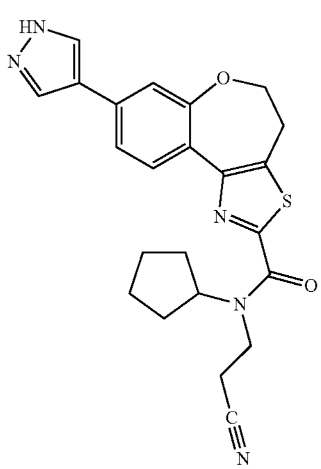 [SMILES: N#CCCN(C(=O)c1nc2c(s1)CCOc1cc(-c3cn[nH]c3)ccc1-2)C1CCCC1] | 8-(1H-Pyrazol-4-yl)-4,5-dihydro-6-oxa-3-thia-1-aza-benzo[e]azulene-2-carboxylic acid (2-cyano-ethyl)-cyclopentyl-amide |

TABLE 1-continued

| No. | Structure | Name |
|---|---|---|
| 143 | 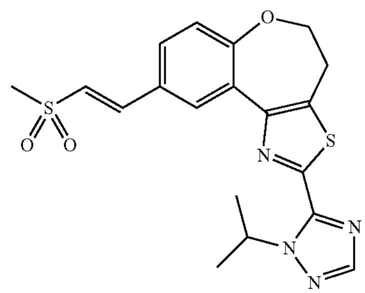 [SMILES: CC(C)n1ncnc1-c1nc2c(s1)CCOc1ccc(/C=C/S(C)(=O)=O)cc1-2] | 2-(2-Isopropyl-2H-[1,2,4]triazol-3-yl)-9-((E)-2-methanesulfonyl-vinyl)-4,5-dihydro-6-oxa-3-thia-1-aza-benzo[e]azulene |
| 144 | 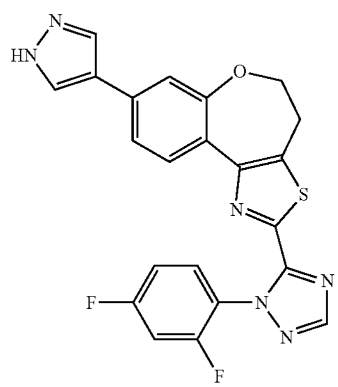 [SMILES: Fc1ccc(-n2ncnc2-c2nc3c(s2)CCOc2cc(-c4cn[nH]c4)ccc2-3)c(F)c1] | 2-[2-(2,4-Difluoro-phenyl)-2H-[1,2,4]triazol-3-yl]-8-(1H-pyrazol-4-yl)-4,5-dihydro-6-oxa-3-thia-1-aza-benzo[e]azulene |
| 145 | 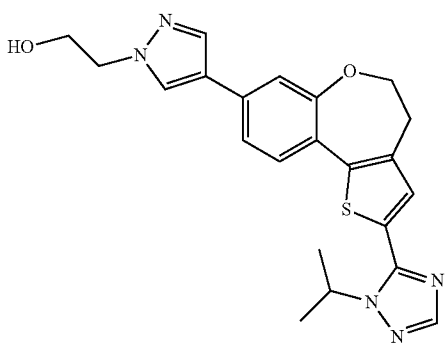 [SMILES: CC(C)n1ncnc1-c1cc2c(s1)-c1ccc(-c3cnn(CCO)c3)cc1OCC2] | 2-(4-(2-(1-isopropyl-1H-1,2,4-triazol-5-yl)-4,5-dihydrobenzo[b]thieno[2,3-d]oxepin-8-yl)-1H-pyrazol-1-yl)ethanol |
| 146 | 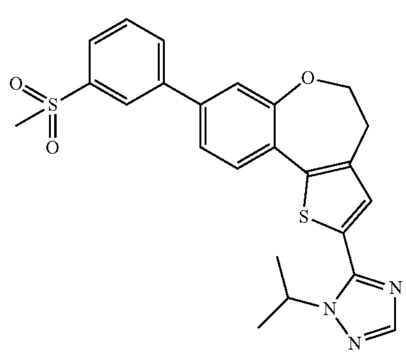 [SMILES: CC(C)n1ncnc1-c1cc2c(s1)-c1ccc(-c3cccc(S(C)(=O)=O)c3)cc1OCC2] | 1-isopropyl-5-(8-(3-(methylsulfonyl)phenyl)-4,5-dihydrobenzo[b]thieno[2,3-d]oxepin-2-yl)-1H-1,2,4-triazole |

TABLE 1-continued

| No. | Structure | Name |
|---|---|---|
| 147 | 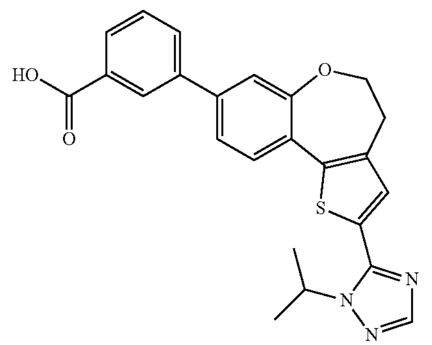 [SMILES: CC(C)n1ncnc1-c1cc2c(s1)-c1ccc(-c3cccc(C(=O)O)c3)cc1OCC2] | 3-(2-(1-isopropyl-1H-1,2,4-triazol-5-yl)-4,5-dihydrobenzo[b]thieno[2,3-d]oxepin-8-yl)benzoic acid |
| 148 | 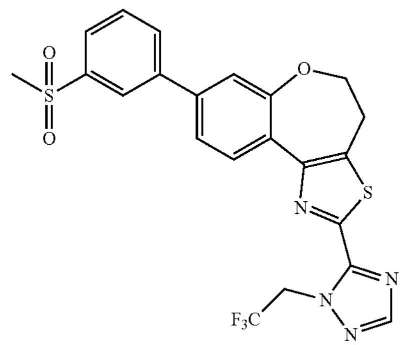 [SMILES: CS(=O)(=O)c1cccc(-c2ccc3c(c2)OCCc2sc(-c4ncnn4CC(F)(F)F)nc2-3)c1] | 8-(3-Methanesulfonyl-phenyl)-2-[2-(2,2,2-trifluoro-ethyl)-2H-[1,2,4]triazol-3-yl]-4,5-dihydro-6-oxa-3-thia-1-aza-benzo[e]azulene |
| 149 | 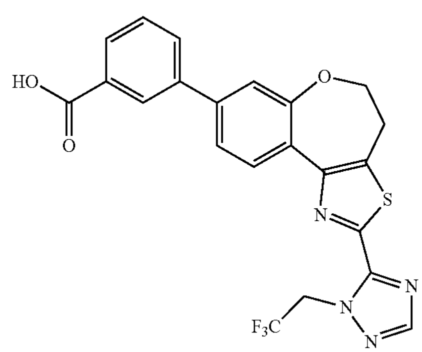 [SMILES: O=C(O)c1cccc(-c2ccc3c(c2)OCCc2sc(-c4ncnn4CC(F)(F)F)nc2-3)c1] | 3-{2-[2-(2,2,2-Trifluoro-ethyl)-2H-[1,2,4]triazol-3-yl]-4,5-dihydro-6-oxa-3-thia-1-aza-benzo[e]azulen-8-yl}-benzoic acid |
| 150 | 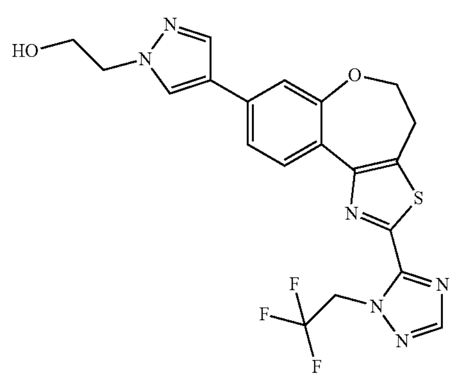 [SMILES: OCCn1cc(-c2ccc3c(c2)OCCc2sc(-c4ncnn4CC(F)(F)F)nc2-3)cn1] | 2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-ethanol |

TABLE 1-continued

| No. | Structure | Name |
|-----|-----------|------|
| 151 | 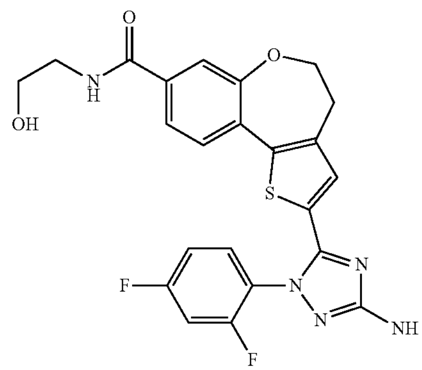 [SMILES: Nc1nc(-c2cc3c(s2)-c2ccc(C(=O)NCCO)cc2OCC3)n(-c2ccc(F)cc2F)n1] | 2-(3-amino-1-(2,4-difluorophenyl)-1H-1,2,4-triazol-5-yl)-N-(2-hydroxyethyl)-4,5-dihydrobenzo[b]thieno[2,3-d]oxepine-8-carboxamide |
| 152 | 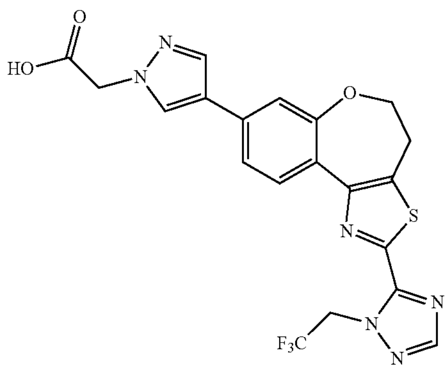 [SMILES: O=C(O)Cn1cc(-c2ccc3c(c2)OCCc2sc(-c4ncnn4CC(F)(F)F)nc2-3)cn1] | (4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-acetic acid |
| 153 | 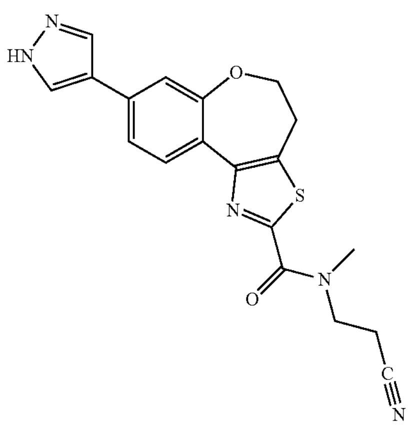 [SMILES: CN(CCC#N)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid (2-cyano-ethyl)-methyl-amide |
| 154 | 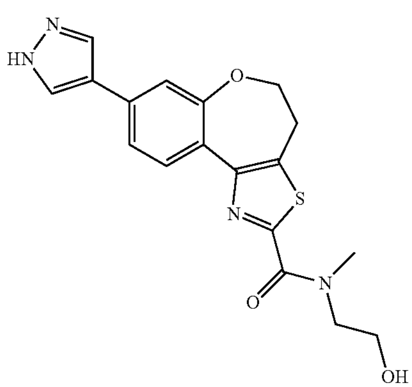 [SMILES: CN(CCO)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid (2-hydroxy-ethyl)-methyl-amide |

TABLE 1-continued

| No. | Structure | Name |
|---|---|---|
| 155 | 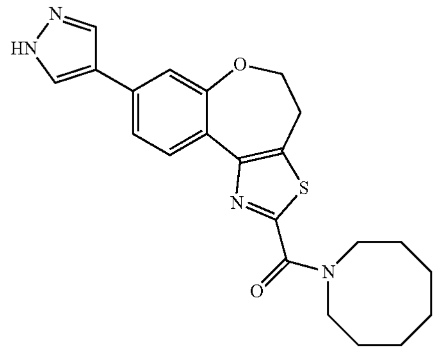 [SMILES: O=C(c1nc2c(s1)CCOc1cc(-c3cn[nH]c3)ccc1-2)N1CCCCCCC1] | Azocan-1-yl-[8-(1H-pyrazol-4-yl)-4,5-dihydro-6-oxa-3-thia-1-aza-benzo[e]azulen-2-yl]-methanone |
| 156 | 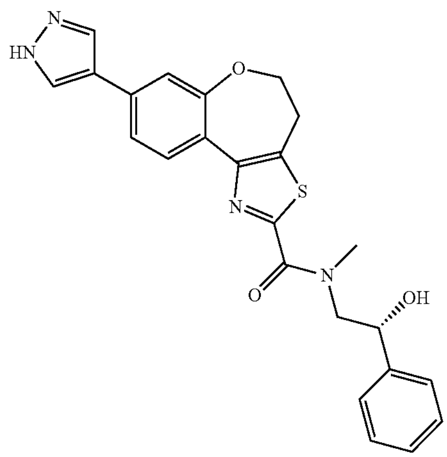 [SMILES: CN(C[C@H](O)c1ccccc1)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid ((R)-2-hydroxy-2-phenyl-ethyl)-methyl-amide |
| 157 | 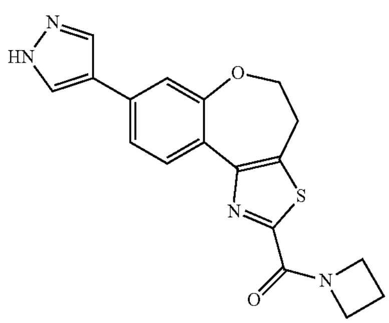 [SMILES: O=C(c1nc2c(s1)CCOc1cc(-c3cn[nH]c3)ccc1-2)N1CCC1] | Azetidin-1-yl-[8-(1H-pyrazol-4-yl)-4,5-dihydro-6-oxa-3-thia-1-aza-benzo[e]azulen-2-yl]-methanone |
| 158 | 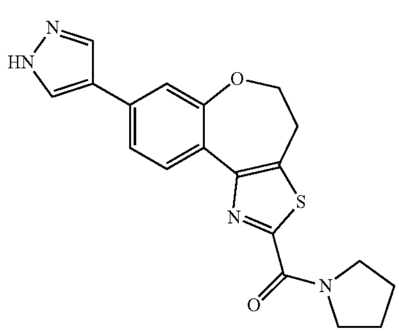 [SMILES: O=C(c1nc2c(s1)CCOc1cc(-c3cn[nH]c3)ccc1-2)N1CCCC1] | [8-(1H-Pyrazol-4-yl)-4,5-dihydro-6-oxa-3-thia-1-aza-benzo[e]azulen-2-yl]-pyrrolidin-1-yl-methanone |

TABLE 1-continued

| No. | Structure | Name |
|---|---|---|
| 159 | 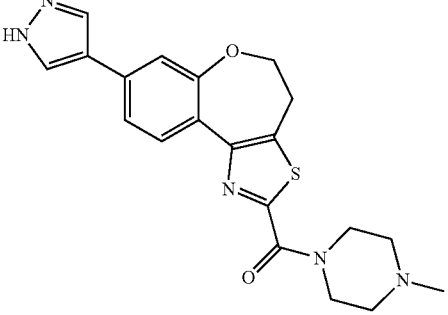 | (4-Methyl-piperazin-1-yl)-[8-(1H-pyrazol-4-yl)-4,5-dihydro-6-oxa-3-thia-1-aza-benzo[e]azulen-2-yl]-methanone |
| 160 | 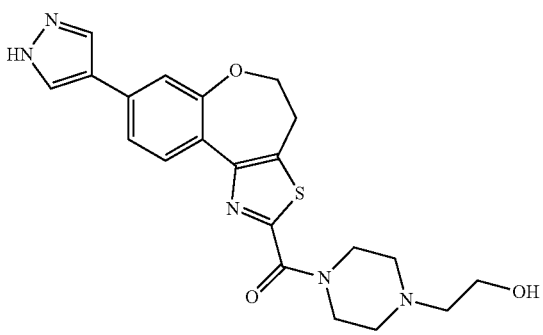 [SMILES: O=C(c1nc2c(s1)CCOc1cc(-c3cn[nH]c3)ccc1-2)N1CCN(CCO)CC1] | [4-(2-Hydroxy-ethyl)-piperazin-1-yl]-[8-(1H-pyrazol-4-yl)-4,5-dihydro-6-oxa-3-thia-1-aza-benzo[e]azulen-2-yl]-methanone |
| 161 | 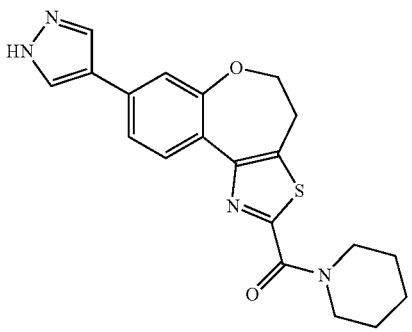 [SMILES: O=C(c1nc2c(s1)CCOc1cc(-c3cn[nH]c3)ccc1-2)N1CCCCC1] | Piperidin-1-yl-[8-(1H-pyrazol-4-yl)-4,5-dihydro-6-oxa-3-thia-1-aza-benzo[e]azulen-2-yl]-methanone |
| 162 | 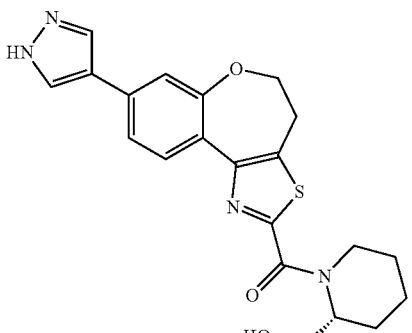 | ((R)-2-Hydroxymethyl-piperidin-1-yl)-[8-(1H-pyrazol-4-yl)-4,5-dihydro-6-oxa-3-thia-1-aza-benzo[c]azulen-2-yl]-methanone |

TABLE 1-continued

| No. | Structure | Name |
|---|---|---|
| 163 | 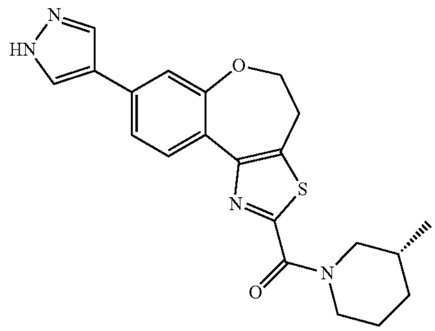 [SMILES: C[C@@H]1CCCN(C(=O)c2nc3c(s2)CCOc2cc(-c4cn[nH]c4)ccc2-3)C1] | ((R)-3-Methyl-piperidin-1-yl)-[8-(1H-pyrazol-4-yl)-4,5-dihydro-6-oxa-3-thia-1-aza-benzo[e]azulen-2-yl]-methanone |
| 164 | 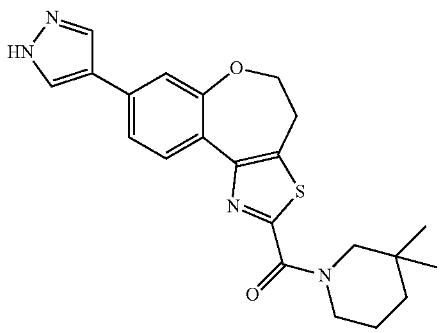 [SMILES: CC1(C)CCCN(C(=O)c2nc3c(s2)CCOc2cc(-c4cn[nH]c4)ccc2-3)C1] | (3,3-Dimethyl-piperidin-1-yl)-[8-(1H-pyrazol-4-yl)-4,5-dihydro-6-oxa-3-thia-1-aza-benzo[e]azulen-2-yl]-methanone |
| 165 | 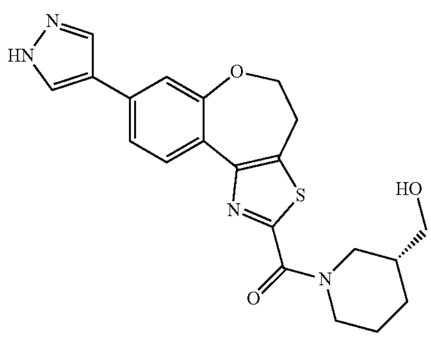 [SMILES: O=C(c1nc2c(s1)CCOc1cc(-c3cn[nH]c3)ccc1-2)N1CCC[C@@H](CO)C1] | ((R)-3-Hydroxymethyl-piperidin-1-yl)-[8-(1H-pyrazol-4-yl)-4,5-dihydro-6-oxa-3-thia-1-aza-benzo[e]azulen-2-yl]-methanone |
| 166 | 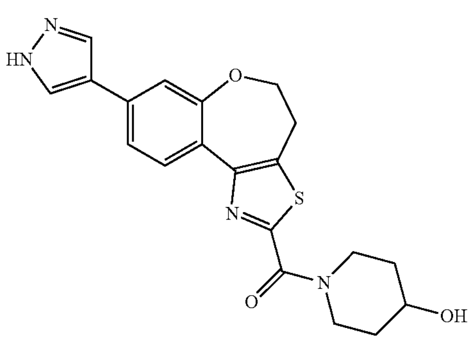 | (4-Hydroxy-piperidin-1-yl)-[8-(1H-pyrazol-4-yl)-4,5-dihydro-6-oxa-3-thia-1-aza-benzo[e]azulen-2-yl]-methanone |

TABLE 1-continued

| No. | Structure | Name |
|---|---|---|
| 167 | 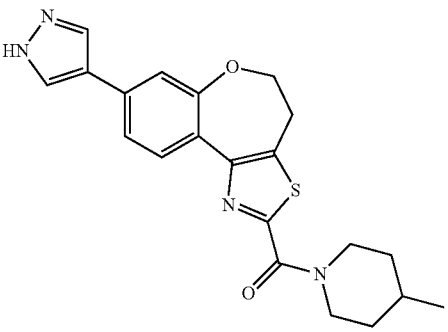 [SMILES: CC1CCN(C(=O)c2nc3c(s2)CCOc2cc(-c4cn[nH]c4)ccc2-3)CC1] | (4-Methyl-piperidin-1-yl)-[8-(1H-pyrazol-4-yl)-4,5-dihydro-6-oxa-3-thia-1-aza-benzo[e]azulen-2-yl]-methanone |
| 168 | 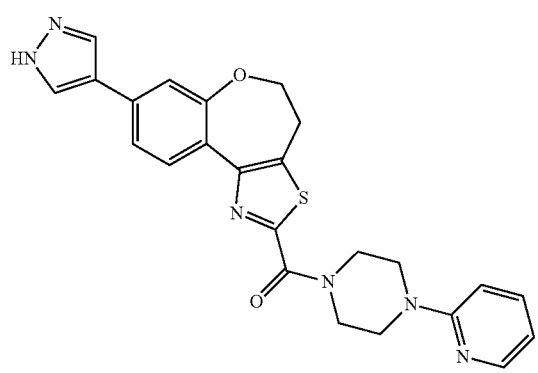 [SMILES: O=C(c1nc2c(s1)CCOc1cc(-c3cn[nH]c3)ccc1-2)N1CCN(c2ccccn2)CC1] | [8-(1H-Pyrazol-4-yl)-4,5-dihydro-6-oxa-3-thia-1-aza-benzo[e]azulen-2-yl]-(4-pyridin-2-yl-piperazin-1-yl)-methanone |
| 169 | 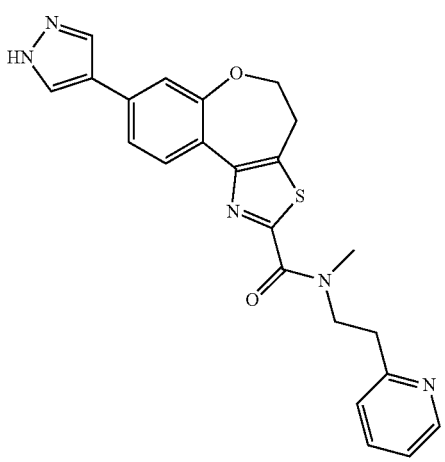 [SMILES: CN(CCc1ccccn1)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid methyl-(2-pyridin-2-yl-ethyl)-amide |
| 170 | 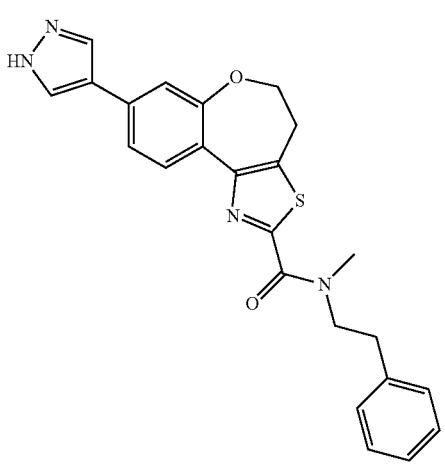 [SMILES: CN(CCc1ccccc1)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid methyl-phenethyl-amide |

TABLE 1-continued

| No. | Structure | Name |
|---|---|---|
| 171 | 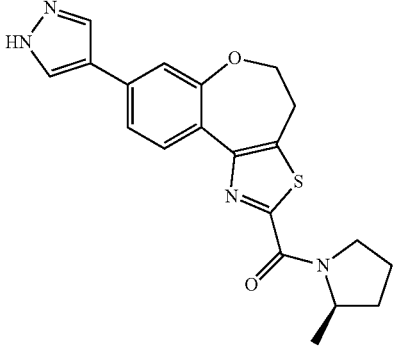 [SMILES: C[C@@H]1CCCN1C(=O)c1nc2c(s1)CCOc1cc(-c3cn[nH]c3)ccc1-2] | ((R)-2-Methyl-pyrrolidin-1-yl)-[8-(1H-pyrazol-4-yl)-4,5-dihydro-6-oxa-3-thia-1-aza-benzo[e]azulen-2-yl]-methanone |
| 172 | 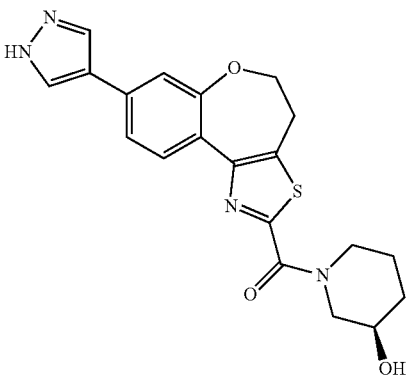 [SMILES: O=C(c1nc2c(s1)CCOc1cc(-c3cn[nH]c3)ccc1-2)N1CCC[C@@H](O)C1] | ((R)-3-Hydroxy-piperidin-1-yl)-[8-(1H-pyrazol-4-yl)-4,5-dihydro-6-oxa-3-thia-1-aza-benzo[e]azulen-2-yl]-methanone |
| 173 | 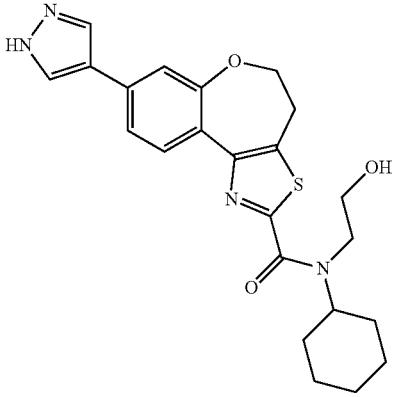 [SMILES: O=C(c1nc2c(s1)CCOc1cc(-c3cn[nH]c3)ccc1-2)N(CCO)C1CCCCC1] | 8-(1H-Pyrazol-4-yl)-4,5-dihydro-6-oxa-3-thia-1-aza-benzo[e]azulene-2-carboxylic acid cyclohexyl-(2-hydroxy-ethyl)-amide |
| 174 | 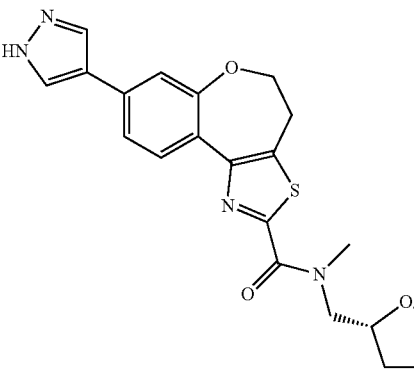 | 8-(1H-Pyrazol-4-yl)-4,5-dihydro-6-oxa-3-thia-1-aza-benzo[e]azulene-2-carboxylic acid methyl-[(R)-1-(tetrahydro-furan-2-yl)methyl]-amide |

TABLE 1-continued

| No. | Structure | Name |
|---|---|---|
| 175 | 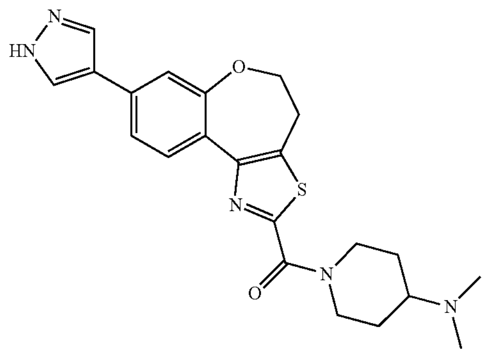 [SMILES: CN(C)C1CCN(C(=O)c2nc3c(s2)CCOc2cc(-c4cn[nH]c4)ccc2-3)CC1] | (4-Dimethylamino-piperidin-1-yl)-[8-(1H-pyrazol-4-yl)-4,5-dihydro-6-oxa-3-thia-1-aza-benzo[e]azulen-2-yl]-methanone |
| 176 | 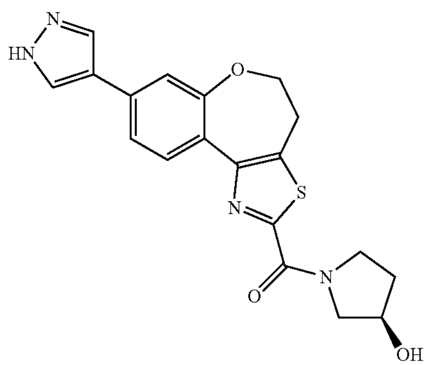 [SMILES: O=C(c1nc2c(s1)CCOc1cc(-c3cn[nH]c3)ccc1-2)N1CC[C@@H](O)C1] | ((R)-3-Hydroxy-pyrrolidin-1-yl)-[8-(1H-pyrazol-4-yl)-4,5-dihydro-6-oxa-3-thia-1-aza-benzo[e]azulen-2-yl]-methanone |
| 177 | 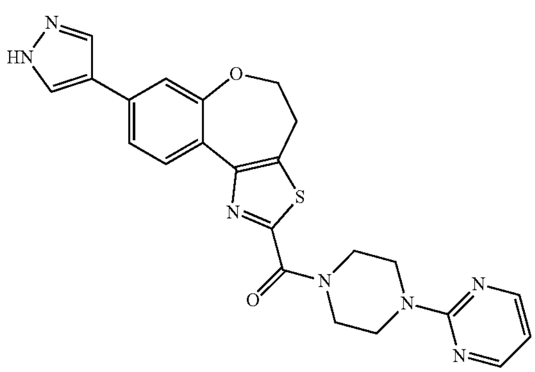 [SMILES: O=C(c1nc2c(s1)CCOc1cc(-c3cn[nH]c3)ccc1-2)N1CCN(c2ncccn2)CC1] | [8-(1H-Pyrazol-4-yl)-4,5-dihydro-6-oxa-3-thia-1-aza-benzo[e]azulen-2-yl]-(4-pyrimidin-2-yl-piperazin-1-yl)-methanone |
| 178 | 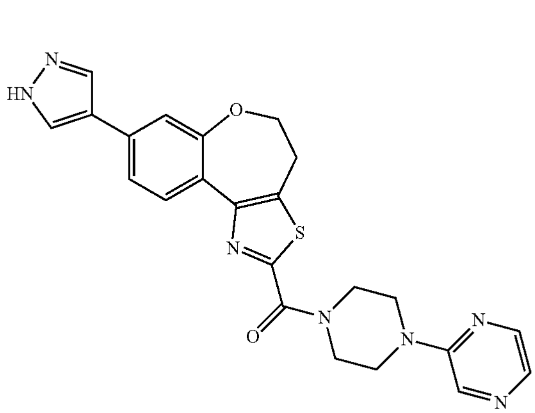 [SMILES: O=C(c1nc2c(s1)CCOc1cc(-c3cn[nH]c3)ccc1-2)N1CCN(c2cnccn2)CC1] | [8-(1H-Pyrazol-4-yl)-4,5-dihydro-6-oxa-3-thia-1-aza-benzo[e]azulen-2-yl]-(2,3,5,6-tetrahydro-[1,2']bipyrazinyl-4-yl)-methanone |

TABLE 1-continued

| No. | Structure | Name |
|---|---|---|
| 179 | 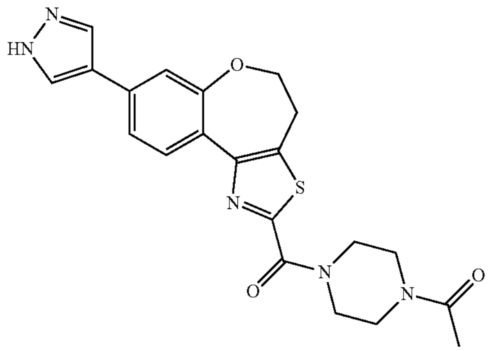 [SMILES: CC(=O)N1CCN(C(=O)c2nc3c(s2)CCOc2cc(-c4cn[nH]c4)ccc2-3)CC1] | 1-{4-[8-(1H-Pyrazol-4-yl)-4,5-dihydro-6-oxa-3-thia-1-aza-benzo[e]azulene-2-carbonyl]-piperazin-1-yl}-ethanone |
| 180 | 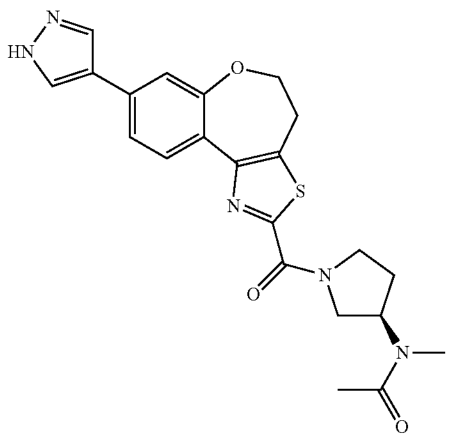 [SMILES: CC(=O)N(C)[C@@H]1CCN(C(=O)c2nc3c(s2)CCOc2cc(-c4cn[nH]c4)ccc2-3)C1] | N-Methyl-N-{(R)-1-[8-(1H-pyrazol-4-yl)-4,5-dihydro-6-oxa-3-thia-1-aza-benzo[e]azulene-2-carbonyl]-pyrrolidin-3-yl}-acetamide |
| 181 | 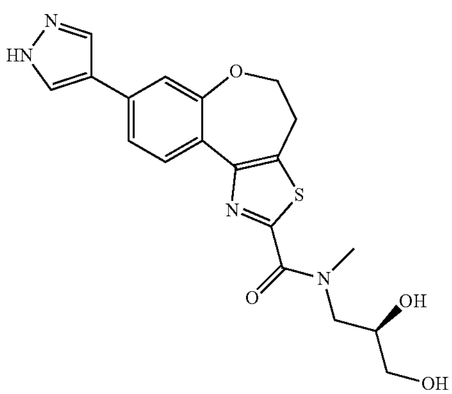 [SMILES: CN(C[C@@H](O)CO)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid ((R)-2,3-dihydroxy-propyl)-methyl-amide |
| 182 | 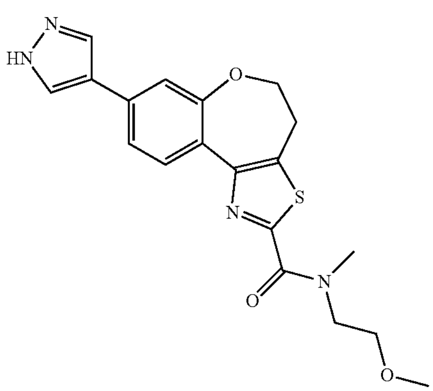 [SMILES: COCCN(C)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid (2-methoxy-ethyl)-methyl-amide |

TABLE 1-continued

| No. | Structure | Name |
|---|---|---|
| 183 | 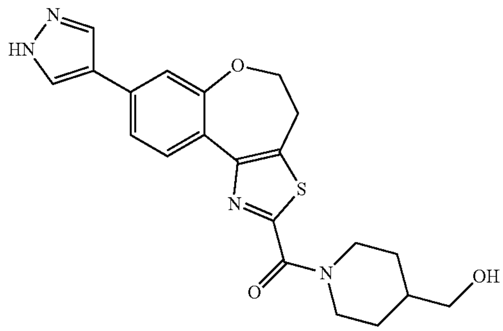 [SMILES: O=C(c1nc2c(s1)CCOc1cc(-c3cn[nH]c3)ccc1-2)N1CCC(CO)CC1] | (4-Hydroxymethyl-piperidin-1-yl)-[8-(1H-pyrazol-4-yl)-4,5-dihydro-6-oxa-3-thia-1-aza-benzo[e]azulen-2-yl]-methanone |
| 184 | 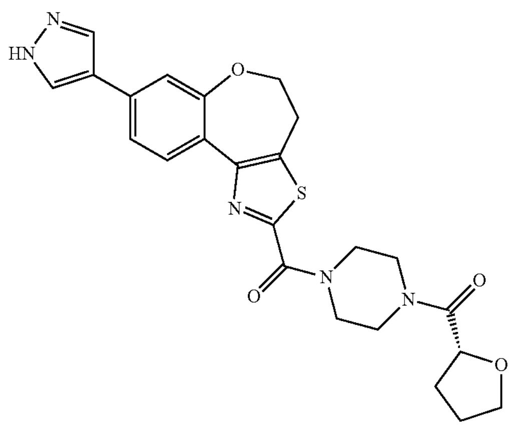 [SMILES: O=C(c1nc2c(s1)CCOc1cc(-c3cn[nH]c3)ccc1-2)N1CCN(C(=O)[C@H]2CCCO2)CC1] | [8-(1H-Pyrazol-4-yl)-4,5-dihydro-6-oxa-3-thia-1-aza-benzo[e]azulen-2-yl]-[4-((R)-tetrahydro-furan-2-carbonyl)-piperazin-1-yl]-methanone |
| 185 | 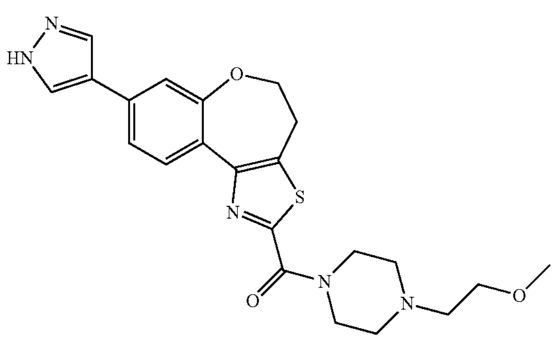 [SMILES: COCCN1CCN(C(=O)c2nc3c(s2)CCOc2cc(-c4cn[nH]c4)ccc2-3)CC1] | [4-(2-Methoxy-ethyl)-piperazin-1-yl]-[8-(1H-pyrazol-4-yl)-4,5-dihydro-6-oxa-3-thia-1-aza-benzo[e]azulen-2-yl]-methanone |
| 186 | 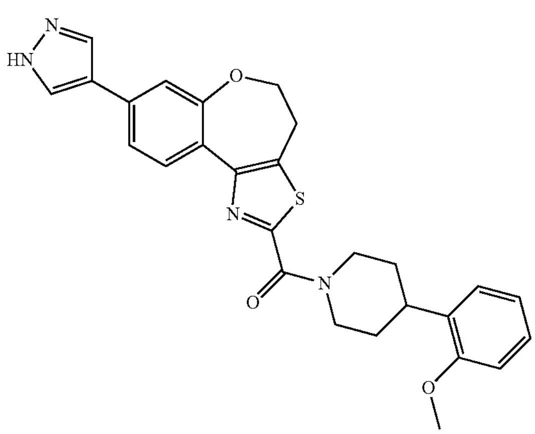 [SMILES: COc1ccccc1C1CCN(C(=O)c2nc3c(s2)CCOc2cc(-c4cn[nH]c4)ccc2-3)CC1] | [4-(2-Methoxy-phenyl)-piperidin-1-yl]-[8-(1H-pyrazol-4-yl)-4,5-dihydro-6-oxa-3-thia-1-aza-benzo[e]azulen-2-yl]-methanone |

TABLE 1-continued

| No. | Structure | Name |
|---|---|---|
| 187 | 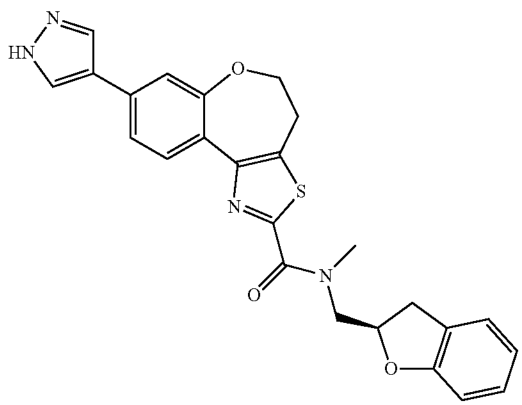 [SMILES: CN(C[C@H]1Cc2ccccc2O1)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid [(R)-1-(2,3-dihydro-benzofuran-2-yl)methyl]-methyl-amide |
| 188 | 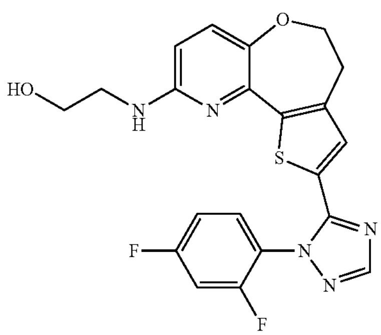 [SMILES: OCCNc1ccc2c(n1)-c1sc(-c3ncnn3-c3ccc(F)cc3F)cc1CCO2] | 2-{2-[2-(2,4-Difluoro-phenyl)-2H-[1,2,4]triazol-3-yl]-4,5-dihydro-6-oxa-1-thia-10-aza-benzo[e]azulen-9-ylamino}-ethanol |
| 189 | 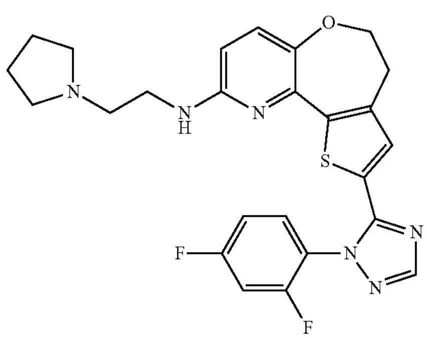 [SMILES: Fc1ccc(-n2ncnc2-c2cc3c(s2)-c2nc(NCCN4CCCC4)ccc2OCC3)c(F)c1] | {2-[2-(2,4-Difluoro-phenyl)-2H-[1,2,4]triazol-3-yl]-4,5-dihydro-6-oxa-1-thia-10-aza-benzo[e]azulen-9-yl}-(2-pyrrolidin-1-yl-ethyl)-amine |
| 190 | 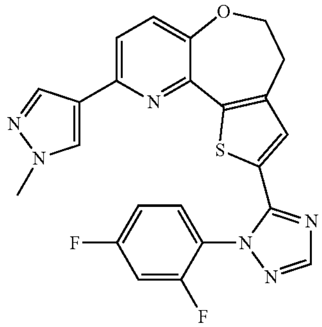 [SMILES: Cn1cc(-c2ccc3c(n2)-c2sc(-c4ncnn4-c4ccc(F)cc4F)cc2CCO3)cn1] | 2-[2-(2,4-Difluoro-phenyl)-2H-[1,2,4]triazol-3-yl]-9-(1-methyl-1H-pyrazol-4-yl)-4,5-dihydro-6-oxa-1-thia-10-aza-benzo[e]azulene |

TABLE 1-continued

| No. | Structure | Name |
| --- | --- | --- |
| 191 | 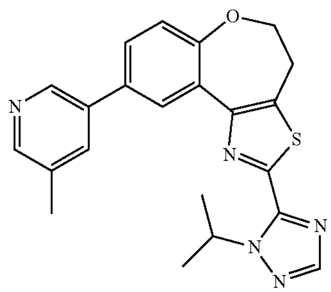 [SMILES: Cc1cncc(-c2ccc3c(c2)-c2nc(-c4ncnn4C(C)C)sc2CCO3)c1] | 2-(2-Isopropyl-2H-[1,2,4]triazol-3-yl)-9-(5-methyl-pyridin-3-yl)-4,5-dihydro-6-oxa-3-thia-1-aza-benzo[e]azulene |
| 192 | 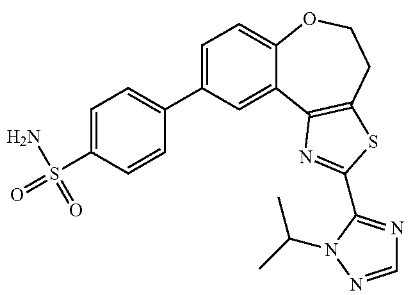 [SMILES: CC(C)n1ncnc1-c1nc2c(s1)CCOc1ccc(-c3ccc(S(N)(=O)=O)cc3)cc1-2] | 4-[2-(2-Isopropyl-2H-[1,2,4]triazol-3-yl)-4,5-dihydro-6-oxa-3-thia-1-aza-benzo[e]azulen-9-yl]-benzenesulfonamide |
| 193 | 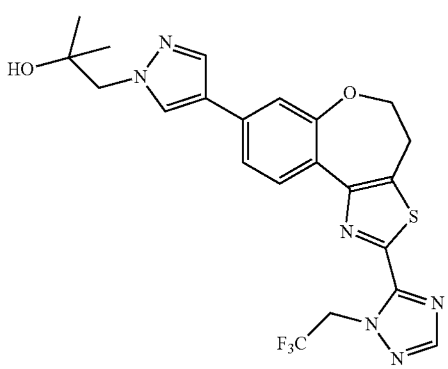 [SMILES: CC(C)(O)Cn1cc(-c2ccc3c(c2)OCCc2sc(-c4ncnn4CC(F)(F)F)nc2-3)cn1] | 2-Methyl-1-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propan-2-ol |
| 194 | 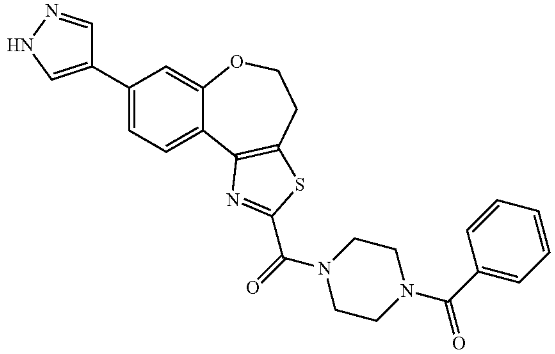 [SMILES: O=C(c1ccccc1)N1CCN(C(=O)c2nc3c(s2)CCOc2cc(-c4cn[nH]c4)ccc2-3)CC1] | (4-Benzoyl-piperazin-1-yl)-[8-(1H-pyrazol-4-yl)-4,5-dihydro-6-oxa-3-thia-1-aza-benzo[e]azulen-2-yl]-methanone |

TABLE 1-continued

| No. | Structure | Name |
| --- | --- | --- |
| 195 | 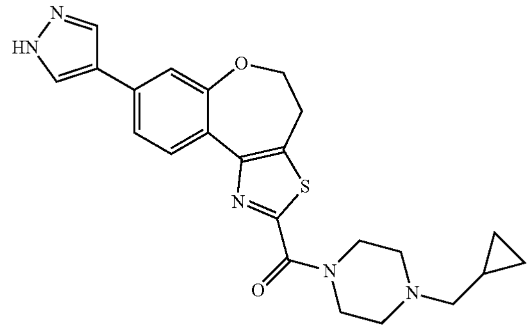 [SMILES: O=C(c1nc2c(s1)CCOc1cc(-c3cn[nH]c3)ccc1-2)N1CCN(CC2CC2)CC1] | (4-Cyclopropylmethyl-piperazin-1-yl)-[8-(1H-pyrazol-4-yl)-4,5-dihydro-6-oxa-3-thia-1-aza-benzo[e]azulen-2-yl]-methanone |
| 196 | 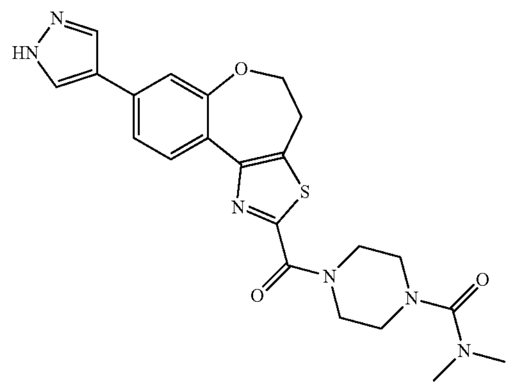 [SMILES: CN(C)C(=O)N1CCN(C(=O)c2nc3c(s2)CCOc2cc(-c4cn[nH]c4)ccc2-3)CC1] | 4-[8-(1H-Pyrazol-4-yl)-4,5-dihydro-6-oxa-3-thia-1-aza-benzo[e]azulene-2-carbonyl]-piperazine-1-carboxylic acid dimethylamide |
| 197 | 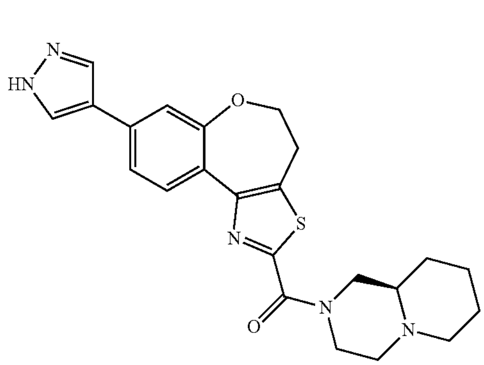 [SMILES: O=C(c1nc2c(s1)CCOc1cc(-c3cn[nH]c3)ccc1-2)N1CCN2CCCC[C@@H]2C1] | (R)-Octahydro-pyrido[1,2-a]pyrazin-2-yl-[8-(1H-pyrazol-4-yl)-4,5-dihydro-6-oxa-3-thia-1-aza-benzo[e]azulen-2-yl]-methanone |
| 198 | 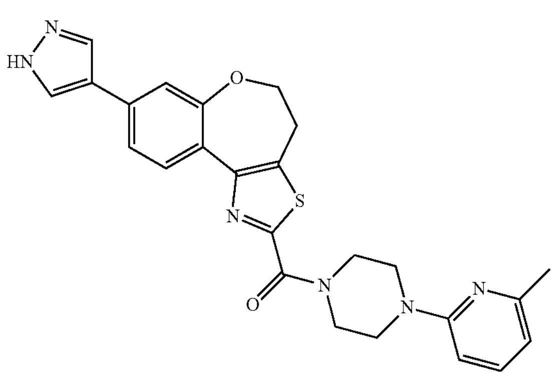 [SMILES: Cc1cccc(N2CCN(C(=O)c3nc4c(s3)CCOc3cc(-c5cn[nH]c5)ccc3-4)CC2)n1] | [4-(6-Methyl-pyridin-2-yl)-piperazin-1-yl]-[8-(1H-pyrazol-4-yl)-4,5-dihydro-6-oxa-3-thia-1-aza-benzo[e]azulen-2-yl]-methanone |

TABLE 1-continued

| No. | Structure | Name |
|---|---|---|
| 199 | 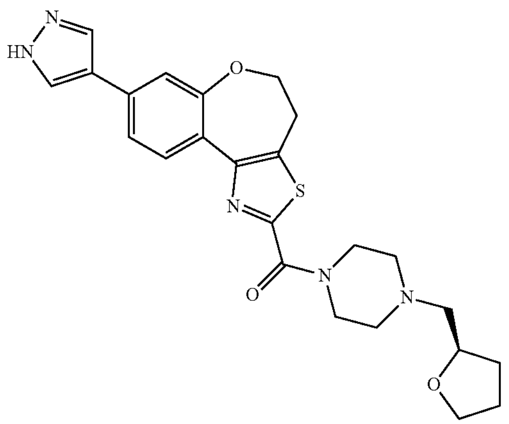 [SMILES: O=C(c1nc2c(s1)CCOc1cc(-c3cn[nH]c3)ccc1-2)N1CCN(C[C@H]2CCCO2)CC1] | [8-(1H-Pyrazol-4-yl)-4,5-dihydro-6-oxa-3-thia-1-aza-benzo[e]azulen-2-yl]-{4-[(R)-1-(tetrahydro-furan-2-yl)methyl]-piperazin-1-yl}-methanone |
| 200 | 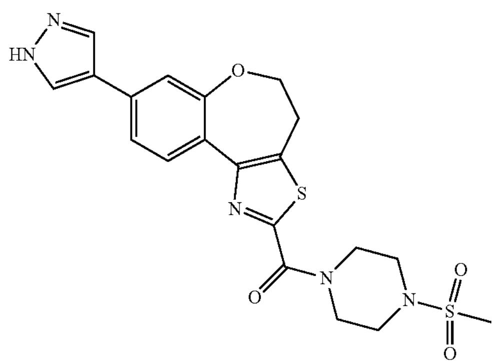 [SMILES: CS(=O)(=O)N1CCN(C(=O)c2nc3c(s2)CCOc2cc(-c4cn[nH]c4)ccc2-3)CC1] | (4-Methanesulfonyl-piperazin-1-yl)-[8-(1H-pyrazol-4-yl)-4,5-dihydro-6-oxa-3-thia-1-aza-benzo[e]azulen-2-yl]-methanone |
| 201 | 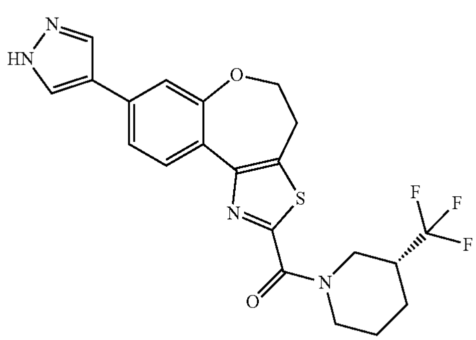 [SMILES: O=C(c1nc2c(s1)CCOc1cc(-c3cn[nH]c3)ccc1-2)N1CCC[C@@H](C(F)(F)F)C1] | [8-(1H-Pyrazol-4-yl)-4,5-dihydro-6-oxa-3-thia-1-aza-benzo[e]azulen-2-yl]-((R)-3-trifluoromethyl-piperidin-1-yl)-methanone |
| 202 | 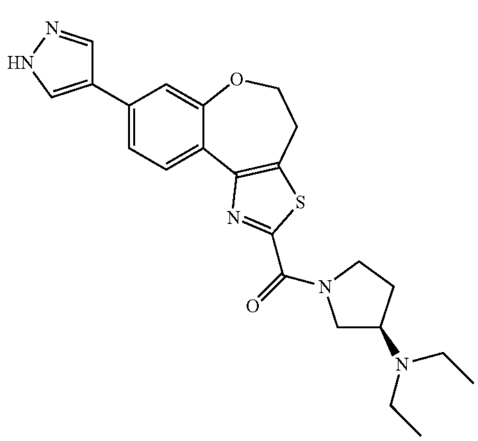 [SMILES: CCN(CC)[C@@H]1CCN(C(=O)c2nc3c(s2)CCOc2cc(-c4cn[nH]c4)ccc2-3)C1] | ((R)-3-Diethylamino-pyrrolidin-1-yl)-[8-(1H-pyrazol-4-yl)-4,5-dihydro-6-oxa-3-thia-1-aza-benzo[e]azulen-2-yl]-methanone |

TABLE 1-continued

| No. | Structure | Name |
|---|---|---|
| 203 | 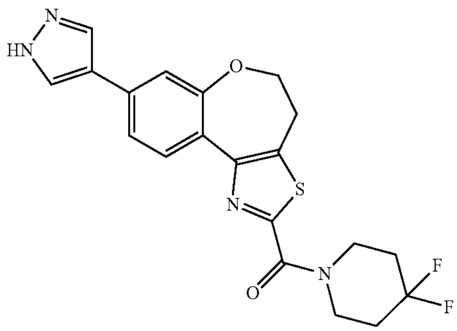 [SMILES: O=C(c1nc2c(s1)CCOc1cc(-c3cn[nH]c3)ccc1-2)N1CCC(F)(F)CC1] | (4,4-Difluoro-piperidin-1-yl)-[8-(1H-pyrazol-4-yl)-4,5-dihydro-6-oxa-3-thia-1-aza-benzo[e]azulen-2-yl]-methanone |
| 204 | 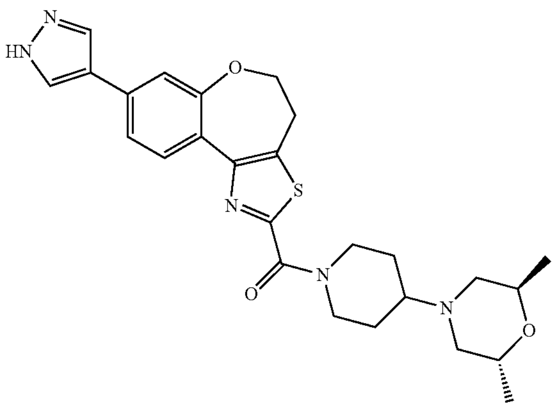 [SMILES: C[C@@H]1CN(C2CCN(C(=O)c3nc4c(s3)CCOc3cc(-c5cn[nH]c5)ccc3-4)CC2)C[C@@H](C)O1] | [4-((2R,6R)-2,6-Dimethyl-morpholin-4-yl)-piperidin-1-yl]-[8-(1H-pyrazol-4-yl)-4,5-dihydro-6-oxa-3-thia-1-aza-benzo[e]azulen-2-yl]-methanone |
| 205 | 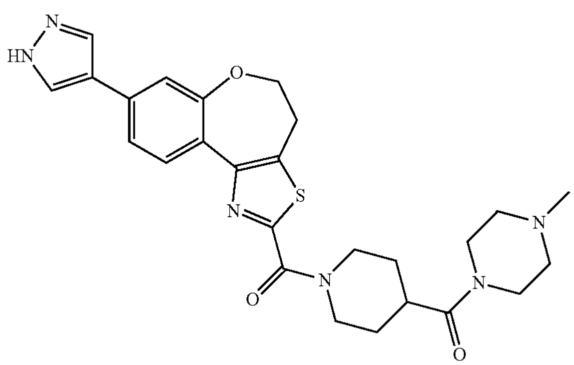 [SMILES: CN1CCN(C(=O)C2CCN(C(=O)c3nc4c(s3)CCOc3cc(-c5cn[nH]c5)ccc3-4)CC2)CC1] | [4-(4-Methyl-piperazine-1-carbonyl)-piperidin-1-yl]-[8-(1H-pyrazol-4-yl)-4,5-dihydro-6-oxa-3-thia-1-aza-benzo[e]azulen-2-yl]-methanone |
| 206 | 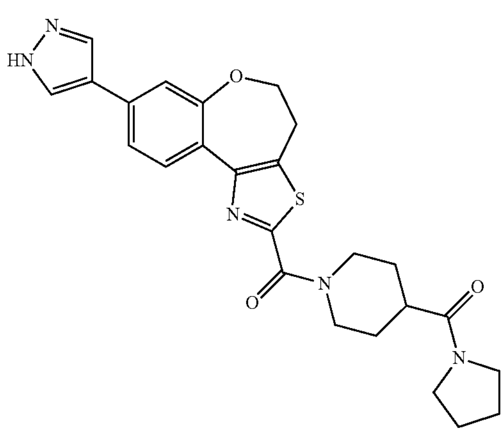 [SMILES: O=C(c1nc2c(s1)CCOc1cc(-c3cn[nH]c3)ccc1-2)N1CCC(C(=O)N2CCCC2)CC1] | [8-(1H-Pyrazol-4-yl)-4,5-dihydro-6-oxa-3-thia-1-aza-benzo[e]azulen-2-yl]-[4-(pyrrolidine-1-carbonyl)-piperidin-1-yl]-methanone |

TABLE 1-continued

| No. | Structure | Name |
|---|---|---|
| 207 | 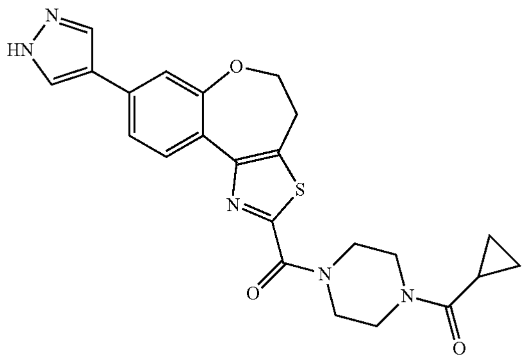 [SMILES: O=C(c1nc2c(s1)CCOc1cc(-c3cn[nH]c3)ccc1-2)N1CCN(C(=O)C2CC2)CC1] | (4-Cyclopropanecarbonyl-piperazin-1-yl)-[8-(1H-pyrazol-4-yl)-4,5-dihydro-6-oxa-3-thia-1-aza-benzo[e]azulen-2-yl]-methanone |
| 208 | 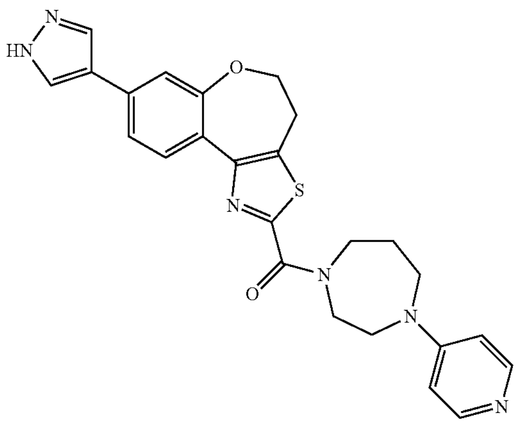 [SMILES: O=C(c1nc2c(s1)CCOc1cc(-c3cn[nH]c3)ccc1-2)N1CCCN(c2ccncc2)CC1] | [8-(1H-Pyrazol-4-yl)-4,5-dihydro-6-oxa-3-thia-1-aza-benzo[e]azulen-2-yl]-(4-pyridin-4-yl-[1,4]diazepan-1-yl)-methanone |
| 209 | 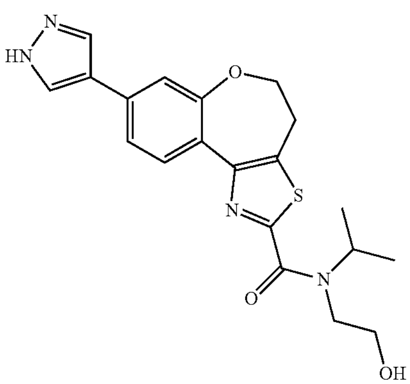 [SMILES: CC(C)N(CCO)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid (2-hydroxy-ethyl)-isopropyl-amide |
| 210 | 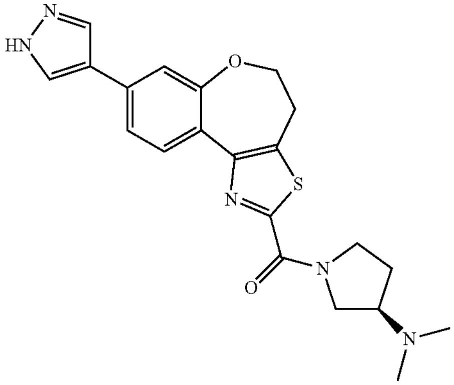 [SMILES: CN(C)[C@@H]1CCN(C(=O)c2nc3c(s2)CCOc2cc(-c4cn[nH]c4)ccc2-3)C1] | ((R)-3-Dimethylamino-pyrrolidin-1-yl)-[8-(1H-pyrazol-4-yl)-4,5-dihydro-6-oxa-3-thia-1-aza-benzo[e]azulen-2-yl]-methanone |

TABLE 1-continued

| No. | Structure | Name |
|---|---|---|
| 211 | 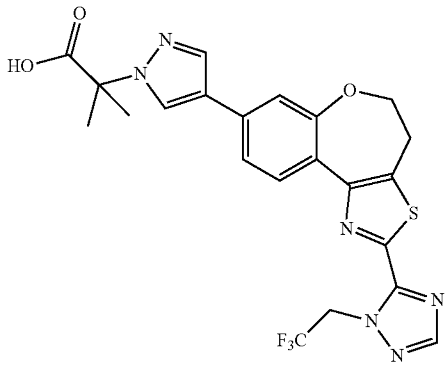 [SMILES: CC(C)(C(=O)O)n1cc(-c2ccc3c(c2)OCCc2sc(-c4ncnn4CC(F)(F)F)nc2-3)cn1] | 2-Methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propionic acid |
| 212 | 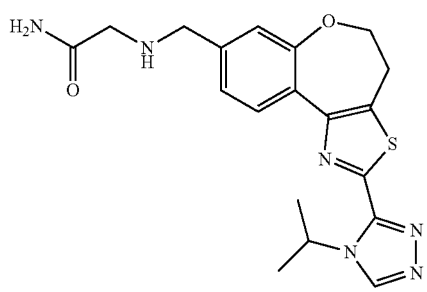 [SMILES: CC(C)n1cnnc1-c1nc2c(s1)CCOc1cc(CNCC(N)=O)ccc1-2] | 2-{[2-(4-Isopropyl-4H-[1,2,4]triazol-3-yl)-4,5-dihydro-6-oxa-3-thia-1-aza-benzo[e]azulen-8-ylmethyl]-amino}-acetamide |
| 213 | 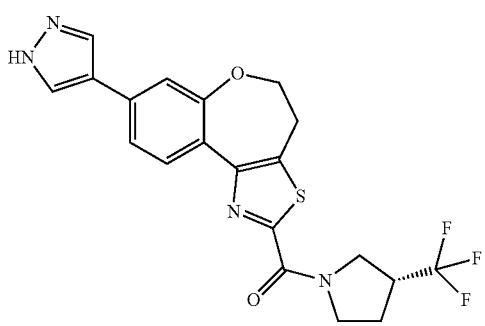 [SMILES: O=C(c1nc2c(s1)CCOc1cc(-c3cn[nH]c3)ccc1-2)N1CC[C@@H](C(F)(F)F)C1] | [8-(1H-Pyrazol-4-yl)-4,5-dihydro-6-oxa-3-thia-1-aza-benzo[e]azulen-2-yl]-((R)-3-trifluoromethyl-pyrrolidin-1-yl)-methanone |
| 214 | 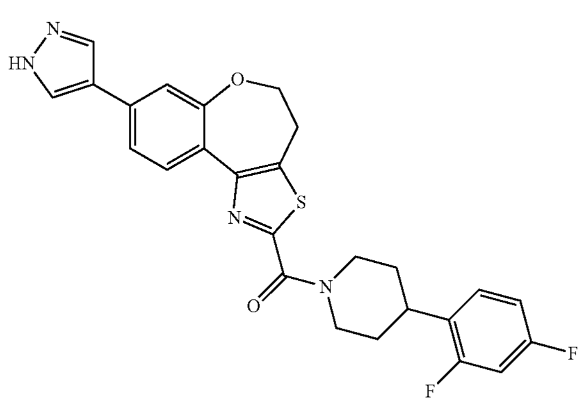 [SMILES: O=C(c1nc2c(s1)CCOc1cc(-c3cn[nH]c3)ccc1-2)N1CCC(c2ccc(F)cc2F)CC1] | [4-(2,4-Difluoro-phenyl)-piperidin-1-yl]-[8-(1H-pyrazol-4-yl)-4,5-dihydro-6-oxa-3-thia-1-aza-benzo[e]azulen-2-yl]-methanone |

TABLE 1-continued

| No. | Structure | Name |
|---|---|---|
| 215 | 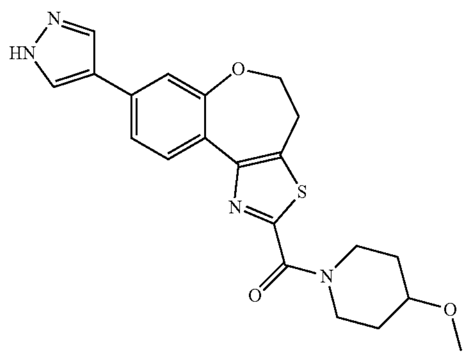 [SMILES: COC1CCN(C(=O)c2nc3c(s2)CCOc2cc(-c4cn[nH]c4)ccc2-3)CC1] | (4-Methoxy-piperidin-1-yl)-[8-(1H-pyrazol-4-yl)-4,5-dihydro-6-oxa-3-thia-1-aza-benzo[e]azulen-2-yl]-methanone |
| 216 | 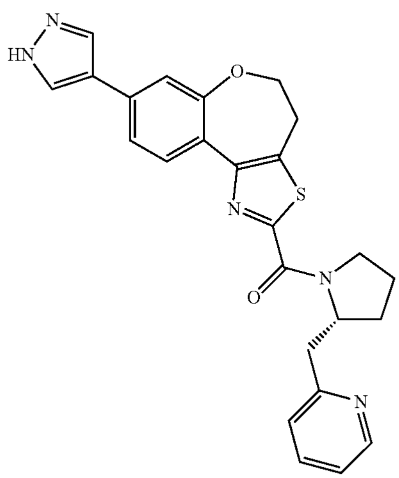 [SMILES: O=C(c1nc2c(s1)CCOc1cc(-c3cn[nH]c3)ccc1-2)N1CCC[C@@H]1Cc1ccccn1] | [8-(1H-Pyrazol-4-yl)-4,5-dihydro-6-oxa-3-thia-1-aza-benzo[e]azulen-2-yl]-((R)-2-pyridin-2-ylmethyl-pyrrolidin-1-yl)-methanone |
| 217 | 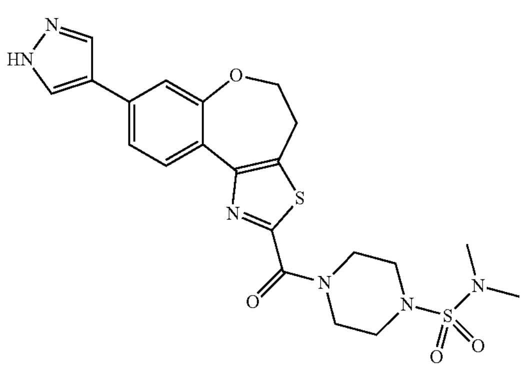 [SMILES: CN(C)S(=O)(=O)N1CCN(C(=O)c2nc3c(s2)CCOc2cc(-c4cn[nH]c4)ccc2-3)CC1] | 4-[8-(1H-Pyrazol-4-yl)-4,5-dihydro-6-oxa-3-thia-1-aza-benzo[e]azulene-2-carbonyl]-piperazine-1-sulfonic acid dimethylamide |
| 218 | 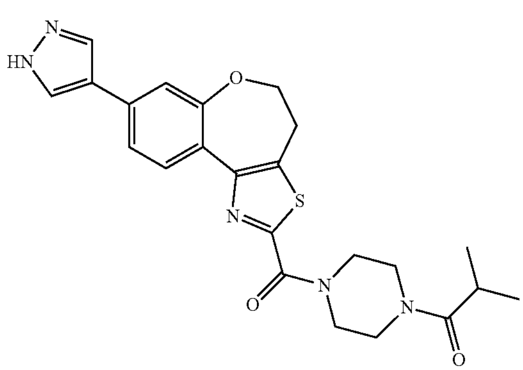 [SMILES: CC(C)C(=O)N1CCN(C(=O)c2nc3c(s2)CCOc2cc(-c4cn[nH]c4)ccc2-3)CC1] | 2-Methyl-1-{4-[8-(1H-pyrazol-4-yl)-4,5-dihydro-6-oxa-3-thia-1-aza-benzo[e]azulene-2-carbonyl]-piperazin-1-yl}-propan-1-one |

TABLE 1-continued

| No. | Structure | Name |
|---|---|---|
| 219 | 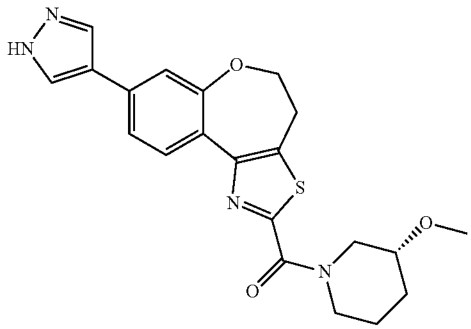 [SMILES: CO[C@@H]1CCCN(C(=O)c2nc3c(s2)CCOc2cc(-c4cn[nH]c4)ccc2-3)C1] | ((R)-3-Methoxy-piperidin-1-yl)-[8-(1H-pyrazol-4-yl)-4,5-dihydro-6-oxa-3-thia-1-aza-benzo[e]azulen-2-yl]-methanone |
| 220 | 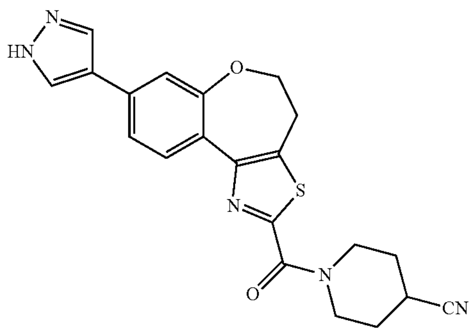 [SMILES: N#CC1CCN(C(=O)c2nc3c(s2)CCOc2cc(-c4cn[nH]c4)ccc2-3)CC1] | 1-[8-(1H-Pyrazol-4-yl)-4,5-dihydro-6-oxa-3-thia-1-aza-benzo[e]azulene-2-carbonyl]-piperidine-4-carbonitrile |
| 221 | 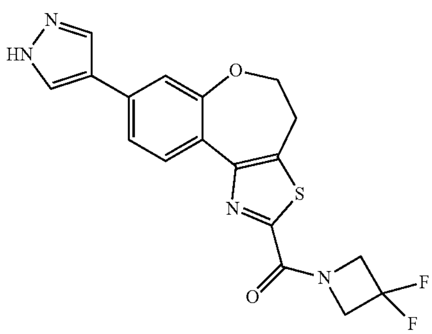 [SMILES: O=C(c1nc2c(s1)CCOc1cc(-c3cn[nH]c3)ccc1-2)N1CC(F)(F)C1] | (3,3-Difluoro-azetidin-1-yl)-[8-(1H-pyrazol-4-yl)-4,5-dihydro-6-oxa-3-thia-1-aza-benzo[e]azulen-2-yl]-methanone |
| 222 | 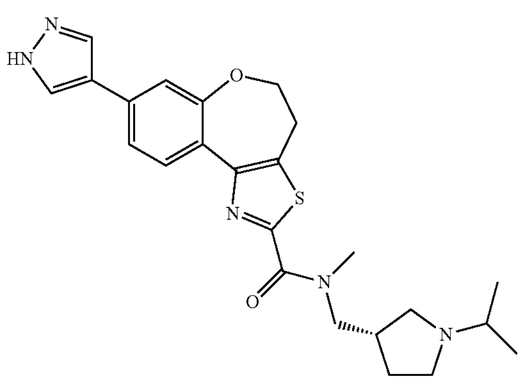 [SMILES: CC(C)N1CC[C@H](CN(C)C(=O)c2nc3c(s2)CCOc2cc(-c4cn[nH]c4)ccc2-3)C1] | 8-(1H-Pyrazol-4-yl)-4,5-dihydro-6-oxa-3-thia-1-aza-benzo[e]azulene-2-carboxylic acid ((S)-1-isopropyl-pyrrolidin-3-ylmethyl)-methyl-amide |

TABLE 1-continued

| No. | Structure | Name |
|---|---|---|
| 223 | 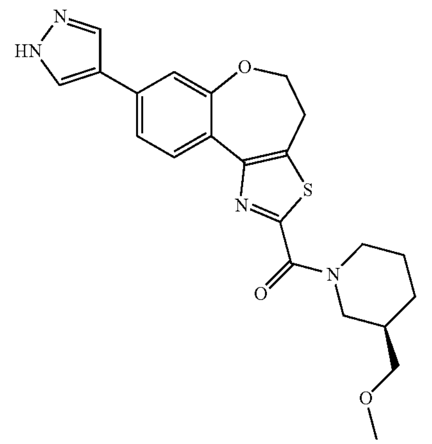 [SMILES: COC[C@@H]1CCCN(C(=O)c2nc3c(s2)CCOc2cc(-c4cn[nH]c4)ccc2-3)C1] | ((R)-3-Methoxymethyl-piperidin-1-yl)-[8-(1H-pyrazol-4-yl)-4,5-dihydro-6-oxa-3-thia-1-aza-benzo[e]azulen-2-yl]-methanone |
| 224 | 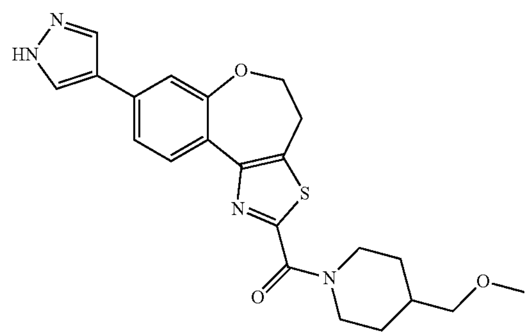 [SMILES: COCC1CCN(C(=O)c2nc3c(s2)CCOc2cc(-c4cn[nH]c4)ccc2-3)CC1] | (4-Methoxymethyl-piperidin-1-yl)-[8-(1H-pyrazol-4-yl)-4,5-dihydro-6-oxa-3-thia-1-aza-benzo[e]azulen-2-yl]-methanone |
| 225 | 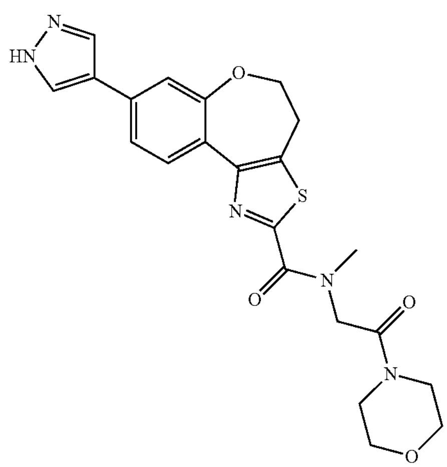 [SMILES: CN(CC(=O)N1CCOCC1)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid methyl-(2-morpholin-4-yl-2-oxo-ethyl)-amide |
| 226 | 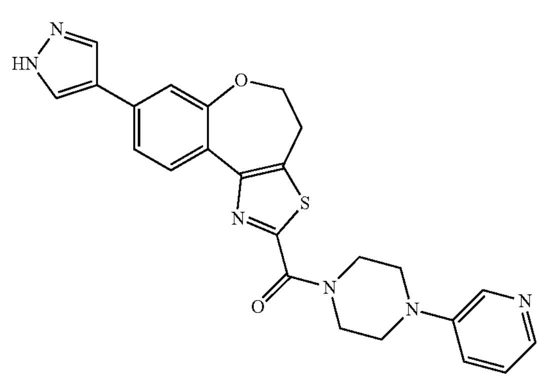 [SMILES: O=C(c1nc2c(s1)CCOc1cc(-c3cn[nH]c3)ccc1-2)N1CCN(c2cccnc2)CC1] | [8-(1H-Pyrazol-4-yl)-4,5-dihydro-6-oxa-3-thia-1-aza-benzo[e]azulen-2-yl]-(4-pyridin-3-yl-piperazin-1-yl)-methanone |

TABLE 1-continued

| No. | Structure | Name |
|---|---|---|
| 227 | 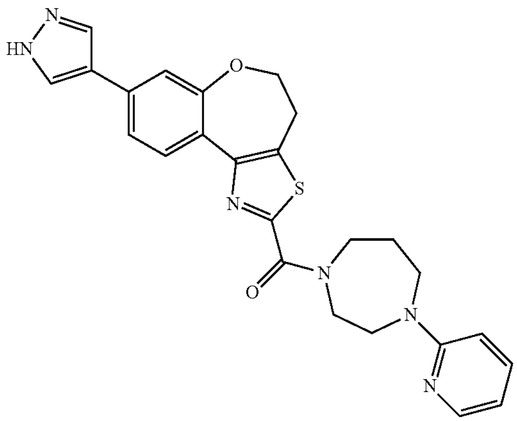 [SMILES: O=C(c1nc2c(s1)CCOc1cc(-c3cn[nH]c3)ccc1-2)N1CCCN(c2ccccn2)CC1] | [8-(1H-Pyrazol-4-yl)-4,5-dihydro-6-oxa-3-thia-1-aza-benzo[e]azulen-2-yl]-(4-pyridin-2-yl-[1,4]diazepan-1-yl)-methanone |
| 228 | 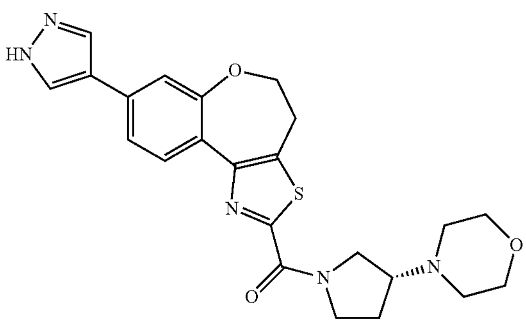 [SMILES: O=C(c1nc2c(s1)CCOc1cc(-c3cn[nH]c3)ccc1-2)N1CC[C@@H](N2CCOCC2)C1] | ((R)-3-Morpholin-4-yl-pyrrolidin-1-yl)-[8-(1H-pyrazol-4-yl)-4,5-dihydro-6-oxa-3-thia-1-aza-benzo[e]azulen-2-yl]-methanone |
| 229 | 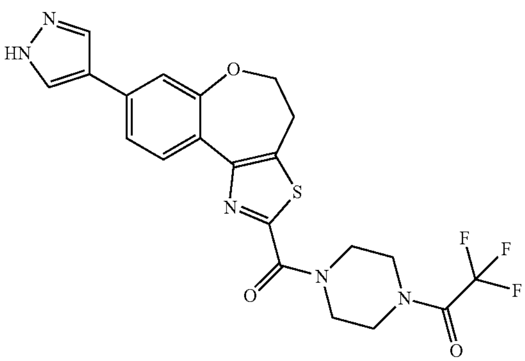 [SMILES: O=C(c1nc2c(s1)CCOc1cc(-c3cn[nH]c3)ccc1-2)N1CCN(C(=O)C(F)(F)F)CC1] | 2,2,2-Trifluoro-1-{4-[8-(1H-pyrazol-4-yl)-4,5-dihydro-6-oxa-3-thia-1-aza-benzo[e]azulene-2-carbonyl]-piperazin-1-yl}-ethanone |
| 230 | 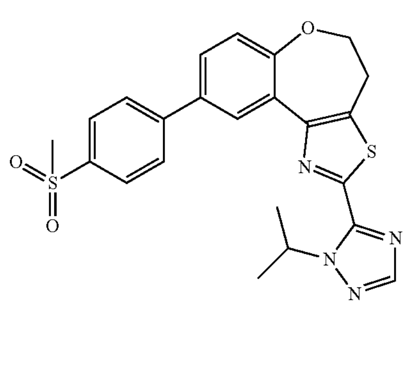 [SMILES: CC(C)n1ncnc1-c1nc2c(s1)CCOc1ccc(-c3ccc(S(C)(=O)=O)cc3)cc1-2] | 2-(2-Isopropyl-2H-[1,2,4]triazol-3-yl)-9-(4-methanesulfonyl-phenyl)-4,5-dihydro-6-oxa-3-thia-1-aza-benzo[e]azulene |

TABLE 1-continued

| No. | Structure | Name |
|---|---|---|
| 231 | 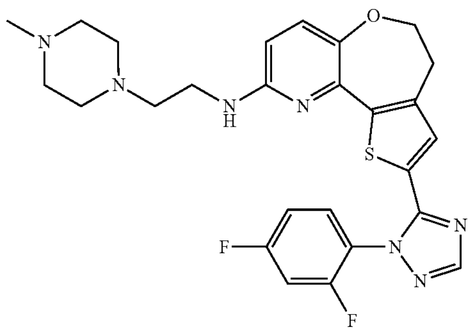 [SMILES: CN1CCN(CCNc2ccc3c(n2)-c2sc(-c4ncnn4-c4ccc(F)cc4F)cc2CCO3)CC1] | {2-[2-(2,4-Difluoro-phenyl)-2H-[1,2,4]triazol-3-yl]-4,5-dihydro-6-oxa-1-thia-10-aza-benzo[e]azulen-9-yl}-[2-(4-methyl-piperazin-1-yl)-ethyl]-amine |
| 232 | 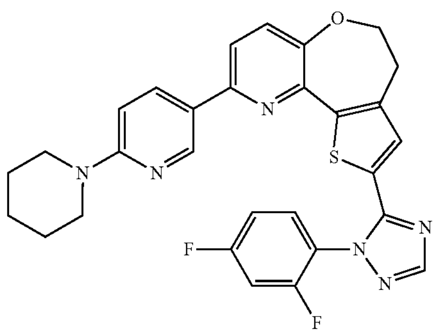 [SMILES: Fc1ccc(-n2ncnc2-c2cc3c(s2)-c2nc(-c4ccc(N5CCCCC5)nc4)ccc2OCC3)c(F)c1] | 2-[2-(2,4-Difluoro-phenyl)-2H-[1,2,4]triazol-3-yl]-9-(3,4,5,6-tetrahydro-2H-[1,2']bipyridinyl-5'-yl)-4,5-dihydro-6-oxa-1-thia-10-aza-benzo[e]azulene |
| 233 | 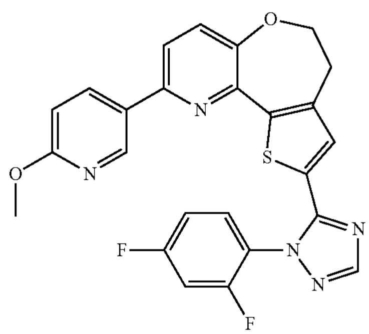 [SMILES: COc1ccc(-c2ccc3c(n2)-c2sc(-c4ncnn4-c4ccc(F)cc4F)cc2CCO3)cn1] | 2-[2-(2,4-Difluoro-phenyl)-2H-[1,2,4]triazol-3-yl]-9-(6-methoxy-pyridin-3-yl)-4,5-dihydro-6-oxa-1-thia-10-aza-benzo[e]azulene |
| 234 | 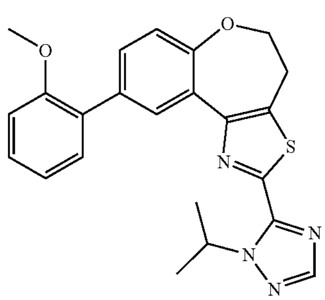 [SMILES: COc1ccccc1-c1ccc2c(c1)-c1nc(-c3ncnn3C(C)C)sc1CCO2] | 2-(2-Isopropyl-2H-[1,2,4]triazol-3-yl)-9-(2-methoxy-phenyl)-4,5-dihydro-6-oxa-3-thia-1-aza-benzo[e]azulene |
| 235 | 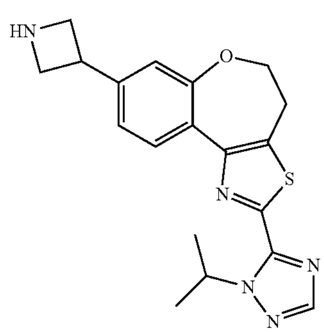 [SMILES: CC(C)n1ncnc1-c1nc2c(s1)CCOc1cc(C3CNC3)ccc1-2] | 8-Azetidin-3-yl-2-(2-isopropyl-2H-[1,2,4]triazol-3-yl)-4,5-dihydro-6-oxa-3-thia-1-aza-benzo[e]azulene |

TABLE 1-continued

| No. | Structure | Name |
|---|---|---|
| 236 | 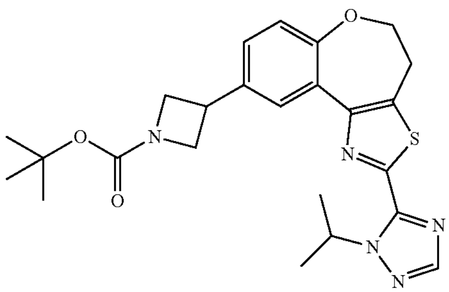 [SMILES: CC(C)n1ncnc1-c1nc2c(s1)CCOc1ccc(C3CN(C(=O)OC(C)(C)C)C3)cc1-2] | 3-[2-(2-Isopropyl-2H-[1,2,4]triazol-3-yl)-4,5-dihydro-6-oxa-3-thia-1-aza-benzo[e]azulen-9-yl]-azetidine-1-carboxylic acid tert-butyl ester |
| 237 | 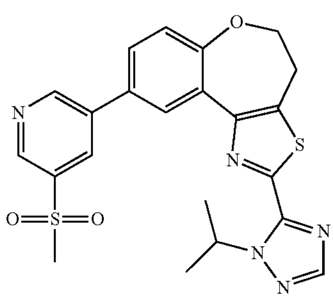 [SMILES: CC(C)n1ncnc1-c1nc2c(s1)CCOc1ccc(-c3cncc(S(C)(=O)=O)c3)cc1-2] | 2-(2-Isopropyl-2H-[1,2,4]triazol-3-yl)-9-(5-methanesulfonyl-pyridin-3-yl)-4,5-dihydro-6-oxa-3-thia-1-aza-benzo[e]azulene |
| 238 | 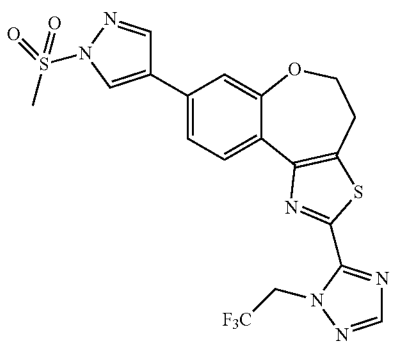 [SMILES: CS(=O)(=O)n1cc(-c2ccc3c(c2)OCCc2sc(-c4ncnn4CC(F)(F)F)nc2-3)cn1] | 8-(1-Methanesulfonyl-1H-pyrazol-4-yl)-2-[2-(2,2,2-trifluoro-ethyl)-2H-[1,2,4]triazol-3-yl]-4,5-dihydro-6-oxa-3-thia-1-aza-benzo[e]azulene |
| 239 | 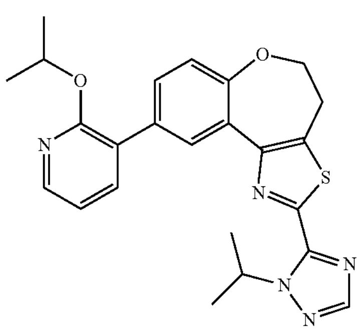 [SMILES: CC(C)Oc1ncccc1-c1ccc2c(c1)-c1nc(-c3ncnn3C(C)C)sc1CCO2] | 9-(2-Isopropoxy-pyridin-3-yl)-2-(2-isopropyl-2H-[1,2,4]triazol-3-yl)-4,5-dihydro-6-oxa-3-thia-1-aza-benzo[e]azulene |

TABLE 1-continued

| No. | Structure | Name |
|---|---|---|
| 240 | 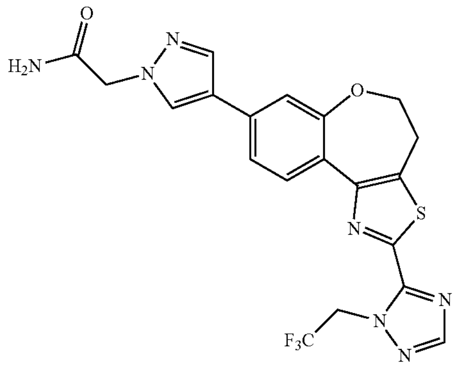 [SMILES: NC(=O)Cn1cc(-c2ccc3c(c2)OCCc2sc(-c4ncnn4CC(F)(F)F)nc2-3)cn1] | 2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-acetamide |
| 241 | 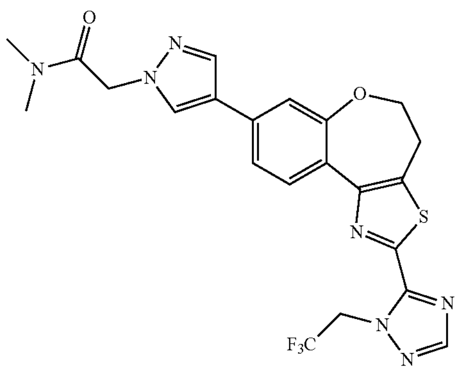 [SMILES: CN(C)C(=O)Cn1cc(-c2ccc3c(c2)OCCc2sc(-c4ncnn4CC(F)(F)F)nc2-3)cn1] | N,N-Dimethyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-acetamide |
| 242 | 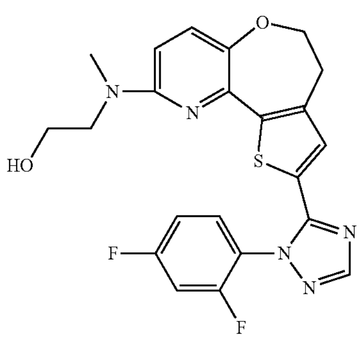 [SMILES: CN(CCO)c1ccc2c(n1)-c1sc(-c3ncnn3-c3ccc(F)cc3F)cc1CCO2] | 2-({2-[2-(2,4-Difluoro-phenyl)-2H-[1,2,4]triazol-3-yl]-4,5-dihydro-6-oxa-1-thia-10-aza-benzo[e]azulen-9-yl}-methyl-amino)-ethanol |
| 243 | 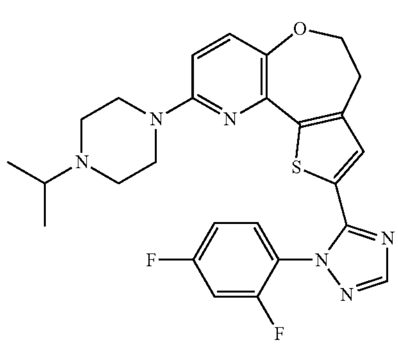 [SMILES: CC(C)N1CCN(c2ccc3c(n2)-c2sc(-c4ncnn4-c4ccc(F)cc4F)cc2CCO3)CC1] | 2-[2-(2,4-Difluoro-phenyl)-2H-[1,2,4]triazol-3-yl]-9-(4-isopropyl-piperazin-1-yl)-4,5-dihydro-6-oxa-1-thia-10-aza-benzo[e]azulene |

TABLE 1-continued

| No. | Structure | Name |
|---|---|---|
| 244 | 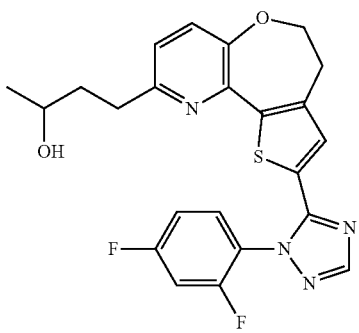 [SMILES: CC(O)CCc1ccc2c(n1)-c1sc(-c3ncnn3-c3ccc(F)cc3F)cc1CCO2] | 4-{2-[2-(2,4-Difluoro-phenyl)-2H-[1,2,4]triazol-3-yl]-4,5-dihydro-6-oxa-1-thia-10-aza-benzo[e]azulen-9-yl}-butan-2-ol |
| 245 | 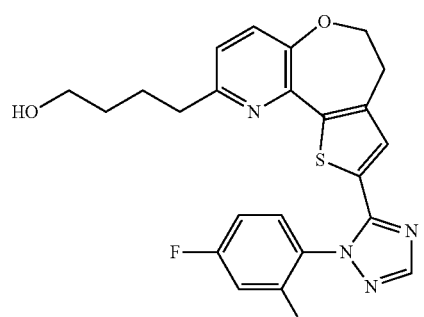 | 4-{2-[2-(2,4-Difluoro-phenyl)-2H-[1,2,4]triazol-3-yl]-4,5-dihydro-6-oxa-1-thia-10-aza-benzo[e]azulen-9-yl}-butan-1-ol |
| 246 | 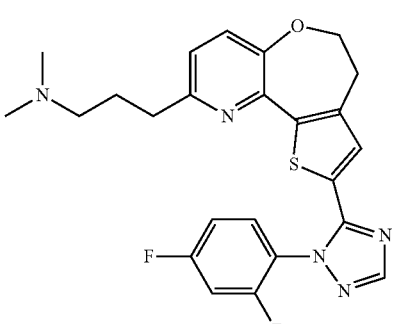 | (3-{2-[2-(2,4-Difluoro-phenyl)-2H-[1,2,4]triazol-3-yl]-4,5-dihydro-6-oxa-1-thia-10-aza-benzo[e]azulen-9-yl}-propyl)-dimethyl-amine |
| 247 | 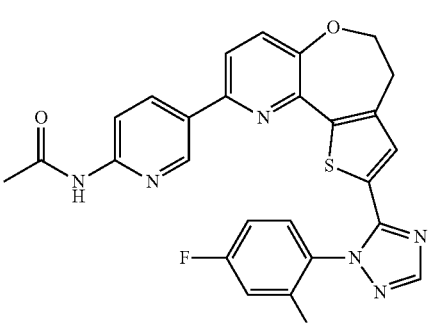 | N-(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-acetamide |

TABLE 1-continued

| No. | Structure | Name |
|---|---|---|
| 248 | 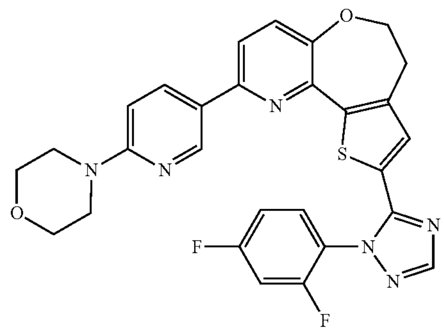 [SMILES: Fc1ccc(-n2ncnc2-c2cc3c(s2)-c2nc(-c4ccc(N5CCOCC5)nc4)ccc2OCC3)c(F)c1] | 2-[2-(2,4-Difluoro-phenyl)-2H-[1,2,4]triazol-3-yl]-9-(6-morpholin-4-yl-pyridin-3-yl)-4,5-dihydro-6-oxa-1-thia-10-aza-benzo[e]azulene |
| 249 | 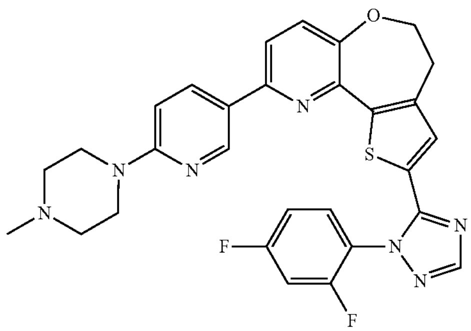 [SMILES: CN1CCN(c2ccc(-c3ccc4c(n3)-c3sc(-c5ncnn5-c5ccc(F)cc5F)cc3CCO4)cn2)CC1] | 2-[2-(2,4-Difluoro-phenyl)-2H-[1,2,4]triazol-3-yl]-9-[6-(4-methyl-piperazin-1-yl)-pyridin-3-yl]-4,5-dihydro-6-oxa-1-thia-10-aza-benzo[e]azulene |
| 250 | 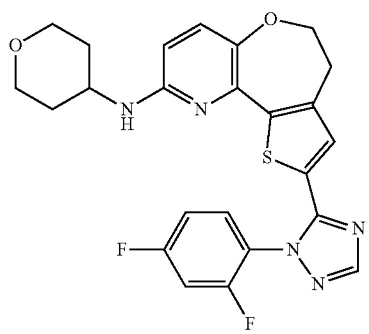 [SMILES: Fc1ccc(-n2ncnc2-c2cc3c(s2)-c2nc(NC4CCOCC4)ccc2OCC3)c(F)c1] | {2-[2-(2,4-Difluoro-phenyl)-2H-[1,2,4]triazol-3-yl]-4,5-dihydro-6-oxa-1-thia-10-aza-benzo[e]azulen-9-yl}-(tetrahydro-pyran-4-yl)-amine |
| 251 | 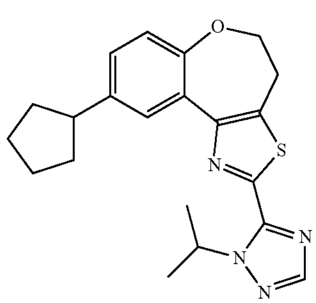 [SMILES: CC(C)n1ncnc1-c1nc2c(s1)CCOc1ccc(C3CCCC3)cc1-2] | 9-Cyclopentyl-2-(2-isopropyl-2H-[1,2,4]triazol-3-yl)-4,5-dihydro-6-oxa-3-thia-1-aza-benzo[e]azulene |

TABLE 1-continued

| No. | Structure | Name |
|---|---|---|
| 252 | 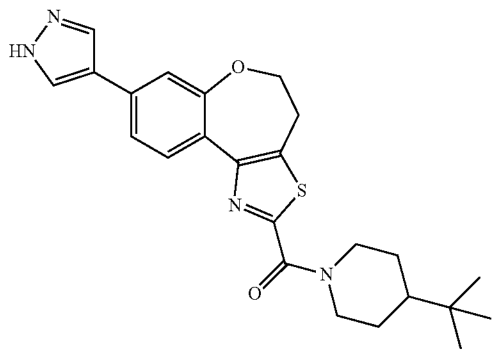 [SMILES: CC(C)(C)C1CCN(C(=O)c2nc3c(s2)CCOc2cc(-c4cn[nH]c4)ccc2-3)CC1] | (4-tert-Butyl-piperidin-1-yl)-[8-(1H-pyrazol-4-yl)-4,5-dihydro-6-oxa-3-thia-1-aza-benzo[e]azulen-2-yl]-methanone |
| 253 | 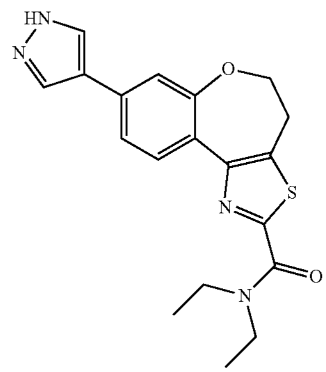 [SMILES: CCN(CC)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid diethylamide |
| 254 | 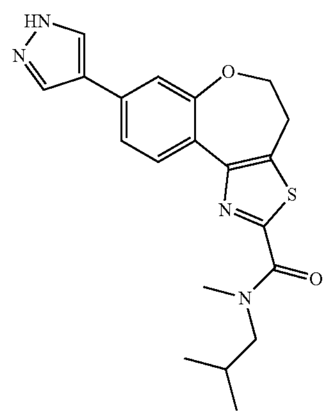 [SMILES: CC(C)CN(C)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid isobutyl-methyl-amide |
| 255 | 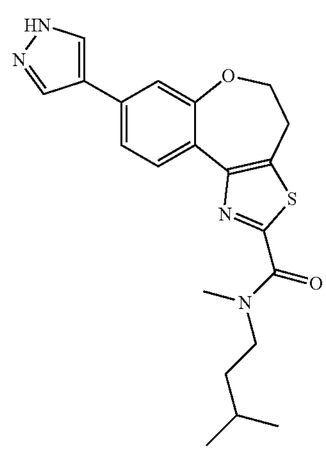 [SMILES: CC(C)CCN(C)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid methyl-(3-methyl-butyl)-amide |

TABLE 1-continued

| No. | Structure | Name |
|---|---|---|
| 256 | 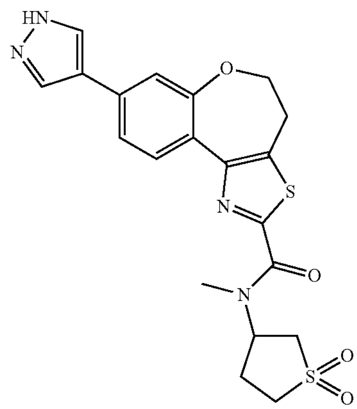 [SMILES: CN(C(=O)c1nc2c(s1)CCOc1cc(-c3cn[nH]c3)ccc1-2)C1CCS(=O)(=O)C1] | 8-(1H-Pyrazol-4-yl)-4,5-dihydro-6-oxa-3-thia-1-aza-benzo[e]azulene-2-carboxylic acid (1,1-dioxo-tetrahydro-thiophen-3-yl)-methyl-amide |
| 257 | 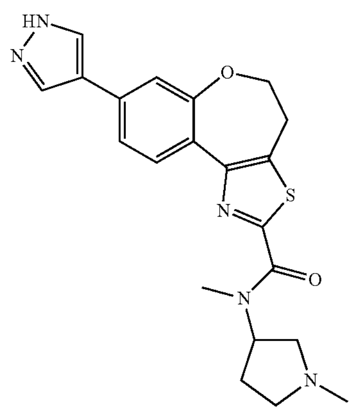 [SMILES: CN1CCC(N(C)C(=O)c2nc3c(s2)CCOc2cc(-c4cn[nH]c4)ccc2-3)C1] | 8-(1H-Pyrazol-4-yl)-4,5-dihydro-6-oxa-3-thia-1-aza-benzo[e]azulene-2-carboxylic acid methyl-(1-methyl-pyrrolidin-3-yl)-amide |
| 258 | 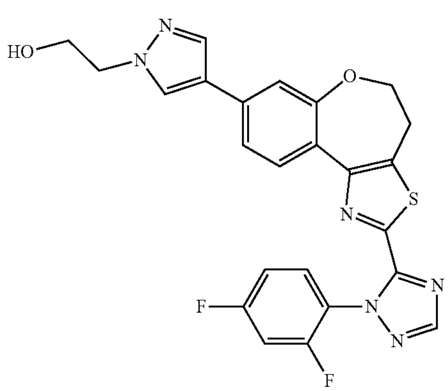 [SMILES: OCCn1cc(-c2ccc3c(c2)OCCc2sc(-c4ncnn4-c4ccc(F)cc4F)nc2-3)cn1] | 2-(4-{2-[2-(2,4-Difluoro-phenyl)-2H-[1,2,4]triazol-3-yl]-4,5-dihydro-6-oxa-3-thia-1-aza-benzo[e]azulen-8-yl}-pyrazol-1-yl)-ethanol |
| 259 | 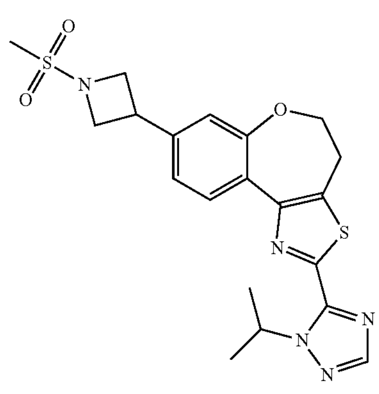 [SMILES: CC(C)n1ncnc1-c1nc2c(s1)CCOc1cc(C3CN(S(C)(=O)=O)C3)ccc1-2] | 2-(2-Isopropyl-2H-[1,2,4]triazol-3-yl)-8-(1-methanesulfonyl-azetidin-3-yl)-4,5-dihydro-6-oxa-3-thia-1-aza-benzo[e]azulene |

TABLE 1-continued

| No. | Structure | Name |
|---|---|---|
| 260 | 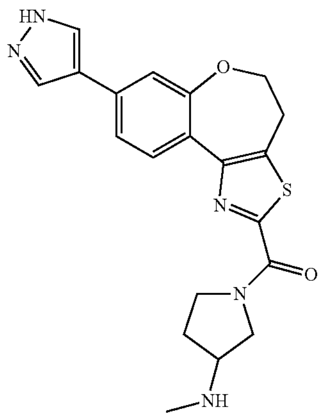 [SMILES: CNC1CCN(C(=O)c2nc3c(s2)CCOc2cc(-c4cn[nH]c4)ccc2-3)C1] | (3-Methylamino-pyrrolidin-1-yl)-[8-(1H-pyrazol-4-yl)-4,5-dihydro-6-oxa-3-thia-1-aza-benzo[e]azulen-2-yl]-methanone |
| 261 | 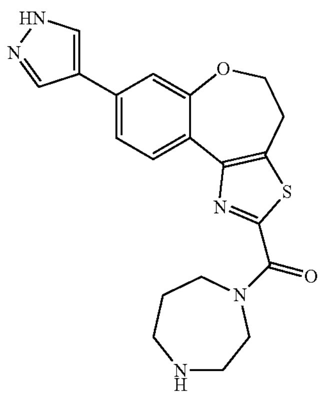 [SMILES: O=C(c1nc2c(s1)CCOc1cc(-c3cn[nH]c3)ccc1-2)N1CCCNCC1] | [1,4]Diazepan-1-yl-[8-(1H-pyrazol-4-yl)-4,5-dihydro-6-oxa-3-thia-1-aza-benzo[e]azulen-2-yl]-methanone |
| 262 | 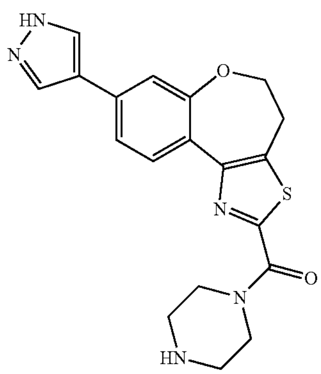 [SMILES: O=C(c1nc2c(s1)CCOc1cc(-c3cn[nH]c3)ccc1-2)N1CCNCC1] | Piperazin-1-yl-[8-(1H-pyrazol-4-yl)-4,5-dihydro-6-oxa-3-thia-1-aza-benzo[e]azulen-2-yl]-methanone |
| 263 | 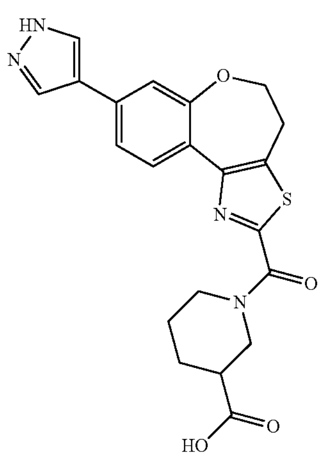 [SMILES: O=C(O)C1CCCN(C(=O)c2nc3c(s2)CCOc2cc(-c4cn[nH]c4)ccc2-3)C1] | 1-[8-(1H-Pyrazol-4-yl)-4,5-dihydro-6-oxa-3-thia-1-aza-benzo[e]azulene-2-carbonyl]-piperidine-3-carboxylic acid |

TABLE 1-continued

| No. | Structure | Name |
|---|---|---|
| 264 | 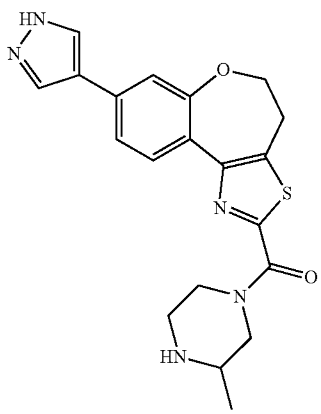 [SMILES: CC1CN(C(=O)c2nc3c(s2)CCOc2cc(-c4cn[nH]c4)ccc2-3)CCN1] | (3-Methyl-piperazin-1-yl)-[8-(1H-pyrazol-4-yl)-4,5-dihydro-6-oxa-3-thia-1-aza-benzo[e]azulen-2-yl]-methanone |
| 265 | 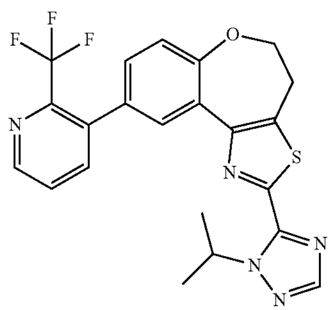 [SMILES: CC(C)n1ncnc1-c1nc2c(s1)CCOc1ccc(-c3cccnc3C(F)(F)F)cc1-2] | 2-(2-Isopropyl-2H-[1,2,4]triazol-3-yl)-9-(2-trifluoromethyl-pyridin-3-yl)-4,5-dihydro-6-oxa-3-thia-1-aza-benzo[e]azulene |
| 266 | 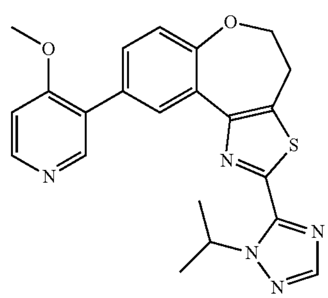 [SMILES: COc1ccncc1-c1ccc2c(c1)-c1nc(-c3ncnn3C(C)C)sc1CCO2] | 2-(2-Isopropyl-2H-[1,2,4]triazol-3-yl)-9-(4-methoxy-pyridin-3-yl)-4,5-dihydro-6-oxa-3-thia-1-aza-benzo[e]azulene |
| 267 | 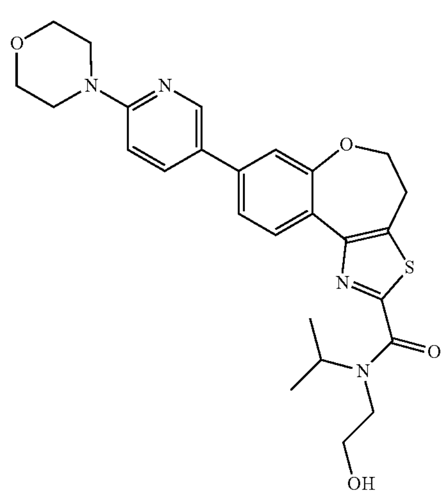 [SMILES: CC(C)N(CCO)C(=O)c1nc2c(s1)CCOc1cc(-c3ccc(N4CCOCC4)nc3)ccc1-2] | 8-(6-Morpholin-4-yl-pyridin-3-yl)-4,5-dihydro-6-oxa-3-thia-1-aza-benzo[e]azulene-2-carboxylic acid (2-hydroxyethyl)-isopropylamide |

TABLE 1-continued

| No. | Structure | Name |
|-----|-----------|------|
| 268 | 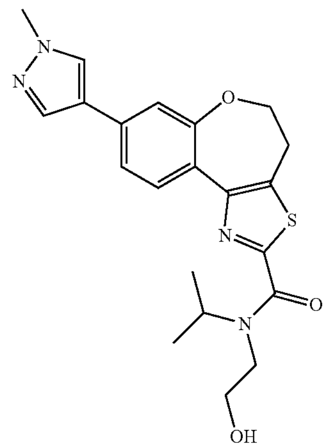 [SMILES: CC(C)N(CCO)C(=O)c1nc2c(s1)CCOc1cc(-c3cnn(C)c3)ccc1-2] | 8-(1-Methyl-1H-pyrazol-4-yl)-4,5-dihydro-6-oxa-3-thia-1-aza-benzo[e]azulene-2-carboxylic acid (2-hydroxy-ethyl)-isopropyl-amide |
| 269 | 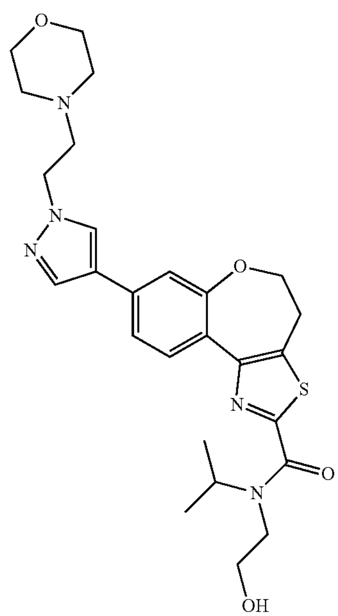 [SMILES: CC(C)N(CCO)C(=O)c1nc2c(s1)CCOc1cc(-c3cnn(CCN4CCOCC4)c3)ccc1-2] | 8-[1-(2-Morpholin-4-yl-ethyl)-1H-pyrazol-4-yl]-4,5-dihydro-6-oxa-3-thia-1-aza-benzo[e]azulene-2-carboxylic acid (2-hydroxy-ethyl)-isopropyl-amide |
| 270 | 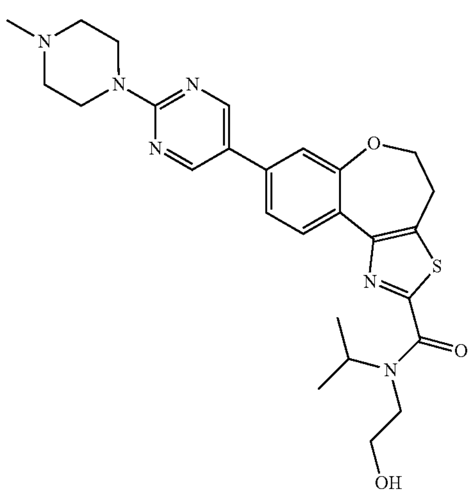 [SMILES: CC(C)N(CCO)C(=O)c1nc2c(s1)CCOc1cc(-c3cnc(N4CCN(C)CC4)nc3)ccc1-2] | 8-[2-(4-Methyl-piperazin-1-yl)-pyrimidin-5-yl]-4,5-dihydro-6-oxa-3-thia-1-aza-benzo[e]azulene-2-carboxylic acid (2-hydroxy-ethyl)-isopropyl-amide |

TABLE 1-continued

| No. | Structure | Name |
|---|---|---|
| 271 | 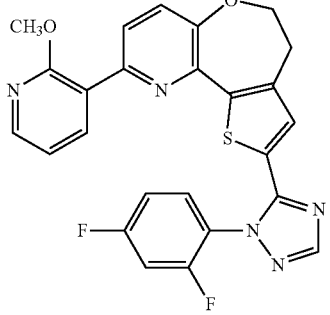 | 2-[2-(2,4-Difluoro-phenyl)-2H-[1,2,4]triazol-3-yl]-9-(2-methoxy-pyridin-3-yl)-4,5-dihydro-6-oxa-1-thia-10-aza-benzo[e]azulene |
| 272 | 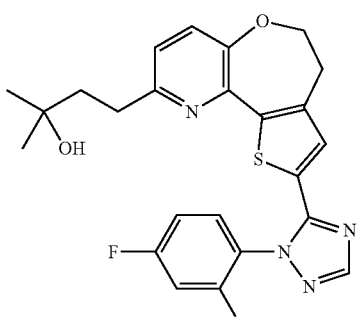 | 4-{2-[2-(2,4-Difluoro-phenyl)-2H-[1,2,4]triazol-3-yl]-4,5-dihydro-6-oxa-1-thia-10-aza-benzo[e]azulen-9-yl}-2-methyl-butan-2-ol |
| 273 | 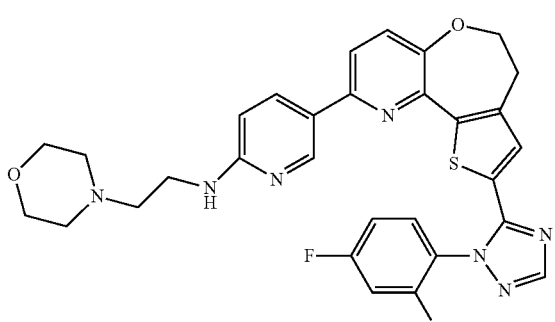 | (5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-(2-morpholin-4-yl-ethyl)-amine |
| 274 | 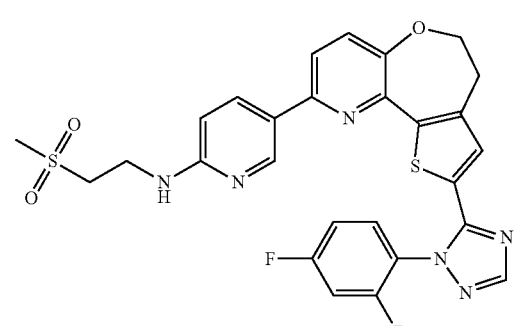 | (5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-(2-methanesulfonyl-ethyl)-amine |

TABLE 1-continued

| No. | Structure | Name |
|---|---|---|
| 275 | 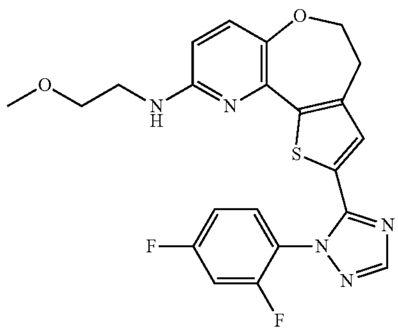 [SMILES: COCCNc1ccc2c(n1)-c1sc(-c3ncnn3-c3ccc(F)cc3F)cc1CCO2] | {2-[2-(2,4-Difluoro-phenyl)-2H-[1,2,4]triazol-3-yl]-4,5-dihydro-6-oxa-1-thia-10-aza-benzo[e]azulen-9-yl}-(2-methoxy-ethyl)-amine |
| 276 | 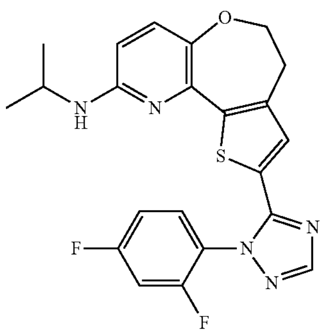 [SMILES: CC(C)Nc1ccc2c(n1)-c1sc(-c3ncnn3-c3ccc(F)cc3F)cc1CCO2] | {2-[2-(2,4-Difluoro-phenyl)-2H-[1,2,4]triazol-3-yl]-4,5-dihydro-6-oxa-1-thia-10-aza-benzo[e]azulen-9-yl}-isopropyl-amine |
| 277 | 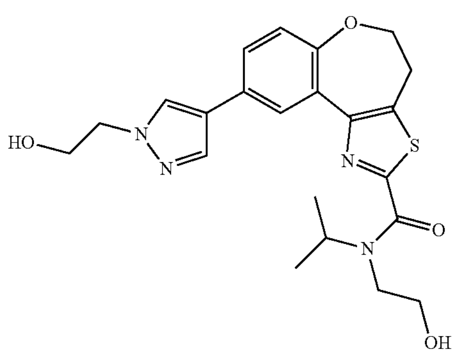 [SMILES: CC(C)N(CCO)C(=O)c1nc2c(s1)CCOc1ccc(-c3cnn(CCO)c3)cc1-2] | 9-[1-(2-Hydroxy-ethyl)-1H-pyrazol-4-yl]-4,5-dihydro-6-oxa-3-thia-1-aza-benzo[e]azulene-2-carboxylic acid (2-hydroxy-ethyl)-isopropyl-amide |
| 278 | 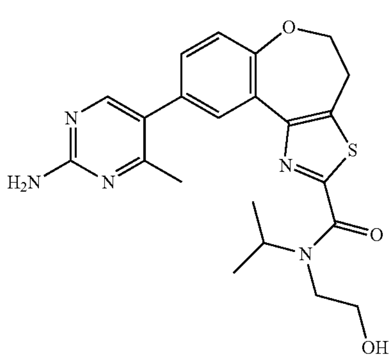 [SMILES: Cc1nc(N)ncc1-c1ccc2c(c1)-c1nc(C(=O)N(CCO)C(C)C)sc1CCO2] | 9-(2-Amino-4-methyl-pyrimidin-5-yl)-4,5-dihydro-6-oxa-3-thia-1-aza-benzo[e]azulene-2-carboxylic acid (2-hydroxy-ethyl)-isopropyl-amide |

TABLE 1-continued

| No. | Structure | Name |
|---|---|---|
| 279 | 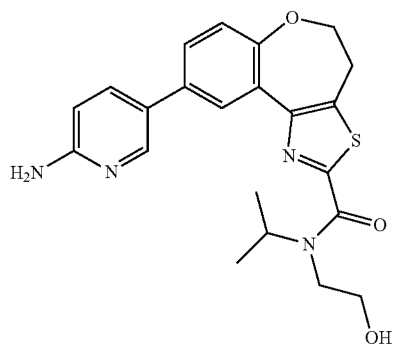 [SMILES: CC(C)N(CCO)C(=O)c1nc2c(s1)CCOc1ccc(-c3ccc(N)nc3)cc1-2] | 9-(6-Amino-pyridin-3-yl)-4,5-dihydro-6-oxa-3-thia-1-aza-benzo[e]azulene-2-carboxylic acid (2-hydroxy-ethyl)-isopropyl-amide |
| 280 | 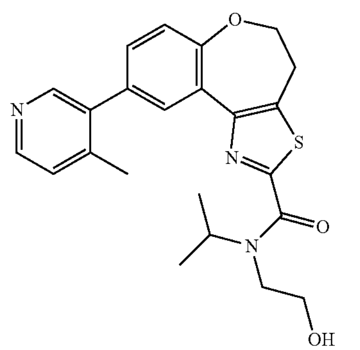 [SMILES: Cc1ccncc1-c1ccc2c(c1)-c1nc(C(=O)N(CCO)C(C)C)sc1CCO2] | 9-(4-Methyl-pyridin-3-yl)-4,5-dihydro-6-oxa-3-thia-1-aza-benzo[e]azulene-2-carboxylic acid (2-hydroxy-ethyl)-isopropyl-amide |
| 281 | 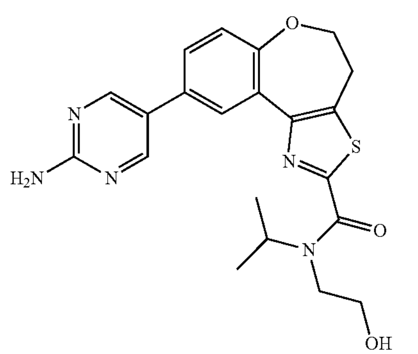 [SMILES: CC(C)N(CCO)C(=O)c1nc2c(s1)CCOc1ccc(-c3cnc(N)nc3)cc1-2] | 9-(2-Amino-pyrimidin-5-yl)-4,5-dihydro-6-oxa-3-thia-1-aza-benzo[e]azulene-2-carboxylic acid (2-hydroxy-ethyl)-isopropyl-amide |
| 282 | 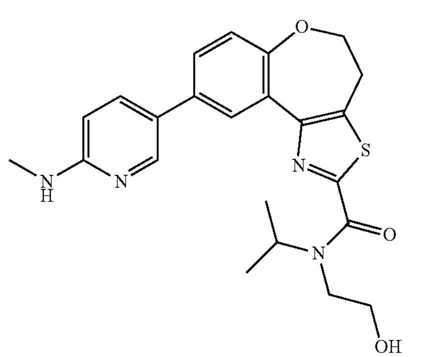 [SMILES: CNc1ccc(-c2ccc3c(c2)-c2nc(C(=O)N(CCO)C(C)C)sc2CCO3)cn1] | 9-(6-Methylamino-pyridin-3-yl)-4,5-dihydro-6-oxa-3-thia-1-aza-benzo[e]azulene-2-carboxylic acid (2-hydroxy-ethyl)-isopropyl-amide |

TABLE 1-continued

| No. | Structure | Name |
|---|---|---|
| 283 | 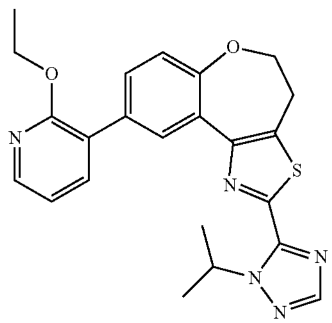 [SMILES: CCOc1ncccc1-c1ccc2c(c1)-c1nc(-c3ncnn3C(C)C)sc1CCO2] | 9-(2-Ethoxy-pyridin-3-yl)-2-(2-isopropyl-2H-[1,2,4]triazol-3-yl)-4,5-dihydro-6-oxa-3-thia-1-aza-benzo[e]azulene |
| 284 | 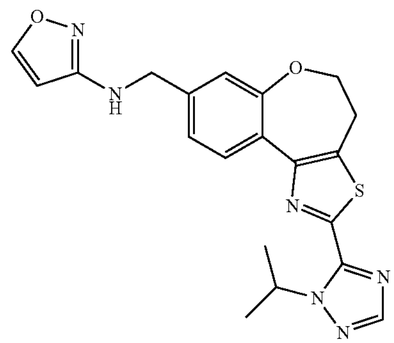 [SMILES: CC(C)n1ncnc1-c1nc2c(s1)CCOc1cc(CNc3ccon3)ccc1-2] | [2-(2-Isopropyl-2H-[1,2,4]triazol-3-yl)-4,5-dihydro-6-oxa-3-thia-1-aza-benzo[e]azulen-8-ylmethyl]-isoxazol-3-yl-amine |
| 285 | 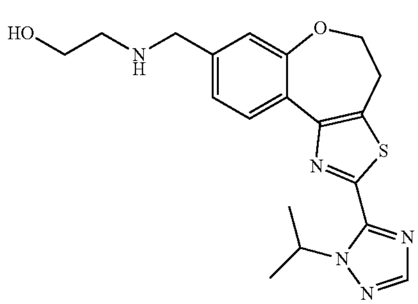 [SMILES: CC(C)n1ncnc1-c1nc2c(s1)CCOc1cc(CNCCO)ccc1-2] | 2-{[2-(2-Isopropyl-2H-[1,2,4]triazol-3-yl)-4,5-dihydro-6-oxa-3-thia-1-aza-benzo[e]azulen-8-ylmethyl]-amino}-ethanol |
| 286 | 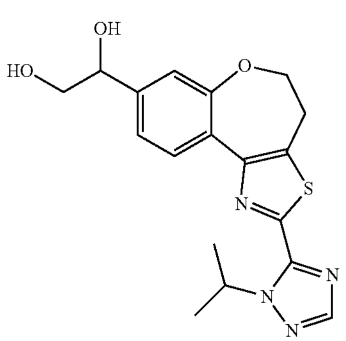 [SMILES: CC(C)n1ncnc1-c1nc2c(s1)CCOc1cc(C(O)CO)ccc1-2] | 1-[2-(2-Isopropyl-2H-[1,2,4]triazol-3-yl)-4,5-dihydro-6-oxa-3-thia-1-aza-benzo[e]azulen-8-yl]-ethane-1,2-diol |

TABLE 1-continued

| No. | Structure | Name |
|---|---|---|
| 287 | 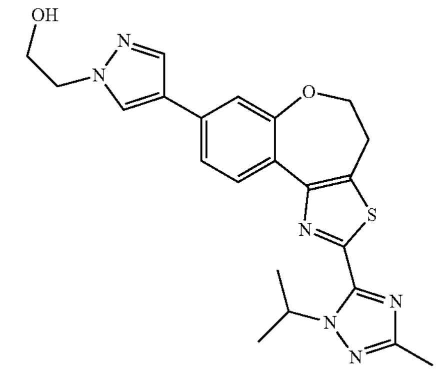 [SMILES: Cc1nc(-c2nc3c(s2)CCOc2cc(-c4cnn(CCO)c4)ccc2-3)n(C(C)C)n1] | 2-{4-[2-(2-Isopropyl-5-methyl-2H-[1,2,4]triazol-3-yl)-4,5-dihydro-6-oxa-3-thia-1-aza-benzo[e]azulen-8-yl]-pyrazol-1-yl}-ethanol |
| 288 | 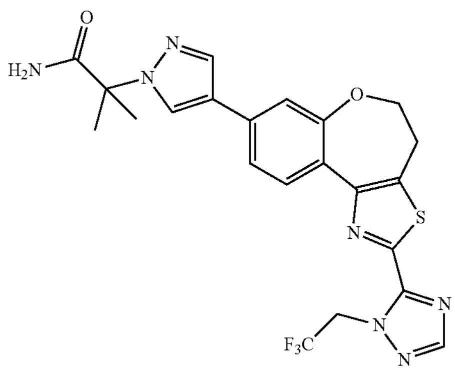 [SMILES: CC(C)(C(N)=O)n1cc(-c2ccc3c(c2)OCCc2sc(-c4ncnn4CC(F)(F)F)nc2-3)cn1] | 2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-isobutyramide |
| 289 | 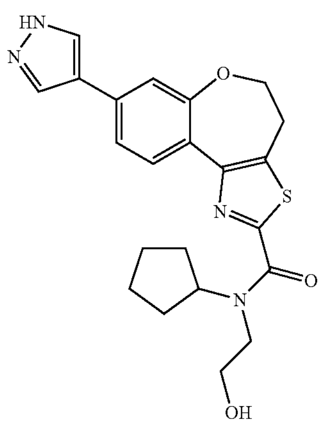 [SMILES: O=C(c1nc2c(s1)CCOc1cc(-c3cn[nH]c3)ccc1-2)N(CCO)C1CCCC1] | 8-(1H-Pyrazol-4-yl)-4,5-dihydro-6-oxa-3-thia-1-aza-benzo[e]azulene-2-carboxylic acid cyclopentyl-(2-hydroxy-ethyl)-amide |
| 290 | 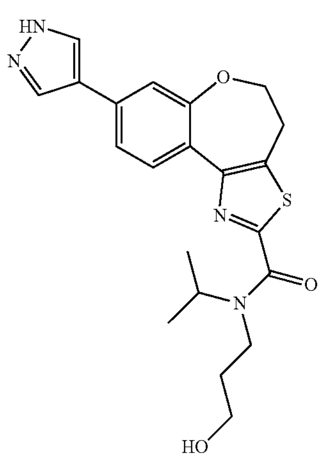 [SMILES: CC(C)N(CCCO)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid (3-hydroxy-propyl)-isopropyl-amide |

TABLE 1-continued

| No. | Structure | Name |
|---|---|---|
| 291 | 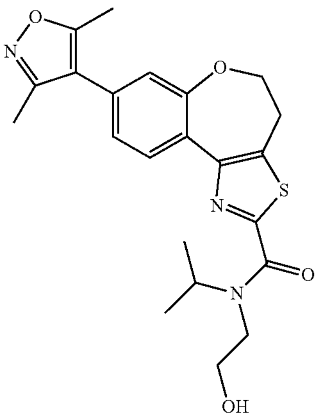 [SMILES: Cc1noc(C)c1-c1ccc2c(c1)OCCc1sc(C(=O)N(CCO)C(C)C)nc1-2] | 8-(3,5-Dimethyl-isoxazol-4-yl)-4,5-dihydro-6-oxa-3-thia-1-aza-benzo[e]azulene-2-carboxylic acid (2-hydroxy-ethyl)-isopropyl-amide |
| 292 | 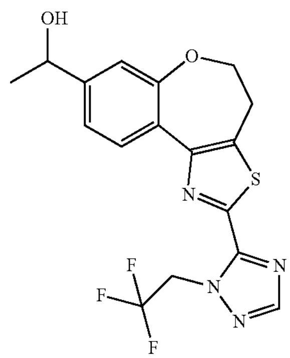 [SMILES: CC(O)c1ccc2c(c1)OCCc1sc(-c3ncnn3CC(F)(F)F)nc1-2] | 1-{2-[2-(2,2,2-Trifluoro-ethyl)-2H-[1,2,4]triazol-3-yl]-4,5-dihydro-6-oxa-3-thia-1-aza-benzo[e]azulen-8-yl}-ethanol |
| 293 | 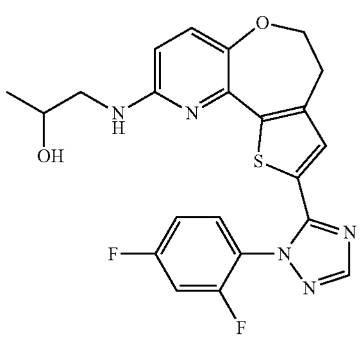 [SMILES: CC(O)CNc1ccc2c(n1)-c1sc(-c3ncnn3-c3ccc(F)cc3F)cc1CCO2] | 1-{2-[2-(2,4-Difluoro-phenyl)-2H-[1,2,4]triazol-3-yl]-4,5-dihydro-6-oxa-1-thia-10-aza-benzo[e]azulen-9-ylamino}-propan-2-ol |
| 294 | 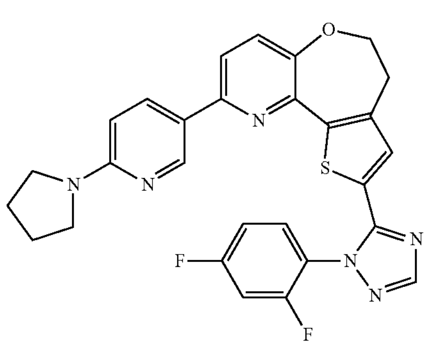 [SMILES: Fc1ccc(-n2ncnc2-c2cc3c(s2)-c2nc(-c4ccc(N5CCCC5)nc4)ccc2OCC3)c(F)c1] | 2-[2-(2,4-Difluoro-phenyl)-2H-[1,2,4]triazol-3-yl]-9-(6-pyrrolidin-1-yl-pyridin-3-yl)-4,5-dihydro-6-oxa-1-thia-10-aza-benzo[e]azulene |

| No. | Structure | Name |
|---|---|---|
| 295 | 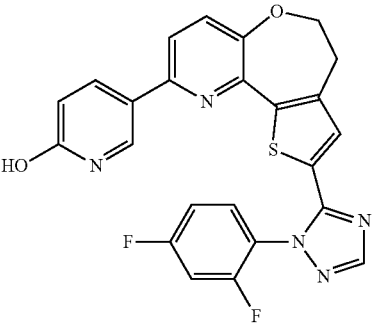 [SMILES: Oc1ccc(-c2ccc3c(n2)-c2sc(-c4ncnn4-c4ccc(F)cc4F)cc2CCO3)cn1] | 5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-ol |
| 296 | 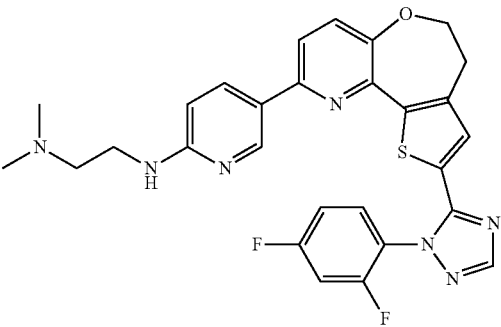 [SMILES: CN(C)CCNc1ccc(-c2ccc3c(n2)-c2sc(-c4ncnn4-c4ccc(F)cc4F)cc2CCO3)cn1] | N'-(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-N,N-dimethyl-ethane-1,2-diamine |
| 297 | 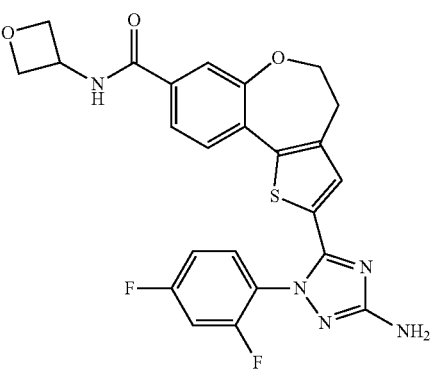 [SMILES: Nc1nc(-c2cc3c(s2)-c2ccc(C(=O)NC4COC4)cc2OCC3)n(-c2ccc(F)cc2F)n1] | 2-[5-Amino-2-(2,4-difluoro-phenyl)-2H-[1,2,4]triazol-3-yl]-4,5-dihydro-6-oxa-1-thia-benzo[e]azulene-8-carboxylic acid oxetan-3-ylamide |
| 298 | 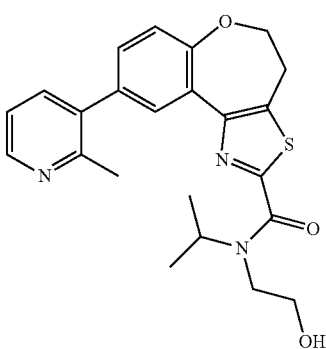 [SMILES: Cc1ncccc1-c1ccc2c(c1)-c1nc(C(=O)N(CCO)C(C)C)sc1CCO2] | 9-(2-Methyl-pyridin-3-yl)-4,5-dihydro-6-oxa-3-thia-1-aza-benzo[e]azulene-2-carboxylic acid (2-hydroxy-ethyl)-isopropyl-amide |

TABLE 1-continued

| No. | Structure | Name |
|---|---|---|
| 299 | 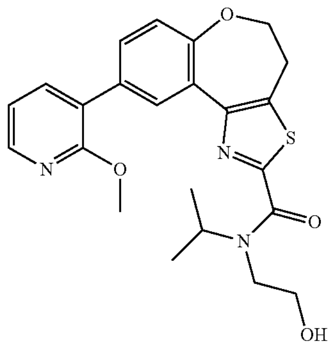 [SMILES: COc1ncccc1-c1ccc2c(c1)-c1nc(C(=O)N(CCO)C(C)C)sc1CCO2] | 9-(2-Methoxy-pyridin-3-yl)-4,5-dihydro-6-oxa-3-thia-1-aza-benzo[e]azulene-2-carboxylic acid (2-hydroxy-ethyl)-isopropyl-amide |
| 300 | 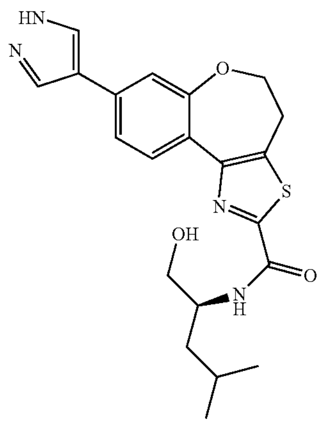 [SMILES: CC(C)C[C@@H](CO)NC(=O)c1nc2c(s1)CCOc1cc(/C(C=N)=C/N)ccc1-2] | 8-(1H-Pyrazol-4-yl)-4,5-dihydro-6-oxa-3-thia-1-aza-benzo[e]azulene-2-carboxylic acid ((S)-1-hydroxymethyl-3-methyl-butyl)-amide |
| 301 | 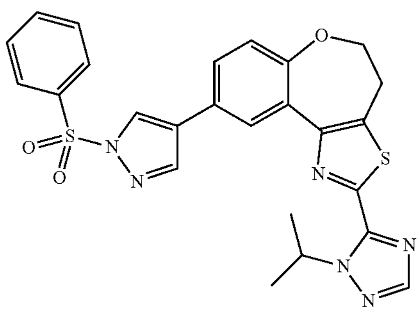 [SMILES: CC(C)n1ncnc1-c1nc2c(s1)CCOc1ccc(-c3cnn(S(=O)(=O)c4ccccc4)c3)cc1-2] | 9-(1-Benzenesulfonyl-1H-pyrazol-4-yl)-2-(2-isopropyl-2H-[1,2,4]triazol-3-yl)-4,5-dihydro-6-oxa-3-thia-1-aza-benzo[e]azulene |
| 302 | 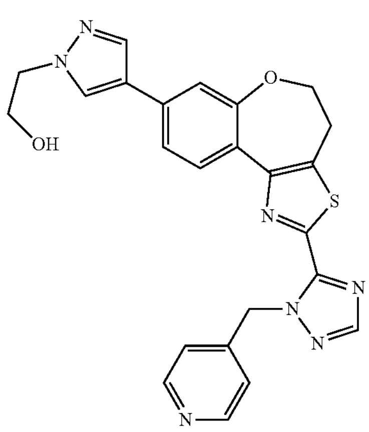 [SMILES: OCCn1cc(-c2ccc3c(c2)OCCc2sc(-c4ncnn4Cc4ccncc4)nc2-3)cn1] | 2-{4-[2-(2-Pyridin-4-ylmethyl-2H-[1,2,4]triazol-3-yl)-4,5-dihydro-6-oxa-3-thia-1-aza-benzo[e]azulen-8-yl]-pyrazol-1-yl}-ethanol |

TABLE 1-continued

| No. | Structure | Name |
|---|---|---|
| 303 | 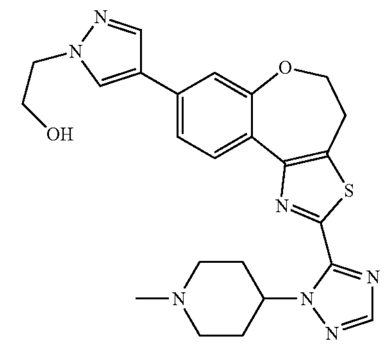 [SMILES: CN1CCC(n2ncnc2-c2nc3c(s2)CCOc2cc(-c4cnn(CCO)c4)ccc2-3)CC1] | 2-(4-{2-[2-(1-Methyl-piperidin-4-yl)-2H-[1,2,4]triazol-3-yl]-4,5-dihydro-6-oxa-3-thia-1-aza-benzo[e]azulen-8-yl}-pyrazol-1-yl)-ethanol |
| 304 | 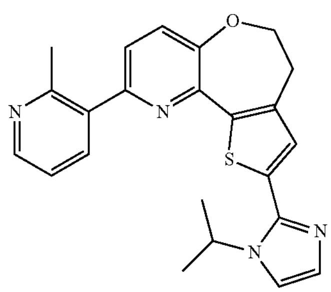 [SMILES: Cc1ncccc1-c1ccc2c(n1)-c1sc(-c3nccn3C(C)C)cc1CCO2] | 2-(1-Isopropyl-1H-imidazol-2-yl)-9-(2-methyl-pyridin-3-yl)-4,5-dihydro-6-oxa-1-thia-10-aza-benzo[e]azulene |
| 305 | 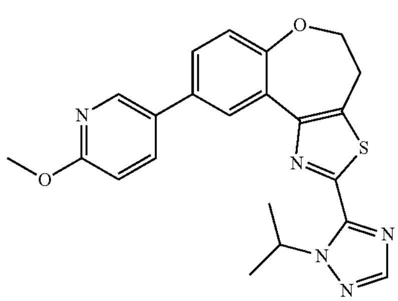 [SMILES: COc1ccc(-c2ccc3c(c2)-c2nc(-c4ncnn4C(C)C)sc2CCO3)cn1] | 2-(2-Isopropyl-2H-[1,2,4]triazol-3-yl)-9-(6-methoxy-pyridin-3-yl)-4,5-dihydro-6-oxa-3-thia-1-aza-benzo[e]azulene |
| 306 | 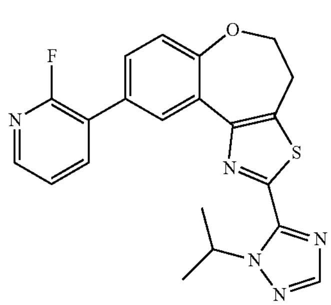 | 9-(2-Fluoro-pyridin-3-yl)-2-(2-isopropyl-2H-[1,2,4]triazol-3-yl)-4,5-dihydro-6-oxa-3-thia-1-aza-benzo[e]azulene |

TABLE 1-continued

| No. | Structure | Name |
|---|---|---|
| 307 | 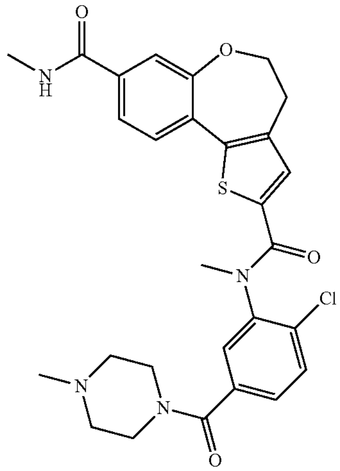 [SMILES: CNC(=O)c1ccc2c(c1)OCCc1cc(C(=O)N(C)c3cc(C(=O)N4CCN(C)CC4)ccc3Cl)sc1-2] | 4,5-Dihydro-6-oxa-1-thia-benzo[e]azulene-2,8-dicarboxylic acid 2-{[2-chloro-5-(4-methyl-piperazine-1-carbonyl)-phenyl]-methyl-amide} 8-methylamide |
| 308 | 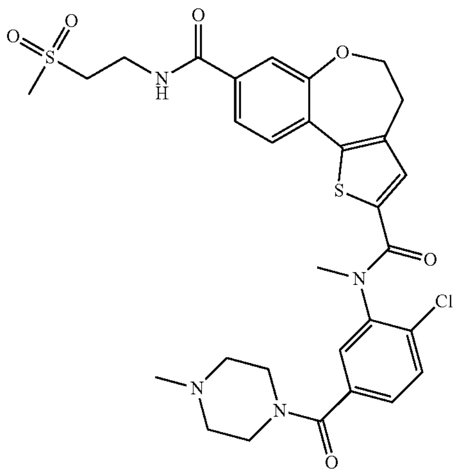 [SMILES: CN1CCN(C(=O)c2ccc(Cl)c(N(C)C(=O)c3cc4c(s3)-c3ccc(C(=O)NCCS(C)(=O)=O)cc3OCC4)c2)CC1] | 4,5-Dihydro-6-oxa-1-thia-benzo[e]azulene-2,8-dicarboxylic acid 2-{[2-chloro-5-(4-methyl-piperazine-1-carbonyl)-phenyl]-methyl-amide} 8-[(2-methanesulfonyl-ethyl)-amide] |
| 309 | 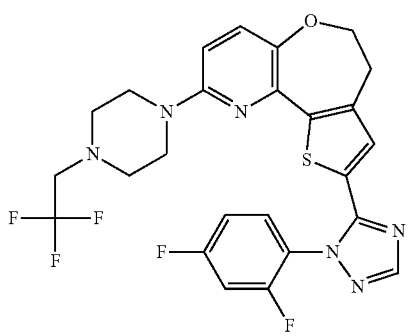 [SMILES: Fc1ccc(-n2ncnc2-c2cc3c(s2)-c2nc(N4CCN(CC(F)(F)F)CC4)ccc2OCC3)c(F)c1] | 2-[2-(2,4-Difluoro-phenyl)-2H-[1,2,4]triazol-3-yl]-9-[4-(2,2,2-trifluoro-ethyl)-piperazin-1-yl]-4,5-dihydro-6-oxa-1-thia-10-aza-benzo[e]azulene |
| 310 | 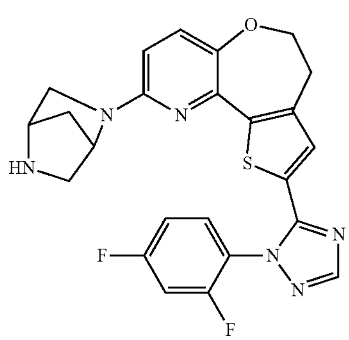 [SMILES: Fc1ccc(-n2ncnc2-c2cc3c(s2)-c2nc(N4CC5CC4CN5)ccc2OCC3)c(F)c1] | 9-(2,5-Diaza-bicyclo[2.2.1]hept-2-yl)-2-[2-(2,4-difluoro-phenyl)-2H-[1,2,4]triazol-3-yl]-4,5-dihydro-6-oxa-1-thia-10-aza-benzo[e]azulene |

TABLE 1-continued

| No. | Structure | Name |
|---|---|---|
| 311 | 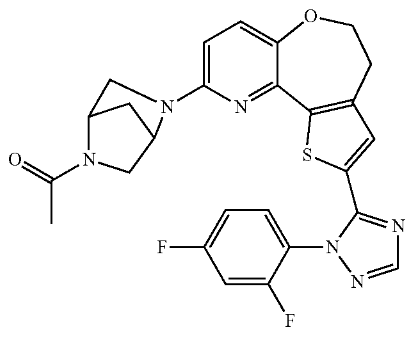 [SMILES: CC(=O)N1CC2CC1CN2c1ccc2c(n1)-c1sc(-c3ncnn3-c3ccc(F)cc3F)cc1CCO2] | 1-(5-{2-[2-(2,4-Difluoro-phenyl)-2H-[1,2,4]triazol-3-yl]-4,5-dihydro-6-oxa-1-thia-10-aza-benzo[e]azulen-9-yl}-2,5-diaza-bicyclo[2.2.1]hept-2-yl)-ethanone |
| 312 | 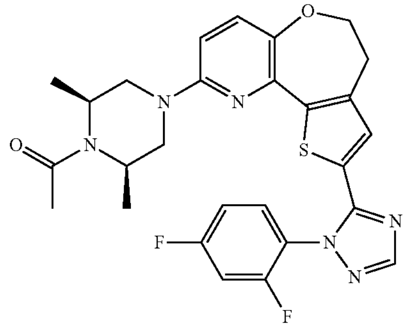 [SMILES: CC(=O)N1[C@H](C)CN(c2ccc3c(n2)-c2sc(-c4ncnn4-c4ccc(F)cc4F)cc2CCO3)C[C@@H]1C] | 1-((2R,6S)-4-{2-[2-(2,4-Difluoro-phenyl)-2H-[1,2,4]triazol-3-yl]-4,5-dihydro-6-oxa-1-thia-10-aza-benzo[e]azulen-9-yl}-2,6-dimethyl-piperazin-1-yl)-ethanone |
| 313 | 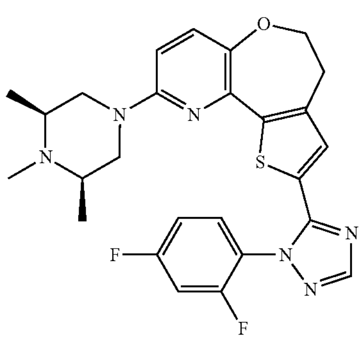 | 2-[2-(2,4-Difluoro-phenyl)-2H-[1,2,4]triazol-3-yl]-9-((3R,5S)-3,4,5-trimethyl-piperazin-1-yl)-4,5-dihydro-6-oxa-1-thia-10-aza-benzo[e]azulene |
| 314 | 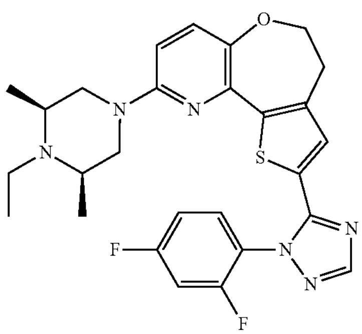 [SMILES: CCN1[C@H](C)CN(c2ccc3c(n2)-c2sc(-c4ncnn4-c4ccc(F)cc4F)cc2CCO3)C[C@@H]1C] | 2-[2-(2,4-Difluoro-phenyl)-2H-[1,2,4]triazol-3-yl]-9-((3R,5S)-4-ethyl-3,5-dimethyl-piperazin-1-yl)-4,5-dihydro-6-oxa-1-thia-10-aza-benzo[e]azulene |

TABLE 1-continued

| No. | Structure | Name |
|---|---|---|
| 315 | 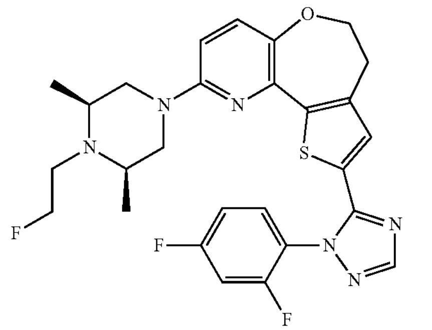 [SMILES: C[C@@H]1CN(c2ccc3c(n2)-c2sc(-c4ncnn4-c4ccc(F)cc4F)cc2CCO3)C[C@H](C)N1CCF] | 2-[2-(2,4-Difluoro-phenyl)-2H-[1,2,4]triazol-3-yl]-9-[(3R,5S)-4-(2-fluoro-ethyl)-3,5-dimethyl-piperazin-1-yl]-4,5-dihydro-6-oxa-1-thia-10-aza-benzo[e]azulene |
| 316 | 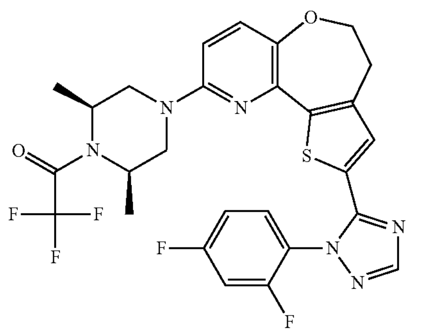 [SMILES: C[C@@H]1CN(c2ccc3c(n2)-c2sc(-c4ncnn4-c4ccc(F)cc4F)cc2CCO3)C[C@H](C)N1C(=O)C(F)(F)F] | 1-((2R,6S)-4-{2-[2-(2,4-Difluoro-phenyl)-2H-[1,2,4]triazol-3-yl]-4,5-dihydro-6-oxa-1-thia-10-aza-benzo[e]azulen-9-yl}-2,6-dimethyl-piperazin-1-yl)-2,2,2-trifluoro-ethanone |
| 317 | 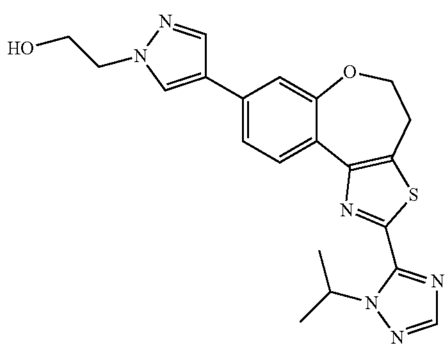 [SMILES: CC(C)n1ncnc1-c1nc2c(s1)CCOc1cc(-c3cnn(CCO)c3)ccc1-2] | 2-{4-[2-(1-Isopropyl-1H-imidazol-2-yl)-4,5-dihydro-6-oxa-3-thia-1-aza-benzo[e]azulen-8-yl]-pyrazol-1-yl}-ethanol |
| 318 | 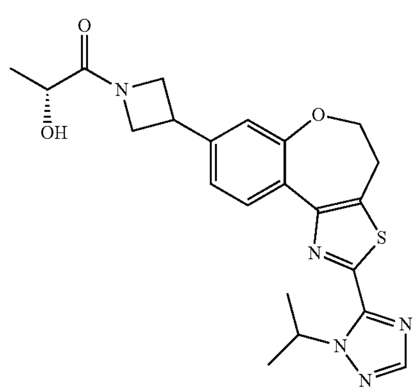 [SMILES: CC(C)n1ncnc1-c1nc2c(s1)CCOc1cc(C3CN(C(=O)[C@@H](C)O)C3)ccc1-2] | (R)-2-Hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-propan-1-one |

TABLE 1-continued

| No. | Structure | Name |
|-----|-----------|------|
| 319 | 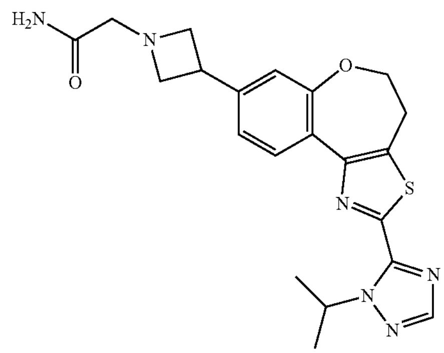 [SMILES: CC(C)n1ncnc1-c1nc2c(s1)CCOc1cc(C3CN(CC(N)=O)C3)ccc1-2] | 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-acetamide |
| 320 | 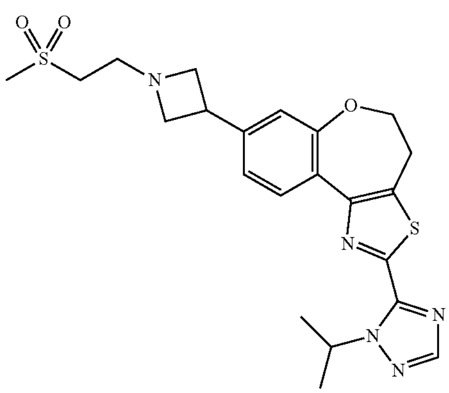 [SMILES: CC(C)n1ncnc1-c1nc2c(s1)CCOc1cc(C3CN(CCS(C)(=O)=O)C3)ccc1-2] | 2-(2-Isopropyl-2H-[1,2,4]triazol-3-yl)-8-[1-(2-methanesulfonyl-ethyl)-azetidin-3-yl]-4,5-dihydro-6-oxa-3-thia-1-aza-benzo[e]azulene |
| 321 | 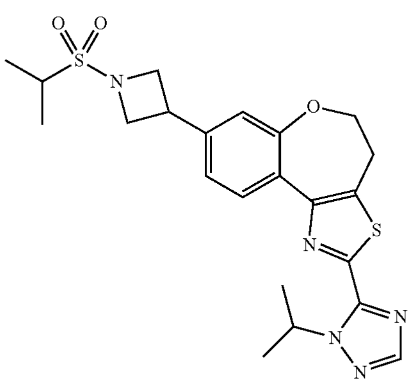 [SMILES: CC(C)n1ncnc1-c1nc2c(s1)CCOc1cc(C3CN(S(=O)(=O)C(C)C)C3)ccc1-2] | 2-(2-Isopropyl-2H-[1,2,4]triazol-3-yl)-8-[1-(propane-2-sulfonyl)-azetidin-3-yl]-4,5-dihydro-6-oxa-3-thia-1-aza-benzo[e]azulene |
| 322 | 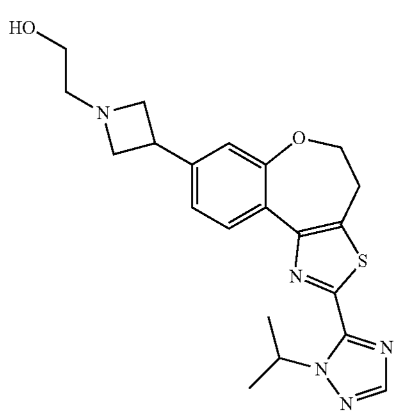 [SMILES: CC(C)n1ncnc1-c1nc2c(s1)CCOc1cc(C3CN(CCO)C3)ccc1-2] | 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-ethanol |

TABLE 1-continued

| No. | Structure | Name |
|---|---|---|
| 323 | 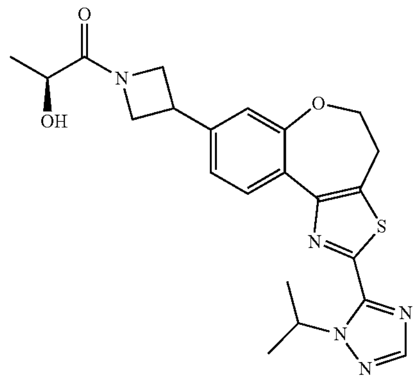 [SMILES: CC(C)n1ncnc1-c1nc2c(s1)CCOc1cc(C3CN(C(=O)[C@H](C)O)C3)ccc1-2] | (S)-2-Hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-propan-1-one |
| 324 | 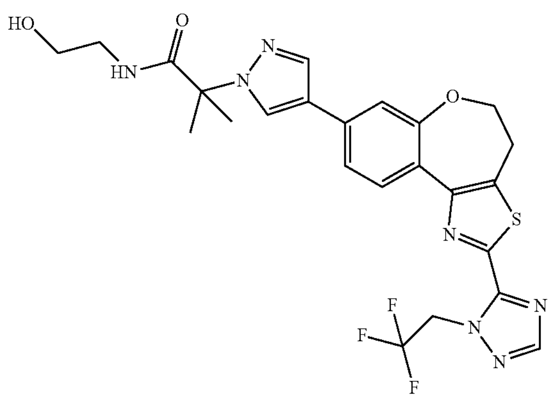 [SMILES: CC(C)(C(=O)NCCO)n1cc(-c2ccc3c(c2)OCCc2sc(-c4ncnn4CC(F)(F)F)nc2-3)cn1] | N-(2-Hydroxy-ethyl)-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-isobutyramide |
| 325 | 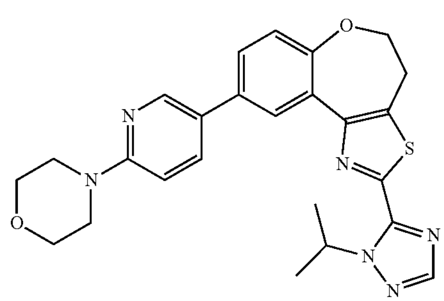 [SMILES: CC(C)n1ncnc1-c1nc2c(s1)CCOc1ccc(-c3ccc(N4CCOCC4)nc3)cc1-2] | 2-(2-Isopropyl-2H-[1,2,4]triazol-3-yl)-9-(6-morpholin-4-yl-pyridin-3-yl)-4,5-dihydro-6-oxa-3-thia-1-aza-benzo[e]azulene |
| 326 | 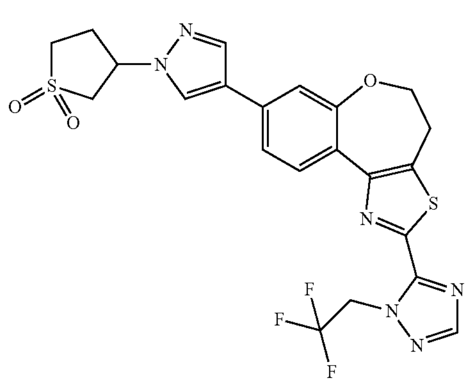 [SMILES: O=S1(=O)CCC(n2cc(-c3ccc4c(c3)OCCc3sc(-c5ncnn5CC(F)(F)F)nc3-4)cn2)C1] | 8-[1-(1,1-Dioxo-tetrahydro-1S-thiophen-3-yl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene |

TABLE 1-continued

| No. | Structure | Name |
|---|---|---|
| 327 | 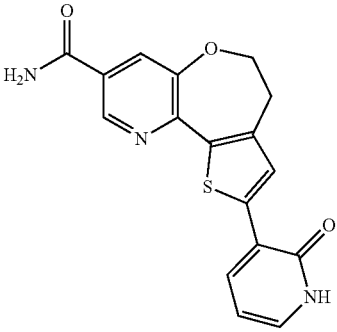 [SMILES: NC(=O)c1cnc2c(c1)OCCc1cc(-c3ccc[nH]c3=O)sc1-2] | 2-(2-Oxo-1,2-dihydro-pyridin-3-yl)-4,5-dihydro-6-oxa-1-thia-10-aza-benzo[e]azulene-8-carboxylic acid amide |
| 328 | 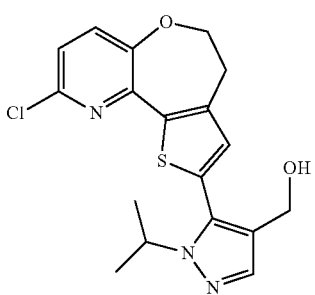 [SMILES: CC(C)n1ncc(CO)c1-c1cc2c(s1)-c1nc(Cl)ccc1OCC2] | [5-(9-Chloro-4,5-dihydro-6-oxa-1-thia-10-aza-benzo[e]azulen-2-yl)-1-isopropyl-1H-pyrazol-4-yl]-methanol |
| 329 | 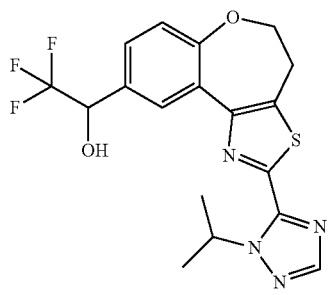 [SMILES: CC(C)n1ncnc1-c1nc2c(s1)CCOc1ccc(C(O)C(F)(F)F)cc1-2] | 2,2,2-Trifluoro-1-[2-(2-isopropyl-2H-[1,2,4]triazol-3-yl)-4,5-dihydro-6-oxa-3-thia-1-aza-benzo[e]azulen-9-yl]-ethanol |
| 330 | 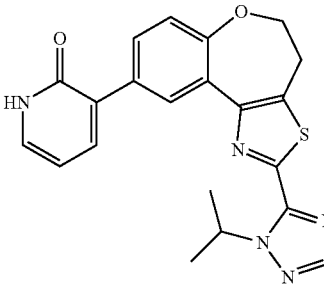 | 3-[2-(2-Isopropyl-2H-[1,2,4]triazol-3-yl)-4,5-dihydro-6-oxa-3-thia-1-aza-benzo[e]azulen-9-yl]-1H-pyridin-2-one |
| 331 | 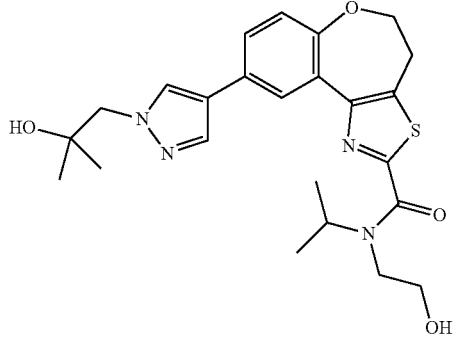 [SMILES: CC(C)N(CCO)C(=O)c1nc2c(s1)CCOc1ccc(-c3cnn(CC(C)(C)O)c3)cc1-2] | 9-[1-(2-Hydroxy-2-methyl-propyl)-1H-pyrazol-4-yl]-4,5-dihydro-6-oxa-3-thia-1-aza-benzo[e]azulene-2-carboxylic acid (2-hydroxy-ethyl)-isopropyl-amide |

TABLE 1-continued

| No. | Structure | Name |
| --- | --- | --- |
| 332 | 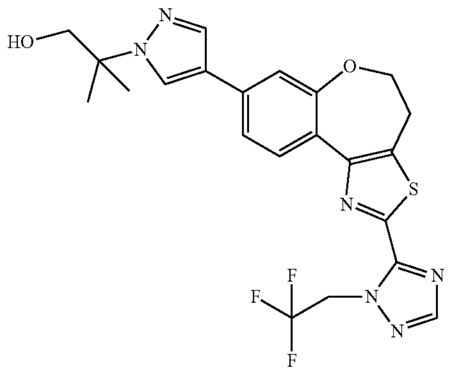 [SMILES: CC(C)(CO)n1cc(-c2ccc3c(c2)OCCc2sc(-c4ncnn4CC(F)(F)F)nc2-3)cn1] | 2-Methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propan-1-ol |
| 333 | 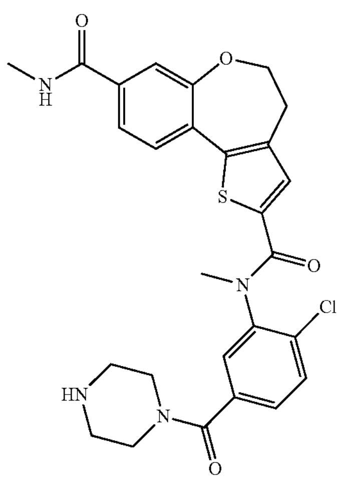 [SMILES: CNC(=O)c1ccc2c(c1)OCCc1cc(C(=O)N(C)c3cc(C(=O)N4CCNCC4)ccc3Cl)sc1-2] | N2-(2-chloro-5-(piperazine-1-carbonyl)phenyl)-N2,N8-dimethyl-4,5-dihydrobenzo[b]thieno[2,3-d]oxepine-2,8-dicarboxamide |
| 334 | 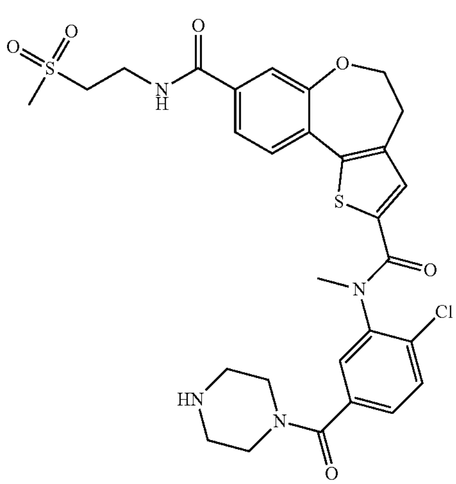 [SMILES: CN(C(=O)c1cc2c(s1)-c1ccc(C(=O)NCCS(C)(=O)=O)cc1OCC2)c1cc(C(=O)N2CCNCC2)ccc1Cl] | N2-(2-chloro-5-(piperazine-1-carbonyl)phenyl)-N2-methyl-N8-(2-(methylsulfonyl)ethyl)-4,5-dihydrobenzo[b]thieno[2,3-d]oxepine-2,8-dicarboxamide |

TABLE 1-continued

| No. | Structure | Name |
|---|---|---|
| 335 | 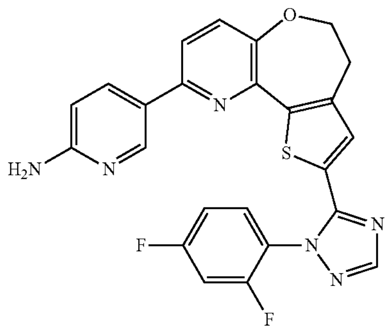 [SMILES: Nc1ccc(-c2ccc3c(n2)-c2sc(-c4ncnn4-c4ccc(F)cc4F)cc2CCO3)cn1] | 5-{2-[2-(2,4-Difluoro-phenyl)-2H-[,2,4]triazol-3-yl]-4,5-dihydro-6-oxa-1-thia-10-aza-benzo[e]azulen-9-yl}-pyridin-2-ylamine |
| 336 | 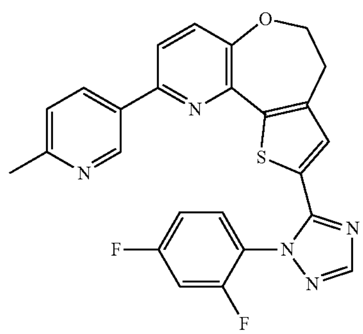 [SMILES: Cc1ccc(-c2ccc3c(n2)-c2sc(-c4ncnn4-c4ccc(F)cc4F)cc2CCO3)cn1] | 2-[2-(2,4-Difluoro-phenyl)-2H-[1,2,4]triazol-3-yl]-9-(6-methyl-pyridin-3-yl)-4,5-dihydro-6-oxa-1-thia-10-aza-benzo[e]azulene |
| 337 | 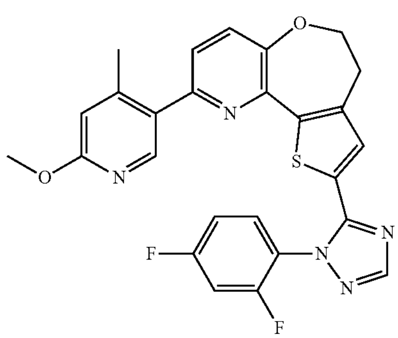 [SMILES: COc1cc(C)c(-c2ccc3c(n2)-c2sc(-c4ncnn4-c4ccc(F)cc4F)cc2CCO3)cn1] | 2-[2-(2,4-Difluoro-phenyl)-2H-[1,2,4]triazol-3-yl]-9-(6-methoxy-4-methyl-pyridin-3-yl)-4,5-dihydro-6-oxa-1-thia-10-aza-benzo[e]azulene |
| 338 | 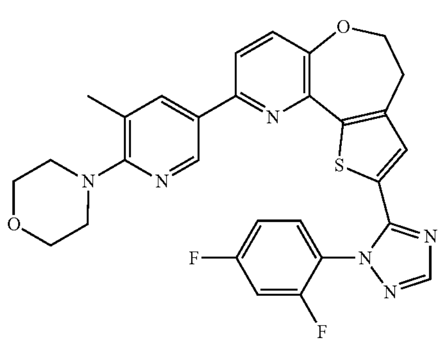 [SMILES: Cc1cc(-c2ccc3c(n2)-c2sc(-c4ncnn4-c4ccc(F)cc4F)cc2CCO3)cnc1N1CCOCC1] | 2-[2-(2,4-Difluoro-phenyl)-2H-[1,2,4]triazol-3-yl]-9-(5-methyl-6-morpholin-4-yl-pyridin-3-yl)-4,5-dihydro-6-oxa-1-thia-10-aza-benzo[e]azulene |

TABLE 1-continued

| No. | Structure | Name |
|---|---|---|
| 339 | 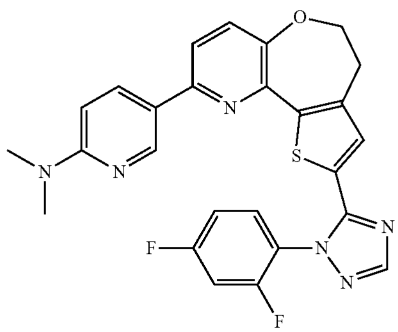 [SMILES: CN(C)c1ccc(-c2ccc3c(n2)-c2sc(-c4ncnn4-c4ccc(F)cc4F)cc2CCO3)cn1] | (5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-dimethyl-amine |
| 340 | 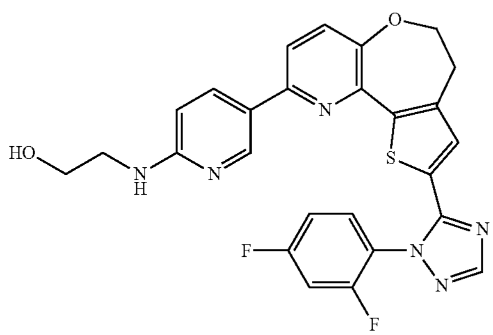 [SMILES: OCCNc1ccc(-c2ccc3c(n2)-c2sc(-c4ncnn4-c4ccc(F)cc4F)cc2CCO3)cn1] | 2-(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-ylamino)-ethanol |
| 341 | 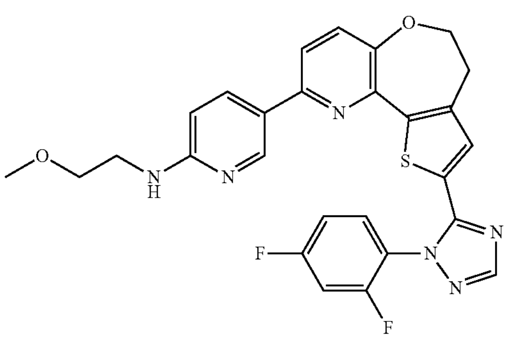 [SMILES: COCCNc1ccc(-c2ccc3c(n2)-c2sc(-c4ncnn4-c4ccc(F)cc4F)cc2CCO3)cn1] | (5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-(2-methoxy-ethyl)-amine |
| 342 | 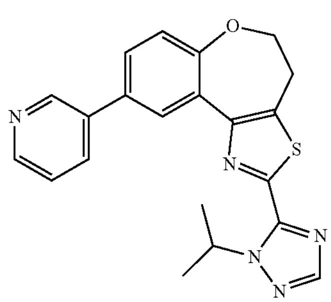 [SMILES: CC(C)n1ncnc1-c1nc2c(s1)CCOc1ccc(-c3cccnc3)cc1-2] | 2-(2-Isopropyl-2H-[1,2,4]triazol-3-yl)-9-pyridin-3-yl-4,5-dihydro-6-oxa-3-thia-1-aza-benzo[e]azulene |
| 343 | 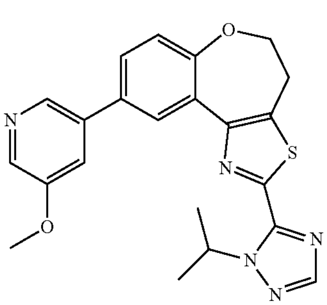 [SMILES: COc1cncc(-c2ccc3c(c2)-c2nc(-c4ncnn4C(C)C)sc2CCO3)c1] | 2-(2-Isopropyl-2H-[1,2,4]triazol-3-yl)-9-(5-methoxy-pyridin-3-yl)-4,5-dihydro-6-oxa-3-thia-1-aza-benzo[e]azulene |

TABLE 1-continued

| No. | Structure | Name |
|---|---|---|
| 344 | 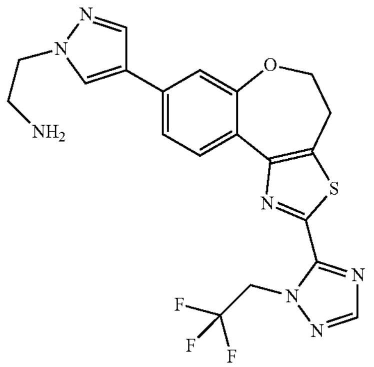 [SMILES: NCCn1cc(-c2ccc3c(c2)OCCc2sc(-c4ncnn4CC(F)(F)F)nc2-3)cn1] | 2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-ethylamine |
| 345 | 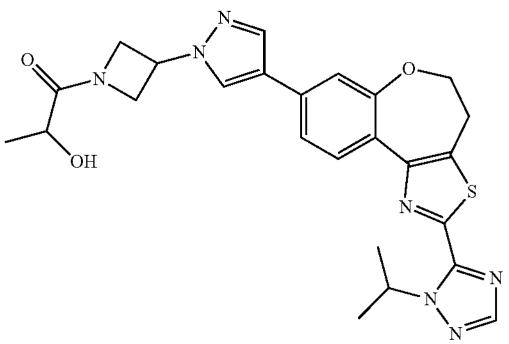 [SMILES: CC(O)C(=O)N1CC(n2cc(-c3ccc4c(c3)OCCc3sc(-c5ncnn5C(C)C)nc3-4)cn2)C1] | 2-Hydroxy-1-(3-{4-[2-(2-isopropyl-2H-[1,2,4]triazol-3-yl)-4,5-dihydro-6-oxa-3-thia-1-aza-benzo[e]azulen-8-yl]-pyrazol-1-yl}-azetidin-1-yl)-propan-1-one |
| 346 | 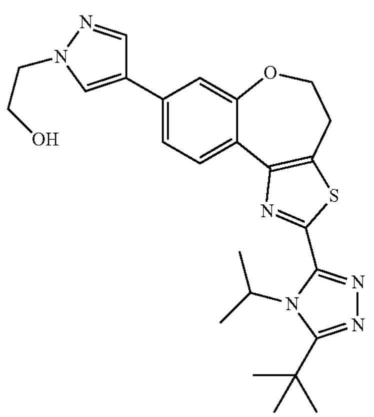 [SMILES: CC(C)n1c(-c2nc3c(s2)CCOc2cc(-c4cnn(CCO)c4)ccc2-3)nnc1C(C)(C)C] | 2-{4-[2-(4-Isopropyl-5-trifluoromethyl-4H-[1,2,4]triazol-3-yl)-4,5-dihydro-6-oxa-3-thia-1-aza-benzo[e]azulen-8-yl]-pyrazol-1-yl}-ethanol |
| 347 | 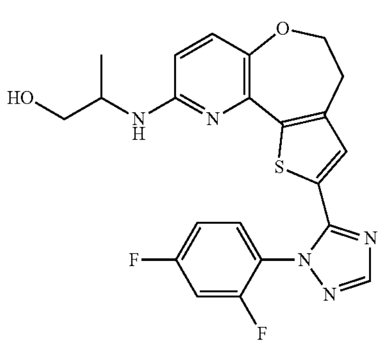 [SMILES: CC(CO)Nc1ccc2c(n1)-c1sc(-c3ncnn3-c3ccc(F)cc3F)cc1CCO2] | 2-{2-[2-(2,4-Difluoro-phenyl)-2H-[1,2,4]triazol-3-yl]-4,5-dihydro-6-oxa-1-thia-10-aza-benzo[e]azulen-9-ylamino}-propan-1-ol |

TABLE 1-continued

| No. | Structure | Name |
|---|---|---|
| 348 | 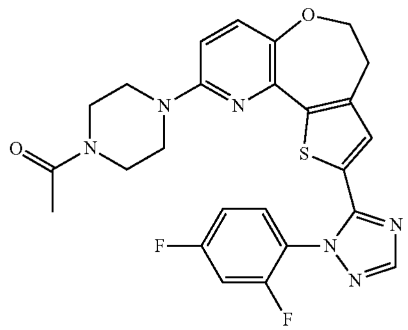 [SMILES: CC(=O)N1CCN(c2ccc3c(n2)-c2sc(-c4ncnn4-c4ccc(F)cc4F)cc2CCO3)CC1] | 1-(4-{2-[2-(2,4-Difluoro-phenyl)-2H-[1,2,4]triazol-3-yl]-4,5-dihydro-6-oxa-1-thia-10-aza-benzo[e]azulen-9-yl}-piperazin-1-yl)-ethanone |
| 349 | 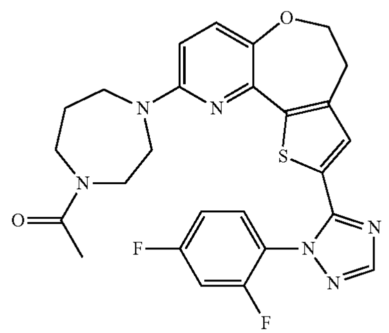 [SMILES: CC(=O)N1CCCN(c2ccc3c(n2)-c2sc(-c4ncnn4-c4ccc(F)cc4F)cc2CCO3)CC1] | 1-(4-{2-[2-(2,4-Difluoro-phenyl)-2H-[1,2,4]triazol-3-yl]-4,5-dihydro-6-oxa-1-thia-10-aza-benzo[e]azulen-9-yl}-[1,4]diazepan-1-yl)-ethanone |
| 350 | 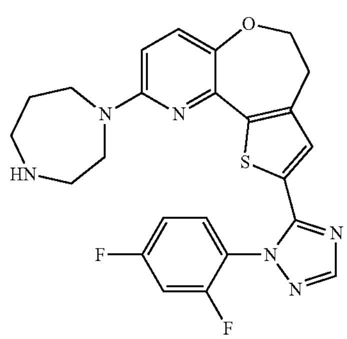 [SMILES: Fc1ccc(-n2ncnc2-c2cc3c(s2)-c2nc(N4CCCNCC4)ccc2OCC3)c(F)c1] | 9-[1,4]Diazepan-1-yl-2-[2-(2,4-difluoro-phenyl)-2H-[1,2,4]triazol-3-yl]-4,5-dihydro-6-oxa-1-thia-10-aza-benzo[e]azulene |
| 351 | 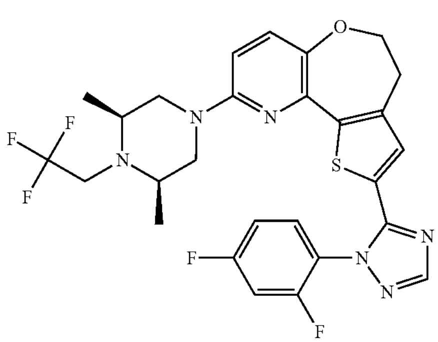 [SMILES: C[C@@H]1CN(c2ccc3c(n2)-c2sc(-c4ncnn4-c4ccc(F)cc4F)cc2CCO3)C[C@H](C)N1CC(F)(F)F] | 2-[2-(2,4-Difluoro-phenyl)-2H-[1,2,4]triazol-3-yl]-9-[(3R,5S)-3,5-dimethyl-4-(2,2,2-trifluoro-ethyl)-piperazin-1-yl]-4,5-dihydro-6-oxa-1-thia-10-aza-benzo[e]azulene |

TABLE 1-continued

| No. | Structure | Name |
|---|---|---|
| 352 | 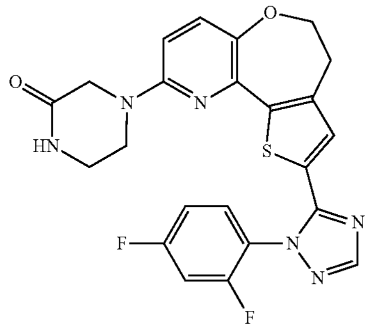 [SMILES: O=C1CN(c2ccc3c(n2)-c2sc(-c4ncnn4-c4ccc(F)cc4F)cc2CCO3)CCN1] | 4-{2-[2-(2,4-Difluoro-phenyl)-2H-[1,2,4]triazol-3-yl]-4,5-dihydro-6-oxa-1-thia-10-aza-benzo[e]azulen-9-yl}-piperazin-2-one |
| 353 | 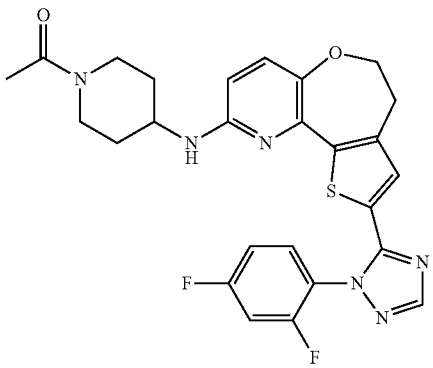 [SMILES: CC(=O)N1CCC(Nc2ccc3c(n2)-c2sc(-c4ncnn4-c4ccc(F)cc4F)cc2CCO3)CC1] | 1-(4-{2-[2-(2,4-Difluoro-phenyl)-2H-[1,2,4]triazol-3-yl]-4,5-dihydro-6-oxa-1-thia-10-aza-benzo[e]azulen-9-ylamino}-piperidin-1-yl)-ethanone |
| 354 | 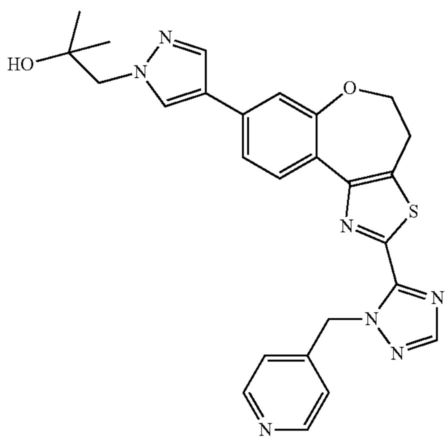 [SMILES: CC(C)(O)Cn1cc(-c2ccc3c(c2)OCCc2sc(-c4ncnn4Cc4ccncc4)nc2-3)cn1] | 2-Methyl-1-{4-[2-(2-pyridin-4-ylmethyl-2H-[1,2,4]triazol-3-yl)-4,5-dihydro-6-oxa-3-thia-1-aza-benzo[e]azulen-8-yl]-pyrazol-1-yl}-propan-2-ol |
| 355 | 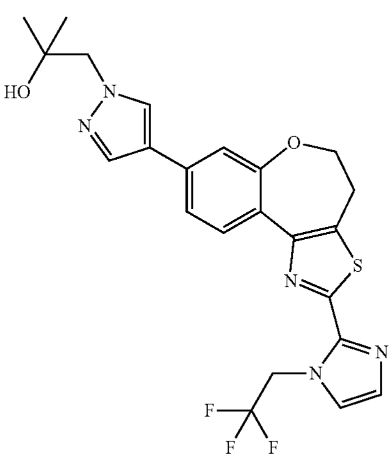 [SMILES: CC(C)(O)Cn1cc(-c2ccc3c(c2)OCCc2sc(-c4nccn4CC(F)(F)F)nc2-3)cn1] | 2-Methyl-1-(4-{2-[1-(2,2,2-trifluoro-ethyl)-1H-imidazol-2-yl]-4,5-dihydro-oxa-3-thia-1-aza-benzo[e]azulen-8-yl}pyrazol-1-yl)-propan-2-ol |

TABLE 1-continued

| No. | Structure | Name |
|---|---|---|
| 356 | 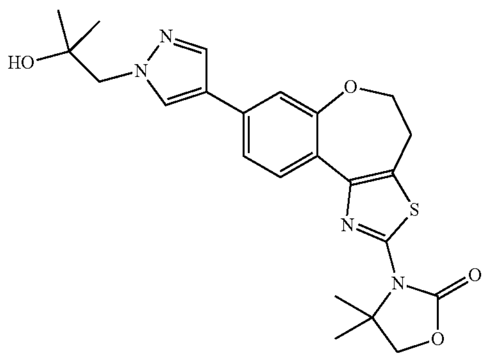 [SMILES: CC(C)(O)Cn1cc(-c2ccc3c(c2)OCCc2sc(N4C(=O)OCC4(C)C)nc2-3)cn1] | 3-{8-[1-(2-Hydroxy-2-methyl-propyl)-1H-pyrazol-4-yl]-4,5-dihydro-6-oxa-3-thia-1-aza-benzo[e]azulen-2-yl}-4,4-dimethyl-oxazolidin-2-one |
| 357 | 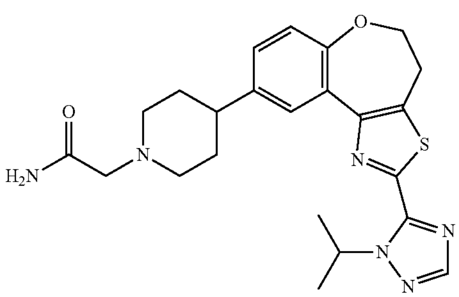 [SMILES: CC(C)n1ncnc1-c1nc2c(s1)CCOc1ccc(C3CCN(CC(N)=O)CC3)cc1-2] | 2-{4-[2-(2-Isopropyl-2H-[1,2,4]triazol-3-yl)-4,5-dihydro-6-oxa-3-thia-1-aza-benzo[e]azulen-9-yl]-piperidin-1-yl}-acetamide |
| 358 | 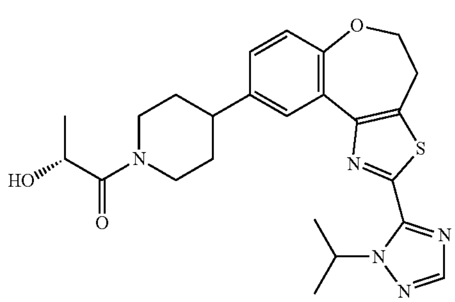 [SMILES: CC(C)n1ncnc1-c1nc2c(s1)CCOc1ccc(C3CCN(C(=O)[C@@H](C)O)CC3)cc1-2] | (R)-2-Hydroxy-1-{4-[2-(2-isopropyl-2H-[1,2,4]triazol-3-yl)-4,5-dihydro-6-oxa-3-thia-1-aza-benzo[e]azulen-9-yl]-piperidin-1-yl}-propan-1-one |
| 359 | 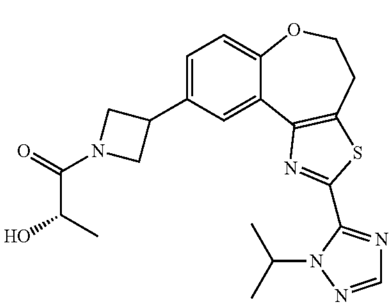 [SMILES: CC(C)n1ncnc1-c1nc2c(s1)CCOc1ccc(C3CN(C(=O)[C@H](C)O)C3)cc1-2] | (S)-2-Hydroxy-1-{3-[2-(2-isopropyl-2H-[1,2,4]triazol-3-yl)-4,5-dihydro-6-oxa-3-thia-1-aza-benzo[e]azulen-9-yl]-azetidin-1-yl}-propan-1-one |

TABLE 1-continued

| No. | Structure | Name |
|---|---|---|
| 360 | 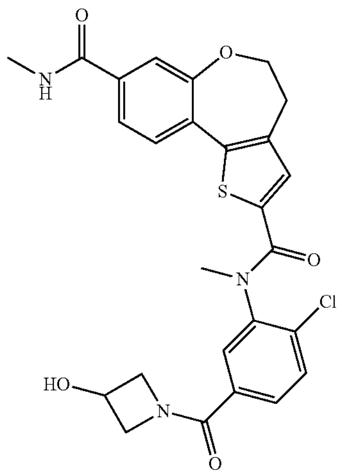 [SMILES: CNC(=O)c1ccc2c(c1)OCCc1cc(C(=O)N(C)c3cc(C(=O)N4CC(O)C4)ccc3Cl)sc1-2] | N2-(2-chloro-5-(3-hydroxyazetidine-1-carbonyl)phenyl)-N2,N8-dimethyl-4,5-dihydrobenzo[b]thieno[2,3-d]oxepine-2,8-dicarboxamide |
| 361 | 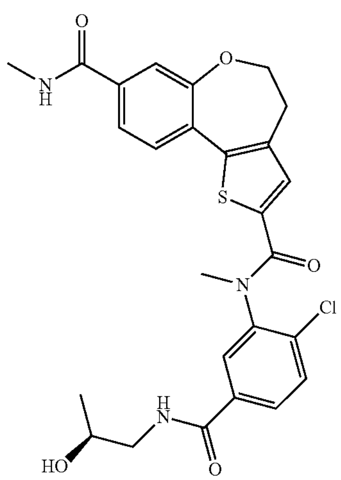 [SMILES: CNC(=O)c1ccc2c(c1)OCCc1cc(C(=O)N(C)c3cc(C(=O)NC[C@H](C)O)ccc3Cl)sc1-2] | N2-(2-chloro-5-((S)-2-hydroxypropylcarbamoyl)phenyl)-N2,N8-dimethyl-4,5-dihydrobenzo[b]thieno[2,3-d]oxepine-2,8-dicarboxamide |
| 362 | 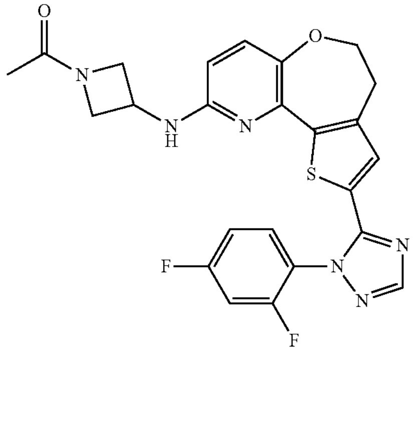 [SMILES: CC(=O)N1CC(Nc2ccc3c(n2)-c2sc(-c4ncnn4-c4ccc(F)cc4F)cc2CCO3)C1] | 1-(3-{2-[2-(2,4-Difluoro-phenyl)-2H-[1,2,4]triazol-3-yl]-4,5-dihydro-6-oxa-1-thia-10-aza-benzo[e]azulen-9-ylamino}-azetidin-1-yl)-ethanone |

TABLE 1-continued

| No. | Structure | Name |
|---|---|---|
| 363 | 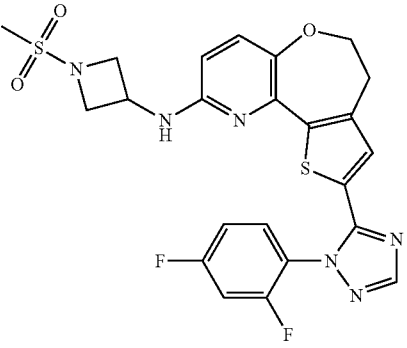 [SMILES: CS(=O)(=O)N1CC(Nc2ccc3c(n2)-c2sc(-c4ncnn4-c4ccc(F)cc4F)cc2CCO3)C1] | {2-[2-(2,4-Difluoro-phenyl)-2H-[1,2,4]triazol-3-yl]-4,5-dihydro-6-oxa-1-thia-10-aza-benzo[e]azulen-9-yl}-(1-methanesulfonyl-azetidin-3-yl)-amine |
| 364 | 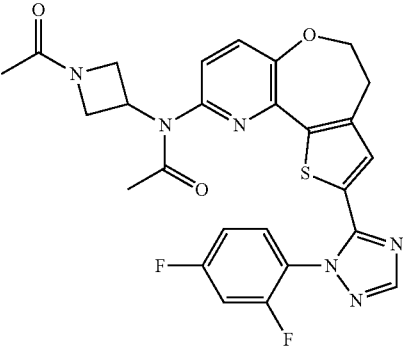 [SMILES: CC(=O)N1CC(N(C(C)=O)c2ccc3c(n2)-c2sc(-c4ncnn4-c4ccc(F)cc4F)cc2CCO3)C1] | N-(1-Acetyl-azetidin-3-yl)-N-{2-[2-(2,4-difluoro-phenyl)-2H-[1,2,4]triazol-3-yl]-4,5-dihydro-6-oxa-1-thia-10-aza-benzo[e]azulen-9-yl)-acetamide |
| 365 | 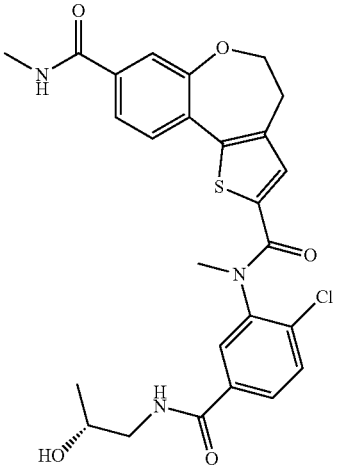 [SMILES: CNC(=O)c1ccc2c(c1)OCCc1cc(C(=O)N(C)c3cc(C(=O)NC[C@@H](C)O)ccc3Cl)sc1-2] | 4,5-Dihydro-6-oxa-1-thia-benzo[e]azulene-2,8-dicarboxylic acid 2-{[2-chloro-5-((R)-2-hydroxy-propylcarbamoyl)-phenyl]-methyl-amide} 8-methylamide |
| 366 | 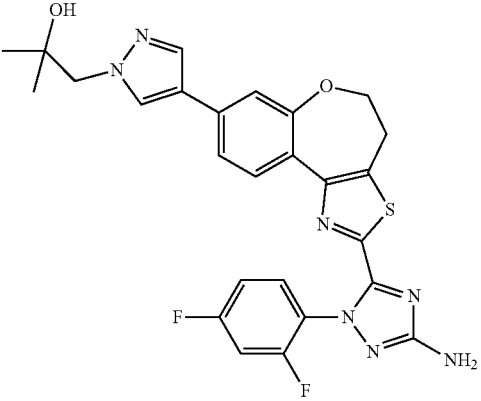 [SMILES: CC(C)(O)Cn1cc(-c2ccc3c(c2)OCCc2sc(-c4nc(N)nn4-c4ccc(F)cc4F)nc2-3)cn1] | 1-(4-{2-[5-Amino-2-(2,4-difluoro-phenyl)-2H-[1,2,4]triazol-3-yl]-4,5-dihydro-6-oxa-3-thia-1-aza-benzo[e]azulen-8-yl}-pyrazol-1-yl)-2-methyl-propan-2-ol |

TABLE 1-continued

| No. | Structure | Name |
|---|---|---|
| 367 | 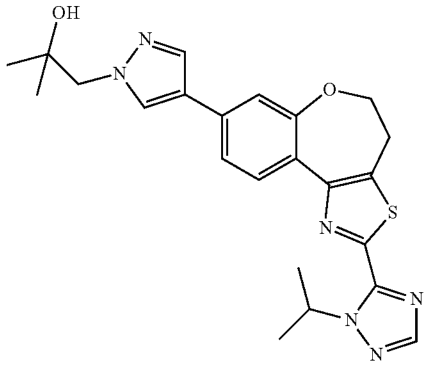 [SMILES: CC(C)n1ncnc1-c1nc2c(s1)CCOc1cc(-c3cnn(CC(C)(C)O)c3)ccc1-2] | 1-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-2-methyl-propan-2-ol |
| 368 | 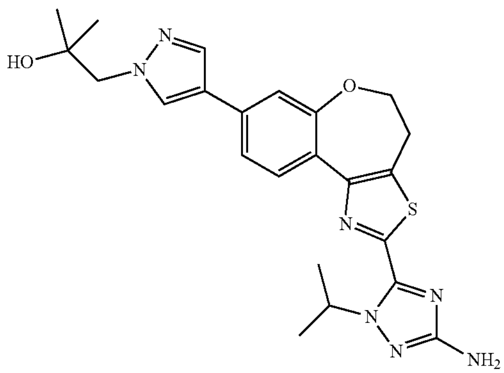 [SMILES: CC(C)n1nc(N)nc1-c1nc2c(s1)CCOc1cc(-c3cnn(CC(C)(C)O)c3)ccc1-2] | 1-{4-[2-(5-Amino-2-isopropyl-2H-[1,2,4]triazol-3-yl)-4,5-dihydro-6-oxa-3-thia-1-aza-benzo[e]azulen-8-yl]-pyrazol-1-yl}-2-methyl-propan-2-ol |
| 369 | 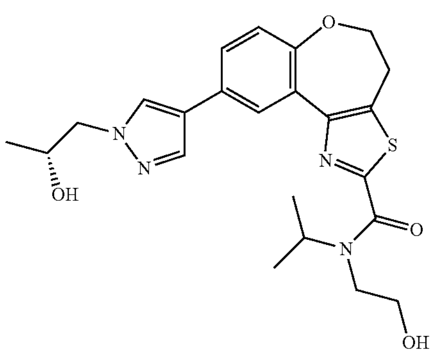 [SMILES: CC(C)N(CCO)C(=O)c1nc2c(s1)CCOc1ccc(-c3cnn(C[C@@H](C)O)c3)cc1-2] | 9-[1-((R)-2-Hydroxy-propyl)-1H-pyrazol-4-yl]-4,5-dihydro-6-oxa-3-thia-1-aza-benzo[e]azulene-2-carboxylic acid (2-hydroxy-ethyl)-isopropyl-amide |
| 370 | 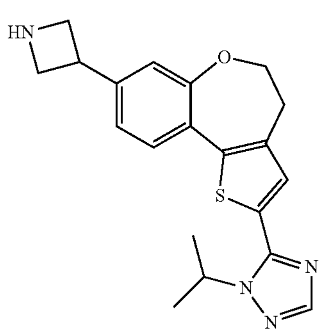 [SMILES: CC(C)n1ncnc1-c1cc2c(s1)-c1ccc(C3CNC3)cc1OCC2] | 5-(8-Azetidin-3-yl-4,5-dihydro-6-oxa-1-thia-benzo[e]azulen-2-yl)-1-isopropyl-1H-[1,2,4]triazole |

TABLE 1-continued

| No. | Structure | Name |
|---|---|---|
| 371 | 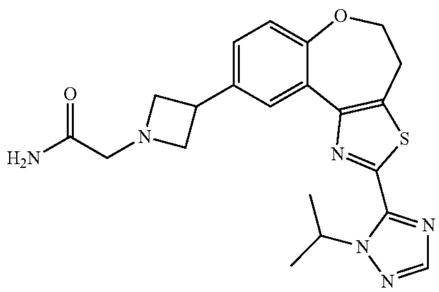 [SMILES: CC(C)n1ncnc1-c1nc2c(s1)CCOc1ccc(C3CN(CC(N)=O)C3)cc1-2] | 2-{3-[2-(2-Isopropyl-2H-[1,2,4]triazol-3-yl)-4,5-dihydro-6-oxa-3-thia-1-aza-benzo[e]azulen-9-yl]-azetidin-1-yl}-acetamide |
| 372 | 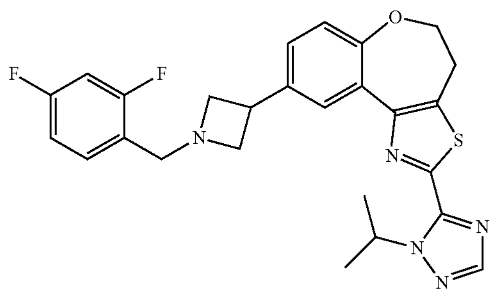 [SMILES: CC(C)n1ncnc1-c1nc2c(s1)CCOc1ccc(C3CN(Cc4ccc(F)cc4F)C3)cc1-2] | 9-[1-(2,4-Difluoro-benzyl)-azetidin-3-yl]-2-(2-isopropyl-2H-[1,2,4]triazol-3-yl)-4,5-dihydro-6-oxa-3-thia-1-aza-benzo[e]azulene |
| 373 | 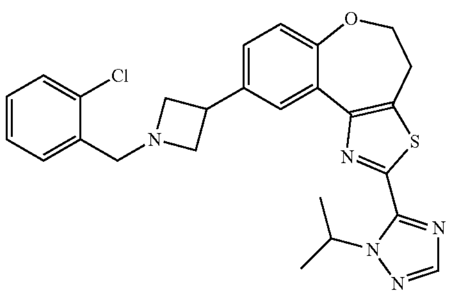 [SMILES: CC(C)n1ncnc1-c1nc2c(s1)CCOc1ccc(C3CN(Cc4ccccc4Cl)C3)cc1-2] | 9-[1-(2-Chloro-benzyl)-azetidin-3-yl]-2-(2-isopropyl-2H-[1,2,4]triazol-3-yl)-4,5-dihydro-6-oxa-3-thia-1-aza-benzo[e]azulene |
| 374 | 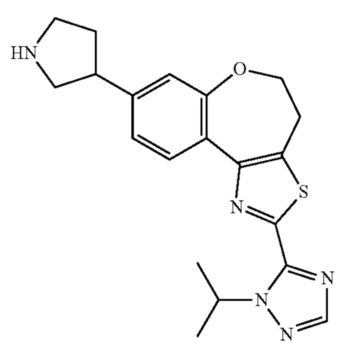 [SMILES: CC(C)n1ncnc1-c1nc2c(s1)CCOc1cc(C3CCNC3)ccc1-2] | 2-(2-Isopropyl-2H-[1,2,4]triazol-3-yl)-8-pyrrolidin-3-yl-4,5-dihydro-6-oxa-3-thia-1-aza-benzo[e]azulene |
| 375 | 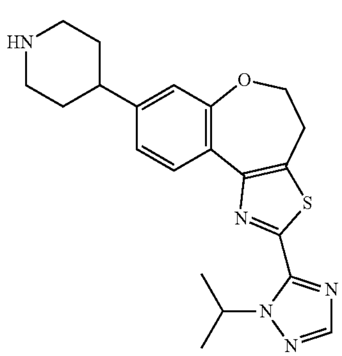 [SMILES: CC(C)n1ncnc1-c1nc2c(s1)CCOc1cc(C3CCNCC3)ccc1-2] | 2-(2-Isopropyl-2H-[1,2,4]triazol-3-yl)-8-piperidin-4-yl-4,5-dihydro-6-oxa-3-thia-1-aza-benzo[e]azulene |

TABLE 1-continued

| No. | Structure | Name |
|---|---|---|
| 376 | 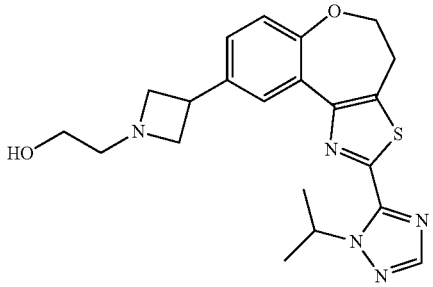 [SMILES: CC(C)n1ncnc1-c1nc2c(s1)CCOc1ccc(C3CN(CCO)C3)cc1-2] | 2-{3-[2-(2-Isopropyl-2H-[1,2,4]triazol-3-yl)-4,5-dihydro-6-oxa-3-thia-1-aza-benzo[e]azulen-9-yl]-azetidin-1-yl}-ethanol |
| 377 | 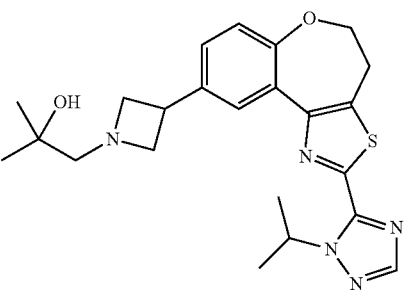 [SMILES: CC(C)n1ncnc1-c1nc2c(s1)CCOc1ccc(C3CN(CC(C)(C)O)C3)cc1-2] | 1-{3-[2-(2-Isopropyl-2H-[1,2,4]triazol-3-yl)-4,5-dihydro-6-oxa-3-thia-1-aza-benzo[e]azulen-9-yl]-azetidin-1-yl}-2-methyl-propan-2-ol |
| 378 | 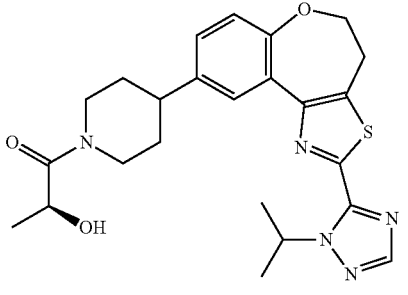 [SMILES: CC(C)n1ncnc1-c1nc2c(s1)CCOc1ccc(C3CCN(C(=O)[C@H](C)O)CC3)cc1-2] | (S)-2-Hydroxy-1-{4-[2-(2-isopropyl-2H-[1,2,4]triazol-3-yl)-4,5-dihydro-6-oxa-3-thia-1-aza-benzo[e]azulen-9-yl]-piperidin-1-yl}-propan-1-one |
| 379 | | |
| 380 | 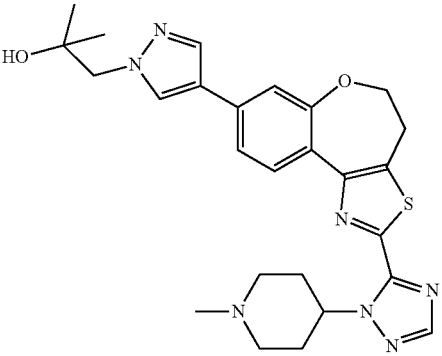 [SMILES: CN1CCC(n2ncnc2-c2nc3c(s2)CCOc2cc(-c4cnn(CC(C)(C)O)c4)ccc2-3)CC1] | 2-Methyl-1-(4-{2-[2-(1-methyl-piperidin-4-yl)-2H-[1,2,4]triazol-3-yl]-4,5-dihydro-6-oxa-3-thia-1-aza-benzo[e]azulen-8-yl}-pyrazol-1-yl)-propan-2-ol |

TABLE 1-continued

| No. | Structure | Name |
|---|---|---|
| 381 | 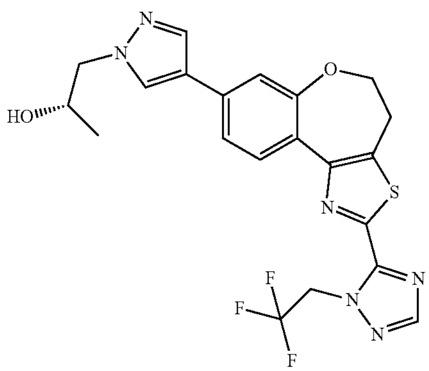 [SMILES: C[C@H](O)Cn1cc(-c2ccc3c(c2)OCCc2sc(-c4ncnn4CC(F)(F)F)nc2-3)cn1] | (S)-1-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-propan-2-ol |
| 382 | 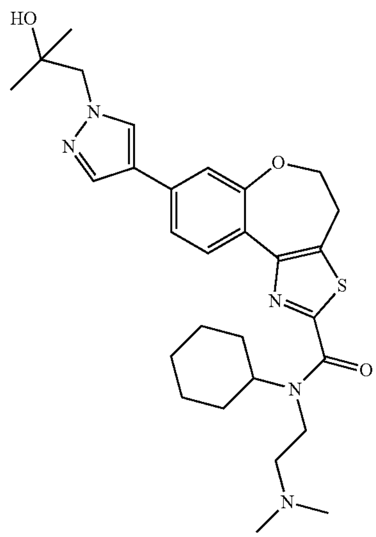 [SMILES: CN(C)CCN(C(=O)c1nc2c(s1)CCOc1cc(-c3cnn(CC(C)(C)O)c3)ccc1-2)C1CCCCC1] | 8-[1-(2-Hydroxy-2-methyl-propyl)-1H-pyrazol-4-yl]-4,5-dihydro-6-oxa-3-thia-1-aza-benzo[e]azulene-2-carboxylic acid cyclohexyl-(2-dimethylamino-ethyl)-amide |
| 383 | 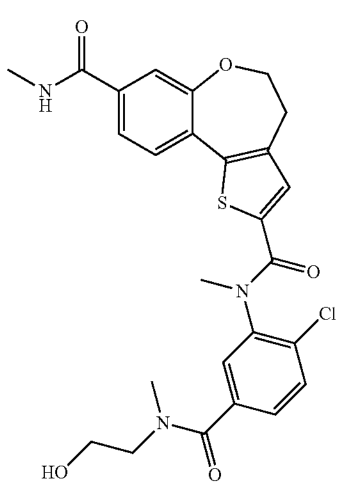 [SMILES: CNC(=O)c1ccc2c(c1)OCCc1cc(C(=O)N(C)c3cc(C(=O)N(C)CCO)ccc3Cl)sc1-2] | N2-(2-chloro-5-((2-hydroxyethyl)(methyl)carbamoyl)phenyl)-N2,N8-dimethyl-4,5-dihydrobenzo[b]thieno[2,3-d]oxepine-2,8-dicarboxamide |

TABLE 1-continued

| No. | Structure | Name |
|-----|-----------|------|
| 384 | 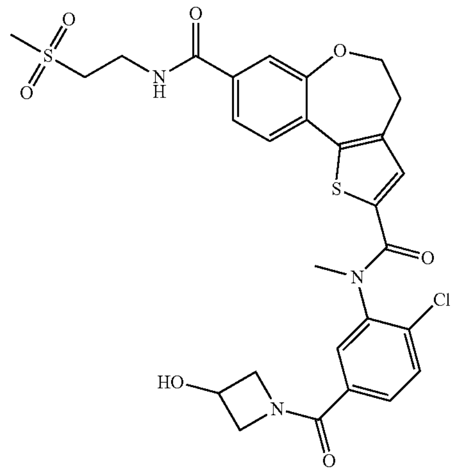 [SMILES: CN(C(=O)c1cc2c(s1)-c1ccc(C(=O)NCCS(C)(=O)=O)cc1OCC2)c1cc(C(=O)N2CC(O)C2)ccc1Cl] | N2-(2-chloro-5-(3-hydroxyazetidine-1-carbonyl)phenyl)-N2-methyl-N8-(2-(methylsulfonyl)ethyl)-4,5-dihydrobenzo[b]thieno[2,3-d]oxepine-2,8-dicarboxamide |
| 385 | 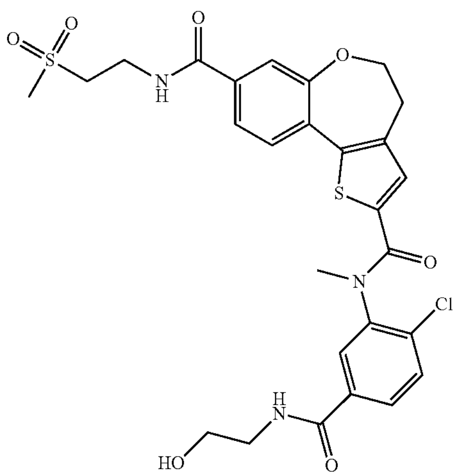 [SMILES: CN(C(=O)c1cc2c(s1)-c1ccc(C(=O)NCCS(C)(=O)=O)cc1OCC2)c1cc(C(=O)NCCO)ccc1Cl] | N2-(2-chloro-5-(2-hydroxyethylcarbamoyl)phenyl)-N2-methyl-N8-(2-(methylsulfonyl)ethyl)-4,5-dihydrobenzo[b]thieno[2,3-d]oxepine-2,8-dicarboxamide |
| 386 | 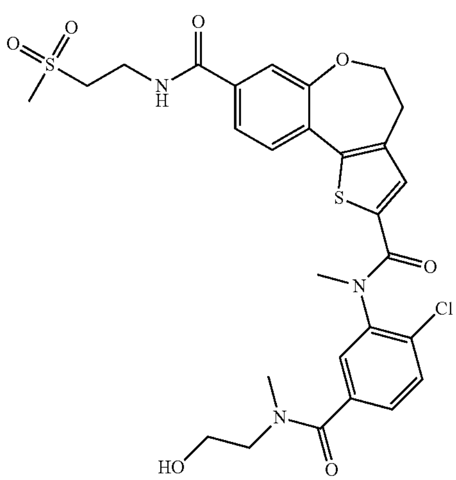 [SMILES: CN(CCO)C(=O)c1ccc(Cl)c(N(C)C(=O)c2cc3c(s2)-c2ccc(C(=O)NCCS(C)(=O)=O)cc2OCC3)c1] | N2-(2-chloro-5-((2-hydroxyethyl)(methyl)carbamoyl)phenyl)-N2-methyl-N8-(2-(methylsulfonyl)ethyl)-4,5-dihydrobenzo[b]thieno[2,3-d]oxepine-2,8-dicarboxamide |

TABLE 1-continued

| No. | Structure | Name |
|---|---|---|
| 387 | 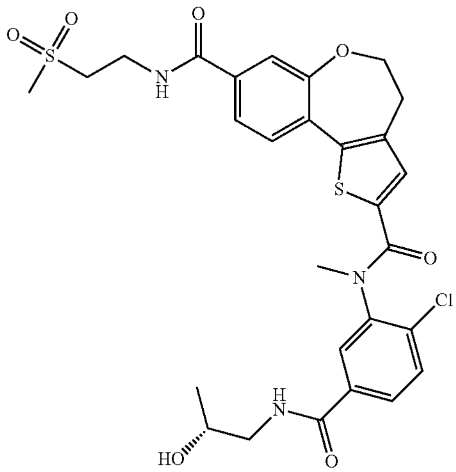 [SMILES: C[C@@H](O)CNC(=O)c1ccc(Cl)c(N(C)C(=O)c2cc3c(s2)-c2ccc(C(=O)NCCS(C)(=O)=O)cc2OCC3)c1] | N2-(2-chloro-5-((R)-2-hydroxypropylcarbamoyl)phenyl)-N2-methyl-N8-(2-(methylsulfonyl)ethyl)-4,5-dihydrobenzo[b]thieno[2,3-d]oxepine-2,8-dicarboxamide |
| 388 | 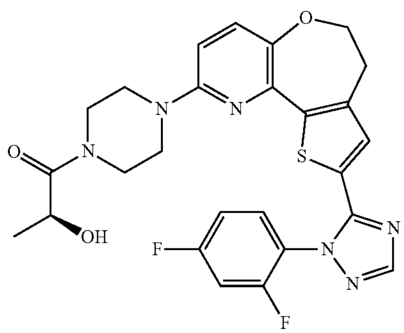 [SMILES: C[C@H](O)C(=O)N1CCN(c2ccc3c(n2)-c2sc(-c4ncnn4-c4ccc(F)cc4F)cc2CCO3)CC1] | (S)-1-(4-{2-[2-(2,4-Difluoro-phenyl)-2H-[1,2,4]triazol-3-yl]-4,5-dihydro-6-oxa-1-thia-10-aza-benzo[e]azulen-9-yl}-piperazin-1-yl)-2-hydroxy-propan-1-one |
| 389 | 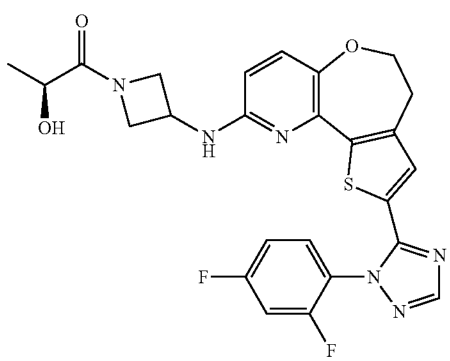 [SMILES: C[C@H](O)C(=O)N1CC(Nc2ccc3c(n2)-c2sc(-c4ncnn4-c4ccc(F)cc4F)cc2CCO3)C1] | (S)-1-(3-(2-[2-(2,4-Difluoro-phenyl)-2H-[1,2,4]triazol-3-yl]-4,5-dihydro-6-oxa-1-thia-10-aza-benzo[e]azulen-9-ylamino}-azetidin-1-yl)-2-hydroxy-propan-1-one |
| 390 | 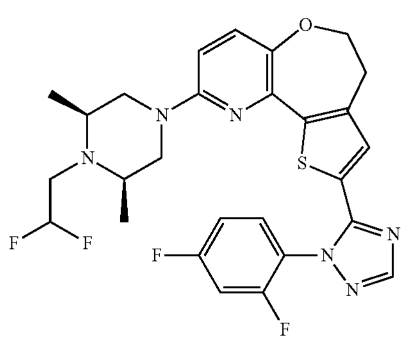 [SMILES: C[C@@H]1CN(c2ccc3c(n2)-c2sc(-c4ncnn4-c4ccc(F)cc4F)cc2CCO3)C[C@H](C)N1CC(F)F] | 9-[(3R,5S)-4-(2,2-Difluoro-ethyl)-3,5-dimethyl-piperazin-1-yl]-2-[2-(2,4-difluoro-phenyl)-2H-[1,2,4]triazol-3-yl]-4,5-dihydro-6-oxa-1-thia-10-aza-benzo[e]azulene |

TABLE 1-continued

| No. | Structure | Name |
|---|---|---|
| 391 | 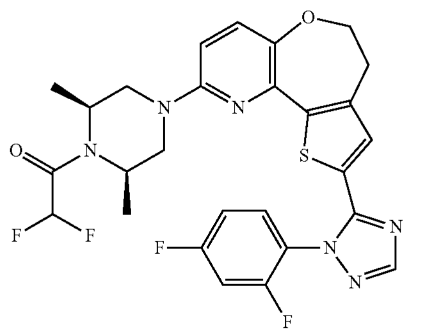 [SMILES: C[C@@H]1CN(c2ccc3c(n2)-c2sc(-c4ncnn4-c4ccc(F)cc4F)cc2CCO3)C[C@H](C)N1C(=O)C(F)F] | 1-((2R,6S)-4-{2-[2-(2,4-Difluoro-phenyl)-2H-[1,2,4]triazol-3-yl]-4,5-dihydro-6-oxa-1-thia-10-aza-benzo[e]azulen-9-yl}-2,6-dimethyl-piperazin-1-yl)-2,2-difluoro-ethanone |
| 392 | 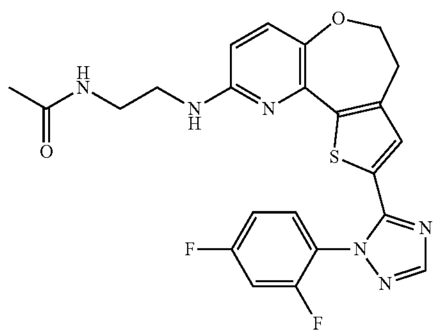 [SMILES: CC(=O)NCCNc1ccc2c(n1)-c1sc(-c3ncnn3-c3ccc(F)cc3F)cc1CCO2] | N-(2-{2-[2-(2,4-Difluoro-phenyl)-2H-[1,2,4]triazol-3-yl]-4,5-dihydro-6-oxa-1-thia-10-aza-benzo[e]azulen-9-ylamino}-ethyl)-acetamide |
| 393 | 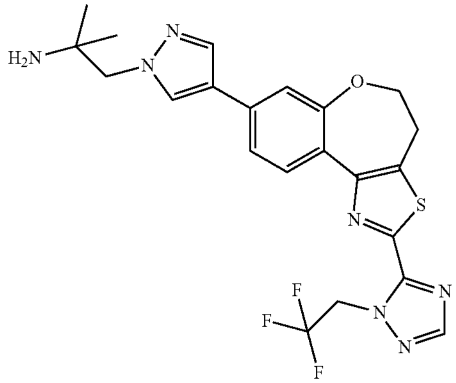 [SMILES: CC(C)(N)Cn1cc(-c2ccc3c(c2)OCCc2sc(-c4ncnn4CC(F)(F)F)nc2-3)cn1] | 1,1-Dimethyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-ethylamine |
| 394 | 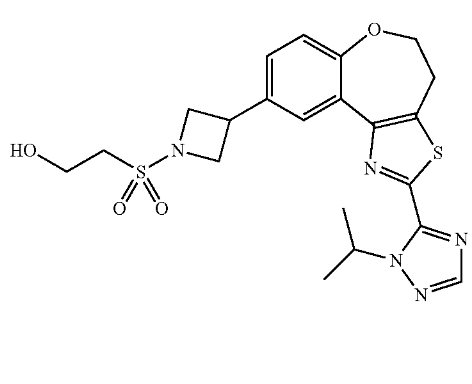 [SMILES: CC(C)n1ncnc1-c1nc2c(s1)CCOc1ccc(C3CN(S(=O)(=O)CCO)C3)cc1-2] | 2-{3-[2-(2-Isopropyl-2H-[1,2,4]triazol-3-yl)-4,5-dihydro-6-oxa-3-thia-1-aza-benzo[e]azulen-9-yl]-azetidine-1-sulfonyl}-ethanol |

TABLE 1-continued

| No. | Structure | Name |
|---|---|---|
| 395 | 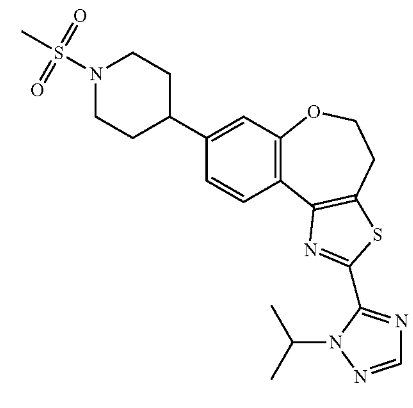 [SMILES: CC(C)n1ncnc1-c1nc2c(s1)CCOc1cc(C3CCN(S(C)(=O)=O)CC3)ccc1-2] | 2-(2-Isopropyl-2H-[1,2,4]triazol-3-yl)-8-(1-methanesulfonyl-piperidin-4-yl)-4,5-dihydro-6-oxa-3-thia-1-aza-benzo[e]azulene |
| 396 | 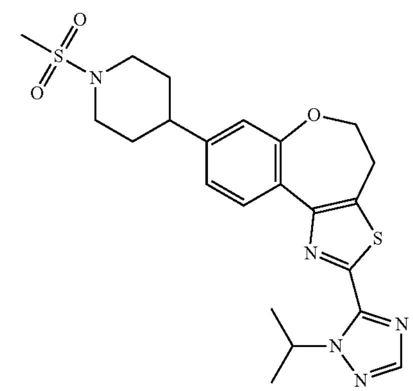 [SMILES: CC(C)n1ncnc1-c1nc2c(s1)CCOc1cc(C3CCN(S(C)(=O)=O)CC3)ccc1-2] | 2-(2-Isopropyl-2H-[1,2,4]triazol-3-yl)-8-(1-methanesulfonyl-pyrrolidin-3-yl)-4,5-dihydro-6-oxa-3-thia-1-aza-benzo[e]azulene |
| 397 | 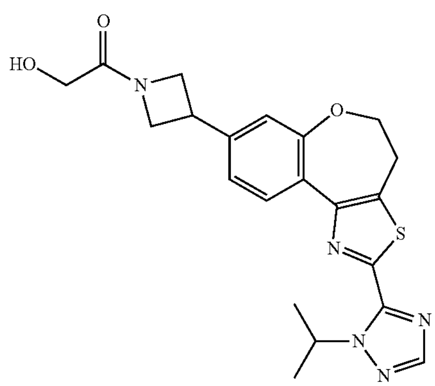 [SMILES: CC(C)n1ncnc1-c1nc2c(s1)CCOc1cc(C3CN(C(=O)CO)C3)ccc1-2] | 2-Hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-ethanone |
| 398 | 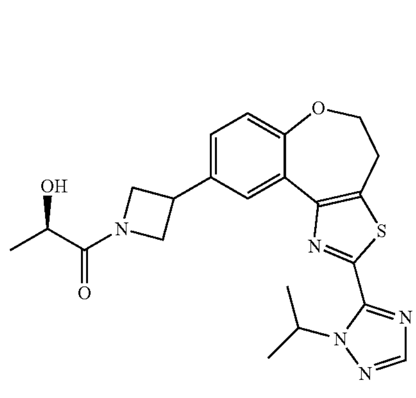 [SMILES: CC(C)n1ncnc1-c1nc2c(s1)CCOc1ccc(C3CN(C(=O)[C@@H](C)O)C3)cc1-2] | (R)-2-Hydroxy-1-{3-[2-(2-isopropyl-2H-[1,2,4]triazol-3-yl)-4,5-dihydro-6-oxa-3-thia-1-aza-benzo[e]azulen-9-yl]-azetidin-1-yl}-propan-1-one |

TABLE 1-continued

| No. | Structure | Name |
|---|---|---|
| 399 | 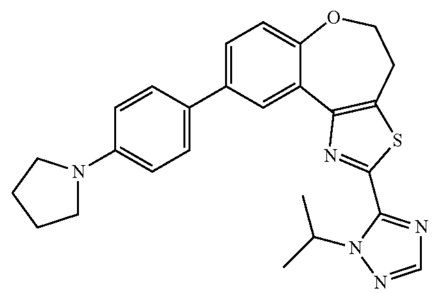 [SMILES: CC(C)n1ncnc1-c1nc2c(s1)CCOc1ccc(-c3ccc(N4CCCC4)cc3)cc1-2] | 2-(2-Isopropyl-2H-[1,2,4]triazol-3-yl)-9-(6-pyrrolidin-1-yl-pyridin-3-yl)-4,5-dihydro-6-oxa-3-thia-1-aza-benzo[e]azulene |
| 400 | 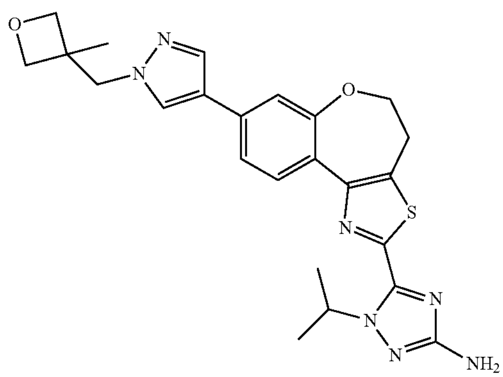 [SMILES: CC(C)n1nc(N)nc1-c1nc2c(s1)CCOc1cc(-c3cnn(CC4(C)COC4)c3)ccc1-2] | 1-Isopropyl-5-(8-[1-(3-methyl-oxetan-3-ylmethyl)-1H-pyrazol-4-yl]-4,5-dihydro-6-oxa-3-thia-1-aza-benzo[e]azulen-2-yl}-1H-[1,2,4]triazol-3-ylamine |
| 401 | 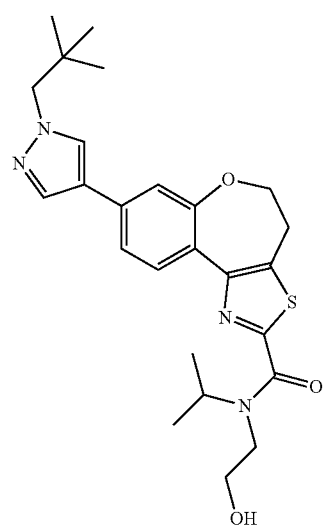 [SMILES: CC(C)N(CCO)C(=O)c1nc2c(s1)CCOc1cc(-c3cnn(CC(C)(C)C)c3)ccc1-2] | 8-[1-(2-Hydroxy-2-methyl-propyl)-1H-pyrazol-4-yl]-4,5-dihydro-6-oxa-3-thia-1-aza-benzo[e]azulene-2-carboxylic acid (2-hydroxy-ethyl)-isopropyl-amide |
| 402 | 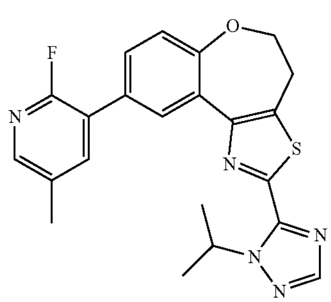 [SMILES: Cc1cnc(F)c(-c2ccc3c(c2)-c2nc(-c4ncnn4C(C)C)sc2CCO3)c1] | 9-(2-Fluoro-5-methyl-pyridin-3-yl)-2-(2 isopropyl-2H-[1,2,4]triazol-3-yl)-4,5-dihydro-6-oxa-3-thia-1-aza-benzo[e]azulene |

TABLE 1-continued

| No. | Structure | Name |
|---|---|---|
| 403 | 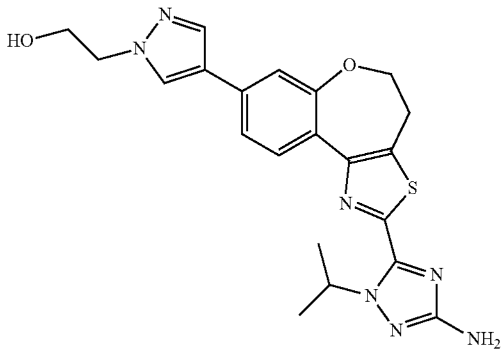 [SMILES: CC(C)n1nc(N)nc1-c1nc2c(s1)CCOc1cc(-c3cnn(CCO)c3)ccc1-2] | 2-{4-[2-(5-Amino-2-isopropyl-2H-[1,2,4]triazol-3-yl)-4,5-dihydro-6-oxa-3-thia-1-aza-benzo[e]azulen-8-yl]-pyrazol-1-yl}-ethanol |
| 404 | 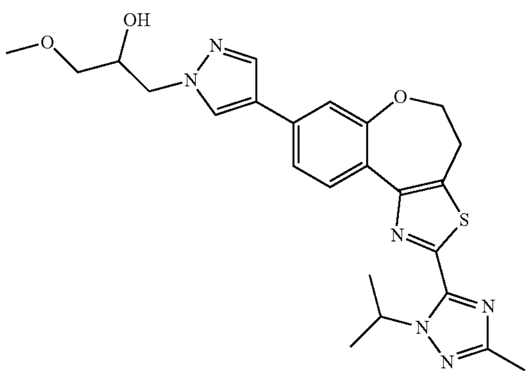 | 1-(4-[2-(2-Isopropyl-5-methyl-2H-[1,2,4]triazol-3-yl)-4,5-dihydro-6-oxa-3-thia-1-aza-benzo[e]azulen-8-yl]-pyrazol-1-yl}-3-methoxy-propan-2-ol |
| 405 | 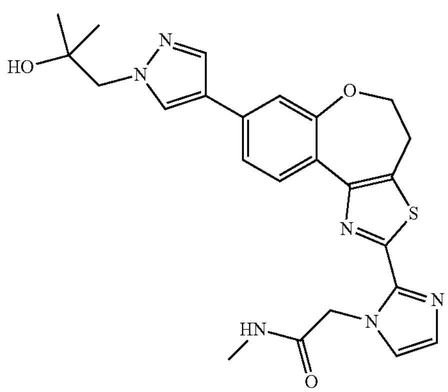 [SMILES: CNC(=O)Cn1ccnc1-c1nc2c(s1)CCOc1cc(-c3cnn(CC(C)(C)O)c3)ccc1-2] | 2-(2-{8-[1-(2-Hydroxy-2-methyl-propyl)-1H-pyrazol-4-yl]-4,5-dihydro-6-oxa-3-thia-1-aza-benzo[e]azulen-2-yl}-imidazol-1-yl)-N-methyl-acetamide |
| 406 | 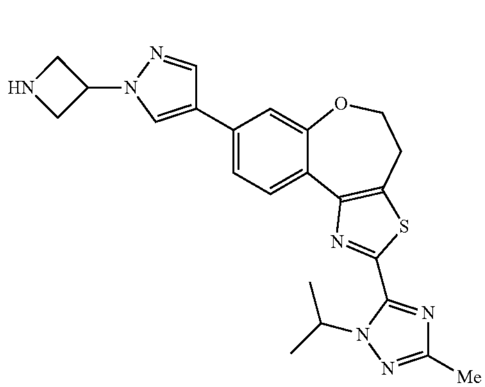 [SMILES: Cc1nc(-c2nc3c(s2)CCOc2cc(-c4cnn(C5CNC5)c4)ccc2-3)n(C(C)C)n1] | 8-(1-Azetidin-3-yl-1H-pyrazol-4-yl)-2-(2-isopropyl-5-methyl-2H-[1,2,4]triazol-3-yl)-4,5-dihydro-6-oxa-3-thia-1-aza-benzo[e]azulene |

TABLE 1-continued

| No. | Structure | Name |
|---|---|---|
| 407 | 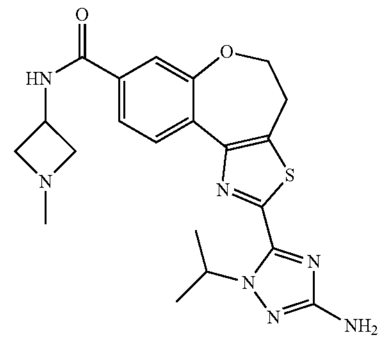 [SMILES: CC(C)n1nc(N)nc1-c1nc2c(s1)CCOc1cc(C(=O)NC3CN(C)C3)ccc1-2] | 2-(5-Amino-2-isopropyl-2H-[1,2,4]triazol-3-yl)-4,5-dihydro-6-oxa-3-thia-1-aza-benzo[e]azulene-8-carboxylic acid (1-methyl-azetidin-3-yl)-amide |
| 408 | 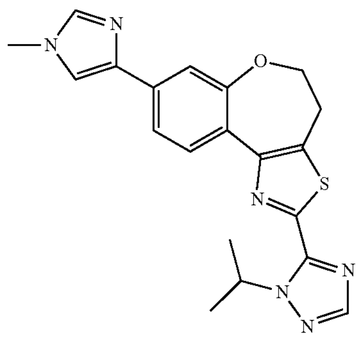 [SMILES: CC(C)n1ncnc1-c1nc2c(s1)CCOc1cc(-c3cn(C)cn3)ccc1-2] | 2-(2-Isopropyl-2H-[1,2,4]triazol-3-yl)-8-(1-methyl-1H-imidazol-4-yl)-4,5-dihydro-6-oxa-3-thia-1-aza-benzo[e]azulene |
| 409 | 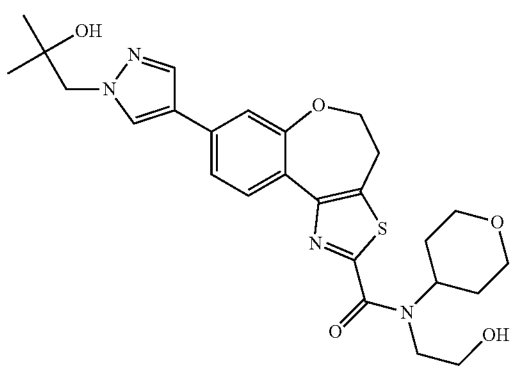 [SMILES: CC(C)(O)Cn1cc(-c2ccc3c(c2)OCCc2sc(C(=O)N(CCO)C4CCOCC4)nc2-3)cn1] | 8-[1-(2-Hydroxy-2-methyl-propyl)-1H-pyrazol-4-yl]-4,5-dihydro-6-oxa-3-thia-1-aza-benzo[e]azulene-2-carboxylic acid (2-hydroxy-ethyl)-(tetrahydro-pyran-4-yl)-amide |
| 410 | 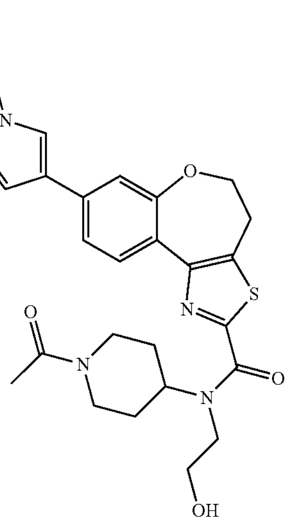 | 8-[1-(2-Hydroxy-2-methyl-propyl)-1H-pyrazol-4-yl]-4,5-dihydro-6-oxa-3-thia-1-aza-benzo[e]azulene-2-carboxylic acid (1-acetyl-piperidin-4-yl)-(2-hydroxy-ethyl)-amide |

TABLE 1-continued

| No. | Structure | Name |
|---|---|---|
| 411 | 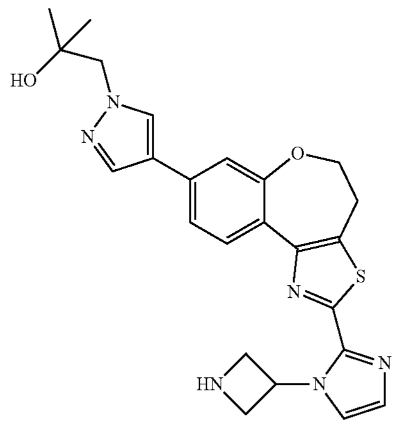 [SMILES: CC(C)(O)Cn1cc(-c2ccc3c(c2)OCCc2sc(-c4nccn4C4CNC4)nc2-3)cn1] | 1-(4-[2-(1-azetidin-3-yl-1H-imidazol-2-yl)-4,5-dihydro-6-oxa-3-thia-1-aza-benzo[e]azulen-8-yl]-pyrazol-1-yl}-2-methyl-propan-2-ol |
| 412 | 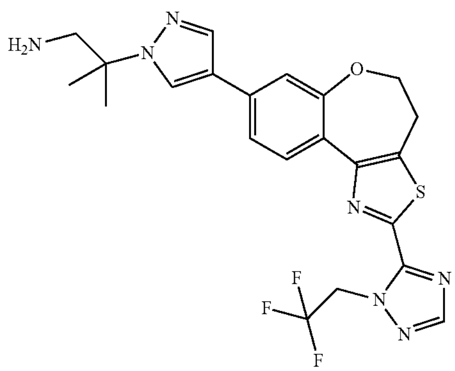 [SMILES: CC(C)(CN)n1cc(-c2ccc3c(c2)OCCc2sc(-c4ncnn4CC(F)(F)F)nc2-3)cn1] | 2-methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propylamine |
| 413 | 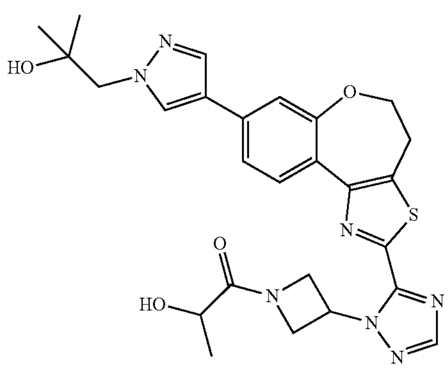 [SMILES: CC(O)C(=O)N1CC(n2ncnc2-c2nc3c(s2)CCOc2cc(-c4cnn(CC(C)(C)O)c4)ccc2-3)C1] | 2-hydroxy-1-[3-(2-{8-[1-(2-hydroxy-2-methyl-propyl)-1H-pyrazol-4-yl]-4,5-dihydro-6-oxa-3-thia-1-aza-benzo[e]azulen-2-yl}-imidazol-1-yl)-azetidin-1-yl]-propan-1-one |
| 414 | 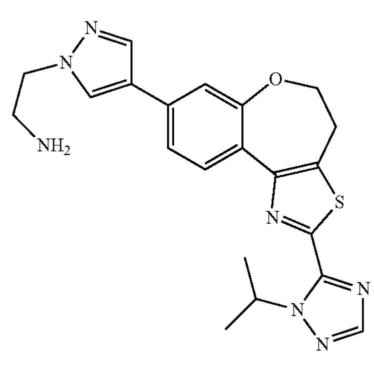 [SMILES: CC(C)n1ncnc1-c1nc2c(s1)CCOc1cc(-c3cnn(CCN)c3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-ethylamine |

TABLE 1-continued

| No. | Structure | Name |
| --- | --- | --- |
| 415 | 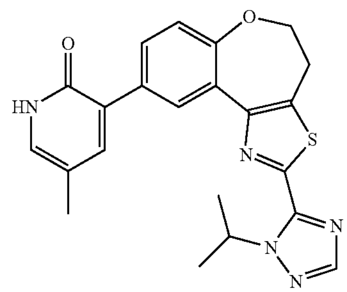 [SMILES: Cc1c[nH]c(=O)c(-c2ccc3c(c2)-c2nc(-c4ncnn4C(C)C)sc2CCO3)c1] | 3-[2-(2-Isopropyl-2H-[1,2,4]triazol-3-yl)-4,5-dihydro-6-oxa-3-thia-1-aza-benzo[e]azulen-9-yl]-5-methyl-1H-pyridin-2-one |
| 416 | 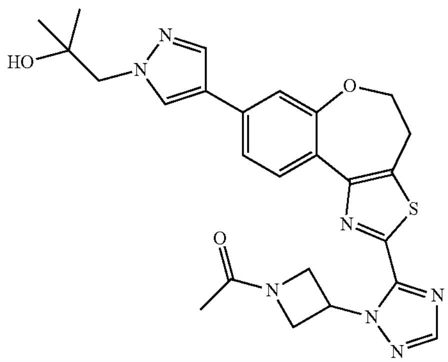 [SMILES: CC(=O)N1CC(n2ncnc2-c2nc3c(s2)CCOc2cc(-c4cnn(CC(C)(C)O)c4)ccc2-3)C1] | 1-[3-(2-{8-[1-(2-Hydroxy-2-methyl-propyl)-1H-pyrazol-4-yl]-4,5-dihydro-6-oxa-3-thia-1-aza-benzo[e]azulen-2-yl}-imidazol-1-yl)-azetidin-1-yl]-ethanone |
| 417 | 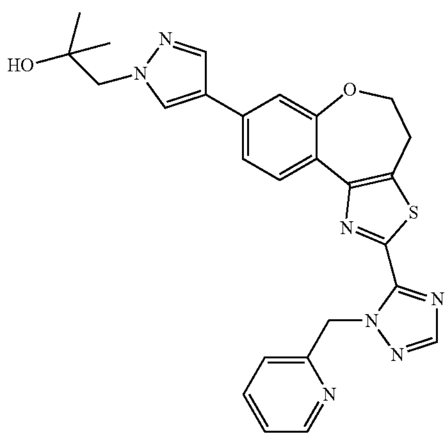 [SMILES: CC(C)(O)Cn1cc(-c2ccc3c(c2)OCCc2sc(-c4ncnn4Cc4ccccn4)nc2-3)cn1] | 2-Methyl-1-{4-[2-(2-pyridin-2-ylmethyl-2H-[1,2,4]triazol-3-yl)-4,5-dihydro-6-oxa-3-thia-1-aza-benzo[e]azulen-8-yl]-pyrazol-1-yl}-propan-2-ol |
| 418 | 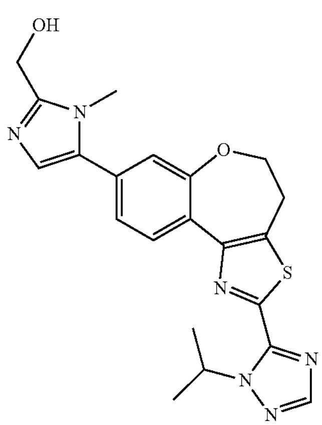 [SMILES: CC(C)n1ncnc1-c1nc2c(s1)CCOc1cc(-c3cnc(CO)n3C)ccc1-2] | {5-[2-(2-Isopropyl-2H-[1,2,4]triazol-yl)-4,5-dihydro-6-oxa-3-thia-1-aza-benzo[e]azulen-8-yl]-1-methyl-1H-imidazol-2-yl}-methanol |

TABLE 1-continued

| No. | Structure | Name |
|---|---|---|
| 419 | 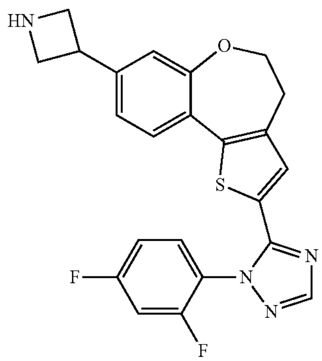 [SMILES: Fc1ccc(-n2ncnc2-c2cc3c(s2)-c2ccc(C4CNC4)cc2OCC3)c(F)c1] | 5-(8-azetidin-3-yl-4,5-dihydro-6-oxa-1-thia-benzo[e]azulen-2-yl)-1-(2,4-difluoro-phenyl)-1H-[1,2,4]triazole |
| 420 | 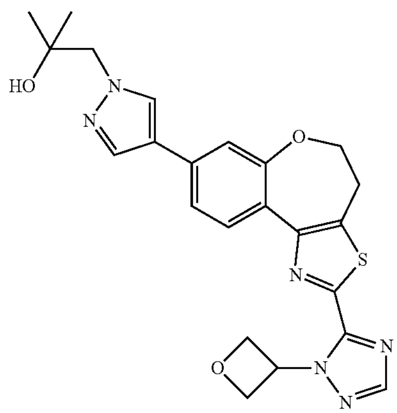 [SMILES: CC(C)(O)Cn1cc(-c2ccc3c(c2)OCCc2sc(-c4ncnn4C4COC4)nc2-3)cn1] | 2-Methyl-1-{4-[2-(1-oxetan-3-yl-1H-imidazol-2-yl)-4,5-dihydro-6-oxa-3-thia-1-aza-benzo[e]azulen-8-yl]-pyrazol-1-yl}-propan-2-ol |
| 421 | 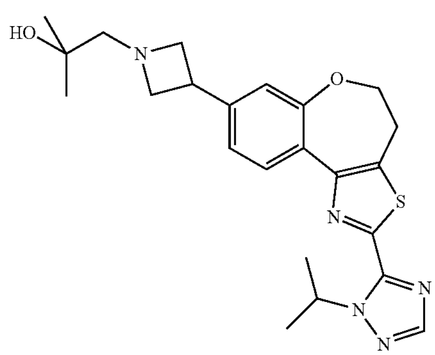 [SMILES: CC(C)n1ncnc1-c1nc2c(s1)CCOc1cc(C3CN(CC(C)(C)O)C3)ccc1-2] | 1-{3-[2-(2-Isopropyl-2H-[1,2,4]triazol-3-yl)-4,5-dihydro-6-oxa-3-thia-1-aza-benzo[e]azulen-8-yl]-azetidin-1-yl}-2-methyl-propan-2-ol |
| 422 | 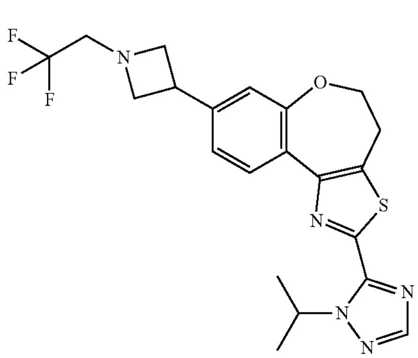 [SMILES: CC(C)n1ncnc1-c1nc2c(s1)CCOc1cc(C3CN(CC(F)(F)F)C3)ccc1-2] | 2-(2-Isopropyl-2H-[1,2,4]triazol-3-yl)-8-[1-(2,2,2-trifluoro-ethyl)-azetidin-3-yl]-4,5-dihydro-6-oxa-3-thia-1-aza-benzo[e]azulene |

TABLE 1-continued

| No. | Structure | Name |
|-----|-----------|------|
| 423 | 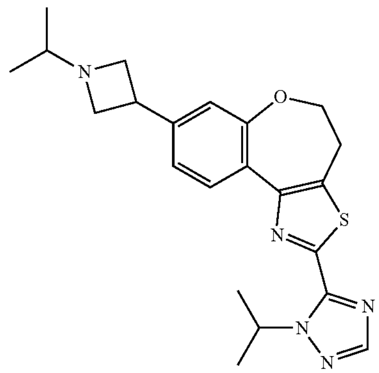 [SMILES: CC(C)N1CC(c2ccc3c(c2)OCCc2sc(-c4ncnn4C(C)C)nc2-3)C1] | 8-(1-Isopropyl-azetidin-3-yl)-2-(2-isopropyl-2H-[1,2,4]triazol-3-yl)-4,5-dihydro-6-oxa-3-thia-1-aza-benzo[e]azulene |
| 424 | 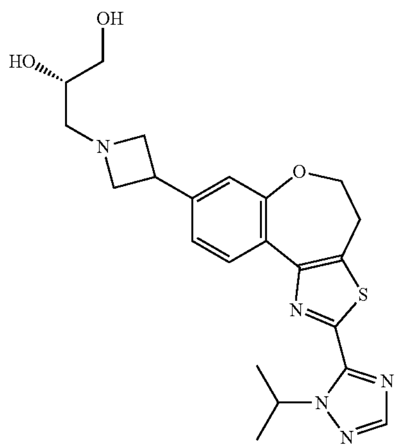 [SMILES: CC(C)n1ncnc1-c1nc2c(s1)CCOc1cc(C3CN(C[C@H](O)CO)C3)ccc1-2] | (S)-3-{3-[2-(2-Isopropyl-2H-[1,2,4]triazol-3-yl)-4,5-dihydro-6-oxa-3-thia-1-aza-benzo[e]azulen-8-yl]-azetidin-1-yl}-propane-1,2-diol |
| 425 | 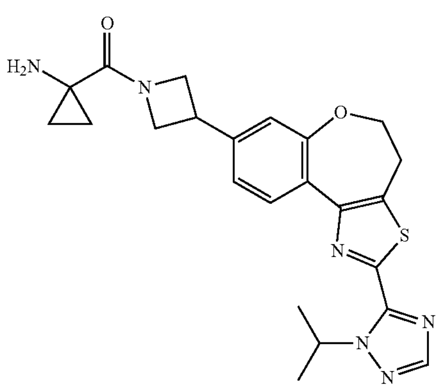 [SMILES: CC(C)n1ncnc1-c1nc2c(s1)CCOc1cc(C3CN(C(=O)C4(N)CC4)C3)ccc1-2] | (1-Amino-cyclopropyl)-{3-[2-(2-isopropyl-2H-[1,2,4]triazol-3-yl)-4,5-dihydro-6-oxa-3-thia-1-aza-benzo[e]azulen-8-yl]-azetidin-1-yl}-methanone |
| 426 | 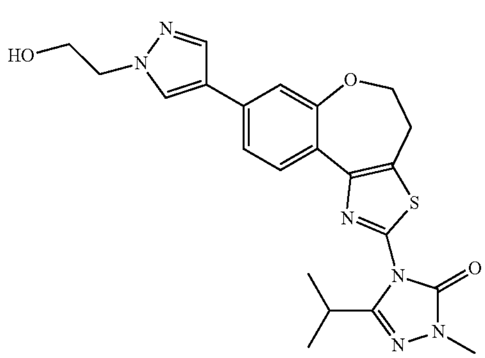 [SMILES: CC(C)c1nn(C)c(=O)n1-c1nc2c(s1)CCOc1cc(-c3cnn(CCO)c3)ccc1-2] | 4-(8-[1-(2-Hydroxy-ethyl)-1H-pyrazol-4-yl]-4,5-dihydro-6-oxa-3-thia-1-aza-benzo[e]azulen-2-yl}-5-isopropyl-2-methyl-2,4-dihydro-[1,2,4]triazol-3-one |

TABLE 1-continued

| No. | Structure | Name |
|---|---|---|
| 427 | 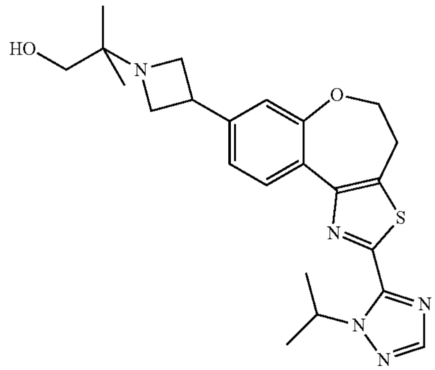 [SMILES: CC(C)n1ncnc1-c1nc2c(s1)CCOc1cc(C3CN(C(C)(C)CO)C3)ccc1-2] | 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-2-methyl-propan-1-ol |
| 428 | 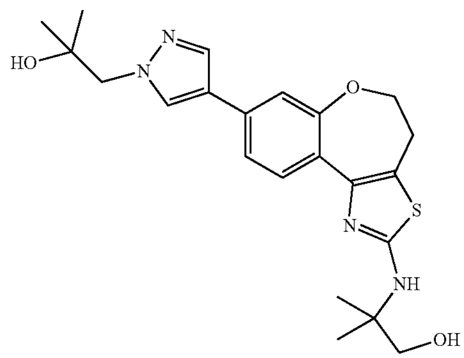 [SMILES: CC(C)(O)Cn1cc(-c2ccc3c(c2)OCCc2sc(NC(C)(C)CO)nc2-3)cn1] | 2-{8-[1-(2-Hydroxy-2-methyl-propyl)-1H-pyrazol-4-yl]-4,5-dihydro-6-oxa-3-thia-1-aza-benzo[e]azulen-2-ylamino}-2-methyl-propan-1-ol |
| 429 | 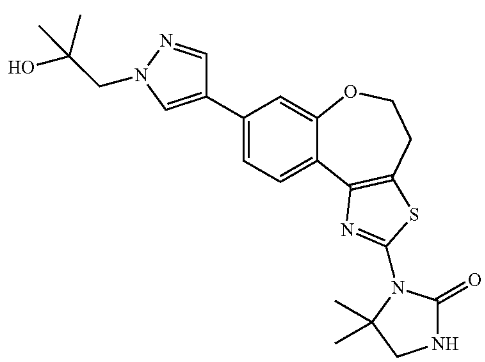 [SMILES: CC(C)(O)Cn1cc(-c2ccc3c(c2)OCCc2sc(N4C(=O)NCC4(C)C)nc2-3)cn1] | 1-{8-[1-(2-Hydroxy-2-methyl-propyl)-1H-pyrazol-4-yl]-4,5-dihydro-6-oxa-3-thia-1-aza-benzo[e]azulen-2-yl}-5,5-dimethyl-imidazolidin-2-one |
| 430 | 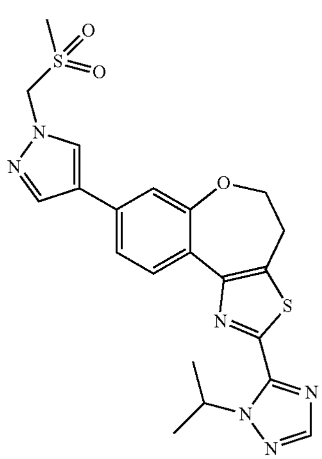 [SMILES: CC(C)n1ncnc1-c1nc2c(s1)CCOc1cc(-c3cnn(CS(C)(=O)=O)c3)ccc1-2] | 2-(2-Isopropyl-2H-[1,2,4]triazol-3-yl)-8-(1-methanesulfonylmethyl-1H-pyrazol-4-yl)-4,5-dihydro-6-oxa-3-thia-1-aza-benzo[e]azulene |

TABLE 1-continued

| No. | Structure | Name |
|-----|-----------|------|
| 431 | 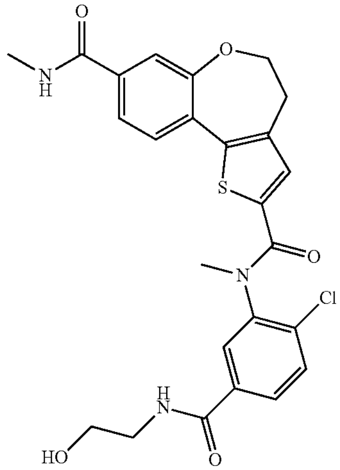 | N2-(2-chloro-5-(2-hydroxyethylcarbamoyl)phenyl)-N2,N8-dimethyl-4,5-dihydrobenzo[b]thieno[2,3-d]oxepine-2,8-dicarboxamide |
| 432 | 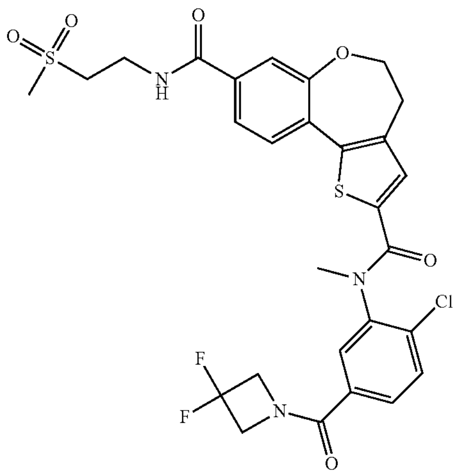 [SMILES: CN(C(=O)c1cc2c(s1)-c1ccc(C(=O)NCCS(C)(=O)=O)cc1OCC2)c1cc(C(=O)N2CC(F)(F)C2)ccc1Cl] | N2-(2-chloro-5-(3,3-difluoroazetidine-1-carbonyl)phenyl)-N2-methyl-N8-(2-(methylsulfonyl)ethyl)-4,5-dihydrobenzo[b]thieno[2,3-d]oxepine-2,8-dicarboxamide |
| 433 | 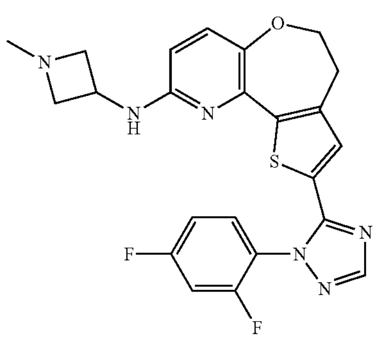 [SMILES: CN1CC(Nc2ccc3c(n2)-c2sc(-c4ncnn4-c4ccc(F)cc4F)cc2CCO3)C1] | {2-[2-(2,4-Difluoro-phenyl)-2H-[1,2,4]triazol-3-yl]-4,5-dihydro-6-oxa-thia-10-aza-benzo[e]azulen-9-yl}-(1-methyl-azetidin-3-yl)-amine |
| 434 | 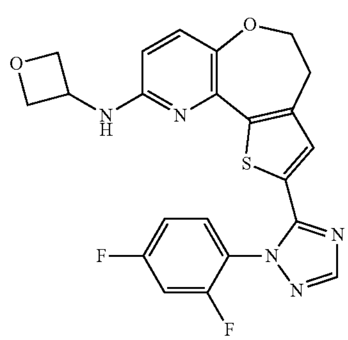 [SMILES: Fc1ccc(-n2ncnc2-c2cc3c(s2)-c2nc(NC4COC4)ccc2OCC3)c(F)c1] | {2-[2-(2,4-Difluoro-phenyl)-2H-[1,2,4]triazol-3-yl]-4,5-dihydro-6-oxa-1-thia-10-aza-benzo[e]azulen-9-yl}-oxetan-3-yl-amine |

TABLE 1-continued

| No. | Structure | Name |
|-----|-----------|------|
| 435 | 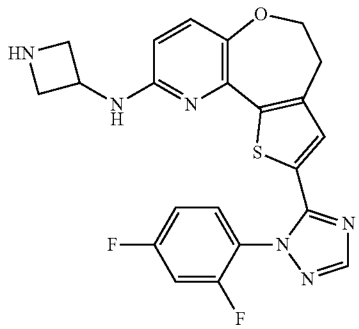 [SMILES: Fc1ccc(-n2ncnc2-c2cc3c(s2)-c2nc(NC4CNC4)ccc2OCC3)c(F)c1] | Azetidin-3-yl-{2-[2-(2,4-difluoro-phenyl)-2H-[1,2,4]triazol-3-yl]-4,5-dihydro-6-oxa-1-thia-10-aza-benzo[e]azulen-9-yl}-amine |
| 436 | 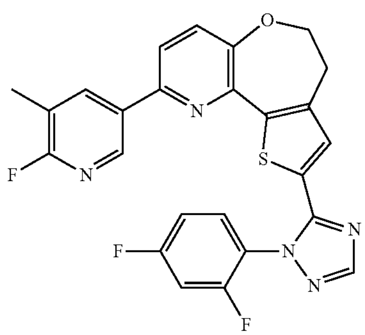 [SMILES: Cc1cc(-c2ccc3c(n2)-c2sc(-c4ncnn4-c4ccc(F)cc4F)cc2CCO3)cnc1F] | 2-[2-(2,4-Difluoro-phenyl)-2H-[1,2,4]triazol-3-yl]-9-(6-fluoro-5-methyl-pyridin-3-yl)-4,5-dihydro-6-oxa-1-thia-10-aza-benzo[e]azulene |
| 437 | 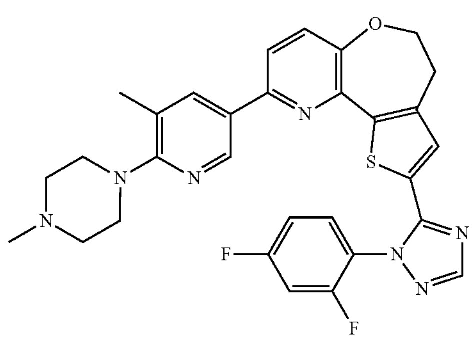 [SMILES: Cc1cc(-c2ccc3c(n2)-c2sc(-c4ncnn4-c4ccc(F)cc4F)cc2CCO3)cnc1N1CCN(C)CC1] | 2-[2-(2,4-Difluoro-phenyl)-2H-[1,2,4]triazol-3-yl]-9-[5-methyl-6-(4-methyl-piperazin-1-yl)-pyridin-3-yl]-4,5-dihydro-6-oxa-1-thia-10-aza-benzo[e]azulene |
| 438 | 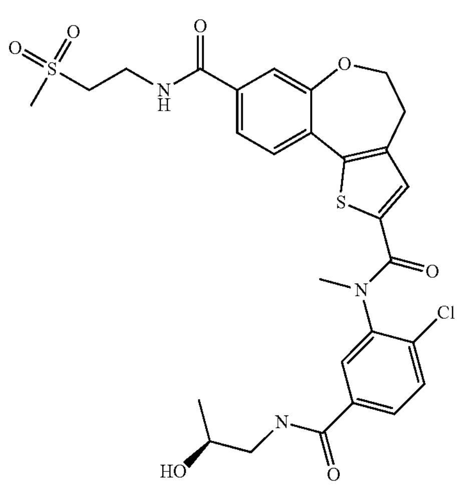 [SMILES: C[C@H](O)CNC(=O)c1ccc(Cl)c(N(C)C(=O)c2cc3c(s2)-c2ccc(C(=O)NCCS(C)(=O)=O)cc2OCC3)c1] | N2-(2-chloro-5-((S)-2-hydroxypropylcarbamoyl)phenyl)-N2-methyl-N8-(2-(methylsulfonyl)ethyl)-4,5-dihydrobenzo[b]thieno[2,3-d]oxepine-2,8-dicarboxamide |

TABLE 1-continued

| No. | Structure | Name |
|---|---|---|
| 439 | 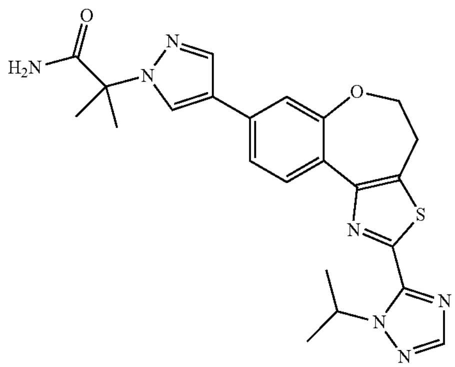 [SMILES: CC(C)n1ncnc1-c1nc2c(s1)CCOc1cc(-c3cnn(C(C)(C)C(N)=O)c3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-isobutyramide |
| 440 | 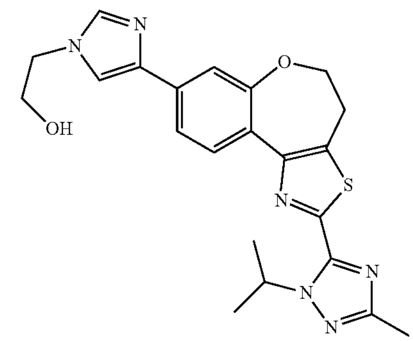 [SMILES: Cc1nc(-c2nc3c(s2)CCOc2cc(-c4cn(CCO)cn4)ccc2-3)n(C(C)C)n1] | 2-{4-[2-(2-Isopropyl-5-methyl-2H-[1,2,4]triazol-3-yl)-4,5-dihydro-6-oxa-3-thia-1-aza-benzo[e]azulen-8-yl]-imidazol-1-yl}-ethanol |
| 441 | 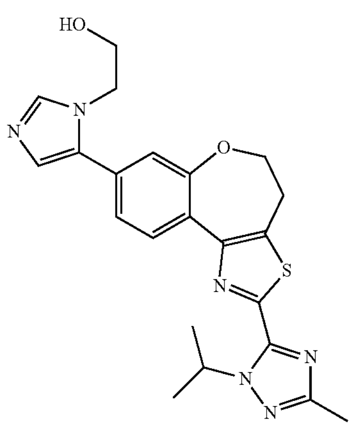 [SMILES: Cc1nc(-c2nc3c(s2)CCOc2cc(-c4cncn4CCO)ccc2-3)n(C(C)C)n1] | 2-{5-[2-(2-Isopropyl-5-methyl-2H-[1,2,4]triazol-3-yl)-4,5-dihydro-6-oxa-3-thia-1-aza-benzo[e]azulen-8-yl]-imidazol-1-yl}-ethanol |
| 442 | 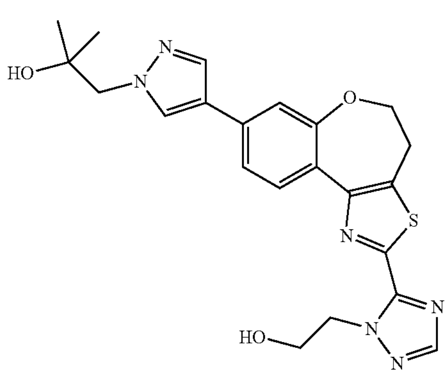 [SMILES: CC(C)(O)Cn1cc(-c2ccc3c(c2)OCCc2sc(-c4ncnn4CCO)nc2-3)cn1] | 1-(4-{2-[2-(2-Hydroxy-ethyl)-2H-[1,2,4]triazol-3-yl]-4,5-dihydro-6-oxa-3-thia-1-aza-benzo[e]azulen-8-yl}-pyrazol-1-yl)-2-methyl-propan-2-ol |

TABLE 1-continued

| No. | Structure | Name |
|---|---|---|
| 443 | 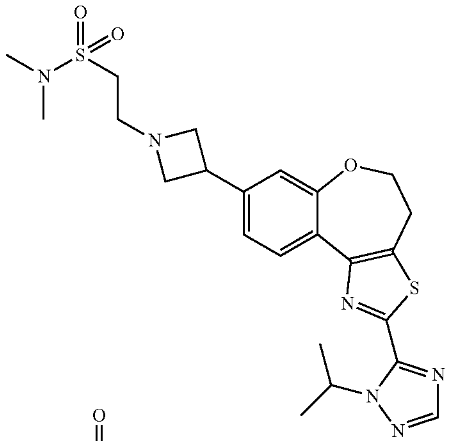 [SMILES: CC(C)n1ncnc1-c1nc2c(s1)CCOc1cc(C3CN(CCS(=O)(=O)N(C)C)C3)ccc1-2] | 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-ethanesulfonic acid dimethylamide |
| 444 | 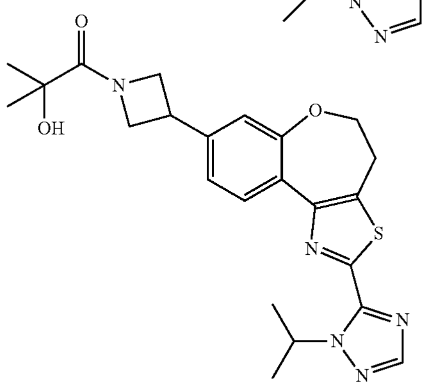 | 2-Hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-2-methyl-propan-1-one |
| 445 | 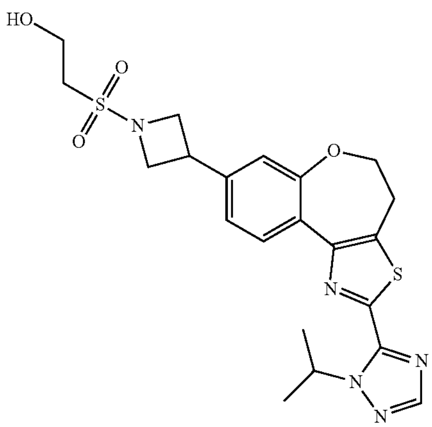 [SMILES: CC(C)n1ncnc1-c1nc2c(s1)CCOc1cc(C3CN(S(=O)(=O)CCO)C3)ccc1-2] | 2-{3-[2-(2-Isopropyl-2H-[1,2,4]triazol-3-yl)-4,5-dihydro-6-oxa-3-thia-1-aza-benzo[e]azulen-8-yl]-azetidine-1-sulfonyl}-ethanol |
| 446 | 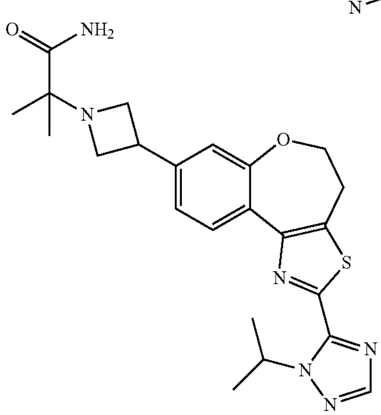 | 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-isobutyramide |

TABLE 1-continued

| No. | Structure | Name |
| --- | --- | --- |
| 447 | 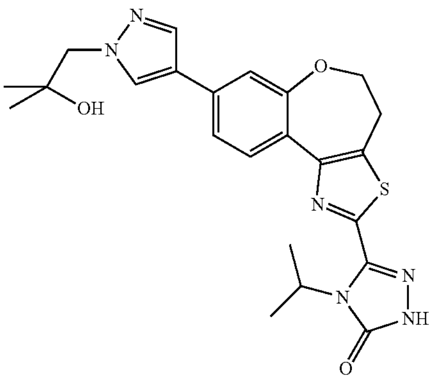 [SMILES: CC(C)n1c(-c2nc3c(s2)CCOc2cc(-c4cnn(CC(C)(C)O)c4)ccc2-3)n[nH]c1=O] | 5-{8-[1-(2-Hydroxy-2-methyl-propyl)-1H-pyrazol-4-yl]-4,5-dihydro-6-oxa-3-thia-1-aza-benzo[e]azulen-2-yl}-4-isopropyl-2,4-dihydro-[1,2,4]triazol-3-one |
| 448 | 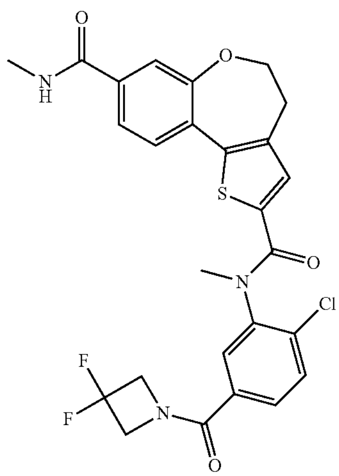 [SMILES: CNC(=O)c1ccc2c(c1)OCCc1cc(C(=O)N(C)c3cc(C(=O)N4CC(F)(F)C4)ccc3Cl)sc1-2] | N2-(2-chloro-5-(3,3-difluoroazetidine-1-carbonyl)phenyl)-N2,N8-dimethyl-4,5-dihydrobenzo[b]thieno[2,3-d]oxepine-2,8-dicarboxamide |
| 449 | 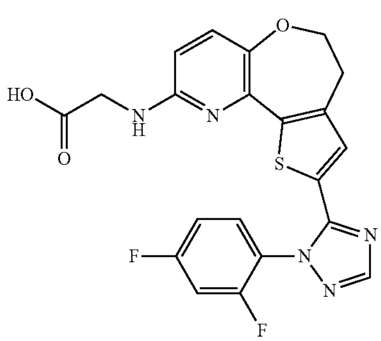 [SMILES: O=C(O)CNc1ccc2c(n1)-c1sc(-c3ncnn3-c3ccc(F)cc3F)cc1CCO2] | {2-[2-(2,4-Difluoro-phenyl)-2H-[1,2,4]triazol-3-yl]-4,5-dihydro-6-oxa-1-thia-10-aza-benzo[e]azulen-9-ylamino}-acetic acid |
| 450 | 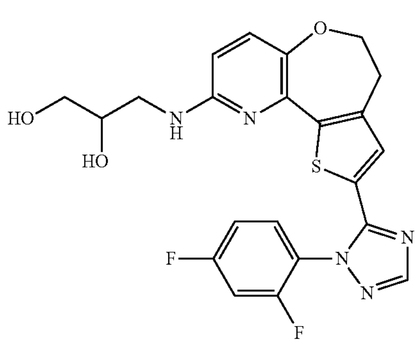 [SMILES: OCC(O)CNc1ccc2c(n1)-c1sc(-c3ncnn3-c3ccc(F)cc3F)cc1CCO2] | 3-{2-[2-(2,4-Difluoro-phenyl)-2H-[1,2,4]triazol-3-yl]-4,5-dihydro-6-oxa-1-thia-10-aza-benzo[e]azulen-9-ylamino}-propane-1,2-diol |

TABLE 1-continued

| No. | Structure | Name |
|---|---|---|
| 451 | 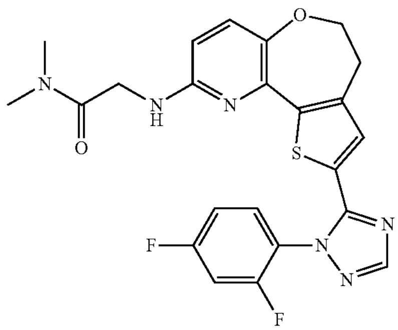 [SMILES: CN(C)C(=O)CNc1ccc2c(n1)-c1sc(-c3ncnn3-c3ccc(F)cc3F)cc1CCO2] | 2-{2-[2-(2,4-Difluoro-phenyl)-2H-[1,2,4]triazol-3-yl]-4,5-dihydro-6-oxa-1-thia-10-aza-benzo[e]azulen-9-ylamino}-N,N-dimethyl-acetamide |
| 452 | 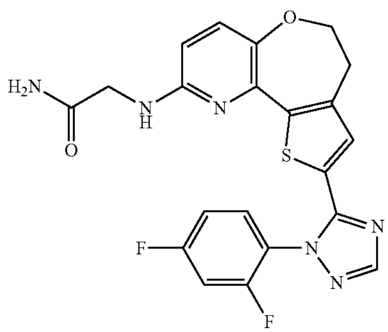 [SMILES: NC(=O)CNc1ccc2c(n1)-c1sc(-c3ncnn3-c3ccc(F)cc3F)cc1CCO2] | 2-{2-[2-(2,4-Difluoro-phenyl)-2H-[1,2,4]triazol-3-yl]-4,5-dihydro-6-oxa-1-thia-10-aza-benzo[e]azulen-9-ylamino}-acetamide |
| 453 | 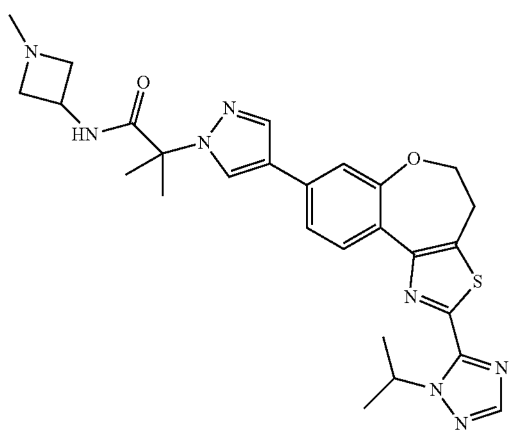 [SMILES: CC(C)n1ncnc1-c1nc2c(s1)CCOc1cc(-c3cnn(C(C)(C)C(=O)NC4CN(C)C4)c3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-N-(1-methyl-azetidin-3-yl)-isobutyramide |
| 454 | 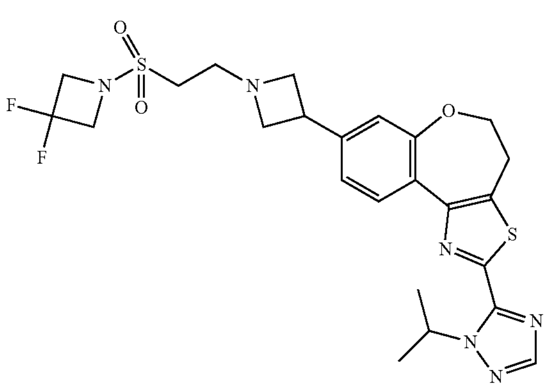 [SMILES: CC(C)n1ncnc1-c1nc2c(s1)CCOc1cc(C3CN(CCS(=O)(=O)N4CC(F)(F)C4)C3)ccc1-2] | 8-{1-[2-(3,3-Difluoro-azetidine-1-sulfonyl)-ethyl]-azetidin-3-yl}-2-(2-isopropyl-2H-[1,2,4]triazol-3-yl)-4,5-dihydro-6-oxa-3-thia-1-aza-benzo[e]azulene |

US 9,175,009 B2

TABLE 1-continued

| No. | Structure | Name |
|---|---|---|
| 455 | 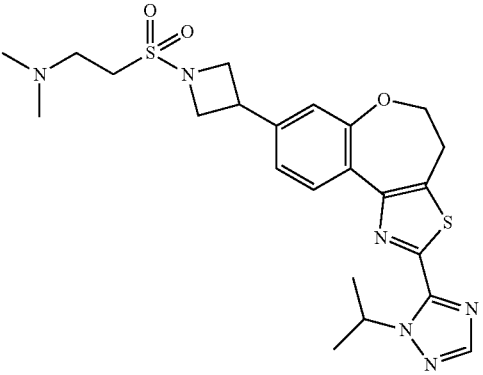 [SMILES: CC(C)n1ncnc1-c1nc2c(s1)CCOc1cc(C3CN(S(=O)(=O)CCN(C)C)C3)ccc1-2] | (2-{3-[2-(2-Isopropyl-2H-[1,2,4]triazol-3-yl)-4,5-dihydro-6-oxa-3-thia-1-aza-benzo[e]azulen-8-yl]-azetidine-1-sulfonyl}-ethyl)-dimethyl-amine |
| 456 | 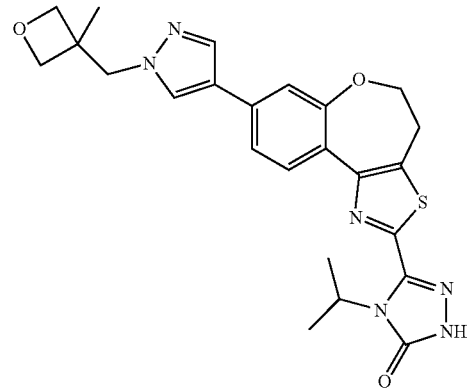 [SMILES: CC(C)n1c(-c2nc3c(s2)CCOc2cc(-c4cnn(CC5(C)COC5)c4)ccc2-3)n[nH]c1=O] | 4-Isopropyl-5-(8-[1-(3-methyl-oxetan-3-ylmethyl)-1H-pyrazol-4-yl]-4,5-dihydro-6-oxa-3-thia-1-aza-benzo[e]azulen-2-yl}-2,4-dihydro-[1,2,4]triazol-3-one |
| 457 | 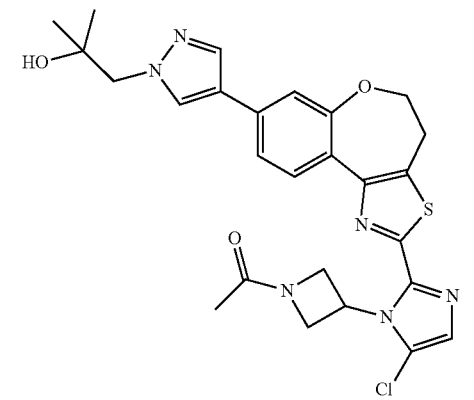 [SMILES: CC(=O)N1CC(n2c(Cl)cnc2-c2nc3c(s2)CCOc2cc(-c4cnn(CC(C)(C)O)c4)ccc2-3)C1] | 1-[3-(5-Chloro-2-{8-[1-(2-hydroxy-2-methyl-propyl)-1H-pyrazol-4-yl]-4,5-dihydro-6-oxa-3-thia-1-aza-benzo[e]azulen-2-yl}-imidazol-1-yl)-azetidin-1-yl]-ethanone |
| 458 | 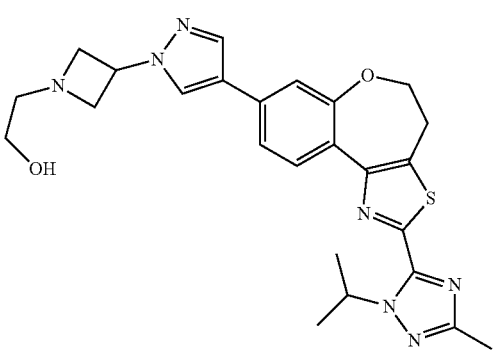 [SMILES: Cc1nc(-c2nc3c(s2)CCOc2cc(-c4cnn(C5CN(CCO)C5)c4)ccc2-3)n(C(C)C)n1] | 2-(3-{4-[2-(2-Isopropyl-5-methyl-2H-[1,2,4]triazol-3-yl)-4,5-dihydro-6-oxa-3-thia-1-aza-benzo[e]azulen-8-yl]-pyrazol-1-yl}-azetidin-1-yl)-ethanol |

TABLE 1-continued

| No. | Structure | Name |
|---|---|---|
| 459 | 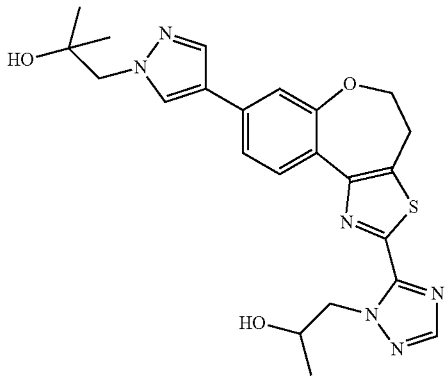 [SMILES: CC(O)Cn1ncnc1-c1nc2c(s1)CCOc1cc(-c3cnn(CC(C)(C)O)c3)ccc1-2] | 1-(4-{2-[2-(2-Hydroxy-propyl)-2H-[1,2,4]triazol-3-yl]-4,5-dihydro-6-oxa-3-thia-1-aza-benzo[e]azulen-8-yl}-pyrazol-1-yl)-2-methyl-propan-2-ol |
| 460 | 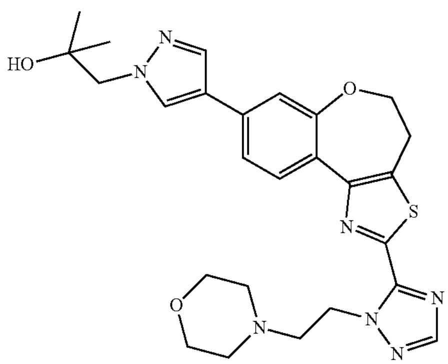 [SMILES: CC(C)(O)Cn1cc(-c2ccc3c(c2)OCCc2sc(-c4ncnn4CCN4CCOCC4)nc2-3)cn1] | 2-Methyl-1-(4-(2-[2-(2-morpholin-4-ethyl)-2H-[1,2,4]triazol-3-yl]-4,5-dihydro-6-oxa-3-thia-1-aza-benzo[e]azulen-8-yl}-pyrazol-1-yl)-propan-2-ol |
| 461 | 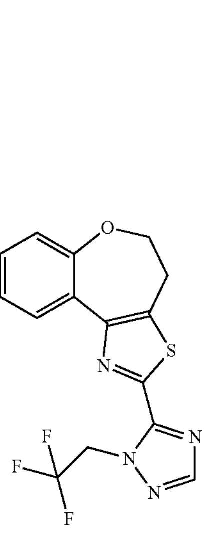 | Oxetan-3-yl-[2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-ethyl]-amine |

TABLE 1-continued

| No. | Structure | Name |
|---|---|---|
| 462 | 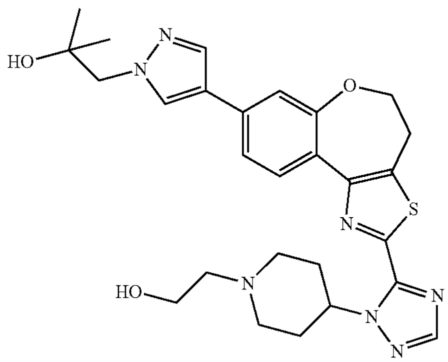 [SMILES: CC(C)(O)Cn1cc(-c2ccc3c(c2)OCCc2sc(-c4ncnn4C4CCN(CCO)CC4)nc2-3)cn1] | 1-[4-(2-{2-[1-(2-Hydroxy-ethyl)-piperidin-4-yl]-2H-[1,2,4]triazol-3-yl}-4,5-dihydro-6-oxa-3-thia-1-aza-benzo[e]azulen-8-yl)-pyrazol-1-yl]-2-methyl-propan-2-ol |
| 463 | 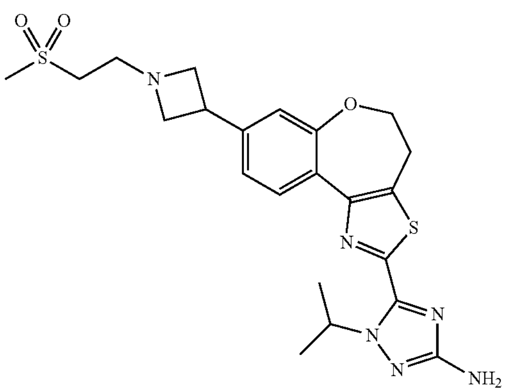 [SMILES: CC(C)n1nc(N)nc1-c1nc2c(s1)CCOc1cc(C3CN(CCS(C)(=O)=O)C3)ccc1-2] | 1-Isopropyl-5-{8-[1-(2-methanesulfonyl-ethyl)-azetidin-3-yl]-4,5-dihydro-6-oxa-3-thia-1-aza-benzo[e]azulen-2-yl}-1H-[1,2,4]triazol-3-ylamine |
| 464 | 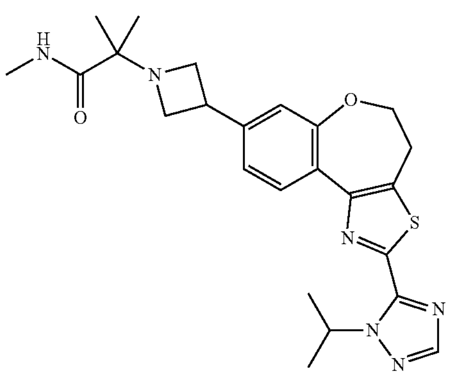 [SMILES: CNC(=O)C(C)(C)N1CC(c2ccc3c(c2)OCCc2sc(-c4ncnn4C(C)C)nc2-3)C1] | 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-N-methyl-isobutyramide |
| 465 | 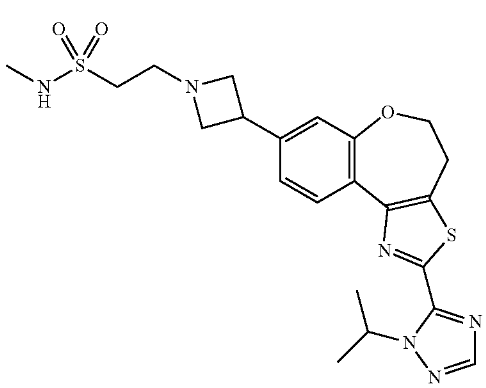 [SMILES: CNS(=O)(=O)CCN1CC(c2ccc3c(c2)OCCc2sc(-c4ncnn4C(C)C)nc2-3)C1] | 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-ethanesulfonic acid Diethylamide |

TABLE 1-continued

| No. | Structure | Name |
|---|---|---|
| 466 | 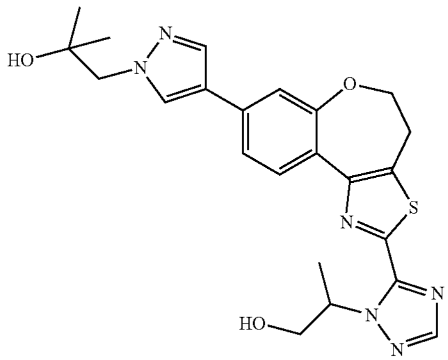 [SMILES: CC(CO)n1ncnc1-c1nc2c(s1)CCOc1cc(-c3cnn(CC(C)(C)O)c3)ccc1-2] | 2-(5-{8-[1-(2-Hydroxy-2-methyl-propyl)-1H-pyrazol-4-yl]-4,5-dihydro-6-oxa-3-thia-1-aza-benzo[e]azulen-2-yl}-[1,2,4]triazol-1-yl)-propan-1-ol |
| 467 | 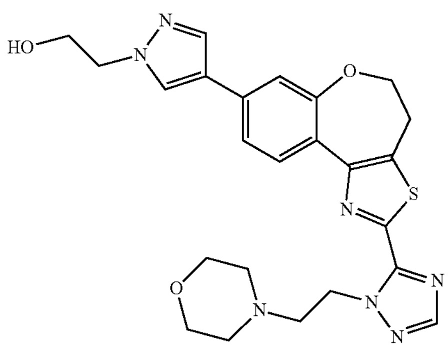 [SMILES: OCCn1cc(-c2ccc3c(c2)OCCc2sc(-c4ncnn4CCN4CCOCC4)nc2-3)cn1] | 2-(4-{2-[2-(2-Morpholin-4-yl-ethyl)-2H-[1,2,4]triazol-3-yl]-4,5-dihydro-6-oxa-3-thia-1-aza-benzo[e]azulen-8-yl}-pyrazol-1-yl)-ethanol |
| 468 | 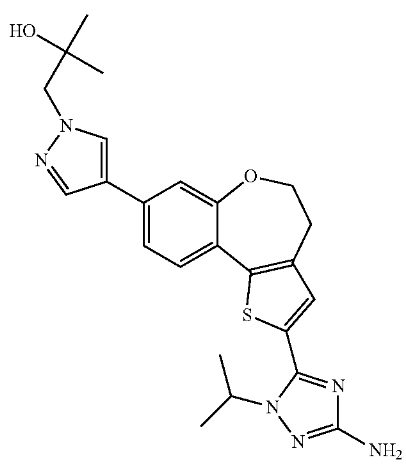 [SMILES: CC(C)n1nc(N)nc1-c1cc2c(s1)-c1ccc(-c3cnn(CC(C)(C)O)c3)cc1OCC2] | 1-(4-(2-(3-amino-1-isopropyl-1H-1,2,4-triazol-5-yl)-4,5-dihydrobenzo[b]thieno[2,3-d]oxepin-8-yl)-1H-pyrazol-1-yl)-2-methylpropan-2-ol |
| 469 | 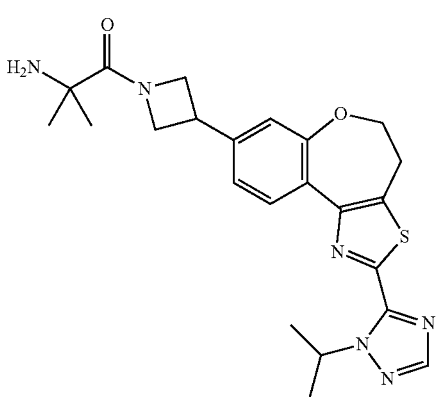 [SMILES: CC(C)n1ncnc1-c1nc2c(s1)CCOc1cc(C3CN(C(=O)C(C)(C)N)C3)ccc1-2] | 2-Amino-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-2-methyl-propan-1-one |

TABLE 1-continued

| No. | Structure | Name |
|---|---|---|
| 470 | 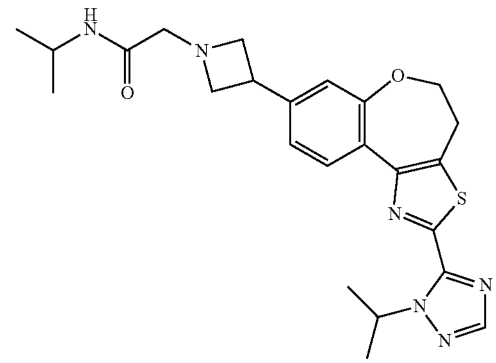 [SMILES: CC(C)NC(=O)CN1CC(c2ccc3c(c2)OCCc2sc(-c4ncnn4C(C)C)nc2-3)C1] | N-Isopropyl-2-{3-[2-(2-isopropyl-2H-[1,2,4]triazol-3-yl)-4,5-dihydro-6-oxa-3-thia-1-aza-benzo[e]azulen-8-yl]-azetidin-1-yl}-acetamide |
| 471 | 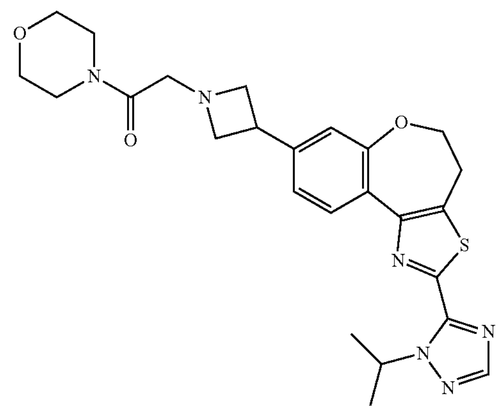 [SMILES: CC(C)n1ncnc1-c1nc2c(s1)CCOc1cc(C3CN(CC(=O)N4CCOCC4)C3)ccc1-2] | 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-1-morpholin-4-yl-ethanone |
| 472 | 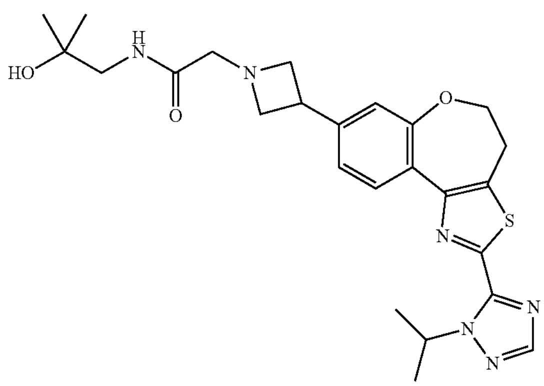 [SMILES: CC(C)n1ncnc1-c1nc2c(s1)CCOc1cc(C3CN(CC(=O)NCC(C)(C)O)C3)ccc1-2] | N-(2-Hydroxy-2-methyl-propyl)-2-{3-[2-(2-isopropyl-2H-[1,2,4]triazol-3-yl)-4,5-dihydro-6-oxa-3-thia-1-aza-benzo[e]azulen-8-yl]-azetidin-1-yl}-acetamide |
| 473 | 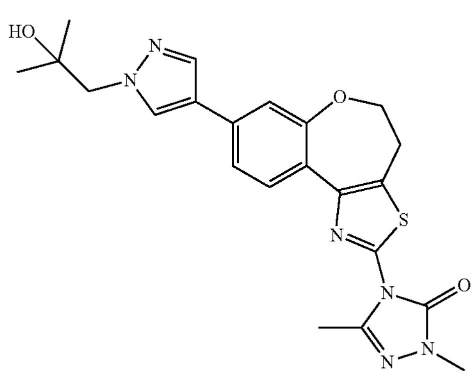 [SMILES: Cc1nn(C)c(=O)n1-c1nc2c(s1)CCOc1cc(-c3cnn(CC(C)(C)O)c3)ccc1-2] | 4-{8-[1-(2-Hydroxy-2-methyl-propyl)-1H-pyrazol-4-yl]-4,5-dihydro-6-oxa-3-thia-1-aza-benzo[e]azulen-2-yl}-2,5-dimethyl-2,4-dihydro-[1,2,4]triazol-3-one |

TABLE 1-continued

| No. | Structure | Name |
|---|---|---|
| 474 | 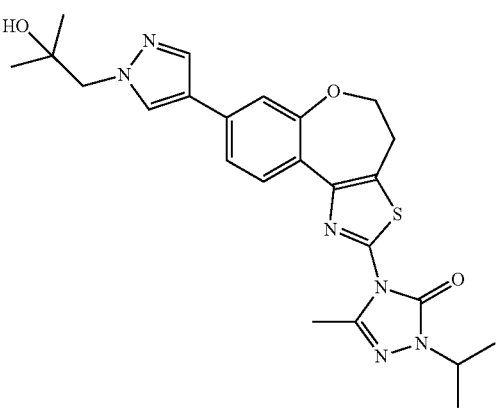 [SMILES: Cc1nn(C(C)C)c(=O)n1-c1nc2c(s1)CCOc1cc(-c3cnn(CC(C)(C)O)c3)ccc1-2] | 4-{8-[1-(2-Hydroxy-2-methyl-propyl)-1H-pyrazol-4-yl]-4,5-dihydro-6-oxa-3-thia-1-aza-benzo[e]azulen-2-yl}-2-isopropyl-5-methyl-2,4-dihydro-[1,2,4]triazol-3-one |
| 475 | 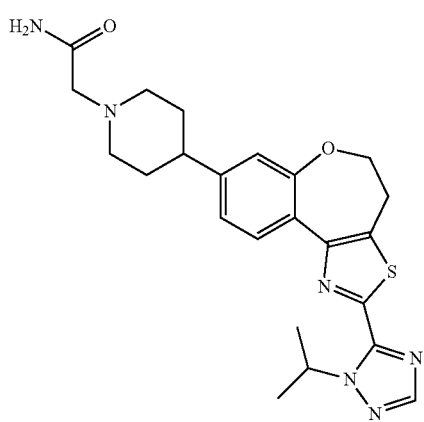 [SMILES: CC(C)n1ncnc1-c1nc2c(s1)CCOc1cc(C3CCN(CC(N)=O)CC3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-acetamide |
| 476 | 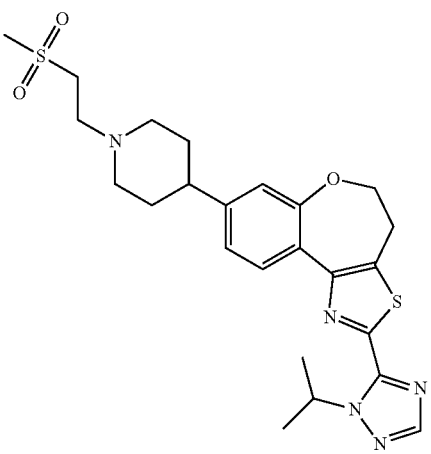 [SMILES: CC(C)n1ncnc1-c1nc2c(s1)CCOc1cc(C3CCN(CCS(C)(=O)=O)CC3)ccc1-2] | 2-(2-Isopropyl-2H-[1,2,4]triazol-3-yl)-8-[1-(2-methanesulfonyl-ethyl)-piperidin-4-yl]-4,5-dihydro-6-oxa-3-thia-1-aza-benzo[e]azulene |
| 477 | 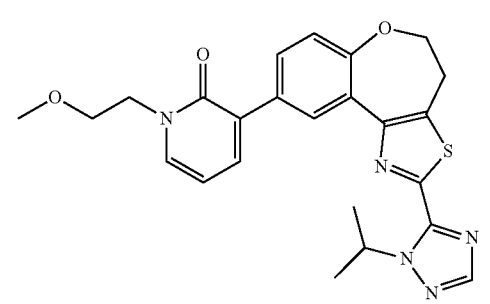 [SMILES: COCCn1cccc(-c2ccc3c(c2)-c2nc(-c4ncnn4C(C)C)sc2CCO3)c1=O] | 3-[2-(2-Isopropyl-2H-[1,2,4]triazol-3-yl)-4,5-dihydro-6-oxa-3-thia-1-aza-benzo[e]azulen-9-yl]-1-(2-methoxy-ethyl)-1H-pyridin-2-one |

TABLE 1-continued

| No. | Structure | Name |
|---|---|---|
| 478 | 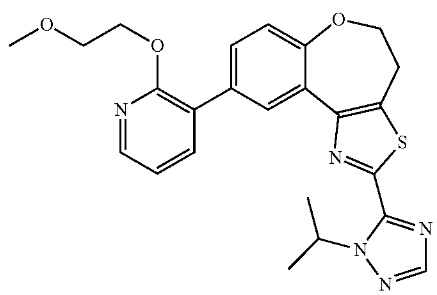 [SMILES: COCCOc1ncccc1-c1ccc2c(c1)-c1nc(-c3ncnn3C(C)C)sc1CCO2] | 2-(2-isopropyl-2H-[1,2,4]triazol-3-yl)-9-[2-(2-methoxy-ethoxy)-pyridin-3-yl]-4,5-dihydro-6-oxa-3-thia-1-aza-benzo[e]azulene |
| 479 | 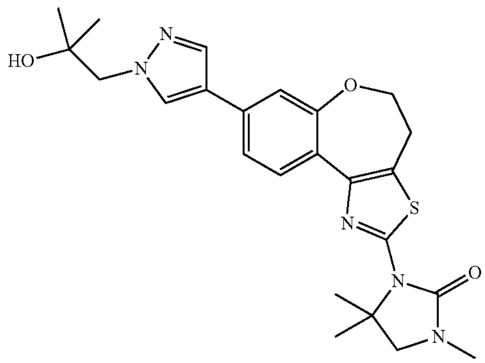 [SMILES: CN1CC(C)(C)N(c2nc3c(s2)CCOc2cc(-c4cnn(CC(C)(C)O)c4)ccc2-3)C1=O] | 3-(8-[1-(2-hydroxy-2-methyl-propyl)-1H-pyrazol-4-yl]-4,5-dihydro-6-oxa-3-thia-1-aza-benzo[e]azulen-2-yl}-1,4,4-trimethyl-imidazolidin-2-one |
| 480 | 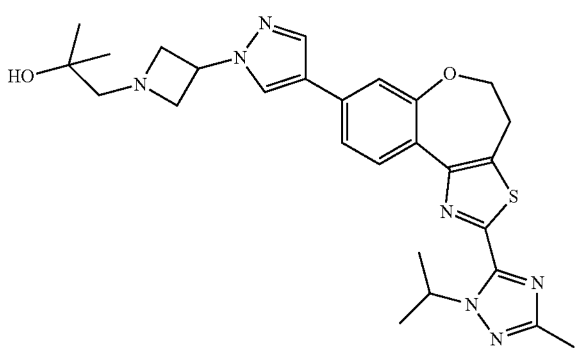 [SMILES: Cc1nc(-c2nc3c(s2)CCOc2cc(-c4cnn(C5CN(CC(C)(C)O)C5)c4)ccc2-3)n(C(C)C)n1] | 1-(3-{4-[2-(2-isopropyl-5-methyl-2H-[1,2,4]triazol-3-yl)-4,5-dihydro-6-oxa-3-thia-1-aza-benzo[e]azulen-8-yl]-pyrazol-1-yl}-azetidin-1-yl)-2-methyl-propan-2-ol |
| 481 | 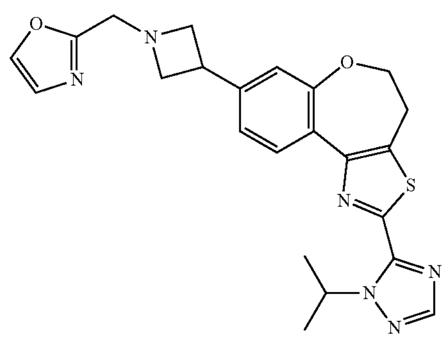 [SMILES: CC(C)n1ncnc1-c1nc2c(s1)CCOc1cc(C3CN(Cc4ncco4)C3)ccc1-2] | 2-(2-isopropyl-2H-[1,2,4]triazol-3-yl)-8-(1-oxazol-2-ylmethyl-azetidin-3-yl)-4,5-dihydro-6-oxa-3-thia-1-aza-benzo[e]azulene |

TABLE 1-continued

| No. | Structure | Name |
| --- | --- | --- |
| 482 | 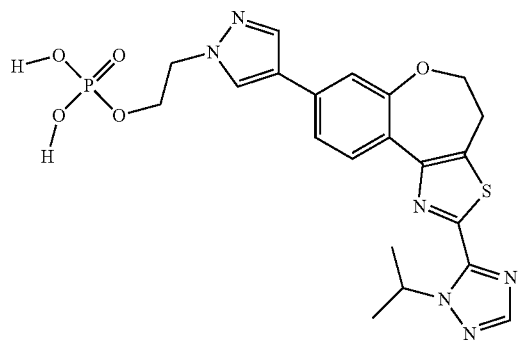 [SMILES: CC(C)n1ncnc1-c1nc2c(s1)CCOc1cc(-c3cnn(CCOP(=O)(O)O)c3)ccc1-2] | phosphoric acid mono-(2-{4-[2-(2-isopropyl-2H-[1,2,4]triazol-3-yl)-4,5-dihydro-6-oxa-3-thia-1-aza-benzo[e]azulen-8-yl]-pyrazol-1-yl}-ethyl) ester |
| 483 | 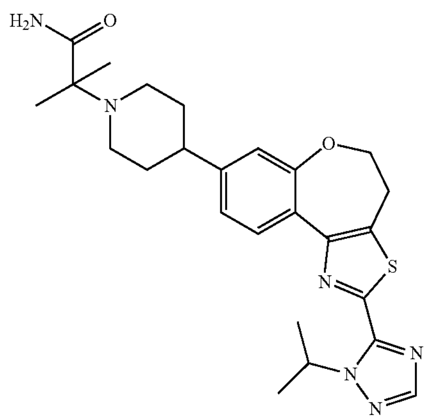 [SMILES: CC(C)n1ncnc1-c1nc2c(s1)CCOc1cc(C3CCN(C(C)(C)C(N)=O)CC3)ccc1-2] | 2-{4-[2-(2-isopropyl-2H-[1,2,4]triazol-3-yl)-4,5-dihydro-6-oxa-3-thia-1-aza-benzo[e]azulen-8-yl]-piperidin-1-yl}-isobutyramide |
| 484 | 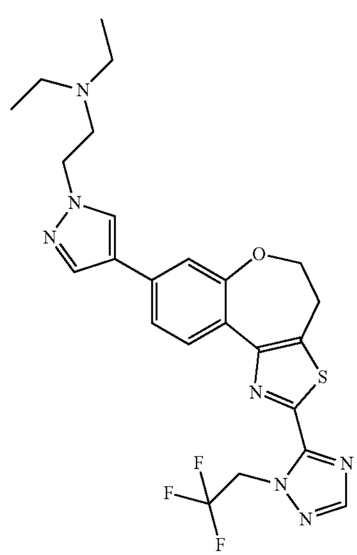 [SMILES: CCN(CC)CCn1cc(-c2ccc3c(c2)OCCc2sc(-c4ncnn4CC(F)(F)F)nc2-3)cn1] | diethyl-[2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-ethyl]-amine |

TABLE 1-continued

| No. | Structure | Name |
|---|---|---|
| 485 | 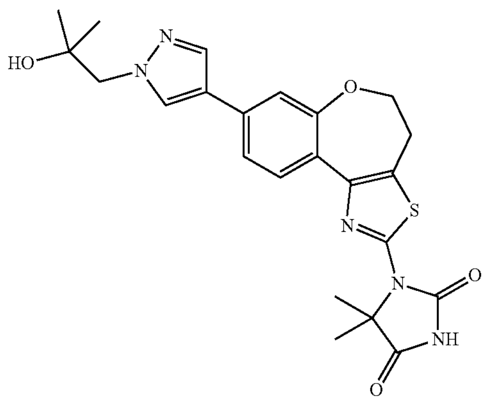 [SMILES: CC(C)(O)Cn1cc(-c2ccc3c(c2)OCCc2sc(N4C(=O)NC(=O)C4(C)C)nc2-3)cn1] | 1-{8-[1-(2-Hydroxy-2-methyl-propyl)-1H-pyrazol-4-yl]-4,5-dihydro-6-oxa-3-thia-1-aza-benzo[e]azulen-2-yl}-5,5-dimethyl-imidazolidine-2,4-dione |
| 486 | 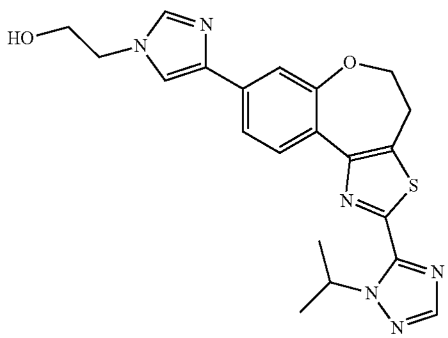 [SMILES: CC(C)n1ncnc1-c1nc2c(s1)CCOc1cc(-c3cn(CCO)cn3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-imidazol-1-yl}-ethanol |
| 487 | 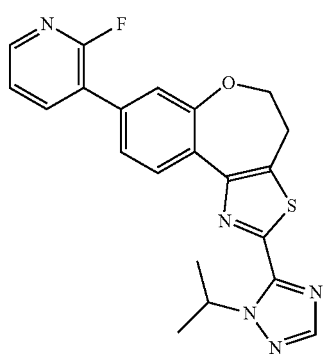 [SMILES: CC(C)n1ncnc1-c1nc2c(s1)CCOc1cc(-c3cccnc3F)ccc1-2] | 8-(2-Fluoro-pyridin-3-yl)-2-(2-isopropyl-2H-[1,2,4]triazol-3-yl)-4,5-dihydro-6-oxa-3-thia-1-aza-benzo[e]azulene |
| 488 | 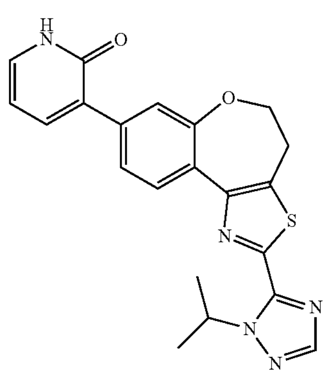 [SMILES: CC(C)n1ncnc1-c1nc2c(s1)CCOc1cc(-c3ccc[nH]c3=O)ccc1-2] | 3-[2-(2-Isopropyl-2H-[1,2,4]triazol-3-yl)-4,5-dihydro-6-oxa-3-thia-1-aza-benzo[e]azulen-8-yl]-1H-pyridin-2-one |

TABLE 1-continued

| No. | Structure | Name |
|---|---|---|
| 489 | 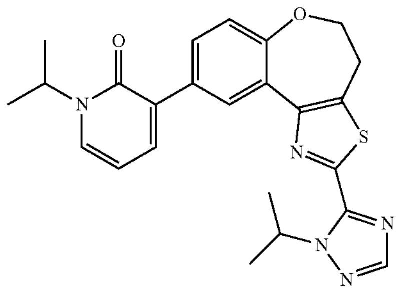 [SMILES: CC(C)n1ncnc1-c1nc2c(s1)CCOc1ccc(-c3cccn(C(C)C)c3=O)cc1-2] | 1-Isopropyl-3-[2-(2-isopropyl-2H-[1,2,4]triazol-3-yl)-4,5-dihydro-6-oxa-3-thia-1-aza-benzo[e]azulen-9-yl]-1H-pyridin-2-one |
| 490 | 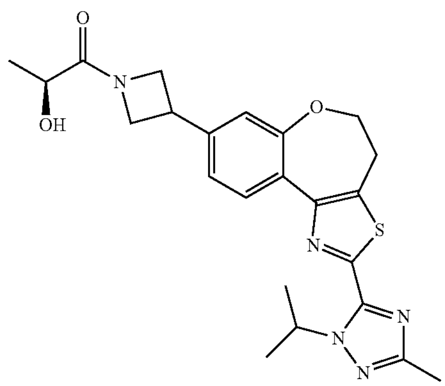 [SMILES: Cc1nc(-c2nc3c(s2)CCOc2cc(C4CN(C(=O)[C@H](C)O)C4)ccc2-3)n(C(C)C)n1] | (S)-2-Hydroxy-1-{3-[2-(2-isopropyl-5-methyl-2H-[1,2,4]triazol-3-yl)-4,5-dihydro-6-oxa-3-thia-1-aza-benzo[e]azulen-8-yl]-azetidin-1-yl}-propan-1-one |
| 491 | 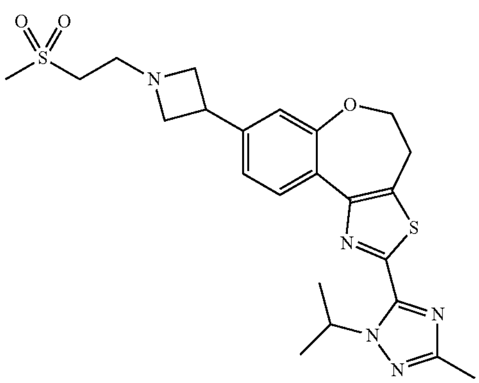 | 2-(2-Isopropyl-5-methyl-2H-[1,2,4]triazol-3-yl)-8-[1-(2-methanesulfonyl-ethyl)-azetidin-3-yl]-4,5-dihydro-6-oxa-3-thia-1-aza-benzo[e]azulene |
| 492 | 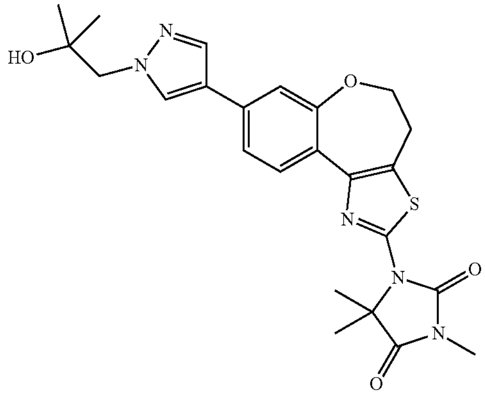 [SMILES: CN1C(=O)N(c2nc3c(s2)CCOc2cc(-c4cnn(CC(C)(C)O)c4)ccc2-3)C(C)(C)C1=O] | 1-{8-[1-(2-Hydroxy-2-methyl-propyl)-1H-pyrazol-4-yl]-4,5-dihydro-6-oxa-3-thia-1-aza-benzo[e]azulen-2-yl}-3,5,5-trimethyl-imidazolidine-2,4-dione |

TABLE 1-continued

| No. | Structure | Name |
|---|---|---|
| 493 | 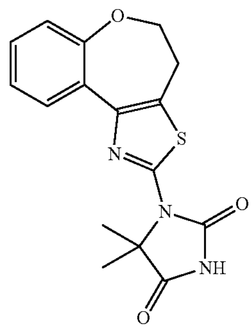 [SMILES: CC1(C)C(=O)NC(=O)N1c1nc2c(s1)CCOc1ccccc1-2] | 1-(4,5-Dihydro-6-oxa-3-thia-1-aza-benzo[e]azulen-2-yl)-5,5-dimethyl-imidazolidine-2,4-dione |
| 494 | 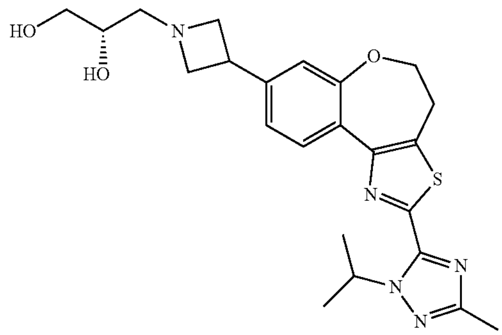 [SMILES: Cc1nc(-c2nc3c(s2)CCOc2cc(C4CN(C[C@H](O)CO)C4)ccc2-3)n(C(C)C)n1] | (S)-3-{3-[2-(2-Isopropyl-5-methyl-2H-[1,2,4]triazol-3-yl)-4,5-dihydro-6-oxa-3-thia-1-aza-benzo[e]azulen-8-yl]-azetidin-1-yl}-propane-1,2-diol |
| 495 | 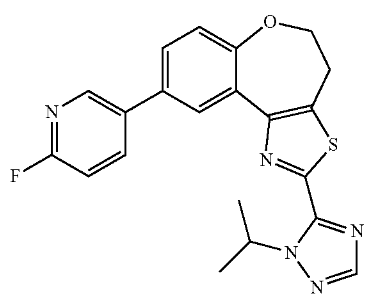 [SMILES: CC(C)n1ncnc1-c1nc2c(s1)CCOc1ccc(-c3ccc(F)nc3)cc1-2] | 9-(6-Fluoro-pyridin-3-yl)-2-(2-isopropyl-2H-[1,2,4]triazol-3-yl)-4,5-dihydro-6-oxa-3-thia-1-aza-benzo[e]azulene |
| 496 | 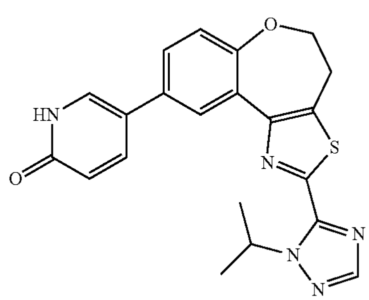 [SMILES: CC(C)n1ncnc1-c1nc2c(s1)CCOc1ccc(-c3ccc(=O)[nH]c3)cc1-2] | 5-[2-(2-Isopropyl-2H-[1,2,4]triazol-3-yl)-4,5-dihydro-6-oxa-3-thia-1-aza-benzo[e]azulen-9-yl]-1H-pyridin-2-one |
| 497 | 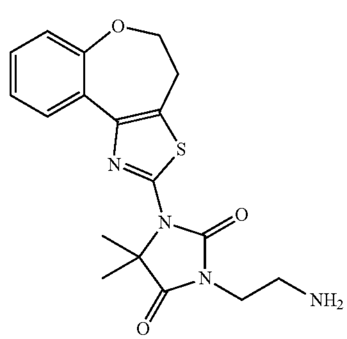 [SMILES: CC1(C)C(=O)N(CCN)C(=O)N1c1nc2c(s1)CCOc1ccccc1-2] | 3-(2-Amino-ethyl)-1-(4,5-dihydro-6-oxa-3-thia-1-aza-benzo[e]azulen-2-yl)-5,5-dimethyl-imidazolidine-2,4-dione |

TABLE 1-continued

| No. | Structure | Name |
|---|---|---|
| 498 | 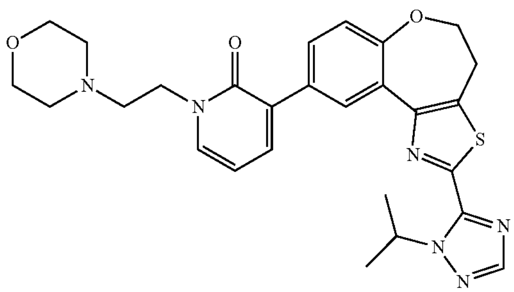 [SMILES: CC(C)n1ncnc1-c1nc2c(s1)CCOc1ccc(-c3cccn(CCN4CCOCC4)c3=O)cc1-2] | 3-[2-(2-Isopropyl-2H-[1,2,4]triazol-3-yl)-4,5-dihydro-6-oxa-3-thia-1-aza-benzo[e]azulen-9-yl]-1-(2-morpholin-4-yl-ethyl)-1H-pyridin-2-one |
| 499 | 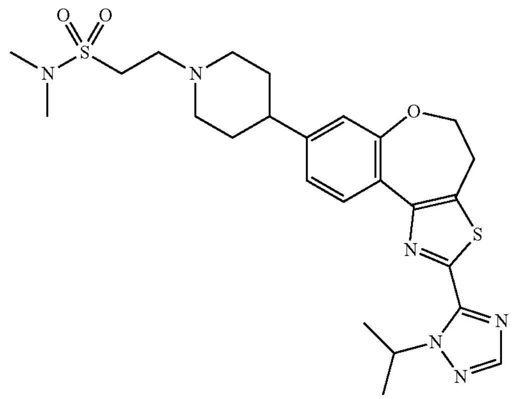 [SMILES: CC(C)n1ncnc1-c1nc2c(s1)CCOc1cc(C3CCN(CCS(=O)(=O)N(C)C)CC3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-ethanesulfonic acid dimethylamide |
| 500 | 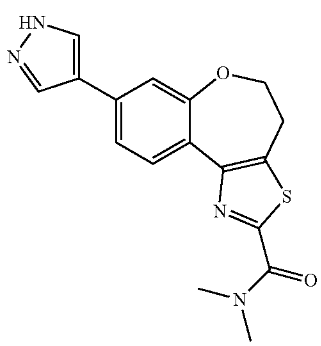 [SMILES: CN(C)C(=O)c1nc2c(s1)CCOc1cc(-c3cn[nH]c3)ccc1-2] | 8-(1H-Pyrazol-4-yl)-4,5-dihydro-6-oxa-3-thia-1-aza-benzo[e]azulene-2-carboxylic acid dimethylamide |
| 501 | 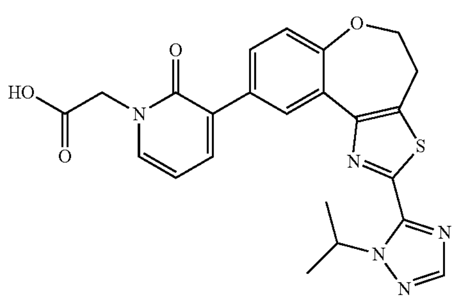 [SMILES: CC(C)n1ncnc1-c1nc2c(s1)CCOc1ccc(-c3cccn(CC(=O)O)c3=O)cc1-2] | {3-[2-(2-Isopropyl-2H-[1,2,4]triazol-3-yl)-4,5-dihydro-6-oxa-3-thia-1-aza-benzo[e]azulen-9-yl]-2-oxo-2H-pyridin-1-yl}-acetic acid |
| 502 | 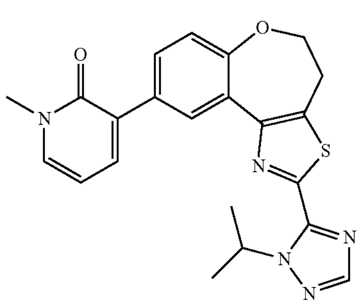 [SMILES: CC(C)n1ncnc1-c1nc2c(s1)CCOc1ccc(-c3cccn(C)c3=O)cc1-2] | 3-[2-(2-Isopropyl-2H-[1,2,4]triazol-3-yl)-4,5-dihydro-6-oxa-3-thia-1-aza-benzo[e]azulen-9-yl]-1-methyl-1H-pyridin-2-one |

TABLE 1-continued

| No. | Structure | Name |
|---|---|---|
| 503 | 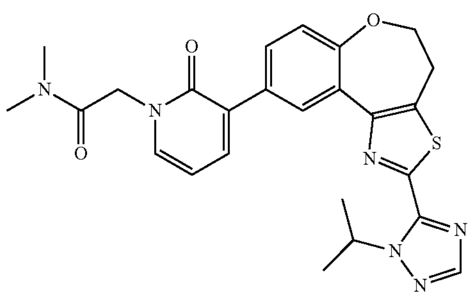 | 2-{3-[2-(2-Isopropyl-2H-[1,2,4]triazol-3-yl)-4,5-dihydro-6-oxa-3-thia-1-aza-benzo[e]azulen-9-yl]-2-oxo-2H-pyridin-1-yl}-N,N-dimethyl-acetamide |
| 504 | 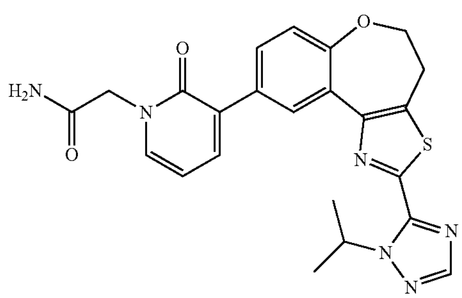 [SMILES: CC(C)n1ncnc1-c1nc2c(s1)CCOc1ccc(-c3cccn(CC(N)=O)c3=O)cc1-2] | 2-{3-[2-(2-Isopropyl-2H-[1,2,4]triazol-3-yl)-4,5-dihydro-6-oxa-3-thia-1-aza-benzo[e]azulen-9-yl]-2-oxo-2H-pyridin-1-yl}-acetamide |
| 505 | 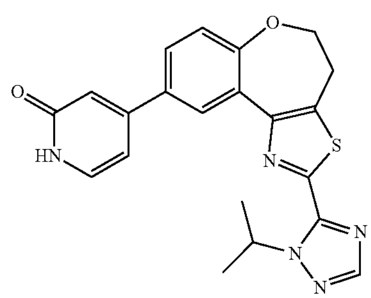 [SMILES: CC(C)n1ncnc1-c1nc2c(s1)CCOc1ccc(-c3cc[nH]c(=O)c3)cc1-2] | 4-[2-(2-Isopropyl-2H-[1,2,4]triazol-3-yl)-4,5-dihydro-6-oxa-3-thia-1-aza-benzo[e]azulen-9-yl]-1H-pyridin-2-one |
| 506 | 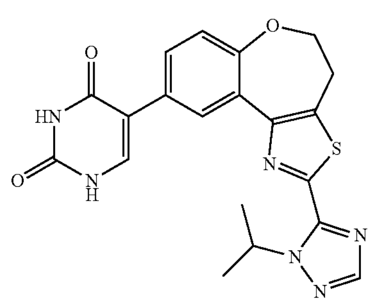 [SMILES: CC(C)n1ncnc1-c1nc2c(s1)CCOc1ccc(-c3c[nH]c(=O)[nH]c3=O)cc1-2] | 5-[2-(2-Isopropyl-2H-[1,2,4]triazol-3-yl)-4,5-dihydro-6-oxa-3-thia-1-aza-benzo[e]azulen-9-yl]-1H-pyrimidine-2,4-dione |
| 507 | 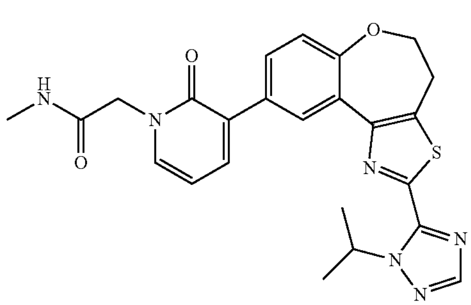 [SMILES: CNC(=O)Cn1cccc(-c2ccc3c(c2)-c2nc(-c4ncnn4C(C)C)sc2CCO3)c1=O] | 2-{3-[2-(2-Isopropyl-2H-[1,2,4]triazol-3-yl)-4,5-dihydro-6-oxa-3-thia-1-aza-benzo[e]azulen-9-yl]-2-oxo-2H-pyridin-1-yl}-N-methyl-acetamide |

TABLE 1-continued

| No. | Structure | Name |
|---|---|---|
| 508 | 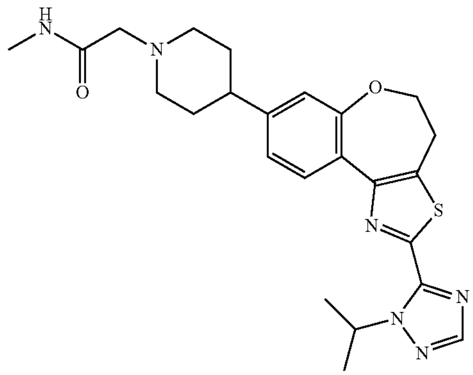 [SMILES: CNC(=O)CN1CCC(c2ccc3c(c2)OCCc2sc(-c4ncnn4C(C)C)nc2-3)CC1] | 2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-N-methyl-acetamide |
| 509 | 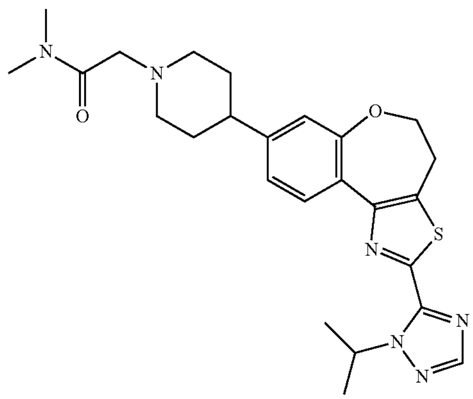 [SMILES: CC(C)n1ncnc1-c1nc2c(s1)CCOc1cc(C3CCN(CC(=O)N(C)C)CC3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-N,N-dimethyl-acetamide |
| 510 | 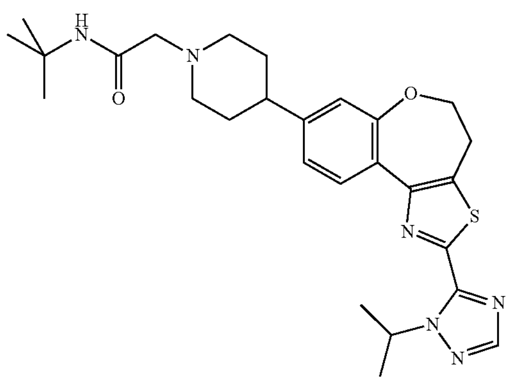 [SMILES: CC(C)n1ncnc1-c1nc2c(s1)CCOc1cc(C3CCN(CC(=O)NC(C)(C)C)CC3)ccc1-2] | N-tert-Butyl-2-{4-[2-(2-isopropyl-2H-[1,2,4]triazol-3-yl)-4,5-dihydro-6-oxa-3-thia-1-aza-benzo[e]azulen-8-yl]-piperidin-1-yl}-acetamide |
| 511 | 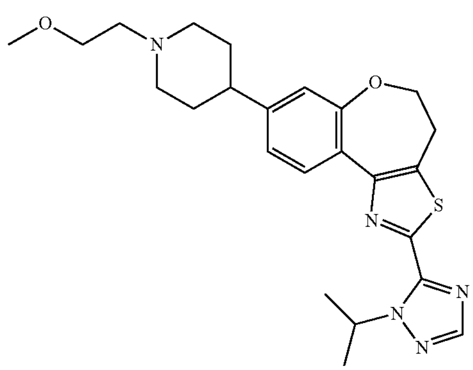 [SMILES: COCCN1CCC(c2ccc3c(c2)OCCc2sc(-c4ncnn4C(C)C)nc2-3)CC1] | 2-(2-Isopropyl-2H-[1,2,4]triazol-3-yl)-8-[1-(2-methoxy-ethyl)-piperidin-4-yl]-4,5-dihydro-6-oxa-3-thia-1-aza-benzo[e]azulene |

TABLE 1-continued

| No. | Structure | Name |
|---|---|---|
| 512 | 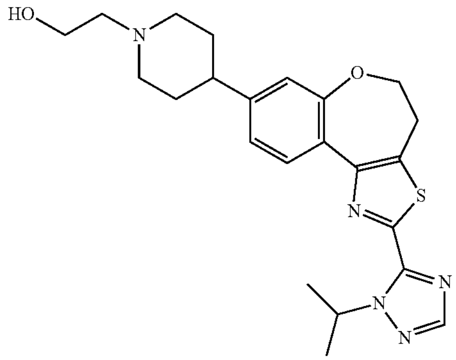 [SMILES: CC(C)n1ncnc1-c1nc2c(s1)CCOc1cc(C3CCN(CCO)CC3)ccc1-2] | 2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-ethanol |

TABLE 2

| No. | Structure | Name |
|---|---|---|
| 513 | 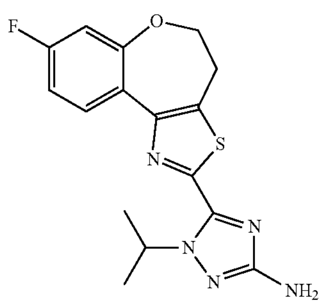 [SMILES: CC(C)n1nc(N)nc1-c1nc2c(s1)CCOc1cc(F)ccc1-2] | 2-(2-Isopropyl-2H-5-amino[1,2,4]triazol-3-yl)-8-fluoro-4,5-dihydro-6-oxa-3-thia-1-aza-benzo[e]azulene |
| 514 | 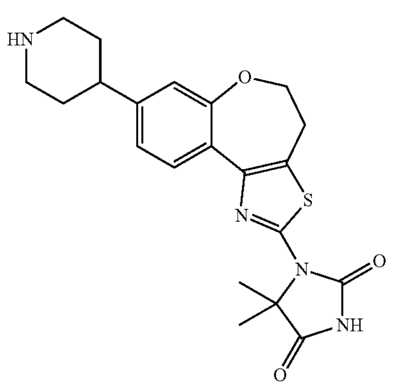 [SMILES: CC1(C)C(=O)NC(=O)N1c1nc2c(s1)CCOc1cc(C3CCNCC3)ccc1-2] | 1-(8-Piperidin-4-yl-4,5-dihydrothiazolo[4,5-d]benzo[b]oxepin-2-yl)-5,5-dimethylimidazolidin-2,4-dione |
| 515 | 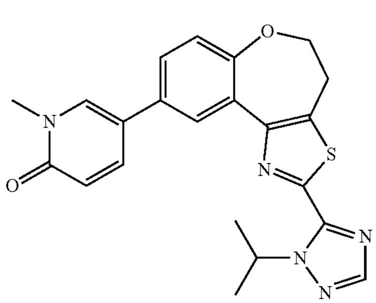 [SMILES: CC(C)n1ncnc1-c1nc2c(s1)CCOc1ccc(-c3ccc(=O)n(C)c3)cc1-2] | 5-[2-(2-Isopropyl-2H-[1,2,4]triazol-3-yl)-4,5-dihydro-6-oxa-3-thia-1-aza-benzo[e]azulen-9-yl]-1H-N-methylpyridin-2-one |

TABLE 2-continued

| No. | Structure | Name |
|---|---|---|
| 516 | 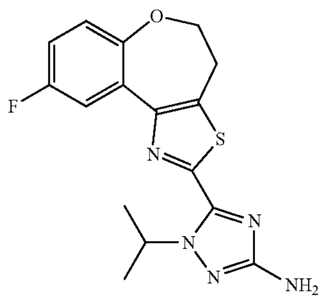 [SMILES: CC(C)n1nc(N)nc1-c1nc2c(s1)CCOc1ccc(F)cc1-2] | 2-(2-Isopropyl-2H-5-amino[1,2,4]triazol-3-yl)-9-fluoro-4,5-dihydro-6-oxa-3-thia-1-aza-benzo[e]azulene |
| 517 | 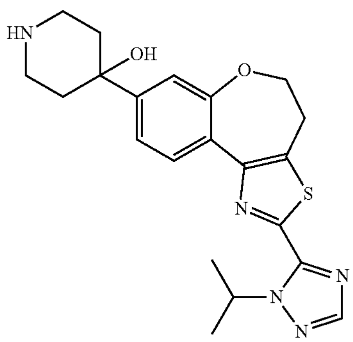 [SMILES: CC(C)n1ncnc1-c1nc2c(s1)CCOc1cc(C3(O)CCNCC3)ccc1-2] | 4-[2-(2-Isopropyl-2H-[1,2,4]triazol-3-yl)-4,5-dihydro-6-oxa-3-thia-1-aza-benzo[e]azulen-8-yl]-piperidin-4-ol hydrochloride |
| 518 | 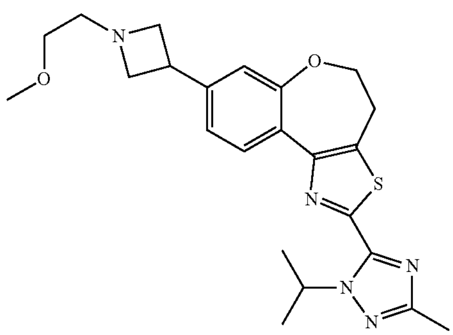 | 2-(2-Isopropyl-5-methyl-2H-[1,2,4]triazol-3-yl)-8-[1-(2-methoxy-ethyl)-azetidin-3-yl]-4,5-dihydro-6-oxa-3-thia-1-aza-benzo[e]azulene |
| 519 | 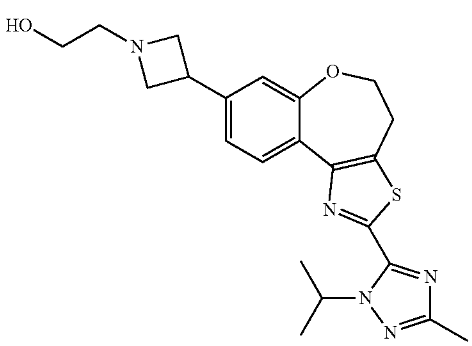 [SMILES: Cc1nc(-c2nc3c(s2)CCOc2cc(C4CN(CCO)C4)ccc2-3)n(C(C)C)n1] | 2-{3-[2-(2-Isopropyl-5-methyl-2H-[1,2,4]triazol-3-yl)-4,5-dihydro-6-oxa-3-thia-1-aza-benzo[e]azulen-8-yl]-azetidin-1-yl}-ethanol |

| No. | Structure | Name |
| --- | --- | --- |
| 520 | 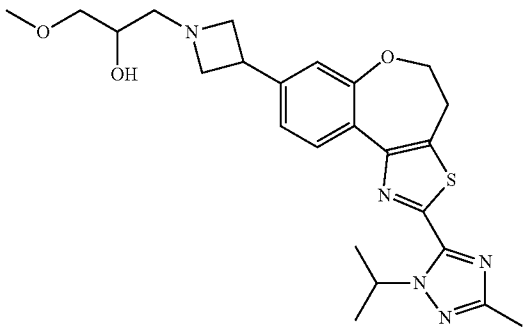 | 1-{3-[2-(2-Isopropyl-5-methyl-2H-[1,2,4]triazol-3-yl)-4,5-dihydro-6-oxa-3-thia-1-aza-benzo[e]azulen-8-yl]-azetidin-1-yl}-3-methoxy-propan-2-ol |
| 521 | 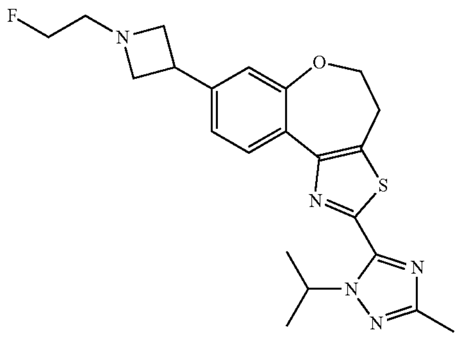 [SMILES: Cc1nc(-c2nc3c(s2)CCOc2cc(C4CN(CCF)C4)ccc2-3)n(C(C)C)n1] | 8-[1-(2-Fluoro-ethyl)-azetidin-3-yl]-2-(2-isopropyl-5-methyl-2H-[1,2,4]triazol-3-yl)-4,5-dihydro-6-oxa-3-thia-1-aza-benzo[e]azulene |
| 522 | 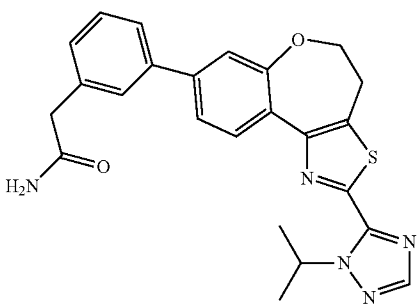 [SMILES: CC(C)n1ncnc1-c1nc2c(s1)CCOc1cc(-c3cccc(CC(N)=O)c3)ccc1-2] | 2-{3-[2-(2-Isopropyl-2H-[1,2,4]triazol-3-yl)-4,5-dihydro-6-oxa-3-thia-1-aza-benzo[e]azulen-8-yl]-phenyl}-acetamide |
| 523 | 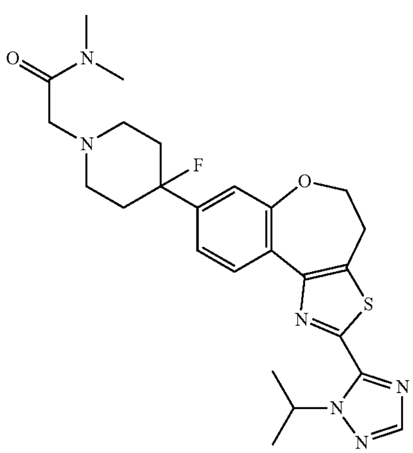 [SMILES: CC(C)n1ncnc1-c1nc2c(s1)CCOc1cc(C3(F)CCN(CC(=O)N(C)C)CC3)ccc1-2] | 2-{4-Fluoro-4-[2-(2-isopropyl-2H-[1,2,4]triazol-3-yl)-4,5-dihydro-6-oxa-3-thia-1-aza-benzo[e]azulen-8-yl]-piperidin-1-yl}-N,N-dimethyl-acetamide |

TABLE 2-continued

| No. | Structure | Name |
|---|---|---|
| 524 | 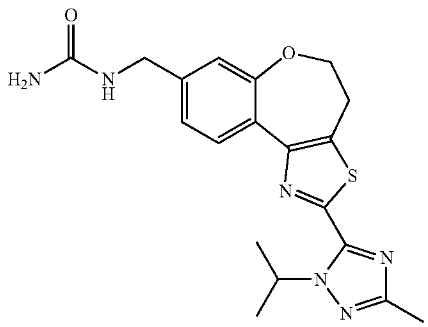 [SMILES: Cc1nc(-c2nc3c(s2)CCOc2cc(CNC(N)=O)ccc2-3)n(C(C)C)n1] | {1-[2-(2-Isopropyl-5-methyl-2H-[1,2,4]triazol-3-yl)-4,5-dihydro-6-oxa-3-thia-1-aza-benzo[e]azulen-8-yl]-methyl}-urea |
| 525 | 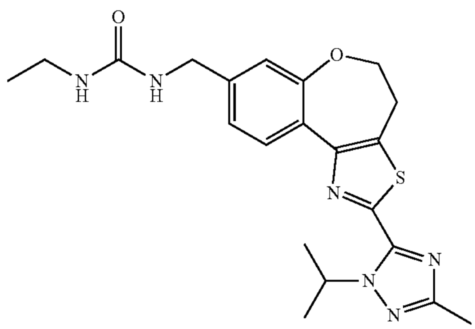 [SMILES: CCNC(=O)NCc1ccc2c(c1)OCCc1sc(-c3nc(C)nn3C(C)C)nc1-2] | 1-ethyl-3-[2-(2-isopropyl-5-methyl-2H-[1,2,4]triazol-3-yl)-4,5-dihydro-6-oxa-3-thia-1-aza-benzo[e]azulen-8-ylmethyl]-urea |
| 526 | 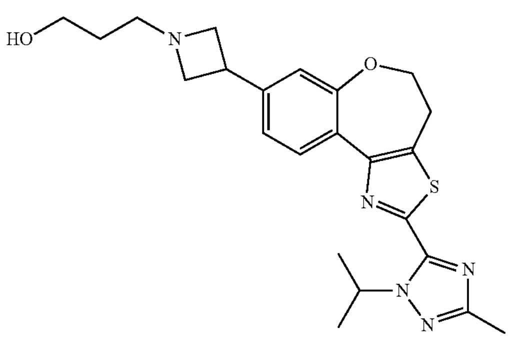 [SMILES: Cc1nc(-c2nc3c(s2)CCOc2cc(C4CN(CCCO)C4)ccc2-3)n(C(C)C)n1] | 3-{3-[2-(2-Isopropyl-5-methyl-2H-[1,2,4]triazol-3-yl)-4,5-dihydro-6-oxa-3-thia-1-aza-benzo[e]azulen-8-yl]-azetidin-1-yl}-propan-1-ol |
| 527 | 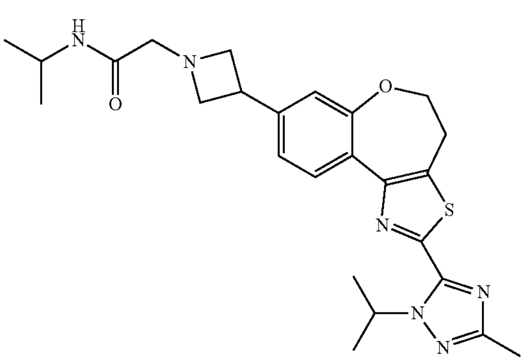 [SMILES: Cc1nc(-c2nc3c(s2)CCOc2cc(C4CN(CC(=O)NC(C)C)C4)ccc2-3)n(C(C)C)n1] | N-Isopropyl-2-{3-[2-(2-isopropyl-5-methyl-2H-[1,2,4]triazol-3-yl)-4,5-dihydro-6-oxa-3-thia-1-aza-benzo[e]azulen-8-yl]-azetidin-1-yl}-acetamide |

TABLE 2-continued

| No. | Structure | Name |
|---|---|---|
| 528 | 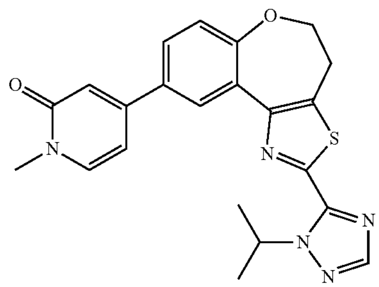 [SMILES: CC(C)n1ncnc1-c1nc2c(s1)CCOc1ccc(-c3ccn(C)c(=O)c3)cc1-2] | 4-[2-(2-Isopropyl-2H-[1,2,4]triazol-3-yl)-4,5-dihydro-6-oxa-3-thia-1-aza-benzo[e]azulen-9-yl]-1H-N-methylpyridin-2-one |
| 529 | 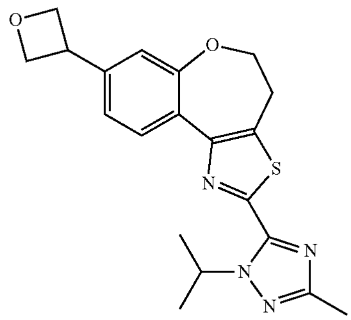 [SMILES: Cc1nc(-c2nc3c(s2)CCOc2cc(C4COC4)ccc2-3)n(C(C)C)n1] | 2-(2-Isopropyl-5-methyl-2H-[1,2,4]triazol-3-yl)-8-oxetan-3-yl-4,5-dihydro-6-oxa-3-thia-1-aza-benzo[e]azulene |
| 530 | 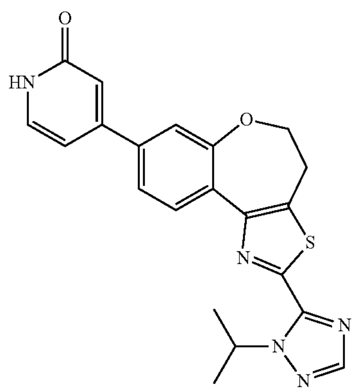 [SMILES: CC(C)n1ncnc1-c1nc2c(s1)CCOc1cc(-c3cc[nH]c(=O)c3)ccc1-2] | 4-[2-(2-Isopropyl-2H-[1,2,4]triazol-3-yl)-4,5-dihydro-6-oxa-3-thia-1-aza-benzo[e]azulen-8-yl]-1H-pyridin-2-one |
| 531 | 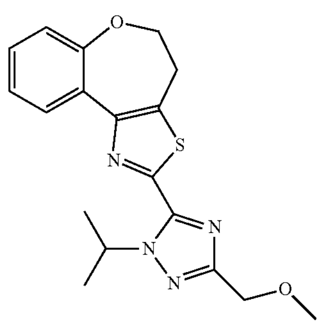 [SMILES: COCc1nc(-c2nc3c(s2)CCOc2ccccc2-3)n(C(C)C)n1] | 2-(2-Isopropyl-2H-5-methoxymethyl[1,2,4]triazol-3-yl)-4,5-dihydro-6-oxa-3-thia-1-aza-benzo[e]azulene |
| 532 | 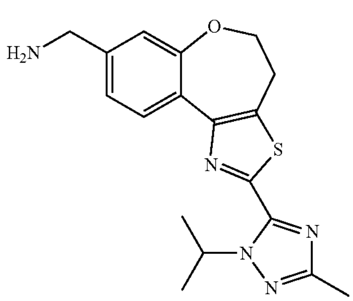 [SMILES: Cc1nc(-c2nc3c(s2)CCOc2cc(CN)ccc2-3)n(C(C)C)n1] | C-[2-(2-Isopropyl-5-methyl-2H-[1,2,4]triazol-3-yl)-4,5-dihydro-6-oxa-3-thia-1-aza-benzo[e]azulen-8-yl]-methylamine |

TABLE 2-continued

| No. | Structure | Name |
|---|---|---|
| 533 | 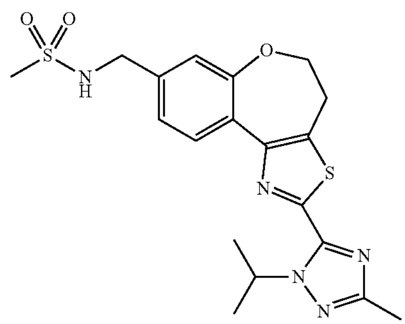 | N-[2-(2-isopropyl-5-methyl-2H-[1,2,4]triazol-3-yl)-4,5-dihydro-6-oxa-3-thia-1-aza-benzo[e]azulen-8-ylmethyl]-methanesulfonamide |
| 534 | 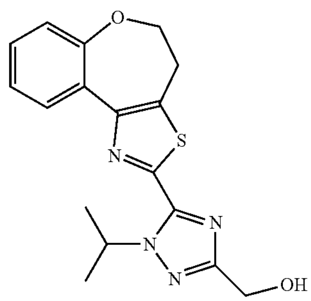 [SMILES: CC(C)n1nc(CO)nc1-c1nc2c(s1)CCOc1ccccc1-2] | 2-(2-Isopropyl-2H-5-hydroxymethyl[1,2,4]triazol-3-yl)-4,5-dihydro-6-oxa-3-thia-1-aza-benzo[e]azulene |
| 535 | 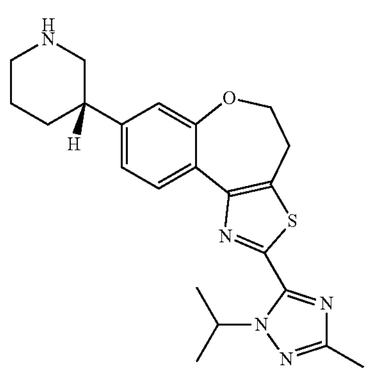 [SMILES: Cc1nc(-c2nc3c(s2)CCOc2cc([C@@H]4CCCNC4)ccc2-3)n(C(C)C)n1] | 2-(2-Isopropyl-5-methyl-2H-[1,2,4]triazol-3-yl)-8-piperidin-3S-yl-4,5-dihydro-6-oxa-3-thia-1-aza-benzo[e]azulene |
| 536 | 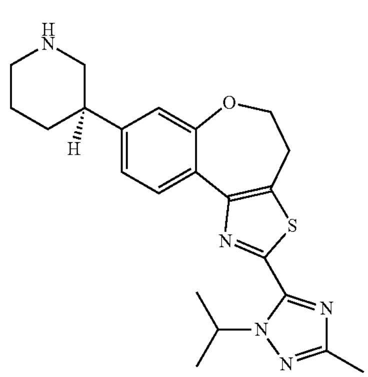 [SMILES: Cc1nc(-c2nc3c(s2)CCOc2cc([C@H]4CCCNC4)ccc2-3)n(C(C)C)n1] | 2-(2-Isopropyl-5-methyl-2H-[1,2,4]triazol-3-yl)-8-piperidin-3R-yl-4,5-dihydro-6-oxa-3-thia-1-aza-benzo[e]azulene |

TABLE 2-continued

| No. | Structure | Name |
|---|---|---|
| 537 | 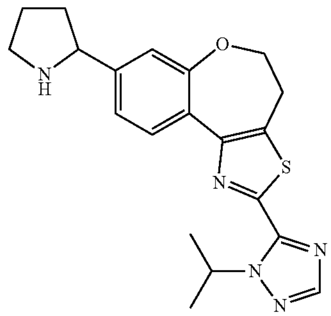 [SMILES: CC(C)n1ncnc1-c1nc2c(s1)CCOc1cc(C3CCCN3)ccc1-2] | 2-(2-Isopropyl-2H-[1,2,4]triazol-3-yl)-8-pyrrolidin-2-yl-4,5-dihydro-6-oxa-3-thia-1-aza-benzo[e]azulene |
| 538 | 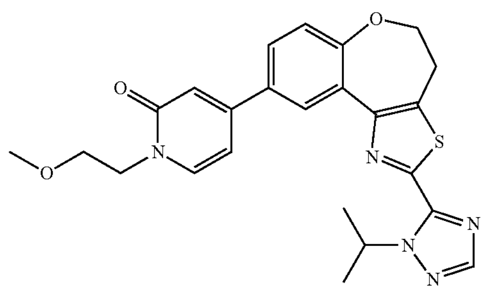 [SMILES: COCCn1ccc(-c2ccc3c(c2)-c2nc(-c4ncnn4C(C)C)sc2CCO3)cc1=O] | 4-[2-(2-Isopropyl-2H-[1,2,4]triazol-3-yl)-4,5-dihydro-6-oxa-3-thia-1-aza-benzo[e]azulen-9-yl]-1H-N-2-methoxyethylpyridin-2-one |
| 539 | 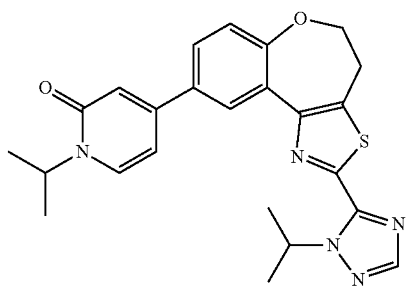 [SMILES: CC(C)n1ncnc1-c1nc2c(s1)CCOc1ccc(-c3ccn(C(C)C)c(=O)c3)cc1-2] | 4-[2-(2-Isopropyl-2H-[1,2,4]triazol-3-yl)-4,5-dihydro-6-oxa-3-thia-1-aza-benzo[e]azulen-9-yl]-1H-N-isopropylpyridin-2-one |
| 540 | 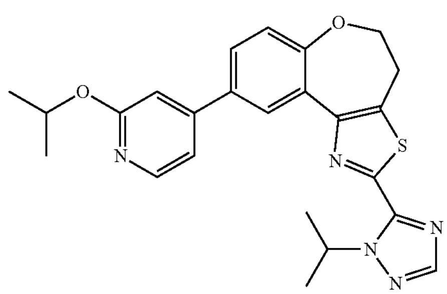 [SMILES: CC(C)Oc1cc(-c2ccc3c(c2)-c2nc(-c4ncnn4C(C)C)sc2CCO3)ccn1] | 4-[2-(2-Isopropyl-2H-[1,2,4]triazol-3-yl)-4,5-dihydro-6-oxa-3-thia-1-aza-benzo[e]azulen-9-yl]-(2-isopropoxy)pyridine |
| 541 | 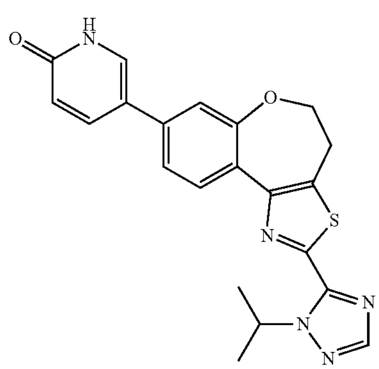 [SMILES: CC(C)n1ncnc1-c1nc2c(s1)CCOc1cc(-c3ccc(=O)[nH]c3)ccc1-2] | 5-[2-(2-Isopropyl-2H-[1,2,4]triazol-3-yl)-4,5-dihydro-6-oxa-3-thia-1-aza-benzo[e]azulen-8-yl]-1H-pyridin-2-one |

TABLE 2-continued

| No. | Structure | Name |
|---|---|---|
| 542 | 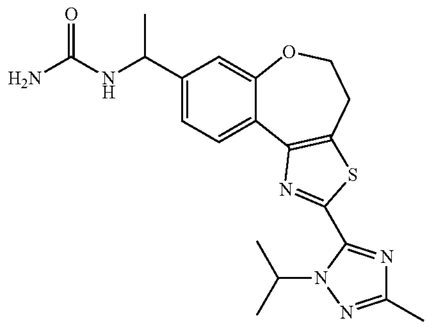 [SMILES: Cc1nc(-c2nc3c(s2)CCOc2cc(C(C)NC(N)=O)ccc2-3)n(C(C)C)n1] | {1-[2-(2-Isopropyl-5-methyl-2H-[1,2,4]triazol-3-yl)-4,5-dihydro-6-oxa-3-thia-1-aza-benzo[e]azulen-8-yl]-ethyl}-urea |
| 543 | 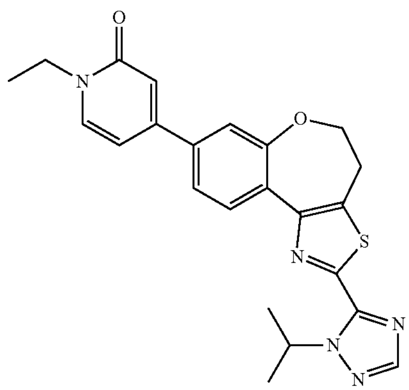 [SMILES: CCn1ccc(-c2ccc3c(c2)OCCc2sc(-c4ncnn4C(C)C)nc2-3)cc1=O] | 4-[2-(2-Isopropyl-2H-[1,2,4]triazol-3-yl)-4,5-dihydro-6-oxa-3-thia-1-aza-benzo[e]azulen-8-yl]-1-ethyl-pyridin-2-one |
| 544 | 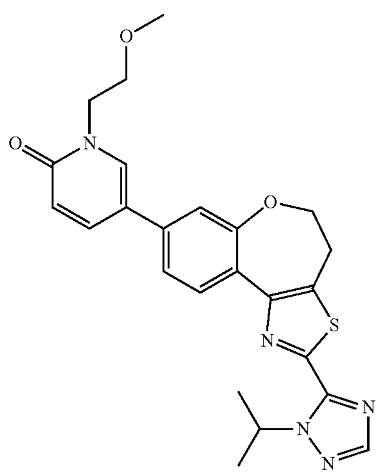 [SMILES: COCCn1cc(-c2ccc3c(c2)OCCc2sc(-c4ncnn4C(C)C)nc2-3)ccc1=O] | 5-[2-(2-Isopropyl-2H-[1,2,4]triazol-3-yl)-4,5-dihydro-6-oxa-3-thia-1-aza-benzo[e]azulen-8-yl]-1-(2-methoxyethyl)-pyridin-2-one |
| 545 | 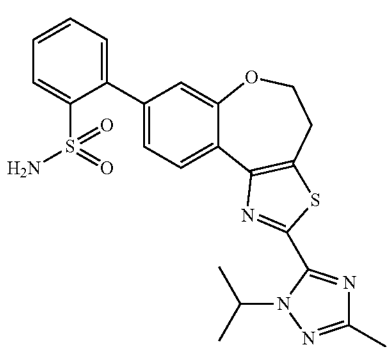 [SMILES: Cc1nc(-c2nc3c(s2)CCOc2cc(-c4ccccc4S(N)(=O)=O)ccc2-3)n(C(C)C)n1] | 2-[2-(2-Isopropyl-5-methyl-2H-[1,2,4]triazol-3-yl)-4,5-dihydro-6-oxa-3-thia-1-aza-benzo[e]azulen-8-yl]-benzenesulfonamide |

TABLE 2-continued

| No. | Structure | Name |
|-----|-----------|------|
| 546 | 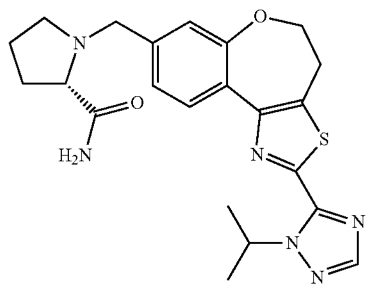 [SMILES: CC(C)n1ncnc1-c1nc2c(s1)CCOc1cc(CN3CCC[C@H]3C(N)=O)ccc1-2] | (S)-1-[2-(2-Isopropyl-2H-[1,2,4]triazol-3-yl)-4,5-dihydro-6-oxa-3-thia-1-aza-benzo[e]azulen-8-ylmethyl]-pyrrolidine-2-carboxylic acid amide |
| 547 | 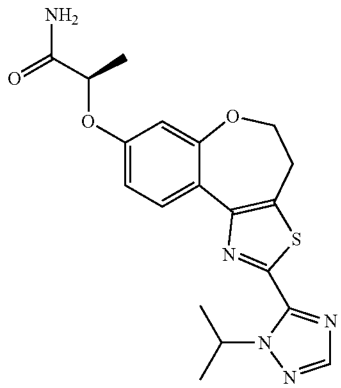 [SMILES: CC(C)n1ncnc1-c1nc2c(s1)CCOc1cc(O[C@H](C)C(N)=O)ccc1-2] | (R)-2-(2-Isopropyl-2H-[1,2,4]triazol-3-yl)-8-(1-amino-1-oxopropan-2-yloxy)-4,5-dihydro-6-oxa-3-thia-1-aza-benzo[e]azulene |
| 548 | 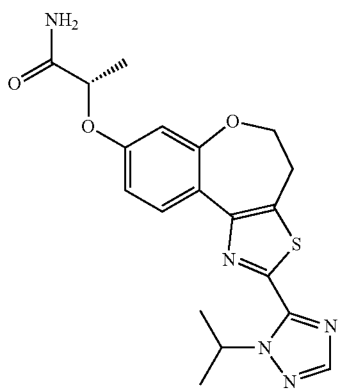 [SMILES: CC(C)n1ncnc1-c1nc2c(s1)CCOc1cc(O[C@@H](C)C(N)=O)ccc1-2] | (S)-2-(2-Isopropyl-2H-[1,2,4]triazol-3-yl)-8-(1-amino-1-oxopropan-2-yloxy)-4,5-dihydro-6-oxa-3-thia-1-aza-benzo[e]azulene |

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with e.g. the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Compounds of the present invention are useful for treating hyperproliferative diseases, conditions and/or disorders including, but not limited to, those characterized by over expression of lipid kinases, e.g. PI3 kinase. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, e.g., a human, suffering from such disease or condition. Also provided is the use of a compound of this invention in the preparation of a medicament for the treatment of the diseases and conditions described herein in a warm-blooded animal, such as a mammal, e.g. a human, suffering from such disorder.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. E.g., the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. E.g., a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, e.g., by coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (e.g., poly(2-hydroxyethylmethacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, e.g., inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. E.g., a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, e.g., 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. E.g., a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. E.g., an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, e.g. about 0.5 to 10% w/w, e.g. about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising e.g. cocoa butter or a salicylate.

Formulations suitable for intrapulmonary or nasal administration have a particle size e.g. in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, e.g. sealed ampoules and vials, and may be stored in a freeze-dried (lyophilized) condition requiring only the addition of the sterile liquid carrier, e.g. water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result e.g. from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic. The container may hold a compound of Formula I or II or a formulation thereof which is effective for treating the condition and may have a sterile access port (e.g., the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. E.g., if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I or II, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, e.g. in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Benzoxepin compounds of Formula I may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

In certain embodiments, compounds of Formula I may be readily prepared using well-known procedures to prepare benzoxepin compounds (Sekhar et al (1989) Sulfur Letters 9(6):271-277; Katsura et al (2000 J. Med. Chem. 43:3315-3321; Rueeger et al (2004) Biorganic & Med. Chem. Letters 14:2451-2457; Reiter et al (2007) Biorganic & Med. Chem. Letters 17:5447-5454; Banaszak et al (2006) Tetrahedron Letters 47:6235-6238) and other heterocycles, which are described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990).

Compounds of Formula I may be prepared singly or as compound libraries comprising at least 2, e.g. 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, the General Procedures show general methods which may be applied for preparation of Formula I compounds, as well as key intermediates. The Figures and Examples sections contain more detailed description of individual reaction steps. Those skilled in the art will appreciate that other synthetic routes may be used to synthesize the inventive compounds. Although certain starting materials and routes are depicted in the Schemes, General Procedures and Examples, other similar starting materials and routes can be substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, Third Ed., 1999.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, e.g.: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. E.g., boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (–) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the ¹H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures

General Procedure A

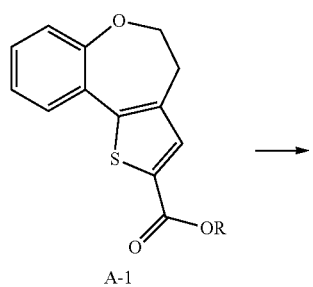

A-1

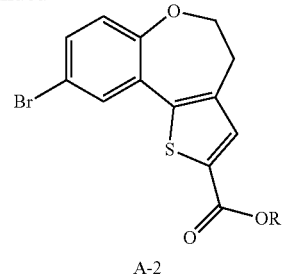

A-2

Benzoxepin intermediates, 4,5-dihydrobenzo[b]thieno[2,3-d]oxepine-2-carboxylate esters, A-1 can be selectively brominated with N-bromosuccinimide (NBS) in DMF to give 9-bromo-4,5-dihydrobenzo[b]thieno[2,3-d]oxepine-2-carboxylate esters A-2.

General Procedure B

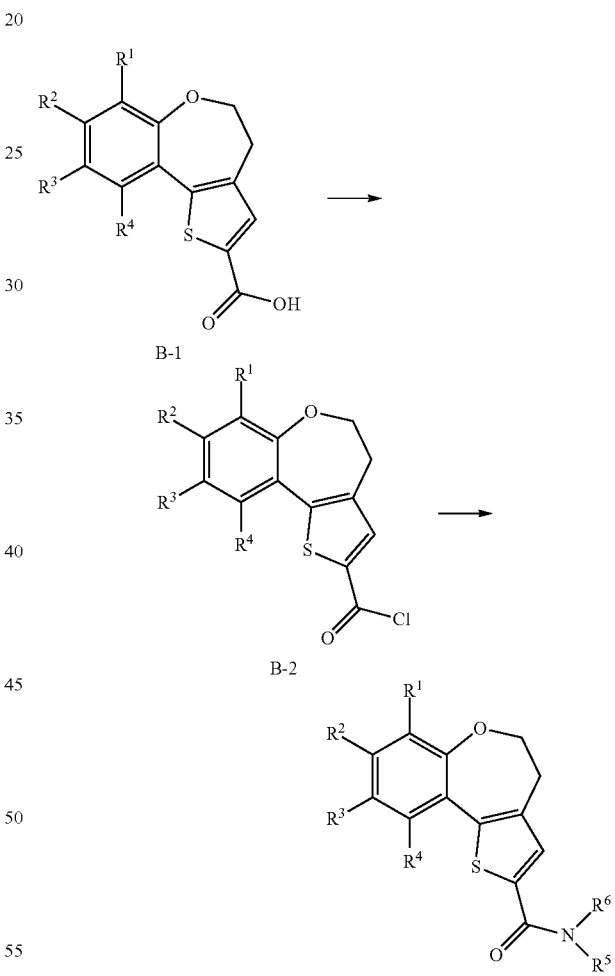

B-1

B-2

B-3

Benzoxepin carboxylic acid intermediates B-1 are converted to the acid chloride B-2 and reacted with primary or secondary amines with triethylamine, DMAP, and solvent such as dichloromethane. Reaction with a primary amine may be followed by N-alkylation, e.g. with methyl iodide and sodium hydride, to generate 4,5-dihydrobenzo[b]thieno[2,3-d]oxepine-2-carboxamide B-3.

E.g., to a suspension of carboxylic acid (0.4 mmol) in anhydrous dichloromethane, is added oxalyl chloride (0.7 mmol) and one drop of dimethyl formamide. After 30 minutes, concentrate in-vacuo. Residue is dissolved in acetonitrile, and potassium carbonate (0.9 mmol) and an amine, e.g. aniline (0.48 mmol) are added. Reaction mixture is stirred overnight at room temperature before diluting with water and ethylacetate. Organic phase is dried (MgSO$_4$) and concentrated in-vacuo.

Alternatively, other active esters of benzoxepin carboxylic acid intermediates B-1 can be formed as anhydrides, acyl imidazolides, acyl azides, and NHS esters to react with amines. Also, benzoxepin carboxylic acid intermediates B-1 can be coupled with amines by in situ formation of active ester intermediates under the broad array of known peptide coupling reagents and methodology.

E.g., to a solution of the carboxylic acid (1 eq) in DMF (6 mL) is added the amine (1.3 eq), HATU (1.3 eq) and diisopropylethyl amine (1.3 eq+1.3 eq for each HCl salt of the amine) and the reaction stirred at room temperature for 16 h. The mixture is partitioned between ethyl acetate and water. The organic layer was washed with brine (3×), dried (MgSO$_4$), reduced in vacuo and purified on silica to give the final amide.

General Procedure C

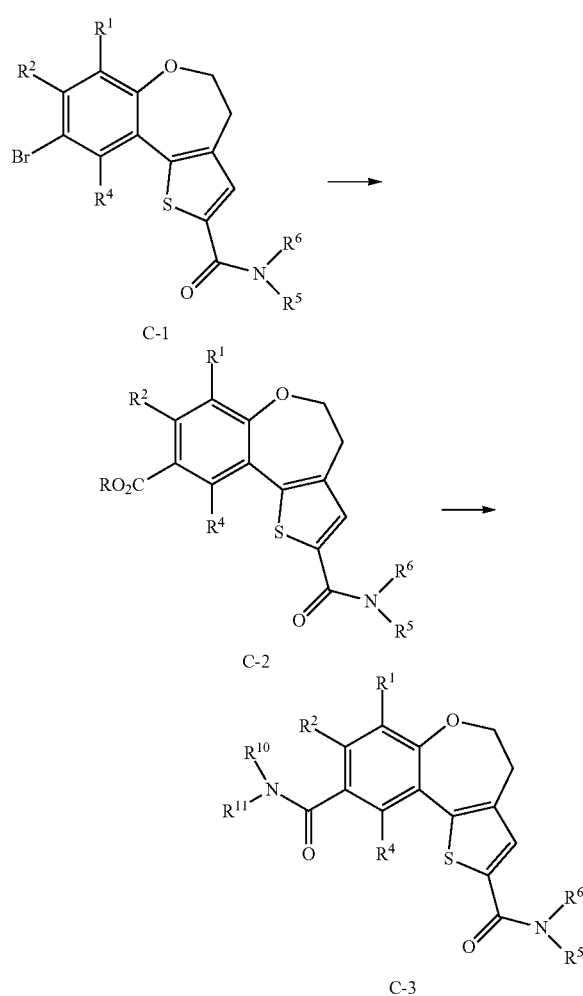

as Pd(OAc)$_2$, and an alcohol, such as methanol to give the carboxamide intermediate C-2. Saponification with lithium hydroxide, sodium hydroxide or other aqueous base to the 8-carboxylic acid intermediate, followed by coupling of a primary or secondary amine with a coupling reagent, such as HATU or DCC gives the 9-carboxamide intermediate C-3.

Alternatively, intermediate C-3 may be prepared directly from bromo intermediate C-1 by aminocarbonylation, following the procedures of Wannberg et al (2003) J. Org. Chem. 68:5750-5753.

General Procedure D

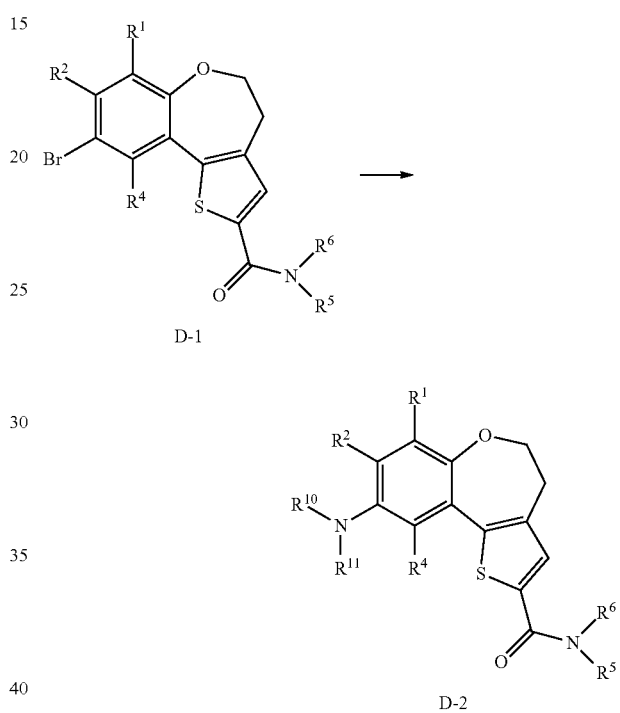

9-Bromo-4,5-dihydrobenzo[b]thieno[2,3-d]oxepine-2-carboxamide intermediates D-1 are aminated with primary or secondary amines (HNR$^{10}$R$^{11}$) or amides (H$_2$NC(=O)R$^{10}$), palladium complexes such as Pd$_2$(dba)$_3$, catalysts such as xantphos and BINAP, alkoxides such as NaOt-Bu or carbonates such as cesium carbonate, in toluene or dioxane, and heating to give aminated products D-2.

General Procedure E

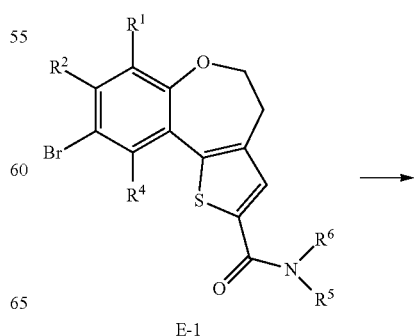

9-Bromo-4,5-dihydrobenzo[b]thieno[2,3-d]oxepine-2-carboxamide intermediates C-1 are carbonylated with carbon monoxide under high pressure with palladium catalysis, such

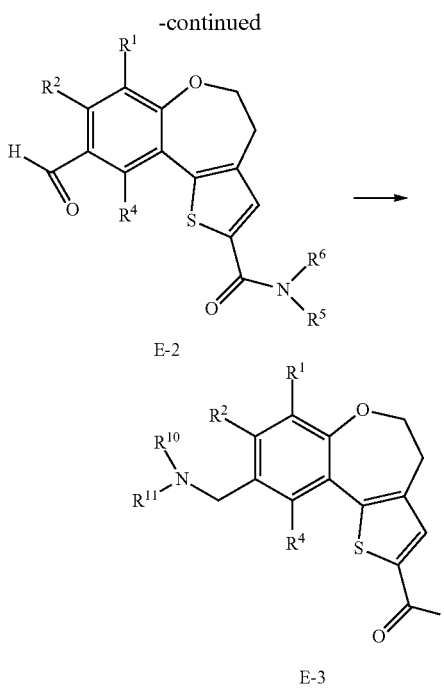

E-2

E-3

8-Bromo-4H-thieno[3,2-c]chromene-2-carboxamide intermediates E-1 are formylated with butyl lithium and dimethylformamide (DMF) to give E-2 which is reductively aminated with a hydride such as sodium acetoxyborohydride and a primary or secondary amine (HNR$^{10}$R$^{11}$).

FIGS. 1-15 show general methods for preparation of Formula I benzoxepin compounds and intermediates.

FIG. 1 shows a synthetic route to 2-Bromo-4,5-dihydro-6-oxa-1-thia-10-aza-benzo[e]azulene 5.

Figure 2:
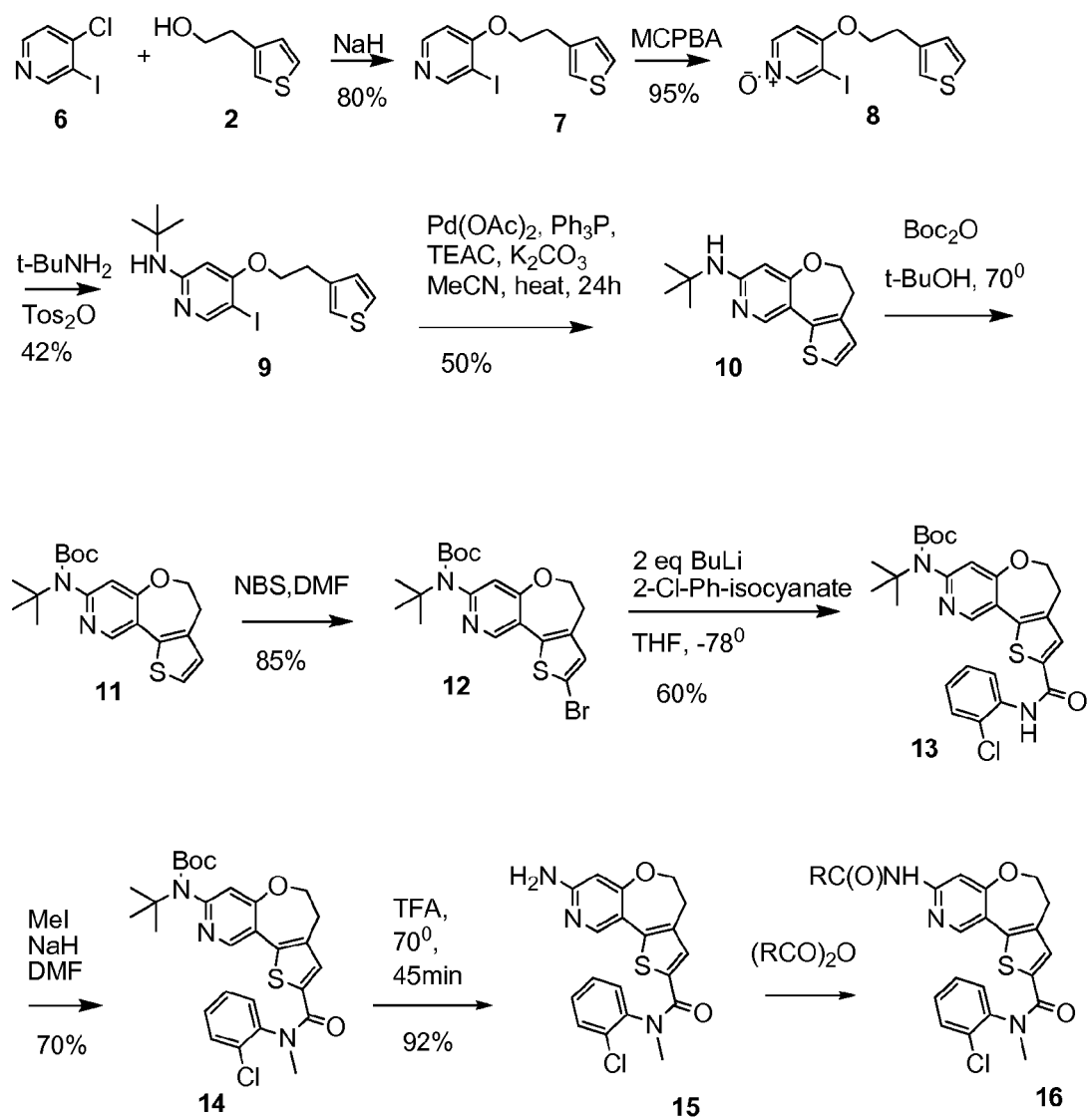
FIG. 2 shows a synthetic route to 8-Amino-4,5-dihydro-6-oxa-1-thia-9-aza-benzo[e]azulene-2-carboxylic acid (2-chloro-phenyl)-amide 15 and amide intermediates 16.

FIG. 2 shows a synthetic route to 8-Amino-4,5-dihydro-6-oxa-1-thia-9-aza-benzo[e]azulene-2-carboxylic acid (2-chloro-phenyl)-amide 15 and amide intermediates 16.

Figure 3:
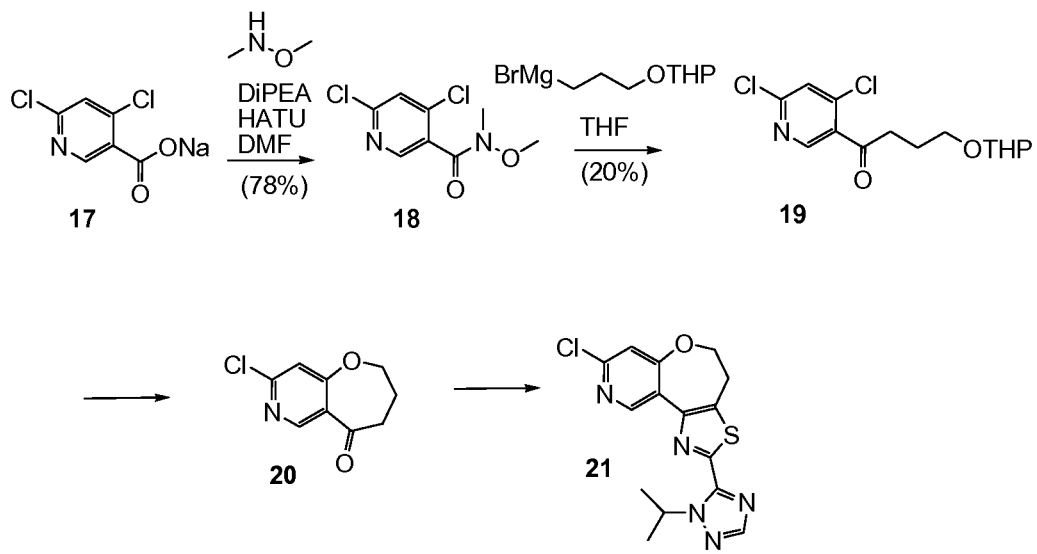
FIG. 3 shows a synthetic route to 8-Chloro-2-(2-isopropyl-2H-[1,2,4]triazol-3-yl)-4,5-dihydro-6-oxa-3-thia-1,9-diaza-benzo[e]azulene 21.

FIG. 3 shows a synthetic route to 8-Chloro-2-(2-isopropyl-2H-[1,2,4]triazol-3-yl)-4,5-dihydro-6-oxa-3-thia-1,9-diazabenzo[e]azulene 21.

Figure 4:
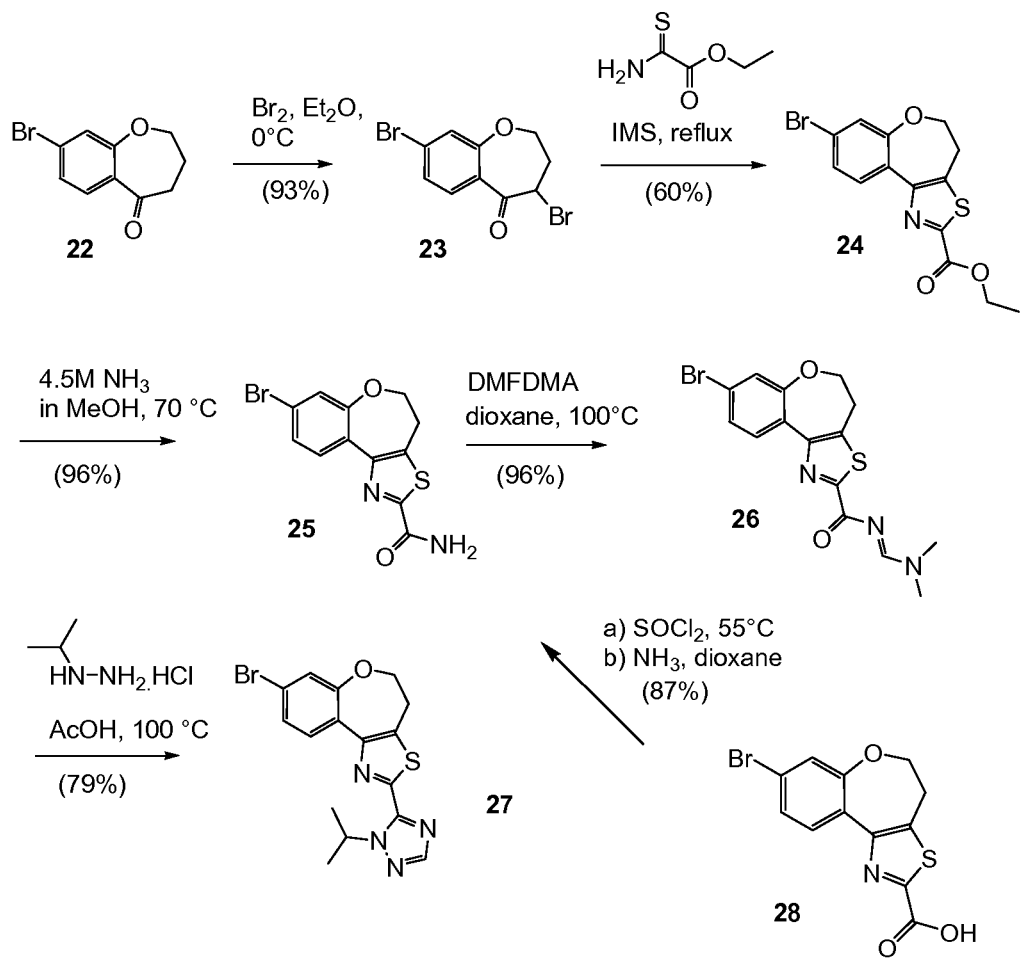
FIG. 4 shows a synthetic route to 8-Bromo-2-(2-isopropyl-2H-[1,2,4]triazol-3-yl)-4,5-dihydro-6-oxa-3-thia-1-aza-benzo[e]azulene 27 from 8-Bromo-4,5-dihydro-6-oxa-3-thia-1-aza-benzo[e]azulene-2-carboxylic acid amide 25

FIG. 4 shows a synthetic route to 8-Bromo-2-(2-isopropyl-2H-[1,2,4]triazol-3-yl)-4,5-dihydro-6-oxa-3-thia-1-aza-benzo[e]azulene 27 from 8-Bromo-4,5-dihydro-6-oxa-3-thia-1-aza-benzo[e]azulene-2-carboxylic acid amide 25

Figure 5:
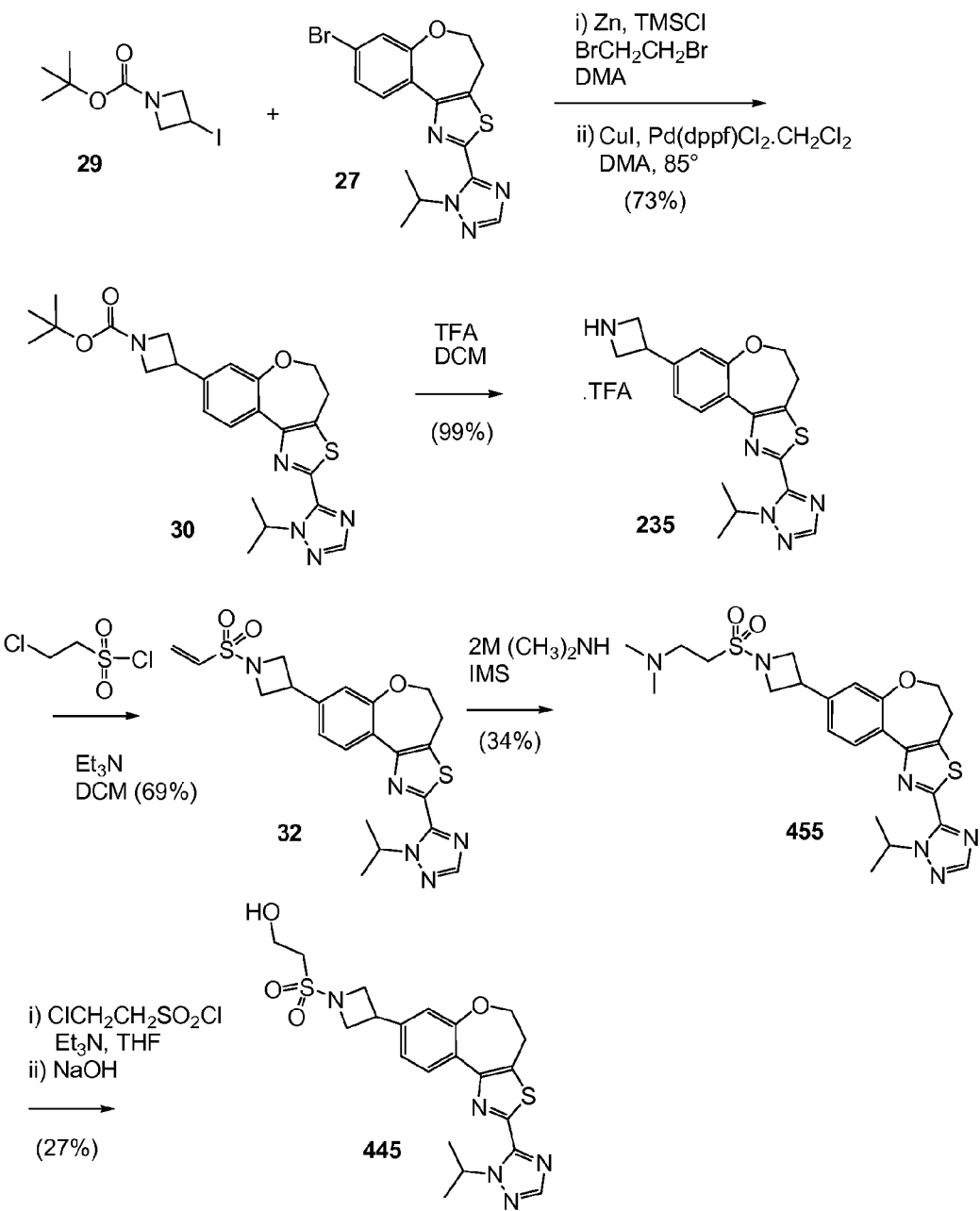
FIG. 5 shows a synthetic route to 8-Azetidin-3-yl-2-(2-isopropyl-2H-[1,2,4]triazol-3-yl)-4,5-dihydro-6-oxa-3-thia-1-aza-benzo[e]azulene 235, and sulfonamides 32, 445, 455.

FIG. 5 shows a synthetic route to 8-Azetidin-3-yl-2-(2-isopropyl-2H-[1,2,4]triazol-3-yl)-4,5-dihydro-6-oxa-3-thia-1-aza-benzo[e]azulene 235, and sulfonamides 32, 445, 455.

Figure 6:
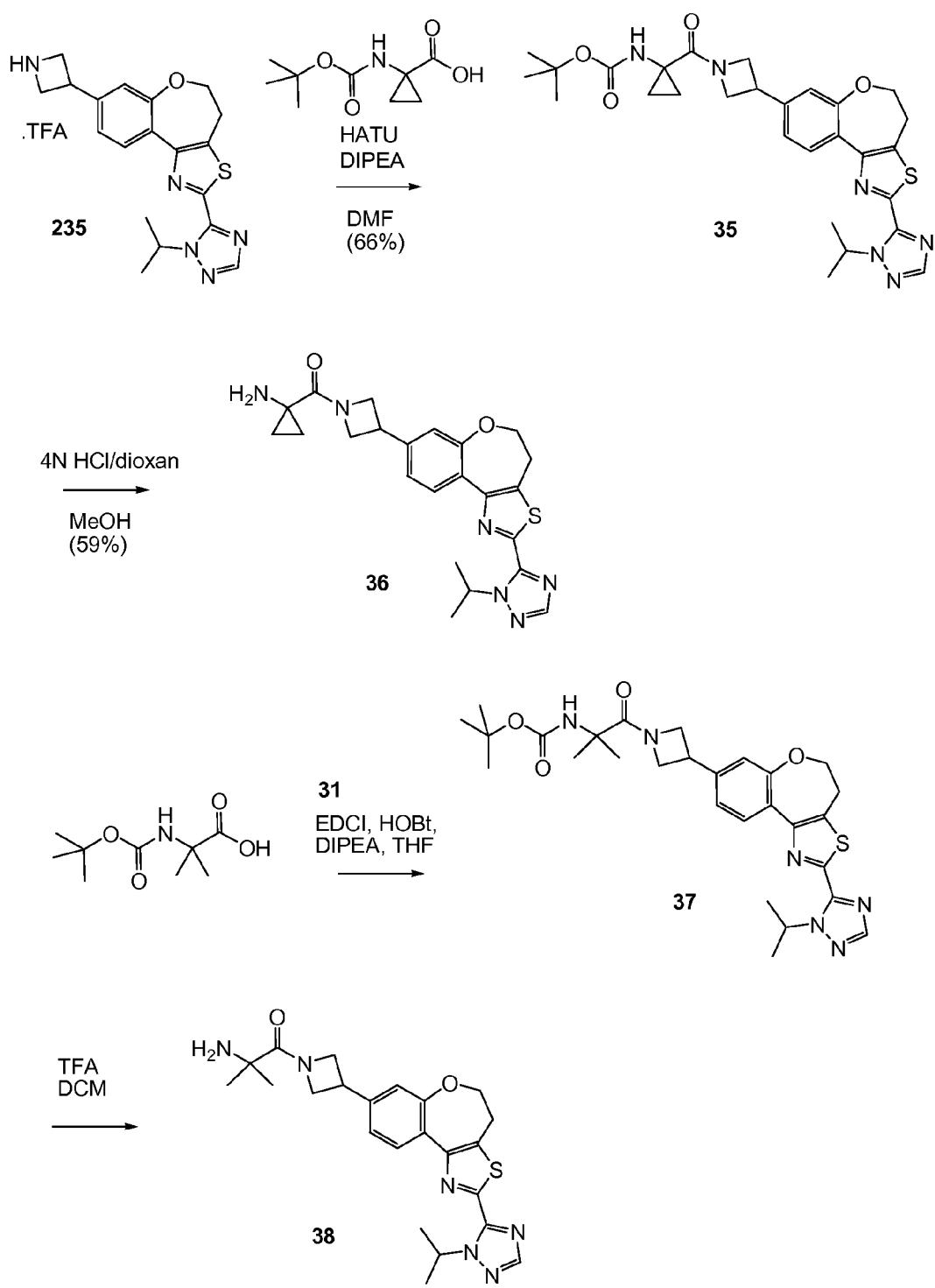
FIG. 6 shows a synthetic route to 36 and 38 from 8-Azetidin-3-yl-2-(2-isopropyl-2H-[1,2,4]triazol-3-yl)-4,5-dihydro-6-oxa-3-thia-1-aza-benzo[e]azulene 235

FIG. 6 shows a synthetic route to 36 and 38 from 8-Azetidin-3-yl-2-(2-isopropyl-2H-[1,2,4]triazol-3-yl)-4,5-dihydro-6-oxa-3-thia-1-aza-benzo[e]azulene 235

Figure 7:
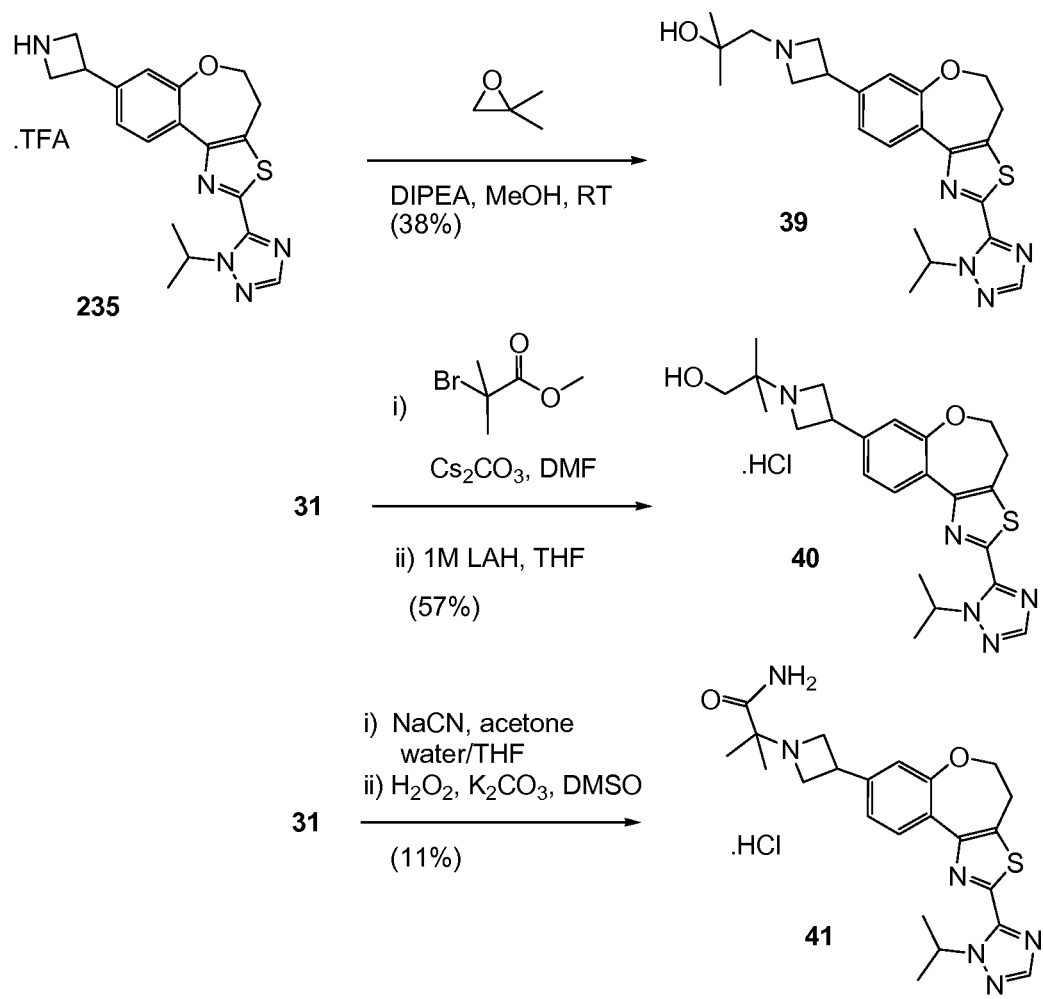
FIG. 7 shows a synthetic route to 39, 40, and 41 from 8-Azetidin-3-yl-2-(2-isopropyl-2H-[1,2,4]triazol-3-yl)-4,5-dihydro-6-oxa-3-thia-1-aza-benzo[e]azulene 235

FIG. 7 shows a synthetic route to 39, 40, and 41 from 8-Azetidin-3-yl-2-(2-isopropyl-2H-[1,2,4]triazol-3-yl)-4,5-dihydro-6-oxa-3-thia-1-aza-benzo[e]azulene 235

Figure 8:
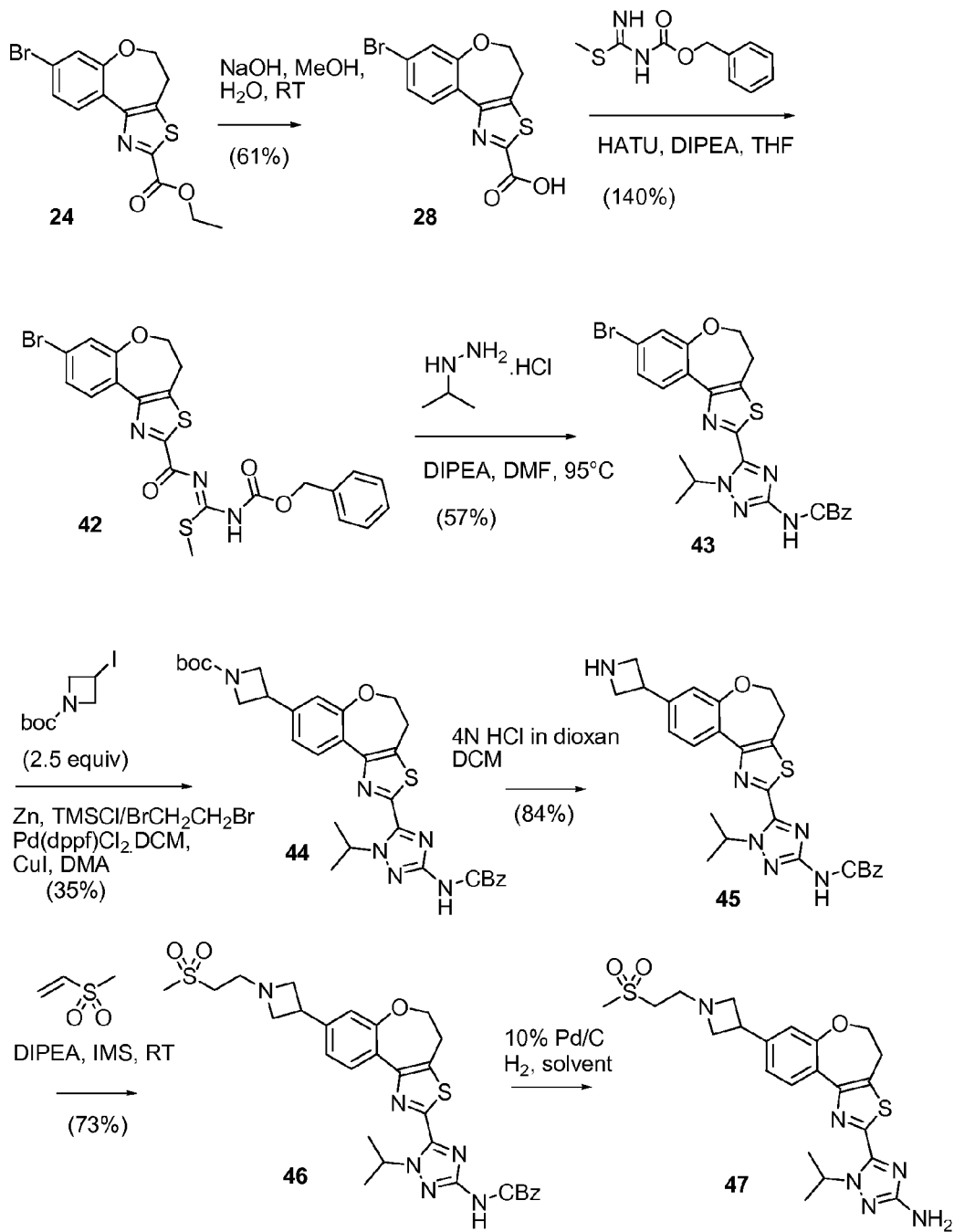
FIG. 8 shows a synthetic route to 47 from 24

FIG. 8 shows a synthetic route to 47 from 24

Figure 9:
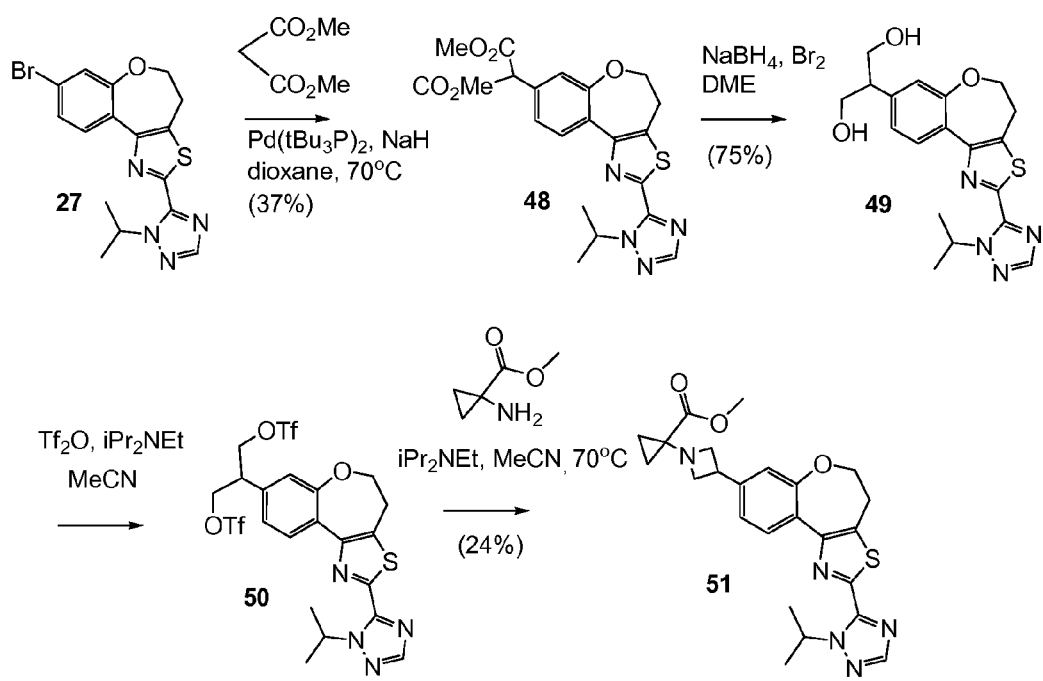
FIG. 9 shows a synthetic route to 51 from 27

FIG. 9 shows a synthetic route to 51 from 27

Figure 10:
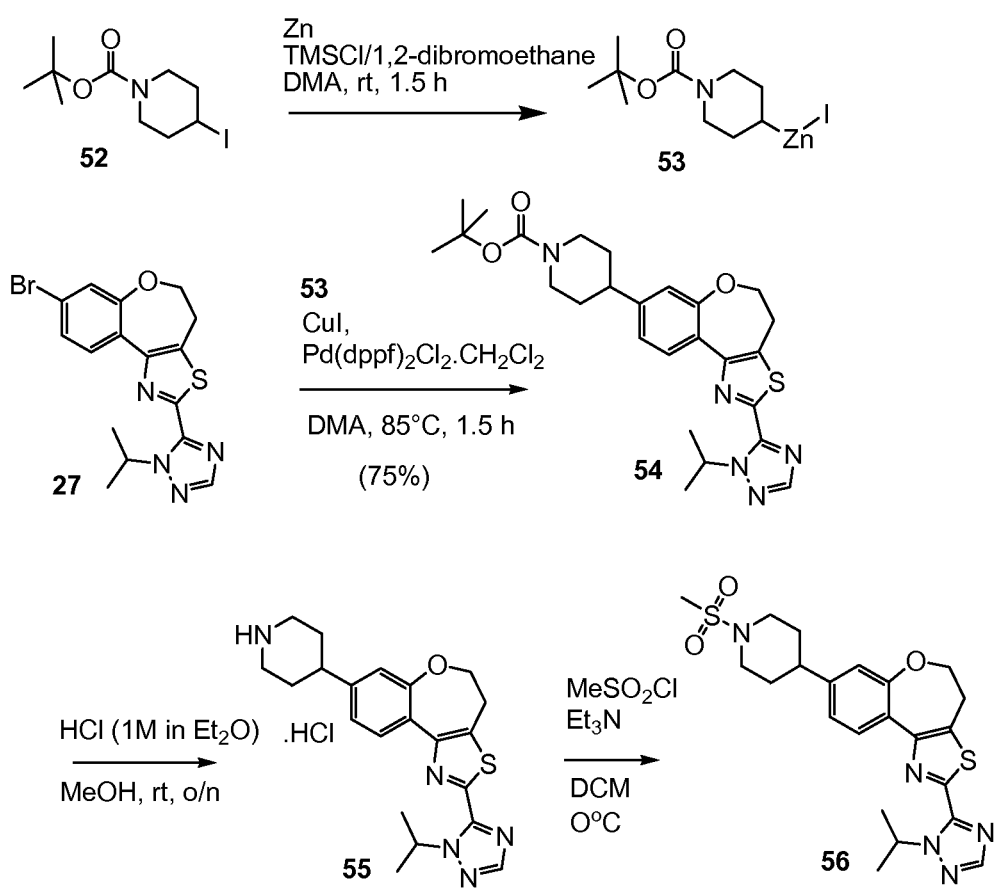
FIG. 10 shows a synthetic route to 56 from 53 and 27

FIG. 10 shows a synthetic route to 56 from 53 and 27

Figure 11:
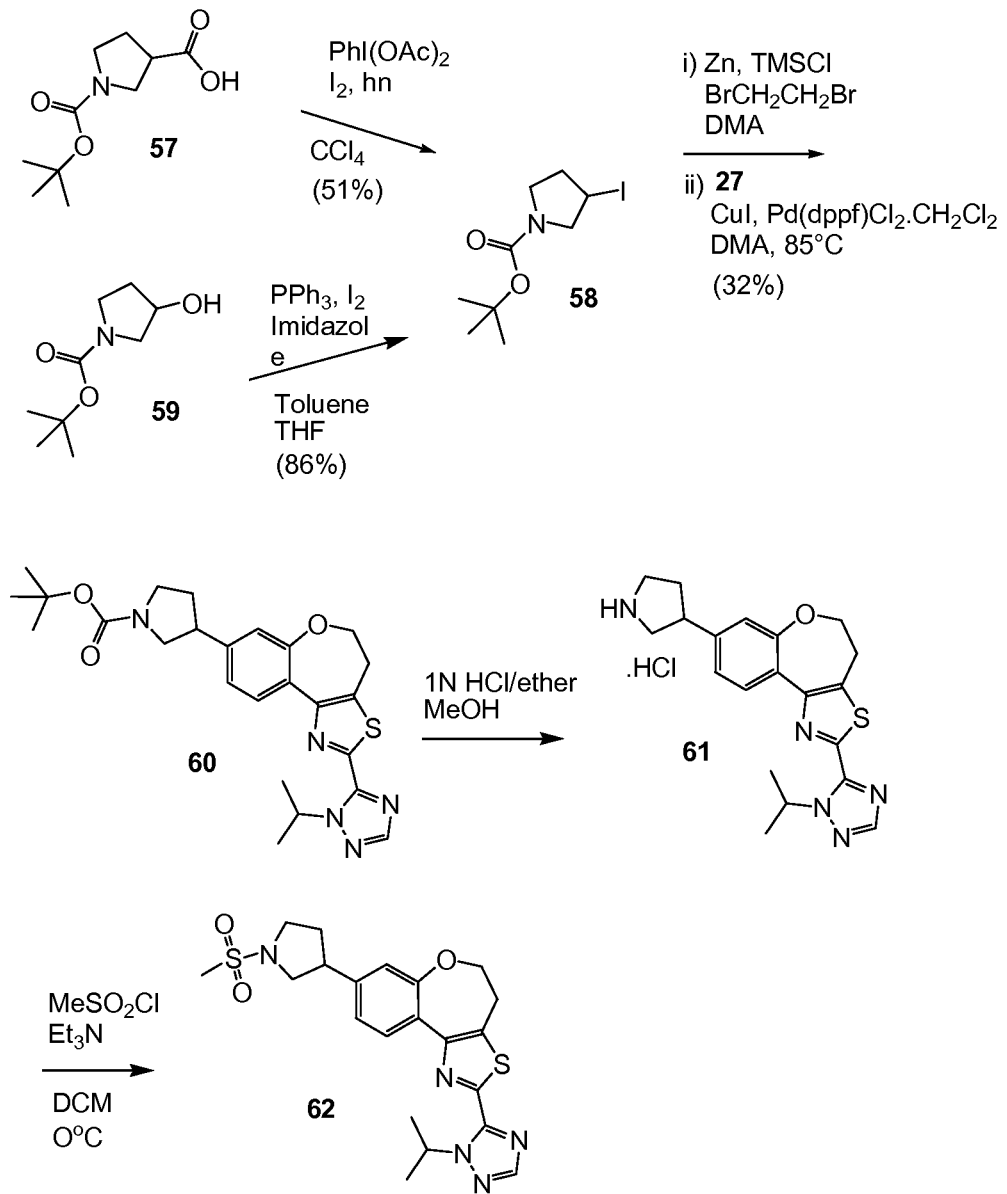
FIG. 11 shows a synthetic route to 62 from 58 and 27

FIG. 11 shows a synthetic route to 62 from 58 and 27

Figure 12:
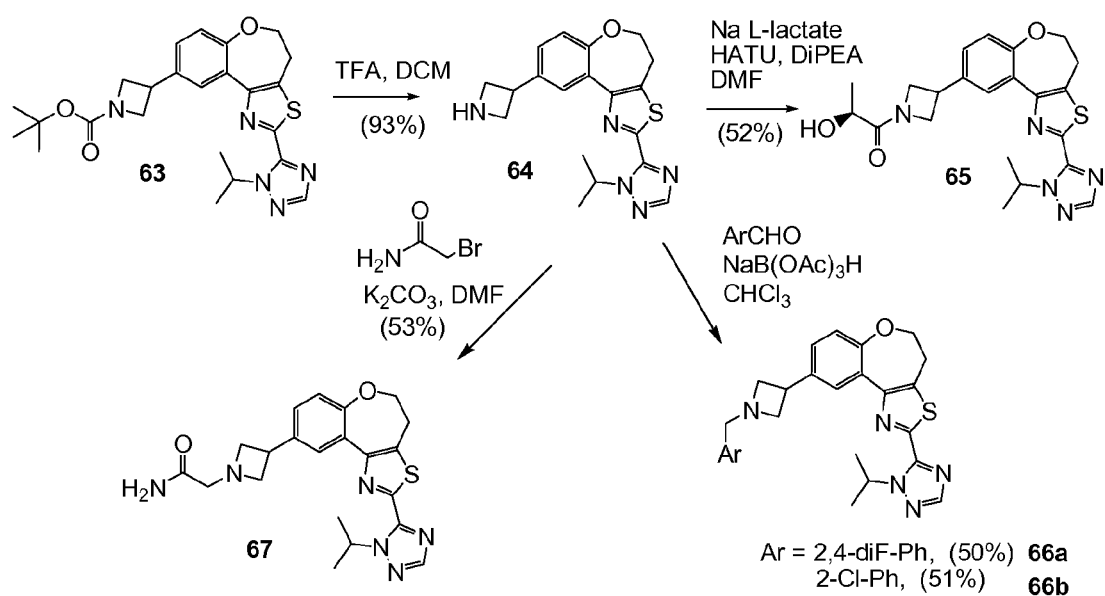
FIG. 12 shows a synthetic route to 66a and 66b from 63

FIG. 12 shows a synthetic route to 66a and 66b from 63

Figure 13:
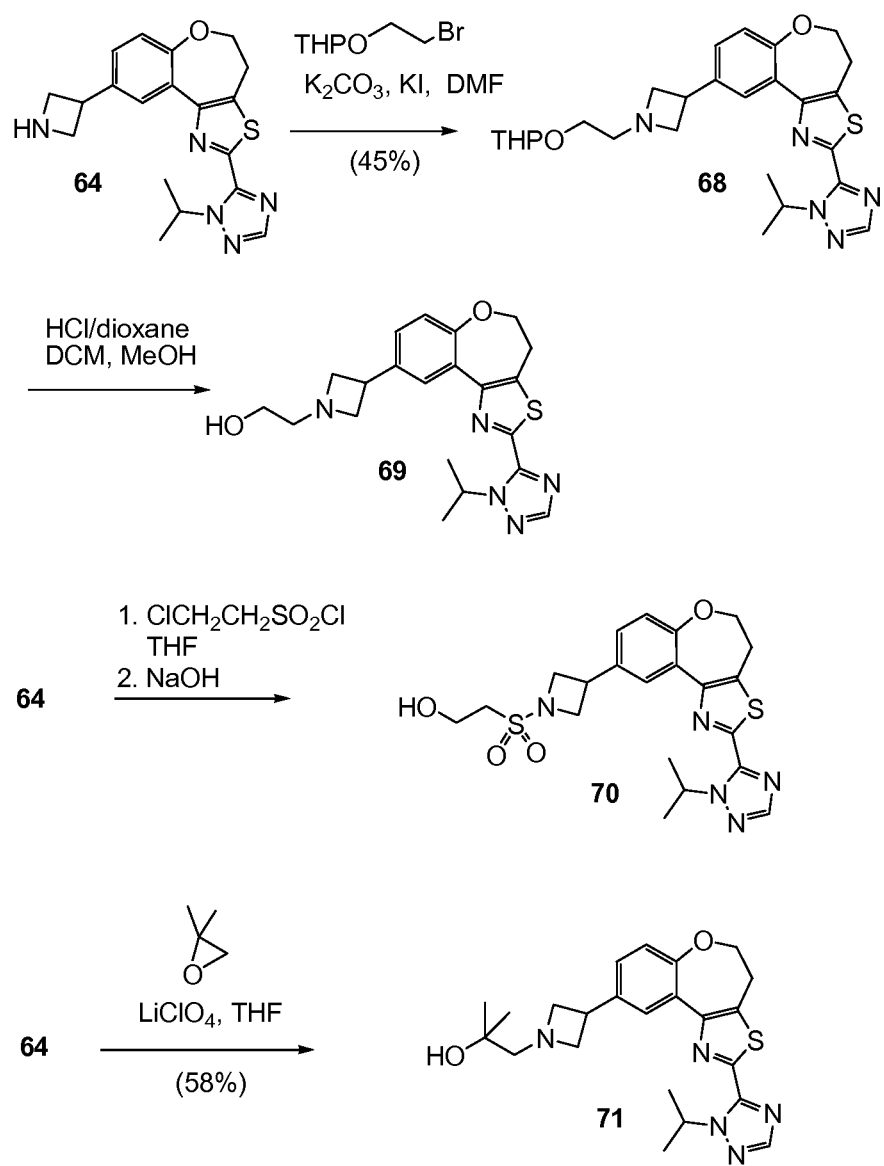
FIG. 13 shows a synthetic route to 69, 70, and 71 from 64

FIG. 13 shows a synthetic route to 69, 70, and 71 from 64

Figure 14:
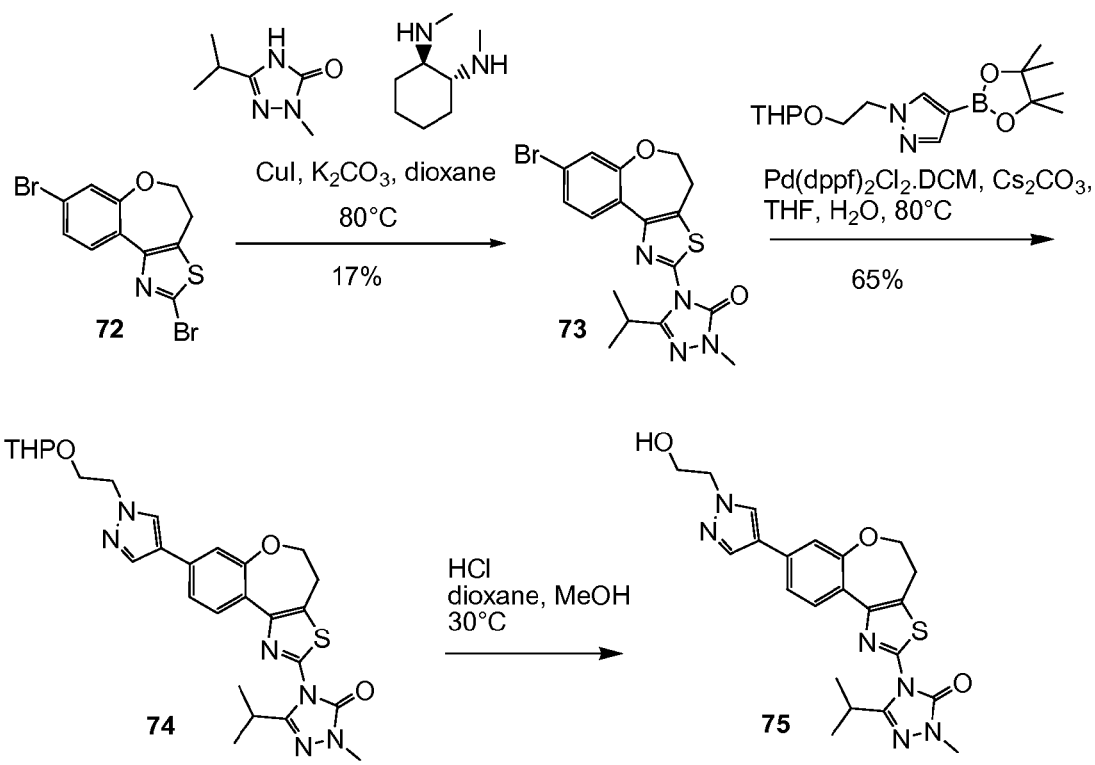
FIG. 14 shows a synthetic route to 75

FIG. 14 shows a synthetic route to 75

Figure 15:
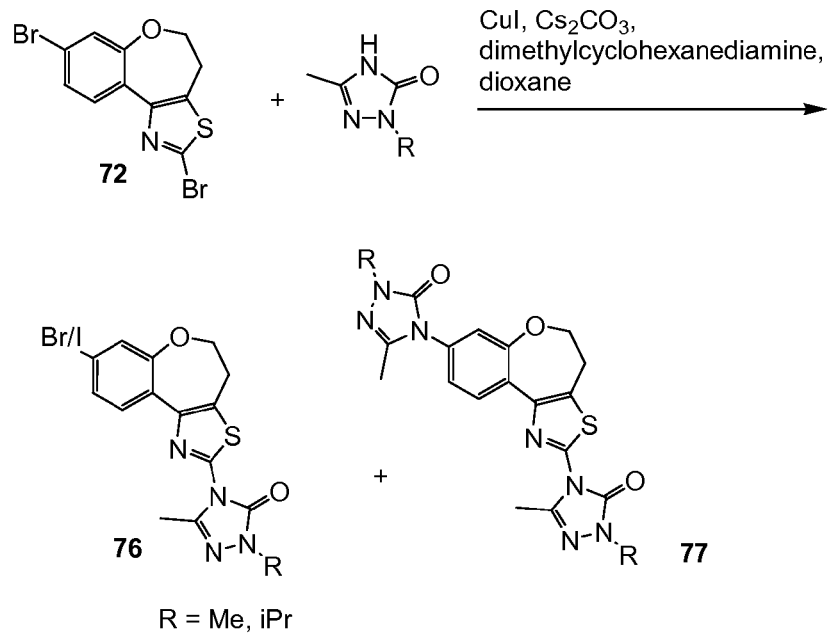
FIG. 15 shows a synthetic route to 76 and 77

FIG. 15 shows a synthetic route to 76 and 77

EXAMPLES

The chemical reactions described in the Examples may be readily adapted to prepare a number of other PI3K inhibitors of the invention, and alternative methods for preparing the compounds of this invention are deemed to be within the scope of this invention. E.g., the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma Aldrich Chemical Company, and were used without further purification unless otherwise indicated. The reactions set forth below were conducted generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). $^1$H NMR spectra were obtained at 400 MHz in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz). Chemical structures were named according to: vendor designation; IUPAC convention; ChemDraw Ultra, Version 9.0.1, CambridgeSoft Corp., Cambridge Mass.; or Autonom 2000 Name, MDL Inc. It is recognized by those skilled in the art that a compound may have more than one name, according to different conventions.

Example 1

4,8-dibromo-3,4-dihydrobenzo[b]oxepin-5(2H)-one

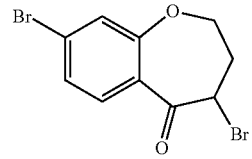 [SMILES: O=C1c2ccc(Br)cc2OCCC1Br]

Step 1: ethyl 4-(3-bromophenoxyl)butanoate

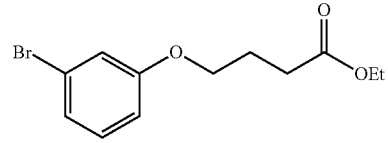 [SMILES: CCOC(=O)CCCOc1cccc(Br)c1]

Solid 3-bromophenol (10.0 g, 58 mmol) was added portion wise to a stirred suspension of K$_2$CO$_3$ in acetone (100 mL) at room temperature. Sodium iodide (NaI, 1.0 g) was added, followed by ethyl-4-bromobutyrate (9.2 mL, 64 mmol). The reaction mixture was heated at 80° C. overnight, cooled to room temperature, diluted with water and extracted with ethylacetate to give ethyl 4-(3-bromophenoxyl)butanoate.

Step 2: 4-(3-bromophenoxy)butanoic acid

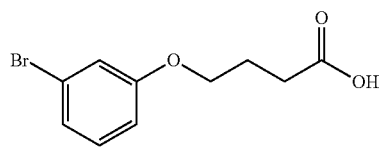

Ethyl 4-(3-bromophenoxyl)butanoate was taken up in 100 mL THF and 50 mL water and treated with lithium hydroxide LiOH (hydrate, 4.9 g). The whole was heated at 50° C. for 2 days. The mixture was cooled to room temperature and acidified to pH 1 with 2N HCl. The aqueous was extracted with ethylacetate. The combined organics were washed with brine and dried over sodium sulfate to give crude 4-(3-Bromophenoxy)butanoic acid as a sticky solid. $^1$H NMR (DMSO-d6, 500 MHz) 7.24 (m, 1H), 7.13 (m, 1H), 7.11 (m, 1H), 6.95 (m, 1H), 3.99 (m, 2H), 2.37 (m, 2H), 1.94 (m, 2H).

Step 3: 8-bromo-3,4-dihydrobenzo[b]oxepin-5(2H)-one

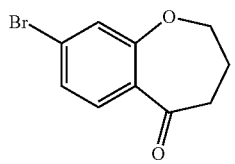 [SMILES: O=C1CCCOc2cc(Br)ccc21]

To a stirred suspension of polyphosphoric acid (PPA, ca. 60 g) and celite (ca. 40 g) in 100 mL toluene was added crude 4-(3-bromophenoxy)butanoic acid (ca. 58 mmol) in one portion, 10 mL toluene rinse. The resultant suspension was heated at 110° C. for 5 hr. The toluene was decanted through a plug of celite and the remaining slurry was washed repeatedly with toluene and ethylacetate. The eluent was concentrated and purified by flash column chromatography (4:1 hex:EtOAc) to give 8-bromo-3,4-dihydrobenzo[b]oxepin-5(2H)-one (7 g, ca. 50% yield). $^1$H NMR (DMSO-d6, 500 MHz) 7.55 (d, J=8.5 Hz, 1H), 7.37 (d, J=1.5 Hz, 1H), 7.35 (dd, J=8.5, 1.5 Hz, 1H), 4.24 (t, J=6.5 Hz, 2H), 2.79 (t, J=7.0 Hz, 2H), 2.14 (m, 2H).

Step 4: 4,8-dibromo-3,4-dihydrobenzo[b]oxepin-5(2H)-one

To a stirred solution of 8-bromo-3,4-dihydro-2H-benzo[b] oxepin-5-one (3.10 g; 12.8 mmol) in Et$_2$O at 0° C. was added Br$_2$ (625 µl; 12.2 mmol) and the reaction mixture was allowed to warm to r.t. over 2 h. Volatiles were evaporated and the residue purified by flash column chromatography (0-20% EtOAc in hexanes) to give 4,8-dibromo-3,4-dihydrobenzo[b] oxepin-5(2H)-one as a colorless solid (4.0 g, 96% yield). $^1$H NMR (400 MHz, CDCl$_3$) δ 7.18-7.21 (m, 2H), 7.55 (d, J=8.0, 1H), 4.87 (app. t, J=5.2, 2H), 4.33-4.39 (m, 1H), 4.09-4.16 (m, 1H), 2.78-2.91 (m, 1H), 2.40-2.49 (m, 1H).

Example 2

8-Bromo-2-ethynyl-4,5-dihydro-6-oxa-3-thia-1-aza-benzo[e]azulene

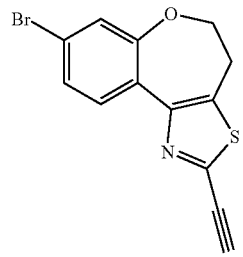 [SMILES: C#Cc1nc2c(s1)CCOc1cc(Br)ccc1-2]

Step 1: 8-Bromo-4,5-dihydro-6-oxa-3-thia-1-aza-benzo[e]azulene-2-carboxylic acid ethyl ester

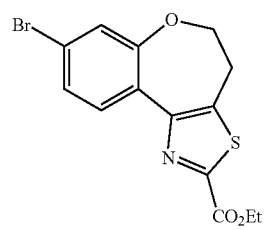 [SMILES: CCOC(=O)c1nc2c(s1)CCOc1cc(Br)ccc1-2]

To a stirred solution of 4,8-dibromo-3,4-dihydrobenzo[b] oxepin-5(2H)-one (2.17 g; 6.8 mmol) in EtOH (70 ml) was added ethyl thiooxamate (2.72 g; 20.4 mmol) and the reaction mixture was heated at reflux temperature over 4 d. The reaction mixture was concentrated and the residue purified by flash column chromatography (0-20% EtOAc in hexanes) to give 8-Bromo-4,5-dihydro-6-oxa-3-thia-1-aza-benzo[e]azulene-2-carboxylic acid ethyl ester as a yellow solid (1.08 g, 45% yield). $^1$H NMR (400 MHz, CDCl$_3$) δ 8.36 (d, J=8.4, 1H), 7.16-7.22 (m, 2H), 4.42 (q, J=7.2, 2H), 4.31 (app. t, J=5.2, 2H), 3.32 (app. t, J=5.2, 2H), 1.38 (t, J=7.2, 3H).

Step 2: 8-Bromo-4,5-dihydro-6-oxa-3-thia-1-aza-benzo[e]azulene-2-carboxylic acid

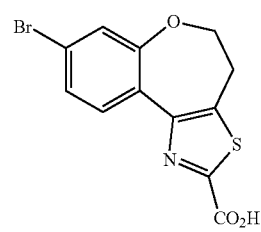 [SMILES: O=C(O)c1nc2c(s1)CCOc1cc(Br)ccc1-2]

To a stirred solution of 8-Bromo-4,5-dihydro-6-oxa-3-thia-1-aza-benzo[e]azulene-2-carboxylic acid ethyl ester in THF (10 ml) and MeOH (5 ml) was added a solution of NaOH (117 mg, 2.9 mmol) in water (2 ml). The reaction mixture was stirred at room temperature for 2 h upon which time it was acidified with 2M HCl. The aqueous was extracted with CH$_2$Cl$_2$ and the combined organics dried (MgSO$_4$) and concentrated to give 8-Bromo-4,5-dihydro-6-oxa-3-thia-1-aza-benzo[e]azulene-2-carboxylic acid as a colorless solid (396 mg; 83%). $^1$H NMR (400 MHz, CDCl$_3$) δ 8.22 (d, J=8.4, 1H), 7.19-7.24 (m, 2H), 4.33 (t, J=5.2, 2H), 3.36 (t, J=5.2, 2H).

Step 3: (8-Bromo-4,5-dihydro-6-oxa-3-thia-1-aza-benzo[e]azulen-2-yl)-methanol

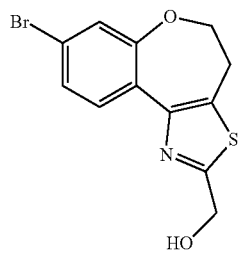 [SMILES: OCc1nc2c(s1)CCOc1cc(Br)ccc1-2]

Lithium tetrahydroaluminate (0.363 g, 9.56 mmol) was suspended in tetrahydrofuran (30 mL) and cooled to 0° C. A solution of 8-Bromo-4,5-dihydro-6-oxa-3-thia-1-aza-benzo[e]azulene-2-carboxylic acid (1.04 g, 3.19 mmol) in tetrahydrofuran (1 mL) was then added dropwise over a 10 min period. The resulting reaction mixture was stirred while warming to r.t. for 12 h. LCMS indicated that the reaction was completely converted with a minor uncharacterized impurity present (<5%). The reaction was quenched by diluting with saturated Rochelle's salt solution and EtOAc (1:1, 200 mL). The mixture was stirred very vigorously until the phases separated. The layers were then partitioned and the aqueous layer was extracted with EtOAc (3x). The combined organic portions were dried over MgSO$_4$, filtered and concentrated. The crude residue was purified by ISCO chromatography (40 g column, 0-75% EtOAc/heptane) to provide 0.63 g (63% yield) of (8-Bromo-4,5-dihydro-6-oxa-3-thia-1-aza-benzo[e]azulen-2-yl)-methanol. LC/MS (ESI+): m/z 313.2 (M+H).

Step 4: 8-Bromo-4,5-dihydro-6-oxa-3-thia-1-aza-benzo[e]azulene-2-carbaldehyde

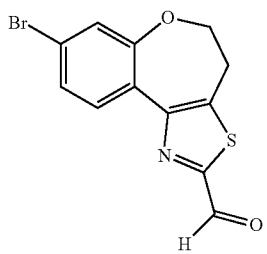 [SMILES: O=Cc1nc2c(s1)CCOc1cc(Br)ccc1-2]

Oxalyl chloride (0.24 mL, 2.9 mmol) was added dropwise to a solution of methyl sulfoxide (0.20 mL, 2.9 mmol) in dry dichloromethane (5 mL) and the resulting mixture was stirred 5 min. A solution of (8-Bromo-4,5-dihydro-6-oxa-3-thia-1-aza-benzo[e]azulen-2-yl)-methanol (0.60 g, 1.9 mmol) in dichloromethane (5 mL) was added portion-wise to the mixture and followed immediately by triethylamine (0.8 mL, 5.8 mmol). The reaction mixture was stirred and monitored by the disappearance of the starting alcohol. The reaction was quenched by the addition of water and EtOAc. The aqueous layer was extracted with EtOAc, dried over MgSO$_4$, filtered and concentrated in vacuo. The residue was purified by ISCO chromatography (0-50% EtOAc/heptane) to provide 8-Bromo-4,5-dihydro-6-oxa-3-thia-1-aza-benzo[e]azulene-2-carbaldehyde (0.41 g, 69% yield). $^1$H NMR (400 MHz, CDCl$_3$) δ 9.97 (s, 1H), 8.39 (dd, J=8.5, 6.8, 1H), 7.37-7.15 (m, 2H), 4.38 (m, 2H), 4.12 (d, J=9.5, 1H)

Step 5: 8-Bromo-2-ethynyl-4,5-dihydro-6-oxa-3-thia-1-aza-benzo[e]azulene

8-Bromo-4,5-dihydro-6-oxa-3-thia-1-aza-benzo[e]azulene-2-carbaldehyde (0.688 g, 2.2 mmol) was dissolved in methanol (8 mL) and methyl 2-diazo-2-(dimethoxyphosphoryl)acetate (0.923 g, 4.44 mmol) was added followed by potassium carbonate (0.613 g, 4.44 mmol). The resulting mixture was stirred 12 h at ambient temperature and quenched by the addition of sat. NH$_4$Cl aqueous solution and stirred 5 min. Diluted with H$_2$O and EtOAc, extracted the aqueous layer with EtOAc (2x) and the combined organic portions were washed with brine. Dried over MgSO$_4$, filtered and concentrated in vacuo. The residue was purified by ISCO chromatography (24 g column, 0-25% EtOAc/heptane) to provide 8-Bromo-2-ethynyl-4,5-dihydro-6-oxa-3-thia-1-aza-benzo[e]azulene as an oil (0.26 g, 38% yield). $^1$H NMR (400 MHz, CDCl$_3$) δ 8.35 (d, J=8.5, 1H), 7.31-7.18 (m, 2H), 4.37 (t, J=5.1, 2H), 3.49 (s, 1H), 3.33 (t, J=5.1, 2H)

Example 3

9-Bromo-4,5-dihydro-6-oxa-3-thia-1-aza-benzo[e]azulene-2-carboxylic acid

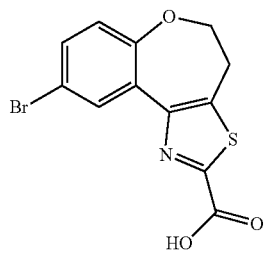 [SMILES: O=C(O)c1nc2c(s1)CCOc1ccc(Br)cc1-2]

Step 1:
1-(5-bromo-2-(2-bromoethoxy)phenyl)ethanone

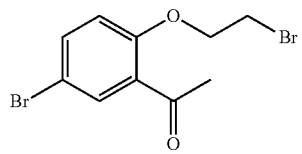

To a stirred solution of 5'-bromo-2'-hydroxyacetophenone (10 g, 46.5 mmol) in methyl ethyl ketone (100 mL) was added K$_2$CO$_3$ (13.5 g, 97.7 mmol) followed by 1,2-dibromoethane (20 mL, 232.5 mmol). The reaction mixture was heated at a mild reflux temperature (ca. 80° C.) for 16 h at which point the reaction flask was cooled to room temperature. The resultant

Step 2:
7-bromo-3,4-dihydrobenzo[b]oxepin-5(2H)-one

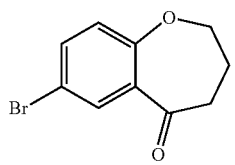 [SMILES: O=C1CCCOc2ccc(Br)cc21]

To a slurry of NaH (60% dispersion in mineral oil) (1.48 g, 37.1 mmol) in THF (~50 mL) at room temperature was added 1-(5-bromo-2-(2-bromoethoxyl)phenyl)ethanone (8.07 g, 25.1 mmol). The reaction mixture was slowly heated to reflux and allowed to stir for 20 h. The solvent was removed under vacuum pressure and the concentrated residue was absorbed onto silica gel and purified by column chromatography (4:1 ethyl acetate/petroleum ether). The product was afforded as a yellow oil after the solvents were removed, providing 4.22 g (70%) of 7-bromo-3,4-dihydrobenzo[b]oxepin-5(2H)-one. $^1$H NMR (CDCl$_3$) δ 7.87 (d, J=2.6 Hz, 1H), 7.50 (dd, J=2.6, 8.1 Hz, 1H), 6.97 (d, J=8.8 Hz, 2H), 4.24 (t, J=6.6 Hz, 2H), 2.89 (t, J=7.0 Hz, 2H), 2.15-2.29 (m, 2H).

Step 3:
4,7-dibromo-3,4-dihydrobenzo[b]oxepin-5(2H)-one

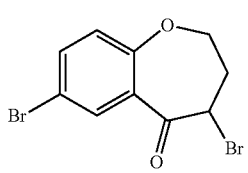 [SMILES: O=C1c2cc(Br)ccc2OCCC1Br]

To 7-bromo-3,4-dihydrobenzo[b]oxepin-5(2H)-one (3 g, 12 mmol) in ether (110 mL) was added bromine (0.7 mL, 14 mmol) and allowed to stir at room temperature overnight. The reaction mixture was concentrated under reduced pressure and purified via ISCO chromatography (hexane to 20% hexane in EtOAc over 45 minutes). Collected fractions and concentrated to give 4,7-dibromo-3,4-dihydrobenzo[b]oxepin-5(2H)-one (3.53 g, 89%). $^1$H NMR (500 MHz, CDCl$_3$) δ 7.86 (d, J=2.5, 1H), 7.52 (dt, J=28.5, 14.2, 1H), 6.97 (d, J=8.7, 1H), 4.95 (dd, J=7.6, 6.8, 1H), 4.53-4.36 (m, 1H), 4.17 (ddd, J=12.8, 9.9, 4.4, 1H), 3.04-2.84 (m, 1H), 2.52 (ddt, J=14.7, 7.8, 4.5, 1H)

Step 4: 9-Bromo-4,5-dihydro-6-oxa-3-thia-1-aza-benzo[e]azulene-2-carboxylic acid ethyl ester

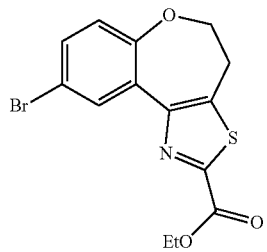 [SMILES: CCOC(=O)c1nc2c(s1)CCOc1ccc(Br)cc1-2]

To 4,7-dibromo-3,4-dihydrobenzo[b]oxepin-5(2H)-one (3.4 g, 11 mmol) and ethyl thioamidooxalate (4.2 g, 32 mmol) was added ethanol (81 mL) and heated at reflux (at 80° C.) for 4 days. The reaction mixture was cooled to room temperature and cooled in an ice bath. The precipitate was collected by filtration to give 9-Bromo-4,5-dihydro-6-oxa-3-thia-1-aza-benzo[e]azulene-2-carboxylic acid ethyl ester (2.59 g, 69%). LC/MS (ESI+): m/z 355 (M+H).

Step 5: 9-Bromo-4,5-dihydro-6-oxa-3-thia-1-aza-benzo[e]azulene-2-carboxylic acid To 9-Bromo-4,5-dihydro-6-oxa-3-thia-1-aza-benzo[e]azulene-2-carboxylic acid ethyl ester (2.52 g, 7.11 mmol) and LiOH (1.53 g, 36.6 mmol) was added THF (6.5 mL) and water (6.5 mL) and allowed to stir at room temperature overnight. The reaction mixture was concentrated under reduced pressure to remove the THF. The reaction mixture was diluted with EtOAc and 1 N HCl and warmed in a water bath to solubilize the solid. The layers were separated and the organic extract was washed sequentially with water and brine. The combined organic extracts were dried over MgSO$_4$ and filtered. The filtrate was concentrated under reduced pressure to give 9-Bromo-4,5-dihydro-6-oxa-3-thia-1-aza-benzo[e]azulene-2-carboxylic acid. LC/MS (ESI+): m/z 327 (M+H)

Example 4

9-Bromo-4,5-dihydro-6-oxa-3-thia-1-aza-benzo[e]azulene-2-carboxylic acid (2-hydroxy-ethyl)-isopropyl-amide

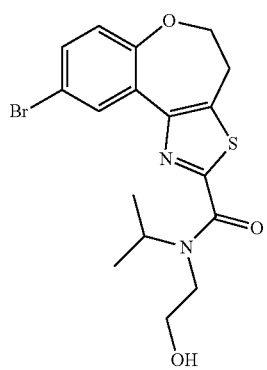 [SMILES: CC(C)N(CCO)C(=O)c1nc2c(s1)CCOc1ccc(Br)cc1-2]

9-Bromo-4,5-dihydro-6-oxa-3-thia-1-aza-benzo[e]azulene-2-carboxylic acid (2.4 g, 7.4 mmol) was dissolved in N,N-Dimethylformamide (DMF, 50 mL, 600 mmol). Added N,N,N'N'-Tetramethyl-O-(7-azabenzotriazol-1-yl)uranium Hexafluorophosphate (3.1 g, 8.1 mmol) and N,N-Diisopropylethylamine (6.4 mL, 37 mmol) and let stir for 10 minutes. Added 2-(isopropylamino)ethanol (1.5 g, 15 mmol) and let the reaction stir for 2 hours. More N,N,N'N'-Tetramethyl-O-(7-azabenzotriazol-1-yl)uranium Hexafluorophosphate was added to the reaction (2.8 g, 7.4 mmol) and let the reaction stir for another 3 hours. Reaction was complete by LCMS. Concentrated in vacuo and flash purified on the ISCO 0 to 50% ethyl acetate in hexanes two times to give 9-Bromo-4,5-dihydro-6-oxa-3-thia-1-aza-benzo[e]azulene-2-carboxylic acid (2-hydroxy-ethyl)-isopropyl-amide (2.05 g, 68% yield).

Example 5

9-Bromo-4,5-dihydro-6-oxa-3-thia-1-aza-benzo[e]azulene-2-carboxylic acid amide

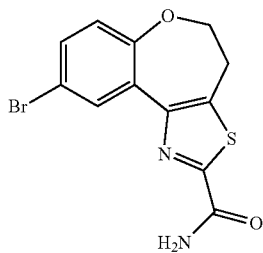

To 9-Bromo-4,5-dihydro-6-oxa-3-thia-1-aza-benzo[e]azulene-2-carboxylic acid (2.13 g, 6.53 mmol) in THF (22 mL) was added ammonium chloride (1.40 g, 26.1 mmol), DIEA (2.27 mL, 13.1 mmol), and then HATU (2.73 g, 7.18 mmol). The reaction mixture was allowed to stir at room temperature for 16 h. The reaction mixture was diluted with sodium bicarbonate and ethyl acetate. The mixture was filtered and the filtrate was extracted with EtOAc. The combined organic extracts were washed with water, brine, dried over MgSO$_4$, filtered, and concentrated under reduced pressure to give 9-Bromo-4,5-dihydro-6-oxa-3-thia-1-aza-benzo[e]azulene-2-carboxylic acid amide (2.12, quantitative yield). LC/MS (ESI+): m/z 327 (M+H)

Example 6

9-Bromo-2-(2-isopropyl-2H-[1,2,4]triazol-3-yl)-4,5-dihydro-6-oxa-3-thia-1-aza-benzo[e]azulene

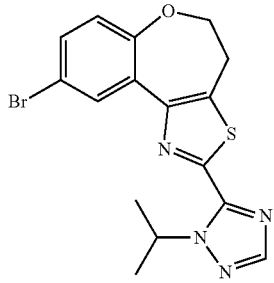 [SMILES: CC(C)n1ncnc1-c1nc2c(s1)CCOc1ccc(Br)cc1-2]

To 9-Bromo-4,5-dihydro-6-oxa-3-thia-1-aza-benzo[e]azulene-2-carboxylic acid amide (2.12 g, 6.52 mmol) in toluene (35 mL) was added 1,1-dimethoxy-N,N-dimethylmethaneamine (7.3 mL, 54.8 mmol). The reaction mixture was allowed to stir and heat to 95° C. for 3 hours. The reaction mixture was cooled to room temperature and concentrated under reduced pressure. The crude residue was treated with a suspension of isopropylhydrazine hydrochloride (0.865 g, 7.82 mmol) in acetic acid (18.5 mL) and water (2.35 mL). The mixture was heated in a sealed vial at 95° C. overnight. The reaction mixture was slowly poured onto a mixture of ice, sodium bicarbonate, and ethyl acetate. The mixture was extracted with ethyl acetate carefully after bubbling subsided. The layers were separated and the organic extract was washed sequentially with water and brine. The combined organic extracts were dried over MgSO$_4$, filtered, and concentrated under reduced pressure. The crude residue was dissolved in a minimal amount of ethyl acetate and purified via ISCO chromatography (hexane to 20% hexane in EtOAc over 45 minutes). Collected fractions and concentrated to give 9-Bromo-2-(2-isopropyl-2H-[1,2,4]triazol-3-yl)-4,5-dihydro-6-oxa-3-thia-1-aza-benzo[e]azulene (0.897 g, 35%). LC/MS (ESI+): m/z 393 (M+H). $^1$H NMR (400 MHz, CDCl$_3$) δ 8.51 (d, J=2.5, 1H), 7.93 (s, 1H), 7.34 (dd, J=8.6, 2.5, 1H), 6.96 (d, J=8.6, 1H), 5.84 (dt, J=13.5, 6.8, 1H), 4.40 (t, J=5.0, 2H), 3.42 (t, J=5.0, 2H), 1.66 (d, J=6.6, 6H)

Example 7

(Z)-8-bromo-5-chloro-2,3-dihydrobenzo[b]oxepine-4-carbaldehyde

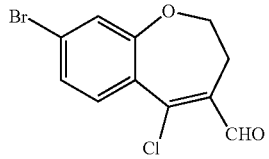 [SMILES: O=CC1=C(Cl)c2ccc(Br)cc2OCC1]

Phosphorus oxychloride, POCl$_3$ (1.88 mL, 20.8 mmol) was added dropwise to DMF (5 mL) at 0° C. After 30 min a solution of 8-bromo-3,4-dihydrobenzo[b]oxepin-5(2H)-one (2.0 g, 8.3 mmol) in 8 mL DMF was added dropwise. The reaction mixture was allowed to reach room temperature to stir 2 hr, then poured slowly over rapidly stirred ice water. The aqueous phase was extracted with ethylacetate and the combined organics were washed with brine, dried over sodium sulfate and concentrated to give (Z)-8-bromo-5-chloro-2,3-dihydrobenzo[b]oxepine-4-carbaldehyde.

Example 8 methyl 8-bromo-4,5-dihydrobenzo[b]thieno[2,3-d]oxepine-2-carboxylate

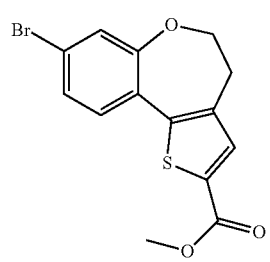

(Z)-8-Bromo-5-chloro-2,3-dihydrobenzo[b]oxepine-4-carbaldehyde 9 was dissolved in 10 mL DMF and treated sequentially with potassium carbonate (2.20 g, 16.6 mmol) and methyl thioglycolate (0.83 mL). The whole was heated at 50° C. overnight, cooled to room temperature, diluted with water and extracted with ethylacetate. The combined organics were washed with brine, dried over sodium sulfate and concentrated. The crude residue was purified by flash column chromatography (20-50% ethylacetate in hexanes) to give 2.20 g (78% yield) 10 as a colorless solid. $^1$H NMR (DMSO-d6, 500 MHz) 7.70 (s, 1H), 7.67 (d, J=8.5 Hz, 1H), 7.31-7.28 (m, 2H), 4.32 (t, J=5.0 Hz, 2H), 3.84 (s, 3H), 3.21 (t, J=5.0 Hz, 2H).

Example 9

8-bromo-4,5-dihydrobenzo[b]thieno[2,3-d]oxepine-2-carboxylic acid 11

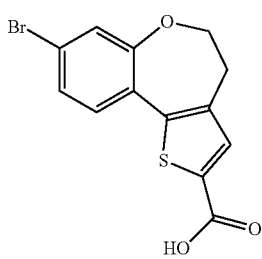

Methyl 8-bromo-4,5-dihydrobenzo[b]thieno[2,3-d]oxepine-2-carboxylate 10 was treated with lithium hydroxide in water and tetrahydrofuran (THF) to give 11.

Example 10

10-aza-4,5-dihydrobenzo[b]thieno[2,3-d]oxepine-2-carboxylic acid

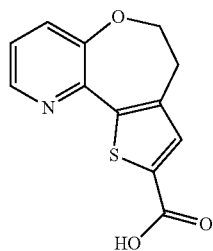 [SMILES: O=C(O)c1cc2c(s1)-c1ncccc1OCC2]

Step 1: 2-Iodo-3-(2-thiophen-3yl-ethoxy)-pyridine

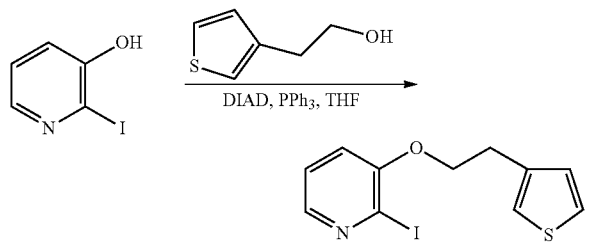

To a solution containing 2-iodo-3-hydroxypyridine (1.85 g, 8.37 mmol), 2-(3-thienyl)ethanol (1.20 mL, 10.9 mmol), and triphenylphosphine (2.85 g, 10.9 mmol) in tetrahydrofuran (46.2 mL, 5.70 mmol) was added diisopropyl azodicarboxylate (2.14 mL, 10.9 mmol) dropwise. The reaction mixture was stirred at room temperature for 18 h. The reaction mixture was concentrated and purified by flash chromatography EtOAc/Hex (0-100%) eluted at 30% to give 2-Iodo-3-(2-thiophen-3yl-ethoxy)-pyridine (yield 90%). MS: (ESI+) 332.2

Step 2: 10-aza-4,5-dihydrobenzo[b]thieno[2,3-d]oxepine

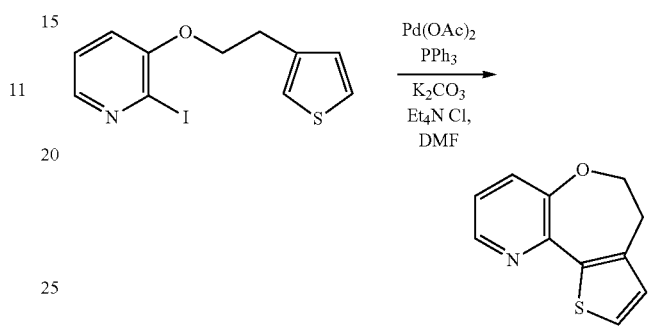

To a solution of 2-iodo-3-(2-thiophen-3yl-ethoxy)-pyridine (1.15 g, 4.05 mmol) in N,N-dimethylformamide (60.9 mL, 787 mmol) was added potassium carbonate (2.80 g, 20.2 mmol), triphenylphosphine (212 mg, 0.809 mmol), tetraethylammonium chloride (4.05 mmol) and palladium acetate (90.8 mg, 0.405 mmol). The reaction mixture was stirred at 90° C. 8 h. The reaction mixture was diluted with DCM then filtered through celite. The filtrate was concentrated and wash water. The crude product was purified by flash chromatography EtOAc/Hex (0-100%) product eluted at 30% to give 10-aza-4,5-dihydrobenzo[b]thieno[2,3-d]oxepine (yield 60%). MS: (ESI+) 204.3

Step 3: 2-bromo-(10-aza-4,5-dihydrobenzo[b]thieno[2,3-d]oxepine)

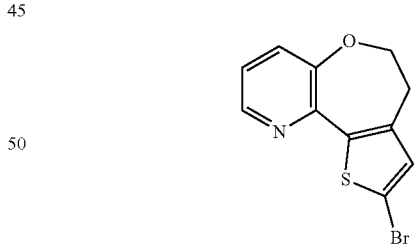

10-aza-4,5-dihydrobenzo[b]thieno[2,3-d]oxepine (1.73 g, 8.51 mmol) was dissolved in methylene chloride (20 mL, 400 mmol) and acetic acid (20 mL, 400 mmol) and cooled to 0° C. N-Bromosuccinimide (1.67 g, 9.36 mmol) was added portionwise to the mixture. The reaction was stirred for 18 hours. Solvents were rotary evaporated, the residue partitioned between ethyl acetate and sat. sodium carbonate aqueous solution. The organic layer was washed with water, brine and dried over sodium sulfate. After rotary evaporation the crude product was chromatographed on Isco (hexane-EtOAc gradient, 0-100%) eluted 20% EtOAc to give 2-bromo-(10-aza-4,5-dihydrobenzo[b]thieno[2,3-d]oxepine). MS: (ESI+) 283.2

Step 4: 10-aza-4,5-dihydrobenzo[b]thieno[2,3-d]oxepine-2-carboxylic acid

To a solution of 2-bromo-(10-aza-4,5-dihydrobenzo[b]thieno[2,3-d]oxepine) (0.700 g, 2.48 mmol) in tetrahydrofuran (25.0 mL, 308 mmol) was added 2.50 M of n-butyllithium in hexane (1.19 mL) dropwise at −78° C. The reaction mixture was stirred at −78° C. for 1 h. The mixture was added to a slurry of dry ice in THF (15 ml) then stirred 2 h. The reaction mixture was quenched with water then slightly basified and extracted EtOAc (2×). The aqueous layer was acidified to pH 2 then extracted with DCM (2×). The organic layers were combined and concentrated to give 10-aza-4,5-dihydrobenzo[b]thieno[2,3-d]oxepine-2-carboxylic acid (yield 62%). MS: (ESI+) 248.3

Example 11

9-Chloro-4,5-dihydro-6-oxa-1-thia-10-aza-benzo[e]azulene-2-carboxylic acid amide

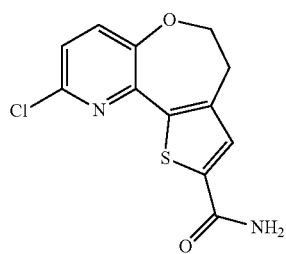 [SMILES: NC(=O)c1cc2c(s1)-c1nc(Cl)ccc1OCC2]

Step 1: 6-chloro-2-iodopyridin-3-ol

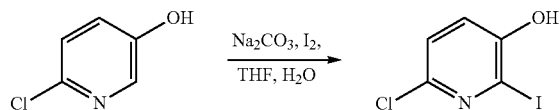 [SMILES: Oc1ccc(Cl)nc1 ; Oc1ccc(Cl)nc1I]

To solution of 6-chloro-pyridin-3-ol (112 g, 868 mmol) in THF (800 mL)/Water (800 mL) was added sodium carbonate (92.0 g, 1.736 mol) and iodine (244.2 g, 1.04 mol). The reaction mixture was stirred rt 4 h. The aqueous layer containing product was separated and washed with hexane (400 mL×2). The aqueous layer was neutralized to pH=7 with HCl and then extracted EtOAc (500 mL×4). The combined organic layers were dried over $Na_2SO_4$, and filtered. The filtrate was concentrated to the crude product, which was washed with EtOAc to afford 163 g of 6-chloro-2-iodopyridin-3-ol, yield: 75%. $^1H$ NMR (DMSO, 400 MHz): δ11.13 (s, 1H, OH), 7.31 (dd, J=8.4, 12.8 Hz, 2H).

Step 2: 2-(thiophen-3-yl)ethanol

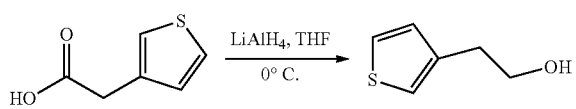 [SMILES: O=C(O)Cc1ccsc1 ; OCCc1ccsc1]

Tetrahydrofuran (200 mL) was added to $LiAlH_4$ (4.56 g, 0.12 mol) and the mixture was stirred at 0° C. 2-(thiophen-3-yl) acetic acid (14.2 g, 0.1 mol) in THF (100 mL) was added dropwise at this temperature. After the addition, the reaction mixture was stirred at 0° C. for further 2 hours. To the reaction mixture was added EtOAc (200 mL) slowly and then 5 mL of water. The suspension was filtered though ceilite, the filtrate was dried over anhydrous sodium sulfate and concentrated to dryness to afford 2-(thiophen-3-yl)ethanol (12.44 g, yield: 99%). $^1H$ NMR (MeOD, 400 MHz): δ5.92-5.87 (m, 1H), 5.69-5.66 (m, 1H), 5.57 (s, 1H) 2.90 (d, J=14.0 Hz, 1H), 2.38 (d, J=14 Hz, 1H), 1.55-1.42 (m, 2H).

Step 3: 6-chloro-2-iodo-3-(2-(thiophen-3-yl)ethoxy)pyridine

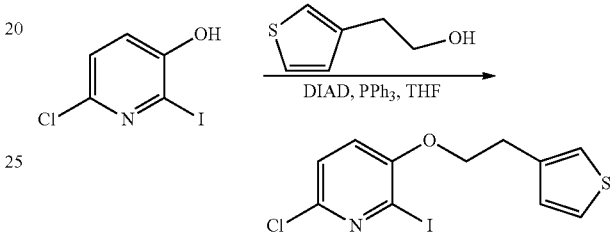

To a solution 6-chloro-2-iodopyridin-3-ol (6.75 g, 26.4 mmol), 2-(3-thienyl) ethanol (3.79 mL, 34.4 mmol), and triphenylphosphine (9.01 g, 34.4 mmol) in tetrahydrofuran (140 mL) was added diisopropyl azodicarboxylate (6.76 mL, 34.4 mmol) dropwise. The reaction mixture was stirred at room temperature overnight. The reaction mixture was concentrated and purified by column on silica gel (eluted at EtOAc/Hexanes=1:20) to give 5.5 g of 6-chloro-2-iodo-3-(2-(thiophen-3-yl)ethoxy)pyridine. Yield: 58%. $^1H$ NMR (DMSO, 400 MHz): δ7.50-7.43 (m, 3H), 7.34 (d, J=1.6 Hz, 1H), 7.17 (d, J=4.8 Hz, 1H), 4.29 (t, J=6.4 Hz, 2H), 3.10 (t, J=6.4 Hz, 2H). LC-MS (ESI): m/z=366 [M+H]+

Step 4: 9-Chloro-4,5-dihydro-6-oxa-1-thia-10-aza-benzo[e]azulene

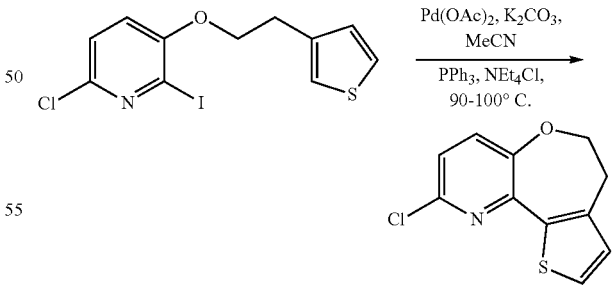

To a solution of 6-chloro-2-iodo-3-(2-(thiophen-3-yl)ethoxy)pyridine (9.14 g, 25.0 mmol) in acetonitrile (150 mL) was added tetraethylammonium chloride (4.14 g, 25.0 mmol), potassium carbonate (6.91 g, 50.0 mmol) and triphenylphosphine (1.31 g, 5.00 mmol) The reaction mixture was degassed and then charged with $N_2$ three times. Palladium acetate (0.561 g, 2.50 mmol) was added to the reaction mixture. The reaction mixture was stirred under $N_2$ at 80° C. for 3 h. The reaction mixture was diluted with DCM then filtered through celite. The filtrate was concentrated to get the crude product, which was purified by column on silica gel (EtOAc/Hexanes=1:10) to afford 54.6 g of 9-Chloro-4,5-dihydro-6-oxa-1-thia-10-aza-benzo[e]azulene (Yield: 89%) $^1$H NMR (DMSO, 400 MHz): δ7.60 (d, J=5.2 Hz, 1H), 7.48 (d, J=6.0 Hz, 1H), 7.26 (d, J=6.0 Hz, 1H), 7.03 (d, J=5.2 Hz, 1H), 4.32 (t, J=4.4 Hz, 2H), 3.20 (t, J=4.4 Hz, 2H). LC-MS (ESI): m/z=238 [M+H]$^+$ Step 5: 2-Bromo-9-chloro-4,5-dihydro-6-oxa-1-thia-10-aza-benzo[e]azulene

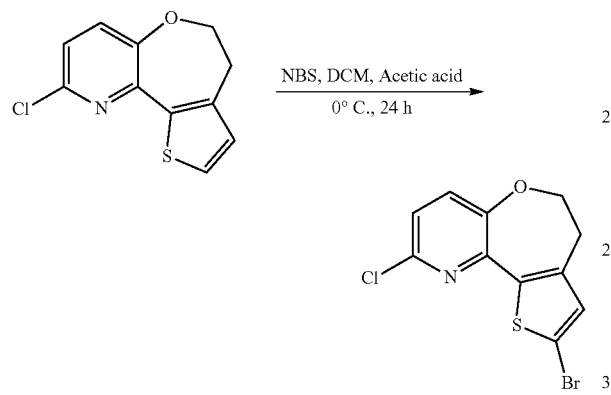

9-Chloro-4,5-dihydro-6-oxa-1-thia-10-aza-benzo[e]azulene (4.33 g, 18.2 mmol) was dissolved in methylene chloride (40 mL, 600 mmol)/acetic acid (40 mL, 700 mmol). The solution was cooled down to 0-5° C. and added a solution of N-Bromosuccinimide (3.57 g, 20.0 mmol) in 10 mL of DCM slowly. The reaction mixture was stirred for 18 hours. After removal of the solvents, the residue was partitioned between ethyl acetate and saturated sodium carbonate aqueous solution. The organic layer was washed with water, brine and dried over sodium sulfate. After filtration, the filtrate was concentrated to give 2-Bromo-9-chloro-4,5-dihydro-6-oxa-1-thia-10-aza-benzo[e]azulene. $^1$HNMR (DMSO, 400 MHz): δ 7.48 (d, J=8.4 Hz, 1H, ArH), 7.28 (d, J=8.4 Hz, 1H, ArH), 7.18 (s, 1H, =CH), 4.32 (t, J=4.4 Hz, 2H, CH$_2$), 3.17 (t, J=4.4 Hz, 2H, CH$_2$).

Step 6: 9-Chloro-4,5-dihydro-6-oxa-1-thia-10-aza-benzo[e]azulene-2-carboxylic acid

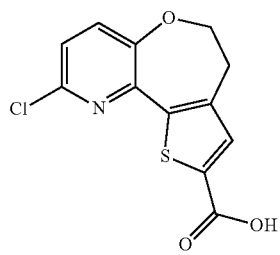 [SMILES: O=C(O)c1cc2c(s1)-c1nc(Cl)ccc1OCC2]

To a solution of 2-Bromo-9-chloro-4,5-dihydro-6-oxa-1-thia-10-aza-benzo[e]azulene (0.440 g, 1.56 mmol) in tetrahydrofuran (24.0 mL, 296 mmol) was added 2.50 M of n-Butyllithium in hexane (0.748 mL) dropwise at −78° C. The reaction mixture was stirred at −78° C. for 1 h. The mixture was bubbled by dried CO$_2$ gas for 0.5-1 hour. The reaction mixture was quenched with water then slightly basified and extracted EtOAc (2×). The aqueous layer was acidified to pH=2 then extracted with DCM (2×) to yield 0.34 g of 9-Chloro-4,5-dihydro-6-oxa-1-thia-10-aza-benzo[e]azulene-2-carboxylic acid (Yield: 76%) $^1$H NMR (DMSO, 400 MHz): δ13.28 (br s, 1H, COOH), 7.64-7.35 (m, 3H, ArH), 4.36 (t, J=4.4 Hz, 2H, CH$_2$), 3.24 (t, J=4.4 Hz, 2H, CH$_2$).

Step 7: 9-Chloro-4,5-dihydro-6-oxa-1-thia-10-aza-benzo[e]azulene-2-carboxylic acid amide A mixture of 9-Chloro-4,5-dihydro-6-oxa-1-thia-10-aza-benzo[e]azulene-2-carboxylic acid (24.6 g, 87.5 mmol), N,N-Diisopropylethylamine (68 g, 525 mmol), ammonium chloride (18.7 g, 350 mmol) and HATU (66.5 g, 175 mmol) in N,N-Dimethyl-formamide (200 mL) was stirred at r.t. for overnight. The reaction mixture was added saturated sodium bicarbonate. After filtered, the filtrate was concentrated to 23 g of 9-Chloro-4,5-dihydro-6-oxa-1-thia-10-aza-benzo[e]azulene-2-carboxylic acid amide (yield: 94%) $^1$H-NMR (DMSO, 400 MHz): δ7.96 (d, J=18.4 Hz, 1H), 7.56 (s, 1H), 7.49 (d, J=8.4 Hz, 1H), 7.43 (s, 1H), 7.31 (d, J=4.8 Hz, 1H), 4.33 (t, J=4.8 Hz, 2H), 3.19 (t, J=4.8 Hz, 2H). LC-MS (ESI): m/z=281 [M+H]$^+$ Example 12

9-Chloro-2-[2-(2,4-difluoro-phenyl)-2H-[1,2,4]triazol-3-yl]-4,5-dihydro-6-oxa-1-thia-10-aza-benzo[e]azulene

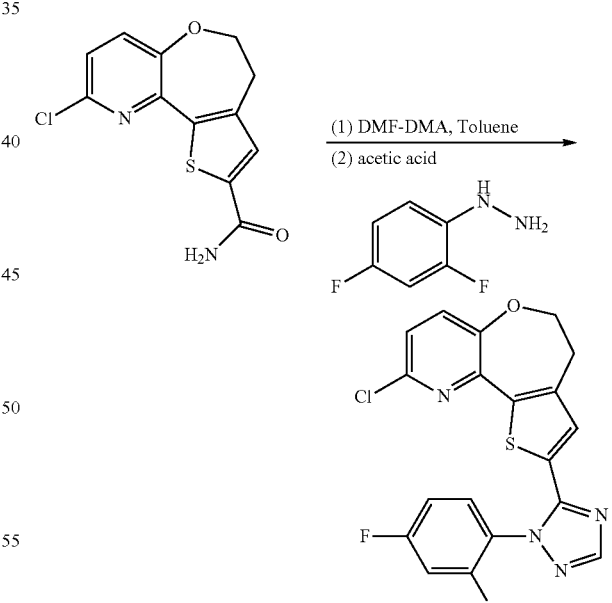

To a suspension of 9-Chloro-4,5-dihydro-6-oxa-1-thia-10-aza-benzo[e]azulene-2-carboxylic acid amide (22 g, 76.8 mmol) in dry toluene (250 mL) was added DMA-DMF (56.1 g, 471.4 mmol). The resulting mixture was heated to 90° C. for 2 h. After removal of the solvent and excess of DMA-DMF, the residue (13.6 g, 94.3 mmol) was dissolved in acetic acid (250 mL) and (2,4-difluorophenyl)hydrazine (16.6 g, 115.2 mmol) was added into the mixture. The mixture was stirred at 90° C. for 2 hours. After removal of the solvents, the residue was treated with EtOAc-water (500 mL, 5:1 (v/v)). The mixture was neutralized with sodium bicarbonate aqueous solution until pH=7. The suspension was filtered and the solid was washed with EtOAc (500 mL). The combined organic layers were washed with saturate sodium bicarbonate aqueous solution (300 mL), dried over sodium sulfate and filtered. The filtrate was concentrated to the crude product, which was purified by flash column (EtOAc/Hexanes=1:3) to give 9-Chloro-2-[2-(2,4-difluoro-phenyl)-2H-[1,2,4]triazol-3-yl]-4,5-dihydro-6-oxa-1-thia-10-aza-benzo[e]azulene (21.4 g, yield: 67%) $^1$H NMR (DMSO, 400 MHz): δ8.35 (s, 1H), 7.98-7.48 (m, 4H), 7.39 (d, J=8.8 Hz, 1H), 7.05 (s, 1H), 4.38 (t, J=4.4 Hz, 2H), 3.2 (t, J=4.4 Hz, 2H). LC-MS (ESI): m/z=417 [M+H]$^+$ Example 13

8-Bromo-2-[1,3,4]oxadiazol-2-yl-4,5-dihydro-6-oxa-3-thia-1-aza-benzo[e]azulene

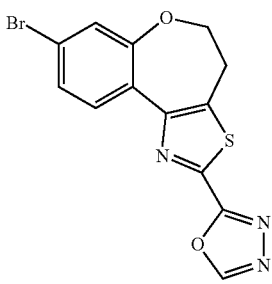 [SMILES: Brc1ccc2c(c1)OCCc1sc(-c3nnco3)nc1-2]

To a solution of 8-bromo-4,5-dihydro-6-oxa-3-thia-1-aza-benzo[e]azulene-2-carboxylic acid (22.2 g, 68.1 mmol) in THF (360 mL) was added (isocyanoimino)triphenylphosphorane (20.6 g, 68.1 mmol) portionwise over 1 hour. The resultant mixture was stirred at RT for 18 hours before being concentrated in vacuo and triturated with 1:1 DCM/cyclohexane (200 mL). The title compound was collected by filtration as a yellow solid (14.5 g, 61%). LCMS: R$_T$=4.03 min, M+H$^+$=350/352.

Example 14

2-(4-Isopropyl-4H-[1,2,4]triazol-3-yl)-4,5-dihydro-6-oxa-3-thia-1-aza-benzo[e]azulene-8-carboxylic acid

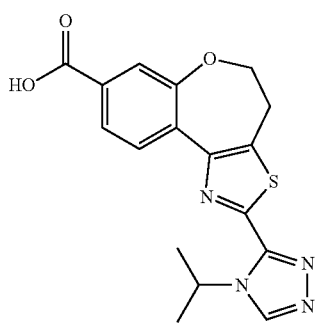 [SMILES: CC(C)n1cnnc1-c1nc2c(s1)CCOc1cc(C(=O)O)ccc1-2]

Step 1: 8-Bromo-2-(4-isopropyl-4H-[1,2,4]triazol-3-yl)-4,5-dihydro-6-oxa-3-thia-1-aza-benzo[e]azulene

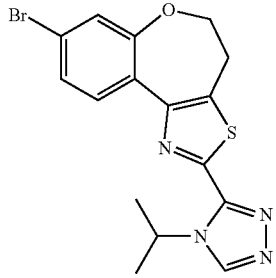 [SMILES: CC(C)n1cnnc1-c1nc2c(s1)CCOc1cc(Br)ccc1-2]

To a solution of 8-bromo-2-[1,3,4]oxadiazol-2-yl-4,5-dihydro-6-oxa-3-thia-1-aza-benzo[e]azulene (4.38 g, 12.51 mmol) in pyridine (12 mL) was added isopropylamine hydrochloride (1.38 g, 12.51 mmol). The reaction mixture was heated at 160° C. for 30 minutes using microwave irradiation before being concentrated in vacuo. The residue was taken up into DCM then washed with 1M HCl then brine before being dried (Na$_2$SO$_4$) and concentrated in vacuo. The resultant residue was purified by flash chromatography (SiO$_2$, gradient 0-3% methanol in DCM then further purified, gradient 0-4% MeOH in EtOAc) to yield the title compound as an orange solid (1.97 g, 40%). LCMS: R$_T$=4.67 min, M+H$^+$=391/393.

Step 2: 2-(4-Isopropyl-4H-[1,2,4]triazol-3-yl)-4,5-dihydro-6-oxa-3-thia-1-aza-benzo[e]azulene-8-carboxylic acid methyl ester

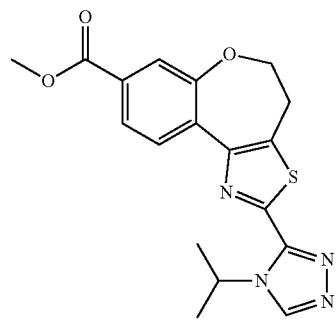 [SMILES: COC(=O)c1ccc2c(c1)OCCc1sc(-c3nncn3C(C)C)nc1-2]

A microwave vial was charged with 8-bromo-2-(4-isopropyl-4H[1,2,4]triazol-3-yl)-4,5-dihydro-6-oxa-3-thia-1-aza-benzo[e]azulene (1.0 g, 2.56 mmol), molybdenum hexacarbonyl (338 mg, 1.28 mmol), Herrmann's catalyst [trans-bis(acetato)bis[o-(di-o-tolylphosphino)benzyl]dipalladium(II)] (122 mg, 0.13 mmol), tri-tert-butylphosphonium tetrafluoroborate (75 mg, 0.26 mmol), DBU (0.38 mL, 2.56 mmol), 1,4-dioxan (6 mL) and MeOH (6 mL), flushed with nitrogen then sealed. The mixture was heated at 150° C. for 45 minutes using microwave irradiattion then filtered through a pad of Celite®, washing the pad with MeOH. The filtrate was concentrated in vacuo and the residue purified by flash chromatography (SiO$_2$, 0-5% MeOH in EtOAc) to give the title compound as a yellow solid (0.51 g, 54%). LCMS: R$_T$=4.28 min, [M+H]$^+$=371

Step 3: [2-(4-Isopropyl-4H-[1,2,4]triazol-3-yl)-4,5-dihydro-6-oxa-3-thia-1-aza-benzo[e]azulen-8-yl]-methanol

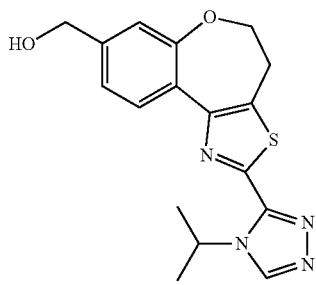 [SMILES: CC(C)n1cnnc1-c1nc2c(s1)CCOc1cc(CO)ccc1-2]

To a solution of 2-(4-isopropyl-4H-[1,2,4]triazol-3-yl)-4,5-dihydro-6-oxa-3-thia-1-aza-benzo[e]azulene-8-carboxylic acid methyl ester (620 mg, 1.67 mmol) in THF (12 mL) at 0° C. was added LiAlH$_4$ (152 mg, 4.02 mmol). The reaction mixture was stirred for 4 hours at RT before being quenched with H$_2$O (0.15 mL), 15% NaOH$_{(aq)}$ (0.15 mL) and H$_2$O (0.45 mL). The precipitate was removed by filtration, washing with methanol/DCM, and then the filtrate was concentrated in vacuo to yield the title compound as an orange solid (563 mg, 98%). LCMS: R$_T$=3.71 min, [M+H]$^+$=343

Step 4: 2-(4-Isopropyl-4H-[1,2,4]triazol-3-yl)-4,5-dihydro-6-oxa-3-thia-1-aza-benzo[e]azulene-8-carbaldehyde

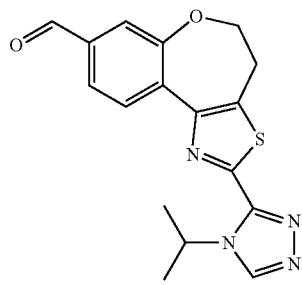 [SMILES: CC(C)n1cnnc1-c1nc2c(s1)CCOc1cc(C=O)ccc1-2]

To a solution of [2-(4-isopropyl-4H-[1,2,4]triazol-3-yl)-4,5-dihydro-6-oxa-3-thia-1-aza-benzo[e]azulen-8-yl]-methanol (565 mg, 1.65 mmol) in DCM (20 mL) was added Dess-Martin periodinane (1,1,1-Triacetoxy-1,1-dihydro-1,2-benziodoxol-3(1H)-one, 763 mg, 1.80 mmol). The reaction mixture was stirred at RT for 2 hours before being concentrated in vacuo. The resultant residue was purified by flash chromatography (SiO$_2$, gradient 0-3% MeOH in DCM) to yield the title compound as a white solid (547 mg, 98%). LCMS: R$_T$=4.00 min, [M+H]$^+$=341

Step 5: 2-(4-Isopropyl-4H-[1,2,4]triazol-3-yl)-4,5-dihydro-6-oxa-3-thia-1-aza-benzo[e]azulene-8-carboxylic acid To a suspension of 2-(4-isopropyl-4H-[1,2,4]triazol-3-yl)-4,5-dihydro-6-oxa-3-thia-1-aza-benzo[e]azulene-8-carboxylic acid methyl ester in THF (6 mL) and water (1.5 mL) was added an aqueous 1N lithium hydroxide solution (1.0 mL, 1.0 mmol). The reaction mixture was stirred for 65 hours then an aqueous 1N HCl solution (2 mL) was added and the mixture was concentrated in vacuo to remove THF. A small quantity of MeOH was added to the resultant mixture and the solid was collected by filtration to give the title compound as an off-white solid (226 mg, 95%). LCMS: R$_T$=3.88 min, [M+H]$^+$=357

Example 15

2-(2-Isopropyl-2H-[1,2,4]triazol-3-yl)-4,5-dihydro-6-oxa-3-thia-1-aza-benzo[e]azulene-8-carboxylic acid methyl ester

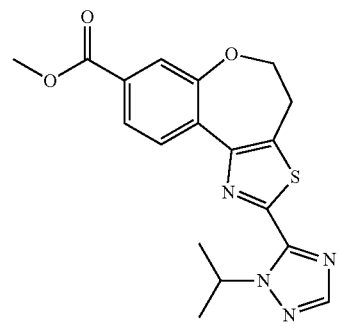 [SMILES: COC(=O)c1ccc2c(c1)OCCc1sc(-c3ncnn3C(C)C)nc1-2]

The title compound was prepared by a similar procedure to 2-(4-isopropyl-4H-[1,2,4]triazol-3-yl)-4,5-dihydro-6-oxa-3-thia-1-aza-benzo[e]azulene-8-carboxylic acid methyl ester using 8-bromo-2-(2-isopropyl-2H-[1,2,4]triazol-3-yl)-4,5-dihydro-6-oxa-3-thia-1-aza-benzo[e]azulene 27 instead of 8-bromo-2-(4-isopropyl-4H[1,2,4]triazol-3-yl)-4,5-dihydro-6-oxa-3-thia-1-aza-benzo[e]azulene. The title compound was isolated as a beige solid (0.61 g, 64%). LCMS: R$_T$=4.71 min, [M+H]$^+$=371

Example 16

[2-(2-Isopropyl-2H-[1,2,4]triazol-3-yl)-4,5-dihydro-6-oxa-3-thia-1-aza-benzo[e]azulen-8-yl]-methanol

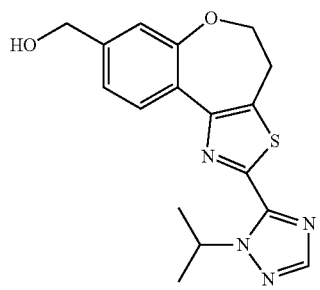 [SMILES: CC(C)n1ncnc1-c1nc2c(s1)CCOc1cc(CO)ccc1-2]

To a suspension of 2-(2-isopropyl-2H-[1,2,4]triazol-3-yl)-4,5-dihydro-6-oxa-3-thia-1-aza-benzo[e]azulene-8-carboxylic acid methyl ester (778 mg, 2.1 mmol) in THF (20 mL) at −78° C. under nitrogen was added dropwise diisobutyl aluminum hydride (1.5M in toluene, 4.2 mL, 6.3 mmol) and the reaction mixture was stirred at 0° C. for 2 hours. MeOH (10 mL) was added cautiously followed by an aqueous 1M potassium sodium tartrate solution (7 mL) at RT. The mixture was concentrated in vacuo to remove organic solvent and the aqueous phase was extracted with DCM (×3). The combined organic extracts were dried (MgSO$_4$) and concentrated in vacuo to give the title compound as an off-white solid (713 mg, 99%). LCMS: R$_T$=4.14 min, [M+H]$^+$=343

Example 17

2-(2-Isopropyl-2H-[1,2,4]triazol-3-yl)-4,5-dihydro-6-oxa-3-thia-1-aza-benzo[e]azulene-8-carbaldehyde

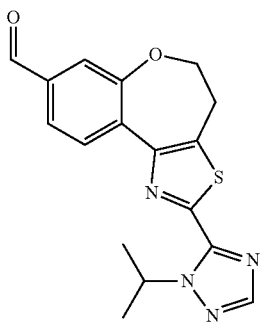 [SMILES: CC(C)n1ncnc1-c1nc2c(s1)CCOc1cc(C=O)ccc1-2]

To a solution of [2-(2-isopropyl-2H-[1,2,4]triazol-3-yl)-4,5-dihydro-6-oxa-3-thia-1-aza-benzo[e]azulen-8-yl]-methanol (713 mg, 2.1 mmol) in DCM (25 mL) was added Dess-Martin periodinane (1,1,1-Triacetoxy-1,1-dihydro-1,2-benziodoxol-3(1H)-one, 971 mg, 2.3 mmol) portionwise. The reaction mixture was stirred for 5 h then diluted with DCM (50 mL) and washed with an aqueous saturated sodium bicarbonate solution (×3). The organic layer was dried (MgSO$_4$) and concentrated in vacuo. The resultant residue was purified by flash chromatography (SiO$_2$, 0-10% EtOAc in DCM) to give the title compound as an off-white solid (736 mg, quant.). LCMS: R$_T$=4.39 min, [M+H]$^+$=341

Example 18

1-[2-(Tetrahydro-pyran-2-yloxy)-ethyl]-4-(4,4,5,5-tetramethyl-[1,3,2]dioxaborolan-2-yl)-1H-pyrazole

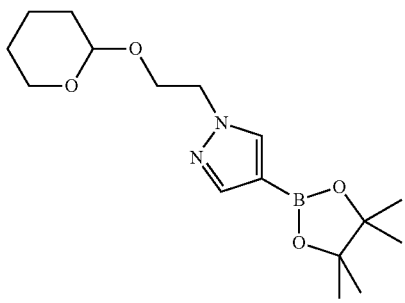 [SMILES: CC1(C)OB(c2cnn(CCOC3CCCCO3)c2)OC1(C)C]

To a solution of 4-pyrazole boronic acid pinacol ester (2.0 g, 10.3 mmol) in anhydrous DMF (20 mL) was added cesium carbonate (4.03 g, 12.4 mmol) and the mixture stirred at RT for 10 minutes. 2-(2-Bromoethoxyl)tetrahydro-2H-pyran (1.87 mL, 12.4 mmol) was added in two portions and the mixture was heated to 70° C. After heating for 18 hours the mixture was allowed to cool to RT and partitioned between water (100 mL) and EtOAc (100 mL). The aqueous layer was washed with EtOAc (3×20 mL) and the combined organic layers washed with water (3×100 mL) followed by brine, dried (Na$_2$SO$_4$) and concentrated in vacuo. The resultant residue was purified by flash chromatography (SiO$_2$, gradient 0-100% EtOAc in cyclohexane) to afford the title compound (2.15 g, 65%). LCMS: R$_T$=3.97 min, [M+Na]$^+$=345

Example 19

2-(1-Isopropyl-1H-imidazol-2-yl)-8-{1-[2-(tetrahydro-pyran-2-yloxy)-ethyl]-1H-pyrazol-4-yl}-4,5-dihydro-6-oxa-3-thia-1-aza-benzo[e]azulene

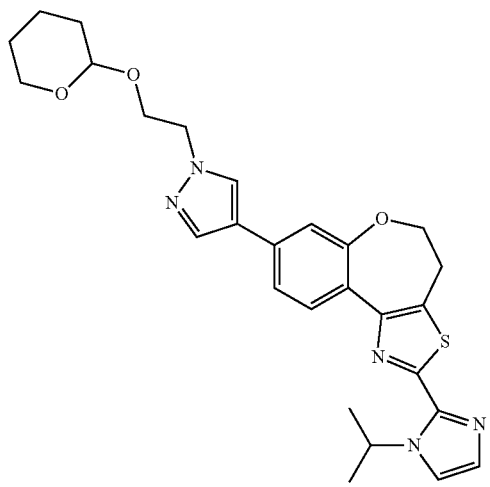 [SMILES: CC(C)n1ccnc1-c1nc2c(s1)CCOc1cc(-c3cnn(CCOC4CCCCO4)c3)ccc1-2]

Step 1: 8-bromo-4,5-dihydro-6-oxa-3-thia-1-aza-benzo[e]azulene-2-carbonitrile

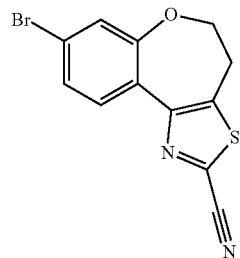 [SMILES: N#Cc1nc2c(s1)CCOc1cc(Br)ccc1-2]

To a suspension of 8-bromo-4,5-dihydro-6-oxa-3-thia-1-aza-benzo[e]azulene-2-carboxylic acid amide 25 (11.44 g, 35.2 mmol) in pyridine (115 mL) at −30° C. was added phosphorus oxychloride (8.4 mL, 91 mmol) dropwise over 10 minutes. The mixture was stirred at −30° C. for 1 hour then allowed to warm to RT and stirred for 2 hours. The mixture was poured into water, stirred for 10 minutes and the solid was collected by filtration. The solid was dissolved in EtOAc and washed with copper sulfate solution. The organic layer was passed through a silica pad eluting with EtOAc and the solvent was removed in vacuo to afford 8-bromo-4,5-dihydro-6-oxa-3-thia-1-aza-benzo[e]azulene-2-carbonitrile (7.78 g, 72%). $^1$H NMR δ (ppm) (DMSO-d6): 8.25 (1H, d, J=8.61

Hz), 7.38 (1H, dd, J=8.68, 2.23 Hz), 7.32-7.30 (1H, m), 4.39 (2H, t, J=5.01 Hz), 3.50-3.44 (2H, m)

Step 2: 8-Bromo-2-(1H-imidazol-2-yl)-4,5-dihydro-6-oxa-3-thia-1-aza-benzo[e]azulene

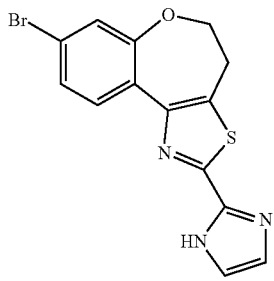 [SMILES: Brc1ccc2c(c1)OCCc1sc(-c3ncc[nH]3)nc1-2]

To a solution of 8-bromo-4,5-dihydro-6-oxa-3-thia-1-aza-benzo[e]azulene-2-carbonitrile (0.100 g, 0.326 mmol) in 1.0 ml of Methanol was added 25% Sodium methoxide (0.020 mL, 0.087 mmol) in Methanol. The reaction was stirred 1 h rt. Aminoacetaldehyde dimethyl acetal (0.0390 mL, 0.358 mmol) was added to the reaction mixture followed by Acetic acid (0.0370 mL, 0.651 mmol). The reaction was heated at 50° C. for 1 h and then cooled to rt. Methanol (0.650 mL, 16.0 mmol) and 6.00 M of Hydrogen chloride in Water (0.163 mL) were added, the reaction was heated 100 for 12 h. The reaction mixture was concentrated then added EtOAc and water. The combined organic layers was concentrated to give 8-Bromo-2-(1H-imidazol-2-yl)-4,5-dihydro-6-oxa-3-thia-1-aza-benzo[e]azulene. MS: (ESI+)=349.1

Step 3: 8-bromo-4,5-dihydro-6-oxa-3-thia-1-aza-benzo[e]azulene-2-carboximidic acid ethyl ester hydrochloride

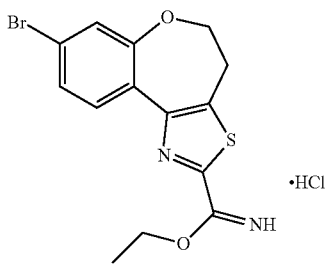 [SMILES: CCOC(=N)c1nc2c(s1)CCOc1cc(Br)ccc1-2 ; Cl]

A mixture of 8-bromo-4,5-dihydro-6-oxa-3-thia-1-aza-benzo[e]azulene-2-carbonitrile (4.63 g, 15 mmol) and sodium ethoxide (136 g, 20 mmol) in IMS (45 mL) was heated to 85° C. After heating for 24 hours the mixture was allowed to cool to RT and the solvent was removed in vacuo. The residue was dissolved 1.25 M HCl in MeOH and stirred at RT for 20 minutes, the resulting solid was collected by filtration to afford the title compound (4.46 g, 76%). $^{1}$H NMR δ (ppm) (DMSO-d6): 9.12 (1H, s), 8.45 (1H, dd, J=8.64, 2.98 Hz), 7.35 (1H, dd, J=8.61, 2.10 Hz), 7.27-7.24 (1H, m), 4.38-4.32 (4H, m), 3.39 (2H, t, J=5.03 Hz), 1.38-1.29 (3H, m)

Step 4: 8-bromo-N-isopropyl-4,5-dihydro-6-oxa-3-thia-1-aza-benzo[e]azulene-2-carboxamidine

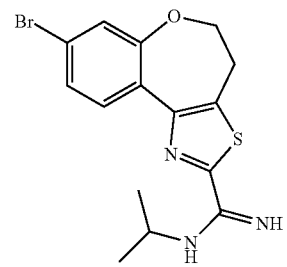 [SMILES: CC(C)NC(=N)c1nc2c(s1)CCOc1cc(Br)ccc1-2]

A mixture of 8-bromo-4,5-dihydro-6-oxa-3-thia-1-aza-benzo[e]azulene-2-carboximidic acid ethyl ester hydrochloride (200 mg, 0.513 mmol) and isopropyl-amine (437 μL, 5.13 mmol) in IMS (3 mL) was heated at 140° C. for 90 minutes using microwave irradiation. The reaction mixture was concentrated in vacuo and the residue dissolved in DCM, washed with water and the organic layer dried (Na$_2$SO$_4$). The organic extract was concentrated in vacuo and the residue was purified by flash chromatography (SiO$_2$, gradient 0-30% MeOH in EtOAc) to afford the title compound (878 mg, 46%). LCMS: R$_T$=3.26 min, [M+H]$^{+}$=366/368

Step 5: 8-Bromo-2-(1-isopropyl-1H-imidazol-2-yl)-4,5-dihydro-6-oxa-3-thia-1-aza-benzo[e]azulene To a solution of 8-bromo-N-isopropyl-4,5-dihydro-6-oxa-3-thia-1-aza-benzo[e]azulene-2-carboxamidine (878 mg, 2.4 mmol) in THF (15 mL) was added chloroacetaldehyde solution (~50 wt. % in H$_2$O, 7.53 mL, 47.9 mmol) and aqueous saturated sodium bicarbonate solution (6 mL) at RT. The mixture was heated to 80° C. with rapid stirring. After heating for 20 hours the mixture was allowed to cool to RT and was extracted with DCM (150 mL). The organic layer was washed with water followed by brine, dried (Na$_2$SO$_4$) and concentrated in vacuo. The resultant residue was purified by flash chromatography (SiO$_2$, gradient 0-100% EtOAc in cyclohexane) to afford the title compound (900 mg, 96%). LCMS R$_T$=4.90 min, [M+H]$^{+}$=390/392

Step 6: 2-(1-Isopropyl-1H-imidazol-2-yl)-8-{1-[2-(tetrahydro-pyran-2-yloxy)-ethyl]-1H-pyrazol-4-yl}-4,5-dihydro-6-oxa-3-thia-1-aza-benzo[e]azulene 8-Bromo-2-(1-isopropyl-1H-imidazol-2-yl)-4,5-dihydro-6-oxa-3-thia-1-aza-benzo[e]azulene and 1-[2-(Tetrahydropyran-2-yloxy)-ethyl]-4-(4,4,5,5-tetramethyl-[1,3,2]diox-aborolan-2-yl)-1H-pyrazole were reacted under Suzuki conditions to give 2-(1-Isopropyl-1H-imidazol-2-yl)-8-{1-[2-(tetrahydro-pyran-2-yloxy)-ethyl]-1H-pyrazol-4-yl}-4,5-dihydro-6-oxa-3-thia-1-aza-benzo[e]azulene. LCMS: $R_T$=4.56 min, $[M+H]^+$=506

Example 20

2-(2-Isopropyl-2H-[1,2,4]triazol-3-yl)-8-{1-[2-(tetrahydro-pyran-2-yloxy)-ethyl]-azetidin-3-yl}-4,5-dihydro-6-oxa-3-thia-1-aza-benzo[e]azulene

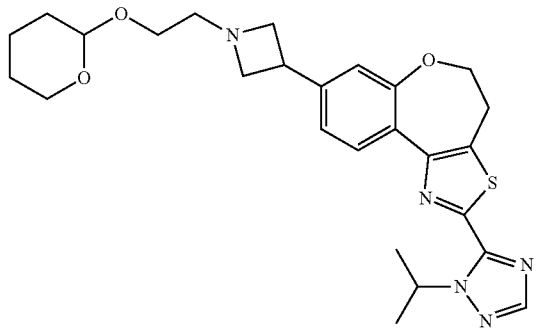 [SMILES: CC(C)n1ncnc1-c1nc2c(s1)CCOc1cc(C3CN(CCOC4CCCCO4)C3)ccc1-2]

The title compound was prepared by a similar method to 2-{3-[2-(2-isopropyl-2H-[1,2,4]triazol-3-yl)-4,5-dihydro-6-oxa-3-thia-1-aza-benzo[e]azulen-8-yl]-azetidin-1-yl}-acetamide using 2-(2-bromoethoxyl)tetrahydro-2H-pyran instead of 2-bromoacetamide and DMF instead of THF and performing the reaction at 60° C. The title compound was isolated as an amber gum (104 mg, 29%). LCMS: $R_T$=3.24, 3.35 min, $[M+H]^+$=496

Example 21

2-(2-Isopropyl-2H-[1,2,4]triazol-3-yl)-9-{1-[2-(tetrahydro-pyran-2-yloxy)-ethyl]-azetidin-3-yl}-4,5-dihydro-6-oxa-3-thia-1-aza-benzo[e]azulene

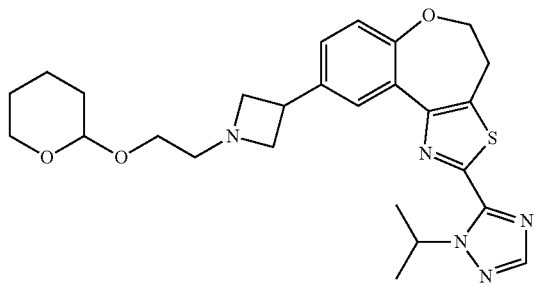 [SMILES: CC(C)n1ncnc1-c1nc2c(s1)CCOc1ccc(C3CN(CCOC4CCCCO4)C3)cc1-2]

The title compound (110 mg, 45%) was prepared by a similar method to 2-(2-isopropyl-2H-[1,2,4]triazol-3-yl)-8-{1-[2-(tetrahydro-pyran-2-yloxy)-ethyl]-azetidin-3-yl}-4,5-dihydro-6-oxa-3-thia-1-aza-benzo[e]azulene using 9-azetidin-3-yl-2-(2-isopropyl-2H-[1,2,4]triazol-3-yl)-4,5-dihydro-6-oxa-3-thia-1-aza-benzo[e]azulene instead of 8-azetidin-3-yl-2-(2-isopropyl-2H-[1,2,4]triazol-3-yl)-4,5-dihydro-6-oxa-3-thia-1-aza-benzo[e]azulene TFA salt 235 and adding potassium iodide (0.2 eq.) to the reaction mixture. LCMS: $R_T$=3.57 min, $[M+H]^+$=496

Example 22

3-Azetidine-1-carboxylic acid tert-butyl ester zinc iodide

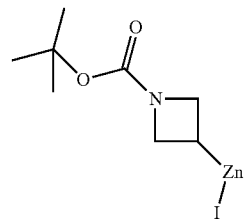

In a sealed flask were placed zinc dust (1.76 g, 27.1 mmol) and Celpure P65 filter agent (380 mg) and the mixture heated under vacuum with a heat gun for 5 minutes. The flask was purged with argon and allowed to cool to RT. To the mixture was added anhydrous DMA (12 mL), followed by a mixture of TMSCl and 1,2-dibromoethane (0.54 mL, 7:5 v:v), causing a large exotherm and vigorous effervescence. The reaction mixture was allowed to cool to RT over 15 minutes before the dropwise addition of 3-iodo-azetidine-1-carboxylic acid tert-butyl ester (6.16 g, 21.8 mmol) as a solution in anhydrous DMA (8.5 mL). The reaction mixture was stirred at RT for 1.5 hours before being filtered to give the title compound as a colourless solution in DMA.

Example 23

3-[2-(2-Isopropyl-2H-[1,2,4]triazol-3-yl)-4,5-dihydro-6-oxa-3-thia-1-aza-benzo[e]azulen-8-yl]-azetidine-1-carboxylic acid tert-butyl ester

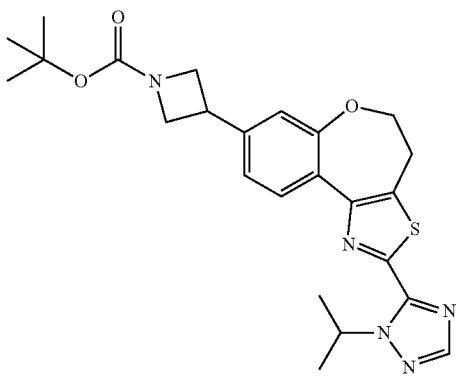 [SMILES: CC(C)n1ncnc1-c1nc2c(s1)CCOc1cc(C3CN(C(=O)OC(C)(C)C)C3)ccc1-2]

A solution of 8-bromo-2-(2-isopropyl-2H-[1,2,4]triazol-3-yl)-4,5-dihydro-6-oxa-3-thia-1-aza-benzo[e]azulene 27 (5.67 g, 14.5 mmol), [1,1'-bis(diphenylphosphino)ferrocene] dichloropalladium(II), complex with dichloromethane (1.18 g, 1.5 mmol) and copper (I) iodide (0.36 g, 1.9 mmol) in anhydrous DMA (64 mL) was degassed by vacuum purging then bubbling argon through the mixture (×3). To the dark red mixture was added 3-azetidine-1-carboxylic acid tert-butyl ester zinc iodide (7.57 g, 21.8 mmol) as a solution in DMA (20.5 mL) and the mixture was heated at 85° C. for 1.75 hours.

During the reaction the mixture turned green, then brown. The reaction mixture was diluted with EtOAc and an aqueous saturated ammonium chloride solution. Water was added to dissolve most of the solids and the mixture was filtered through Celite®. The organic phase of the filtrate was separated and the aqueous phase extracted with EtOAc (×2). The combined organic extracts were washed with brine, dried (Na$_2$SO$_4$) and concentrated in vacuo. The resultant residue was purified by flash chromatography (SiO$_2$, 5-40% EtOAc in cyclohexane) to give the title compound as a pink solid (4.96 g, 73%). LCMS: R$_T$=5.13 min, [M+H]$^+$=468

Example 24

4-Piperidine-1-carboxylic acid tert-butyl ester zinc iodide

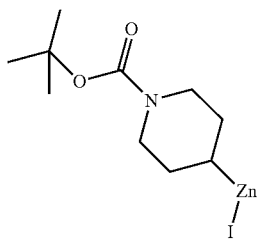

The title compound was prepared by a similar procedure to 3-azetidine-1-carboxylic acid tert-butyl ester zinc iodide using 4-iodo-piperidine-1-carboxylic acid tert-butyl ester instead of 3-iodo-azetidine-1-carboxylic acid tert-butyl ester.

Example 25

4-[2-(2-Isopropyl-2H-[1,2,4]triazol-3-yl)-4,5-dihydro-6-oxa-3-thia-1-aza-benzo[e]azulen-8-yl]-piperidine-1-carboxylic acid tert-butyl ester

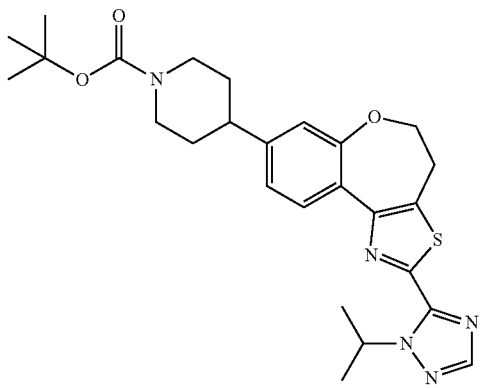 [SMILES: CC(C)n1ncnc1-c1nc2c(s1)CCOc1cc(C3CCN(C(=O)OC(C)(C)C)CC3)ccc1-2]

The title compound was prepared by a similar procedure to 3-[2-(2-isopropyl-2H-[1,2,4]triazol-3-yl)-4,5-dihydro-6-oxa-3-thia-1-aza-benzo[e]azulen-8-yl]-azetidine-1-carboxylic acid tert-butyl ester using 4-piperidine-1-carboxylic acid tert-butyl ester zinc iodide instead of 3-azetidine-1-carboxylic acid tert-butyl ester zinc iodide. The title compound was isolated as a brown solid (480 mg, 76%). LCMS: R$_T$=5.24 min, [M+H]$^+$=496

Example 26

3-Pyrrolidine-1-carboxylic acid tert-butyl ester zinc iodide

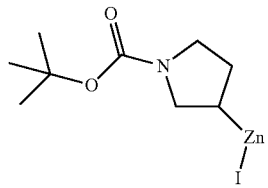

The title compound was prepared by a similar procedure to 3-azetidine-1-carboxylic acid tert-butyl ester zinc iodide using 3-iodo-pyrrolidine-1-carboxylic acid tert-butyl ester instead of 3-iodo-azetidine-1-carboxylic acid tert-butyl ester.

Example 27

3-[2-(2-Isopropyl-2H-[1,2,4]triazol-3-yl)-4,5-dihydro-6-oxa-3-thia-1-aza-benzo[e]azulen-8-yl]-pyrrolidine-1-carboxylic acid tert-butyl ester

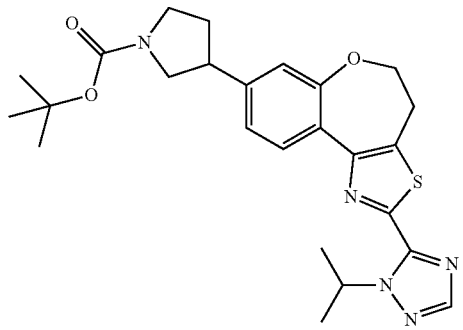 [SMILES: CC(C)n1ncnc1-c1nc2c(s1)CCOc1cc(C3CCN(C(=O)OC(C)(C)C)C3)ccc1-2]

The title compound was prepared by a similar procedure to 3-[2-(2-isopropyl-2H-[1,2,4]triazol-3-yl)-4,5-dihydro-6-oxa-3-thia-1-aza-benzo[e]azulen-8-yl]-azetidine-1-carboxylic acid tert-butyl ester using 3-pyrrolidine-1-carboxylic acid tert-butyl ester zinc iodide instead of 3-azetidine-1-carboxylic acid tert-butyl ester zinc iodide. The title compound was isolated as a red-brown gummy solid (22 mg, 6%). LCMS: R$_T$=5.20 min, [M+H]$^+$=482

Example 28

4-[2-(2-Isopropyl-2H-[1,2,4]triazol-3-yl)-4,5-dihydro-6-oxa-3-thia-1-aza-benzo[e]azulen-9-yl]-piperidine-1-carboxylic acid tert-butyl ester

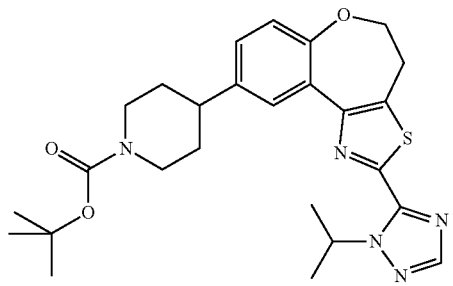 [SMILES: CC(C)n1ncnc1-c1nc2c(s1)CCOc1ccc(C3CCN(C(=O)OC(C)(C)C)CC3)cc1-2]

The title compound was prepared by a similar procedure to 3-[2-(2-isopropyl-2H-[1,2,4]triazol-3-yl)-4,5-dihydro-6-oxa-3-thia-1-aza-benzo[e]azulen-8-yl]-azetidine-1-carboxylic acid tert-butyl ester using 9-bromo-2-(2-isopropyl-2H-[1,2,4]triazol-3-yl)-4,5-dihydro-6-oxa-3-thia-1-aza-benzo[e]azulene from Example 6 instead of 8-bromo-2-(2-isopropyl-2H-[1,2,4]triazol-3-yl)-4,5-dihydro-6-oxa-3-thia-1-aza-benzo[e]azulene 27 and 4-piperidine-1-carboxylic acid tert-butyl ester zinc iodide instead of 3-azetidine-1-carboxylic acid tert-butyl ester zinc iodide. LCMS: $R_T$=5.12 min, $[M+H]^+$=496

Example 29

2-(2-Isopropyl-2H-[1,2,4]triazol-3-yl)-9-piperidin-4-yl-4,5-dihydro-6-oxa-3-thia-1-aza-benzo[e]azulene TFA salt

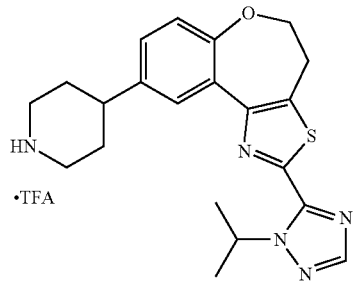 [SMILES: CC(C)n1ncnc1-c1nc2c(s1)CCOc1ccc(C3CCNCC3)cc1-2]

The title compound was prepared by a similar procedure to 8-azetidin-3-yl-2-(2-isopropyl-2H-[1,2,4]triazol-3-yl)-4,5-dihydro-6-oxa-3-thia-1-aza-benzo[e]azulene TFA salt 235 using 4-[2-(2-isopropyl-2H-[1,2,4]triazol-3-yl)-4,5-dihydro-6-oxa-3-thia-1-aza-benzo[e]azulen-9-yl]-piperidine-1-carboxylic acid tert-butyl ester instead of 3-[2-(2-isopropyl-2H-[1,2,4]triazol-3-yl)-4,5-dihydro-6-oxa-3-thia-1-aza-benzo[e]azulen-8-yl]-azetidine-1-carboxylic acid tert-butyl ester. The title compound was isolated as a beige solid (1.75 g, 93%). LCMS: $R_T$=3.28 min, $[M+H]^+$=396

Example 30

8-[1-((S)-2,2-Dimethyl-[1,3]dioxolan-4-ylmethyl)-azetidin-3-yl]-2-(2-isopropyl-2H-[1,2,4]triazol-3-yl)-4,5-dihydro-6-oxa-3-thia-1-aza-benzo[e]azulene

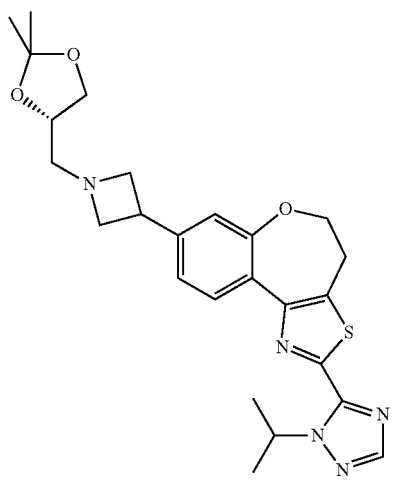 [SMILES: CC(C)n1ncnc1-c1nc2c(s1)CCOc1cc(C3CN(C[C@H]4COC(C)(C)O4)C3)ccc1-2]

The title compound was prepared by a similar procedure to 8-(1-isopropyl-azetidin-3-yl)-2-(2-isopropyl-2H-[1,2,4]triazol-3-yl)-4,5-dihydro-6-oxa-3-thia-1-aza-benzo[e]azulene using (R)-(+)-2,2-dimethyl-1,3-dioxolane-4-carboxaldehyde instead of acetone and adding 1.0 eq. diisopropylethylamine to the reaction mixture. The product was isolated as a colourless oil (127 mg, 32%). LCMS: $R_T$=3.37 min, $[M+H]^+$=482

Example 31

(1-{3-[2-(2-Isopropyl-2H-[1,2,4]triazol-3-yl)-4,5-dihydro-6-oxa-3-thia-1-aza-benzo[e]azulen-8-yl]-azetidine-1-carbonyl}-cyclopropyl)-carbamic acid tert-butyl ester

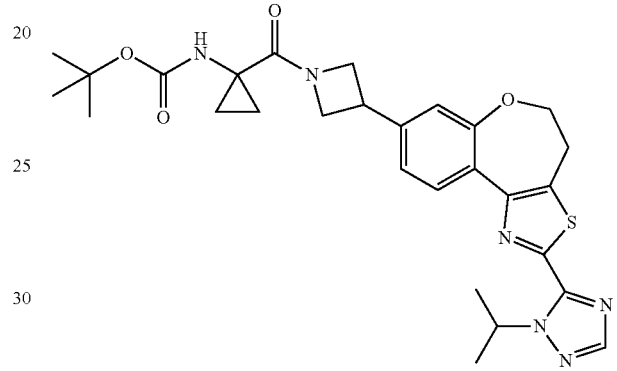

The title compound was prepared by a similar procedure to (R)-2-hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-propan-1-one using 1-(Boc-amino)cyclopropane carboxylic acid and DMF to give (1-{3-[2-(2-Isopropyl-2H-[1,2,4]triazol-3-yl)-4,5-dihydro-6-oxa-3-thia-1-aza-benzo[e]azulen-8-yl]-azetidine-1-carbonyl}-cyclopropyl)-carbamic acid tert-butyl ester isolated as a white solid (228 mg, 66%). LCMS: $R_T$=4.72 min, $[M+H]^+$=551

Example 32

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-2-methyl-propionic acid methyl ester

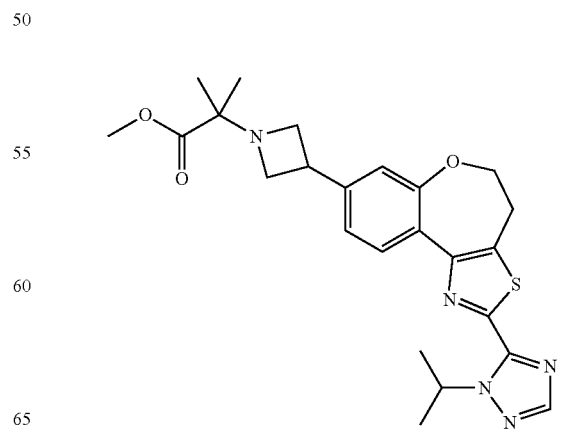

The title compound was prepared by a similar procedure to 2-{3-[2-(2-isopropyl-2H-[1,2,4]triazol-3-yl)-4,5-dihydro-6-oxa-3-thia-1-aza-benzo[e]azulen-8-yl]-azetidin-1-yl}-acetamide using methyl 2-bromoisobutyrate, cesium carbonate instead of potassium carbonate and DMF. The reaction was performed at 80° C. to give 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-2-methyl-propionic acid methyl ester isolated as a white solid (147 mg, 60%). LCMS: $R_T$=3.16 min, [M+H]$^+$=468

Example 33

8-(1-Ethenesulfonyl-azetidin-3-yl)-2-(2-isopropyl-2H-[1,2,4]triazol-3-yl)-4,5-dihydro-6-oxa-3-thia-1-aza-benzo[e]azulene

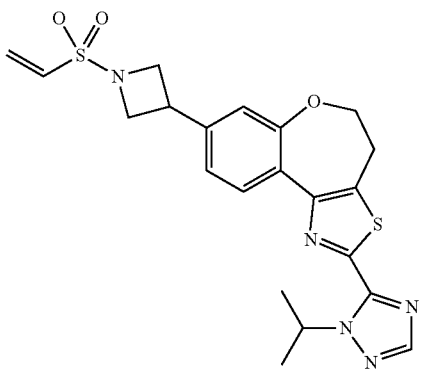

To a mixture of 8-azetidin-3-yl-2-(2-isopropyl-2H-[1,2,4]triazol-3-yl)-4,5-dihydro-6-oxa-3-thia-1-aza-benzo[e]azulene TFA salt 235 (100 mg, 0.2 mmol) in dry DCM (2 mL) was added triethylamine (60 μL, 0.4 mmol) and the reaction mixture was stirred for 1 hour. The mixture was washed with water followed by brine, dried (Na$_2$SO$_4$) and then treated with triethylamine (30 μL, 0.2 mmol) followed by 2-chloroethanesulfonyl chloride (42 μL, 0.4 mmol) in dry DCM (1 mL). The reaction mixture was stirred at RT for 18 hours then diluted with DCM and washed with water followed by brine, dried (Na$_2$SO$_4$) and concentrated in vacuo to give 8-(1-Ethenesulfonyl-azetidin-3-yl)-2-(2-isopropyl-2H-[1,2,4]triazol-3-yl)-4,5-dihydro-6-oxa-3-thia-1-aza-benzo[e]azulene as a light brown oil (75 mg, 82%). $^1$H NMR δ (ppm) (CDCl$_3$): 8.39 (1H, d, J=8.22 Hz), 7.93 (1H, s), 7.16 (1H, dd, J=8.22, 1.98 Hz), 7.02 (1H, d, J=1.91 Hz), 6.61 (1H, dd, J=16.50, 9.95 Hz), 6.39 (1H, d, J=16.66 Hz), 6.18 (1H, d, J=9.95 Hz), 5.93-5.87 (1H, m), 4.45-4.39 (2H, m), 4.28-4.22 (2H, m), 4.07-3.97 (2H, m), 3.81 (1H, t, J=7.81 Hz), 3.46-3.40 (2H, m), 1.64 (6H, d, J=6.65 Hz)

Example 34

8-bromo-4,5-dihydro-6-oxa-3-thia-1-aza-benzo[e]azulene-2-carboxylic acid

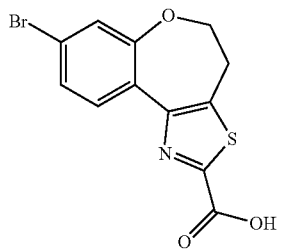 [SMILES: O=C(O)c1nc2c(s1)CCOc1cc(Br)ccc1-2]

A mixture of 8-bromo-4,5-dihydro-6-oxa-3-thia-1-aza-benzo[e]azulene-2-carboxylic acid ethyl ester (3.32 g, 9.38 mmol), MeOH (75 mL) and water (50 mL) was treated with sodium hydroxide (562 mg, 14.06 mmol) at RT. After 90 minutes THF (20 mL) was added to aid dissolution. After 60 minutes the mixture was concentrated in vacuo, dissolved in water (200 mL) and carefully acidified to pH1 with 2N HCl. The resulting solid was collected by filtration, washed with water and dried under vacuum to afford 8-bromo-4,5-dihydro-6-oxa-3-thia-1-aza-benzo[e]azulene-2-carboxylic acid (1.86 g, 61%). LCMS $R_T$=4.91 min, no [M+H]$^+$=326/328

Example 35

[5-(8-Bromo-4,5-dihydro-6-oxa-3-thia-1-aza-benzo[e]azulen-2-yl)-1-isopropyl-1H-[1,2,4]triazol-3-yl]-carbamic acid benzyl ester

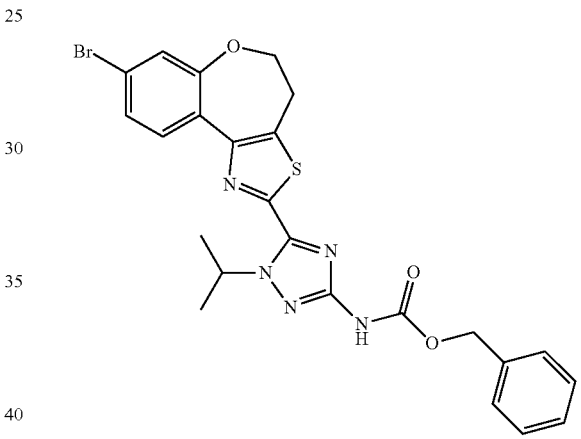

To a suspension of 8-bromo-4,5-dihydro-6-oxa-3-thia-1-aza-benzo[e]azulene-2-carboxylic acid (1.86 g, 5.70 mmol) in anhydrous THF (75 mL) was added diisopropylethylamine (2 mL, 11.4 mmol), HATU (2.39 g, 6.27 mmol) and 1-benzyloxycarbonyl-2-methyl-isothiourea (1.47 g, 6.56 mmol) at RT. After stirring for 24 hours an aqueous saturated sodium bicarbonate solution was added and the mixture extracted with 1:1 EtOAc/THF solution (×2). The organic layers were combined, washed with brine, dried (Na$_2$SO$_4$) and concentrated in vacuo. The resulting solid was added to DMF (50 mL) and treated with diisopropylethylamine (4 mL, 22.8 mmol) and isopropylhydrazine hydrochloride (941 mg, 8.55 mmol). The mixture was heated to 95° C. and scrubbed with 1N NaOH solution and NaOCl solution. After 2 hours the mixture was allowed to cool to RT, extracted with EtOAc and washed with water. The organic layer was dried (Na$_2$SO$_4$) and concentrated in vacuo. The resultant residue was purified by flash chromatography (SiO$_2$, gradient 0-50% EtOAc in cyclohexane) to afford [5-(8-Bromo-4,5-dihydro-6-oxa-3-thia-1-aza-benzo[e]azulen-2-yl)-1-isopropyl-1H-[1,2,4]triazol-3-yl]-carbamic acid benzyl ester (1.75 g, 57%). LCMS: $R_T$=5.11 min, [M+H]$^+$=540/542

Example 36

3-[2-(5-Benzyloxycarbonylamino-2-isopropyl-2H-[1,2,4]-triazol-3-yl)-4,5-dihydro-6-oxa-3-thia-1-aza-benzo[e]azulen-8-yl]-azetidine-1-carboxylic acid tert-butyl ester

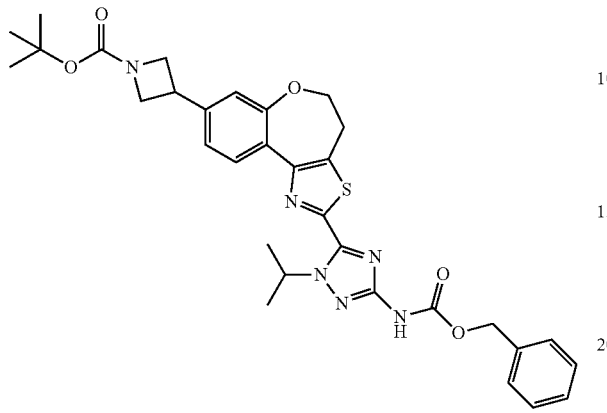

Following a similar procedure to 3-[2-(2-isopropyl-2H-[1,2,4]triazol-3-yl)-4,5-dihydro-6-oxa-3-thia-1-aza-benzo[e]azulen-8-yl]-azetidine-1-carboxylic acid tert-butyl ester using [5-(8-bromo-4,5-dihydro-6-oxa-3-thia-1-aza-benzo[e]azulen-2-yl)-1-isopropyl-1H-[1,2,4]triazol-3-yl]-carbamic acid benzyl ester, 3-[2-(5-Benzyloxycarbonylamino-2-isopropyl-2H-[1,2,4]-triazol-3-yl)-4,5-dihydro-6-oxa-3-thia-1-aza-benzo[e]azulen-8-yl]-azetidine-1-carboxylic acid tert-butyl ester was prepared (394 mg, 36%). LCMS: $R_T$=4.98 min, $[M+H]^+$=617

Example 37

[5-(8-azetidin-3-yl-4,5-dihydro-6-oxa-3-thia-1-aza-benzo[e]azulen-2-yl)-1-isopropyl-1H-[1,2,4]triazol-3-yl]-carbamic acid benzyl ester hydrochloride salt

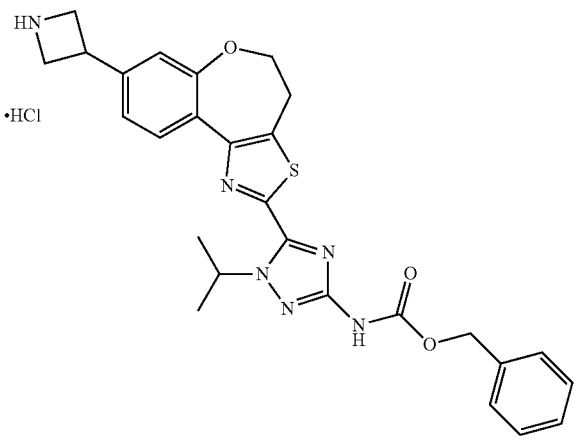 [SMILES: Cl ; CC(C)n1nc(NC(=O)OCc2ccccc2)nc1-c1nc2c(s1)CCOc1cc(C3CNC3)ccc1-2]

To a solution of 3-[2-(5-benzyloxycarbonylamino-2-isopropyl-2H-[1,2,4]-triazol-3-yl)-4,5-dihydro-6-oxa-3-thia-1-aza-benzo[e]azulen-8-yl]-azetidine-1-carboxylic acid tert-butyl ester (504 mg, 0.82 mmol) in DCM (10 mL) was added 4N HCl in dioxan (2 mL) at RT. After stirring for 2 hours MeOH (2 mL) and 4N HCl in dioxan (3 mL) were added to the mixture. After stirring for 60 minutes the reaction mixture was concentrated in vacuo. The resulting solid was treated with ether, collected by filtration and dried under vacuum to afford [5-(8-azetidin-3-yl-4,5-dihydro-6-oxa-3-thia-1-aza-benzo[e]azulen-2-yl)-1-isopropyl-1H-[1,2,4]triazol-3-yl]-carbamic acid benzyl ester hydrochloride salt (379 mg, 84%). LCMS: $R_T$=3.04 min, $[M+H]^+$=517

Example 38

(1-Isopropyl-5-{8-[1-(2-methanesulfonyl-ethyl)-azetidin-3-yl]-4,5-dihydro-6-oxa-3-thia-1-aza-benzo[e]azulen-2-yl}-1H-[1,2,4]triazol-3-yl)-carbamic acid benzyl ester

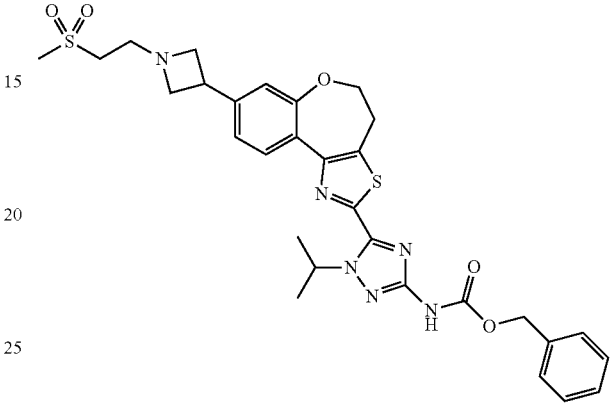

The title compound was prepared by a similar procedure to 2-(2-isopropyl-2H-[1,2,4]triazol-3-yl)-8-[1-(2-methanesulfonyl-ethyl)-azetidin-3-yl]-4,5-dihydro-6-oxa-3-thia-1-aza-benzo[e]azulene using 8-azetidin-3-yl-2-(2-isopropyl-2H-[1,2,4]triazol-3-yl)-4,5-dihydro-6-oxa-3-thia-1-aza-benzo[e]azulene 235 HCl salt and diisopropylethylamine. The reaction mixture was diluted with DCM and water. The organic phase dried (Na$_2$SO$_4$) and concentrated in vacuo. The residue was purified by flash chromatography (SiO$_2$, 0-4% MeOH in DCM) to give (1-Isopropyl-5-{8-[1-(2-methanesulfonyl-ethyl)-azetidin-3-yl]-4,5-dihydro-6-oxa-3-thia-1-aza-benzo[e]azulen-2-yl}-1H-[1,2,4]triazol-3-yl)-carbamic acid benzyl ester (157 mg, 73%). LCMS: $R_T$=3.04 min, $[M+H]^+$=623

Example 39

(2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-1,1-dimethyl-2-oxo-ethyl)-carbamic acid tert-butyl ester

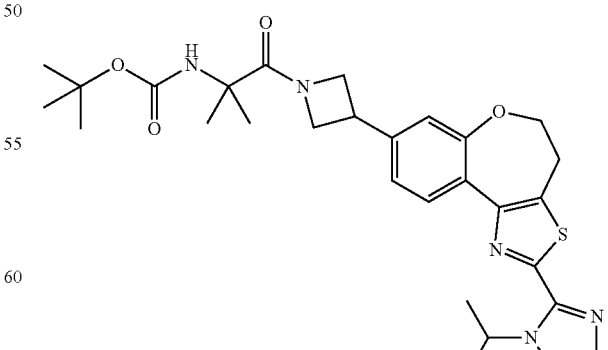

Following a similar method to N-(2-hydroxy-2-methyl-propyl)-2-{3-[2-(2-isopropyl-2H-[1,2,4]triazol-3-yl)-4,5-dihydro-6-oxa-3-thia-1-aza-benzo[e]azulen-8-yl]-azetidin-1-yl}-acetamide using Boc-Aib-OH, (2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-1,1-dimethyl-2-oxo-ethyl)-carbamic acid tert-butyl ester was isolated as a colourless oil (203 mg, 59%). LCMS: $R_T$=4.77 min, [M+H]$^+$=553

Example 40

{3-[2-(2-Isopropyl-2H-[1,2,4]triazol-3-yl)-4,5-dihydro-6-oxa-3-thia-1-aza-benzo[e]azulen-8-yl]-azetidin-1-yl}-acetic acid tert-butyl ester

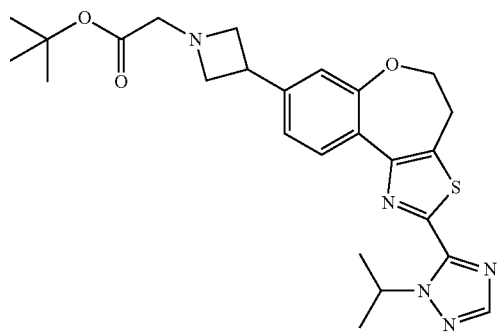 [SMILES: CC(C)n1ncnc1-c1nc2c(s1)CCOc1cc(C3CN(CC(=O)OC(C)(C)C)C3)ccc1-2]

Following a similar procedure to 2-{3-[2-(2-isopropyl-2H-[1,2,4]triazol-3-yl)-4,5-dihydro-6-oxa-3-thia-1-aza-benzo[e]azulen-8-yl]-azetidin-1-yl}-acetamide using tert-butyl bromoacetate, {3-[2-(2-Isopropyl-2H-[1,2,4]triazol-3-yl)-4,5-dihydro-6-oxa-3-thia-1-aza-benzo[e]azulen-8-yl]-azetidin-1-yl}-acetic acid tert-butyl ester was isolated as a colourless oil (97 mg, 33%). LCMS: $R_T$=3.63 min, [M+H]$^+$=482

Example 41

{3-[2-(2-Isopropyl-2H-[1,2,4]triazol-3-yl)-4,5-dihydro-6-oxa-3-thia-1-aza-benzo[e]azulen-8-yl]-azetidin-1-yl}-acetic acid TFA salt

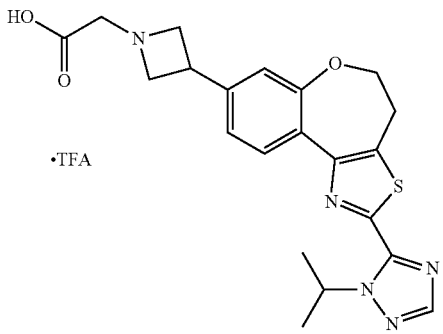 [SMILES: CC(C)n1ncnc1-c1nc2c(s1)CCOc1cc(C3CN(CC(=O)O)C3)ccc1-2]

Following a similar procedure to 8-azetidin-3-yl-2-(2-isopropyl-2H-[1,2,4]triazol-3-yl)-4,5-dihydro-6-oxa-3-thia-1-aza-benzo[e]azulene TFA salt 235 using {3-[2-(2-isopropyl-2H-[1,2,4]triazol-3-yl)-4,5-dihydro-6-oxa-3-thia-1-aza-benzo[e]azulen-8-yl]-azetidin-1-yl}-acetic acid tert-butyl ester and TFA:DCM (1:2), {3-[2-(2-Isopropyl-2H-[1,2,4]triazol-3-yl)-4,5-dihydro-6-oxa-3-thia-1-aza-benzo[e]azu-len-8-yl]-azetidin-1-yl}-acetic acid TFA salt was isolated as a white solid (75 mg, 90%). $^1$H NMR δ (ppm) (DMSO-d6): 8.35 (1H, d, J=8.20 Hz), 8.11 (1H, d, J=0.75 Hz), 7.29 (1H, d, J=8.33 Hz), 7.21 (1H, s), 5.85-5.77 (1H, m), 4.48-4.39 (2H, m), 4.41-4.35 (2H, m), 4.36-4.22 (3H, m), 3.48-3.42 (2H, m), 1.55 (6H, d, J=6.59 Hz) plus 2 protons obscured by the water peak and 2 exchangeable protons not observed.

Example 42

2-Methyl-1-[4-(4,4,5,5-tetramethyl-[1,3,2]dioxaborolan-2-yl)-pyrazol-1-yl]-propan-2-ol

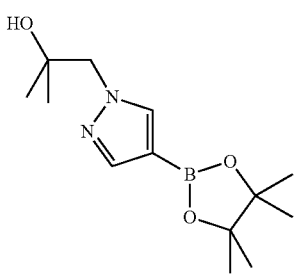 [SMILES: CC(C)(O)Cn1cc(B2OC(C)(C)C(C)(C)O2)cn1]

To a solution of 4-(4,4,5,5-tetramethyl-[1,3,2]dioxaborolan-2-yl)-1H-pyrazole (500 mg, 2.58 mmol) in 2,2-dimethyl-oxirane (3 mL) was added cesium carbonate (130 mg, 0.40 mmol). The reaction was heated at 120° C. for 30 minutes using microwave irradiation. The reaction was cooled then filtered through a plug of cotton wool, flushing with DCM. The filtrate was concentrated in vacuo giving 2-Methyl-1-[4-(4,4,5,5-tetramethyl-[1,3,2]dioxaborolan-2-yl)-pyrazol-1-yl]-propan-2-ol as a beige solid (620 mg, 90%). $^1$H NMR δ (ppm) (CDCl$_3$): 7.82 (1H, d, J=0.65 Hz), 7.69 (1H, s), 4.07 (2H, s), 1.32 (12H, s), 1.15 (6H, s). 1 Exchangeable proton not observed

Example 43

8-Bromo-4,5-dihydro-6-oxa-3-thia-1-aza-benzo[e]azulen-2-ylamine

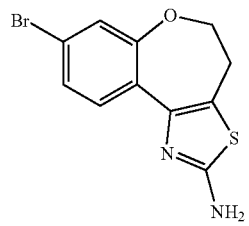 [SMILES: Nc1nc2c(s1)CCOc1cc(Br)ccc1-2]

To a solution of 8-bromo-4,5-dihydro-6-oxa-3-thia-1-aza-benzo[e]azulene-2-carboxylic acid (12.5 g, 38.3 mmol) in tert-butanol (250 mL) were added triethylamine (5.5 mL, 40 mmol) and diphenylphosphoryl-azide (8.6 mL, 40 mmol). The reaction mixture was stirred at 95° C. for 16 hours, then allowed to cool down to RT, and concentrated in vacuo. The resultant residue was dissolved in EtOAc, washed successively with water, aqueous saturated sodium bicarbonate solution followed by brine, dried (MgSO$_4$) and concentrated in vacuo. The resultant residue was dissolved in DCM (150 mL) and treated with TFA (50 mL). The reaction mixture was stirred at RT for 3 hours then concentrated in vacuo. The resulting residue was triturated with 20% EtOAc/cyclohexane and filtered to afford 8-Bromo-4,5-dihydro-6-oxa-3-thia-1-aza-benzo[e]azulen-2-ylamine as an off-white solid (7.94 g, 70%). LCMS: $R_T$=3.13 min, $[M+H]^+$=297/299

Example 44

2,8-Dibromo-4,5-dihydro-6-oxa-3-thia-1-aza-benzo[e]azulene

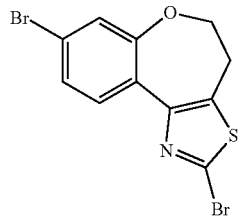 [SMILES: Brc1ccc2c(c1)OCCc1sc(Br)nc1-2]

To a solution of 8-bromo-4,5-dihydro-6-oxa-3-thia-1-aza-benzo[e]azulen-2-ylamine (1.69 g, 5.68 mmol) in MeCN (60 mL) was added $CuBr_2$ (2.54 g, 11.36 mmol). The reaction was purged with argon and cooled to 0° C. before the dropwise addition of 2-methyl-2-nitrosooxy-propane (1.35 mL, 11.36 mL). The reaction was warmed to RT and stirred for 20 hours, then quenched with an aqueous saturated sodium bicarbonate solution (30 mL) and extracted with DCM (3×50 mL). The combined organic phases were washed with brine (30 mL), dried ($Na_2SO_4$) and concentrated in vacuo. The residue was subjected to flash chromatography ($SiO_2$, 0-10% DCM in cyclohexane) to give 2,8-Dibromo-4,5-dihydro-6-oxa-3-thia-1-aza-benzo[e]azulene as a white solid (1.45 g, 70%). LCMS: $R_T$=4.54 min, $[M+H]^+$=360/362/364.

Example 45

Mixture of 4-(8-Bromo-4,5-dihydro-6-oxa-3-thia-1-aza-benzo[e]azulen-2-yl)-2,5-dimethyl-2,4-dihydro-[1,2,4]triazol-3-one and 4-(8-Iodo-4,5-dihydro-6-oxa-3-thia-1-aza-benzo[e]azulen-2-yl)-2,5-dimethyl-2,4-dihydro-[1,2,4]triazol-3-one (~1:1)

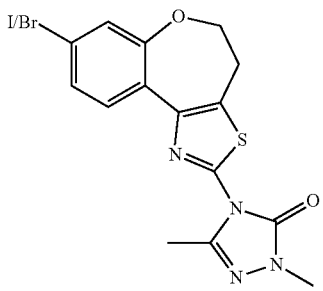

A microwave vial was charged with 2,8-dibromo-4,5-dihydro-6-oxa-3-thia-1-aza-benzo[e]azulene (429 mg, 1.2 mmol), 2,5-dimethyl-2,4-dihydro-[1,2,4]triazol-3-one (188 mg, 1.7 mmol), trans-1,2-dimethylamino-cyclohexane (187 μL, 1.2 mmol), copper (I) iodide (227 mg, 1.2 mmol), cesium carbonate (540 mg, 1.7 mmol) and 1,4-dioxan (20 mL) and sealed. The vial was evacuated and purged with argon (×3) then the reaction mixture was heated at 100° C. for 18 h. The mixture was concentrated in vacuo and the residue purified by flash chromatography ($SiO_2$, 0-10% EtOAc in DCM) to give the mixture of 4-(8-Bromo-4,5-dihydro-6-oxa-3-thia-1-aza-benzo[e]azulen-2-yl)-2,5-dimethyl-2,4-dihydro-[1,2,4]triazol-3-one and 4-(8-Iodo-4,5-dihydro-6-oxa-3-thia-1-aza-benzo[e]azulen-2-yl)-2,5-dimethyl-2,4-dihydro-[1,2,4]triazol-3-one (~1:1) as an off-white solid (41 mg). LCMS: $R_T$=4.39, 4.44 min, $[M+H]^+$=393/395 and 441

Example 46

2-Isopropyl-5-methyl-2,4-dihydro-[1,2,4]triazol-3-one

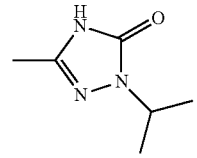

To a solution of [1-ethoxy-eth-(Z)-ylidene]-carbamic acid ethyl ester (834 mg, 5.24 mmol) in toluene (15 mL) was added isopropyl hydrazine hydrochloride (637 mg, 5.76 mmol) followed by triethylamine (803 μL, 5.76 mmol). The reaction vessel was sealed and stirred at 45° C. for 45 minutes before the addition of triethylamine (803 μL, 5.76 mmol). The resultant mixture was heated to 90° C. and stirred for 17 hours, then cooled and concentrated in vacuo. The resultant residue was purified by flash chromatography ($SiO_2$, gradient 0% to 8% 2M $NH_3$/MeOH in DCM) to give 2-Isopropyl-5-methyl-2,4-dihydro-[1,2,4]triazol-3-one as an off white solid (329 mg, 44%). LCMS: $R_T$=2.16 min, $[M+Na]^+$=164

Example 47

Mixture of 4-(8-Bromo-4,5-dihydro-6-oxa-3-thia-1-aza-benzo[e]azulen-2-yl)-2-isopropyl-5-methyl-2,4-dihydro-[1,2,4]triazol-3-one and 4-(8-Iodo-4,5-dihydro-6-oxa-3-thia-1-aza-benzo[e]azulen-2-yl)-2-isopropyl-5-methyl-2,4-dihydro-[1,2,4]triazol-3-one (~1:1)

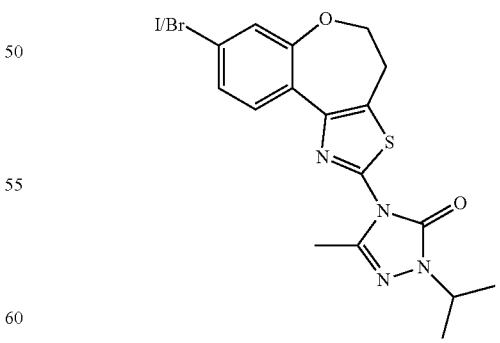

Following a similar procedure for the mixture of 4-(8-bromo-4,5-dihydro-6-oxa-3-thia-1-aza-benzo[e]azulen-2-yl)-2,5-dimethyl-2,4-dihydro-[1,2,4]triazol-3-one and 4-(8-iodo-4,5-dihydro-6-oxa-3-thia-1-aza-benzo[e]azulen-2-yl)-2,5-dimethyl-2,4-dihydro-[1,2,4]triazol-3-one using 2-isopropyl-5-methyl-2,4-dihydro-[1,2,4]triazol-3-one, the mixture of 4-(8-Bromo-4,5-dihydro-6-oxa-3-thia-1-aza-benzo[e]azulen-2-yl)-2-isopropyl-5-methyl-2,4-dihydro-[1,2,4]triazol-3-one and 4-(8-Iodo-4,5-dihydro-6-oxa-3-thia-1-aza-benzo[e]azulen-2-yl)-2-isopropyl-5-methyl-2,4-dihydro-[1,2,4]triazol-3-one (~1:1) was isolated as an off-white solid (49 mg). LCMS: $R_T$=5.17 min, [M+H]$^+$=421/423 and 469

Example 48

4-(8-Bromo-4,5-dihydro-6-oxa-3-thia-1-aza-benzo[e]azulen-2-yl)-5-isopropyl-2-methyl-2,4-dihydro-[1,2,4]triazol-3-one

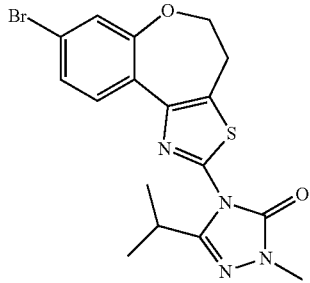 [SMILES: CC(C)c1nn(C)c(=O)n1-c1nc2c(s1)CCOc1cc(Br)ccc1-2]

The title compound was prepared by a similar method to the mixture of 4-(8-bromo-4,5-dihydro-6-oxa-3-thia-1-aza-benzo[e]azulen-2-yl)-2,5-dimethyl-2,4-dihydro-[1,2,4]triazol-3-one and 4-(8-iodo-4,5-dihydro-6-oxa-3-thia-1-aza-benzo[e]azulen-2-yl)-2,5-dimethyl-2,4-dihydro-[1,2,4]triazol-3-one using 5-isopropyl-2-methyl-2,4-dihydro-[1,2,4]triazol-3-one and potassium carbonate. 4-(8-Bromo-4,5-dihydro-6-oxa-3-thia-1-aza-benzo[e]azulen-2-yl)-5-isopropyl-2-methyl-2,4-dihydro-[1,2,4]triazol-3-one was isolated as a yellow solid (11 mg, 17%). LCMS: $R_T$=5.19 min, [M+H]$^+$=421/423

Example 49

5-Isopropyl-2-methyl-4-(8-{1-[2-(tetrahydro-pyran-2-yloxy)-ethyl]-1H-pyrazol-4-yl}-4,5-dihydro-6-oxa-3-thia-1-aza-benzo[e]azulen-2-yl)-2,4-dihydro-[1,2,4]triazol-3-one

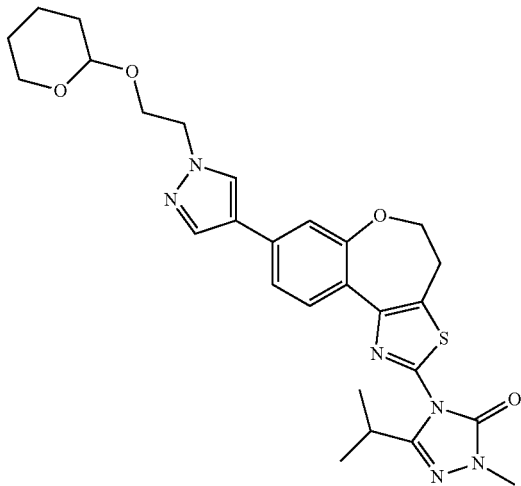 [SMILES: CC(C)c1nn(C)c(=O)n1-c1nc2c(s1)CCOc1cc(-c3cnn(CCOC4CCCCO4)c3)ccc1-2]

The title compound was prepared by a similar procedure to 4-{8-[1-(2-hydroxy-2-methyl-propyl)-1H-pyrazol-4-yl]-4,5-dihydro-6-oxa-3-thia-1-aza-benzo[e]azulen-2-yl}-2,5-dimethyl-2,4-dihydro-[1,2,4]triazol-3-one using 1-[2-(tetrahydro-pyran-2-yloxy)-ethyl]-4-(4,4,5,5-tetramethyl-[1,3,2]dioxaborolan-2-yl)-1H-pyrazole. 5-Isopropyl-2-methyl-4-(8-{1-[2-(tetrahydro-pyran-2-yloxy)-ethyl]-1H-pyrazol-4-yl}-4,5-dihydro-6-oxa-3-thia-1-aza-benzo[e]azulen-2-yl)-2,4-dihydro-[1,2,4]triazol-3-one was isolated as a white solid (9 mg, 65%). LCMS: $R_T$=4.84 min, [M+H]$^+$=537

Example 50

1-Ethenesulfonyl-3,3-difluoro-azetidine

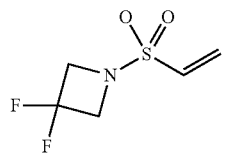

The title compound was prepared by a similar procedure to 8-(1-ethenesulfonyl-azetidin-3-yl)-2-(2-isopropyl-2H-[1,2,4]triazol-3-yl)-4,5-dihydro-6-oxa-3-thia-1-aza-benzo[e]azulene using 3,3-difluoroazetidine hydrochloride salt. 1-Ethenesulfonyl-3,3-difluoro-azetidine was isolated as a light brown oil after flash chromatography (SiO$_2$, DCM) (171 mg, 61%). $^1$H NMR δ (ppm) (CDCl$_3$): 6.56 (1H, dd, J=16.56, 9.83 Hz), 6.40 (1H, d, J=16.59 Hz), 6.20 (1H, d, J=9.83 Hz), 4.32-4.17 (4H, m)

Example 51

8-Bromo-2-[2-(2,2,2-trifluoro-ethyl)-2H-[1,2,4]triazol-3-yl]-4,5-dihydro-6-oxa-3-thia-1-aza-benzo[e]azulene

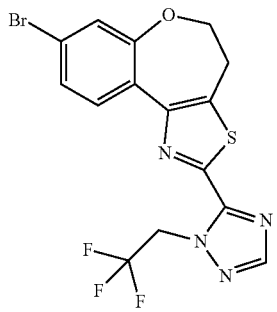 [SMILES: FC(F)(F)Cn1ncnc1-c1nc2c(s1)CCOc1cc(Br)ccc1-2]

To a solution of 8-Bromo-4,5-dihydro-6-oxa-3-thia-1-aza-benzo[e]azulene-2-carboxylic acid amide 25 (10.76 g, 0.03308 mol) in toluene (200 mL) was added methanamine, 1,1-Dimethoxy-N,N-dimethyl-(19.683 g, 0.1640 moles). The reaction was heated to 95° C. for 3 hours. The toluene was removed in vacuo to give a beige powder. The crude (12.58 g, 0.03308 mol) was redissolved in acetic acid (120 mL) and trifluoroethyl hydrazine (6.269 mL, 0.04962 mol) was added. The reaction was heated to 95° C. for 4 h. The AcOH was removed in vacuo. The product was loaded as a solid onto silica and purified by flash chromatography (5-70% EtOAc in hexanes). The appropriate fractions were combined and concentrated to give 8-Bromo-2-[2-(2,2,2-trifluoro-ethyl)-2H-

[1,2,4]triazol-3-yl]-4,5-dihydro-6-oxa-3-thia-1-aza-benzo[e]azulene (6.176 g) as an off-white solid. MS(ESI+) 431.0/433.0.

2-(2-pyridin-4-ylmethyl-2H-[1,2,4]triazol-3-yl)-4,5-dihydro-6-oxa-3-thia-1-aza-benzo[e]azulene.

Example 52

8-Bromo-2-[2-(2,2,2-trifluoro-1-methyl-ethyl)-2H-[1,2,4]triazol-3-yl]-4,5-dihydro-6-oxa-3-thia-1-aza-benzo[e]azulene

Example 54

8-Bromo-2-(2-pyridin-2-ylmethyl-2H-[1,2,4]triazol-3-yl)-4,5-dihydro-6-oxa-3-thia-1-aza-benzo[e]azulene

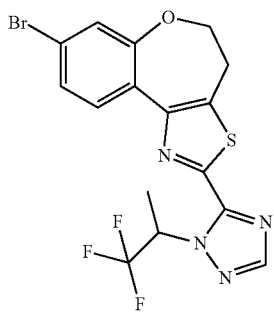 [SMILES: CC(n1ncnc1-c1nc2c(s1)CCOc1cc(Br)ccc1-2)C(F)(F)F]

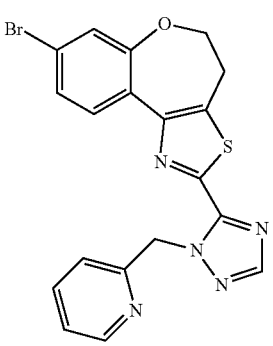

Following the procedure for 8-Bromo-2-[2-(2,2,2-trifluoro-ethyl)-2H-[1,2,4]triazol-3-yl]-4,5-dihydro-6-oxa-3-thia-1-aza-benzo[e]azulene, 8-Bromo-4,5-dihydro-6-oxa-3-thia-1-aza-benzo[e]azulene-2-carboxylic acid amide 25 was reacted with (2,2,2-Trifluoro-1-methyl-ethyl)-hydrazine to give 8-Bromo-2-[2-(2,2,2-trifluoro-1-methyl-ethyl)-2H-[1,2,4]triazol-3-yl]-4,5-dihydro-6-oxa-3-thia-1-aza-benzo[e]azulene. MS(ESI+) 445.0/447.0.

Following the procedure for 8-Bromo-2-[2-(2,2,2-trifluoro-ethyl)-2H-[1,2,4]triazol-3-yl]-4,5-dihydro-6-oxa-3-thia-1-aza-benzo[e]azulene, 8-Bromo-4,5-dihydro-6-oxa-3-thia-1-aza-benzo[e]azulene-2-carboxylic acid amide 25 was reacted with Pyridin-2-ylmethyl-hydrazine to give 8-Bromo-2-(2-pyridin-2-ylmethyl-2H-[1,2,4]triazol-3-yl)-4,5-dihydro-6-oxa-3-thia-1-aza-benzo[e]azulene. MS(ESI+) 440.0/442.0.

Example 53

8-Bromo-2-(2-pyridin-4-ylmethyl-2H-[1,2,4]triazol-3-yl)-4,5-dihydro-6-oxa-3-thia-1-aza-benzo[e]azulene

Example 55

8-Bromo-2-[2-(1-methyl-piperidin-4-yl)-2H-[1,2,4]triazol-3-yl]-4,5-dihydro-6-oxa-3-thia-1-aza-benzo[e]azulene

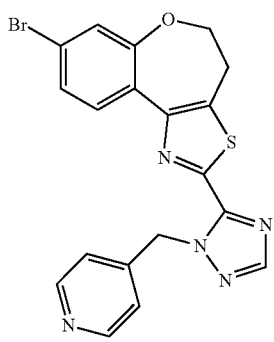 [SMILES: Brc1ccc2c(c1)OCCc1sc(-c3ncnn3Cc3ccncc3)nc1-2]

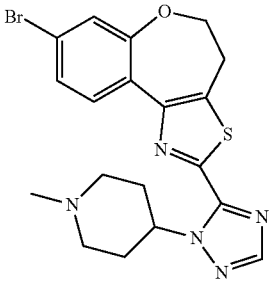 [SMILES: CN1CCC(n2ncnc2-c2nc3c(s2)CCOc2cc(Br)ccc2-3)CC1]

Following the procedure for 8-Bromo-2-[2-(2,2,2-trifluoro-ethyl)-2H-[1,2,4]triazol-3-yl]-4,5-dihydro-6-oxa-3-thia-1-aza-benzo[e]azulene, 8-Bromo-4,5-dihydro-6-oxa-3-thia-1-aza-benzo[e]azulene-2-carboxylic acid amide 25 was reacted with pyridin-4-ylmethyl-hydrazine to give 8-Bromo- Following the procedure for 8-Bromo-2-[2-(2,2,2-trifluoro-ethyl)-2H-[1,2,4]triazol-3-yl]-4,5-dihydro-6-oxa-3-thia-1-aza-benzo[e]azulene, 8-Bromo-4,5-dihydro-6-oxa-3-thia-1-aza-benzo[e]azulene-2-carboxylic acid amide 25 was reacted with (1-methyl-piperidin-4-yl)-hydrazine to give 8-Bromo-2-[2-(1-methyl-piperidin-4-yl)-2H-[1,2,4]triazol-3-yl]-4,5-dihydro-6-oxa-3-thia-1-aza-benzo[e]azulene.

Example 56

2-[5-(8-Bromo-4,5-dihydro-6-oxa-3-thia-1-aza-benzo[e]azulen-2-yl)-[1,2,4]triazol-1-yl]-ethanol

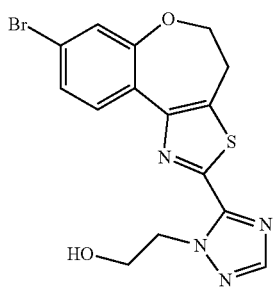 [SMILES: OCCn1ncnc1-c1nc2c(s1)CCOc1cc(Br)ccc1-2]

Following the procedure for 8-Bromo-2-[2-(2,2,2-trifluoro-ethyl)-2H-[1,2,4]triazol-3-yl]-4,5-dihydro-6-oxa-3-thia-1-aza-benzo[e]azulene, 8-Bromo-4,5-dihydro-6-oxa-3-thia-1-aza-benzo[e]azulene-2-carboxylic acid amide 25 was reacted with 2-hydrazino-ethanol to give 2-[5-(8-Bromo-4,5-dihydro-6-oxa-3-thia-1-aza-benzo[e]azulen-2-yl)-[1,2,4]triazol-1-yl]-ethanol. MS(ESI+) 393.0/395.0.

Example 57

1-[5-(8-Bromo-4,5-dihydro-6-oxa-3-thia-1-aza-benzo[e]azulen-2-yl)-[1,2,4]triazol-1-yl]-propan-2-ol

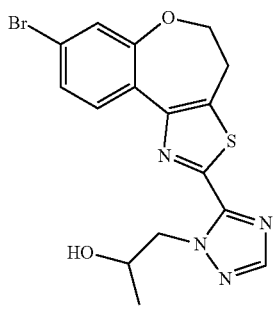 [SMILES: CC(O)Cn1ncnc1-c1nc2c(s1)CCOc1cc(Br)ccc1-2]

Following the procedure for 8-Bromo-2-[2-(2,2,2-trifluoro-ethyl)-2H-[1,2,4]triazol-3-yl]-4,5-dihydro-6-oxa-3-thia-1-aza-benzo[e]azulene, 8-Bromo-4,5-dihydro-6-oxa-3-thia-1-aza-benzo[e]azulene-2-carboxylic acid amide 25 was reacted with 1-hydrazino-propan-2-ol to give 1-[5-(8-Bromo-4,5-dihydro-6-oxa-3-thia-1-aza-benzo[e]azulen-2-yl)-[1,2,4]triazol-1-yl]-propan-2-ol. MS(ESI+) 407.0/409.0.

Example 58

Acetic acid 2-[5-(8-bromo-4,5-dihydro-6-oxa-3-thia-1-aza-benzo[e]azulen-2-yl)-[1,2,4]triazol-1-yl]-propyl ester

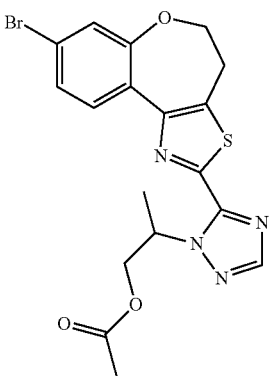 [SMILES: CC(=O)OCC(C)n1ncnc1-c1nc2c(s1)CCOc1cc(Br)ccc1-2]

Following the procedure for 8-Bromo-2-[2-(2,2,2-trifluoro-ethyl)-2H-[1,2,4]triazol-3-yl]-4,5-dihydro-6-oxa-3-thia-1-aza-benzo[e]azulene, 8-Bromo-4,5-dihydro-6-oxa-3-thia-1-aza-benzo[e]azulene-2-carboxylic acid amide 25 was reacted with 1-hydrazino-propan-1-ol to give Acetic acid 2-[5-(8-bromo-4,5-dihydro-6-oxa-3-thia-1-aza-benzo[e]azulen-2-yl)-[1,2,4]triazol-1-yl]-propyl ester. MS(ESI+) 449.0/451.0.

Example 59

8-bromo-2-[2-(2-morpholin-4-yl-ethyl)-2H-[1,2,4]triazol-3-yl]-4,5-dihydro-6-oxa-3-thia-1-aza-benzo[e]azulene

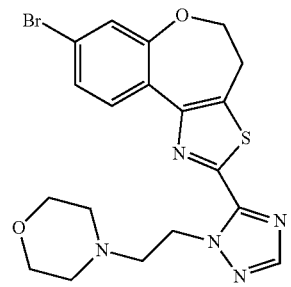 [SMILES: Brc1ccc2c(c1)OCCc1sc(-c3ncnn3CCN3CCOCC3)nc1-2]

Following the procedure for 8-Bromo-2-[2-(2,2,2-trifluoro-ethyl)-2H-[1,2,4]triazol-3-yl]-4,5-dihydro-6-oxa-3-thia-1-aza-benzo[e]azulene, 8-Bromo-4,5-dihydro-6-oxa-3-thia-1-aza-benzo[e]azulene-2-carboxylic acid amide 25 was reacted with (2-morpholin-4-yl-ethyl)-hydrazine to give 8-bromo-2-[2-(2-morpholin-4-yl-ethyl)-2H-[1,2,4]triazol-3-yl]-4,5-dihydro-6-oxa-3-thia-1-aza-benzo[e]azulene. MS(ESI+) 462.1/464.1.

Example 60

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-2-methyl-propionitrile

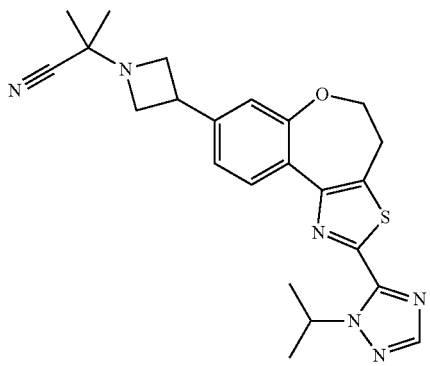 [SMILES: CC(C)n1ncnc1-c1nc2c(s1)CCOc1cc(C3CN(C(C)(C)C#N)C3)ccc1-2]

8-Azetidin-3-yl-2-(2-isopropyl-2H-[1,2,4]triazol-3-yl)-4,5-dihydro-6-oxa-3-thia-1-aza-benzo[e]azulene TFA salt 235 (0.32 g, 0.6 mmol) was suspended in water (2.5 mL) and treated with sodium cyanide (50 mg, 0.6 mmol). A solution of acetone (60 mg, 0.9 mmol) in water (0.25 mL) was added followed by THF (~2 mL) to aid dissolution. The reaction mixture was stirred at RT for 18 hours then extracted with DCM (×2). The combined organic extracts were washed with brine, dried (Na$_2$SO$_4$) and concentrated in vacuo to afford 2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-2-methyl-propionitrile (0.26 g, quant.) LCMS: R$_T$=4.66 min, [M+H]$^+$=435

Example 61

2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-2-methyl-propionitrile

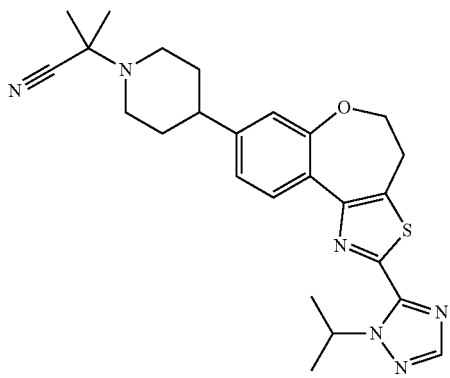 [SMILES: CC(C)n1ncnc1-c1nc2c(s1)CCOc1cc(C3CCN(C(C)(C)C#N)CC3)ccc1-2]

The title compound was prepared by a similar procedure to 2-{3-[2-(2-isopropyl-2H-[1,2,4]triazol-3-yl)-4,5-dihydro-6-oxa-3-thia-1-aza-benzo[e]azulen-8-yl]-azetidin-1-yl}-2-methyl-propionitrile using 2-(2-isopropyl-2H-[1,2,4]triazol-3-yl)-8-piperidin-4-yl-4,5-dihydro-6-oxa-3-thia-1-aza-benzo[e]azulene TFA salt to give 2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-2-methyl-propionitrile isolated as an orange oil (346 mg) as a roughly 1:1 mixture with 2-(2-isopropyl-2H-[1,2,4]triazol-3-yl)-8-piperidin-4-yl-4,5-dihydro-6-oxa-3-thia-1-aza-benzo[e]azulene and was used without further purification. LCMS: R$_T$=4.71 min, [M+H]$^+$=463

Example 62

4,5-dihydrobenzo[b]thieno[2,3-d]oxepine-8-carbonitrile

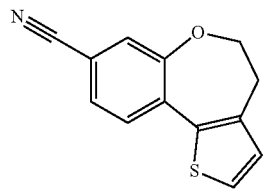 [SMILES: N#Cc1ccc2c(c1)OCCc1ccsc1-2]

A solution of 8-bromo-4,5-dihydro-6-oxa-1-thia-benzo[e]azulene (0.500 grams, 1.77 mmol) and copper cyanide (0.48 grams, 5.30 mmol) in 10 ml of DMF was flash heated on Biotage microwave. The reaction mixture was diluted with a large volume of EtOAc and this solution was filtered through celite by vacuum filtration. The filtrate was plated onto a 1/1 mixture on silica/celite and dry load purified by MPLC on a 14 gram silica column eluting with 10 to 80% EtOAc/heptanes to give 500 mg (123%) of 4,5-dihydrobenzo[b]thieno[2,3-d]oxepine-8-carbonitrile as determined by LC/MS.

Example 63

2-bromo-4,5-dihydrobenzo[b]thieno[2,3-d]oxepine-8-carbonitrile

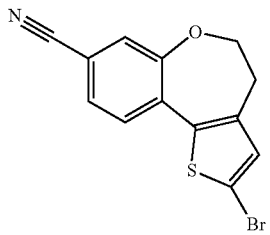 [SMILES: N#Cc1ccc2c(c1)OCCc1cc(Br)sc1-2]

A solution of 4,5-dihydrobenzo[b]thieno[2,3-d]oxepine-8-carbonitrile (240 mg, 1.05 mmol) in 3 ml of DMF was treated with NBS (206 mg, 1.16 mmol) at room temperature for 15 hours. The reaction mixture was diluted with a large volume of EtOAc and the organic was washed with water and saline and concentrated in vacuo to a solid. This residue was filtered onto celite and purified by MPLC on a 14 gram silica column, eluting with 20-80% EtOAc/heptanes to give 200 mg (62%) of 2-bromo-4,5-dihydrobenzo[b]thieno[2,3-d]oxepine-8-carbonitrile as a white powder in high purity as determined by LC/MS.

Example 64

2-(2-methylpyridin-4-yl)-4,5-dihydrobenzo[b]thieno[2,3-d]oxepine-8-carbonitrile

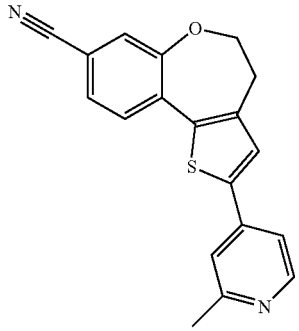 [SMILES: Cc1cc(-c2cc3c(s2)-c2ccc(C#N)cc2OCC3)ccn1]

A 2 ml microwave vial was loaded with a slurry of 2-Bromo-4,5-dihydro-6-oxa-1-thia-benzo[e]azulene-8-carbonitrile (170 mg, 0.55 mmol) and pyridine-2-amino boronic acid pinacolester (130 mg, 0.61 mmol) in 0.800 ml of aqueous 2M Sodium carbonate and 1.2 ml of ACN. The reaction mixture was degassed by bubbling nitrogen through the solution for several minutes. Next palladium tetrakis (51 mg, 2 mmol) was added to the reaction mixture and the vial was tightly capped and flash heated a Biotage microwave at 180 C for 10 minutes. The cooled reaction mixture was diluted with a large volume of EtOAc and the organic was washed with water and saline and concentrated in vacuo. The resulting residue was taken into DMF and purified by preparative RP-HPLC to give 32 mg (17%) of 2-(2-methylpyridin-4-yl)-4,5-dihydrobenzo[b]thieno[2,3-d]oxepine-8-carbonitrile

Example 65

9-Chloro-2-[5-(2,4-difluoro-phenyl)-3H-imidazol-4-yl]-4,5-dihydro-6-oxa-1-thia-10-aza-benzo[e]azulene

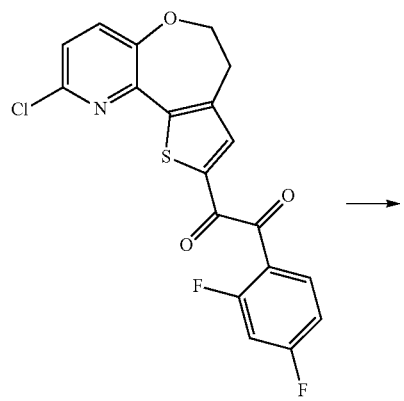

-continued

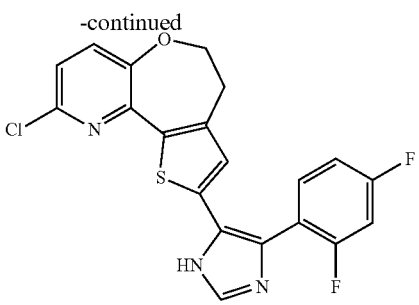

To a solution of 1-(9-Chloro-4,5-dihydro-6-oxa-1-thia-10-aza-benzo[e]azulen-2-yl)-2-(2,4-difluoro-phenyl)-ethane-1,2-dione (200 mg, 0.483 mmol) in 1.2 ml of acetic acid was added paraformaldehyde (14.8 mg, 0.493 mmol) and ammonium acetate (380 mg, 4.83 mmol). The reaction mixture was flash heated on a Biotage microwave. The cooled reaction mixture was dilute with EtOAc and washed with saline and the organics was concentrated in vacuo to solid. The crude was purified by MPLC on a 14 gram silica column eluting with 10-70% EtOAc/heptanes to give 9-chloro-2-[5-(2,4-difluoro-phenyl)-3H-imidazol-4-yl]-4,5-dihydro-6-oxa-1-thia-10-aza-benzo[e]azulene (150 mg, 73%) as a yellow powder.

Example 101

((R)-2-Hydroxymethyl-pyrrolidin-1-yl)-[8-(1H-pyrazol-4-yl)-4,5-dihydro-6-oxa-3-thia-1-aza-benzo[e]azulen-2-yl]-methanone 101

To an ice water cooled slurry of 8-bromo-4,5-dihydro-6-oxa-3-thia-1-aza-benzo[e]azulene-2-carboxylic acid (1.0 g, 0.003 mol) in methylene chloride (0.5 mL) was added two drops of anhydrous DMF followed by the drop-wise addition of oxalyl chloride (0.5 mL, 0.006 mol). The mixture was stirred for 1 hour, concentrated in vacuo and the corresponding acid chloride, 8-Bromo-4,5-dihydro-6-oxa-3-thia-1-aza-benzo[e]azulene-2-carbonyl chloride, was used without purification.

To a solution of D-(−)-Prolinol (0.205 g, 2.03 mmol) in N,N-Diisopropylamine (0.758 mL, 4.35 mmol) and N,N-Dimethylformamide (4.49 mL, 58.0 mmol) at room temperature was added 8-Bromo-4,5-dihydro-6-oxa-3-thia-1-aza-benzo[e]azulene-2-carbonyl chloride (0.500 g, 1.45 mmol) portionwise. The reaction mixture was stirred at room temperature for 1 hour. The reaction mixture was diluted with ethyl acetate, washed with brine, and concentrated in vacuo to give (8-Bromo-4,5-dihydro-6-oxa-3-thia-1-aza-benzo[e]azulen-2-yl)-((R)-2-hydroxymethyl-pyrrolidin-1-yl)-methanone which was not further purified.

(8-Bromo-4,5-dihydro-6-oxa-3-thia-1-aza-benzo[e]azulen-2-yl)-((R)-2-hydroxymethyl-pyrrolidin-1-yl)-methanone (0.297 g, 0.726 mmol), 4,4,5,5-Tetramethyl-2-(1H-pyrazol-4-yl)-1,3,2-dioxaborolane (0.211 g, 1.09 mmol), 2 M Sodium bicarbonate in water (1 mL, 2.0 mmol) and acetonitrile (2 mL, 40 mmol) were combined in a microwave vial and thoroughly purged with nitrogen. Added Tetrakis(triphenylphosphine)palladium(0) (0.0838 g, 0.0726 mmol) and heated on the Emrys microwave at 150° C. for 10 minutes. Cooled to room temperature, diluted with ethyl acetate, washed with brine and concentrated the organic layer in vacuo. Purified by HPLC to give 101 (48 mg, 17% yield, M+1 397.1)

Example 102

8-(1H-Pyrazol-4-yl)-4,5-dihydro-6-oxa-3-thia-1-aza-benzo[e]azulene-2-carboxylic acid isopropyl-methyl-amide 102

To a solution of N-methylpropan-2-amine (0.265 g, 3.63 mmol) in N,N-Diisopropylamine (0.758 mL, 4.35 mmol) and N,N-Dimethylformamide (4.49 mL, 58.0 mmol) at room temperature was added 8-Bromo-4,5-dihydro-6-oxa-3-thia-1-aza-benzo[e]azulene-2-carbonyl chloride (0.500 g, 1.45 mmol) portionwise. The reaction mixture was stirred at room temperature for 1 hour, diluted with ethyl acetate, washed with brine, and concentrated in vacuo to give 8-Bromo-4,5-dihydro-6-oxa-3-thia-1-aza-benzo[e]azulene-2-carboxylic acid isopropyl-methyl-amide which was not further purified.

8-Bromo-4,5-dihydro-6-oxa-3-thia-1-aza-benzo[e]azulene-2-carboxylic acid isopropyl-methyl-amide (0.292 g, 0.766 mmol), 4,4,5,5-Tetramethyl-2-(1H-pyrozol-4-yl)-1,3,2-dioxaborolane (0.208 g, 1.07 mmol), 2 M Sodium bicarbonate in water (1 mL, 2.0 mmol) and acetonitrile (2 mL, 40 mmol) were combined ion a microwave vial and thoroughly purged with nitrogen. Added Tetrakis(triphenylphosphine) palladium(0) (0.0824 g, 0.0714 mmol) and heated on the Emrys microwave at 150° C. for 10 minutes. Cooled to room temperature, diluted with ethyl acetate, washed with brine and concentrated the organic layer in vacuo. Purified by HPLC to give 102 (50 mg, 18% yield, M+1 369.0)

Example 103

8-(1H-Pyrazol-4-yl)-4,5-dihydro-6-oxa-3-thia-1-aza-benzo[e]azulene-2-carboxylic acid (2-hydroxy-ethyl)-isopropyl-amide 103

To a degassed solution of 8-bromo-4,5-dihydro-6-oxa-3-thia-1-aza-benzo[e]azulene-2-carboxylic acid (1.40 g, 4.29 mmol), 4,4,5,5-Tetramethyl-2-(1H-pyrazol-4-yl)-1,3,2-dioxaborolane (1.0 g, 5.0 mmol), 2 M Sodium bicarbonate in water (6.0 mL, 10.0 mmol) and acetonitrile (8.0 mL, 200 mmol) in a microwave vial was added Tetrakis(triphenylphosphine)palladium(0) (0.499 g, 0.432 mmol). The vial was heated on the Emrys microwave at 150° C. for 20 minutes. Cooled to room temperature and diluted with ethyl acetate, the precipitate was filtered off, washed with ethyl acetate and water and dried under vacuum to give 8-(1H-Pyrazol-4-yl)-4,5-dihydro-6-oxa-3-thia-1-aza-benzo[e]azulene-2-carboxylic acid (1.4 g, 103% yield).

To a solution of 8-(1H-Pyrazol-4-yl)-4,5-dihydro-6-oxa-3-thia-1-aza-benzo[e]azulene-2-carboxylic acid (363.8 mg, 1.161 mmol) in N,N-dimethylformamide (39-60 equiv.) and N,N-Diisopropylamine (1.5 equiv.) was added 2-(isopropylamino)ethanol (133.1 mg, 1.29 mmol) followed by the addition of N,N,N'N'-tetramethyl-O-(7-azabenzotriazol-1-yl) uranium hexafluorophosphate (1.1 equiv.). The reaction mixture was heated at 50° C. for 2 hrs to 24 hours depending on when complete by LCMS. Reaction mixture was concentrated on the genevac and purified by HPLC or diluted with ethyl acetate, washed with brine, dried over sodium sulfate and concentrated in vacuo prior to purification by HPLC to give 103 (70 mg, 15% yield, M+1 399.1)

Example 104

2-(2-Isopropyl-2H-[1,2,4]triazol-3-yl)-4,5-dihydro-6-oxa-3-thia-1-aza-benzo[e]azulene-8-carboxylic acid (2-methoxy-ethyl)-amide 104

Similar to as described in General procedure F, 8-Bromo-2-(2-isopropyl-2H-[1,2,4]triazol-3-yl)-4,5-dihydro-6-oxa-3-thia-1-aza-benzo[e]azulene 27 was reacted with 2-methoxy-ethylamine to give 104 after purification by reverse phase HPLC (368 mg). LCMS: 414.1

Example 105

2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-ethanol 105

Similarly to as described in General Procedure C, 8-bromo-2-(2-isopropyl-2H-[1,2,4]triazol-3-yl)-4,5-dihydro-6-oxa-3-thia-1-aza-benzo[e]azulene 27 was reacted with ethyl 2-(4-(4,4,5,5-tetramethyl-1,3,2-dioxaborolan-2-yl)-1H-pyrazol-1-yl)acetate to give {4-[2-(2-Isopropyl-2H-[1,2,4]triazol-3-yl)-4,5-dihydro-6-oxa-3-thia-1-benzo[e] azulen-8-yl]-pyrazol-1-yl}-acetic acid ethyl ester as a colorless solid. LCMS: 466.

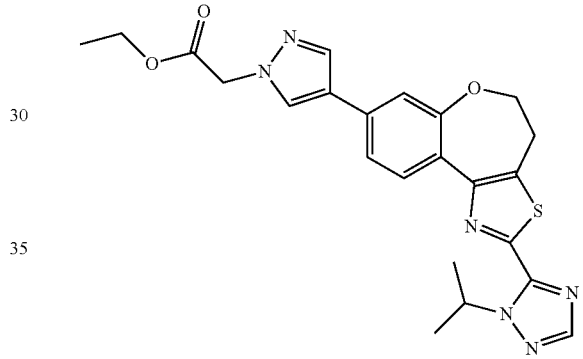

A solution of {4-[2-(2-Isopropyl-2H-[1,2,4]triazol-3-yl)-4,5-dihydro-6-oxa-3-thia-1-aza-benzo[e]azulen-8-yl]-pyrazol-1-yl}-acetic acid ethyl ester in THF (200 mL) was cooled to 0° C. and treated dropwise with a solution of 1M LiAlH₄ (in THF, 23 mL, 23 mmol, 2.5 eq). After 1 h, LCMS indicated consumption of starting material. A solution of saturated sodium sulfate was added slowly until H₂ evolution ceased. ~30 g of solid magnesium sulfate was added and the whole was stirred for 20 min. Filtration over celite (EtOAc and DCM) followed by concentration of the filtrant gave a crude residue that was purified by reverse-phase HPLC to give 1.4 g of 105 (43%). LCMS: 423.1. $^1$H NMR (400 MHz, DMSO) δ 8.32 (d, J=8.3 Hz, 1H), 8.22 (s, 1H), 8.10 (s, 1H), 7.95 (s, 1H), 7.43 (dd, J=8.3, 1.6 Hz, 1H), 7.30 (d, J=1.6 Hz, 1H), 5.84 (dt, J=13.2, 6.6 Hz, 1H), 4.91 (t, J=5.3 Hz, 1H), 4.39 (t, J=4.9 Hz, 2H), 4.16 (t, J=5.6 Hz, 2H), 3.77 (q, J=5.5 Hz, 2H), 3.44 (t, J=4.9 Hz, 2H), 1.56 (d, J=6.6 Hz, 6H).

Alternatively, following the procedure for 376, 2-(1-isopropyl-1H-imidazol-2-yl)-8-{1-[2-(tetrahydro-pyran-2-yloxy)-ethyl]-1H-pyrazol-4-yl}-4,5-dihydro-6-oxa-3-thia-1-aza-benzo[e]azulene and MeOH as the solvent gave 105 as a solid (134 mg). LCMS: R$_T$=10.20 min, [M+H]$^+$=422. $^1$H NMR δ (ppm) (DMSO-d6): 8.25 (1H, d, J=8.27 Hz), 8.17 (1H, s), 7.90 (1H, d, J=0.76 Hz), 7.81 (1H, s), 7.39-7.35 (2H, m), 7.24 (1H, d, J=1.82 Hz), 5.66-5.56 (1H, m), 4.33 (2H, t, J=5.05 Hz), 4.11 (2H, t, J=5.77 Hz), 3.72 (2H, t, J=5.66 Hz), 3.41-3.32 (2H, m), 1.51 (6H, d, J=6.67 Hz). 1 Exchangeable proton not observed Example 106

1H-Pyrazole-4-carboxylic acid {2-[2-(2,2,2-trifluoro-ethyl)-2H-[1,2,4]triazol-3-yl]-4,5-dihydro-6-oxa-3-thia-1-aza-benzo[e]azulen-8-ylmethyl}-amide 106

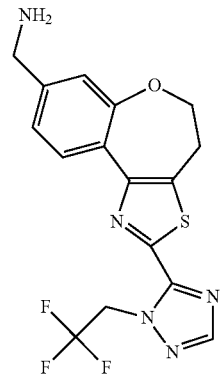 [SMILES: NCc1ccc2c(c1)OCCc1sc(-c3ncnn3CC(F)(F)F)nc1-2]

To a solution of {2-[2-(2,2,2-Trifluoro-ethyl)-2H-[1,2,4]triazol-3-yl]-4,5-dihydro-6-oxa-3-thia-1-aza-benzo[e]azulen-8-yl}-methylamine in tetrahydrofuran was added diisopropylethylamine followed by 1H-pyrazole-4-carboxylic acid and O-(7-azabenzotriazol-1-yl)-N,N,N',N'-tetramethyluronium hexafluorophosphate. The reaction was stirred at room temperature for about 3 hours. The mixture was partitioned between saturated sodium bicarbonate and ethyl acetate and extracted 3 times with ethyl acetate. The organic layers were combined, dried with MgSO₄, and concentrated. The crude was purified by reverse-phase HPLC to give was reacted with to give 106. MS(ESI+) 476.1. ¹H NMR (400 MHz, DMSO) δ 13.03 (br, 1H), 8.60 (m, 1H), 8.32-8.22 (m, 2H), 8.07 (s, 2H), 7.15 (dd, J=16.3, 8.3, 1H), 7.00 (s, 1H), 5.84 (q, J=8.7, 2H), 4.43 (d, J=5.9, 2H), 4.36 (t, J=4.9, 2H), 3.45 (t, J=4.9, 2H)

Example 107

2-[2-(2,2,2-Trifluoro-ethyl)-2H-[1,2,4]triazol-3-yl]-4,5-dihydro-6-oxa-3-thia-1-aza-benzo[e]azulene-8-carboxylic acid ((S)-2-hydroxy-propyl)-amide 107

To a solution of (S)-1-Amino-propan-2-ol in degassed toluene (2.32 mL) under nitrogen atmosphere was added 8-Bromo-2-[2-(2,2,2-trifluoro-ethyl)-2H-[1,2,4]triazol-3-yl]-4,5-dihydro-6-oxa-3-thia-1-aza-benzo[e]azulene, Pd(OAc)2, 4,5-Bis(diphenylphosphino)-9,9-dimethylxanthene and sodium carbonate. The mixture was purged with carbon monoxide and heated to 90° C. under a carbon monoxide balloon for 24 hours. The reaction was diluted with ethyl acetate, filtered through celite, and purified by reverse-phase HPLC to give 107. MS(ESI+) 454.0

Example 108

2-(2-Isopropyl-2H-[1,2,4]triazol-3-yl)-4,5-dihydro-6-oxa-3-thia-1-aza-benzo[e]azulene-8-carboxylic acid [2-(2-hydroxy-ethoxy)-ethyl]-amide 108

Similar to as described in General procedure F, 8-Bromo-2-(2-isopropyl-2H-[1,2,4]triazol-3-yl)-4,5-dihydro-6-oxa-3-thia-1-aza-benzo[e]azulene 27 was reacted with 3-(2-aminoethoxyl)propan-1-ol to give 108 after purification by reverse phase HPLC (140 mg). LCMS: 444.1.

Example 109

{2-[2-(2,4-Difluoro-phenyl)-2H-[1,2,4]triazol-3-yl]-4,5-dihydro-6-oxa-1-thia-10-aza-benzo[e]azulen-9-yl}-[2-(1,1-dioxo-1S-thiomorpholin-4-yl)-ethyl]-amine 109

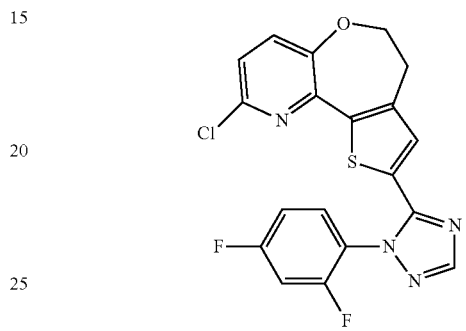

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 2-(1,1-Dioxo-1l6-thiomorpholin-4-yl)-ethylamine (210 mg, 1.2 mmol), Pd(OAc)₂ (23 mg, 0.10 mmol), Xphos (47 mg, 0.10 mmol), t-BuONa (230 mg, 2.0 mmol) and dioxane (4 mL) were added in a 10 mL of sealed tube, and the mixture was heated by microwave at 112° C. for 7 min under N₂. The reaction mixture was filtered to gather the solution and water was added. The mixture was extracted by DCM (20 mL×3). The combined organic layers were dried over Na₂SO₄, concentrated in vacuo, and purified by preparative HPLC to 109 (47 mg, yield: 8.4%). ¹HNMR (DMSO-d₆, 400 MHz): δ8.25 (s, 1H), 7.91-7.85 (m, 1H), 7.72 (t, J=10 Hz, 1H), 7.42 (t, J=0.8 Hz, 1H), 7.07-7.03 (m, 2H), 6.40 (d, J=4.8 Hz, 1H), 4.13 (t, J=4.4 Hz, 2H), 3.52-3.34 (m, 2H), 3.28-3.11 (m, 6H), 3.01-3.96 (m, 6H). ESI-MS: m/z=559 [M+H⁺]

Example 110

2-[2-(2,4-Difluoro-phenyl)-2H-[1,2,4]triazol-3-yl]-9-(4-methyl-piperazin-1-yl)-4,5-dihydro-6-oxa-1-thia-10-aza-benzo[e]azulene 110

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)₂ (49 mg, 0.3 mmol), morpholine (130 mg, 1.44 mmol), 2,8,9-tributyl-2,5,8,9-tetraaza-1-phosphabicyclo[3.3.3]undecane (99 mg, 0.29 mmol), tert-butoxide (140 mg, 1.44 mmol) in dioxane (2 mL) was bubbled N₂ for 10 min and then stirred at 120° C. for 1 h under the irradition of microwave. The mixture was filtered over ceilite. The filtrate was concentrated to dryness and purified by pre-HPLC to afford 115 mg of 110 (yield=31%). ¹H NMR (CDCl₃, 400 MHz): δ8.12-8.10 (m, 1H), 7.58-7.52 (m, 1H), 7.15-7.05 (m, 4H), 6.55 (d, J=9.2 Hz, 1H), 4.25-4.23 (m, 2H), 3.75-3.63 (m, 5H), 3.12-3.10 (m, 2H), 2.93-2.91 (m, 4H), 2.62-2.57 (m, 3H). LC-MS (ESI): m/z=480 [M+H]⁺

Example 111

2-(2-Isopropyl-2H-[1,2,4]triazol-3-yl)-4,5-dihydro-6-oxa-3-thia-1-aza-benzo[e]azulene-9-carboxylic acid (2-hydroxy-ethyl)-amide 111

9-Bromo-2-(2-isopropyl-2H-[1,2,4]triazol-3-yl)-4,5-dihydro-6-oxa-3-thia-1-aza-benzo[e]azulene from Example 6 (0.350 g, 0.894 mmol), ethanolamine (0.162 mL, 2.68 mmol), 4,5-bis(diphenylphosphino)-9,9-dimethylxanthene (0.054 g, 0.093 mmol), and sodium carbonate (0.569 g, 5.37 mmol) were added to a nitrogen flushed flask. To the mixture was added toluene (20 mL) and nitrogen was bubbled through the reaction mixture for 2 minutes. To the reaction mixture was added $Pd(OAc)_2$ (0.021 g, 0.093 mmol), then CO was bubbled through the reaction mixture for 1 minute and the reaction was placed under a CO balloon and stirred and heated at 85° C. for 18 hours. LCMS showed very little conversion from starting material to product. To the reaction mixture was added ethanolamine (0.162 mL, 2.68 mmol), 4,5-bis(diphenylphosphino)-9,9-dimethylxanthene (0.054 g, 0.093 mmol), sodium carbonate (0.569 g, 5.37 mmol), and $Pd(OAc)_2$ (0.021 g, 0.093 mmol), then CO was bubbled through the reaction mixture for 1 minute and the reaction was placed under a CO balloon and stirred and heated at 85° C. for 18 hours. The reaction mixture was cooled to room temperature, diluted with EtOAc, and filtered through a pad of celite. The filtrate was concentrated under reduced pressure and diluted with EtOAc. The solution was washed sequentially with water, and brine, before drying over $MgSO_4$ and concentrating under reduced pressure. The crude material was dissolved in DMF and purified by reverse phase HPLC provide 111 (3 mg, 8%). $^1$H NMR (400 MHz, DMSO) δ 8.92 (d, J=2.1, 1H), 8.37 (t, J=5.5, 1H), 8.08 (d, J=21.9, 1H), 7.75 (dd, J=8.4, 2.1, 1H), 7.12 (d, J=8.4, 1H), 5.83 (dt, J=13.0, 6.6, 1H), 4.70 (t, J=5.4, 1H), 4.42 (t, J=4.8, 2H), 3.56-3.44 (m, 4H), 3.38-3.33 (m, 2H), 1.57 (d, J=6.6, 6H). MS (ESI(+)): m/z 400.1 (M+H)

Example 112

2-[2-(2,2,2-Trifluoro-ethyl)-2H-[1,2,4]triazol-3-yl]-4,5-dihydro-6-oxa-3-thia-1-aza-benzo[e]azulene-8-carboxylic acid (2-hydroxy-ethyl)-amide 112

Following the procedure for 107, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with ethanolamine to give 112. MS(ESI+) 440.0. $^1$H NMR (400 MHz, DMSO) δ 8.47 (t, J=5.4, 1H), 8.37 (d, J=8.3, 1H), 8.30 (s, 1H), 7.68 (dd, J=8.3, 1.4, 1H), 7.57 (d, J=1.3, 1H), 5.85 (q, J=8.7, 2H), 4.71 (br, 1H), 4.41 (t, J=4.9, 2H), 3.58-3.44 (m, 4H), 3.36-3.30 (m, 2H).

Example 113

2-[2-(2,2,2-Trifluoro-ethyl)-2H-[1,2,4]triazol-3-yl]-4,5-dihydro-6-oxa-3-thia-1-aza-benzo[e]azulene-8-carboxylic acid (2,2-difluoro-ethyl)-amide 113

Following the procedure for 107, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with 2,2-difluoro-ethylamine to give 113. MS(ESI+) 460.0. $^1$H NMR (400 MHz, DMSO) δ 8.90 (t, J=5.8, 1H), 8.40 (d, J=8.3, 1H), 8.30 (s, 1H), 7.71 (dd, J=8.3, 1.6, 1H), 7.60 (d, J=1.5, 1H), 6.12 (tt, J=55.9, 3.9, 1H), 5.86 (q, J=8.8, 2H), 4.42 (t, J=4.9, 2H), 3.77-3.58 (m, 2H), 3.51 (t, J=4.9, 2H)

Example 114

8-[1-(2-Morpholin-4-yl-ethyl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene 114

To a microwave vial was added 8-bromo-2-[2-(2,2,2-trifluoro-ethyl)-2H-[1,2,4]triazol-3-yl]-4,5-dihydro-6-oxa-3-thia-1-aza-benzo[e]azulene and potassium acetate in acetonitrile and water. The solution was thoroughly purged and degassed with nitrogen for 5 minutes. 4-{2-[4-(4,4,5,5-Tetramethyl-[1,3,2]dioxaborolan-2-yl)-pyrazol-1-yl]-ethyl}-morpholine and Tetrakis(triphenylphosphine)palladium were added the vial was sealed immediately. The reaction was heated in the microwave for about 20 minutes at 140° C.

The mixture was diluted with methylene chloride and filtered through celite. Saturated $NH_4Cl$ was added and the mixture was extracted 3 times with methylene chloride. The organic layers were combined, dried with $MgSO_4$ and concentrated. The crude was purified by reverse-phase HPLC to give 114. MS(ESI+) 532.2. $^1$H NMR (400 MHz, DMSO) δ 8.30-8.25 (m, 3H), 7.96 (s, 1H), 7.43 (dd, J=8.3, 1.6, 1H), 7.30 (d, J=1.5, 1H), 5.86 (q, J=8.7, 2H), 4.40 (t, J=4.9, 2H), 4.24 (t, J=6.5, 2H), 3.61-3.51 (m, 4H), 3.47 (t, J=4.9, 2H), 2.75 (t, J=6.5, 2H), 2.46-2.35 (m, 4H)

Example 115

9-[1-(2-Morpholin-4-yl-ethyl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene 115

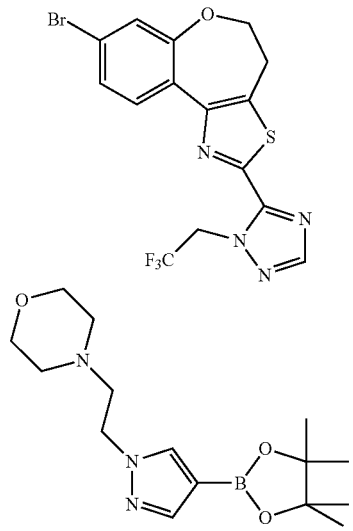

8-Bromo-2-[2-(2,2,2-trifluoro-ethyl)-2H-[1,2,4]triazol-3-yl]-4,5-dihydro-6-oxa-3-thia-1-aza-benzo[e]azulene and 4-(2-(4-(4,4,5,5-tetramethyl-1,3,2-dioxaborolan-2-yl)-1H-pyrazol-1-yl)ethyl)morpholine were reacted under palladium Suzuki conditions to give 115 (17% yield). LC/MS (ESI+): m/z 532 (M+H). $^1$H NMR (400 MHz, DMSO) δ 8.48 (d, J=2.1, OH), 8.30 (s, OH), 8.07 (s, OH), 7.76 (s, OH), 7.49 (dd, J=8.3, 2.2, OH), 7.09 (d, J=8.3, OH), 5.89 (q, J=8.6, OH), 4.38 (t, J=4.9, OH), 4.25 (t, J=6.6, OH), 3.61-3.51 (m, 1H), 3.48 (t, J=4.9, OH), 2.75 (t, J=6.6, OH), 2.45-2.35 (m, 1H)

Example 116

(2-Morpholin-4-yl-ethyl)-(5-{2-[2-(2,2,2-trifluoro-ethyl)-2H-[1,2,4]triazol-3-yl]-4,5-dihydro-6-oxa-3-thia-1-aza-benzo[e]azulen-8-yl}-pyridin-2-yl)-amine 116

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with (2-Morpholin-4-yl-ethyl)-[5-(4,4,5,5-tetramethyl-[1,3,2]dioxaborolan-2-yl)-pyridin-2-yl]-amine to give 116. MS(ESI+) 558.2. $^1$H NMR (400 MHz, DMSO) δ 8.41 (d, J=2.1, 1H), 8.32 (d, J=8.4, 1H), 8.29 (s, 1H), 7.79 (dd, J=8.8, 2.4, 1H), 7.45 (dd, J=8.4, 1.7, 1H), 7.30 (d, J=1.6, 1H), 6.59 (dd, J=10.9, 7.1, 2H), 5.87 (q, J=8.7, 2H), 4.41 (t, J=4.9, 2H), 3.64-3.54 (m, 4H), 3.47 (t, J=4.9, 2H), 3.42 (dd, J=12.5, 6.4, 2H), 2.50-2.47, (m, 2H), 2.40-2.44 (m, 4H)

Example 117

{2-[2-(2,4-Difluoro-phenyl)-2H-[1,2,4]triazol-3-yl]-4,5-dihydro-6-oxa-1-thia-10-aza-benzo[e]azulen-9-yl}-(1-methyl-pyrrolidin-3-ylmethyl)-amine 117

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (49 mg, 0.3 mmol), C-(1-Methyl-pyrrolidin-3-yl)-methylamine (164 mg, 1.44 mmol), 2,8,9-tributyl-2,5,8,9-tetraaza-1-phosphabicyclo[3.3.3]undecane (99 mg, 0.29 mmol) tert-butoxide (140 mg, 1.44 mmol) in dioxane (2 mL) was bubbled N$_2$ for 10 min and then stirred at 120° C. for 1 h under the irradition of microwave. The mixture was filtered over ceilite. The filtrate was concentrated to dryness and purified by pre-HPLC to afford 120 mg of 117 (yield=34%). $^1$H NMR (CDCl$_3$, 400 MHz): δ8.67-8.52 (m, 1H), 8.11-8.06 (m, 1H), 7.58-7.50 (m, 1H), 7.16-7.02 (m, 3H), 6.96-6.90 (m, 1H), 6.42-6.31 (m, 1H), 4.28-4.21 (m, 2H), 3.50-2.84 (m, 8H), 2.72-2.64 (m, 3H), 2.38-2.22 (m, 1H), 1.94-1.82 (m, 1H). LC-MS (ESI): m/z=495 [M+H]$^+$ Example 118

{2-[2-(2,4-Difluoro-phenyl)-2H-[1,2,4]triazol-3-yl]-4,5-dihydro-6-oxa-1-thia-10-aza-benzo[e]azulen-9-yl}-(1-methyl-piperidin-4-ylmethyl)-amine 118

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (49 mg, 0.3 mmol), C-(1-Methyl-piperidin-4-yl)-methylamine (184 mg, 1.44 mmol), 2,8,9-tributyl-2,5,8,9-tetraaza-1-phosphabicyclo[3.3.3]undecane (99 mg, 0.29 mmol), tert-butoxide (140 mg, 1.44 mmol) in dioxane (2 mL) was bubbled N$_2$ for 10 min and then stirred at 120° C. for 1 h under the irradition of microwave. The mixture was filtered over ceilite. The filtrate was concentrated to dryness and purified by pre-HPLC to afford 135 mg of 118 (yield=37%). $^1$H NMR (CDCl$_3$, 400 MHz) δ: 8.49 (s, 1H), 8.01 (s, 1H), 7.48-7.45 (m, 1H), 7.08-6.98 (m, 3H), 6.88 (s, 1H), 6.24-6.00 (m, 1H), 4.16-4.12 (m, 1H), 3.42-2.84 (m, 4H), 3.02-2.96 (m, 2H), 2.55 (s, 3H), 2.38-2.32 (m, 2H), 1.82-1.80 (m, 1H), 1.76-1.70 (m, 2H), 1.68-1.59 (m, 2H). LC-MS (ESI): m/z=509 [M+H]$^+$ Example 119

[2-(4-Isopropyl-4H-[1,2,4]triazol-3-yl)-4,5-dihydro-6-oxa-3-thia-1-aza-benzo[e]azulen-8-ylmethyl]-(2,2,2-trifluoro-ethyl)-amine 119

To a solution of 2-(4-isopropyl-4H-[1,2,4]triazol-3-yl)-4,5-dihydro-6-oxa-3-thia-1-aza-benzo[e]azulene-8-carbaldehyde (180 mg, 0.53 mmol) in DCE (7 mL+5% AcOH) was added trifluoroethylamine (46 µL, 0.58 mmol) and the mixture was stirred for 30 minutes. Sodium triacetoxyborohydride (134 mg, 0.64 mmol) was added and the solution was stirred under nitrogen for 65 hours. The reaction mixture was diluted with aqueous saturated sodium bicarbonate solution and DCM and the phases were separated. The organic layer was washed with brine, dried (Na$_2$SO$_4$) and concentrated in vacuo. The resultant residue was purified by flash chromatography (SiO$_2$, 0-5% 2M NH$_3$/MeOH in DCM) to give a colourless oil. The oil was triturated with ether/cyclohexane to give 119 as a grey solid (138 mg, 61%). LCMS: R$_T$=9.52 min, [M+H]$^+$=424. $^1$H NMR δ (ppm) (DMSO-d6): 8.91 (1H, s), 8.22 (1H, d, J=8.10 Hz), 7.09 (1H, dd, J=8.16, 1.68 Hz), 7.00 (1H, d, J=1.64 Hz), 5.49-5.39 (1H, m), 4.33-4.27 (2H, m), 3.74 (2H, s), 3.40-3.32 (2H, m), 3.21-3.09 (2H, m), 2.92 (1H, s), 1.52 (6H, d, J=6.71 Hz)

Example 120

[2-(4-Isopropyl-4H-[1,2,4]triazol-3-yl)-4,5-dihydro-6-oxa-3-thia-1-aza-benzo[e]azulen-8-ylmethyl]-(2-methoxy-ethyl)-amine 120

Following the procedure for 119, 2-(4-isopropyl-4H-[1,2,4]triazol-3-yl)-4,5-dihydro-6-oxa-3-thia-1-aza-benzo[e]azulene-8-carbaldehyde and 2-methoxyethylamine were reacted. After purification by flash chromatography the resulting oil was dissolved in ether and treated with 1M HCl in ether to give a solid that was filtered off and dried to give 120 as a yellow solid (129 mg, 56%). LCMS: R$_T$=6.11 min, [M+H]$^+$=400. $^1$H NMR δ (ppm) (DMSO-d6): 9.17 (2H, s), 8.93-8.90 (1H, m), 8.29 (1H, d, J=8.13 Hz), 7.28 (1H, dd, J=8.22, 1.81 Hz), 7.24 (1H, d, J=1.76 Hz), 5.47-5.38 (1H, m), 4.33 (2H, t, J=4.98 Hz), 4.10 (2H, t, J=5.38 Hz), 3.56 (2H, t, J=5.15 Hz), 3.43-3.30 (2H, m), 3.25 (3H, s), 3.02 (2H, t, J=5.63 Hz), 1.56-1.49 (6H, m)

Example 121

Dimethyl-[3-(5-{2-[2-(2,2,2-trifluoro-ethyl)-2H-[1,2,4]triazol-3-yl]-4,5-dihydro-6-oxa-3-thia-1-aza-benzo[e]azulen-8-yl}-pyridin-2-yloxy)-propyl]-amine 121

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with dimethyl-{3-[5-(4,4,5,5-tetramethyl-[1,3,2]dioxaborolan-2-yl)-pyridin-2-yloxy]-propyl}-amine to give 121. MS(ESI+) 531.2. $^1$H NMR (400 MHz, DMSO) δ 8.56 (d, J=2.2, 1H), 8.38 (d, J=8.3, 1H), 8.30 (s, 1H), 8.09 (dd, J=8.7, 2.5, 1H), 7.54 (dd, J=8.3, 1.8, 1H), 7.41 (d, J=1.7, 1H), 6.89 (d, J=8.6, 1H), 5.87

(q, J=8.7, 2H), 4.43 (t, J=4.9, 2H), 4.33 (t, J=6.6, 2H), 3.49 (t, J=4.9, 2H), 2.37 (t, J=7.1, 2H), 2.16 (s, 6H), 1.87 (p, J=6.8, 2H)

Example 122

1-tert-Butyl-5-[8-(1H-pyrazol-4-yl)-4,5-dihydro-6-oxa-3-thia-1-aza-benzo[e]azulen-2-yl]-1H-[1,2,4]triazol-3-ylamine 122

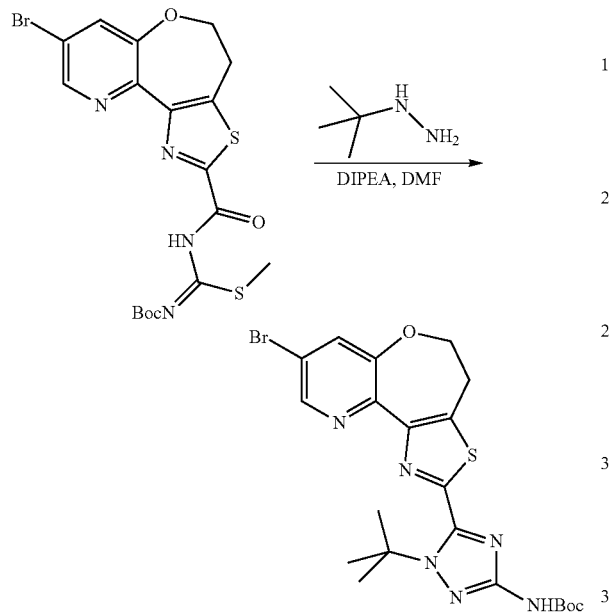

1-(8-Bromo-4,5-dihydro-6-oxa-3-thia-1-aza-benzo[e]azulene-2-carbonyl)-2-methyl-N-Boc-isothiourea (1.0 g, 2.0 mmol) was dissolved in DMF (5 mL) and treated with DIPEA (1.07 mL, 6.14 mmol). This was followed by the addition of t-butylhydrazine hydrochloride (0.32 g, 2.6 mmol). The reaction mixture was heated at 85° C. for 2 h. Cooled to r.t. and diluted with EtOAc and H₂O. Extracted twice with EtOAc and the combined organic layers were washed with brine, dried over Na₂SO₄, filtered and concentrated. The solid residue was adsorbed onto Celite and purified by ISCO chromatography (80 g column, 0-100% EtOAc/heptane) to provide [5-(8-Bromo-4,5-dihydro-6-oxa-3-thia-1-aza-benzo[e]azulen-2-yl)-1-tert-butyl-1H-[1,2,4]triazol-3-yl]-carbamic acid tert-butyl ester (940 mg, 90% yield).

[5-(8-Bromo-4,5-dihydro-6-oxa-3-thia-1-aza-benzo[e]azulen-2-yl)-1-tert-butyl-1H-[1,2,4]triazol-3-yl]-carbamic acid tert-butyl ester (0.94 g, 1.8 mmol) was dissolved in MeCN (20 mL) and H₂O (20 mL) and added potassium acetate (601 mg, 6.12 mmol). The reaction flask was degassed by bubbling N₂ for 5 min. Charged with 4,4,5,5-tetramethyl-2-(1H-pyrazol-4-yl)-1,3,2-dioxaborolane (456 mg, 2.53 mmol) and then tetrakis(triphenylphosphine)palladium(0) (280 mg, 0.24 mmol). The reaction was subjected to microwave irradiation at 140° C. for 20 min. The reaction was cooled to r.t., filtered through a plug of Celite and diluted with water. Extracted three times with EtOAc and the combined organic portions were dried over MgSO₄, filtered and concentrated. The crude residue was taken up in DCM (10 mL) and treated with trifluoroacetic acid (5 mL). Stirred at room temperature for 1 h and concentrated in vacuo. The resultant residue was taken up in a minimal amount of DMF/DMSO (1:1) and purified by rp-HPLC to provide 58 mg (10% yield) of 122. LC/MS (ESI+): m/z 408 (M+H). $^1$H NMR (400 MHz, DMSO) δ 12.96 (bs, 1H), 8.31 (m, 2H), 7.99 (bs, 1H), 7.50-7.39 (m, 2H), 7.34 (d, J=1.5, 2H), 5.47 (s, 2H), 4.47-4.24 (m, 4H), 3.39 (dd, J=15.8, 10.7, 4H), 1.78 (s, J=18.7, 9H).

Example 123

Cyclopentylmethyl-{2-[2-(2,4-difluoro-phenyl)-2H-[1,2,4]triazol-3-yl]-4,5-dihydro-6-oxa-1-thia-10-aza-benzo[e]azulen-9-yl}-amine 123

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (360 mg, 0.81 mmol), Pd(OAc)₂ (58 mg, 0.26 mmol), Cyclopentyl-methylamine HCl salt (236 mg, 1.74 mmol), 2,8,9-tributyl-2,5,8,9-tetraaza-1-phosphabicyclo[3.3.3]undecane (99 mg, 0.29 mmol), tert-butoxide (256 mg, 2.61 mmol) in dioxane (2 mL) was bubbled N₂ for 10 min and then stirred at 130° C. for 5 min under the irradiation of microwave. The mixture was filtered over ceilite. The filtrate was concentrated to dryness and purified by pre-TLC (EtOAc:hexanes=1:1) to afford 51 mg of 123. (yield=13%). $^1$H NMR (CDCl₃, 400 MHz) δ: 8.01 (s, 1H), 7.50-7.44 (m, 1H), 7.04-6.98 (m, 4H), 6.18-6.15 (d, J=8.8 Hz, 1H), 4.16-4.14 (m, 2H), 3.12-3.03 (m, 4H), 2.09-2.02 (m, 1H), 1.77-1.70 (m, 2H), 1.60-1.47 (m, 4H), 1.24-1.18 (m, 2H). LC-MS (ESI): m/z=480 [M+H]⁺

Example 124

1-{2-[2-(2,4-Difluoro-phenyl)-2H-[1,2,4]triazol-3-yl]-4,5-dihydro-6-oxa-1-thia-10-aza-benzo[e]azulen-9-yl}-piperidin-4-ol 124

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)₂ (49 mg, 0.3 mmol), 4-Tri-methylsilanyloxy-piperidine (186 mg, 1.44 mmol), 2,8,9-tributyl-2,5,8,9-tetraaza-1-phosphabicyclo[3.3.3]undecane (99 mg, 0.29 mmol), tert-butoxide (140 mg, 1.44 mmol) in dioxane (2 mL) was bubbled N₂ for 10 min and then stirred at 120° C. for 6 min under the irradiation of microwave. The mixture was filtered over ceilite. The filtrate was concentrated to dryness and purified by pre-HPLC to afford 130 mg of 124 (yield=38%). $^1$H NMR (MeOD, 400 MHz): δ8.11 (s, 1H), 7.68-7.66 (m, 1H), 7.33-7.23 (m, 3H), 7.10-7.08 (m, 1H), 6.54-6.52 (m, 1H), 4.16-4.13 (m, 2H), 3.90-3.86 (m, 2H), 3.76-3.72 (m, 2H), 3.07-3.04 (m, 2H), 2.95-2.89 (m, 2H), 1.86-1.82 (m, 2H), 1.44-1.41 (m, 2H). LC-MS (ESI): m/z=482 [M+H]⁺

Example 125

2-[2-(2,4-Difluoro-phenyl)-2H-[1,2,4]triazol-3-yl]-9-(1,1-dioxo-S-thiomorpholin-4-yl)-4,5-dihydro-6-oxa-1-thia-10-aza-benzo[e]azulene 125

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)₂ (49 mg, 0.3 mmol), Thiomorpholine 1,1-dioxide (194 mg, 1.44 mmol), 2,8,9-tributyl-2,5,8,9-tetraaza-1-phosphabicyclo[3.3.3]undecane (99 mg, 0.29 mmol), tert-butoxide (140 mg, 1.44 mmol) in dioxane (2 mL) was bubbled N₂ for 10 min and then stirred at 120° C. for 1 h under the irradiation of microwave. The mixture was filtered over ceilite. The filtrate was concentrated to dryness and purified by pre-TLC (EtOAc:hexanes=1:1) to afford 85 mg of 125. (yield=24%). $^1$H NMR (CDCl$_3$, 400 MHz): δ8.03 (s, 1H), 7.52-7.46 (m, 1H), 7.18-7.16 (m, 1H), 7.08-6.95 (m, 3H), 4.21-4.19 (m, 2H), 4.05-3.98 (m, 4H), 3.07-3.05 (m, 2H), 2.99-2.97 (m, 4H) LC-MS (ESI): m/z=516 [M+H]$^+$ Example 126

{2-[2-(2,4-Difluoro-phenyl)-2H-[1,2,4]triazol-3-yl]-4,5-dihydro-6-oxa-1-thia-10-aza-benzo[e]azulen-9-yl}-phenethyl-amine 126

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (49 mg, 0.3 mmol), phenethylamine (174 mg, 1.44 mmol), 2,8,9-tributyl-2,5,8,9-tetraaza-1-phosphabicyclo[3.3.3]undecane (99 mg, 0.29 mmol), tert-butoxide (140 mg, 1.44 mmol) in dioxane (2 mL) was bubbled N$_2$ for 10 min and then stirred at 120° C. for 1 h under the irradiation of microwave. The mixture was filtered over ceilite. The filtrate was concentrated to dryness and purified by pre-HPLC to afford 90 mg of 126 (yield=25%). $^1$H NMR (CDCl$_3$, 400 MHz): δ8.02 (s, 1H), 7.47-7.45 (m, 1H), 7.40-7.32 (m, 2H), 7.20-7.12 (m, 2H), 7.09 (s, 1H), 7.00-7.90 (m, 3H), 6.11 (d, J=8.4 Hz, 1H), 4.18-4.16 (m, 2H), 3.53-3.47 (m, 2H), 3.07-3.03 (m, 2H), 2.87-2.82 (m, 2H). LC-MS (ESI): m/z=502 [M+H]$^+$ Example 127

2-(3-amino-1-(2,4-difluorophenyl)-1H-1,2,4-triazol-5-yl)-N-methyl-4,5-dihydrobenzo[b]thieno[2,3-d]oxepine-8-carboxamide 127

Similarly to as described in General Procedure D, 2-[5-Amino-2-(2,4-difluoro-phenyl)-2H-[1,2,4]triazol-3-yl]-4,5-dihydro-6-oxa-1-thia-benzo[e]azulene-8-carboxylic acid was reacted with methylamine hydrochloride to give 127 as a colorless solid after reverse phase HPLC (140 mg). LCMS: 454.1

Example 128

2-(2-Isopropyl-2H-[1,2,4]triazol-3-yl)-9-(2-methyl-pyridin-3-yl)-4,5-dihydro-6-oxa-3-thia-1-aza-benzo[e]azulene 128

To 9-Bromo-2-(2-isopropyl-2H-[1,2,4]triazol-3-yl)-4,5-dihydro-6-oxa-3-thia-1-aza-benzo[e]azulene from Example 6 (0.388 g, 0.992 mmol), 2-methylpyridin-3-ylboronic acid (0.176 g, 1.29 mmol), potassium acetate (0.389 g, 3.96 mmol), and tetrakis(triphenylphosphine)palladium(0) (57 mg, 0.049 mmol) was added DMF (20 mL) and water (1 mL). Nitrogen was bubbled through the reaction mixture for 5 minutes. The reaction mixture was allowed to stir at 105° C. for 24 hours before cooling, diluting with EtOAc, and filtering through a pad of celite. The filtrate was concentrated under reduced pressure and diluted with EtOAc. The solution was washed sequentially with water, and brine, before drying over MgSO$_4$ and concentrating under reduced pressure. The crude material was dissolved in DMF and purified by reverse phase HPLC to provide 128 (115 mg, 28%). $^1$H NMR (400 MHz, DMSO) δ 8.44 (dd, J=24.8, 2.7, 2H), 8.10 (s, 1H), 7.69 (t, J=8.1, 1H), 7.35 (ddd, J=12.5, 7.9, 3.6, 2H), 7.19 (d, J=8.3, 1H), 5.74 (dt, J=13.2, 6.7, 1H), 4.44 (t, J=4.9, 2H), 3.49 (t, J=4.9, 2H), 2.53 (s, 3H), 1.48 (d, J=6.6, 6H). MS (ESI(+)): m/z 404.1 (M+H).

Example 129

2-(2-Isopropyl-2H-[1,2,4]triazol-3-yl)-9-(2-methoxy-pyridin-3-yl)-4,5-dihydro-6-oxa-3-thia-1-aza-benzo[e]azulene 129

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 2-methoxypyridin-3-ylboronic acid were reacted. The crude material was dissolved in DMF and purified by reverse phase HPLC to provide 129 (200 mg, 60%). $^1$H NMR (400 MHz, DMSO) δ 8.66 (d, J=2.2, 1H), 8.19 (dd, J=4.9, 1.7, 1H), 8.10 (s, 1H), 7.79 (dd, J=7.3, 1.8, 1H), 7.50 (dd, J=8.4, 2.3, 1H), 7.21-7.09 (m, 2H), 5.75 (dt, J=13.3, 6.7, 1H), 4.42 (t, J=4.9, 2H), 3.91 (s, 3H), 3.47 (t, J=4.9, 2H), 1.52 (d, J=6.6, 6H). MS (ESI(+)): m/z 420.1 (M+H).

Example 130

2-[2-(2,4-Difluoro-phenyl)-2H-[1,2,4]triazol-3-yl]-9-(4-methanesulfonyl-piperazin-1-yl)-4,5-dihydro-6-oxa-1-thia-10-aza-benzo[e]azulene 130

2-[2-(2,4-Difluoro-phenyl)-2H-[1,2,4]triazol-3-yl]-9-piperazin-1-yl-4,5-dihydro-6-oxa-1-thia-10-aza-benzo[e]azulene (150 mg, 0.3 mmol) was dissolved in THF, DIPEA (155 mg, 1.2 mmol) was added. Methanesulfonyl chloride (41 mg, 0.36 mmol) was added dropwise into the solution, and the reaction mixture was stirred at room temperature for 12 h. The reaction mixture was concentrated in vacuo, and then dissolved in DCM. The mixture was washed by water, dried over Na$_2$SO$_4$, concentrated in vacuo, and purified by prep. TLC (DCM/EtOAc=10:1) to give 130 (42.0 mg, yield: 26%). $^1$HNMR (Acetone, 400 MHz): δ8.00 (s, 1H), 7.73-7.71 (m, 1H), 7.36-7.10 (m, 2H), 7.12 (s, 2H), 6.69 (d, J=9.2 Hz, 1H), 4.14 (s, 1H), 3.49 (s, 4H), 3.22 (s, 4H), 3.00 (s, 2H), 2.79 (s, 3H). ESI-MS: m/z=545 [M+H$^+$]

Example 131

2-{[2-(4-Isopropyl-4H-[1,2,4]triazol-3-yl)-4,5-dihydro-6-oxa-3-thia-1-aza-benzo[e]azulen-8-ylmethyl]-amino}-ethanol 131

Following the procedure for 119, 2-(4-isopropyl-4H-[1,2,4]triazol-3-yl)-4,5-dihydro-6-oxa-3-thia-1-aza-benzo[e]azulene-8-carbaldehyde and ethanolamine were reacted. After aqueous work-up the resulting gum was triturated with DCM/ether/pentane to give a solid that was filtered off and dried to give 131 as an off-white solid (55 mg, 27%). LCMS: R$_T$=5.54 min, [M+H]$^+$=386. $^1$H NMR δ (ppm) (CDCl$_3$): 8.37 (1H, s), 8.30 (1H, d, J=8.11 Hz), 7.13 (1H, dd, J=8.15, 1.72 Hz), 7.05 (1H, d, J=1.68 Hz), 5.70-5.63 (1H, m), 4.41 (2H, t, J=5.06 Hz), 3.84 (2H, s), 3.68 (2H, t, J=5.17 Hz), 3.42 (2H, t, J=5.07 Hz), 2.85 (2H, t, J=5.16 Hz), 1.65 (6H, d, J=6.74 Hz). 2 Exchangeable protons not seen Example 132

{2-[2-(2,4-Difluoro-phenyl)-2H-[1,2,4]triazol-3-yl]-4,5-dihydro-6-oxa-1-thia-10-aza-benzo[e]azulen-9-yl}-(2-morpholin-4-yl-ethyl)-amine 132

A mixture of 9-Chloro-2-[2-(2,4-difluoro-phenyl)-2H-[1,2,4]triazol-3-yl]-4,5-dihydro-6-oxa-1-thia-10-aza-benzo[e]

azulene (300 mg, 0.72 mmol), Pd(OAc)$_2$ (49 mg, 0.3 mmol), 2-Morpholin-4-yl-ethylamine (200 mg, 1.44 mmol), 2,8,9-tributyl-2,5,8,9-tetraaza-1-phosphabicyclo[3.3.3]undecane (99 mg, 0.29 mmol), tert-butoxide (140 mg, 1.44 mmol) in dioxane (2 mL) was bubbled N$_2$ for 10 min and then stirred at 120° C. for 6 min under the irradition of microwave. The mixture was filtered over ceilite. The filtrate was concentrated to dryness and purified by pre-HPLC to afford 47 mg of 132. (yield=13%). $^1$H NMR (CDCl$_3$, 400 MHz): δ8.01 (s, 1H), 7.50-7.44 (m, 1H), 7.05-6.97 (m, 4H), 6.23-6.21 (d, J=8.4 Hz, 1H), 4.76-4.74 (m, 1H), 4.17-4.14 (m, 2H), 3.68-3.66 (m, 4H), 3.30-3.26 (m, 2H), 3.04-3.02 (m, 2H), 2.55-2.52 (m, 2H), 2.48-2.42 (m, 4H). LC-MS (ESI): m/z=511 [M+H]$^+$ Example 134

2-[2-(2,4-Difluoro-phenyl)-2H-[1,2,4]triazol-3-yl]-4,5-dihydro-6-oxa-1-thia-10-aza-benzo[e]azulen-9-ylamine 134

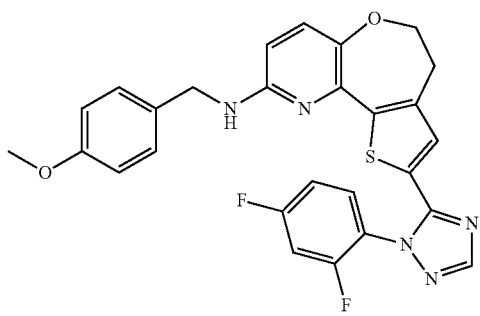 [SMILES: COc1ccc(CNc2ccc3c(n2)-c2sc(-c4ncnn4-c4ccc(F)cc4F)cc2CCO3)cc1]

9-Chloro-2-[2-(2,4-difluoro-phenyl)-2H-[1,2,4]triazol-3-yl]-4,5-dihydro-6-oxa-1-thia-10-aza-benzo[e]azulene (1.23 g, 3.0 mmol), 4-Methoxy-benzylamine (493 mg, 3.6 mmol), Pd$_2$(dba)$_3$ (210 mg, 0.3 mmol), Xphos (142 mg, 0.3 mmol), t-BuONa (576 mg, 6 mmol) and dioxane (6 mL) was added in a 10 mL of sealed tube, and the reaction mixture was heated by microwave at 112° C. for 7 min under N$_2$. The reaction mixture was filtered to gather the solution. Then water was added into the solution and extracted by DCM (50 mL×3). The combined organic layer was dried by Na$_2$SO$_4$, concentrated in vacuo, separated by TLC (DCM:EtOAc=4:1) to give {2-[2-(2,4-Difluoro-phenyl)-2H-[1,2,4]triazol-3-yl]-4,5-dihydro-6-oxa-1-thia-10-aza-benzo[e]azulen-9-yl}-(4-methoxy-benzyl)-amine (1.2 g, yield: 77%). $^1$H NMR (DMSO-d$_6$, 400 MHz): δ 8.36 (s, 1H), 7.96 (d, J=2.0 Hz, 1H), 7.69 (s, 1H), 7.39 (s, 1H), 7.31 (s, 1H), 7.29 (s, 2H), 7.14 (s, 1H), 6.97-6.90 (m, 3H), 6.46 (d, J=8.8 Hz, 1H), 4.34 (d, J=6.4 Hz, 2H), 4.20 (s, 2H), 3.77 (s, 3H), 3.12 (s, 2H). LC-MS (ESI): m/z=518 [M+H]$^+$ {2-[2-(2,4-Difluoro-phenyl)-2H-[1,2,4]triazol-3-yl]-4,5-dihydro-6-oxa-1-thia-10-aza-benzo[e]azulen-9-yl}-(4-methoxy-benzyl)-amine (1.2 g, 2.3 mmol) was dissolved in TFA (20 mL). The reaction mixture was stirred at 80° C. for 2 h. The reaction mixture was concentrated in vacuo, and dissolved in DCM (30 mL). The organic layer was washed by water, dried by Na$_2$SO$_4$, concentrated in vacuo, and separated by preparative TLC (DCM/EtOAc=4:1) to give 134 (800 mg, yield: 87%)$^1$H NMR (D$_2$O, 400 MHz): δ8.05 (s, 2H), 7.05 (d, J=8.8 Hz, 1H), 7.23 (t, J=2.0 Hz, 1H), 7.14 (s, 1H), 6.99-6.97 (m, 3H), 6.51 (d, J=8.8 Hz, 1H). LC-MS (ESI): m/z=398 [M+H]$^+$ Example 135

2-(2-Isopropyl-2H-[1,2,4]triazol-3-yl)-9-(6-methyl-pyridin-3-yl)-4,5-dihydro-6-oxa-3-thia-1-aza-benzo[e]azulene 135

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 6-methylpyridin-3-yl-boronic acid were reacted. The crude material was diluted with DMF and the solids were collected by filtration to provide 135 (58 mg, 23%). $^1$H NMR (400 MHz, DMSO) δ 8.73 (dd, J=32.7, 2.1, 2H), 8.11 (s, 1H), 7.96 (dd, J=8.1, 2.4, 1H), 7.65 (dd, J=8.4, 2.3, 1H), 7.38 (d, J=8.1, 1H), 7.20 (d, J=8.4, 1H), 5.78 (dt, J=13.0, 6.5, 1H), 4.52-4.32 (m, 2H), 3.48 (t, J=4.9, 2H), 2.52 (s, 3H), 1.57 (d, J=6.6, 6H). MS (ESI(+)): m/z 404.1 (M+H).

Example 136

2-(2-Isopropyl-2H-[1,2,4]triazol-3-yl)-4,5-dihydro-6-oxa-3-thia-1-aza-benzo[e]azulene-9-carbonitrile 136

9-Bromo-2-(2-isopropyl-2H-[1,2,4]triazol-3-yl)-4,5-dihydro-6-oxa-3-thia-1-aza-benzo[e]azulene from Example 6 (120 mg, 0.31 mmol) was dissolved in DMF (1.6 mL) in a 10-mL microwave vial. Purged with N$_2$ and added zinc cyanide (36 mg, 0.31 mmol) followed by tetrakis(triphenylphosphine)palladium(0) (18 mg, 0.015 mmol). Sealed the vial and evacuated and recycled twice with N$_2$. The vessel was subjected to microwave irradiation with stirring for 10 min at 175° C. The vessel was then cooled to r.t. and the reaction mixture was diluted with dichloromethane and water. The phases were separated and the organic layer was washed once with water, dried over MgSO$_4$, filtered and concentrated in vacuo. The crude residue was purified by ISCO chromatography (40 g column, 0-10% MeOH/DCM) to provide 76 mg (73% yield) of 136. LC/MS (ESI+): m/z 338 (M+H)

Example 137

(S)-1-[8-(1H-Pyrazol-4-yl)-4,5-dihydro-6-oxa-3-thia-1-aza-benzo[e]azulene-2-carbonyl]-pyrrolidine-2-carbonitrile 137

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (S)-pyrrolidine-2-carbonitrile (1.2 equiv) to give 137 (14.2 mg, M+1 392.1)

Example 138

((S)-3-Methyl-morpholin-4-yl)-[8-(1H-pyrazol-4-yl)-4,5-dihydro-6-oxa-3-thia-1-aza-benzo[e]azulen-2-yl]-methanone 138

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (S)-3-methylmorpholine (1.2 equiv) to give 138 (14.9 mg, M+1 397.1)

Example 139

2-(2-Isopropyl-2H-[1,2,4]triazol-3-yl)-9-(4-methyl-pyridin-3-yl)-4,5-dihydro-6-oxa-3-thia-1-aza-benzo[e]azulene 139

Following the procedure for 128, 9-Bromo-2-(2-isopropyl-2H-[1,2,4]triazol-3-yl)-4,5-dihydro-6-oxa-3-thia-1-azabenzo[e]azulene from Example 6 and 4-methylpyridin-3-yl-boronic acid were reacted. The crude material was dissolved in DMF and purified by reverse phase HPLC to provide 139 (89 mg, 35%). $^1$H NMR (400 MHz, DMSO) δ 8.57-8.29 (m, 3H), 8.12 (d, J=15.0, 1H), 7.38 (dd, J=8.3, 2.4, 2H), 7.20 (d, J=8.3, 1H), 5.73 (dt, J=13.1, 6.6, 1H), 4.45 (t, J=4.9, 2H), 3.49 (t, J=4.9, 2H), 2.37 (s, 3H), 1.48 (d, J=6.6, 6H). MS (ESI(+)): m/z 404.1 (M+H).

Example 140

2-(4-Isopropyl-4H-[1,2,4]triazol-3-yl)-4,5-dihydro-6-oxa-3-thia-1-aza-benzo[e]azulene-8-carboxylic acid isoxazol-3-ylamide 140

To a suspension of 2-(4-isopropyl-4H-[1,2,4]triazol-3-yl)-4,5-dihydro-6-oxa-3-thia-1-aza-benzo[e]azulene-8-carboxylic acid (226 mg, 0.63 mmol) in DCM (5 mL) at 0° C. was added DMF (4 drops, catalytic) then oxalyl chloride (115 μL, 1.32 mmol) dropwise. The reaction mixture was stirred at room temperature for 18 hours. 3-Amino-isoxazole (233 μL, 3.15 mmol) was added followed by triethylamine (176 μL, 1.26 mmol) and the reaction mixture was stirred for 4 hours. Aqueous saturated sodium bicarbonate solution was added and then ether and the mixture was filtered. The filtrate was concentrated in vacuo to remove the organics and the resulting aqueous phase was extracted with DCM (×3). The combined organic extracts were dried (Na$_2$SO$_4$) and concentrated in vacuo. The resultant residue was purified by flash chromatography (SiO$_2$, 0-5% MeOH in EtOAc) then trituration with EtOAc to give 140 as an off-white solid (126 mg, 47%). LCMS: R$_T$=9.86 min, [M+H]$^+$=423. $^1$H NMR δ (ppm) (DMSO-d6): 11.39 (1H, s), 8.94 (1H, s), 8.81 (1H, d, J=1.76 Hz), 8.39 (1H, d, J=8.33 Hz), 7.79 (1H, dd, J=8.34, 1.90 Hz), 7.70 (1H, d, J=1.87 Hz), 7.00 (1H, d, J=1.76 Hz), 5.51-5.41 (1H, m), 4.41-4.35 (2H, m), 3.47-3.41 (2H, m), 1.54 (6H, d, J=6.70 Hz)

Example 141

((R)-3-Methyl-pyrrolidin-1-yl)-[8-(1H-pyrazol-4-yl)-4,5-dihydro-6-oxa-3-thia-1-aza-benzo[e]azulen-2-yl]-methanone 141

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (R)-3-methylpyrrolidine (1.2 equiv) to give 141 (2.4 mg, M+1 381.1)

Example 142

8-(1H-Pyrazol-4-yl)-4,5-dihydro-6-oxa-3-thia-1-aza-benzo[e]azulene-2-carboxylic acid (2-cyano-ethyl)-cyclopentyl-amide 142

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with N-(but-3-ynyl)cyclopentanamine (1.2 equiv) to give 142 (2.4 mg, M+1 434.1)

Example 143

2-(2-Isopropyl-2H-[1,2,4]triazol-3-yl)-9-((E)-2-methanesulfonyl-vinyl)-4,5-dihydro-6-oxa-3-thia-1-aza-benzo[e]azulene 143

A mixture of 9-Bromo-2-(2-isopropyl-2H-[1,2,4]triazol-3-yl)-4,5-dihydro-6-oxa-3-thia-1-aza-benzo[e]azulene from Example 6 (0.36 g, 0.92 mmol), methyl vinyl sulfone (0.24 mL, 2.8 mmol), bis(triphenylphosphine)palladium(II) chloride (64 mg, 0.092 mmol) and triethylamine (0.64 mL, 4.6 mmol) in DMF (10 mL) was heated under an argon atmosphere for 16 h. The reaction mixture was concentrated and purified by column chromatography (40 g column, 0-100% EtOAc/heptane) to provide 280 mg (73% yield) of 143. LC/MS (ESI+): m/z 417 (M+H). $^1$H NMR (400 MHz, DMSO) δ 8.59 (d, J=2.0, 1H), 8.11 (s, 1H), 7.71 (dd, J=8.4, 2.1, 1H), 7.59-7.26 (m, 2H), 7.17 (d, J=8.4, 1H), 5.88-5.67 (m, 1H), 4.43 (t, J=4.8, 2H), 3.48 (dd, J=12.3, 7.5, 2H), 3.12 (s, 1H), 1.58 (d, J=6.6, 6H)

Example 144

2-[2-(2,4-Difluoro-phenyl)-2H-[1,2,4]triazol-3-yl]-8-(1H-pyrazol-4-yl)-4,5-dihydro-6-oxa-3-thia-1-aza-benzo[e]azulene 144

Following the procedure for 114, 8-Bromo-2-[2-(2,4-difluoro-phenyl)-2H-[1,2,4]triazol-3-yl]-4,5-dihydro-6-oxa-3-thia-1-aza-benzo[e]azulene was reacted with 4-(4,4,5,5-Tetramethyl-[1,3,2]dioxaborolan-2-yl)-1H-pyrazole to give 144. MS(ESI+) 449.0. $^1$H NMR (400 MHz, DMSO) δ 12.96 (s, 1H), 8.42 (s, 1H), 8.25 (s, 1H), 7.94 (s, 1H), 7.90-7.83 (m, 1H), 7.74-7.66 (m, 1H), 7.45-7.35 (m, 2H), 7.26 (d, J=1.5, 1H), 7.16 (dd, J=8.3, 1.6, 1H), 4.33 (t, J=4.9, 2H), 3.41 (t, J=4.9, 2H)

Example 145

2-(4-(2-(1-isopropyl-1H-1,2,4-triazol-5-yl)-4,5-dihydrobenzo[b]thieno[2,3-d]oxepin-8-yl)-1H-pyrazol-1-yl)ethanol 145

A solution of 1-Isopropyl-5-[8-(1H-pyrazol-4-yl)-4,5-dihydro-6-oxa-1-thia-benzo[e]azulen-2-yl]-1H-[1,2,4]triazole (0.23 g, 0.61 mmol) and cesium carbonate (0.40 g, 0.0012 mol) in N,N-dimethylformamide (1.8 mL, 0.023 mol) was stirred at room temperature for 5 minutes. 2-Bromoethanol (0.086 mL, 0.0012 mol) was added and the reaction was heated to 110° C. overnight. The mixture was cooled to room temperature. Ethyl acetate and water were added and the aqueous layer was extracted 3× with ethyl acetate. The organic phases were combined, dried with MgSO$_4$, and concentrated. The crude was purified by reverse-phase HPLC to give 101.8 mg of 145 as a colorless solid. MS(ESI+) 422.1. $^1$H NMR (400 MHz, DMSO) δ 8.21 (s, 1H), 8.00 (s, 1H), 7.93 (s, 1H), 7.66 (d, J=8.2, 1H), 7.52 (s, 1H), 7.32 (dd, J=8.2, 1.6, 1H), 7.27 (d, J=1.5, 1H), 5.10-4.95 (m, 1H), 4.90 (t, J=5.3, 1H), 4.34 (t, J=5.0, 2H), 4.15 (t, J=5.6, 2H), 3.77 (q, J=5.5, 2H), 3.29-3.24 (m, 2H), 1.48 (d, J=6.5, 6H)

Example 146

1-isopropyl-5-(8-(3-(methylsulfonyl)phenyl)-4,5-dihydrobenzo[b]thieno[2,3-d]oxepin-2-yl)-1H-1,2,4-triazole 146

Following the procedure for 114, 5 5-(8-Bromo-4,5-dihydro-6-oxa-1-thia-benzo[e]azulen-2-yl)-1-isopropyl-1H-[1,2,4]triazole was reacted with 3-methylsulfonylphenylboronic acid to give 146. MS(ESI+) 466.1.

Example 147

3-(2-(1-isopropyl-1H-1,2,4-triazol-5-yl)-4,5-dihydrobenzo[b]thieno[2,3-d]oxepin-8-yl)benzoic acid 147

Following the procedure for 114, 5 5-(8-Bromo-4,5-dihydro-6-oxa-1-thia-benzo[e]azulen-2-yl)-1-isopropyl-1H-[1,2,4]triazole was reacted with 3-carboxyphenylboronic acid to give 147. MS(ESI+) 432.1

Example 148

8-(3-Methanesulfonyl-phenyl)-2-[2-(2,2,2-trifluoro-ethyl)-2H-[1,2,4]triazol-3-yl]-4,5-dihydro-6-oxa-3-thia-1-aza-benzo[e]azulene 148

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with 3-methylsulfonylphenylboronic acid to give 148. MS(ESI+) 507.0. $^1$H NMR (400 MHz, DMSO) δ 8.44 (d, J=8.3, 1H), 8.31 (s, 1H), 8.25 (s, 1H), 8.14 (d, J=8.0, 1H), 7.93 (d, J=7.8, 1H), 7.75 (t, J=7.8, 1H), 7.67 (dd, J=8.3, 1.7, 1H), 7.55 (d, J=1.7, 1H), 5.88 (q, J=8.6, 2H), 4.45 (t, J=4.9, 2H), 3.52 (t, J=4.9, 2H), 3.32 (s, 3H)

Example 149

3-{2-[2-(2,2,2-Trifluoro-ethyl)-2H-[1,2,4]triazol-3-yl]-4,5-dihydro-6-oxa-3-thia-1-aza-benzo[e]azulen-8-yl}-benzoic acid 149

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with 3-carboxyphenylboronic acid to give 149. MS(ESI+) 473.0. $^1$H NMR (400 MHz, DMSO) δ 13.05 (br, 1H), 8.42 (d, J=8.3, 1H), 8.30 (s, 1H), 8.24 (s, 1H), 8.00 (d, J=7.8, 1H), 7.96 (d, J=7.8, 1H), 7.65-7.54 (m, 2H), 7.42 (d, J=1.6, 1H), 5.88 (q, J=8.6, 2H), 4.45 (t, J=4.9, 2H), 3.51 (t, J=4.9, 2H)

Example 150

2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-ethanol 150

A solution of 8-(1H-Pyrazol-4-yl)-2-[2-(2,2,2-trifluoro-ethyl)-2H-[1,2,4]triazol-3-yl]-4,5-dihydro-6-oxa-3-thia-1-aza-benzo[e]azulene (0.30 g, 0.00072 mol) and Cesium Carbonate (0.28 g, 0.00086 mol) in N,N-Dimethylformamide (1.5 mL, 0.019 mol) was stirred at room temperature for 5 minutes. 2-Bromoethanol (0.061 mL, 0.00086 mol) was added and the reaction was stirred at 70° C. overnight. The mixture was cooled to room temperature and ethyl acetate and water were added to the reaction. The aqueous layer was extracted 3 times with ethyl acetate and the combined organics were washed with water, dried with MgSO$_4$, and concentrated. The crude was purified by reverse-phase HPLC to give 150 (48.4 mg) as a colorless solid. MS(ESI+) 463.1. $^1$H NMR (400 MHz, DMSO) δ 8.29 (s, 1H), 8.27 (d, J=8.3, 1H), 8.24 (s, 1H), 7.97 (s, 1H), 7.44 (dd, J=8.3, 1.6, 1H), 7.31 (d, J=1.5, 1H), 5.86 (q, J=8.7, 2H), 4.91 (t, J=5.3, 2H), 4.40 (t, J=4.9, 2H), 4.16 (t, J=5.6, 2H), 3.77 (q, J=5.6, 2H), 3.47 (t, J=4.9, 2H)

Example 151

2-(3-amino-1-(2,4-difluorophenyl)-1H-1,2,4-triazol-5-yl)-N-(2-hydroxyethyl)-4,5-dihydrobenzo[b]thieno[2,3-d]oxepine-8-carboxamide 151

Similarly to as described in General Procedure D, 2-[5-Amino-2-(2,4-difluoro-phenyl)-2H-[1,2,4]triazol-3-yl]-4,5-dihydro-6-oxa-1-thia-benzo[e]azulene-8-carboxylic acid was reacted with ethanolamine to give 151 as a colorless solid after reverse phase HPLC (85 mg). LCMS: 484.1

Example 152

(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-acetic acid 152

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with [4-(4,4,5,5-Tetramethyl-[1,3,2]dioxaborolan-2-yl)-pyrazol-1-yl]-acetic acid ethyl ester to give 152. MS(ESI+) 477.0. $^1$H NMR (400 MHz, DMSO) δ 13.61-12.69 (br, 1H), 8.31-8.26 (m, 2H), 8.25 (s, 1H), 7.99 (s, 1H), 7.44 (dd, J=8.3, 1.6, 1H), 7.31 (d, J=1.5, 1H), 5.86 (q, J=8.7, 2H), 4.95 (s, 2H), 4.40 (t, J=4.9, 2H), 3.47 (t, J=4.9, 2H)

Example 153

8-(1H-Pyrazol-4-yl)-4,5-dihydro-6-oxa-3-thia-1-aza-benzo[e]azulene-2-carboxylic acid (2-cyano-ethyl)-methyl-amide 153

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 3-(methylamono)propanenitrile (1.2 equiv) to give 153 (32.2 mg, M+1 380.1)

Example 154

8-(1H-Pyrazol-4-yl)-4,5-dihydro-6-oxa-3-thia-1-aza-benzo[e]azulene-2-carboxylic acid (2-hydroxy-ethyl)-methyl-amide 154

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 2-(methylamino)ethanol (1.2 equiv) to give 154 (10.4 mg, M+1 371.1)

Example 155

Azocan-1-yl-[8-(1H-pyrazol-4-yl)-4,5-dihydro-6-oxa-3-thia-1-aza-benzo[e]azulen-2-yl]-methanone 155

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with azocane (1.2 equiv) to give 155 (12.1 mg, M+1 409.1)

Example 156

8-(1H-Pyrazol-4-yl)-4,5-dihydro-6-oxa-3-thia-1-aza-benzo[e]azulene-2-carboxylic acid ((R)-2-hydroxy-2-phenyl-ethyl)-methyl-amide 156

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (R)-2-(methylamino)-1-phenylethanol (1.2 equiv) to give 156 (19.1 mg, M+1 447.1)

Example 157

Azetidin-1-yl-[8-(1H-pyrazol-4-yl)-4,5-dihydro-6-oxa-3-thia-1-aza-benzo[e]azulen-2-yl]-methanone 157

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with azetidine (1.2 equiv) to give 157 (15.9 mg, M+1 353.0)

Example 158

[8-(1H-Pyrazol-4-yl)-4,5-dihydro-6-oxa-3-thia-1-aza-benzo[e]azulen-2-yl]-pyrrolidin-1-yl-methanone 158

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with pyrrolidine (1.2 equiv) to give 158 (17.7 mg, M+1 367.1)

Example 159

(4-Methyl-piperazin-1-yl)-[8-(1H-pyrazol-4-yl)-4,5-dihydro-6-oxa-3-thia-1-aza-benzo[e]azulen-2-yl]-methanone 159

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 1-methylpiperazine (1.2 equiv) to give 159 (17.7 mg, M+1 396.0)

Example 160

[4-(2-Hydroxy-ethyl)-piperazin-1-yl]-[8-(1H-pyrazol-4-yl)-4,5-dihydro-6-oxa-3-thia-1-aza-benzo[e]azulen-2-yl]-methanone 160

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 2-(piperazin-1-yl)ethanol (1.2 equiv) to give 160 (20.9 mg, M+1 426.1)

Example 161

Piperidin-1-yl-[8-(1H-pyrazol-4-yl)-4,5-dihydro-6-oxa-3-thia-1-aza-benzo[e]azulen-2-yl]-methanone 161

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with piperidine (1.2 equiv) to give 161 (17.9 mg, M+1 381.2)

Example 162

((R)-2-Hydroxymethyl-piperidin-1-yl)-[8-(1H-pyrazol-4-yl)-4,5-dihydro-6-oxa-3-thia-1-aza-benzo[e]azulen-2-yl]-methanone 162

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (S)-piperidin-2ylmethanol (1.2 equiv) to give 162 (12.1 mg, M+1 411.1)

Example 163

((R)-3-Methyl-piperidin-1-yl)-[8-(1H-pyrazol-4-yl)-4,5-dihydro-6-oxa-3-thia-1-aza-benzo[e]azulen-2-yl]-methanone 163

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (S)-3-methylpiperidine (1.2 equiv) to give 163 (13.8 mg, M+1 395.1)

Example 164

(3,3-Dimethyl-piperidin-1-yl)-[8-(1H-pyrazol-4-yl)-4,5-dihydro-6-oxa-3-thia-1-aza-benzo[e]azulen-2-yl]-methanone 164

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 3,3-dimethylpiperidine (1.2 equiv) to give 164 (12.1 mg, M+1 409.1)

Example 165

((R)-3-Hydroxymethyl-piperidin-1-yl)-[8-(1H-pyrazol-4-yl)-4,5-dihydro-6-oxa-3-thia-1-aza-benzo[e]azulen-2-yl]-methanone 165

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (R)-piperidin-3-ylmethanol (1.2 equiv) via to give 165 (18.1 mg, M+1 411.1)

Example 166

(4-Hydroxy-piperidin-1-yl)-[8-(1H-pyrazol-4-yl)-4,5-dihydro-6-oxa-3-thia-1-aza-benzo[e]azulen-2-yl]-methanone 166

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with piperidin-4-ol (1.2 equiv) to give 166 (16.4 mg, M+1 397.1)

Example 167

(4-Methyl-piperidin-1-yl)-[8-(1H-pyrazol-4-yl)-4,5-dihydro-6-oxa-3-thia-1-aza-benzo[e]azulen-2-yl]-methanone 167

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 4-methylpiperidine (1.2 equiv) to give 167 (15.8 mg, M+1 395.1)

Example 168

[8-(1H-Pyrazol-4-yl)-4,5-dihydro-6-oxa-3-thia-1-aza-benzo[e]azulen-2-yl]-(4-pyridin-2-yl-piperazin-1-yl)-methanone 168

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 1-(pyridine-2-yl) piperazine (1.2 equiv) to give 168 (19.8 mg, M+1 459.1)

Example 169

8-(1H-Pyrazol-4-yl)-4,5-dihydro-6-oxa-3-thia-1-aza-benzo[e]azulene-2-carboxylic acid methyl-(2-pyridin-2-yl-ethyl)-amide 169

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with N-methyl-2-(pyridine-2-yl)ethanamine (1.2 equiv) to give 169 (14.4 mg, M+1 432.1)

Example 170

8-(1H-Pyrazol-4-yl)-4,5-dihydro-6-oxa-3-thia-1-aza-benzo[e]azulene-2-carboxylic acid methyl-phenethyl-amide 170

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with N-methyl-2-phenylethanamine (1.2 equiv) to give 170 (14.5 mg, M+1 431.1)

Example 171

((R)-2-Methyl-pyrrolidin-1-yl)-[8-(1H-pyrazol-4-yl)-4,5-dihydro-6-oxa-3-thia-1-aza-benzo[e]azulen-2-yl]-methanone 171

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with (S)-2-methylpyrrolidine (1.2 equiv) to give 171 (14.8 mg, M+1 381.1)

Example 172

((R)-3-Hydroxy-piperidin-1-yl)-[8-(1H-pyrazol-4-yl)-4,5-dihydro-6-oxa-3-thia-1-aza-benzo[e]azulen-2-yl]-methanone 172

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with (S)-piperidin-3-ol (1.2 equiv) to give 172 (14.1 mg, M+1 397.1)

Example 173

8-(1H-Pyrazol-4-yl)-4,5-dihydro-6-oxa-3-thia-1-aza-benzo[e]azulene-2-carboxylic acid cyclohexyl-(2-hydroxy-ethyl)-amide 173

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with 2-(cyclohexylamino)ethanol (1.2 equiv) to give 173 (14.1 mg, M+1 439.1)

Example 174

8-(1H-Pyrazol-4-yl)-4,5-dihydro-6-oxa-3-thia-1-aza-benzo[e]azulene-2-carboxylic acid methyl-[(R)-1-(tetrahydro-furan-2-yl)methyl]-amide 174

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with (R)—N-methyl-1(tetrahydrofuran-2-yl)methanamine (1.2 equiv) to give 174 (18.4 mg, M+1 411.1)

Example 175

(4-Dimethylamino-piperidin-1-yl)-[8-(1H-pyrazol-4-yl)-4,5-dihydro-6-oxa-3-thia-1-aza-benzo[e]azulen-2-yl]-methanone 175

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with N,N-dimethylpiperdin-4-amine (1.2 equiv) to give 175 (17.9 mg, M+1 424.1)

Example 176

((R)-3-Hydroxy-pyrrolidin-1-yl)-[8-(1H-pyrazol-4-yl)-4,5-dihydro-6-oxa-3-thia-1-aza-benzo[e]azulen-2-yl]-methanone 176

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with (R)-pyrrolidin-3-ol (1.2 equiv) to give 176 (16.8 mg, M+1 383.1)

Example 177

[8-(1H-Pyrazol-4-yl)-4,5-dihydro-6-oxa-3-thia-1-aza-benzo[e]azulen-2-yl]-(4-pyrimidin-2-yl-piperazin-1-yl)-methanone 177

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with 2-(piperazin-1-yl)pyrimidine (1.2 equiv) to give 177 (8.7 mg, M+1 460.1)

Example 178

[8-(1H-Pyrazol-4-yl)-4,5-dihydro-6-oxa-3-thia-1-aza-benzo[e]azulen-2-yl]-(2,3,5,6-tetrahydro-[1,2']bipyrazinyl-4-yl)-methanone 178

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with 2-(piperazin-1-yl)pyrazine (1.2 equiv) to give 178 (8.7 mg, M+1 460.1)

Example 179

1-{4-[8-(1H-Pyrazol-4-yl)-4,5-dihydro-6-oxa-3-thia-1-aza-benzo[e]azulene-2-carbonyl]-piperazin-1-yl}-ethanone 179

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with 1-(piperazin-1-yl)ethanone (1.2 equiv) to give 179 (13.5 mg, M+1 424.1)

Example 180

N-Methyl-N-{(R)-1-[8-(1H-pyrazol-4-yl)-4,5-dihydro-6-oxa-3-thia-1-aza-benzo[e]azulene-2-carbonyl]-pyrrolidin-3-yl}-acetamide 180

Following the procedure for 103, 8-(1H-Pyrazol-4-yl)-4, 5-dihydro-6-oxa-3-thia-1-aza-benzo[e]azulene-2-carboxylic acid (50.0 mg, 0.2 mmol) was reacted with (R)—N-methyl-N-(pyrrolidin-3-yl)acetamide (1.2 equiv) to give 180 (24.3 mg, M+1 438.1)

Example 181

8-(1H-Pyrazol-4-yl)-4,5-dihydro-6-oxa-3-thia-1-aza-benzo[e]azulene-2-carboxylic acid ((R)-2,3-dihydroxy-propyl)-methyl-amide 181

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (S)-3-(methylamino)propane-1,2-diol (1.2 equiv) to give 181 (14.9 mg, M+1 401.1)

Example 182

8-(1H-Pyrazol-4-yl)-4,5-dihydro-6-oxa-3-thia-1-aza-benzo[e]azulene-2-carboxylic acid (2-methoxy-ethyl)-methyl-amide 182

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 2-methoxy-N-methylethanamine (1.2 equiv) to give 182 (15.1 mg, M+1 385.1)

Example 183

(4-Hydroxymethyl-piperidin-1-yl)-[8-(1H-pyrazol-4-yl)-4,5-dihydro-6-oxa-3-thia-1-aza-benzo[e]azulen-2-yl]-methanone 183

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with piperidin-4-yl-methanol (1.2 equiv) to give 183 (15.9 mg, M+1 411.1)

Example 184

[8-(1H-Pyrazol-4-yl)-4,5-dihydro-6-oxa-3-thia-1-aza-benzo[e]azulen-2-yl]-[4-((R)-tetrahydro-furan-2-carbonyl)-piperazin-1-yl]-methanone 184

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with piperazin-1-yl(tetrahydrofuran-2-yl)methanone (1.2 equiv) to give 184 (19.3 mg, M+1 480.1)

Example 185

[4-(2-Methoxy-ethyl)-piperazin-1-yl]-[8-(1H-pyrazol-4-yl)-4,5-dihydro-6-oxa-3-thia-1-aza-benzo[e]azulen-2-yl]-methanone 185

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 1-(2-methoxy-ethyl)piperazine (1.2 equiv) to give 185 (21.8 mg, M+1 440.1)

Example 186

[4-(2-Methoxy-phenyl)-piperidin-1-yl]-[8-(1H-pyrazol-4-yl)-4,5-dihydro-6-oxa-3-thia-1-aza-benzo[e]azulen-2-yl]-methanone 186

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 4-(2-methoxyphenyl)piperidine (1.2 equiv) to give 186 (17.9 mg, M+1 487.1)

Example 187

8-(1H-Pyrazol-4-yl)-4,5-dihydro-6-oxa-3-thia-1-aza-benzo[e]azulene-2-carboxylic acid [(R)-1-(2,3-dihydro-benzofuran-2-yl)methyl]-methyl-amide 187

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (R)-1-(2,3-dihydrobenzofuran-2-yl)-N-methylmethanamine (1.2 equiv) to give 187 (16.8 mg, M+1 459.1)

Example 188

2-{2-[2-(2,4-Difluoro-phenyl)-2H-[1,2,4]triazol-3-yl]-4,5-dihydro-6-oxa-1-thia-10-aza-benzo[e]azulen-9-ylamino}-ethanol 188

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (20 mg, 0.1 mmol), Trimethylsilanyloxy-ethylamine (190 mg, 1.44 mmol), X-phos (70 mg, 0.144 mmol), tert-butoxide (140 mg, 1.44 mmol) in dioxane (2 mL) was bubbled N$_2$ for 10 min and then stirred at 120° C. for 6 min under the irradition of microwave. The mixture was filtered over celite. The filtrate was concentrated to dryness and purified by pre-HPLC to afford 64.8 mg of 188. (yield=21%). $^1$H NMR (CDCl$_3$, 400 MHz): δ8.02 (s, 1H), 7.51-7.45 (m, 1H), 7.08-7.00 (m, 4H), 6.24-6.22 (d, J=8.8 Hz, 1H), 4.17-4.15 (m, 2H), 3.76-3.74 (m, 2H), 3.45-3.42 (m, 2H), 3.06-3.04 (m, 2H). LC-MS (ESI): m/z=442 [M+H]$^+$ Example 190

2-[2-(2,4-Difluoro-phenyl)-2H-[1,2,4]triazol-3-yl]-9-(1-methyl-1H-pyrazol-4-yl)-4,5-dihydro-6-oxa-1-thia-10-aza-benzo[e]azulene 190

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (100 mg, 0.24 mmol), Cs$_2$CO$_3$ (156.4 mg, 0.48 mmol), Pd(dppf)Cl$_2$ (17 mg, 0.024 mmol) and 1-Methyl-4-(4,4,5,5-tetramethyl-[1,3,2]dioxaborolan-2-yl)-1H-pyrazole (65 mg, 0.30 mmol) in acetonitrile/water (3 mL, 3:1) was degassed with N$_2$ for 2 min, then stirred at 150° C. for 15 min under the irradition of microwave. The mixture was filtered over ceilite. The filtrate was concentrated to dryness and purified by pre-TLC to afford 23 mg of 190 (yield=21%). $^1$H NMR (MeOD, 400 MHz): δ8.19 (s, 1H), 7.94 (s, 1H), 7.85 (s, 1H), 7.68-7.62 (m, 2H), 7.44-7.24 (m, 5H), 4.31-4.28 (m, 2H), 3.95 (s, 3H), 3.16-3.14 (m, 2H) LC-MS (ESI): m/z=463 [M+H]$^+$

Example 191

2-(2-Isopropyl-2H-[1,2,4]triazol-3-yl)-9-(5-methyl-pyridin-3-yl)-4,5-dihydro-6-oxa-3-thia-1-aza-benzo[e]azulene 191

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 5-methylpyridin-3-yl-boronic acid were reacted to give 191 (0.027 g, 17%). $^1$H NMR (400 MHz, DMSO) δ 8.73 (d, J=2.4, 2H), 8.42 (s, 1H), 8.12 (s, 1H), 7.89 (s, 1H), 7.69 (dd, J=8.4, 2.3, 1H), 7.20 (d, J=8.4, 1H), 5.82 (dt, J=13.1, 6.5, 1H), 4.43 (t, J=4.8, 2H), 3.56-3.39 (m, 2H), 2.39 (s, 3H), 1.58 (d, J=6.6, 6H). MS (ESI(+)): m/z 404.0 (M+H)

Example 192

4-[2-(2-Isopropyl-2H-[1,2,4]triazol-3-yl)-4,5-dihydro-6-oxa-3-thia-1-aza-benzo[e]azulen-9-yl]-benzenesulfonamide 192

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 4-sulfamoylphenylboronic acid were reacted to give 192 (0.034 g, 19%). $^1$H NMR (400 MHz, CDCl$_3$) δ 8.75 (d, J=2.3, 1H), 8.02 (d, J=8.4, 2H), 7.94 (s, 1H), 7.75 (t, J=12.6, 2H), 7.51 (dt, J=13.0, 6.5, 1H), 7.19 (d, J=8.4, 1H), 5.86 (dt, J=13.3, 6.7, 1H), 4.82 (s, 2H), 4.47 (t, J=4.9, 2H), 3.47 (t, J=4.9, 2H), 1.65 (d, J=6.6, 6H). MS (ESI(+)): m/z 468.1 (M+H)

Example 193

2-Methyl-1-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propan-2-ol 193

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with 2-Methyl-1-[4-(4,4,5,5-tetramethyl-[1,3,2]dioxaborolan-2-yl)-pyrazol-1-yl]-propan-2-ol to give 193. MS(ESI+) 491.1. $^1$H NMR (400 MHz, DMSO) δ 8.29 (s, 1H), 8.27 (d, J=8.3, 1H), 8.18 (s, 1H), 7.96 (s, 1H), 7.45 (dd, J=8.3, 1.8, 1H), 7.31 (d, J=1.7, 1H), 5.86 (q, J=8.7, 2H), 4.71 (s, 1H), 4.39 (t, J=5.0, 2H), 4.03 (s, 2H), 3.47 (t, J=5.0, 2H), 1.10 (s, 6H)

Example 194

(4-Benzoyl-piperazin-1-yl)-[8-(1H-pyrazol-4-yl)-4,5-dihydro-6-oxa-3-thia-1-aza-benzo[e]azulen-2-yl]-methanone 194

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with phenyl(piperazin-1-yl)methanone (1.2 equiv) to give 194 (M+1 486.0)

Example 195

(4-Cyclopropylmethyl-piperazin-1-yl)-[8-(1H-pyrazol-4-yl)-4,5-dihydro-6-oxa-3-thia-1-aza-benzo[e]azulen-2-yl]-methanone 195

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 1-(cyclopropylmethyl)piperazine (1.2 equiv) to give 195 (M+1 436.0)

Example 196

4-[8-(1H-Pyrazol-4-yl)-4,5-dihydro-6-oxa-3-thia-1-aza-benzo[e]azulene-2-carbonyl]-piperazine-1-carboxylic acid dimethylamide 196

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with N,N-dimethylpiperazine-1-carboxamide (1.2 equiv) to give 196 (M+1 453.0)

Example 197

(R)-Octahydro-pyrido[1,2-a]pyrazin-2-yl-[8-(1H-pyrazol-4-yl)-4,5-dihydro-6-oxa-3-thia-1-aza-benzo[e]azulen-2-yl]-methanone 197

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (R)-octahydro-1H-pyrido[1,2-a]pyrazine (1.2 equiv) to give 197 (M+1 436.0)

Example 198

[4-(6-Methyl-pyridin-2-yl)-piperazin-1-yl]-[8-(1H-pyrazol-4-yl)-4,5-dihydro-6-oxa-3-thia-1-aza-benzo[e]azulen-2-yl]-methanone 198

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 1-(6-methylpyridin-2-yl)piperazine (1.2 equiv) to give 198 (M+1 473.0)

Example 199

[8-(1H-Pyrazol-4-yl)-4,5-dihydro-6-oxa-3-thia-1-aza-benzo[e]azulen-2-yl]-{4-[(R)-1-(tetrahydro-furan-2-yl)methyl]-piperazin-1-yl}-methanone 199

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (S)-1-((tetrahydrofuran-2-yl)methyl)piperazine (1.2 equiv) to give 199 (M+1 466.0)

Example 200

(4-Methanesulfonyl-piperazin-1-yl)-[8-(1H-pyrazol-4-yl)-4,5-dihydro-6-oxa-3-thia-1-aza-benzo[e]azulen-2-yl]-methanone 200

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 1-(methylsulfonyl)piperazine (1.2 equiv) to give 200 (M+1 460.0)

Example 201

[8-(1H-Pyrazol-4-yl)-4,5-dihydro-6-oxa-3-thia-1-aza-benzo[e]azulen-2-yl]-((R)-3-trifluoromethyl-piperidin-1-yl)-methanone 201

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (R)-3-(trifluoromethyl)piperidine (1.2 equiv) to give 201 (M+1 449.0)

Example 202

((R)-3-Diethylamino-pyrrolidin-1-yl)-[8-(1H-pyrazol-4-yl)-4,5-dihydro-6-oxa-3-thia-1-aza-benzo[e]azulen-2-yl]-methanone 202

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (R)—N,N-diethylpyrrolidin-3-amine (1.2 equiv) to give 202 (M+1 438.0)

Example 203

(4,4-Difluoro-piperidin-1-yl)-[8-(1H-pyrazol-4-yl)-4,5-dihydro-6-oxa-3-thia-1-aza-benzo[e]azulen-2-yl]-methanone 203

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 4,4-difluoropiperidine (1.2 equiv) to give 203 (M+1 417.0)

Example 204

[4-((2R,6R)-2,6-Dimethyl-morpholin-4-yl)-piperidin-1-yl]-[8-(1H-pyrazol-4-yl)-4,5-dihydro-6-oxa-3-thia-1-aza-benzo[e]azulen-2-yl]-methanone 204

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (3S,5S-3,5-dimethyl-4-(piperidin-4-yl)morpholine (1.2 equiv) to give 204 (M+1 494.0)

Example 205

[4-(4-Methyl-piperazine-1-carbonyl)-piperidin-1-yl]-[8-(1H-pyrazol-4-yl)-4,5-dihydro-6-oxa-3-thia-1-aza-benzo[e]azulen-2-yl]-methanone 205

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (4-methylpiperazin-1-yl)(piperidin-4-yl)methanone (1.2 equiv) to give 205 (M+1 507.0)

Example 206

[8-(1H-Pyrazol-4-yl)-4,5-dihydro-6-oxa-3-thia-1-aza-benzo[e]azulen-2-yl]-[4-(pyrrolidine-1-carbonyl)-piperidin-1-yl]-methanone 206

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with piperidin-4-yl (pyrrolidin-1-yl)methanone (1.2 equiv) to give 206 (M+1 478.0)

Example 207

(4-Cyclopropanecarbonyl-piperazin-1-yl)-[8-(1H-pyrazol-4-yl)-4,5-dihydro-6-oxa-3-thia-1-aza-benzo[e]azulen-2-yl]-methanone 207

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with cyclopropyl(piperidin-4-yl)methanone (1.2 equiv) to give 207 (M+1 450.0)

Example 208

[8-(1H-Pyrazol-4-yl)-4,5-dihydro-6-oxa-3-thia-1-aza-benzo[e]azulen-2-yl]-(4-pyridin-4-yl-[1,4]diazepan-1-yl)-methanone 208

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 1-(pyridin-4-yl)-1,4-diazepane (1.2 equiv) to give 208 (M+1 473.0)

Example 209

8-(1H-Pyrazol-4-yl)-4,5-dihydro-6-oxa-3-thia-1-aza-benzo[e]azulene-2-carboxylic acid (2-hydroxy-ethyl)-isopropyl-amide 209

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 2-(isopropylamino)ethanol (1.2 equiv) to give 209 (10.8 mg, M+1 399.1)

Example 210

((R)-3-Dimethylamino-pyrrolidin-1-yl)-[8-(1H-pyrazol-4-yl)-4,5-dihydro-6-oxa-3-thia-1-aza-benzo[e]azulen-2-yl]-methanone 210

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (R)—N,N-dimethylpyrrolidin-3amine (1.2 equiv) to give 210 (M+1 410.0)

Example 211

2-Methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propionic acid 211

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with 2-Methyl-2-[4-(4,4,5,5-tetramethyl-[1,3,2]dioxaborolan-2-yl)-pyrazol-1-yl]-propionic acid ethyl ester to give 211. MS(ESI+) 505.1

Example 212

2-{[2-(4-Isopropyl-4H-[1,2,4]triazol-3-yl)-4,5-dihydro-6-oxa-3-thia-1-aza-benzo[e]azulen-8-ylmethyl]-amino}-acetamide 212

To a suspension of 2-(2-isopropyl-2H-[1,2,4]triazol-3-yl)-4,5-dihydro-6-oxa-3-thia-1-aza-benzo[e]azulene-8-carbaldehyde (86 mg, 0.25 mmol) in MeOH (4 mL) was added glycinamide hydrochloride (140 mg, 1.26 mmol) and the mixture was stirred for 30 minutes. AcOH (2 drops) was added followed by sodium borohydride (14 mg, 0.38 mmol) and the reaction mixture was stirred for 65 hours. Further sodium borohydride (10 mg) was added and the reaction stirred for another 20 hours. Aqueous saturated sodium bicarbonate solution (15 mL) was added and the MeOH was removed in vacuo. The aqueous phase was extracted with DCM (×3) and the combined organic phase was dried (Na$_2$SO$_4$) and concentrated in vacuo. The resultant residue was purified by flash chromatography (SiO$_2$, 0-6% MeOH in EtOAc then 0-5% 2M NH$_3$/MeOH in DCM) to give 212 as a yellow solid (30 mg, 30%). LCMS: R$_T$=5.43 min, [M+H]$^+$=399. $^1$H NMR δ (ppm) (DMSO-d6): 8.93 (1H, s), 8.23 (1H, d, J=8.10 Hz), 7.25 (1H, s), 7.11 (1H, dd, J=8.16, 1.70 Hz), 7.01 (1H, d, J=1.75 Hz), 5.52-5.40 (1H, m), 4.33 (2H, t, J=5.05 Hz), 3.65 (2H, s), 3.39 (2H, t, J=5.11 Hz), 3.01 (2H, s), 1.54 (6H, d, J=6.71 Hz)

Example 213

[8-(1H-Pyrazol-4-yl)-4,5-dihydro-6-oxa-3-thia-1-aza-benzo[e]azulen-2-yl]-((R)-3-trifluoromethyl-pyrrolidin-1-yl)-methanone 213

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with (S)-3-(trifluoromethyl)pyrrolidine (1.2 equiv) to give 213 (15.8 mg, M+1 435.1)

Example 214

[4-(2,4-Difluoro-phenyl)-piperidin-1-yl]-[8-(1H-pyrazol-4-yl)-4,5-dihydro-6-oxa-3-thia-1-aza-benzo[e]azulen-2-yl]-methanone 214

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 4-(2,4-difluorophenyl)piperidine (1.2 equiv) to give 214 (11.8 mg, M+1 493.1)

Example 215

(4-Methoxy-piperidin-1-yl)-[8-(1H-pyrazol-4-yl)-4,5-dihydro-6-oxa-3-thia-1-aza-benzo[e]azulen-2-yl]-methanone 215

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with 4-methoxypiperidine (1.2 equiv) to give 215 (19.6 mg, M+1 411.1)

Example 216

[8-(1H-Pyrazol-4-yl)-4,5-dihydro-6-oxa-3-thia-1-aza-benzo[e]azulen-2-yl]-((R)-2-pyridin-2-ylmethyl-pyrrolidin-1-yl)-methanone 216

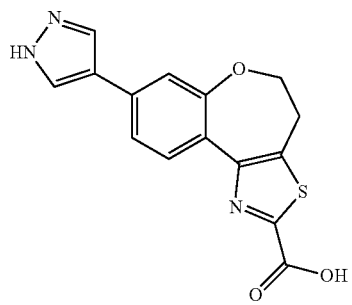 [SMILES: O=C(O)c1nc2c(s1)CCOc1cc(-c3cn[nH]c3)ccc1-2]

Following Example 103, to a well stirred solution of 8-(1H-Pyrazol-4-yl)-4,5-dihydro-6-oxa-3-thia-1-aza-benzo[e]azulene-2-carboxylic acid (50 mg, 0.20 mmol) in DMF at room temperature was added (R)-2-(pyrrolidin-2-ylmethyl)pyridine (0.24 mmol), followed by the addition of DIPEA (0.056 ml, 0.32 mmol). Finally, HATU (0.067 grams, 0.18 mmol) was added and the reaction mixture was heated as a slurry at 50 C for 4 hours. The reaction mixture was conc. in vacuo and taken into a large volume of EtOAc and the organic phase was washed with dilute aqueous bicarb, water and then saline and dried (Na2SO4), then concentrated to a residue. The crude material was purified by preparative RP-HPLC to give 216 as a lyophilized solid. MS: (ESI+)=458.5

Example 217

4-[8-(1H-Pyrazol-4-yl)-4,5-dihydro-6-oxa-3-thia-1-aza-benzo[e]azulene-2-carbonyl]-piperazine-1-sulfonic acid dimethylamide 217

Following Example 216, to a well stirred solution of 8-(1H-Pyrazol-4-yl)-4,5-dihydro-6-oxa-3-thia-1-aza-benzo[e]azulene-2-carboxylic acid and N,N-dimethylpiperazine-1-sulfonamide were reacted to give 217. MS: (ESI+)=489.1

Example 218

2-Methyl-1-{4-[8-(1H-pyrazol-4-yl)-4,5-dihydro-6-oxa-3-thia-1-aza-benzo[e]azulene-2-carbonyl]-piperazin-1-yl}-propan-1-one 218

Following Example 216, to a well stirred solution of 8-(1H-Pyrazol-4-yl)-4,5-dihydro-6-oxa-3-thia-1-aza-benzo[e]azulene-2-carboxylic acid and N,N-dimethylpiperazine-1-carboxamide were reacted to give 218. MS: (ESI+)=452.1

Example 219

((R)-3-Methoxy-piperidin-1-yl)-[8-(1H-pyrazol-4-yl)-4,5-dihydro-6-oxa-3-thia-1-aza-benzo[e]azulen-2-yl]-methanone 219

Following Example 216, to a well stirred solution of 8-(1H-Pyrazol-4-yl)-4,5-dihydro-6-oxa-3-thia-1-aza-benzo[e]azulene-2-carboxylic acid and (R)-2-methoxypiperidine were reacted to give 219. MS: (ESI+)=411.1

Example 220

1-[8-(1H-Pyrazol-4-yl)-4,5-dihydro-6-oxa-3-thia-1-aza-benzo[e]azulene-2-carbonyl]-piperidine-4-carbonitrile 220

Following Example 216, to a well stirred solution of 8-(1H-Pyrazol-4-yl)-4,5-dihydro-6-oxa-3-thia-1-aza-benzo[e]azulene-2-carboxylic acid and piperidine-4-carbonitrile were reacted to give 220. MS: (ESI+)=406.0

Example 221

(3,3-Difluoro-azetidin-1-yl)-[8-(1H-pyrazol-4-yl)-4,5-dihydro-6-oxa-3-thia-1-aza-benzo[e]azulen-2-yl]-methanone 221

Following Example 216, to a well stirred solution of 8-(1H-Pyrazol-4-yl)-4,5-dihydro-6-oxa-3-thia-1-aza-benzo[e]azulene-2-carboxylic acid and 3,3-difluoroazetidine to give 221. MS: (ESI+)=389.0

Example 222

8-(1H-Pyrazol-4-yl)-4,5-dihydro-6-oxa-3-thia-1-aza-benzo[e]azulene-2-carboxylic acid ((S)-1-isopropyl-pyrrolidin-3-ylmethyl)-methyl-amide 222

Following Example 216, to a well stirred solution of 8-(1H-Pyrazol-4-yl)-4,5-dihydro-6-oxa-3-thia-1-aza-benzo[e]azulene-2-carboxylic acid and (S)-1-(1-isopropylpyrrolidin-3-yl)-N-methylmethanamine to give 222. MS: (ESI+)=452.2

Example 223

((R)-3-Methoxymethyl-piperidin-1-yl)-[8-(1H-pyrazol-4-yl)-4,5-dihydro-6-oxa-3-thia-1-aza-benzo[e]azulen-2-yl]-methanone 223

Following Example 216, to a well stirred solution of 8-(1H-Pyrazol-4-yl)-4,5-dihydro-6-oxa-3-thia-1-aza-benzo[e]azulene-2-carboxylic acid and (S)-3-(methoxymethyl)piperidine to give 223. MS: (ESI+)=425.1

Example 224

(4-Methoxymethyl-piperidin-1-yl)-[8-(1H-pyrazol-4-yl)-4,5-dihydro-6-oxa-3-thia-1-aza-benzo[e]azulen-2-yl]-methanone 224

Following Example 216, to a well stirred solution of 8-(1H-Pyrazol-4-yl)-4,5-dihydro-6-oxa-3-thia-1-aza-benzo[e]azulene-2-carboxylic acid and 4-(methoxymethyl)piperidine to give 224. MS: (ESI+)=425.1

Example 225

8-(1H-Pyrazol-4-yl)-4,5-dihydro-6-oxa-3-thia-1-aza-benzo[e]azulene-2-carboxylic acid methyl-(2-morpholin-4-yl-2-oxo-ethyl)-amide 225

Following Example 216, to a well stirred solution of 8-(1H-Pyrazol-4-yl)-4,5-dihydro-6-oxa-3-thia-1-aza-benzo[e]azulene-2-carboxylic acid and 2-(methylamino)-1-morpholino-ethanone to give 225. MS: (ESI+)=454.1

Example 226

[8-(1H-Pyrazol-4-yl)-4,5-dihydro-6-oxa-3-thia-1-aza-benzo[e]azulen-2-yl]-(4-pyridin-3-yl-piperazin-1-yl)-methanone 226

Following Example 216, to a well stirred solution of 8-(1H-Pyrazol-4-yl)-4,5-dihydro-6-oxa-3-thia-1-aza-benzo[e]azulene-2-carboxylic acid and 1-(pyridin-2-yl)piperazine to give 226. MS: (ESI+)=459.2

Example 227

[8-(1H-Pyrazol-4-yl)-4,5-dihydro-6-oxa-3-thia-1-aza-benzo[e]azulen-2-yl]-(4-pyridin-2-yl-[1,4]diazepan-1-yl)-methanone 227

Following Example 216, to a well stirred solution of 8-(1H-Pyrazol-4-yl)-4,5-dihydro-6-oxa-3-thia-1-aza-benzo[e]azulene-2-carboxylic acid and 1-(pyridin-2-yl)-1,4-diazepane to give 227. MS: (ESI+)=473.1

Example 228

((R)-3-Morpholin-4-yl-pyrrolidin-1-yl)-[8-(1H-pyrazol-4-yl)-4,5-dihydro-6-oxa-3-thia-1-aza-benzo[e]azulen-2-yl]-methanone 228

Following Example 216, to a well stirred solution of 8-(1H-Pyrazol-4-yl)-4,5-dihydro-6-oxa-3-thia-1-aza-benzo[e]azulene-2-carboxylic acid and (R)-4-(pyrrolidin-3-yl)morpholine to give 228. MS: (ESI+)=453.1

Example 229

2,2,2-Trifluoro-1-{4-[8-(1H-pyrazol-4-yl)-4,5-dihydro-6-oxa-3-thia-1-aza-benzo[e]azulene-2-carbonyl]-piperazin-1-yl}-ethanone 229

Following Example 216, to a well stirred solution of 8-(1H-Pyrazol-4-yl)-4,5-dihydro-6-oxa-3-thia-1-aza-benzo[e]azulene-2-carboxylic acid and 2,2,2-trifluoro-1-(piperazin-1-yl)ethanone to give 229. MS: (ESI+)=478.1

Example 230

2-(2-Isopropyl-2H-[1,2,4]triazol-3-yl)-9-(4-methanesulfonyl-phenyl)-4,5-dihydro-6-oxa-3-thia-1-aza-benzo[e]azulene 230

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 4-(methylsulfonyl)phenylboronic acid were reacted to give 230 (0.072 g, 40%). $^1$H NMR (400 MHz, CDCl$_3$) δ 8.77 (d, J=2.3, 1H), 8.03 (d, J=8.4, 2H), 7.94 (s, 1H), 7.82 (d, J=8.4, 2H), 7.59-7.48 (m, 1H), 7.20 (d, J=8.4, 1H), 5.94-5.79 (m, 1H), 4.48 (t, J=4.9, 2H), 3.46 (dd, J=10.7, 5.8, 2H), 3.12 (s, 3H), 1.65 (d, J=6.6, 6H). MS (ESI(+)): m/z 467.1 (M+H)

Example 231

{2-[2-(2,4-Difluoro-phenyl)-2H-[1,2,4]triazol-3-yl]-4,5-dihydro-6-oxa-1-thia-10-aza-benzo[e]azulen-9-yl}-[2-(4-methyl-piperazin-1-yl)-ethyl]-amine 231

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (20 mg, 0.1 mmol), 2-(4-methylpiperazin-1-yl)ethanamine (121 mg, 0.936 mmol), X-phos (70 mg, 0.144 mmol), tert-butoxide (140 mg, 1.44 mmol) in dioxane (2 mL) was bubbled N$_2$ for 10 min and then stirred at 120° C. for 5 min under the irradiation of microwave. The mixture was filtered over ceilite. The filtrate was concentrated to dryness and purified by pre-HPLC to afford 180 mg of 231. (yield=48%). $^1$H NMR (CDCl$_3$, 400 MHz): δ8.41 (s, 1H), 8.01 (m, 1H), 7.50-7.45 (m, 1H), 7.06-6.99 (m, 3H), 6.88 (s, 1H), 6.24 (d, J=8.8 Hz, 1H), 4.16-4.14 (m, 2H), 3.42-3.40 (m, 2H), 3.02-3.00 (m, 2H), 2.82-2.70 (m, 10H), 2.42 (s, 3H). LC-MS (ESI): m/z=524 [M+H]$^+$

Example 232

2-[2-(2,4-Difluoro-phenyl)-2H-[1,2,4]triazol-3-yl]-9-(3,4,5,6-tetrahydro-2H-[1,2']bipyridinyl-5'-yl)-4,5-dihydro-6-oxa-1-thia-10-aza-benzo[e]azulene 232

2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo

[e]azulene, from the procedure for 249, (470 mg, 1.0 mmol), Piperidine (102 mg, 1.2 mmol), DIPEA (340 mg, 3 mmol) and NMP (4 mL) were added in a 10 mL of sealed tube, and the mixture was heated by microwave at 150° C. for 120 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 232 (46.2 mg, yield: 8.5%). $^1$HNMR (DMSO-$d_6$, 400 MHz): δ8.74 (s, 1H), 8.31 (s, 1H), 8.10 (d, J=4.8 Hz, 1H), 7.91-7.87 (m, 1H), 7.78-7.77 (m, 2H), 7.50-7.40 (m, 1H), 7.18 (d, J=4.4 Hz, 1H), 7.19 (d, J=8.8 Hz, 1H), 6.93 (d, J=8.8 Hz, 1H), 4.31 (s, 2H), 3.64 (s, 4H), 3.16 (s, 2H), 1.63-1.57 (m, 4H) ESI-MS: m/z=543 [M+H$^+$]

Example 233

2-[2-(2,4-Difluoro-phenyl)-2H-[1,2,4]triazol-3-yl]-9-(6-methoxy-pyridin-3-yl)-4,5-dihydro-6-oxa-1-thia-10-aza-benzo[e]azulene 233

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 2-Methoxy-5-(4,4,5,5-tetramethyl-[1,3,2]dioxaborolan-2-yl)-pyridine (282 mg, 1.2 mmol), $Cs_2CO_3$ (650 mg, 2.0 mmol), Pd(dppf)Cl$_2$ (73 mg, 0.10 mmol) and $CH_3CN—H_2O$ (1:1, 4 mL) were added in a 10 mL of sealed tube, and the mixture was heated by microwave at 120° C. for 20 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 233 (87.2 mg, yield: 17%). $^1$HNMR (DMSO-$d_6$, 400 MHz): δ8.81 (s, 1H), 8.31 (s, 1H), 8.23 (d, J=2.4 Hz, 1H), 7.85 7.78 (m, 2H), 7.49 (d, J=2.4 Hz, 2H), 7.21 (s, 1H), 6.97 (d, J=8.8 Hz, 1H), 4.27 (s, 2H), 3.93 (s, 3H), 3.17 (s, 2H). ESI-MS: m/z=490 [M+H$^+$]

Example 234

2-(2-Isopropyl-2H-[1,2,4]triazol-3-yl)-9-(2-methoxy-phenyl)-4,5-dihydro-6-oxa-3-thia-1-aza-benzo[e]azulene 234

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 2-methoxyphenylboronic acid were reacted to give 234 (0.087 g, 54%). $^1$H NMR (400 MHz, DMSO) δ 8.60 (s, 1H), 8.10 (s, 1H), 7.39 (dd, J=31.7, 7.5, 3H), 7.09 (dt, J=14.7, 9.8, 3H), 5.82-5.69 (m, 1H), 4.41 (s, 2H), 3.79 (s, 3H), 3.47 (s, 2H), 1.51 (d, J=6.5, 6H). MS (ESI(+)): m/z 419.1 (M+H)

Example 235

8-Azetidin-3-yl-2-(2-isopropyl-2H-[1,2,4]triazol-3-yl)-4,5-dihydro-6-oxa-3-thia-1-aza-benzo[e]azulene 235

A solution of 3-[2-(2-isopropyl-2H-[1,2,4]triazol-3-yl)-4,5-dihydro-6-oxa-3-thia-1-aza-benzo[e]azulen-8-yl]-azetidine-1-carboxylic acid tert-butyl ester (0.5 g, 1.1 mmol) in DCM (6.5 mL) was treated with TFA (6.5 mL). The reaction mixture was stirred at RT for 4 hours then concentrated in vacuo. The residue was azeotroped with DCM then dissolved in DCM and washed with an aqueous saturated sodium bicarbonate solution (×2) followed by brine. The mixture was passed through a phase separator cartridge and concentrated in vacuo to give 235 as a pale orange gum (397 mg, quant.). LCMS: R$_T$=3.13 min, [M+H]$^+$=368. 1H NMR δ (ppm) (DMSO-d6): 9.34 (1H, s), 9.05 (1H, s), 8.30 (1H, d, J=8.19 Hz), 8.06 (1H, d, J=0.58 Hz), 7.23 (1H, dd, J=8.24, 1.89 Hz), 7.13 (1H, d, J=1.84 Hz), 5.82-5.72 (1H, m), 4.36-4.30 (2H, m), 4.25-4.17 (2H, m), 4.13-3.97 (3H, m), 3.43-3.37 (2H, m), 1.50 (6H, d, J=6.59 Hz).

Example 236

3-[2-(2-Isopropyl-2H-[1,2,4]triazol-3-yl)-4,5-dihydro-6-oxa-3-thia-1-aza-benzo[e]azulen-9-yl]-azetidine-1-carboxylic acid tert-butyl ester 236

Zinc (151 mg, 2.31 mmol) was stirred in DMA (0.4 mL) under an atmosphere of argon. Chlorotrimethylsilane (25 uL, 0.20 mmol) and 1,2-dibromoethane (20 uL, 0.2 mmol) were added (gentle exotherm) and the mixture stirred at room temperature for 15 min. A solution of tert-butyl 3-iodoazetidine-1-carboxylate (0.5 g, 1.8 mmol) in DMA (1 mL) was introduced and the reaction was allowed to stir at room temperature for an additional 30 min. Meanwhile, [1,1'-Bis(diphenylphosphino)ferrocen]dichloropalladium(II), in complex with dichloromethane (1:1) (68 mg, 0.083 mmol), copper(I) iodide (32 mg, 0.166 mmol) and 9-bromo-2-(2-isopropyl-2H-[1,2,4]triazol-3-yl)-4,5-dihydro-6-oxa-3-thia-1-aza-benzo[e]azulene from Example 6 (0.65 g, 1.66 mmol) were mixed in DMA (2.5 mL) and stirred under argon for 10 min. Subsequently, the organozinc reagent solution was transferred to this mixture via syringe. The resulting green reaction mixture was stirred at 80° C. whereupon it turned yellow. Stirring was continued for 20 h. At this point, LCMS indicated approximately 33% conversion to the title compound. The mixture was diluted with EtOAc (25 mL) and 1 N HCl (25 mL) and the layers were partitioned. The aqueous layer was extracted with EtOAc (2×10 mL) and the combined organic portions were washed once with brine. The extract was dried over MgSO$_4$ and concentrated in vacuo. The residue was purified by rp-HPLC to give 236 (35 mg, 5% yield). LC/MS (ESI+): m/z 468.2 (M+H). $^1$H NMR (400 MHz, DMSO) δ 1.22 8.47 (d, J=2.0 Hz, 1H), 8.10 (s, 1H), 7.20 (dd, J=8.2, 2.1 Hz, 1H), 7.03 (d, J=8.2 Hz, 1H), 5.84 (dt, J=13.2, 6.5 Hz, 1H), 4.35 (dd, J=17.3, 12.5 Hz, 4H), 3.82 (s, 3H), 3.44 (t, J=4.9 Hz, 2H), 1.58 (t, J=9.5 Hz, 6H), 1.41 (s, 9H).

Example 237

2-(2-Isopropyl-2H-[1,2,4]triazol-3-yl)-9-(5-methanesulfonyl-pyridin-3-yl)-4,5-dihydro-6-oxa-3-thia-1-aza-benzo[e]azulene 237

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 5-(methylsulfonyl)pyridin-3-ylboronic acid were reacted to give 237 (0.053 g, 30%). $^1$H NMR (400 MHz, DMSO) δ 9.28 (d, J=2.0, 1H), 9.07 (d, J=1.8, 1H), 8.82 (d, J=2.2, 1H), 8.56 (s, 1H), 8.11 (s, 1H), 7.87 (dd, J=8.4, 2.3, 1H), 7.27 (d, J=8.4, 1H), 5.87 (dt, J=13.0, 6.5, 1H), 4.45 (t, J=4.8, 2H), 3.50 (t, J=4.8, 2H), 3.41 (s, 3H), 1.59 (d, J=6.6, 6H). MS (ESI(+)): m/z 468.1 (M+H)

Example 238

8-(1-Methanesulfonyl-1H-pyrazol-4-yl)-2-[2-(2,2,2-trifluoro-ethyl)-2H-[1,2,4]triazol-3-yl]-4,5-dihydro-6-oxa-3-thia-1-aza-benzo[e]azulene 238

To a round bottom flask containing 8-(1H-Pyrazol-4-yl)-2-[2-(2,2,2-trifluoro-ethyl)-2H-[1,2,4]triazol-3-yl]-4,5-dihydro-6-oxa-3-thia-1-aza-benzo[e]azulene (0.200 g, 0.000478 mol) in methylene chloride (3 mL, 0.05 mol) and chloroform (2 mL, 0.02 mol) was added triethylamine (0.080 mL, 0.00057 mol) and methanesulfonyl chloride (0.088 mL, 0.00114 mol). The reaction was stirred at 40° C. for 6 h. The mixture was washed with water followed by brine, dried with $MgSO_4$ and concentrated. The crude was loaded as a solid onto silica gel and purified by flash chromatography (1-10% MeOH in DCM) followed by reverse-phase HPLC to give 238 (16.5 mg) as a colorless solid. MS(ESI+) 497.0. $^1$H NMR (400 MHz, DMSO) δ 8.88 (s, 1H), 8.56 (s, 1H), 8.33 (d, J=8.3, 1H), 8.30 (s, 1H), 7.65 (dd, J=8.3, 1.6, 1H), 7.55 (d, J=1.5, 1H), 5.86 (q, J=8.7, 2H), 4.42 (t, J=4.9, 2H), 3.58 (s, 3H), 3.49 (t, J=4.9, 2H)

Example 239

9-(2-Isopropoxy-pyridin-3-yl)-2-(2-isopropyl-2H-[1,2,4]triazol-3-yl)-4,5-dihydro-6-oxa-3-thia-1-aza-benzo[e]azulene 239

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 2-isopropoxy-3-(4,4,5,5-tetramethyl-1,3,2-dioxaborolan-2-yl)pyridine were reacted to give 239 (0.102 g, 59%). $^1$H NMR (400 MHz, DMSO) δ 8.53 (d, J=2.2, 1H), 8.23-8.03 (m, 2H), 7.75 (dd, J=7.3, 1.8, 1H), 7.56 (dd, J=8.4, 2.2, 1H), 7.20-7.00 (m, 2H), 5.72 (dt, J=13.3, 6.6, 1H), 5.35 (dt, J=12.3, 6.2, 1H), 4.43 (t, J=4.9, 2H), 3.47 (t, J=4.9, 2H), 1.50 (d, J=6.6, 6H), 1.29 (d, J=6.2, 6H). MS (ESI(+)): m/z 448.1 (M+H)

Example 240

2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-acetamide 240

To a round bottom flask containing (4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-acetic acid (0.150 g, 0.000315 mol) in tetrahydrofuran (2.0 mL, 0.025 mol) was added N,N-diisopropylethylamine (0.33 mL, 0.0019 mol), ammonium chloride (0.10 g, 0.0019 mol) and N,N,N',N'-tetramethyl-O-(7-azabenzotriazol-1-yl)uronium hexafluorophosphate (HATU) (0.24 g, 0.00063 mol). The reaction was stirred at room temperature overnight. The mixture was partitioned between saturated sodium bicarbonate and ethyl acetate. The organic phases were combined, dried with $MgSO_4$, and concentrated. The crude was purified by reverse-phase HPLC to yield 240 (31.5 mg) as a colorless solid. MS(ESI+) 476.1.

Example 241

N,N-Dimethyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-acetamide 241

Following the procedure for 240, (4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-acetic acid was reacted with dimethylamine to give 241. MS(ESI+) 504.1. $^1$H NMR (400 MHz, DMSO) δ 8.31-8.26 (m, 2H), 8.16 (s, 1H), 7.97 (s, 1H), 7.44 (dd, J=8.3, 1.6, 1H), 7.31 (d, J=1.4, 1H), 5.87 (q, J=8.7, 2H), 5.12 (s, 2H), 4.40 (t, J=4.9, 2H), 3.47 (t, J=4.9, 2H), 3.05 (s, 3H), 2.87 (s, 3H)

Example 242

2-({2-[2-(2,4-Difluoro-phenyl)-2H-[1,2,4]triazol-3-yl]-4,5-dihydro-6-oxa-1-thia-10-aza-benzo[e]azulen-9-yl}-methyl-amino)-ethanol 242

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), $Pd(OAc)_2$ (20 mg, 0.1 mmol), Methyl-(2-trimethylsilanyloxy-ethyl)-amine (211 mg, 1.44 mmol), X-phos (70 mg, 0.144 mmol), tert-butoxide (140 mg, 1.44 mmol) in dioxane (2 mL) was bubbled $N_2$ for 10 min and then stirred at 125° C. for 7 min under the irradition of microwave. The mixture was filtered over ceilite. The filtrate was concentrated to dryness and purified by pre-TLC (EtOAc:PE=2:1) to afford 85 mg of 242. (yield=26%). $^1$H NMR ($CDCl_3$, 400 MHz): δ8.01-8.00 (m, 1H), 7.50-7.45 (m, 1H), 7.13-7.00 (m, 4H), 6.36 (d, J=9.2 Hz, 1H), 4.17-4.15 (m, 2H), 3.78-3.75 (m, 1H), 3.63-3.59 (m, 2H), 3.07-3.05 (m, 2H), 2.98 (s, 3H), 2.30-2.26 (m, 1H). LC-MS (ESI): m/z=456 [M+H]$^+$ Example 243

2-[2-(2,4-Difluoro-phenyl)-2H-[1,2,4]triazol-3-yl]-9-(4-isopropyl-piperazin-1-yl)-4,5-dihydro-6-oxa-1-thia-10-aza-benzo[e]azulene 243

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), $Pd(OAc)_2$ (20 mg, 0.1 mmol), 1-Isopropyl-piperazine (164 mg, 1.44 mmol), X-phos (70 mg, 0.144 mmol), tert-butoxide (140 mg, 1.44 mmol) in dioxane (2 mL) was bubbled $N_2$ for 10 min and then stirred at 120° C. for 2.5 min under the irradition of microwave. The mixture was filtered over celite. The filtrate was concentrated to dryness and purified by pre-HPLC to afford 80 mg of 243. (yield=22%). $^1$H NMR ($CDCl_3$, 400 MHz): δ8.02 (s, 1H), 7.50-7.44 (m, 1H), 7.09-6.99 (m, 4H), 6.46 (d, J=8.8 Hz, 1H), 4.18-4.12 (m, 2H), 3.42-3.40 (m, 3H), 3.05-3.03 (m, 2H), 2.12-2.06 (m, 2H), 1.56-1.50 (m, 3H), 1.10-1.04 (m, 3H). LC-MS (ESI): m/z=509 [M+H]$^+$ Example 244

4-{2-[2-(2,4-Difluoro-phenyl)-2H-[1,2,4]triazol-3-yl]-4,5-dihydro-6-oxa-1-thia-10-aza-benzo[e]azulen-9-yl}-butan-2-ol 244

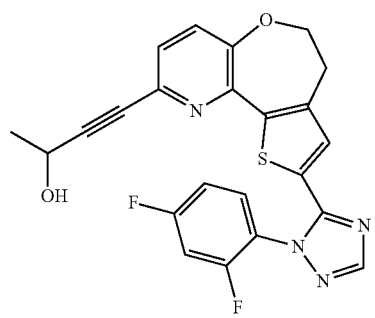 [SMILES: CC(O)C#Cc1ccc2c(n1)-c1sc(-c3ncnn3-c3ccc(F)cc3F)cc1CCO2]

Following the procedures for 246, 4-{2-[2-(2,4-Difluoro-phenyl)-2H-[1,2,4]triazol-3-yl]-4,5-dihydro-6-oxa-1-thia-10-aza-benzo[e]azulen-9-yl}-but-3-yn-2-ol was prepared (Yield: 93%. ¹H NMR (DMSO-d₆, 400 MHz): δ8.32 (s, 1H), 7.93 (dd, J=5.6, 8.4 Hz, 1H), 7.74-7.69 (m, 1H), 7.45-7.40 (m, 2H), 7.33 (d, J=8.0 Hz, 1H), 6.95 (s, 1H), 5.59 (d, J=5.2 Hz, 1H), 4.64 (q, J=5.6, 6.8 Hz, 1H), 4.32 (t, J=4.0 Hz, 2H), 3.13 (t, J=4.4 Hz, 2H), 1.42 (d, J=6.4 Hz, 3H), ESI-MS: (m/z)=451 [M+H]⁺) from 9-Chloro-2-[2-(2,4-difluoro-phenyl)-2H-[1,2,4]triazol-3-yl]-4,5-dihydro-6-oxa-1-thia-10-aza-benzo[e]azulene and but-3-yn-2-ol, and hydrogenated to give 244 Yield: 38%. ¹H NMR (DMSO-d₆, 400 MHz): δ8.26 (s, 1H), 7.89-7.84 (m, 1H), 7.70-7.65 (m, 1H), 7.40 (t, J=8.0 Hz, 1H), 7.28 (d, J=8.4 Hz, 1H), 7.07 (d, J=8.4 Hz, 1H), 7.00 (s, 1H), 4.44 (s, 1H), 4.23 (t, =4.8 Hz, 2H), 3.58-3.56 (m, 1H), 3.13 (t, J=4.8 Hz, 2H), 2.71-2.63 (m, 2H), 1.69-1.61 (m, 2H), 1.05 (d, J=6.4 Hz, 3H). LC-MS (ESI): m/z=455 [M+H]⁺

Example 245

4-{2-[2-(2,4-Difluoro-phenyl)-2H-[1,2,4]triazol-3-yl]-4,5-dihydro-6-oxa-1-thia-10-aza-benzo[e]azulen-9-yl}-butan-1-ol 245

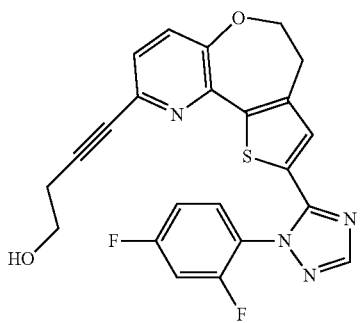 [SMILES: OCCC#Cc1ccc2c(n1)-c1sc(-c3ncnn3-c3ccc(F)cc3F)cc1CCO2]

Following the procedures for 246, 9-Chloro-2-[2-(2,4-difluoro-phenyl)-2H-[1,2,4]triazol-3-yl]-4,5-dihydro-6-oxa-1-thia-10-aza-benzo[e]azulene and but-3-yn-1-ol were reacted under palladium catalysis to give 4-{2-[2-(2,4-Difluoro-phenyl)-2H-[1,2,4]triazol-3-yl]-4,5-dihydro-6-oxa-1-thia-10-aza-benzo[e]azulen-9-yl}-but-3-yn-1-ol (Yield: 81%. ¹H NMR (DMSO-d₆, 400 MHz): δ8.31 (s, 1H), 7.94-7.88 (m, 1H), 7.74-7.68 (m, 1H), 7.43-7.38 (m, 2H), 7.31 (d, J=8.4 Hz, 1H), 6.92 (s, 1H), 4.95 (s, 1H), 4.31 (t, J=4.0 Hz, 2H), 3.62 (m, 2H), 3.12 (t, J=4.4 Hz, 2H), 2.61 (t, J=6.8 Hz, 2H). LC-MS (ESI): m/z=451 [M+H]⁺), which was hydrogenated to give 245 Yield: 43%. ¹H NMR (DMSO-d₆, 400 MHz): δ8.27 (s, 1H), 7.90-7.84 (m, 1H), 7.70-7.65 (m, 1H), 7.41-7.39 (m, 1H), 7.29 (d, J=8.4 Hz, 1H), 7.06 (d, J=8.4 Hz, 1H), 6.99 (s, 1H), 4.37 (s, 1H), 4.23 (t, J=4.8 Hz, 2H), 3.40 (t, J=6.4 Hz, 2H), 3.09 (t, J=4.8 Hz, 2H), 2.64-2.60 (m, 2H), 1.65-1.59 (m, 1H), 1.44-1.38 (m, 1H). LC-MS (ESI): m/z=455 [M+H]⁺

Example 246

(3-{2-[2-(2,4-Difluoro-phenyl)-2H-[1,2,4]triazol-3-yl]-4,5-dihydro-6-oxa-1-thia-10-aza-benzo[e]azulen-9-yl}-propyl)-dimethyl-amine 246

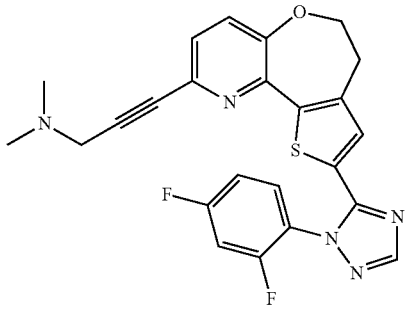 [SMILES: CN(C)CC#Cc1ccc2c(n1)-c1sc(-c3ncnn3-c3ccc(F)cc3F)cc1CCO2]

To a mixture of 9-Chloro-2-[2-(2,4-difluoro-phenyl)-2H-[1,2,4]triazol-3-yl]-4,5-dihydro-6-oxa-1-thia-10-aza-benzo[e]azulene (500 mg, 1.2 mmol), and dimethyl-prop-2-ynyl-amine (150 mg, 1.8 mmol) in dry DMF (3 mL) under nitrogen was added K₂CO₃ (498 mg, 3.6 mmol), CuI (11 mg, 0.06 mmol), 1,3-bis(diphenylphosphino)propane (99 mg, 0.24 mmol) and Pd(OAc)₂ (27 mg, 0.12 mmol). The reaction mixture was heated at 110° C. for 40 min under microwave. Cooled to room temperature, the resulting mixture was poured into water and extracted with EtOAc. Dried organics over sodium sulfate and purified by column chromatography (Hexanes/EtOAc=1:1) to give (3-{2-[2-(2,4-Difluoro-phenyl)-2H-[1,2,4]triazol-3-yl]-4,5-dihydro-6-oxa-1-thia-10-aza-benzo[e]azulen-9-yl}-prop-2-ynyl)-dimethyl-amine as a yellow solid (530 mg, yield 95%). ¹H NMR (DMSO-d₆, 400 MHz): δ8.31 (s, 1H), 7.91 (dd, J=3.2, 8.8 Hz, 1H), 7.73-7.68 (m, 1H), 7.40 (d, J=8.0 Hz, 2H), 7.33 (d, J=8.4 Hz, 1H), 7.07 (s, 1H), 4.31 (t, J=4.8 Hz, 2H), 3.50 (s, 2H), 3.14 (t, J=4.8 Hz, 2H), 2.27 (s, 6H). ESI-MS: (m/z)=464 [M+H]⁺

The mixture of (3-{2-[2-(2,4-Difluoro-phenyl)-2H-[1,2,4]triazol-3-yl]-4,5-dihydro-6-oxa-1-thia-10-aza-benzo[e]azulen-9-yl}-prop-2-ynyl)-dimethyl-amine (200 mg, 0.43 mmol), 10% Pd/C (20 mg) in MeOH (20 mL) was stirred under H₂ atmosphere (50 psi) at room temperature for overnight. Filtered and concentrated to give 246 (26 mg, yield: 13%). ¹H NMR (CDCl₃, 400 MHz): δ8.08 (s, 1H), 7.58-7.52 (m, 1H), 7.19 (d, J=8.0 Hz, 1H), 7.15-7.07 (m, 2H), 6.94 (d, J=8.0 Hz, 1H), 6.90 (s, 1H), 4.29 (t, J=4.4 Hz, 2H), 3.12 (t, J=4.4 Hz, 2H), 2.82-2.77 (m, 4H), 2.57 (s, 6H), 2.15-2.08 (m, 2H). ESI-MS: (m/z)=468 [M+H]⁺

Example 247

N-(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-acetamide 247

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), N-[5-(4,4,5,5-Tetramethyl-[1,3,2]dioxaborolan-2-yl)-pyridin-2-yl]-acetamide (314 mg, 1.2 mmol), Cs₂CO₃ (650 mg, 2.0 mmol), Pd(dppf)Cl₂ (73 mg, 0.10 mmol) and CH₃CN—H₂O (1:1, 4 mL) were added in a 10 mL of sealed tube, and the mixture was heated by microwave at 120° C. for 20 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to 247 (77 mg, yield: 15%). $^1$HNMR (DMSO-$d_6$, 400 MHz): δ10.62 (s, 1H), 8.88 (s, 1H), 8.27 (s, 1H), 8.15 (s, 2H), 7.42 (t, J=0.8 Hz, 1H), 7.89-7.81 (m, 3H), 7.47 (t, J=8.8 Hz, 2H), 7.15 (s, 1H), 4.27 (s, 2H), 3.17 (s, 2H), 2.08 (s, 3H). ESI-MS: m/z=517 [M+H$^+$]

Example 248

2-[2-(2,4-Difluoro-phenyl)-2H-[1,2,4]triazol-3-yl]-9-(6-morpholin-4-yl-pyridin-3-yl)-4,5-dihydro-6-oxa-1-thia-10-aza-benzo[e]azulene 248

9-Chloro-2-[2-(2,4-difluoro-phenyl)-2H-[1,2,4]triazol-3-yl]-4,5-dihydro-6-oxa-1-thia-10-aza-benzo[e]azulene (4.16 mg, 10 mmol), 4-[5-(4,4,5,5-Tetramethyl-[1,3,2]dioxaborolan-2-yl)-pyridin-2-yl]-morpholine (350 mg, 12 mmol), $Cs_2CO_3$ (650 mg, 2.0 mmol), Pd(dppf)$Cl_2$ (73 mg, 0.10 mmol) and $CH_3CN$—$H_2O$ (1:1, 4 mL) were added in a 50 mL of sealed tube, and the mixture was heated by microwave at 80° C. for 60 min under $N_2$. The reaction mixture was filtered to gather the solution and water was added. The mixture was extracted by DCM (50 mL×3). The combined organic layers were dried over $Na_2SO_4$, concentrated in vacuo, and purified by preparative TLC to give 248 (98.1 mg, yield: 18%). $^1$HNMR (DMSO-$d_6$, 400 MHz): δ8.75 (s, 1H), 8.28 (s, 1H), 8.06 (d, J=2.4 Hz, 1H), 7.73-7.71 (m, 1H), 7.45-7.41 (m, 2H), 7.41-7.38 (m, 2H), 7.14 (s, 1H), 6.93 (d, J=8.8 Hz, 1H), 4.27 (s, 2H), 3.74 (s, 4H), 3.53 (s, 4H), 3.11 (s, 2H). ESI-MS: m/z=545 [M+H$^+$]

Example 249

2-[2-(2,4-Difluoro-phenyl)-2H-[1,2,4]triazol-3-yl]-9-[6-(4-methyl-piperazin-1-yl)-pyridin-3-yl]-4,5-dihydro-6-oxa-1-thia-10-aza-benzo[e]azulene 249

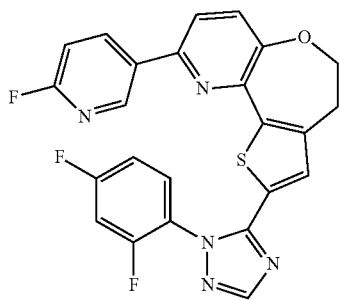 [SMILES: Fc1ccc(-n2ncnc2-c2cc3c(s2)-c2nc(-c4ccc(F)nc4)ccc2OCC3)c(F)c1]

9-Chloro-2-[2-(2,4-difluoro-phenyl)-2H-[1,2,4]triazol-3-yl]-4,5-dihydro-6-oxa-1-thia-10-aza-benzo[e]azulene (4.16 g, 10 mmol), 2-Fluoro-5-(4,4,5,5-tetramethyl-[1,3,2]dioxaborolan-2-yl)-pyridine (2.67 g, 12 mmol), $Cs_2CO_3$ (6.50 g, 20 mmol), Pd(dppf)$Cl_2$ (730 mg, 1.0 mmol) and $CH_3CN$—$H_2O$ (1:1, 40 mL) were added in a 50 mL of sealed tube, and the mixture was heated at 80° C. for 60 min under $N_2$. The reaction mixture was filtered to gather the solution and water was added. The mixture was extracted by DCM (50 mL×3). The combined organic layers were dried over $Na_2SO_4$, concentrated in vacuo, and purified by preparative TLC to give 2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo[e]azulene (4.0 g, yield: 84%). $^1$HNMR (DMSO-$d_6$, 400 MHz): δ8.68 (s, 1H), 8.43 (t, J=4.8 Hz, 2H), 8.12-8.01 (m, 1H), 8.00-7.92 (m, 1H), 7.84 (t, J=2.8 Hz, 1H), 7.58-7.50 (m, 2H), 7.26 (s, 2H), 4.39 (s, 2H), 3.24 (s, 2H), 2.23 (s, 3H). ESI-MS: m/z=478 [M+H$^+$]

2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo[e]azulene (470 mg, 1.0 mmol), 1-Methyl-piperazine (120 mg, 1.2 mmol), DIPEA (340 mg, 3 mmol) and NMP (4 mL) were added in a 10 mL of sealed tube, and the mixture was heated by microwave at 150° C. for 120 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 249 (315 mg, yield: 57%). $^1$HNMR (DMSO-$d_6$, 400 MHz): δ8.71 (s, 1H), 8.27 (s, 1H), 8.04 (d, J=3.2 Hz, 1H), 7.42 (t, J=2 Hz, 1H), 7.90-7.88 (m, 1H), 7.76-7.78 (m, 2H), 7.46-7.40 (m, 1H), 7.38 (d, J=8.4 Hz, 1H), 7.14 (m, 1H), 6.91 (d, J=8.8 Hz, 1H), 4.26 (s, 2H), 3.50 (s, 3H), 3.10 (s, 2H), 2.38 (s, 4H), 2.18 (s, 3H). ESI-MS: m/z=558 [M+H$^+$]

Example 250

{2-[2-(2,4-Difluoro-phenyl)-2H-[1,2,4]triazol-3-yl]-4,5-dihydro-6-oxa-1-thia-10-aza-benzo[e]azulen-9-yl}-(tetrahydro-pyran-4-yl)-amine 250

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (20 mg, 0.1 mmol), Tetrahydro-pyran-4-ylamine (145 mg, 1.44 mmol), X-phos (70 mg, 0.144 mmol), tert-butoxide (140 mg, 1.44 mmol) in dioxane (2 mL) was bubbled $N_2$ for 10 min and then stirred at 120° C. for 2.5 min under the irradition of microwave. The mixture was filtered over ceilite. The filtrate was concentrated to dryness and purified by pre-HPLC to afford 80 mg of 250. (yield=29%). $^1$H NMR (CDCl$_3$, 400 MHz): δ8.03 (s, 1H), 7.50-7.44 (m, 1H), 7.09-6.99 (m, 4H), 6.18 (d, J=8.8 Hz, 1H), 4.06-4.02 (m, 1H), 3.96-3.90 (m, 2H), 3.84-3.76 (m, 1H), 3.50-3.41 (m, 2H), 3.06-3.03 (m, 2H), 1.48-1.40 (m, 2H). LC-MS (ESI): m/z=481 [M+H]$^+$ Example 251

9-Cyclopentyl-2-(2-isopropyl-2H-[1,2,4]triazol-3-yl)-4,5-dihydro-6-oxa-3-thia-1-aza-benzo[e]azulene 251

1,1'-Bis(diphenylphosphino)ferrocene]dichloropalladium (II) complex with DCM (1:1) (8.45 mg, 0.0104 mmol), copper(I) iodide (3.94 mg, 0.0207 mmol) and 9-Bromo-2-(2-isopropyl-2H-[1,2,4]triazol-3-yl)-4,5-dihydro-6-oxa-3-thia-1-aza-benzo[e]azulene from Example 6 (0.081 g, 0.21 mmol) were mixed in DMA (2.5 mL) and stirred under argon for 10 min and cyclopentylzinc bromide (0.5 M in THF, 0.42 mL, 0.21 mmol) was transferred to this mixture via syringe. The reaction was carried out at 80° C. Subsequently cooled to room temp. and diluted with EtOAc and 1 N HCl and worked up. Purified via rp-HPLC to provide 251 (8 mg, 10% yield). LC/MS (ESI+): m/z 381 (M+H). $^1$H NMR (400 MHz, DMSO) δ 8.27 (d, J=2.0, 1H), 8.08 (d, J=16.1, 1H), 7.16 (dd, J=8.2, 2.1, 1H), 6.98 (d, J=8.2, 1H), 5.83 (dt, J=13.2, 6.7, 1H), 4.34 (t, J=5.0, 2H), 3.42 (t, J=5.0, 2H), 3.05 (p, J=8.3, 1H), 2.19-1.98 (m, 2H), 1.73 (ddd, J=11.4, 6.9, 3.8, 4H), 1.61-1.48 (m, 8H).

Example 252

(4-tert-Butyl-piperidin-1-yl)-[8-(1H-pyrazol-4-yl)-4,5-dihydro-6-oxa-3-thia-1-aza-benzo[e]azulen-2-yl]-methanone 252

Following Example 216, to a well stirred solution of 8-(1H-Pyrazol-4-yl)-4,5-dihydro-6-oxa-3-thia-1-aza-benzo[e]azulene-2-carboxylic acid and 4-tert-butylpiperidine to give 252. MS: (ESI+)=427.1

Example 253

8-(1H-Pyrazol-4-yl)-4,5-dihydro-6-oxa-3-thia-1-aza-benzo[e]azulene-2-carboxylic acid diethylamide 253

Following Example 216, to a well stirred solution of 8-(1H-Pyrazol-4-yl)-4,5-dihydro-6-oxa-3-thia-1-aza-benzo[e]azulene-2-carboxylic acid and diethylamine to give 253. MS: (ESI+)=369.1

Example 254

8-(1H-Pyrazol-4-yl)-4,5-dihydro-6-oxa-3-thia-1-aza-benzo[e]azulene-2-carboxylic acid isobutyl-methyl-amide 254

Following Example 216, to a well stirred solution of 8-(1H-Pyrazol-4-yl)-4,5-dihydro-6-oxa-3-thia-1-aza-benzo[e]azulene-2-carboxylic acid and N,2-dimethylpropan-1-amine to give 254. MS: (ESI+)=369.1

Example 255

8-(1H-Pyrazol-4-yl)-4,5-dihydro-6-oxa-3-thia-1-aza-benzo[e]azulene-2-carboxylic acid methyl-(3-methyl-butyl)-amide 255

Following Example 216, to a well stirred solution of 8-(1H-Pyrazol-4-yl)-4,5-dihydro-6-oxa-3-thia-1-aza-benzo[e]azulene-2-carboxylic acid and N,3-dimethylbutan-1-amine to give 255. MS: (ESI+)=397.1

Example 256

8-(1H-Pyrazol-4-yl)-4,5-dihydro-6-oxa-3-thia-1-aza-benzo[e]azulene-2-carboxylic acid (1,1-dioxo-tetrahydro-thiophen-3-yl)-methyl-amide 256

Following Example 216, to a well stirred solution of 8-(1H-Pyrazol-4-yl)-4,5-dihydro-6-oxa-3-thia-1-aza-benzo[e]azulene-2-carboxylic acid and N-(1,1-dioxidotetrahydrothien-3-yl)-N-methylamine to give 256. MS: (ESI+)=445.1

Example 257

8-(1H-Pyrazol-4-yl)-4,5-dihydro-6-oxa-3-thia-1-aza-benzo[e]azulene-2-carboxylic acid methyl-(1-methyl-pyrrolidin-3-yl)-amide 257

Following Example 216, to a well stirred solution of 8-(1H-Pyrazol-4-yl)-4,5-dihydro-6-oxa-3-thia-1-aza-benzo[e]azulene-2-carboxylic acid and 1-methylpyrrolidin-3-amine to give 257. MS: (ESI+)=410.1

Example 258

2-(4-{2-[2-(2,4-Difluoro-phenyl)-2H-[1,2,4]triazol-3-yl]-4,5-dihydro-6-oxa-3-thia-1-aza-benzo[e]azulen-8-yl}-pyrazol-1-yl)-ethanol 258

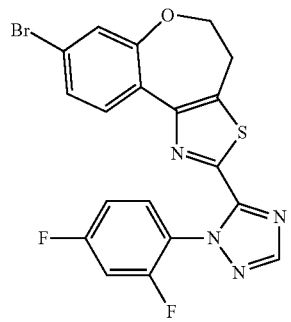 [SMILES: Fc1ccc(-n2ncnc2-c2nc3c(s2)CCOc2cc(Br)ccc2-3)c(F)c1]

To a microwave vial was added 8-Bromo-2-[2-(2,4-difluoro-phenyl)-2H-[1,2,4]triazol-3-yl]-4,5-dihydro-6-oxa-3-thia-1-aza-benzo[e]azulene (0.300 g, 0.000650 mol) and potassium acetate (0.1915 g, 0.001951 mol) in acetonitrile (1 mL, 0.02 mol) and water (2 mL, 0.1 mol). The reaction was thoroughly degassed and purged with $N_2$ for 5 minutes. A solution of 1-[2-(Tetrahydro-pyran-2-yloxy)-ethyl]-4-(4,4,5,5-tetramethyl-[1,3,2]dioxaborolan-2-yl)-1H-pyrazole (0.2724 g, 0.0008455 mol) in acetonitrile (1 mL, 0.02 mol) was added, followed by tetrakis(triphenylphosphine)palladium(0) (0.07515 g, 6.504E-5 mol) and the vial was sealed immediately. The reaction was heated to 140° C. for 20 minutes in the microwave. The mixture was diluted with methylene chloride and filtered through celite. Saturated $NH_4Cl$ was added and the mixture was extracted 3 times with methylene chloride. The organic layers were combined, dried with $MgSO_4$ and concentrated. The crude was dissolved in methylene chloride (7 mL, 0.1 mol) and hydrogen chloride (4N in dioxoane, 0.38 mL, 0.001517 mol) was added dropwise. The reaction was stirred at room temperature for 1 hour.

The mixture was concentrated and partitioned between saturated sodium bicarbonate and methylene chloride and extracted 3 times with methylene chloride. The organic phases were combined, dried with $MgSO_4$, and concentrated. The crude was purified by reverse-phase HPLC to give 258 (156.6 mg) as a solid. MS(ESI+) 493.1. $^1$H NMR (400 MHz, DMSO) δ 8.42 (s, 1H), 8.20 (s, 1H), 7.90 (s, 1H), 7.89-7.83 (m, 1H), 7.76-7.65 (m, 1H), 7.44-7.36 (m, 2H), 7.22 (d, J=1.5, 1H), 7.12 (dd, J=8.3, 1.6, 1H), 4.89 (t, J=5.3, 1H), 4.33 (t, J=4.8, 2H), 4.15 (t, J=5.6, 2H), 3.76 (q, J=5.5, 2H), 3.41 (t, J=4.9, 2H)

Example 259

2-(2-Isopropyl-2H-[1,2,4]triazol-3-yl)-8-(1-methanesulfonyl-azetidin-3-yl)-4,5-dihydro-6-oxa-3-thia-1-aza-benzo[e]azulene 259

Following the procedure for 395, 8-azetidin-3-yl-2-(2-isopropyl-2H-[1,2,4]triazol-3-yl)-4,5-dihydro-6-oxa-3-thia-1-aza-benzo[e]azulene hydrochloride salt and methanesulfonyl chloride were reacted. The reaction mixture was loaded directly onto a silica column with no aqueous work-up to give 259 isolated as a white solid (67 mg, 84%). LCMS: $R_T$=10.97 min, $[M+H]^+$=446. $^1$H NMR δ (ppm) (CDCl$_3$): 8.36 (1H, d, J=8.20 Hz), 7.90 (1H, d, J=0.68 Hz), 7.16 (1H, dd, J=8.24, 1.88 Hz), 7.02 (1H, d, J=1.85 Hz), 5.93-5.83 (1H, m), 4.42-4.36 (2H, m), 4.30-4.22 (2H, m), 4.10-4.03 (2H, m), 3.83-3.73 (1H, m), 3.43-3.37 (2H, m), 2.90 (3H, s), 1.61 (6H, d, J=6.63 Hz)

Example 260

(3-Methylamino-pyrrolidin-1-yl)-[8-(1H-pyrazol-4-yl)-4,5-dihydro-6-oxa-3-thia-1-aza-benzo[e]azulen-2-yl]-methanone 260

Following Example 216, to a well stirred solution of 8-(1H-Pyrazol-4-yl)-4,5-dihydro-6-oxa-3-thia-1-aza-benzo[e]azulene-2-carboxylic acid and N-methylpyrrolidin-3-amine to give 260. MS: (ESI+)=396.1

Example 261

[1,4]Diazepan-1-yl-[8-(1H-pyrazol-4-yl)-4,5-dihydro-6-oxa-3-thia-1-aza-benzo[e]azulen-2-yl]-methanone 261

Following Example 216, to a well stirred solution of 8-(1H-Pyrazol-4-yl)-4,5-dihydro-6-oxa-3-thia-1-aza-benzo[e]azulene-2-carboxylic acid and 1,4-diazepane to give 261. MS: (ESI+)=382.1

Example 262

Piperazin-1-yl-[8-(1H-pyrazol-4-yl)-4,5-dihydro-6-oxa-3-thia-1-aza-benzo[e]azulen-2-yl]-methanone 262

Following Example 216, to a well stirred solution of 8-(1H-Pyrazol-4-yl)-4,5-dihydro-6-oxa-3-thia-1-aza-benzo[e]azulene-2-carboxylic acid and piperazine to give 262. MS: (ESI+)=382.1

Example 263

1-[8-(1H-Pyrazol-4-yl)-4,5-dihydro-6-oxa-3-thia-1-aza-benzo[e]azulene-2-carbonyl]-piperidine-3-carboxylic acid 263

Following Example 216, to a well stirred solution of 8-(1H-Pyrazol-4-yl)-4,5-dihydro-6-oxa-3-thia-1-aza-benzo[e]azulene-2-carboxylic acid and piperidine-3-carboxylic acid to give 263. MS: (ESI+)=396.1

Example 264

(3-Methyl-piperazin-1-yl)-[8-(1H-pyrazol-4-yl)-4,5-dihydro-6-oxa-3-thia-1-aza-benzo[e]azulen-2-yl]-methanone 264

Following Example 216, to a well stirred solution of 8-(1H-Pyrazol-4-yl)-4,5-dihydro-6-oxa-3-thia-1-aza-benzo[e]azulene-2-carboxylic acid and 2-methylpiperazine to give 264. MS: (ESI+)=396.1

Example 265

2-(2-Isopropyl-2H-[1,2,4]triazol-3-yl)-9-(2-trifluoromethyl-pyridin-3-yl)-4,5-dihydro-6-oxa-3-thia-1-aza-benzo[e]azulene 265

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 2-(trifluoromethyl)pyridin-3-ylboronic acid were reacted to give 265 (0.058 g, 25%). $^1$H NMR (400 MHz, DMSO) δ 9.30 (d, J=2.2, 1H), 8.28 (d, J=8.0, 1H), 8.19 (t, J=7.9, 1H), 8.12 (s, 1H), 8.04 (dd, J=8.5, 2.3, 1H), 7.82 (t, J=17.9, 1H), 7.23 (d, J=8.5, 1H), 5.93 (dt, J=13.2, 6.7, 1H), 4.45 (t, J=4.9, 2H), 3.50 (t, J=4.8, 2H), 1.57 (d, J=6.6, 6H). MS (ESI(+)): m/z 458.1 (M+H)

Example 266

2-(2-Isopropyl-2H-[1,2,4]triazol-3-yl)-9-(4-methoxy-pyridin-3-yl)-4,5-dihydro-6-oxa-3-thia-1-aza-benzo[e]azulene 266

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 4-methoxypyridin-3-ylboronic acid were reacted to give 266 (0.045 g, 28%). $^1$H NMR (400 MHz, CDCl$_3$) δ 8.61 (d, J=2.1, 1H), 8.50 (d, J=6.0, 2H), 7.92 (s, 1H), 7.46 (dd, J=8.3, 2.2, 1H), 7.15 (d, J=8.4, 1H), 6.93 (d, J=5.7, 1H), 5.84 (dt, J=13.3, 6.6, 1H), 4.46 (t, J=5.0, 2H), 3.91 (s, 3H), 3.45 (t, J=5.0, 2H), 1.59 (d, J=6.7, 6H). MS (ESI(+)): m/z 420.1 (M+H)

Example 267

8-(6-Morpholin-4-yl-pyridin-3-yl)-4,5-dihydro-6-oxa-3-thia-1-aza-benzo[e]azulene-2-carboxylic acid (2-hydroxyethyl)-isopropylamide 267

To a microwave vial was added 8-Bromo-4,5-dihydro-6-oxa-3-thia-1-aza-benzo[e]azulene-2-carboxylic acid (2-hydroxyethyl)-isopropylamide (0.100 grams, 0.243 mmol) in 2M sodium carbonate (0.500 mL) and ACN (0.636 mL), and then 4-(2-(5-(4,4,5,5-tetramethyl-1,3,2-dioxaborolan-2-yl)pyridin-2-yl)ethyl)morpholine (0.292 mmol) was added. This solution was degassed by bubbling nitrogen through the solution for several minutes. Finally, palladium tetrakis (triphenylphosphine)palladium(0) was added and the vial was tightly capped. The reaction mixture was then flash heated on a Biotage microwave at 140° C. for 20 minutes. The cooled reaction mixture was diluted with EtOAc and the organic was washed with water, then saline and dried (Na2SO4) before concentration to a solid. The crude material was purified by preparative RP-HPLC to give 267. MS: (ESI+)=495.1

Example 268

8-(1-Methyl-1H-pyrazol-4-yl)-4,5-dihydro-6-oxa-3-thia-1-aza-benzo[e]azulene-2-carboxylic acid (2-hydroxy-ethyl)-isopropyl-amide 268

Following Example 267, 8-Bromo-4,5-dihydro-6-oxa-3-thia-1-aza-benzo[e]azulene-2-carboxylic acid (2-hydroxyethyl)-isopropylamide and 1-methyl-4-(4,4,5,5-tetramethyl-1,3,2-dioxaborolan-2-yl)-1H-pyrazole were reacted to give 268. MS: (ESI+)=413.1

Example 269

8-[1-(2-Morpholin-4-yl-ethyl)-1H-pyrazol-4-yl]-4,5-dihydro-6-oxa-3-thia-1-aza-benzo[e]azulene-2-carboxylic acid (2-hydroxy-ethyl)-isopropyl-amide 269

Following Example 267, 8-Bromo-4,5-dihydro-6-oxa-3-thia-1-aza-benzo[e]azulene-2-carboxylic acid (2-hydroxyethyl)-isopropylamide and 4-(2-(4-(4,4,5,5-tetramethyl-1,3,2-dioxaborolan-2-yl)-1H-pyrazol-1-yl)ethyl)morpholine were reacted to give 269. MS: (ESI+)=512.2

Example 270

8-[2-(4-Methyl-piperazin-1-yl)-pyrimidin-5-yl]-4,5-dihydro-6-oxa-3-thia-1-aza-benzo[e]azulene-2-carboxylic acid (2-hydroxy-ethyl)-isopropyl-amide 270

Following Example 267, 8-Bromo-4,5-dihydro-6-oxa-3-thia-1-aza-benzo[e]azulene-2-carboxylic acid (2-hydroxyethyl)-isopropylamide and 2-(4-methylpiperazin-1-yl)-5-(4,4,5,5-tetramethyl-1,3,2-dioxaborolan-2-yl)pyrimidine to give 270. MS: (ESI+)=509.2

Example 271

2-[2-(2,4-Difluoro-phenyl)-2H-[1,2,4]triazol-3-yl]-9-(2-methoxy-pyridin-3-yl)-4,5-dihydro-6-oxa-1-thia-10-aza-benzo[e]azulene 271

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 2-Methoxy-3-(4,4,5,5-tetramethyl-[1,3,2]dioxaborolan-2-yl)-pyridine (282 mg, 1.2 mmol), Cs$_2$CO$_3$ (650 mg, 2.0 mmol), Pd(dppf)Cl$_2$ (73 mg, 0.10 mmol) and CH$_3$CN—H$_2$O (1:1, 4 mL) were added in a 10 mL of sealed tube, and the mixture was heated by microwave at 120° C. for 20 min under N$_2$. The reaction mixture was filtered to gather the solution and water was added. The mixture was extracted by DCM (20 mL×3). The combined organic layers were dried over Na$_2$SO$_4$, concentrated in vacuo, and purified by preparative HPLC to give 271 (270 mg, yield: 46%). $^1$HNMR (DMSO-d$_6$, 400 MHz): δ8.30-8.26 (m, 2H), 8.15 (d, J=6.8 Hz, 1H), 7.94 (d, J=8.4 Hz, 2H), 7.92 (t, J=9.2 Hz, 1H), 7.29-7.18 (m, 2H), 4.33 (s, 2H), 3.96 (s, 3H), 3.16 (s, 2H). ESI-MS: m/z=490 [M+H]$^+$

Example 272

4-{2-[2-(2,4-Difluoro-phenyl)-2H-[1,2,4]triazol-3-yl]-4,5-dihydro-6-oxa-1-thia-10-aza-benzo[e]azulen-9-yl}-2-methyl-butan-2-ol 272

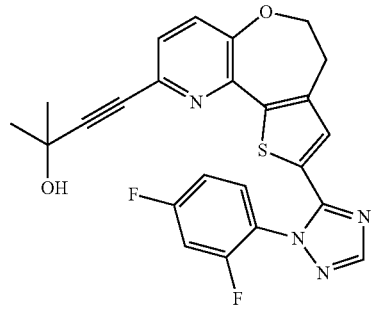 [SMILES: CC(C)(O)C#Cc1ccc2c(n1)-c1sc(-c3ncnn3-c3ccc(F)cc3F)cc1CCO2]

Following the procedures for 246, 4-{2-[2-(2,4-Difluoro-phenyl)-2H-[1,2,4]triazol-3-yl]-4,5-dihydro-6-oxa-1-thia-10-aza-benzo[e]azulen-9-yl}-2-methyl-but-3-yn-2-ol was prepared (Yield: 69%. $^1$H NMR (DMSO-d$_6$, 400 MHz): δ8.30 (s, 1H), 7.93-7.877 (m, 1H), 7.74-7.68 (m, 1H), 7.43-7.37 (m, 2H), 7.29 (d, J=8.4 Hz, 1H), 6.99 (s, 1H), 5.60 (s, 1H), 4.30 (t, J=4.4 Hz, 2H), 3.12 (t, J=4.4 Hz, 2H), 1.21 (s, 6H). ESI-MS: (m/z)=465 [M+H]$^+$) from 9-Chloro-2-[2-(2,4-difluoro-phenyl)-2H-[1,2,4]triazol-3-yl]-4,5-dihydro-6-oxa-1-thia-10-aza-benzo[e]azulene and 2-methylbut-3-yn-2-ol, and hydrogenated to give 272 Yield: 37%. $^1$H NMR (DMSO-d$_6$, 400 MHz): δ8.26 (s, 1H), 7.90-7.84 (m, 1H), 7.69-7.63 (m, 1H), 7.39-7.34 (m, 1H), 7.27 (d, J=8.0 Hz, 1H), 7.06-7.03 (m, 2H), 4.22 (t, J=4.8 Hz, 2H), 3.08 (t, J=4.8 Hz, 2H), 2.68-2.63 (m, 2H), 1.69-1.64 (m, 2H), 1.10 (s, 6H). LC-MS (ESI): m/z=469[M+H]$^+$

Example 273

(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-(2-morpholin-4-yl-ethyl)-amine 273

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), (2-Morpholin-4-yl-ethyl)-[5-(4,4,5,5-tetramethyl-[1,3,2]dioxaborolan-2-yl)-pyridin-2-yl]-amine (400 mg, 1.2 mmol), Cs$_2$CO$_3$ (650 mg, 2.0 mmol), Pd(dppf)Cl$_2$ (73 mg, 0.10 mmol) and CH$_3$CN—H$_2$O (1:1, 4 mL) were added in a 10 mL of sealed tube, and the mixture was heated by microwave at 120° C. for 20 min under N$_2$. The reaction mixture was filtered to gather the solution and water was added. The mixture was extracted by DCM (20 mL×3). The combined organic layers were dried over Na$_2$SO$_4$, concentrated in vacuo, and purified by preparative HPLC to give 273 (97.5 mg, yield: 17%). $^1$HNMR (DMSO-d$_6$, 400 MHz): δ8.61 (s, 1H), 8.27 (s, 1H), 8.09 (s, 1H), 7.91-7.87 (m, 2H), 7.67-7.67 (m, 2H), 7.37-7.35 (m, 2H), 7.16 (s, 2H), 7.21 (s, 1H), 6.85 (s, 1H), 6.60 (d, J=8.8 Hz, 2H), 4.27 (s, 2H), 3.28 (s, 6H), 3.32 (s, 4H), 3.11 (s, 4H). ESI-MS: m/z=588 [M+H]$^+$

Example 274

(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-(2-methanesulfonyl-ethyl)-amine 274

2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo[e]azulene (470 mg, 1.0 mmol), from the procedure for 249, 2-Methanesulfonylethylamine (147, 1.2 mmol), DIPEA (340 mg, 3 mmol) and NMP (4 mL) were added in a 10 mL of sealed tube, and the mixture was heated by microwave at 150° C. for 120 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 274 (23.7 mg, yield: 4.1%). $^1$HNMR (DMSO-$d_6$, 400 MHz): δ8.77 (s, 1H), 8.38 (s, 1H), 8.04-8.00 (m, 2H), 7.84-7.77 (m, 2H), 7.29 (s, 2H), 6.77 (d, J=8.8 Hz, 1H), 4.37 (s, 2H), 3.88-3.81 (m, 2H), 3.50-3.47 (m, 2H), 3.23-3.21 (m, 2H), 3.10 (s, 3H). ESI-MS: m/z=581 [M+H]$^+$

Example 275

{2-[2-(2,4-Difluoro-phenyl)-2H-[1,2,4]triazol-3-yl]-4,5-dihydro-6-oxa-1-thia-10-aza-benzo[e]azulen-9-yl}-(2-methoxy-ethyl)-amine 275

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (20 mg, 0.1 mmol), 2-Methoxy-ethylamine (147 mg, 1.44 mmol), X-phos (70 mg, 0.144 mmol), tert-butoxide (140 mg, 1.44 mmol) in dioxane (2 mL) was bubbled $N_2$ for 10 min and then stirred at 120° C. for 2.5 min under the irradition of microwave. The mixture was filtered over ceilite. The filtrate was concentrated to dryness and purified by pre-HPLC to afford 110 mg of 275. (yield=34%). $^1$H NMR (CDCl$_3$, 400 MHz): δ8.10 (s, 1H), 7.61-7.54 (m, 1H), 7.14-7.06 (m, 4H), 6.30 (d, J=8.8 Hz, 1H), 4.62-4.58 (m, 1H), 4.25-4.24 (m, 2H), 3.60-3.58 (m, 2H), 3.52-3.48 (m, 2H), 3.41 (s, 3H), 3.13-3.10 (m, 2H). LC-MS (ESI): m/z=456 [M+H]$^+$

Example 276

{2-[2-(2,4-Difluoro-phenyl)-2H-[1,2,4]triazol-3-yl]-4,5-dihydro-6-oxa-1-thia-10-aza-benzo[e]azulen-9-yl}-isopropyl-amine 276

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (20 mg, 0.1 mmol), isopropylamine (80 mg, 1.44 mmol), X-phos (70 mg, 0.144 mmol), tert-butoxide (140 mg, 1.44 mmol) in dioxane (2 mL) was bubbled $N_2$ for 10 min and then stirred at 120° C. for 5 min under the irradition of microwave. The mixture was filtered over celite. The filtrate was concentrated to dryness and purified by pre-HPLC to afford 80 mg of 276 (yield=25%). $^1$H NMR (CDCl$_3$, 400 MHz) δ: 8.01 (s, 1H), 7.50-7.44 (m, 1H), 7.18-7.15 (m, 1H), 7.09-6.99 (m, 3H), 6.13 (d, J=8.8 Hz, 1H), 4.19-4.14 (m, 2H), 3.96-3.80 (m, 2H), 3.45-3.41 (m, 1H), 3.06-3.04 (m, 2H), 3.18-3.12 (m, 6H). LC-MS (ESI): m/z=439 [M+H]$^+$

Example 277

9-[1-(2-Hydroxy-ethyl)-1H-pyrazol-4-yl]-4,5-dihydro-6-oxa-3-thia-1-aza-benzo[e]azulene-2-carboxylic acid (2-hydroxy-ethyl)-isopropyl-amide 277

9-Bromo-4,5-dihydro-6-oxa-3-thia-1-aza-benzo[e]azulene-2-carboxylic acid (2-hydroxy-ethyl)-isopropyl-amide (57 mg, 0.138 mmol), 1-(2-(tetrahydro-2H-pyran-2yloxy)ethyl)-4-(4,4,5,5-tetramethyl-1,3,2-dioxaborolan-2-yl)-1H-pyrazole (67 mg, 0.208 mmol), Tetrakis(triphenylphosphine) palladium(0) (16 mg, 0.0138 mmol), 1.5 mL 1 M potassium acetate in water, and 1.5 mL acetonitrile were combined in a microwave vial and placed on the CEM microwave for 20 minutes at 140° C. Complete reaction by LCMS. Diluted reaction with 2 M HCl and extracted product with ethyl acetate. Some of the THP group fell off during work-up. The final Intermediate was in the ethyl acetate layer, which was dried over magnesium sulfate and concentrated in vacuo. Flash purified 0 to 10% MeOH in dichloromethane and again concentrated in vacuo. The THP intermediate was deprotected with 1 M HCl in dioxane (5 mL0 over 72 hours). Complete deprotection by LCMS. Concentrated in vacuo and purified by HPLC to give 277 (3.8 mg, 6% yield, M+1 443.1)

Example 278

9-(2-Amino-4-methyl-pyrimidin-5-yl)-4,5-dihydro-6-oxa-3-thia-1-aza-benzo[e]azulene-2-carboxylic acid (2-hydroxy-ethyl)-isopropyl-amide 278

Following the procedure for 277, 9-Bromo-4,5-dihydro-6-oxa-3-thia-1-aza-benzo[e]azulene-2-carboxylic acid (2-hydroxy-ethyl)-isopropyl-amide (52.2 mg, 0.127 mmol) and 4-methyl-5-(4,4,5,5-tetramethyl-1,3,2-dioxaborolan-2-yl)pyrimidin-2-amine (35.8 mg, 0.152 mmol) were reacted to give 278 (0.6 mg, 1% yield M+1 440.1)

Example 279

9-(6-Amino-pyridin-3-yl)-4,5-dihydro-6-oxa-3-thia-1-aza-benzo[e]azulene-2-carboxylic acid (2-hydroxy-ethyl)-isopropyl-amide 279

Following the procedure for 277, 9-Bromo-4,5-dihydro-6-oxa-3-thia-1-aza-benzo[e]azulene-2-carboxylic acid (2-hydroxy-ethyl)-isopropyl-amide (52.5 mg, 0.128 mmol) and 5-(4,4,5,5-tetramethyl-1,3,2-dioxaborolan-2-yl)pyridin-2-amine (33.7 mg, 0.153 mmol) were reacted to give 279 (7.2 mg, 13% yield, M+1 425.1).

Example 280

9-(4-Methyl-pyridin-3-yl)-4,5-dihydro-6-oxa-3-thia-1-aza-benzo[e]azulene-2-carboxylic acid (2-hydroxy-ethyl)-isopropyl-amide 280

Following the procedure for 277, 9-Bromo-4,5-dihydro-6-oxa-3-thia-1-aza-benzo[e]azulene-2-carboxylic acid (2-hydroxy-ethyl)-isopropyl-amide (52.3 mg, 0.127 mmol) and 4-methylpyridin-3-ylboronic acid (21.0 mg, 0.153 mmol) were reacted to give 280 (4.3 mg, 8% yield, M+1 424.1).

Example 281

9-(2-Amino-pyrimidin-5-yl)-4,5-dihydro-6-oxa-3-thia-1-aza-benzo[e]azulene-2-carboxylic acid (2-hydroxy-ethyl)-isopropyl-amide 281

Following the procedure for 277, 9-Bromo-4,5-dihydro-6-oxa-3-thia-1-aza-benzo[e]azulene-2-carboxylic acid (2-hydroxy-ethyl)-isopropyl-amide (53.4 mg, 0.130 mmol) and 5-(4,4,5,5-tetramethyl-1,3,2-dioxaborolan-2-yl)pyrimidin-2-amine (34.4 mg, 0.156 mmol) were reacted to give 281 (6.6 mg, 12% yield, M+1 426.1)

Example 282

9-(6-Methylamino-pyridin-3-yl)-4,5-dihydro-6-oxa-3-thia-1-aza-benzo[e]azulene-2-carboxylic acid (2-hydroxy-ethyl)-isopropyl-amide 282

Following the procedure for 277, 9-Bromo-4,5-dihydro-6-oxa-3-thia-1-aza-benzo[e]azulene-2-carboxylic acid (2-hydroxy-ethyl)-isopropyl-amide (52.9 mg, 0.129 mmol) and tert-butyl methyl(5-(4,4,5,5-tetramethyl-1,3,2-dioxaborolan-2-yl)pyridine-2-yl)carbamate (51.6 mg, 0.154 mmol) were reacted to give 282, purified by HPLC (1.4 mg, 2.5% yield, M+1 439.1).

Example 283

9-(2-Ethoxy-pyridin-3-yl)-2-(2-isopropyl-2H-[1,2,4]triazol-3-yl)-4,5-dihydro-6-oxa-3-thia-1-aza-benzo[e]azulene 283

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 2-ethoxypyridin-3-yl-boronic acid were reacted to give 283 (0.045 g, 27%). $^1$H NMR (400 MHz, CDCl$_3$) δ 8.62 (d, J=2.2, 1H), 8.15 (dd, J=4.9, 1.8, 1H), 7.92 (s, 1H), 7.65 (dd, J=7.3, 1.8, 1H), 7.55 (dt, J=11.2, 5.6, 1H), 7.13 (d, J=8.4, 1H), 7.02-6.93 (m, 1H), 5.84 (dt, J=13.2, 6.6, 1H), 4.55-4.39 (m, 4H), 3.45 (t, J=5.0, 2H), 1.59 (d, J=6.6, 6H), 1.38 (t, J=7.0, 3H). MS (ESI(+)): m/z 434.1 (M+H)

Example 284

[2-(2-Isopropyl-2H-[1,2,4]triazol-3-yl)-4,5-dihydro-6-oxa-3-thia-1-aza-benzo[e]azulen-8-ylmethyl]-isoxazol-3-yl-amine 284

Following the procedure for 119, 2-(2-isopropyl-2H-[1,2,4]triazol-3-yl)-4,5-dihydro-6-oxa-3-thia-1-aza-benzo[e]azulene-8-carbaldehyde and 3-amino-isoxazole were reacted. Purification by flash chromatography (SiO$_2$, 0-20% EtOAc in DCM) gave 284 as a white solid (154 mg, 52%). LCMS: R$_T$=10.79 min, [M+H]$^+$=409. $^1$H NMR δ (ppm) (CDCl$_3$): 8.33 (1H, d, J=8.10 Hz), 8.04 (1H, d, J=1.68 Hz), 7.90 (1H, s), 7.16 (1H, d, J=8.19 Hz), 7.06 (1H, s), 5.93-5.84 (1H, m), 5.85-5.83 (1H, m), 4.42 (2H, s), 4.38 (2H, t, J=5.02 Hz), 3.42-3.36 (2H, m), 1.60 (6H, d, J=6.62 Hz). 1 Exchangeable proton not seen.

Example 285

2-{[2-(2-Isopropyl-2H-[1,2,4]triazol-3-yl)-4,5-dihydro-6-oxa-3-thia-1-aza-benzo[e]azulen-8-ylmethyl]-amino}-ethanol 285

Following the procedure for 212, 2-(2-isopropyl-2H-[1,2,4]triazol-3-yl)-4,5-dihydro-6-oxa-3-thia-1-aza-benzo[e]azulene-8-carbaldehyde and ethanolamine were reacted to give 285 isolated as a pale yellow solid (131 mg, 47%). LCMS: R$_T$=6.85 min, [M+H]$^+$=386. $^1$H NMR δ (ppm) (CDCl$_3$): 8.31 (1H, d, J=8.11 Hz), 7.89 (1H, s), 7.12 (1H, d, J=8.19 Hz), 7.02 (1H, s), 5.93-5.82 (1H, m), 4.37 (2H, t, J=5.06 Hz), 3.81 (2H, s), 3.66 (2H, t, J=5.12 Hz), 3.38 (2H, t, J=5.06 Hz), 2.81 (2H, t, J=5.11 Hz), 1.60 (6H, d, J=6.63 Hz). 2 Exchangeable protons not seen.

Example 286

1-[2-(2-Isopropyl-2H-[1,2,4]triazol-3-yl)-4,5-dihydro-6-oxa-3-thia-1-aza-benzo[e]azulen-8-yl]-ethane-1,2-diol 286

A solution of 2-(2-Isopropyl-2H-[1,2,4]triazol-3-yl)-8-vinyl-4,5-dihydro-6-oxa-3-thia-1-aza-benzo[e]azulene (1.28 mmol) in acetone, THF and water (15 mL, 1:1:1) was treated with N-methylmorpholine-N-oxide (299 mg, 2.56 mmol) then potassium osmate dihydrate (14 mg, 0.04 mmol). The reaction mixture was stirred at room temperature overnight. Solid sodium sulfite was added and the reaction mixture was extracted with EtOAc. The combined organics were dried over sodium sulfate, concentrated and the residue purified by reverse phase HPLC to give 286 as a colorless solid (222 mg, 46%). LCMS: 373.1. $^1$H NMR (400 MHz, DMSO) δ 8.28 (d, J=8.2 Hz, 1H), 8.09 (s, 1H), 7.16 (d, J=8.1 Hz, 1H), 7.04 (s, 1H), 5.82 (dt, J=13.3, 6.5 Hz, 1H), 5.26 (d, J=4.4 Hz, 1H), 4.70 (t, J=5.8 Hz, 1H), 4.54 (dd, J=10.4, 5.6 Hz, 1H), 4.36 (t, J=5.0 Hz, 2H), 3.53-3.35 (m, 4H), 1.55 (d, J=6.6 Hz, 6H)

Example 287

2-{4-[2-(2-Isopropyl-5-methyl-2H-[1,2,4]triazol-3-yl)-4,5-dihydro-6-oxa-3-thia-1-aza-benzo[e]azulen-8-yl]-pyrazol-1-yl}-ethanol 287

Similarly to as described in General Procedure C: 8-Bromo-2-(2-isopropyl-5-methyl-2H-[1,2,4]triazol-3-yl)-4,5-dihydro-6-oxa-3-thia-1-aza-benzo[e]azulene was reacted with 1-(2-(tetrahydro-2H-pyran-2-yloxy)ethyl)-4-(4,4,5,5-tetramethyl-1,3,2-dioxaborolan-2-yl)-1H-pyrazole. Subsequent to the Suzuki coupling, deprotection of the tetrahydropyranyl ether was accomplished by adding 2N HCl to the crude reaction mixture. Purification by reverse phase HPLC gave 287 as a colorless solid (53 mg). LCMS: 437.1.

Example 288

2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-isobutyramide 288

Following the procedure for 240, 2-Methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propionic acid was reacted with ammonium chloride to give 288. MS(ESI+) 504.1. $^1$H NMR (400 MHz, DMSO) δ 8.44 (s, 1H), 8.3-8.25 (m, 2H), 8.04 (s, 1H), 7.51 (dd, J=8.3, 1.5, 1H), 7.40 (d, J=1.4, 1H), 7.16 (br, 1H), 6.77 (br, 1H), 5.86 (q, J=8.7, 2H), 4.40 (t, J=4.9, 2H), 3.47 (t, J=4.9, 2H), 1.74 (s, 6H)

Example 289

8-(1H-Pyrazol-4-yl)-4,5-dihydro-6-oxa-3-thia-1-aza-benzo[e]azulene-2-carboxylic acid cyclopentyl-(2-hydroxy-ethyl)-amide 289

Following Example 216, to a well stirred solution of 8-(1H-Pyrazol-4-yl)-4,5-dihydro-6-oxa-3-thia-1-aza-benzo[e]azulene-2-carboxylic acid and 2-(cyclopentylamino)ethanol to give 289. MS: (ESI+)=425.1

Example 290

8-(1H-Pyrazol-4-yl)-4,5-dihydro-6-oxa-3-thia-1-aza-benzo[e]azulene-2-carboxylic acid (3-hydroxy-propyl)-isopropyl-amide 290

Following Example 216, to a well stirred solution of 8-(1H-Pyrazol-4-yl)-4,5-dihydro-6-oxa-3-thia-1-aza-benzo[e]azulene-2-carboxylic acid and 3-(isopropylamino)propan-1-ol to give 290. MS: (ESI+)=413.1

Example 291

8-(3,5-Dimethyl-isoxazol-4-yl)-4,5-dihydro-6-oxa-3-thia-1-aza-benzo[e]azulene-2-carboxylic acid (2-hydroxy-ethyl)-isopropyl-amide 291

Following Example 267, 8-Bromo-4,5-dihydro-6-oxa-3-thia-1-aza-benzo[e]azulene-2-carboxylic acid (2-hydroxyethyl)-isopropylamide and 3,5-dimethyl-4-(4,4,5,5-tetramethyl-1,3,2-dioxaborolan-2-yl)isoxazole to give 291. MS: (ESI+)=428.1

Example 292

1-{2-[2-(2,2,2-Trifluoro-ethyl)-2H-[1,2,4]triazol-3-yl]-4,5-dihydro-6-oxa-3-thia-1-aza-benzo[e]azulen-8-yl}-ethanol 292

To a solution of 1-{2-[2-(2,2,2-Trifluoro-ethyl)-2H-[1,2,4]triazol-3-yl]-4,5-dihydro-6-oxa-3-thia-1-aza-benzo[e]azulen-8-yl}-ethanone (0.2357 g, 0.0005976 mol) in ethanol (2.5 mL, 0.043 mol) was added sodium tetrahydroborate (0.02713 g, 0.0007172 mol). The reaction was stirred at room temperature for 5 hours. The reaction was quenched with 2N HCl and diluted with water. Ethyl acetate was added and the aqueous layer was extracted 3× with ethyl acetate. The organic phases were combined, dried with $MgSO_4$, and concentrated. The crude was purified by reverse-phase HPLC to give 292 (74.8 mg) as a white solid. MS(ESI+) 397.0. $^1$H NMR (400 MHz, DMSO) δ 8.28 (s, 1H), 8.25 (d, J=8.2, 1H), 7.16 (dd, J=8.2, 1.1, 1H), 7.05 (m, 1H), 5.85 (q, J=8.7, 2H), 5.19 (d, J=4.4, 1H), 4.79-4.63 (m, 1H), 4.36 (t, J=5.0, 2H), 3.45 (t, J=5.0, 2H), 1.34 (d, J=6.4, 3H)

Example 293

1-{2-[2-(2,4-Difluoro-phenyl)-2H-[1,2,4]triazol-3-yl]-4,5-dihydro-6-oxa-1-thia-10-aza-benzo[e]azulen-9-ylamino}-propan-2-ol 293

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (20 mg, 0.1 mmol) 2-Trimethylsilanyloxy-propylamine (211 mg, 1.44 mmol), X-phos (70 mg, 0.144 mmol), tert-butoxide (140 mg, 1.44 mmol) in dioxane (2 mL) was bubbled N$_2$ for 10 min and then stirred at 125° C. for 7 min under the irradition of microwave. The mixture was filtered over ceilite. The filtrate was concentrated to dryness and purified by pre-TLC (EtOAc/hexanes=2:1) to afford 110 mg of 293. (yield=34%). $^1$H NMR (CDCl$_3$, 400 MHz): δ8.01 (s, 1H), 7.50-7.45 (m, 1H), 7.06-6.98 (m, 4H), 6.23 (d, J=8.8 Hz, 1H), 4.54-4.50 (m, 1H), 4.17-4.15 (m, 2H), 3.98-3.94 (m, 1H), 3.44-3.40 (m, 1H), 3.15-3.00 (m, 3H), 1.21-1.17 (m, 3H). LC-MS (ESI): m/z=456 [M+H]$^+$

Example 294

2-[2-(2,4-Difluoro-phenyl)-2H-[1,2,4]triazol-3-yl]-9-(6-pyrrolidin-1-yl-pyridin-3-yl)-4,5-dihydro-6-oxa-1-thia-10-aza-benzo[e]azulene 294

2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo[e]azulene, from the procedure for 249, (470 mg, 1.0 mmol), Pyrrolidine (85 mg, 1.2 mmol), DIPEA (340 mg, 3 mmol) and NMP (4 mL) were added in a 10 mL of sealed tube, and the mixture was heated by microwave at 150° C. for 120 min under N$_2$. The reaction mixture was filtered to gather the solution and water was added. The mixture was extracted by DCM (20 mL×3). The combined organic layers were dried over Na$_2$SO$_4$, concentrated in vacuo, and purified by preparative HPLC to give 294 (31.3 mg, yield: 5.9%). $^1$HNMR (DMSO-d$_6$, 400 MHz): δ8.81 (s, 1H), 8.38 (s, 1H), 8.12 (d, J=8.8 Hz, 1H), 7.98-7.97 (m, 1H), 7.78-7.77 (m, 1H), 7.76-7.78 (m, 2H), 7.46-7.40 (m, 1H), 7.38 (d, J=8.4 Hz, 1H), 7.51 (t, J=8.8 Hz, 1H), 7.48 (t, J=4.4 Hz, 1H), 7.26 (s, 1H), 6.60 (d, J=8.8 Hz, 1H), 4.38 (s, 2H), 3.54 (s, 3H), 3.22 (s, 2H), 2.07 (s, 4H). ESI-MS: m/z=529 [M+H$^+$]

Example 295

5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-ol 295

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 5-(4,4,5-Trimethyl-[1,3,2]dioxaborolan-2-yl)-pyridin-2-ol (268 mg, 1.2 mmol), Cs$_2$CO$_3$ (650 mg, 2.0 mmol), Pd(dppf)Cl$_2$ (73 mg, 0.10 mmol) and CH$_3$CN—H$_2$O (1:1, 4 mL) were added in a 10 mL of sealed tube, and the mixture was heated by microwave at 120° C. for 20 min under N$_2$. The reaction mixture was filtered to gather the solution and water was added. The mixture was extracted by DCM (20 mL×3). The combined organic layers were dried over Na$_2$SO$_4$, concentrated in vacuo, and purified by preparative HPLC to give 295 (34.7 mg, yield: 7.1%). $^1$HNMR (DMSO-d$_6$, 400 MHz): δ8.30 (s, 1H), 8.10 (s, 1H), 7.98-7.92 (m, 2H), 7.78 (t, J=4.8 Hz, 1H), 7.67 (d, J=8.8 Hz, 1H), 7.49 (t, J=8.8 Hz, 1H), 7.20 (s, 1H), 6.43 (d, J=8.8 Hz, 1H), 4.29 (s, 2H), 3.14 (s, 2H), ESI-MS: m/z=475 [M+H$^+$]

Example 296

N'-(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-N,N-dimethyl-ethane-1,2-diamine 296

2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo

[e]azulene (470 mg, 1.0 mmol), from the procedure for 249, 2-(N,N-Dimethyl)-ethylamine (90 mg, 1.2 mmol), DIPEA (340 mg, 3 mmol) and NMP (4 mL) were added in a 10 mL of sealed tube, and the mixture was heated by microwave at 150° C. for 120 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 296 (69 mg, yield: 13%). $^1$HNMR (DMSO-$d_6$, 400 MHz): δ9.50 (s, 1H), 8.72 (s, 1H), 8.31 (s, 1H), 7.97-7.91 (m, 2H), 7.77-7.72 (m, 2H), 7.48-7.43 (m, 2H), 7.15 (s, 1H), 6.99 (s, 1H), 6.72 (d, J=4.4 Hz, 1H), 4.31 (s, 2H), 3.86 (s, 2H), 3.33 (s, 2H), 3.33 (s, 2H), 3.15 (s, 2H), 2.75 (s, 6H). ESI-MS: m/z=546 [M+H$^+$]

Example 297

2-[5-Amino-2-(2,4-difluoro-phenyl)-2H-[1,2,4]triazol-3-yl]-4,5-dihydro-6-oxa-1-thia-benzo[e]azulene-8-carboxylic acid oxetan-3-ylamide 297

Similarly to as described in General Procedure D, 2-[5-Amino-2-(2,4-difluoro-phenyl)-2H-[1,2,4]triazol-3-yl]-4,5-dihydro-6-oxa-1-thia-benzo[e]azulene-8-carboxylic acid was reacted with 3-aminooxetane hydrochloride to give 297 as a colorless solid after reverse phase HPLC (146 mg). LCMS: 496.1

Example 298

9-(2-Methyl-pyridin-3-yl)-4,5-dihydro-6-oxa-3-thia-1-aza-benzo[e]azulene-2-carboxylic acid (2-hydroxy-ethyl)-isopropyl-amide 298

Following the procedure for 277, 9-Bromo-4,5-dihydro-6-oxa-3-thia-1-aza-benzo[e]azulene-2-carboxylic acid (2-hydroxy-ethyl)-isopropyl-amide (53.4 mg, 0.130 mmol) and 2-methylpyridin-3-ylboronic acid (21.3 mg, 0.156 mmol) were reacted to give 298 (9.2 mg, 17% yield, M+1 424.1)

Example 299

9-(2-Methoxy-pyridin-3-yl)-4,5-dihydro-6-oxa-3-thia-1-aza-benzo[e]azulene-2-carboxylic acid (2-hydroxy-ethyl)-isopropyl-amide 299

Following the procedure for 277, 9-Bromo-4,5-dihydro-6-oxa-3-thia-1-aza-benzo[e]azulene-2-carboxylic acid (2-hydroxy-ethyl)-isopropyl-amide (52.2 mg, 0.127 mmol) and 2-methoxypyridin-3-ylboronic acid (23.3 mg, 0.152 mmol) were reacted to give 299 (4.0 mg, 7% yield, M+1 440.1).

Example 300

8-(1H-Pyrazol-4-yl)-4,5-dihydro-6-oxa-3-thia-1-aza-benzo[e]azulene-2-carboxylic acid ((S)-1-hydroxymethyl-3-methyl-butyl)-amide 300

Following Example 216, to a well stirred solution of 8-(1H-Pyrazol-4-yl)-4,5-dihydro-6-oxa-3-thia-1-aza-benzo[e]azulene-2-carboxylic acid and (S)-3-amino-5-methylhexan-1-ol to give 300. MS: (ESI+)=413.1

Example 301

9-(1-Benzenesulfonyl-1H-pyrazol-4-yl)-2-(2-isopropyl-2H-[1,2,4]triazol-3-yl)-4,5-dihydro-6-oxa-3-thia-1-aza-benzo[e]azulene 301

9-Bromo-2-(2-isopropyl-2H-[1,2,4]triazol-3-yl)-4,5-dihydro-6-oxa-3-thia-1-aza-benzo[e]azulene from Example 6 and 1-(phenylsulfonyl)-4-(4,4,5,5-tetramethyl-1,3,2-dioxaborolan-2-yl)-1H-pyrazole were reacted under palladium Suzuki conditions to give 301 (39% yield). LC/MS (ESI+): m/z 519 (M+H). $^1$H NMR (400 MHz, DMSO) δ 8.85 (s, 1H), 8.62 (d, J=2.1, 1H), 8.28 (s, 1H), 8.11 (s, 1H), 8.03 (d, J=7.6, 2H), 7.81 (t, J=7.5, 1H), 7.75-7.60 (m, 3H), 7.12 (d, J=8.4, 1H), 5.82 (dt, J=13.0, 6.6, 1H), 4.39 (t, J=4.8, 2H), 3.46 (t, J=4.9, 2H), 1.59 (d, J=6.6, 6H)

Example 302

2-{4-[2-(2-Pyridin-4-ylmethyl-2H-[1,2,4]triazol-3-yl)-4,5-dihydro-6-oxa-3-thia-1-aza-benzo[e]azulen-8-yl]-pyrazol-1-yl}-ethanol 302

Similarly to as described in General Procedure C: 8-Bromo-2-(2-pyridin-4-ylmethyl-2H-[1,2,4]triazol-3-yl)-4,5-dihydro-6-oxa-3-thia-1-aza-benzo[e]azulene was reacted with ethyl 2-(4-(4,4,5,5-tetramethyl-1,3,2-dioxaborolan-2-yl)-1H-pyrazol-1-yl)acetate. The crude ester was reduced with lithium aluminum hydride as described for 2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-ethanol. The product was purified by HPLC to give 302 as a colorless solid (32 mg). LCMS: 472.1.

Example 303

2-(4-{2-[2-(1-Methyl-piperidin-4-yl)-2H-[1,2,4]triazol-3-yl]-4,5-dihydro-6-oxa-3-thia-1-aza-benzo[e]azulen-8-yl}-pyrazol-1-yl)-ethanol 303

Similarly to as described in General Procedure C: 8-Bromo-2-[2-(1-methyl-piperidin-4-yl)-2H-[1,2,4]triazol-3-yl]-4,5-dihydro-6-oxa-3-thia-1-aza-benzo[e]azulene was reacted with ethyl 2-(4-(4,4,5,5-tetramethyl-1,3,2-dioxaborolan-2-yl)-1H-pyrazol-1-yl)acetate. The crude ester was reduced with lithium aluminum hydride as described for 2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-ethanol. The product was purified by HPLC to give 303 as a colorless solid (27 mg). LCMS: 478.2.

Example 304

2-(1-Isopropyl-1H-imidazol-2-yl)-9-(2-methyl-pyridin-3-yl)-4,5-dihydro-6-oxa-1-thia-10-aza-benzo[e]azulene 304

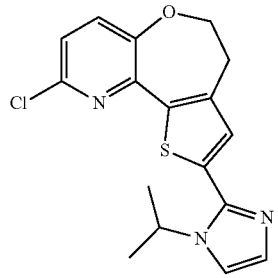 [SMILES: CC(C)n1ccnc1-c1cc2c(s1)-c1nc(Cl)ccc1OCC2]

To a solution of 9-Chloro-2-(1-isopropyl-1H-imidazol-2-yl)-4,5-dihydro-6-oxa-1-thia-10-aza-benzo[e]azulene (63 mg, 0.18 mmol), Potassium acetate (60.2 mg, 0.613 mmol), 2-methylpyridine-3-boronic acid, (32.2 mg, 0.235 mmol) and Tetrakis(triphenylphosphine)palladium(0) (28 mg, 0.024 mmol) in Acetonitrile (2 mL, 30 mmol) and Water (2 mL, 100 mmol) was degassed. The reaction was heated in the microwave at 140° C. for 20 minutes. The reaction was cooled to r.t., then extract with ethyl acetate. The combined organics were concentrated and purified by reverse phase HPLC to give 304. MS: (ESI+)=403.1. $^1$H NMR (400 MHz, DMSO) δ 8.55-8.47 (m, 1H), 7.86 (d, J=7.7 Hz, 1H), 7.54 (d, J=8.3 Hz, 1H), 7.50-7.43 (m, 2H), 7.36 (dd, J=7.7, 4.9 Hz, 1H), 7.29 (s, 1H), 7.00 (s, 1H), 4.82 (dt, J=13.3, 6.5 Hz, 1H), 4.43 (t, J=4.6 Hz, 2H), 2.65 (s, 3H), 1.44 (d, J=6.6 Hz, 6H).

Example 305

2-(2-Isopropyl-2H-[1,2,4]triazol-3-yl)-9-(6-methoxy-pyridin-3-yl)-4,5-dihydro-6-oxa-3-thia-1-azabenzo[e]azulene 305

Following the procedure for 128, 9-Bromo-2-(2-isopropyl-2H-[1,2,4]triazol-3-yl)-4,5-dihydro-6-oxa-3-thia-1-azabenzo[e]azulene from Example 6 and 6-methoxypyridin-3-ylboronic acid were reacted to give 305 (0.027 g, 17%). $^1$H NMR (400 MHz, DMSO) δ 8.62 (d, J=2.3, 1H), 8.48 (d, J=2.0, 1H), 8.11 (s, 1H), 7.99 (dd, J=8.6, 2.5, 1H), 7.60 (dd, J=8.4, 2.3, 1H), 7.18 (d, J=8.4, 1H), 6.96 (d, J=8.6, 1H), 5.77 (dt, J=13.3, 6.8, 1H), 4.42 (t, J=4.9, 2H), 3.91 (s, 3H), 3.48 (t, J=4.8, 2H), 1.57 (d, J=6.6, 6H). MS (ESI(+)): m/z 420.1 (M+H)

Example 306

9-(2-Fluoro-pyridin-3-yl)-2-(2-isopropyl-2H-[1,2,4]triazol-3-yl)-4,5-dihydro-6-oxa-3-thia-1-aza-benzo[e]azulene 306

Following the procedure for 128, 9-Bromo-2-(2-isopropyl-2H-[1,2,4]triazol-3-yl)-4,5-dihydro-6-oxa-3-thia-1-azabenzo[e]azulene from Example 6 and 2-fluoropyridin-3-ylboronic acid were reacted to give 306. MS (ESI(+)): m/z 408.1 (M+H).

Example 307

4,5-Dihydro-6-oxa-1-thia-benzo[e]azulene-2,8-dicarboxylic acid 2-{[2-chloro-5-(4-methyl-piperazine-1-carbonyl)-phenyl]-methyl-amide}8-methylamide 307

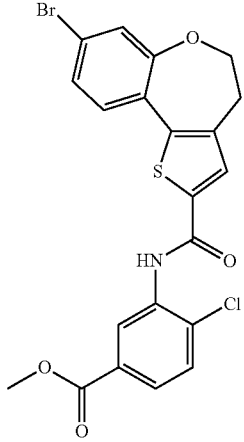 [SMILES: COC(=O)c1ccc(Cl)c(NC(=O)c2cc3c(s2)-c2ccc(Br)cc2OCC3)c1]

A solution of 8-bromo-4,5-dihydro-6-oxa-1-thia-benzo[e]azulene-2-carboxylic acid (25 g, 0.077 mol) in 200 mL of SOCl$_2$ was heated at 80° C. for 3 h. Concentration gave the crude acid chloride. A suspension of the crude acid chloride (ca. 0.077 mol) from above in 1000 mL of THF at 0° C. was treated with a solution of 3-amino-4-chloro-benzoic acid methyl ester (15.7 g, 1.1 eq)/pyridine (30 mL) in 100 mL of THF. The mixture was allowed to reach room temperature overnight. The reaction solution was concentrated to 1/2 volume, diluted with water. The resulting precipitate was filtered, washed with water and Et$_2$O. The filter cake was dried to a constant weight under vacuum to give methyl 3-(8-bromo-4,5-dihydrobenzo[b]thieno[2,3-d]oxepine-2-carboxamido)-4-chlorobenzoate (32.9 g, yield 87%). LC-MS: (ESI, m/z)=494 [M+1]$^+$

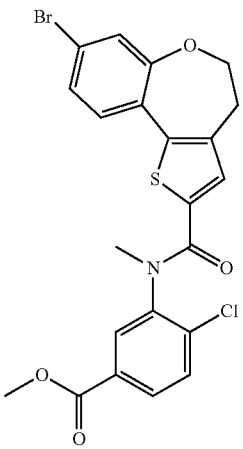 [SMILES: COC(=O)c1ccc(Cl)c(N(C)C(=O)c2cc3c(s2)-c2ccc(Br)cc2OCC3)c1]

To a solution of methyl 3-(8-bromo-4,5-dihydrobenzo[b]thieno[2,3-d]oxepine-2-carboxamido)-4-chlorobenzoate (32 g, 65 mmol) and Cs$_2$CO$_3$ (42.4 g, 130 mmol) in DMF (500 mL) was added CH$_3$I (12 mL, 195 mmol). The reaction mixture was stirred at room temperature overnight. Then it was concentrated to remove the DMF, and water was added into the mixture. The resulting precipitate was filtrated, washed by water, and dried to give methyl 3-(8-bromo-N-methyl-4,5-dihydrobenzo[b]thieno[2,3-d]oxepine-2-carboxamido)-4-chlorobenzoate (31 g, 94%)$^1$H NMR (CDCl$_3$, 400 MHz): δ8.07-7.08 (m, 6H, ArH), 6.81 (s, 1H, =CH), 4.22 (t, J=5.2 Hz, 2H, CH$_2$), 3.94 (s, 3H, OCH$_3$), 3.40 (s, 3H, NCH$_3$), 3.01 (t, J=5.2 Hz, 2H, CH$_2$)

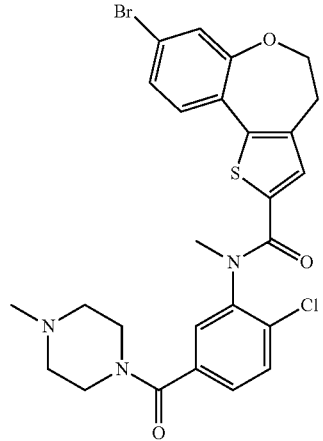 [SMILES: CN1CCN(C(=O)c2ccc(Cl)c(N(C)C(=O)c3cc4c(s3)-c3ccc(Br)cc3OCC4)c2)CC1]

To a suspension of methyl 3-(8-bromo-N-methyl-4,5-dihydrobenzo[b]thieno[2,3-d]oxepine-2-carboxamido)-4- chlorobenzoate (31 g, 61 mmol) in THF (200 mL) and H$_2$O (100 mL) was added LiOH.H$_2$O (6.42 g, 153 mmol). The reaction mixture was stirred at room temperature overnight. Then it was acidified with 2N HCl to pH 2-3, and concentrated to remove most of solvent. The resulting precipitate was washed by water, dried to give the carboxylic acid, 3-(8-bromo-N-methyl-4,5-dihydrobenzo[b]thieno[2,3-d]oxepine-2-carboxamido)-4-chlorobenzoic acid (27.3 g, 91%). LC-MS: (ESI, m/z)=494 [M+1]$^+$ To a mixture of 1-methyl-piperazine (1.22 g, 12.18 mmol), DIPEA (3 mL), HATU (2.78 g, 7.31 mmol) in THF (60 mL) was added 3-(8-bromo-N-methyl-4,5-dihydrobenzo[b]thieno[2,3-d]oxepine-2-carboxamido)-4-chlorobenzoic acid (3.0 g, 6.09 mmol) under nitrogen atmosphere at room temperature. The reaction mixture was stirred overnight, diluted with water, extracted with EtOAc. The organic layer was dried over Na$_2$SO$_4$, concentrated in vacuo to give 8-bromo-N-(2-chloro-5-(4-methylpiperazine-1-carbonyl)phenyl)-N-methyl-4,5-dihydrobenzo[b]thieno[2,3-d]oxepine-2-carboxamide (3.3 g, yield 94%) $^1$H NMR (DMSO-d6, 400 MHz): δ7.74-7.21 (m, 6H, ArH), 6.67 (s, 1H, =CH), 4.18 (t, J=4.4 Hz, 2H, CH$_2$), 3.31-2.12 (m, 16H, CH$_3$, CH$_2$)

A suspension of 8-bromo-N-(2-chloro-5-(4-methylpiperazine-1-carbonyl)phenyl)-N-methyl-4,5-dihydrobenzo[b]thieno[2,3-d]oxepine-2-carboxamide (500 mg, 0.87 mmol), Pd(OAc)$_2$ (10 mg, 0.0435 mmol), Xantphos (50 mg, 0.087 mmol), MeNH$_2$.HCl (88 mg, 1.30 mmol) and Na$_2$CO$_3$ (277 mg, 2.61 mmol) in toluene (10 mL) was heated at 80° C. under atmosphere of CO from balloon for overnight, filtrated and concentrated. The crude product was purified by flash column chromatography on silica gel (DCM/MeOH=40:1-20:1 as eluted solvent) to give 307 (148.6 mg, yield 31%). $^1$H NMR (CDCl$_3$, 400 MHz): δ7.60-6.94 (m, 7H, NH, ArH), 6.23 (s, 1H, =CH), 4.23 (t, J=4.8 Hz, 2H, CH$_2$), 3.79-2.09 (m, 19H, CH$_3$, CH$_2$). LC-MS: (ESI, m/z)=553 [M+1]$^+$ Example 308

4,5-Dihydro-6-oxa-1-thia-benzo[e]azulene-2,8-dicarboxylic acid 2-{[2-chloro-5-(4-methyl-piperazine-1-carbonyl)-phenyl]-methyl-amide} 8-[(2-methanesulfonyl-ethyl)-amide] 308

A suspension of 8-bromo-N-(2-chloro-5-(4-methylpiperazine-1-carbonyl)phenyl)-N-methyl-4,5-dihydrobenzo[b]thieno[2,3-d]oxepine-2-carboxamide (500 mg, 0.87 mmol), Pd(OAc)$_2$ (10 mg, 0.0435 mmol), Xantphos (50 mg, 0.087 mmol), MeSO$_2$(CH$_2$)$_2$NH$_2$.HCl (207 mg, 1.30 mmol) and Na$_2$CO$_3$ (277 mg, 2.61 mmol) in toluene (10 mL) was heated at 80° C. under atmosphere of CO from balloon for overnight. The mixture was filtered, concentrated, and the crude product purified by flash column chromatography on silica gel (DCM/MeOH=40:1-20:1 as eluted solvent) to give 308 (289.2 mg, yield 52%). $^1$HNMR(CDCl$_3$, 400 MHz): δ 7.60-6.97 (m, 8H, ArH), 4.23 (t, J=4.8 Hz, 2H, CH$_2$), 4.01-2.17 (m, 23H, CH$_3$, CH$_2$). LC-MS: (ESI, m/z)=645 [M+1]$^+$ Example 309

2-[2-(2,4-Difluoro-phenyl)-2H-[1,2,4]triazol-3-yl]-9-[4-(2,2,2-trifluoro-ethyl)-piperazin-1-yl]-4,5-dihydro-6-oxa-1-thia-10-aza-benzo[e]azulene 309

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd(OAc)$_2$ (20 mg, 0.1 mmol), 1-(2,2,2-Trifluoro-ethyl)-piperazine (175 mg, 1.44 mmol), X-phos (70 mg, 0.144 mmol), tert-butoxide (140 mg, 1.44 mmol) in dioxane (2 mL) was bubbled N$_2$ for 10 min and then stirred at 125° C. for 9 min under the irradition of microwave. The mixture was filtered over ceilite. The filtrate was concentrated to dryness and purified by pre-HPLC to afford 110 mg of 309. (yield=28%). $^1$H NMR (CDCl$_3$, 400 MHz): δ8.08 (s, 1H), 7.57-7.51 (m, 1H), 7.16-7.06 (m, 4H), 6.52 (d, J=8.8 Hz, 1H), 4.25-4.23 (m, 2H), 3.47-3.44 (m, 4H), 3.12-3.02 (m, 4H), 2.80-2.77 (m, 4H). LC-MS (ESI): m/z=549 [M+H]$^+$ Example 310

9-(2,5-Diaza-bicyclo[2.2.1]hept-2-yl)-2-[2-(2,4-difluoro-phenyl)-2H-[1,2,4]triazol-3-yl]-4,5-dihydro-6-oxa-1-thia-10-aza-benzo[e]azulene 310

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), Pd(OAc)$_2$ (22.4 mg, 0.1 mmol), 2,5-Diaza-bicyclo[2.2.1]heptane (120 mg, 1.2 mmol), X-phos (47 mg, 0.10 mmol), tert-butoxide (200 mg, 20 mmol) in dioxane (2 mL) was bubbled N$_2$ for 10 min and then stirred at 120° C. for 6 min under the irradition of microwave. The mixture was filtered over ceilite. The filtrate was concentrated to dryness and purified by pre-HPLC to afford 310. (61.4 mg, yield=13%). $^1$H NMR (CDCl$_3$, 400 MHz): δ 8.27 (s, 1H), 7.89-7.88 (m, 1H), 7.72-7.99 (m, 1H), 7.41-7.39 (m, 1H), 7.28-7.16 (m, 2H), 6.39 (d, J=8.8 Hz, 1H), 4.41 (s, 1H), 4.16 (s, 2H), 3.46-3.41 (m, 6H), 2.74 (s, 2H), 1.06 (t, J=6.8 Hz, 2H). LC-MS (ESI): m/z=479 [M+H]$^+$ Example 311

1-(5-{2-[2-(2,4-Difluoro-phenyl)-2H-[1,2,4]triazol-3-yl]-4,5-dihydro-6-oxa-1-thia-10-aza-benzo[e]azulen-9-yl}-2,5-diaza-bicyclo[2.2.1]hept-2-yl)-ethanone 311

Compound 310 (479 mg, 1.0 mmol), Acetyl chloride (100 mg, 1.2 mmol), DIPEA (260 mg, 2.0 mmol) was dissolved in THF (10 mL). The reaction mixture was stirred at r.t. for 1 hour. LC-MS indicated the reaction was completed. To the reaction mixture was added 20 mL of water, the mixture was extracted with dichloromethane. The organic layer was dried over anhydrous sodium sulfate, and concentrated to dryness. The crude was purified by pre-HPLC to afford 311 (78.1 mg, yield: 15%). $^1$HNMR (DMSO-d$_6$, 400 MHz): δ8.27 (s, 1H), 7.91-7.90 (m, 1H), 7.74 (s, 1H), 7.43-7.39 (m, 1H), 7.23-7.20 (m, 2H), 6.48 (t, J=4.4 Hz, 1H), 4.77 (s, 2H), 3.53 (s, 2H), 3.53-3.32 (m, 4H), 3.19 (s, 2H), 1.96 (s, 3H), 1.23 (s, 2H). ESI-MS: m/z=521 [M+H$^+$]

Example 312

1-((2R,6S)-4-{2-[2-(2,4-Difluoro-phenyl)-2H-[1,2,4]triazol-3-yl]-4,5-dihydro-6-oxa-1-thia-10-aza-benzo[e]azulen-9-yl}-2,6-dimethyl-piperazin-1-yl)-ethanone 312

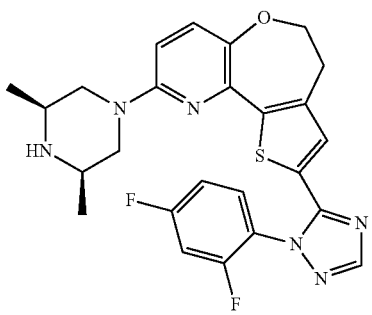 [SMILES: C[C@@H]1CN(c2ccc3c(n2)-c2sc(-c4ncnn4-c4ccc(F)cc4F)cc2CCO3)C[C@H](C)N1]

To a mixture of 2-[2-(2,4-Difluoro-phenyl)-2H-[1,2,4]triazol-3-yl]-9-((3R,5S)-3,5-dimethyl-piperazin-1-yl)-4,5-dihydro-6-oxa-1-thia-10-aza-benzo[e]azulene (150 mg, 0.3 mmol), potassium carbonate (84 mg, 0.6 mmol) in DMF (5 mL) was added acetic anhydride (0.3 mL) at −15° C. The mixture was slowly warmed to room temperature and stirred for 30 min. The reaction mixture was added 30 mL of water. The solid was collected to give 100 mg of 312. Yield=62%. $^1$H NMR (CDCl$_3$, 400 MHz): δ8.03 (s, 1H), 7.51-7.46 (m, 1H), 7.19-7.00 (m, 4H), 6.50 (d, J=8.8 Hz, 1H), 4.19 (t, J=4.4 Hz, 2H), 3.66-3.65 (m, 2H), 3.07 (t, J=4.8 Hz, 2H), 0.93-2.89 (m, 2H), 2.13 (s, 3H), 2.03 (s, 2H), 1.29-1.24 (m, 6H). ESI-MS: m/z=537 [M+H$^+$]

Example 313

2-[2-(2,4-Difluoro-phenyl)-2H-[1,2,4]triazol-3-yl]-9-((3R,5S)-3,4,5-trimethyl-piperazin-1-yl)-4,5-dihydro-6-oxa-1-thia-10-aza-benzo[e]azulene 313

To a mixture of 2-[2-(2,4-Difluoro-phenyl)-2H-[1,2,4]triazol-3-yl]-9-((3R,5S)-3,5-dimethyl-piperazin-1-yl)-4,5-dihydro-6-oxa-1-thia-10-aza-benzo[e]azulene (100 mg, 0.2 mmol), Cesium carbonate (131 mg, 0.4 mmol) in N,N-dimethylformamide (5 mL) was added CH$_3$I (0.025 mL, 0.4 mmol) at −15° C. The mixture was slowly warmed to room temperature and stirred for about 30 min. The reaction mixture was added 30 mL of water. The solid was collected to give 70 mg of 313. Yield=60%. $^1$H NMR (CDCl$_3$, 400 MHz): δ8.02 (s, 1H), 7.51-7.46 (m, 1H), 7.11-6.97 (m, 4H), 6.46 (d, J=8.8 Hz, 1H), 4.18 (t, J=4.8 Hz, 2H), 3.85 (d, J=13.6 Hz, 2H), 3.08 (t, J=4.8 Hz, 2H), 2.59 (t, J=7.2 Hz, 2H), 2.26-2.19 (m, 4H), 1.14 (d, J=6.8 Hz, 6H). ESI-MS: m/z=509 [M+H$^+$]

Example 314

2-[2-(2,4-Difluoro-phenyl)-2H-[1,2,4]triazol-3-yl]-9-((3R,5S)-4-ethyl-3,5-dimethyl-piperazin-1-yl)-4,5-dihydro-6-oxa-1-thia-10-aza-benzo[e]azulene 314

A mixture of 2-[2-(2,4-Difluoro-phenyl)-2H-[1,2,4]triazol-3-yl]-9-((3R,5S)-3,5-dimethyl-piperazin-1-yl)-4,5-dihydro-6-oxa-1-thia-10-aza-benzo[e]azulene (150 mg, 0.3 mmol), 1-Bromo-2-fluoro-ethane (65 mg, 0.45 mmol) and Cesium carbonate (200 mg, 0.6 mmol) in N,N-Dimethylformamide (2 mL) was stirred at 120° C. for 1 h under the irradiation of microwave. The reaction mixture was filtered over celite and purified by pre-TLC (Hexanes/EtOAc=1:1) to afford 314 Yield=56%. $^1$H NMR (CDCl$_3$, 400 MHz): δ8.02 (s, 1H), 7.49-7.46 (m, 1H), 7.11-6.97 (m, 4H), 6.45 (d, J=8.8 Hz, 1H), 4.18 (t, J=4.8 Hz, 2H), 3.86 (d, J=11.6 Hz, 2H), 3.07 (t, J=4.8 Hz, 2H), 2.96 (q, J$_1$=7.2 Hz, J$_2$=5.2 Hz, 2H), 2.64-2.51 (m, 4H), 1.13 (d, J=6.0 Hz, 6H), 0.88-0.81 (m, 3H). ESI-MS: m/z=523 [M+H$^+$]

Example 315

2-[2-(2,4-Difluoro-phenyl)-2H-[1,2,4]triazol-3-yl]-9-[(3R,5S)-4-(2-fluoro-ethyl)-3,5-dimethyl-piperazin-1-yl]-4,5-dihydro-6-oxa-1-thia-10-aza-benzo[e]azulene 315

A mixture of 2-[2-(2,4-Difluoro-phenyl)-2H-[1,2,4]triazol-3-yl]-9-((3R,5S)-3,5-dimethyl-piperazin-1-yl)-4,5-dihydro-6-oxa-1-thia-10-aza-benzo[e]azulene (150 mg, 0.3 mmol), 1-Bromo-2-fluoro-ethane (65 mg, 0.45 mmol) and Cesium carbonate (200 mg, 0.6 mmol) in N,N-Dimethylformamide (2 mL) was stirred at 120° C. for 1 h under the irradiation of microwave. The reaction mixture was filtered over celite and purified by pre-TLC (Hexanes/EtOAc=1:1) to afford 45 mg of 315 (yield: 28%). $^1$H NMR (CDCl$_3$, 400 MHz): δ8.23 (s, 1H), 7.51-7.46 (m, 1H), 7.10-6.93 (m, 4H), 6.46 (d, J=8.8 Hz, 1H), 4.52 (t, J=5.6 Hz, 2H), 4.40 (t, J=5.6 Hz, 2H), 4.18 (t, J=4.8 Hz, 2H), 3.85-3.82 (m, 2H), 3.07-2.94 (m, 4H), 2.70 (d, J=6.0 Hz, 2H), 2.55-2.49 (m, 2H), 1.22-1.34 (d, J=6.0 Hz, 6H). LC-MS (ESI): m/z=541 [M+H]$^+$

Example 316

1-((2R,6S)-4-{2-[2-(2,4-Difluoro-phenyl)-2H-[1,2,4]triazol-3-yl]-4,5-dihydro-6-oxa-1-thia-10-aza-benzo[e]azulen-9-yl}-2,6-dimethyl-piperazin-1-yl)-2,2,2,-trifluoro-ethanone 316

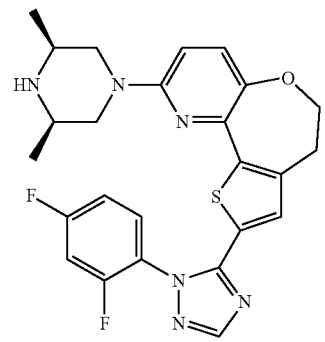 [SMILES: C[C@@H]1CN(c2ccc3c(n2)-c2sc(-c4ncnn4-c4ccc(F)cc4F)cc2CCO3)C[C@H](C)N1]

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), (2S,6R)-2,6-dimethylpiperazine (164 mg, 1.44 mmol), $^t$BuONa (47 mg, 0.48 mmol), Pd(OAc)$_2$ (49 mg, 0.3 mmol) and 2,8,9-tributyl-2,5,8,9-tetraaza-1-phosphabicyclo[3.3.3]undecane (99 mg, 0.29 mmol), in dioxane (2 mL) was bubbled N$_2$ for 10 min and then stirred at 120° C. for 1 h under the irradition of microwave. The mixture was filtered by celite. The filtrate was concentrated to dryness and purified by pre-TLC(EtOAc) to afford 220 mg of 2-[2-(2,4-Difluoro-phenyl)-2H-[1,2,4]triazol-3-yl]-9-((3R,5S)-3,5-dimethyl-piperazin-1-yl)-4,5-dihydro-6-oxa-1-thia-10-aza-benzo[e]azulene. (Yield: 62%) $^1$H NMR (DMSO, 400 MHz): δ8.28 (s, 1H), 8.22 (s, 1H), 7.94-7.88 (m, 1H), 7.72-7.67 (m, 1H), 7.40 (d, J=2.4 Hz, 1H), 7.24 (t, J=2.4 Hz, 1H), 6.79 (d, J=8.8 Hz, 1H), 4.20 (t, J=4.4 Hz, 2H), 3.99 (q, J=2.4, 12.8 Hz, 2H), 3.12 (t, J=4.8 Hz, 2H), 2.87-2.82 (m, 2H), 1.10 (d, J=6.0 Hz, 6H). LC-MS (ESI): m/z=495 [M+H]$^+$ A mixture of 2-[2-(2,4-Difluoro-phenyl)-2H-[1,2,4]triazol-3-yl]-9-((3R,5S)-3,5-dimethyl-piperazin-1-yl)-4,5-dihydro-6-oxa-1-thia-10-aza-benzo[e]azulene (150 mg, 0.3 mmol), potassium carbonate (84 mg, 0.6 mmol) was suspended in N,N-dimethylformamide (5 mL). The mixture was stirred at −15° C. for 10 min and added 2,2,2-trifluoroacetic anhydride dropwise. The mixture was slowly warmed to room temperature and stirred for about 30 min. The reaction mixture was added 30 ml of water. The solid was collected to get 142 mg of 316. (HPLC purity: 95%) $^1$H NMR (CDCl$_3$, 400 MHz): δ8.04 (s, 1H), 7.52-7.47 (m, 1H), 7.19-7.00 (m, 4H), 6.50 (m, J=8.8 Hz, 1H), 4.62 (s, 1H), 4.23-3.88 (m, 5H), 3.07-2.89 (m, 4H), 1.36-1.31 (m, 6H). LC-MS (ESI): m/z=591 [M+H]$^+$ Example 318

(R)-2-Hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-propan-1-one 318

To a suspension of 8-azetidin-3-yl-2-(2-isopropyl-2H-[1,2,4]triazol-3-yl)-4,5-dihydro-6-oxa-3-thia-1-aza-benzo[e]azulene TFA salt 235 (200 mg, 0.42 mmol) in THF (3 mL) was added diisopropylethylamine (0.22 mL, 1.26 mmol), HATU (175 mg, 0.46 mmol) and D-(−)-lactic acid (41 mg, 0.46 mmol). The reaction mixture was stirred at RT for 18 hours and then concentrated in vacuo. The resultant residue was partitioned between DCM and an aqueous saturated sodium bicarbonate solution and the organic layer was washed with water followed by brine, dried (Na$_2$SO$_4$) and concentrated in vacuo. The resultant residue was purified by flash chromatography (SiO$_2$, 0-5% MeOH in DCM) to give a cream solid that was freeze-dried from methanol and water to give 318 as a white solid (59 mg, 32%). LCMS: R$_T$=4.44 min, [M+H]$^+$=440. $^1$H NMR δ (ppm) (DMSO-d6): 8.30 (1H, d, J=8.19 Hz), 8.05 (1H, s), 7.18 (1H, ddd, J=8.24, 4.14, 1.84 Hz), 7.01 (1H, s), 5.82-5.72 (1H, m), 5.04 (1H, s), 4.65-4.55 (1H, m), 4.35-4.29 (2H, m), 4.28-4.17 (2H, m), 4.11 (1H, dd, J=13.38, 6.69 Hz), 3.86-3.75 (2H, m), 3.42-3.36 (2H, m), 1.50 (6H, d, J=6.59 Hz), 1.16 (3H, d, J=6.70 Hz)

Example 319

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-acetamide 319

To a suspension of 8-azetidin-3-yl-2-(2-isopropyl-2H-[1,2,4]triazol-3-yl)-4,5-dihydro-6-oxa-3-thia-1-aza-benzo[e]azulene TFA salt 235 (200 mg, 0.42 mmol) in THF (3 mL) was added potassium carbonate (174 mg, 1.26 mmol) and 2-bromoacetamide (63 mg, 0.46 mmol) and the reaction mixture was stirred at RT for 18 hours. The volatiles were evaporated in vacuo and the residue partitioned between DCM and an aqueous saturated sodium bicarbonate solution. The organic layer was washed with water followed by brine, dried (MgSO$_4$), concentrated in vacuo and the residue purified by flash chromatography (SiO$_2$, 0-5% MeOH in DCM) to give 319 isolated as a cream solid after freeze drying from methanol and water (40 mg, 22%). LCMS: R$_T$=3.03 min, [M+H]$^+$ =425. $^1$H NMR δ (ppm) (DMSO-d6): 8.26 (1H, d, J=8.18 Hz), 8.05 (1H, s), 7.20 (1H, dd, J=8.24, 1.83 Hz), 7.08 (1H, s), 7.00 (2H, d, J=1.87 Hz), 5.83-5.73 (1H, m), 4.34-4.28 (2H, m), 3.69-3.62 (2H, m), 3.63-3.52 (1H, m), 3.41-3.35 (2H, m), 3.21-3.14 (2H, m), 2.99 (2H, s), 1.50 (6H, d, J=6.59 Hz)

Example 320

2-(2-Isopropyl-2H-[1,2,4]triazol-3-yl)-8-[1-(2-methanesulfonyl-ethyl)-azetidin-3-yl]-4,5-dihydro-6-oxa-3-thia-1-aza-benzo[e]azulene 320

To a solution of 8-azetidin-3-yl-2-(2-isopropyl-2H-[1,2,4]triazol-3-yl)-4,5-dihydro-6-oxa-3-thia-1-aza-benzo[e]azulene TFA salt 235 (200 mg, 0.42 mmol) in IMS (industrial methylated spirits, 3 mL) was added triethylamine (0.20 mL, 1.47 mmol) and methyl vinyl sulfone (0.09 mL, 1.05 mmol) and the reaction mixture was stirred at RT (room temperature) for 18 hours. The reaction mixture was concentrated in vacuo and the residue purified by flash chromatography (SiO$_2$, 0-5% MeOH in DCM). Freeze-drying from methanol and water gave 320 as a pale yellow solid (135 mg, 68%). LCMS: R$_T$=3.10 min, [M+H]$^+$=474. $^1$H NMR δ (ppm) (DMSO-d6): 8.35 (1H, d, J=8.19 Hz), 8.11 (1H, s), 7.29 (1H, d, J=8.27 Hz), 7.20 (1H, s), 5.85-5.76 (1H, m), 4.41-4.35 (3H, m), 4.14 (3H, d, J=59.98 Hz), 3.68 (2H, s), 3.53-3.41 (3H, m), 3.13 (3H, s), 1.55 (6H, d, J=6.60 Hz). 2 Protons obscured by water peak Example 321

2-(2-Isopropyl-2H-[1,2,4]triazol-3-yl)-8-[1-(propane-2-sulfonyl)-azetidin-3-yl]-4,5-dihydro-6-oxa-3-thia-1-aza-benzo[e]azulene 321

Following the procedure for 395, 8-azetidin-3-yl-2-(2-isopropyl-2H-[1,2,4]triazol-3-yl)-4,5-dihydro-6-oxa-3-thia-1-aza-benzo[e]azulene free base 235, diisopropylethylamine and isopropylsulfonyl chloride were reacted. The reaction mixture was loaded directly onto a silica column with no aqueous work-up to give 321 isolated as a solid (57 mg, 25%). LCMS: R$_T$=12.20 min, [M+H]$^+$=474. $^1$H NMR δ (ppm) (CDCl$_3$): 8.39 (1H, d, J=8.20 Hz), 7.93 (1H, s), 7.21 (1H, dd, J=8.21, 1.89 Hz), 7.06 (1H, d, J=1.84 Hz), 5.96-5.88 (1H, m), 4.42 (2H, t, J=5.00 Hz), 4.29 (2H, t, J=8.23 Hz), 4.15 (2H, t, J=7.30 Hz), 3.84-3.78 (1H, m), 3.43 (2H, t, J=5.03 Hz), 3.16 (1H, t, J=6.84 Hz), 1.64 (6H, d, J=6.62 Hz), 1.40 (6H, d, J=6.84 Hz)

Example 322

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-ethanol 322

Following the procedure for 376, 2-(2-isopropyl-2H-[1,2,4]triazol-3-yl)-8-{1-[2-(tetrahydro-pyran-2-yloxy)-ethyl]-azetidin-3-yl}-4,5-dihydro-6-oxa-3-thia-1-aza-benzo[e]azulene was reacted with MeOH as the solvent and the reaction mixture was warmed to 30° C. The crude product was triturated with diethyl ether to give 322 as a yellow solid (92 mg, quant.) LCMS: R$_T$=3.03 min, [M+H]$^+$=412. $^1$H NMR δ (ppm) (DMSO-d6): 10.65 (1H, s), 8.34-8.25 (1H, m), 8.06 (1H, s), 7.27-7.20 (1H, m), 7.15 (1H, dd, J=14.90, 1.71 Hz), 5.80-5.71 (1H, m), 4.41-4.21 (5H, m), 4.20-4.08 (1H, m), 3.67-3.56 (2H, m), 3.45-3.30 (2H, m), 3.26 (1H, dd, J=10.12, 5.06 Hz), 1.51-1.46 (6H, m). 2 Protons obscured by water peak and 1 exchangeable not observed

Example 323

(S)-2-Hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-propan-1-one 323

Following the procedure for 318, 8-azetidin-3-yl-2-(2-isopropyl-2H-[1,2,4]triazol-3-yl)-4,5-dihydro-6-oxa-3-thia-1-aza-benzo[e]azulene free base 235 and L-(+)-lactic acid were reacted to give 323 isolated as an off-white solid after freeze-drying (42 mg, 29%). LCMS: R$_T$=10.71 min, [M+H]$^+$=440. $^1$H NMR δ (ppm) (CDCl$_3$): 8.40-8.33 (1H, m), 7.90 (1H, s), 7.10 (1H, t, J=6.16 Hz), 6.99 (1H, d, J=8.83 Hz), 5.91-5.83 (1H, m), 4.62-4.36 (5H, m), 4.21 (3H, m), 4.18-4.08 (1H, m), 3.93-3.84 (1H, m), 3.40 (2H, t, J=5.01 Hz), 1.61 (6H, d, J=6.62 Hz), 1.34 (3H, d, J=6.57 Hz)

Example 324

N-(2-Hydroxy-ethyl)-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-isobutyramide 324

Following the procedure for 453, 2-Methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propionic acid was reacted with ethanolamine to give 324. MS(ESI+) 548.1. $^1$H NMR (400 MHz, DMSO) δ 8.46 (s, 1H), 8.30-8.25 (m, 2H), 8.07 (s, 1H), 7.52 (dd, J=8.3, 1.5, 1H), 7.41 (d, J=1.5, 1H), 7.20 (t, J=5.4, 1H), 5.86 (q, J=8.7, 2H), 4.59 (t, J=5.4, 1H), 4.40 (t, J=4.8, 2H), 3.47 (t, J=4.9, 2H), 3.36 (q, J=6.0, 2H), 3.12 (q, J=6.0, 2H), 1.75 (s, 6H)

Example 325

2-(2-Isopropyl-2H-[1,2,4]triazol-3-yl)-9-(6-morpholin-4-yl-pyridin-3-yl)-4,5-dihydro-6-oxa-3-thia-1-aza-benzo[e]azulene 325

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 4-(5-(4,4,5,5-tetramethyl-1,3,2-dioxaborolan-2-yl)pyridin-2-yl)morpholine were reacted to give 325 (0.106 g, 58%). $^1$H NMR (400 MHz, CDCl$_3$) δ 8.62 (d, J=2.1, 1H), 8.49 (d, J=1.8, 1H), 7.93 (s, 1H), 7.76 (dd, J=8.7, 2.4, 1H), 7.42 (dd, J=8.4, 2.2, 1H), 7.14 (d, J=8.3, 1H), 6.73 (d, J=8.8, 1H), 5.88 (dt, J=13.3, 6.6, 1H), 4.45 (t, J=5.0, 2H), 3.95-3.76 (m, 4H), 3.68-3.52 (m, 4H), 3.45 (t, J=5.0, 2H), 1.65 (d, J=6.6, 6H). MS (ESI+)): m/z 475.2 (M+H)

Example 326

8-[1-(1,1-Dioxo-tetrahydro-1S-thiophen-3-yl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene 326

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with 1-(1,1-Dioxo-tetrahydrothiophen-3-yl)-4-(4,4,5,5-tetramethyl-[1,3,2] dioxaborolan-2-yl)-1H-pyrazole to give 326. MS(ESI+) 537.1. $^1$H NMR (400 MHz, DMSO) δ 8.45 (s, 1H), 8.32-8.26 (m, 2H), 8.10 (s, 1H), 7.46 (dd, J=8.3, 1.3, 1H), 7.35 (d, J=1.2, 1H), 5.86 (q, J=8.7, 2H), 5.25 (p, J=7.4, 1H), 4.40 (t, J=4.9, 2H), 3.76 (dd, J=13.7, 8.1, 1H), 3.60-3.39 (m, 4H), 3.35-3.25 (m, 1H), 2.76-2.53 (m, 2H)

Example 327

2-(2-Oxo-1,2-dihydro-pyridin-3-yl)-4,5-dihydro-6-oxa-1-thia-10-aza-benzo[e]azulene-8-carboxylic acid amide 327

Step 1: Methyl 9-(2-fluoropyridin-3-yl)-6,7-dihydrothieno[2,3-d]pyrido[3,2-b]oxepine-3-carboxylate

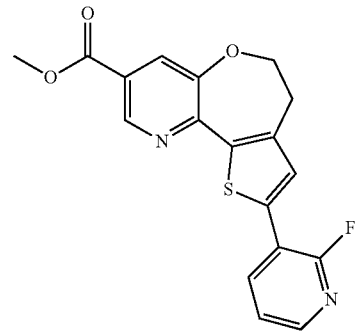 [SMILES: COC(=O)c1cnc2c(c1)OCCc1cc(-c3cccnc3F)sc1-2]

Methyl 9-bromo-6,7-dihydrothieno[2,3-d]pyrido[3,2-b]oxepine-3-carboxylate was coupled with 2-fluoropyridin-3-ylboronic acid under Suzuki conditions to give methyl 9-(2-fluoropyridin-3-yl)-6,7-dihydrothieno[2,3-d]pyrido[3,2-b]oxepine-3-carboxylate. Yield 61%. MS(ESI+): 357.1

Step 2: 2-(2-Oxo-1,2-dihydropyridin-3-yl)-4,5-dihydrobenzooxepino[4,5-d]thiophene-8-carboxylic acid

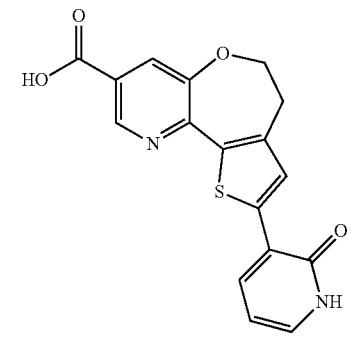 [SMILES: O=C(O)c1cnc2c(c1)OCCc1cc(-c3ccc[nH]c3=O)sc1-2]

A mixture of 120 mg (0.337 mmol) of methyl 9-(2-fluoropyridin-3-yl)-6,7-dihydrothieno[2,3-d]pyrido[3,2-b]oxepine-3-carboxylate in 5 ml of acetic acid and 2 ml of 4 N aqueous hydrogen chloride was heated in a sealed vial at 110° C. for 3 hours. The mixture was concentrated in vacuum and the residue triturated with 5 ml of water. The precipitate was collected and dried in high vacuum for 24 hours. Yield 102 mg (54%). MS(ESI+): 341.1

Step 3

2-(2-Oxo-1,2-dihydropyridin-3-yl)-4,5-dihydrobenzooxepino[4,5-d]thiophene-8-carboxylic acid was coupled with ammonium chloride, and HATU to give 327. Yield 40%. MS(ESI+): 340.1. 1H NMR (400 MHz, DMSO) 12.07 (s, 1H), 8.68 (d, J=1.7, 1H), 8.16-8.03 (m, 2H), 7.78 (d, J=1.7, 1H), 7.68 (s, 1H), 7.52 (s, 1H), 7.43 (t, J=8.8, 1H), 6.36 (t, J=6.7, 1H), 4.36 (s, 2H)

Example 329

2,2,2-Trifluoro-1-[2-(2-isopropyl-2H-[1,2,4]triazol-3-yl)-4,5-dihydro-6-oxa-3-thia-1-aza-benzo[e]azulen-9-yl]-ethanol 329

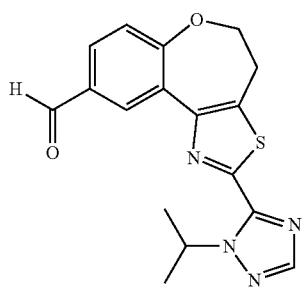 [SMILES: CC(C)n1ncnc1-c1nc2c(s1)CCOc1ccc(C=O)cc1-2]

2-(2-Isopropyl-2H-[1,2,4]triazol-3-yl)-4,5-dihydro-6-oxa-3-thia-1-aza-benzo[e]azulene-9-carbonitrile 136 (0.353 g, 1.05 mmol) was dissolved in DCM (2.5 mL) and cooled at 0° C. A solution of diisobutylaluminum hydride (1M, 1.57 mL, 1.57 mmol) was added dropwise and the mixture was gradually allowed to warm to room temperature with stirring over 2 h. The reaction mixture was then poured into a mixture containing Rochelle's salt aqueous solution and Et$_2$O. The entire mixture was stirred vigorously for an overnight period to aid partitioning of the phases. The phases were separated and the aqueous was extracted 3× with EtOAc. The combined organic layers were washed with brine, dried over MgSO$_4$, filtered and concentrated to provide 354 mg (99%) of the crude aldehyde, 2-(2-Isopropyl-2H-[1,2,4]triazol-3-yl)-4,5-dihydro-6-oxa-3-thia-1-aza-benzo[e]azulene-9-carbaldehyde.

2-(2-Isopropyl-2H-[1,2,4]triazol-3-yl)-4,5-dihydro-6-oxa-3-thia-1-aza-benzo[e]azulene-9-carbaldehyde (0.354 g, 1.04 mmol) was dissolved in THF (7 mL) and treated with (trifluoromethyl)trimethylsilane (0.154 mL, 1.04 mmol) followed by TBAF (1M, 0.02 mL, 0.02 mmol). Stirred the resulting reaction mixture at ambient temperature for 2 h. Concentrated in vacuo and re-dissolved in DMF and purified by reverse phase HPLC to give 25.6 mg (6% yield) of 329. LC/MS (ESI+): m/z 411 (M+H). 1H NMR (400 MHz, DMSO) δ 8.55 (s, 1H), 8.10 (s, 1H), 7.41 (d, J=8.4, 1H), 7.10 (d, J=8.3, 1H), 6.80 (s, 1H), 5.80 (dt, J=13.1, 6.5, 1H), 5.21 (d, J=6.7, 1H), 4.39 (t, J=4.9, 2H), 3.45 (t, J=4.9, 2H), 1.55 (d, J=6.5, 6H).

Example 330

3-[2-(2-Isopropyl-2H-[1,2,4]triazol-3-yl)-4,5-dihydro-6-oxa-3-thia-1-aza-benzo[e]azulen-9-yl]-1H-pyridin-2-one 330

To a solution of 306 (0.275 g, 0.675 mmol) in DME (5 mL) was added 10% aq HCl (5 mL). The reaction mixture was allowed to stir and heat at 80° C. for 18 hours before cooling, concentrating under reduced pressure, and diluting with EtOAc. The solution was washed sequentially with water, and brine, before drying over MgSO$_4$ and concentrating under reduced pressure to 50 mL of EtOAc and the solids were collected by filtration to give 330 (244 mg, 89%). 1H NMR (400 MHz, DMSO) δ 11.79 (s, 1H), 9.00 (t, J=15.9, 1H), 8.10 (s, 1H), 7.67 (ddd, J=16.8, 8.8, 5.2, 2H), 7.37 (d, J=5.1, 1H), 7.08 (d, J=8.4, 1H), 6.31 (t, J=6.7, 1H), 5.88 (dt, J=13.2, 6.6, 1H), 4.58-4.20 (m, 2H), 3.46 (t, J=5.0, 2H), 1.55 (d, J=6.6, 6H). MS (ESI(+)): m/z 406.1 (M+H)

Example 331

9-[1-(2-Hydroxy-2-methyl-propyl)-1H-pyrazol-4-yl]-4,5-dihydro-6-oxa-3-thia-1-aza-benzo[e]azulene-2-carboxylic acid (2-hydroxy-ethyl)-isopropyl-amide 331

Following the procedure for 277, 9-Bromo-4,5-dihydro-6-oxa-3-thia-1-aza-benzo[e]azulene-2-carboxylic acid (2-hydroxy-ethyl)-isopropyl-amide (225 mg, 0.547 mmol) and 2-methyl-1-(4-(4,4,5,5-tetramethyl-1,3,2-dioxaborolan-2-yl)1H-pyrazol-1-yl)propan-2-ol (174.7 mg, 0.656 mmol) were reacted to give 331 (20.0 mg, 8% yield, M+1 471.2).

Example 332

2-Methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propan-1-ol 332

2-Methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propionic acid (0.250 g, 0.000496 mol) in dry tetrahydrofuran (1.0 mL, 0.012 mol) cooled to 0° C. Lithium tetrahydroaluminate (1M solution in THF, 1.0 mL, 0.0010 mol), was added dropwise at 0° C. and the mixture was allowed to warm to room temperature and stirred for 2 h. The reaction was quenched with saturated Na$_2$SO$_4$ until no more hydrogen evolution was observed. MgSO$_4$ was added and the solution was filtered and rinsed with copious amounts of methylene chloride. The solvent was removed in vacuo and the crude material was purified by reverse-phase HPLC to give 332 (35.4 mg) as a colorless solid. MS(ESI+) 491.1.

Example 333

N2-(2-chloro-5-(piperazine-1-carbonyl)phenyl)-N2,N8-dimethyl-4,5-dihydrobenzo[b]thieno[2,3-d]oxepine-2,8-dicarboxamide 333

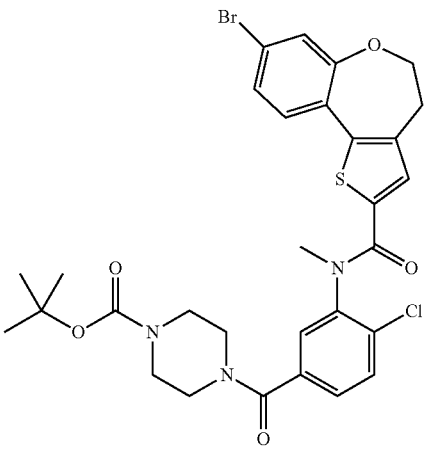 [SMILES: CN(C(=O)c1cc2c(s1)-c1ccc(Br)cc1OCC2)c1cc(C(=O)N2CCN(C(=O)OC(C)(C)C)CC2)ccc1Cl]

To a mixture of tert-butyl piperazine-1-carboxylate (1.7 g, 9.13 mmol), DIPEA (3 mL), HATU (2.78 g, 7.31 mmol) in THF (60 mL) was added 3-(8-bromo-N-methyl-4,5-dihydrobenzo[b]thieno[2,3-d]oxepine-2-carboxamido)-4-chlorobenzoic acid (3.0 g, 6.09 mmol) under nitrogen atmosphere at room temperature. The reaction mixture was stirred overnight, diluted with water, extracted with EtOAc. The organic layer was dried over $Na_2SO_4$, concentrated in vacuo to give tert-butyl 4-(3-(8-bromo-N-methyl-4,5-dihydrobenzo[b]thieno[2,3-d]oxepine-2-carboxamido)-4-chlorobenzoyl)piperazine-1-carboxylate (3.9 g, yield: 97%). LC-MS: (ESI, m/z)=682 [M+Na]$^+$

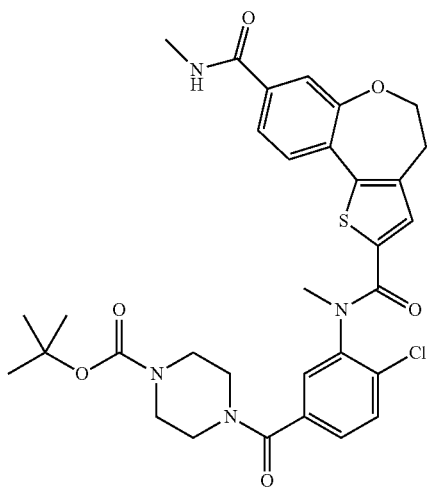 [SMILES: CNC(=O)c1ccc2c(c1)OCCc1cc(C(=O)N(C)c3cc(C(=O)N4CCN(C(=O)OC(C)(C)C)CC4)ccc3Cl)sc1-2]

A suspension of tert-butyl 4-(3-(8-bromo-N-methyl-4,5-dihydrobenzo[b]thieno[2,3-d]oxepine-2-carboxamido)-4-chlorobenzoyl)piperazine-1-carboxylate (500 mg, 0.76 mmol), Pd(OAc)$_2$ (9 mg, 0.038 mmol), Xantphos (44 mg, 0.076 mmol), MeNH$_2$·HCl (77 mg, 1.14 mmol) and Na$_2$CO$_3$ (242 mg, 2.28 mmol) in toluene (10 mL) was heated at 80° C. under atmosphere of CO from balloon for overnight. Then it was filtrated and concentrated, the crude product was purified by pre-TLC (DCM/MeOH=10:1 as eluted solvent) to give tert-butyl 4-(4-chloro-3-(N-methyl-8-(methylcarbamoyl)-4,5-dihydrobenzo[b]thieno[2,3-d]oxepine-2-carboxamido)benzoyl)piperazine-1-carboxylate (390 mg, yield: 80%). $^1$H NMR (DMSO, 400 MHz): δ7.59-7.26 (m, 8H, ArH, NH), 4.26 (t, J=5.2 Hz, 2H, CH$_2$), 3.57-2.80 (m, 18H, CH$_2$, CH$_3$), 1.47 (s, 9H, CH$_3$)

A solution of HCl in EtOAc (4M, 20 mL) was slowly added into a solution of tert-butyl 4-(4-chloro-3-(N-methyl-8-(methylcarbamoyl)-4,5-dihydrobenzo[b]thieno[2,3-d]oxepine-2-carboxamido)benzoyl)piperazine-1-carboxylate (390 mg, 0.61 mmol) in EtOAc (5 mL) at 0° C. The mixture was stirred at room temperature for overnight. The solids were filtered and washed with EtOAc, dried to give 333 (250 mg, yield 71%). $^1$H NMR (MeOD, 400 MHz): δ7.76-7.42 (m, 7H, ArH, NH), 6.90 (s, 1H, =CH), 4.23-2.89 (m, 19H). LC-MS: (ESI, m/z)=539 [M+H]$^+$, 561 [M+Na]$^+$ Example 334

N2-(2-chloro-5-(piperazine-1-carbonyl)phenyl)-N2-methyl-N8-(2-(methylsulfonyl)ethyl)-4,5-dihydrobenzo[b]thieno[2,3-d]oxepine-2,8-dicarboxamide 334

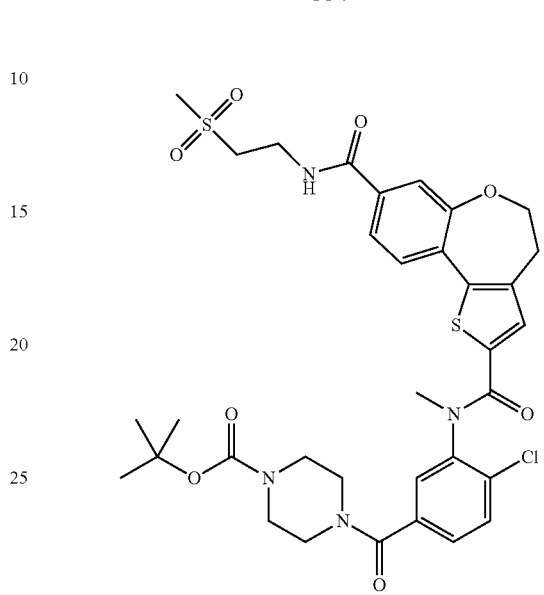

A suspension of tert-butyl 4-(3-(8-bromo-N-methyl-4,5-dihydrobenzo[b]thieno[2,3-d]oxepine-2-carboxamido)-4-chlorobenzoyl)piperazine-1-carboxylate (500 mg, 0.76 mmol), Pd(OAc)$_2$ (9 mg, 0.038 mmol), Xantphos (44 mg, 0.076 mmol), MeSO$_2$(CH$_2$)$_2$NH$_2$·HCl (182 mg, 1.14 mmol) and Na$_2$CO$_3$ (242 mg, 2.28 mmol) in toluene (10 mL) was heated at 80° C. under atmosphere of CO from balloon for overnight. Then it was filtrated and concentrated, the crude product was purified by pre-TLC (DCM:MeOH=10:1 as eluted solvent) to give tert-butyl 4-(4-chloro-3-(N-methyl-8-(2-(methylsulfonyl)ethylcarbamoyl)-4,5-dihydrobenzo[b]thieno[2,3-d]oxepine-2-carboxamido)benzoyl)piperazine-1-carboxylate (350 mg, yield 63%). $^1$H NMR (CDCl$_3$, 400 MHz): δ 7.60-7.34 (m, 8H, ArH, NH), 4.26-2.80 (m, 22H, CH$_2$, CH$_3$), 1.48 (s, 9H, 3CH$_3$).

A solution of HCl in EtOAc (4M, 20 mL) was slowly added into a solution of tert-butyl 4-(4-chloro-3-(N-methyl-8-(2-(methylsulfonyl)ethylcarbamoyl)-4,5-dihydrobenzo[b]thieno[2,3-d]oxepine-2-carboxamido)benzoyl)piperazine-1-carboxylate (350 mg, 0.48 mmol) in EtOAc (5 mL) at 0° C. The mixture was stirred at room temperature for overnight. The solids were filtered and washed with EtOAc, dried to give 334 (176.6 mg, yield: 55%). $^1$H NMR (MeOD, 400 MHz): δ7.77-7.44 (m, 7H, ArH, NH), 6.93 (s, 1H, =CH), 4.24-3.04 (m, 23H). LC-MS: (ESI, m/z)=631 [M+H]$^1$ Example 335

5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-ylamine 335

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 5-(4,4,5,5-Tetramethyl-[1,3,2]dioxaborolan-2-yl)-pyridin-2-ylamine (268 mg, 1.2 mmol), $Cs_2CO_3$ (650 mg, 2.0 mmol), Pd(dppf)$Cl_2$ (73 mg, 0.10 mmol) and $CH_3CN$—$H_2O$ (1:1, 4 mL) were added in a 10 mL of sealed tube, and the mixture was heated by microwave at 120° C. for 20 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 335 (179.7 mg, yield: 38%). $^1$HNMR (DMSO-$d_6$, 400 MHz): δ8.54 (s, 1H), 8.27 (s, 1H), 7.92-7.87 (m, 2H), 7.42 (t, J=0.8 Hz, 1H), 7.73-7.72 (m, 1H), 7.66 (d, J=8.8 Hz, 1H), 7.43 (t, J=8.8 Hz, 1H), 7.17 (s, 1H), 6.54 (d, J=8.8 Hz, 1H), 6.28 (s, 1H), 4.26 (s, 2H), 3.11 (s, 2H). ESI-MS: m/z=475 [M+H$^+$]

Example 336

2-[2-(2,4-Difluoro-phenyl)-2H-[1,2,4]triazol-3-yl]-9-(6-methyl-pyridin-3-yl)-4,5-dihydro-6-oxa-1-thia-10-aza-benzo[e]azulene 336

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 2-Methyl-5-(4,4,5,5-tetramethyl-[1,3,2]dioxaborolan-2-yl)-pyridine (262 mg, 1.2 mmol), $Cs_2CO_3$ (650 mg, 2.0 mmol), Pd(dppf)$Cl_2$ (73 mg, 0.10 mmol) and $CH_3CN$—$H_2O$ (1:1, 4 mL) were added in a 10 mL of sealed tube, and the mixture was heated by microwave at 120° C. for 20 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 336 (168.7 mg, yield: 36%). $^1$HNMR (DMSO-$d_6$, 400 MHz): δ9.04 (s, 1H), 8.28 (s, 1H), 8.16 (d, J=8.4 Hz, 1H), 7.91-7.87 (m, 2H), 7.76-7.71 (m, 1H), 7.48-7.45 (m, 2H), 7.36-7.34 (m, 1H), 7.14 (s, 1H), 4.30 (s, 2H), 3.14 (s, 2H), 2.52 (s, 3H). ESI-MS: m/z=474 [M+H$^+$]

Example 337

2-[2-(2,4-Difluoro-phenyl)-2H-[1,2,4]triazol-3-yl]-9-(6-methoxy-4-methyl-pyridin-3-yl)-4,5-dihydro-6-oxa-1-thia-10-aza-benzo[e]azulene 337

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 2-Methoxy-4-methyl-5-(4,4,5,5-tetramethyl-[1,3,2]dioxaborolan-2-yl)-pyridine (298 mg, 1.2 mmol), $Cs_2CO_3$ (650 mg, 2.0 mmol), Pd(dppf)$Cl_2$ (73 mg, 0.10 mmol) and $CH_3CN$—$H_2O$ (1:1, 4 mL) were added in a 10 mL of sealed tube, and the mixture was heated by microwave at 120° C. for 20 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to afford 337 (120.8 mg, yield: 24%). $^1$HNMR (DMSO-$d_6$, 400 MHz): δ8.29 (s, 1H), 8.20 (s, 1H), 7.92-7.81 (m, 1H), 7.70 (t, J=2.4 Hz, 1H), 7.51-7.41 (m, 3H), 7.24 (s, 2H), 6.75 (s, 1H), 4.31 (s, 2H), 3.89 (s, 3H), 3.19 (s, 2H), 2.32 (s, 3H). ESI-MS: m/z=504 [M+H$^+$]

Example 338

2-[2-(2,4-Difluoro-phenyl)-2H-[1,2,4]triazol-3-yl]-9-(5-methyl-6-morpholin-4-yl-pyridin-3-yl)-4,5-dihydro-6-oxa-1-thia-10-aza-benzo[e]azulene 338

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 4-[4-Methyl-5-(4,4,5,5-tetramethyl-[1,3,2]dioxaborolan-2-yl)-pyridin-2-yl]-morpholine (370 mg, 1.2 mmol), $Cs_2CO_3$ (650 mg, 2.0 mmol), Pd(dppf)$Cl_2$ (73 mg, 0.10 mmol) and $CH_3CN$—$H_2O$ (1:1, 4 mL) were added in a 10 mL of sealed tube, and the mixture was heated by microwave at 120° C. for 20 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 338 (211 mg, yield: 38%). $^1$HNMR (DMSO-$d_6$, 400 MHz): δ8.69 (s, 1H), 8.28 (s, 1H), 7.96-7.90 (m, 1H), 7.85-7.70 (m, 2H), 7.52-7.41 (m, 2H), 7.17 (s, 2H), 3.75-3.72 (m, 4H), 3.13 (s, 6H), 2.32 (s, 3H). ESI-MS: m/z=559 [M+H$^+$]

Example 339

(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-dimethyl-amine 339

2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo[e]azulene (470 mg, 1.0 mmol), from the procedure for 249, Dimethyl-amine (98 mg, 1.2 mmol), DIPEA (340 mg, 3 mmol) and NMP (4 mL) were added in a 10 mL of sealed tube, and the mixture was heated by microwave at 150° C. for 120 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 339 (61.4 mg, yield: 12%). $^1$HNMR (DMSO-$d_6$, 400 MHz): δ8.74 (s, 1H), 8.31 (s, 1H), 8.06 (d, J=9.2 Hz, 1H), 7.91-7.87 (m, 1H), 7.73-7.71 (m, 2H), 7.42-7.40 (m, 2H), 7.19 (d, J=4.4 Hz, 1H), 7.19 (d, J=8.8 Hz, 1H), 6.77 (d, J=8.8 Hz, 1H), 4.31 (s, 2H), 3.16-3.11 (m, 8H). ESI-MS: m/z=503 [M+H$^+$]

Example 340

2-(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-ylamino)-ethanol 340

2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo[e]azulene (470 mg, 1.0 mmol), from the procedure for 249, 2-Methanesulfonyl-ethylamine (147 mg, 1.2 mmol), DIPEA (340 mg, 3 mmol) and NMP (4 mL) were added in a 10 mL of sealed tube, and the mixture was heated by microwave at 150° C. for 120 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 340 (68.9 mg, yield: 14%). $^1$HNMR (DMSO-$d_6$, 400 MHz): δ8.63 (s, 1H), 8.30 (s, 1H), 7.90-7.85 (m, 2H), 7.70-7.70 (m, 2H), 7.41-7.38 (m, 2H), 7.19 (s, 2H), 6.90-6.88 (m, 1H), 6.63 (d, J=8.8 Hz, 1H), 4.75 (s, 1H), 4.29 (s, 2H), 3.56-3.55 (m, 2H), 3.40-3.38 (m, 2H), 3.15 (s, 2H). ESI-MS: m/z=519 [M+H$^+$]

Example 341

(5-{2-[2-(2,4-Difluoro-phenyl)-2H-[1,2,4]triazol-3-yl]-4,5-dihydro-6-oxa-1-thia-10-aza-benzo[e]azulen-9-yl}-pyridin-2-yl)-(2-methoxy-ethyl)-amine 341

2-[2-(2,4-Difluoro-phenyl)-2H-[1,2,4]triazol-3-yl]-9-(6-fluoro-pyridin-3-yl)-4,5-dihydro-6-oxa-1-thia-10-aza-benzo[e]azulene (470 mg, 1.0 mmol), from the procedure for 249, 2-Methoxy-ethylamine (90 mg, 1.2 mmol), DIPEA (340 mg, 3 mmol) and NMP (4 mL) were added in a 10 mL of sealed tube, and the mixture was heated by microwave at 150° C. for 120 min under $N_2$. The reaction mixture was filtered to gather the solution and water was added. The mixture was extracted by DCM (20 mL×3). The combined organic layers were dried over $Na_2SO_4$, concentrated in vacuo, and purified by preparative HPLC to give 341 (105.5 mg, yield: 20%). $^1$HNMR (DMSO-$d_6$, 400 MHz): δ8.63 (s, 1H), 8.31 (s, 1H), 7.94-7.88 (m, 2H), 7.76-7.68 (m, 2H), 7.46-7.38 (m, 2H), 7.21 (s, 2H), 6.99 (s, 1H), 6.63 (d, J=8.8 Hz, 1H), 4.31 (s, 2H), 3.49 (s, 4H), 3.29 (s, 3H), 3.15 (s, 2H). ESI-MS: m/z=533 [M+H$^+$]

Example 342

2-(2-Isopropyl-2H-[1,2,4]triazol-3-yl)-9-pyridin-3-yl-4,5-dihydro-6-oxa-3-thia-1-aza-benzo[e]azulene 342

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and pyridin-3-ylboronic acid were reacted to give 342 (0.120 g, 22%). $^1$H NMR (400 MHz, DMSO) δ 8.91 (d, J=1.7, 1H), 8.72 (d, J=2.3, 1H), 8.57 (dd, J=7.2, 3.7, 1H), 8.11 (s, 1H), 8.07 (d, J=8.0, 1H), 7.69 (dd, J=8.4, 2.3, 1H), 7.53 (dd, J=7.9, 4.8, 1H), 7.22 (d, J=8.4, 1H), 5.79 (dt, J=13.2, 6.6, 1H), 4.44 (t, J=4.9, 2H), 3.49 (t, J=4.9, 2H), 1.57 (d, J=6.6, 6H). MS (ESI(+)): m/z 390.1 (M+H)

Example 343

2-(2-Isopropyl-2H-[1,2,4]triazol-3-yl)-9-(5-methoxy-pyridin-3-yl)-4,5-dihydro-6-oxa-3-thia-1-aza-benzo[e]azulene 343

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 3-methoxy-5-(4,4,5,5-tetramethyl-1,3,2-dioxaborolan-2-yl)pyridine were reacted to give 343 (0.062 g, 60%). $^1$H NMR (500 MHz, DMSO) δ 8.72 (d, J=2.4, 1H), 8.50 (d, J=1.8, 1H), 8.29 (d, J=2.7, 1H), 8.11 (s, 1H), 7.71 (dd, J=8.4, 2.4, 1H), 7.64 (dd, J=2.6, 2.0, 1H), 7.21 (d, J=8.4, 1H), 5.82 (dd, J=13.2, 6.6, 1H), 4.43 (t, J=5.0, 2H), 3.92 (s, 3H), 3.49 (t, J=5.0, 2H), 1.56 (d, J=6.6, 6H). MS (ESI(+)): m/z 420.1 (M+H)

Example 344

2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-ethylamine 344

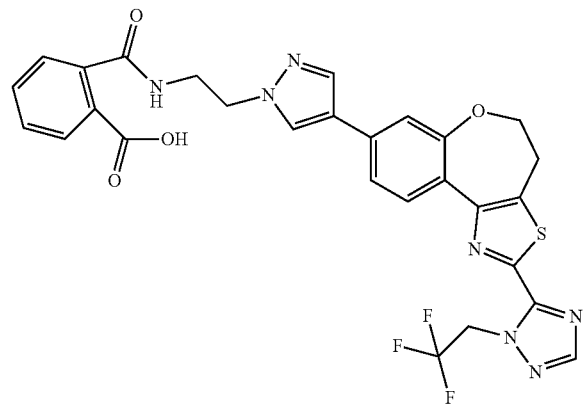 [SMILES: O=C(O)c1ccccc1C(=O)NCCn1cc(-c2ccc3c(c2)OCCc2sc(-c4ncnn4CC(F)(F)F)nc2-3)cn1]

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with 2-{2-[4-(4,4,5,5-Tetramethyl-[1,3,2]dioxaborolan-2-yl)-pyrazol-1-yl]-ethyl}-isoindole-1,3-dione to give N-[2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-ethyl]-phthalamic acid. MS(ESI+) 610.1

To a solution of N-[2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-ethyl]-phthalamic acid (0.2000 g, 0.0003281 mol) in ethanol (3 mL, 0.05 mol) was added hydrazine (0.01133 mL, 0.0003609 mol). The mixture was heated to 60° C. overnight, cooled to room temperature and concentrated in vacuo. The crude was purified by reverse-phase HPLC to give 344 (13.6 mg) as a colorless solid. MS(ESI+) 462.1. $^1$H NMR (400 MHz, DMSO) δ 8.31-8.25 (m, 3H), 7.99 (s, 1H), 7.45 (dd, J=8.3, 1.8, 1H), 7.33 (d, J=1.8, 1H), 5.87 (q, J=8.7, 2H), 4.40 (t, J=5.0, 2H), 4.11 (t, J=6.3, 2H), 3.47 (t, J=5.0, 2H), 2.98 (t, J=6.3, 2H)

Example 345

2-Hydroxy-1-(3-{4-[2-(2-isopropyl-2H-[1,2,4]triazol-3-yl)-4,5-dihydro-6-oxa-3-thia-1-aza-benzo[e]azulen-8-yl]-pyrazol-1-yl}-azetidin-1-yl)-propan-1-one 345

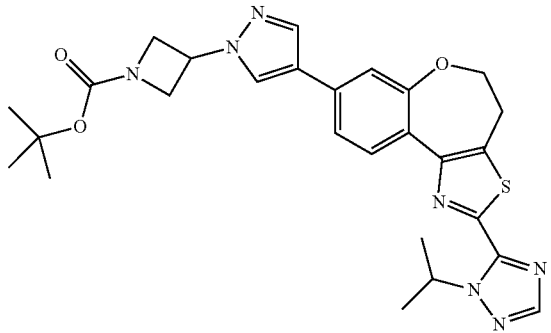 [SMILES: CC(C)n1ncnc1-c1nc2c(s1)CCOc1cc(-c3cnn(C4CN(C(=O)OC(C)(C)C)C4)c3)ccc1-2]

Similarly to as described in General Procedure C, 8-Bromo-2-(2-isopropyl-2H-[1,2,4]triazol-3-yl)-4,5-dihydro-6-oxa-3-thia-1-aza-benzo[e]azulene 27 was reacted with tert-butyl 3-(4-(4,4,5,5-tetramethyl-1,3,2-dioxaborolan-2-yl)-1H-pyrazol-1-yl)azetidine-1-carboxylate to give 3-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-azetidine-1-carboxylic acid tert-butyl ester which was used without purification.

3-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-azetidine-1-carboxylic acid tert-butyl ester (2.2 mmol) was dissolved in 5 mL of methylene chloride and treated with 2 mL of trifluoroacetic acid. After 2 h, aqueous workup and concentration of the organics gave the crude deprotected azetidine as a colorless solid that was used in the next step without purification. Crude 8-(1-Azetidin-3-yl-1H-pyrazol-4-yl)-2-(2-isopropyl-2H-[1,2,4]triazol-3-yl)-4,5-dihydro-6-oxa-3-thia-1-aza-benzo[e]azulene (190 mg) was dissolved in 3 mL of THF and treated sequentially with DIPEA (0.23 mL, 1.3 mmol), lactic acid (0.10 L, 1.3 mmol) and HATU (333 mg, 0.88 mmol). After 2 h at room temperature, aqueous workup and extraction with ethylacetate gave a crude solid that was purified by reverse phase HPLC to give 345 as a colorless solid (35 mg, 16%). LCMS: 506.2. $^1$H NMR (400 MHz, DMSO) δ 8.47 (d, J=2.3 Hz, 1H), 8.33 (d, J=8.3 Hz, 1H), 8.11 (s, 2H), 7.48 (dd, J=8.3, 1.7 Hz, 1H), 7.36 (d, J=1.7 Hz, 1H), 5.84 (m, 1H), 5.28 (m, 1H), 5.23-5.17 (m, 1H), 4.80-4.69 (m, 1H), 4.60-4.50 (m, 1H), 4.39 (t, J=5.0 Hz, 2H), 4.34 (m, 1H), 4.22-4.12 (m, 2H), 3.45 (t, J=5.0 Hz, 2H), 1.56 (d, J=6.6 Hz, 6H), 1.23 (d, J=6.7 Hz, 3H).

Example 346

2-{4-[2-(4-Isopropyl-5-trifluoromethyl-4H-[1,2,4]triazol-3-yl)-4,5-dihydro-6-oxa-3-thia-1-aza-benzo[e]azulen-8-yl]-pyrazol-1-yl}-ethanol 346

Similarly to as described in General Procedure C, 8-bromo-2-(4-isopropyl-5-trifluoromethyl-4H-[1,2,4]triazol-3-yl)-4,5-dihydro-6-oxa-3-thia-1-aza-benzo[e]azulene was reacted with 1-(2-(tetrahydro-2H-pyran-2-yloxy)ethyl)-4-(4,4,5,5-tetramethyl-1,3,2-dioxaborolan-2-yl)-1H-pyrazole. Subsequent to the Suzuki coupling, deprotection of the tetrahydropyranyl ether was accomplished by adding 2N HCl to the crude reaction mixture. Purification by reverse phase HPLC gave 346 as a colorless solid (112 mg). LCMS: 491.1. $^1$H NMR (400 MHz, DMSO) δ 8.27 (d, J=13.7 Hz, 1H), 8.23 (s, 1H), 7.95 (s, 1H), 7.44 (dd, J=8.3, 1.7 Hz, 1H), 7.32 (d, J=1.7 Hz, 1H), 5.45-5.29 (m, 1H), 4.91 (t, J=5.3 Hz, 1H), 4.41 (t, J=5.0 Hz, 2H), 4.16 (t, J=5.6 Hz, 2H), 3.77 (q, J=5.5 Hz, 2H), 3.48 (t, J=5.0 Hz, 2H), 1.70 (t, J=11.9 Hz, 6H)

Example 347

2-{2-[2-(2,4-Difluoro-phenyl)-2H-[1,2,4]triazol-3-yl]-4,5-dihydro-6-oxa-1-thia-10-aza-benzo[e]azulen-9-ylamino}-propan-1-ol 347

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), 1-(trimethylsilyloxy)propan-2-amine (211 mg, 1.44 mmol), $^t$BuONa (47 mg, 0.48 mmol), Pd(OAc)$_2$ (16 mg, 0.1 mmol), and Xphos (68 mg, 0.144 mmol) in dioxane (2 mL) was bubbled N$_2$ for 10 min and then stirred at 125° C. for 7 min under the irradition of microwave. The mixture was filtered over ceilite. The filtrate was concentrated to dryness and purified by pre-TLC (EtOAc) and pre-HPLC to afford 40 mg of 347. (yield: 13%). $^1$H NMR (CDCl$_3$, 400 MHz): δ8.02 (s, 1H), 7.49 (q, J=5.6, 8.8 Hz, 1H), 7.12-6.99 (m, 4H), 6.21 (d, J=4.8 Hz, 1H), 4.20-3.04 (m, 8H), 2.28 (s, 1H), 1.19-1.15 (m, 3H). LC-MS (ESI): m/z=456 [M+H]$^+$ Example 348

1-(4-{2-[2-(2,4-Difluoro-phenyl)-2H-[1,2,4]triazol-3-yl]-4,5-dihydro-6-oxa-1-thia-10-aza-benzo[e]azulen-9-yl}-piperazin-1-yl)-ethanone 348

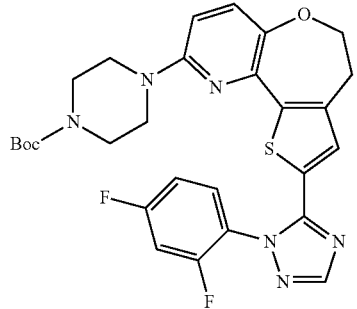 [SMILES: CC(C)(C)OC(=O)N1CCN(c2ccc3c(n2)-c2sc(-c4ncnn4-c4ccc(F)cc4F)cc2CCO3)CC1]

9-Chloro-2-[2-(2,4-difluoro-phenyl)-2H-[1,2,4]triazol-3-yl]-4,5-dihydro-6-oxa-1-thia-10-aza-benzo[e]azulene (208 mg×4, 2.0 mmol), tert-butyl piperazine-1-carboxylate (445 mg, 2.4 mmol), Pd(OAc)$_2$ (45 mg, 0.20 mmol), Xphos (95 mg, 2.0 mmol), t-BuONa (460 mg, 4.0 mmol) and dioxane (4 mL) were added in a 10 mL of sealed tube, and the mixture was heated by microwave at 112° C. for 7 min under N$_2$. The reaction mixture was filtered to gather the solution and water was added. The mixture was extracted by DCM (20 mL×3). The combined organic layers were dried over Na$_2$SO$_4$, concentrated in vacuo, and purified by preparative TLC (DCM/EtOAc=10:1) to give 4-{2-[2-(2,4-Difluoro-phenyl)-2H-[1,2,4]triazol-3-yl]-4,5-dihydro-6-oxa-1-thia-10-aza-benzo[e]azulen-9-yl}-piperazine-1-carboxylic acid tert-butyl ester (612 mg, yield: 54%). $^1$HNMR (DMSO-d$_6$, 400 MHz): δ8.30 (s, 1H), 7.99-7.90 (m, 1H), 7.79-7.70 (m, 2H), 7.32 (s, 1H), 7.27 (s, 1H), 7.25 (s, 1H), 6.78 (d, J=8.8 Hz, 1H), 4.19 (s, 4H), 4.04-4.02 (m, 4H), 3.44 (m, 1H), 3.12 (s, 1H), 1.57 (s, 9H) ESI-MS: m/z=567 [M+H$^+$]

4-{2-[2-(2,4-Difluoro-phenyl)-2H-[1,2,4]triazol-3-yl]-4,5-dihydro-6-oxa-1-thia-10-aza-benzo[e]azulen-9-yl}-piperazine-1-carboxylic acid tert-butyl ester (0.61 g, 1.08 mmol) was dissolved in EtOAc, and EtOAc—HCl was added dropwise into the solution. And them the mixture was stirred at room temperature for 2 h. The reaction mixture was filtered to gather the solid. The resulting solid was washed by DCM (10 mL) to give 2-[2-(2,4-Difluoro-phenyl)-2H-[1,2,4]triazol-3-yl]-9-piperazin-1-yl-4,5-dihydro-6-oxa-1-thia-10-aza-benzo[e]azulene as HCl salt (420 mg, yield: 77%). $^1$HNMR (D$_2$O, 400 MHz): δ8.05 (s, 1H), 7.45-7.39 (m, 1H), 7.23 (t, J=8.8 Hz, 1H), 7.19 (t, J=8.4 Hz, 1H), 7.01 (s, 1H), 6.99 (d, J=1.6 Hz, 1H), 6.99 (d, J=4.8 Hz, 1H), 3.97 (s, 1H), 3.39 (s, 4H), 3.19 (s, 4H), 2.83 (s, 2H) ESI-MS: m/z=503 [M+H$^+$]

2-[2-(2,4-Difluoro-phenyl)-2H-[1,2,4]triazol-3-yl]-9-piperazin-1-yl-4,5-dihydro-6-oxa-1-thia-10-aza-benzo[e]azulene (150 mg, 0.3 mmol) was dissolved in THF (20 mL), and DIPEA (155 mg, 1.2 mmol) was added. Acetyl chloride (28 mg, 0.36 mmol) was added dropwise into the solution. And then the reaction mixture was stirred at room temperature for 12 h. The reaction mixture was concentrated in vacuo, and then dissolved in DCM. The mixture was washed by water, dried by Na$_2$SO$_4$, concentrated in vacuo, and purified by prep. TLC (DCM/EtOAc=10:1) to give 348 (42.6 mg, yield: 28%). $^1$HNMR (DMSO, 400 MHz): δ8.29 (s, 1H), 7.97-7.88 (m, 1H), 7.78 (t, J=2.4 Hz, 1H), 7.47 (t, J=8.4 Hz, 1H), 7.27-7.24 (m, 2H), 6.80 (d, J=8.8 Hz, 1H), 4.20 (s, 1H), 3.63 (s, 4H), 3.33 (s, 4H), 3.11 (s, 2H), 2.07 (s, 3H). ESI-MS: m/z=509 [M+H$^+$]

Example 349

1-(4-{2-[2-(2,4-Difluoro-phenyl)-2H-[1,2,4]triazol-3-yl]-4,5-dihydro-6-oxa-1-thia-10-aza-benzo[e]azulen-9-yl}-[1,4]diazepan-1-yl)-ethanone 349

Compound 350 (70 mg, 0.14 mmol) was dissolved in THF, DIPEA (56 mg, 0.56 mmol) was added, and acetyl chloride (14 mg, 0.17 mmol) was added into the solution. And the reaction mixture was stirred at room temperature for 2 h. The reaction mixture was concentrated in vacuo, then dissolved in DCM. The organic layer was washed by water, dried by Na2SO4, concentrated in vacuo, and purified by TLC (DCM/EtOAc=4:1) to get 349 (51.9 mg, yield: 67%)$^1$HNMR (DMSO-d$_6$, 400 MHz): δ8.30 (s, 1H), 8.16 (s, 1H), 7.96-7.70 (m, 1H), 7.35-7.29 (m, 1H), 7.28-7.25 (m, 1H), 7.21 (s, 1H), 7.20-7.16 (m, 1H), 6.97 (t, J=11.4 Hz, 1H), 4.17 (d, J=5.2 Hz, 2H), 3.68 (s, 2H), 3.30 (s, 6H), 3.10 (s, 2H), 1.70 (s, 3H), 1.28 (t, J=6.0 Hz, 1H). ESI-MS: m/z=523 [M+H$^+$]

Example 350

9-[1,4]Diazepan-1-yl-2-[2-(2,4-difluoro-phenyl)-2H-[1,2,4]triazol-3-yl]-4,5-dihydro-6-oxa-1-thia-10-aza-benzo[e]azulene 350

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol), 1,4-diazepane (120 mg, 1.2 mmol), Pd$_2$(dba)$_3$ (210 mg, 0.3 mmol), Xphos (142 mg, 0.3 mmol), t-BuONa (576 mg, 6 mmol) and dioxane (6 mL) were added into a 10 mL of sealed tube, and the mixture was heated by microwave at 112° C. for 7 min under N$_2$. The reaction mixture was filtered to gather the solution. The water was added and extracted by DCM (50 mL×3). The combined organic layers were dried over Na$_2$SO$_4$, concentrated in vacuo, and separated by column (DCM/EtOAc=4:1) to get 350 (120 mg, yield: 25%). $^1$HNMR (DMSO-d$_6$, 400 MHz): δ8.04 (s, 1H), 7.97 (s, 1H), 7.67-7.65 (m, 1H), 7.50-7.46 (m, 1H), 7.20 (t, J=8 Hz, 1H), 7.02 (s, 1H), 6.97 (d, J=8.8 Hz, 1H), 6.36 (d, J=8.8 Hz, 1H), 3.92 (d, J=4.4 Hz, 2H), 3.37-3.31 (m, 4H), 2.87 (d, J=4.4 Hz, 4H), 2.72 (s, 2H), 2.57 (s, 2H), 1.59 (s, 2H). ESI-MS: m/z=481 [M+H$^+$]

Example 351

2-[2-(2,4-Difluoro-phenyl)-2H-[1,2,4]triazol-3-yl]-9-[(3R,5S)-3,5-dimethyl-4-(2,2,2-trifluoro-ethyl)-piperazin-1-yl]-4,5-dihydro-6-oxa-1-thia-10-aza-benzo[e]azulene 351

To a solution of compound 316 (100 mg, 0.17 mmol) in tetrahydrofuran (5 mL) was added a solution of borane/dimethylsulfane (10 mol/L, 2 mL) dropwise at 0° C. After the addition was completed, the reaction mixture was stirred at that temperature for 30 min and then allowed to warm to 50° C. After stirred for another 1 hour the reaction mixture was quenched by adding 15 mL of methanol and 5 mL of 1 M HCl aqueous solution slowly. The mixture was stirred at room temperature for 2 hours before concentration to the residue. The mixture was treated with dichloromethane and water. The organic layer was concentrated to dryness and the crude was purified by pre-TLC (Hexanes/EtOAc=1:1) to afford 60 mg of 351. (Yield: 61%)$^1$H NMR (CDCl$_3$, 400 MHz): δ8.02 (s, 1H), 7.51-7.46 (m, 1H), 7.09-6.97 (m, 4H), 6.45 (d, J=8.8 Hz, 1H), 4.18 (t, J=4.8 Hz, 2H), 3.84-3.80 (m, 2H), 3.27 (q, J=9.6 Hz, 2H), 3.07 (t, J=4.8 Hz, 2H), 2.84 (d, J=6.8 Hz, 2H), 2.57-2.51 (m, 2H), 1.22-1.34 (d, J=6.0 Hz, 6H). LC-MS (ESI): m/z=577 [M+H]$^+$ Example 352

4-{2-[2-(2,4-Difluoro-phenyl)-2H-[1,2,4]triazol-3-yl]-4,5-dihydro-6-oxa-1-thia-10-aza-benzo[e]azulen-9-yl}-piperazin-2-one 352

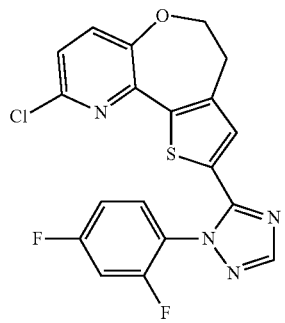 [SMILES: Fc1ccc(-n2ncnc2-c2cc3c(s2)-c2nc(Cl)ccc2OCC3)c(F)c1]

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (100 mg, 0.24 mmol), piperazin-2-one (48 mg, 0.48 mmol), $^t$BuONa (47 mg, 0.48 mmol), Pd$_2$(dba)$_3$ (22 mg, 0.2 mmol) and Xphos (23 mg, 0.048 mmol) in dioxane (2 mL) was bubbled N$_2$ for 10 min and then stirred at 115° C. for 5 min under the irradition of microwave. The mixture was filtered by celite. The filtrate was concentrated to dryness and purified by pre-TLC (EtOAc) and pre-HPLC to afford 15 mg of 352. (yield: 13%)$^1$H NMR (CDCl$_3$, 400 MHz): δ8.02 (s, 1H, ArH), 7.49-6.96 (m, 5H), 6.41 (d, J=8.8 Hz, 1H), 5.95 (s, 1H), 4.19 (t, J=4.8 Hz, 2H), 3.99 (s, 2H), 3.76 (t, J=5.2 Hz, 2H), 3.47 (t, J=5.2 Hz, 2H), 3.06 (t, J=4.8 Hz, 2H). LC-MS (ESI): m/z=481 [M+H]$^+$ Example 353

1-(4-{2-[2-(2,4-Difluoro-phenyl)-2H-[1,2,4]triazol-3-yl]-4,5-dihydro-6-oxa-1-thia-10-aza-benzo[e]azulen-9-ylamino}-piperidin-1-yl)-ethanone 353

9-Chloro-2-[2-(2,4-difluoro-phenyl)-2H-[1,2,4]triazol-3-yl]-4,5-dihydro-6-oxa-1-thia-10-aza-benzo[e]azulene (208 mg, 0.5 mmol), 1-(4-aminopiperidin-1-yl)ethanone (170 mg, 0.6 mmol), Pd(OAc)$_2$ (11 mg, 0.05 mmol), Xphos (14 mg, 0.05 mmol), t-BuONa (115 mg, 1.0 mmol) and dioxane (2.0 ml) was added into a 10 mL of sealed tube, and the mixture was heated by microwave at 112° C. for 7 min under N$_2$. The reaction mixture was filtered to gather the solution and water was added. The mixture was extracted by DCM (20 mL×3). The combined organic layers were dried over Na$_2$SO$_4$, concentrated in vacuo, and purified by preparative TLC (DCM/EtOAc=10:1) to get 353 (115 mg, yield: 44%). $^1$HNMR (DMSO-d$_6$, 400 MHz): δ8.24 (s, 1H), 7.87-7.83 (m, 1H), 7.70 (t, J=2.8 Hz, 1H), 7.69 (t, J=2.8 Hz, 1H), 7.38 (s, 1H), 7.07 (d, J=8.8 Hz, 1H), 6.43 (d, J=11.2 Hz, 1H), 6.37 (d, J=8.8 Hz, 1H), 4.14-4.03 (m, 4H), 3.69-3.66 (m, 2H), 3.06-3.04 (m, 2H), 2.64 (t, J=2.0 Hz, 1H), 2.87 (s, 3H), 1.88-1.78 (m, 2H), 1.23-1.22 (m, 2H). ESI-MS: m/z=523 [M+H$^+$]

Example 354

2-Methyl-1-{4-[2-(2-pyridin-4-ylmethyl-2H-[1,2,4]triazol-3-yl)-4,5-dihydro-6-oxa-3-thia-1-aza-benzo[e]azulen-8-yl]-pyrazol-1-yl}-propan-2-ol 354

Following the procedure for 114, 8-Bromo-2-(2-pyridin-4-ylmethyl-2H-[1,2,4]triazol-3-yl)-4,5-dihydro-6-oxa-3-thia-1-aza-benzo[e]azulene was reacted with 2-Methyl-1-[4-(4,4,5,5-tetramethyl-[1,3,2]dioxaborolan-2-yl)-pyrazol-1-yl]-propan-2-ol to give 354. MS(ESI+) 500.1. $^1$H NMR (400 MHz, DMSO) δ 8.56 (dd, J=4.5, 1.6, 2H), 8.24 (s, 1H), 8.15 (s, 1H), 8.03 (d, J=8.3, 1H), 7.93 (s, 1H), 7.32 (dd, J=8.3, 1.8, 1H), 7.26 (d, J=1.8, 1H), 7.23-7.19 (m, 2H), 6.12 (s, 2H), 4.71 (s, 1H), 4.35 (t, J=5.0, 2H), 4.03 (s, 2H), 3.43 (t, J=5.0, 2H), 1.09 (s, 6H)

Example 355

2-Methyl-1-(4-{2-[1-(2,2,2-trifluoro-ethyl)-1H-imidazol-2-yl]-4,5-dihydro-6-oxa-3-thia-1-aza-benzo[e]azulen-8-yl}-pyrazol-1-yl)-propan-2-ol 355

To a solution of 8-Bromo-2-(1H-imidazol-2-yl)-4,5-dihydro-6-oxa-3-thia-1-aza-benzo[e]azulene (0.430 g, 1.23 mmol) in N,N-Dimethylformamide (17.2 mL, 222 mmol) was added Cesium Carbonate (0.805 g, 2.47 mmol). After 45 min. 2-iodo-1,1,1-trifluoro-ethane (0.241 mL, 2.47 mmol) was added to the reaction mixture. The reaction mixture was stirred at 50C 4 h. The reaction was quenched with water then extracted with EtOAc 2×. The organic layers was combined, dried Na2SO4, concentrated and purified by chromatography (EtOAc/Hex) (eluted at 35%) to give 8-Bromo-2-[1-(2,2,2-trifluoro-ethyl)-1H-imidazol-2-yl]-4,5-dihydro-6-oxa-3-thia-1-aza-benzo[e]azulene. MS: (ESI+)=330.1.

8-Bromo-2-[1-(2,2,2-trifluoro-ethyl)-1H-imidazol-2-yl]-4,5-dihydro-6-oxa-3-thia-1-aza-benzo[e]azulene (110.0 mg, 0.2557 mmol) dissolved in Acetonitrile (0.534 mL, 10.2 mmol) and with dissolved 2.00 M of Potassium carbonate in Water (0.256 mL). Degas by bubbling nitrogen for 5 min. The reaction was charged with 2-methyl-1-(4-(4,4,5,5-tetramethyl-1,3,2-dioxaborolan-2-yl)-1H-pyrazol-1-yl)propan-2-ol (102 mg, 0.384 mmol) then Tetrakis(triphenylphosphine)palladium(0) (41.36 mg, 0.03579 mmol). The reaction was heated in microwave at 140 C for 10 min. The reaction was cooled to r.t. then extracted with ethyl acetate. Combined organics concentrated and purified by reverse phase HPLC to give 355. MS: (ESI+)=490.1. $^1$H NMR (400 MHz, DMSO) δ 8.24 (d, J=8.3 Hz, 1H), 8.17 (s, 1H), 7.95 (s, 1H), 7.55 (s, 1H), 7.41 (dd, J=8.3, 1.8 Hz, 1H), 7.29 (d, J=1.8 Hz, 1H), 7.18 (d, J=1.2 Hz, 1H), 5.74 (q, J=8.9 Hz, 2H), 4.71 (s, 1H), 4.37 (t, J=5.0 Hz, 2H), 4.03 (s, 2H), 3.40 (t, J=5.0 Hz, 2H), 1.09 (s, 6H)

Example 356

3-{8-[1-(2-Hydroxy-2-methyl-propyl)-1H-pyrazol-4-yl]-4,5-dihydro-6-oxa-3-thia-1-aza-benzo[e]azulen-2-yl}-4,4-dimethyl-oxazolidin-2-one 356

Step 1: 1-(1-Hydroxy-2-methylpropan-2-yl)thiourea

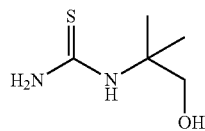

Following the procedure in US2008/45579, 2008, 2-amino-2-methylpropan-1-ol was coupled with benzoyl-isothiocyanate to give N-(1-hydroxy-2-methylpropan-2-ylcarbamothioyl)benzamide which was then reacted with lithium hydroxide to give 1-(1-hydroxy-2-methylpropan-2-yl)thiourea. 1H NMR (400 MHz, DMSO) δ 7.09 (s, 2H), 5.01 (s, 1H), 3.44 (s, 2H), 1.30 (s, 6H)

Step 2: 2-(8-Bromo-4,5-dihydrothiazolo[4,5-d]benzo[b]oxepine-2-ylamino)-2-methylpropan-1-ol

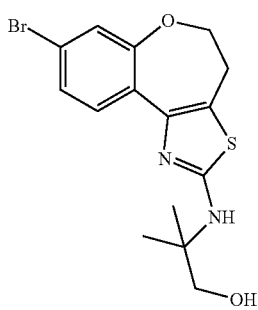 [SMILES: CC(C)(CO)Nc1nc2c(s1)CCOc1cc(Br)ccc1-2]

A mixture of 0.67 g (5.0 mmol) of 1-(1-hydroxy-2-methylpropan-2-yl)thiourea and 1.60 g (5.00 mmol) of 4,8-dibromo-3,4-dihydro-2Hbenzo[b]oxepin-5-one in 30 ml of ethanol was heated under reflux for 3 hours. The mixture was concentrated, the residue purified on silica gel column eluting the product with 10% of methanol in dichloromethane. Yield 1.38 g (75%). MS(ESI+): 369.3

Step 3: 3-(8-Bromo-4,5-dihydrothiazolo[4,5-d]benzo[b]oxepine-2-yl)-4,4-dimethyloxazolidin-2-one

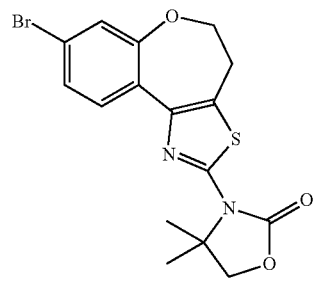 [SMILES: CC1(C)COC(=O)N1c1nc2c(s1)CCOc1cc(Br)ccc1-2]

Triphosgene (148 mg, 0.500 mmol) was added to a mixture of 185 mg (0.500 mmol) of 2-(8-bromo-4,5-dihydrothiazolo[4,5-d]benzo[b]oxepine-2-ylamino)-2-methylpropan-1-ol and 0.522 ml (3.00 mmol) of diisopropylethylamine in 7.0 ml of methylene chloride. The reaction mixture was stirred for 3 hours and concentrated in vacuum. The residue was partitioned between ethyl acetate and 5% aqueous citric acid. The organic extracts were washed with water, brine, dried over magnesium sulfate and concentrated in vacuum. Yield 194 mg (98%). MS(ESI+): 396.3

Step 4

3-(8-bromo-4,5-dihydrothiazolo[4,5-d]benzo[b]oxepine-2-yl)-4,4-dimethyloxazolidin-2-one was coupled with 2-methyl-1-(4-(4,4,5,5-tetramethyl-1,3,2-dioxaborolan-2-yl)-1H-pyrazol-1-yl)propan-2-ol to give 356. Yield 22%. MS(ESI+): 455.1. 1H NMR (400 MHz, DMSO) δ 8.16 (d, J=8.3, 1H), 8.11 (s, 1H), 7.90 (s, 1H), 7.37 (dd, J=8.3, 1.8, 1H), 7.24 (d, J=1.8, 1H), 4.71 (s, 1H), 4.32 (d, J=6.9, 4H), 4.05-4.00 (m, 2H), 3.25 (t, J=5.0, 2H), 1.76 (s, 6H), 1.09 (s, 6H)

Example 357

2-{4-[2-(2-Isopropyl-2H-[1,2,4]triazol-3-yl)-4,5-dihydro-6-oxa-3-thia-1-aza-benzo[e]azulen-9-yl]-piperidin-1-yl}-acetamide 357

Following the procedure for 319, 2-(2-isopropyl-2H-[1,2,4]triazol-3-yl)-9-piperidin-4-yl-4,5-dihydro-6-oxa-3-thia-1-aza-benzo[e]azulene TFA salt was alkylated with bromoacetamide to give 357 isolated as a white solid (167 mg, 86%). LCMS: R$_T$=7.55 min, [M+H]$^+$=453. $^1$H NMR δ (ppm) (DMSO-d6): 8.23 (1H, d, J=2.30 Hz), 8.06 (1H, s), 7.14 (1H, dd, J=8.34, 2.37 Hz), 7.10 (2H, s), 6.95 (1H, d, J=8.26 Hz), 5.79-5.68 (1H, m), 4.33-4.27 (2H, m), 3.41-3.35 (2H, m), 2.92-2.81 (4H, m), 2.50 (1H, m), 2.17 (2H, dd, J=12.36, 10.20 Hz), 1.78 (2H, d, J=12.48 Hz), 1.73-1.61 (2H, m), 1.53 (6H, d, J=6.61 Hz)

Example 358

(R)-2-Hydroxy-1-{4-[2-(2-isopropyl-2H-[1,2,4]triazol-3-yl)-4,5-dihydro-6-oxa-3-thia-1-aza-benzo[e]azulen-9-yl]-piperidin-1-yl}-propan-1-one 358

Following the procedure for 318, 2-(2-isopropyl-2H-[1,2,4]triazol-3-yl)-9-piperidin-4-yl-4,5-dihydro-6-oxa-3-thia-1- aza-benzo[e]azulene TFA salt was reacted to give 358 isolated as a white solid (90 mg, 45%). LCMS: $R_T$=11.57 min, [M+H]$^+$=468. $^1$H NMR δ (ppm) (DMSO-d6): 8.19 (1H, d, J=2.28 Hz), 8.06 (1H, s), 7.14 (1H, d, J=8.35 Hz), 6.96 (1H, d, J=8.24 Hz), 5.78-5.70 (1H, m), 4.83 (1H, s), 4.48 (1H, d, J=12.45 Hz), 4.42 (1H, q, J=6.52 Hz), 4.30 (2H, t, J=5.02 Hz), 4.08 (1H, s), 3.38 (2H, t, J=5.02 Hz), 3.09 (1H, t, J=13.26 Hz), 2.84-2.75 (1H, m), 2.71-2.59 (1H, m), 1.84 (2H, d, J=12.55 Hz), 1.57-1.47 (8H, m), 1.17 (3H, t, J=5.38 Hz)

Example 359

(S)-2-Hydroxy-1-{3-[2-(2-isopropyl-2H-[1,2,4]triazol-3-yl)-4,5-dihydro-6-oxa-3-thia-1-aza-benzo[e]azulen-9-yl]-azetidin-1-yl}-propan-1-one 359

Following the procedure for 318, 9-azetidin-3-yl-2-(2-isopropyl-2H-[1,2,4]triazol-3-yl)-4,5-dihydro-6-oxa-3-thia-1-aza-benzo[e]azulene and sodium L-lactate were reacted in DMF to give 359. LCMS: $R_T$=10.69 min, [M+H]$^+$=440. $^1$H NMR δ (ppm) (CDCl$_3$): 8.36 (1H, s), 7.90 (1H, s), 7.20-7.11 (1H, m), 7.09-7.01 (1H, m), 5.84-5.75 (1H, m), 4.62-4.30 (4H, m), 4.26-4.07 (3H, m), 3.98-3.87 (1H, m), 3.43-3.35 (2H, m), 1.61 (6H, d, J=6.65 Hz), 1.32 (3H, dd, J=10.70, 6.64 Hz). 1 Exchangeable not observed Example 360

N2-(2-chloro-5-(3-hydroxyazetidine-1-carbonyl)phenyl)-N2,N8-dimethyl-4,5-dihydrobenzo[b]thieno[2,3-d]oxepine-2,8-dicarboxamide 360

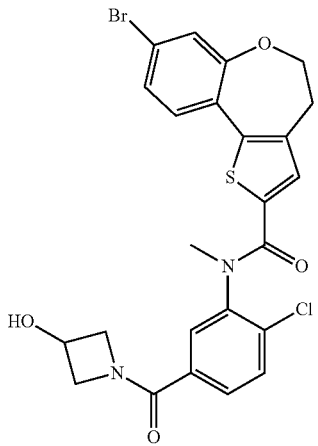 [SMILES: CN(C(=O)c1cc2c(s1)-c1ccc(Br)cc1OCC2)c1cc(C(=O)N2CC(O)C2)ccc1Cl]

To a mixture of 3-(8-bromo-N-methyl-4,5-dihydrobenzo[b]thieno[2,3-d]oxepine-2-carboxamido)-4-chlorobenzoic acid (2.5 g, 5.07 mmol) in THF (50 mL) was added EDCI (1.94 g, 10.14 mmol), HOBt (1.03 g, 7.61 mmol), DIPEA (5 mL) and 3-hydroxyazetidine hydrochloride (0.83 g, 7.61 mmol) by sequence under nitrogen atmosphere at room temperature. The reaction mixture was stirred overnight, diluted with water, extracted with EtOAc. The organic layer was dried over Na$_2$SO$_4$, concentrated in vacuo. The crude product was purified by flash column chromatography on silica gel (eluted by hexanes:EtOAc=1:2) to give 8-bromo-N-(2-chloro-5-(3-hydroxyazetidine-1-carbonyl)phenyl)-N-methyl-4,5-dihydrobenzo[b]thieno[2,3-d]oxepine-2-carboxamide (1.6 g, yield 58%). LC-MS: (ESI, m/z)=547 [M+H]$^+$ A suspension of 8-bromo-N-(2-chloro-5-(3-hydroxyazetidine-1-carbonyl)phenyl)-N-methyl-4,5-dihydrobenzo[b]thieno[2,3-d]oxepine-2-carboxamide (500 mg, 0.91 mmol), Pd(OAc)$_2$ (10 mg, 0.046 mmol), Xantphos (53 mg, 0.091 mmol), MeNH$_2$.HCl (92 mg, 1.37 mmol) and Na$_2$CO$_3$ (289 mg, 2.73 mmol) in toluene (5 mL) and DMF (5 mL) was heated at 80° C. under atmosphere of CO from balloon for overnight. Then it was filtrated and concentrated, the crude product was purified by flash column chromatography on silica gel (DCM:MeOH=20:1 as eluted solvent) to give a white solid which was washed with MeOH and dried to give 360 (221.5 mg, yield 46%). $^1$H NMR (DMSO, 400 MHz): δ8.43 (m, 1H, NH), 7.87-7.43 (m, 6H, ArH), 6.65 (s, 1H, =CH), 5.52 (d, J=6.4 Hz, 1H, OH), 4.48-2.75 (m, 15H). LC-MS: (ESI, m/z)=526 [M+H]$^+$ Example 361

N2-(2-chloro-5-((S)-2-hydroxypropylcarbamoyl)phenyl)-N2,N8-dimethyl-4,5-dihydrobenzo[b]thieno[2,3-d]oxepine-2,8-dicarboxamide 361

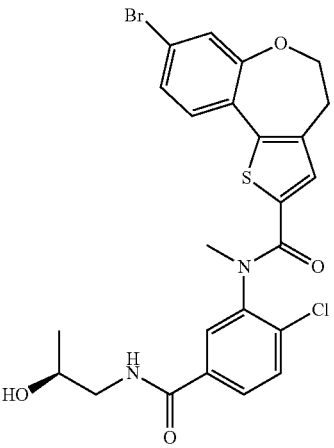 [SMILES: C[C@H](O)CNC(=O)c1ccc(Cl)c(N(C)C(=O)c2cc3c(s2)-c2ccc(Br)cc2OCC3)c1]

To the mixture of 3-(8-bromo-N-methyl-4,5-dihydrobenzo[b]thieno[2,3-d]oxepine-2-carboxamido)-4-chlorobenzoic acid (2.5 g, 5.07 mmol) in THF (50 mL) was added EDCI (1.94 g, 10.14 mmol), HOBt (1.03 g, 7.61 mmol), DIPEA (5 mL) and (S)-1-amino-propan-2-ol (0.57 g, 7.61 mmol) by sequence under nitrogen atmosphere at room temperature. The reaction mixture was stirred overnight, diluted with water. The resulting precipitate was washed with water and EtOAc to give 8-bromo-N-(2-chloro-5-((S)-2-hydroxypropylcarbamoyl)phenyl)-N-methyl-4,5-dihydrobenzo[b]thieno[2,3-d]oxepine-2-carboxamide (2.0 g, yield 72%). $^1$H NMR (DMSO-d6, 400 MHz): δ8.62-6.60 (m, 8H, NH, ArH), 4.77 (d, J=4.8 Hz, 1H, OH), 4.18 (br s, 2H, CH$_2$), 3.79-3.75 (m, 1H, CH), 3.31 (s, 3H, NCH$_3$), 3.19 (br s, 2H, CH$_2$), 2.94 (br s, 2H, CH$_2$), 1.05 (d, J=6.0 Hz, 3H, CH$_3$). LC-MS: (ESI, m/z)=549 [M+H]$^+$ A suspension of 8-bromo-N-(2-chloro-5-((S)-2-hydroxypropylcarbamoyl)phenyl)-N-methyl-4,5-dihydrobenzo[b]thieno[2,3-d]oxepine-2-carboxamide (500 mg, 1.00 mmol), Pd(OAc)$_2$ (11 mg, 0.05 mmol), Xantphos (58 mg, 0.01 mmol), MeNH$_2$.HCl (101 mg, 1.50 mmol) and Na$_2$CO$_3$ (318 mg, 3.00 mmol) in toluene (5 mL) and DMF (5 mL) was heated at 80° C. under atmosphere of CO from balloon overnight. Then it was filtrated and concentrated, diluted with water. The resulting precipitate was washed with water and DCM, dried to give 361 (158.9 mg, yield 30%). $^1$H NMR (DMSO-d6, 400 MHz): δ8.63-7.43 (m, 8H, NH, ArH), 6.62 (s, 1H, =CH), 4.77 (d, J=4.0 Hz, 1H, OH), 4.18 (br s, 2H, CH$_2$), 3.78-3.76 (m, 1H, CH), 3.32 (s, 3H, NCH$_3$), 3.24 (br s, 2H, CH$_2$), 2.98 (br s, 2H, CH$_2$), 2.75 (d, J=4.4 Hz, 3H, NCH$_3$)., 1.06 (d, J=6.4 Hz, 3H, CH$_3$). LC-MS: (ESI, m/z)=528 [M+H]$^+$, 550 [M+Na]$^+$ Example 362

1-(3-{2-[2-(2,4-Difluoro-phenyl)-2H-[1,2,4]triazol-3-yl]-4,5-dihydro-6-oxa-1-thia-10-aza-benzo[e]azulen-9-ylamino}-azetidin-1-yl)-ethanone 362

Compound 435 (150 mg, 0.3 mmol) was dissolved in THF, and DIPEA was added. Acetyl chloride was added dropwise into the solution. After the addition, the reaction mixture was further stirred at room temperature for 12 h. The reaction mixture was concentrated in vacuo, and dissolved in DCM. The organic layer was washed by water, dried by Na$_2$SO$_4$, concentrated in vacuo, and purified by prep. TLC (DCM/EtOAc=10:1) to give 362 (15 mg, 10%). $^1$HNMR (DMSO-d$_6$, 400 MHz): δ8.36 (s, 1H), 8.02-7.92 (m, 1H), 7.83 (t, J=8.8 Hz, 1H), 7.52 (t, J=8.1 Hz, 1H), 7.31 (s, 1H), 7.24 (d, J=8.8 Hz, 1H), 6.50 (d, J=8.4 Hz, 1H), 4.38-4.35 (m, 2H), 4.25-4.16 (m, 4H), 3.74 (s, 1H), 3.24 (s, 2H), 1.89 (s, 3H). ESI-MS: m/z=495 [M+H]$^+$ Example 363

{2-[2-(2,4-Difluoro-phenyl)-2H-[1,2,4]triazol-3-yl]-4,5-dihydro-6-oxa-1-thia-10-aza-benzo[e]azulen-9-yl}-(1-methanesulfonyl-azetidin-3-yl)-amine 363

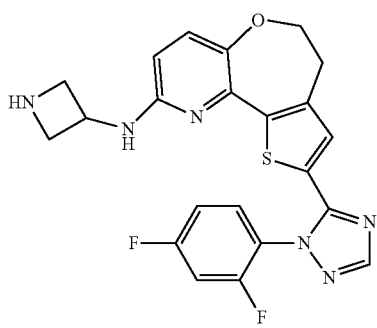 [SMILES: Fc1ccc(-n2ncnc2-c2cc3c(s2)-c2nc(NC4CNC4)ccc2OCC3)c(F)c1]

Azetidin-3-yl-{2-[2-(2,4-difluoro-phenyl)-2H-[1,2,4]triazol-3-yl]-4,5-dihydro-6-oxa-1-thia-10-aza-benzo[e]azulen-9-yl}-amine (452 mg, 1.0 mmol), Methanesulfonyl chloride (136 mg, 1.2 mmol), DIPEA (260 mg, 2.0 mmol) was dissolved in THF (10 mL). The reaction mixture was stirred at room temperature (r.t.) for 1 hour. LC-MS indicated the reaction was completed. To the reaction mixture was added 20 mL of water, the mixture was extracted with dichloromethane. The organic layer was dried over anhydrous sodium sulfate, and concentrated to dryness. The crude was purified by pre-HPLC to afford 363 (57.2 mg, yield: 11%). $^1$HNMR (DMSO-d$_6$, 400 MHz): δ 9.50 (s, 1H), 8.72 (s, 1H), 8.31 (s, 1H), 7.97-7.91 (m, 2H), 7.77-7.72 (m, 2H), 7.48-7.43 (m, 2H), 7.15 (s, 1H), 6.99 (s, 1H), 6.72 (d, J=4.4 Hz, 1H), 4.31 (s, 2H), 3.86 (s, 2H), 3.33 (s, 2H), 3.15 (s, 2H), 2.75 (s, 6H). ESI-MS: m/z=531 [M+H]$^+$ Example 364

N-(1-Acetyl-azetidin-3-yl)-N-{2-[2-(2,4-difluoro-phenyl)-2H-[1,2,4]triazol-3-yl]-4,5-dihydro-6-oxa-1-thia-10-aza-benzo[e]azulen-9-yl}-acetamide 364

Compound 435 (150 mg, 0.3 mmol) was dissolved in THF, and DIPEA was added. Acetyl chloride was added dropwise into the solution. After the addition, the reaction mixture was further stirred at room temperature for 12 h. The reaction mixture was concentrated in vacuo, and dissolved in DCM. The organic layer was washed by water, dried by Na$_2$SO$_4$, concentrated in vacuo, and purified by prep. TLC (DCM/EtOAc=10:1) to give 364 (20 mg, yield: 12%). $^1$HNMR (DMSO-d$_6$, 400 MHz): δ8.02 (s, 1H), 7.74-7.72 (m, 1H), 7.41-7.37 (m, 2H), 7.26 (t, J=8.8 Hz, 1H), 7.18 (d, J=8.4 Hz, 1H), 4.99 (m, 1H), 4.28-4.24 (m, 4H), 4.03 (t, J=8.4 Hz, 1H), 3.96 (t, J=9.6 Hz, 1H), 3.56-3.53 (m, 1H), 3.08 (s, 1H), 3.24 (s 2H), 1.91 (s, 3H), 1.58 (s, 3H). ESI-MS: m/z=536 [M+H$^+$]

Example 365

4,5-Dihydro-6-oxa-1-thia-benzo[e]azulene-2,8-dicarboxylic acid 2-{[2-chloro-5-((R)-2-hydroxy-propyl-carbamoyl)-phenyl]-methyl-amide} 8-methylamide 365

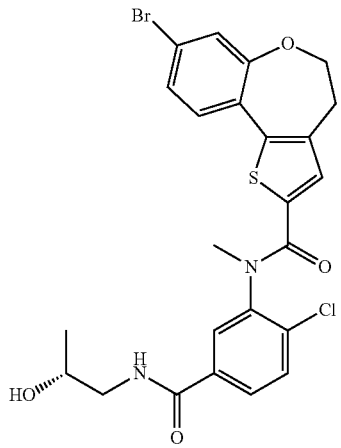 [SMILES: C[C@@H](O)CNC(=O)c1ccc(Cl)c(N(C)C(=O)c2cc3c(s2)-c2ccc(Br)cc2OCC3)c1]

To a mixture of 3-(8-bromo-N-methyl-4,5-dihydrobenzo[b]thieno[2,3-d]oxepine-2-carboxamido)-4-chlorobenzoic acid (3 g, 6.09 mmol) in THF (50 mL) was added EDCI (2.34 g, 12.18 mmol), HOBt (1.23 g, 9.13 mmol), DIPEA (5 mL) and (R)-1-amino-propan-2-ol (0.69 g, 9.13 mmol) by sequence under nitrogen atmosphere at room temperature. The reaction mixture was stirred overnight, diluted with water. The resulting precipitate was washed with water and EtOAc to give 8-bromo-N-(2-chloro-5-((R)-2-hydroxypropylcarbamoyl)phenyl)-N-methyl-4,5-dihydrobenzo[b]thieno[2,3-d]oxepine-2-carboxamide (2.7 g, yield 81%). $^1$H NMR (DMSO-d6, 400 MHz): δ8.62 (t, J=5.2 Hz, 1H, NH), 8.11-6.11 (m, 7H, ArH), 4.77 (d, J=4.4 Hz, 1H, OH), 4.18 (br s, 2H, CH$_2$), 3.81-3.75 (m, 1H, CH), 3.32 (s, 3H, NCH$_3$), 3.19 (br s, 2H, CH$_2$), 2.94 (br s, 2H, CH$_2$), 1.05 (d, J=6.0 Hz, 3H, CH$_3$). LC-MS: (ESI, m/z)=549 [M+H]$^+$ The suspension of 8-bromo-N-(2-chloro-5-((R)-2-hydroxypropylcarbamoyl)phenyl)-N-methyl-4,5-dihydrobenzo[b]thieno[2,3-d]oxepine-2-carboxamide (500 mg, 1.00 mmol), Pd(OAc)$_2$ (11 mg, 0.05 mmol), Xantphos (58 mg, 0.01 mmol), MeNH$_2$.HCl (101 mg, 1.50 mmol) and Na$_2$CO$_3$ (318 mg, 3.00 mmol) in toluene (5 mL) and DMF (5 mL) was heated at 80° C. under atmosphere of CO from balloon overnight. Then it was filtrated and concentrated, diluted with water. The resulting precipitate was washed with water and DCM, the crude product was purified by preparative HPLC to give 365 (52.3 mg, yield 10%). $^1$H NMR (DMSO-d6, 400 MHz): δ8.63-7.43 (m, 8H, NH, ArH), 6.61 (s, 1H, =CH), 4.78 (brs, 1H, OH), 4.20 (brs, 2H, CH$_2$), 3.80-3.79 (m, 1H, CH), 3.35-2.66 (m, 10H, CH$_3$, CH$_2$), 2.98 (brs, 2H, CH$_2$), 2.75 (d, J=4.4 Hz, 3H, NCH$_3$)., 1.07-0.97 (m, 3H, CH$_3$). LC-MS: (ESI, m/z)=528 [M+H]$^+$

Example 366

1-(4-{2-[5-Amino-2-(2,4-difluoro-phenyl)-2H-[1,2,4]triazol-3-yl]-4,5-dihydro-6-oxa-3-thia-1-aza-benzo[e]azulen-8-yl}-pyrazol-1-yl)-2-methyl-propan-2-ol 366

Similarly to as described in General Procedure C, 5-(8-Bromo-4,5-dihydro-6-oxa-3-thia-1-aza-benzo[e]azulen-2-yl)-1-(2,4-difluoro-phenyl)-1H-[1,2,4]triazol-3-ylamine was reacted with 2-methyl-1-(4-(4,4,5,5-tetramethyl-1,3,2-dioxaborolan-2-yl)-1H-pyrazol-1-yl)propan-2-ol. Purification of the crude reaction mixture by reverse phase HPLC gave 366. LCMS: 536.1.

Example 367

1-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-2-methyl-propan-2-ol 367

Similar to as described in General Procedure C, 8-Bromo-2-(2-isopropyl-2H-[1,2,4]triazol-3-yl)-4,5-dihydro-6-oxa-3-thia-1-aza-benzo[e]azulene 27 was reacted with 2-methyl-1-(4-(4,4,5,5-tetramethyl-1,3,2-dioxaborolan-2-yl)-1H-pyrazol-1-yl)propan-2-ol. Purification of the crude reaction mixture by reverse phase HPLC gave 367. LCMS: 451.1

Example 368

1-{4-[2-(5-Amino-2-isopropyl-2H-[1,2,4]triazol-3-yl)-4,5-dihydro-6-oxa-3-thia-1-aza-benzo[e]azulen-8-yl]-pyrazol-1-yl}-2-methyl-propan-2-ol 368

Similar to as described in General Procedure C, 5-(8-Bromo-4,5-dihydro-6-oxa-3-thia-1-aza-benzo[e]azulen-2-yl)-1-isopropyl-1H-[1,2,4]triazol-3-ylamine was reacted with 2-methyl-1-(4-(4,4,5,5-tetramethyl-1,3,2-dioxaborolan-2-yl)-1H-pyrazol-1-yl)propan-2-ol. Purification of the crude reaction mixture by reverse phase HPLC gave 368. LCMS: 466.2.

Example 369

9-[1-((R)-2-Hydroxy-propyl)-1H-pyrazol-4-yl]-4,5-dihydro-6-oxa-3-thia-1-aza-benzo[e]azulene-2-carboxylic acid (2-hydroxy-ethyl)-isopropyl-amide 369

Following the procedure for 277, 9-Bromo-4,5-dihydro-6-oxa-3-thia-1-aza-benzo[e]azulene-2-carboxylic acid (2-hydroxy-ethyl)-isopropyl-amide (418 mg, 1.02 mmol) and (R)-1-(4-(4,4,5,5-tetramethyl-1,3,2-dioxaborolan-2-yl)1H-pyrazol-1-yl)propan-2-ol (307.4 mg, 1.22 mmol) were reacted to give 369 (44.8 mg, 10% yield, M+1 457.1).

Example 370

5-(8-Azetidin-3-yl-4,5-dihydro-6-oxa-1-thia-benzo[e]azulen-2-yl)-1-isopropyl-1H-[1,2,4]triazole 370

Following the procedure for 419, 5-(8-bromo-4,5-dihydrobenzo[b]thieno[2,3-d]oxepin-2-yl)-1-isopropyl-1H-1,2,4-triazole (313.4 mg, 0.803 mmol) was dissolved in N,N-dimethyacetamide and purged with nitrogen. Added [1,1'-Bis(diphenylphosphino)ferrocene]dichloropalladium(II) complex with dichloromethane (1:1) (32.8 mg, 0.04 mmol) and copper(I)iodide (15.3 mg, 0.08 mmol). Bubbled in nitrogen for 10 minutes. Added (1-(tert-butoxycarbonyl)azetidin-3-yl)zinc(II) iodide (279.8 mg, 0.80 mmol) in 2.8 mL DMA. Heated at 80° C. overnight. Complete reaction was confirmed by LCMS. Diluted reaction mixture with 1 M HCl and extracted tert-butyl 3-(2-(1-isopropyl-1H-1,2,4-triazol-5-yl)-4,5-dihydrobenzo[b]thieno[2,3-d]oxepin-8-yl)azetidine-1-carboxylate with ethyl acetate. Dried over magnesium sulfate and concentrated in vacuo. Purified by flash chromatography (0 to 50% ethyl acetate in hexanes). Concentrated in vacuo and re-dissolved the residue in 10 mL 1,4-dioxane. Added 5 mL 4 N HCl in dioxane and let stir for 2 hours. Complete deprotection was confirmed by LCMS. Concentrated in vacuo purified by HPLC to give 370 (33.3 mg, 11% yield, M=1 367.1)

Example 371

2-{3-[2-(2-Isopropyl-2H-[1,2,4]triazol-3-yl)-4,5-dihydro-6-oxa-3-thia-1-aza-benzo[e]azulen-9-yl]-azetidin-1-yl}-acetamide 371

Following the procedure of 319, 9-azetidin-3-yl-2-(2-isopropyl-2H-[1,2,4]triazol-3-yl)-4,5-dihydro-6-oxa-3-thia-1-aza-benzo[e]azulene and bromoacetamide were reacted in DMF to give 371 (111 mg, 53%). LCMS: R$_T$=6.96 min, [M+H]$^+$=425. $^1$H NMR δ (ppm) (CDCl$_3$): 8.31 (1H, d, J=2.35 Hz), 7.90 (1H, s), 7.17 (1H, dd, J=8.28, 2.36 Hz), 7.03 (1H, d, J=8.26 Hz), 7.01-6.85 (1H, m), 5.91-5.83 (1H, m), 5.41 (1H, s), 4.37 (2H, t, J=5.06 Hz), 3.89 (2H, t, J=7.36 Hz), 3.81-3.73 (1H, m), 3.43-3.34 (4H, m), 3.22 (2H, s), 1.63 (6H, d, J=6.65 Hz)

Example 372

9-[1-(2,4-Difluoro-benzyl)-azetidin-3-yl]-2-(2-isopropyl-2H-[1,2,4]triazol-3-yl)-4,5-dihydro-6-oxa-3-thia-1-aza-benzo[e]azulene 372

A mixture of 9-azetidin-3-yl-2-(2-isopropyl-2H-[1,2,4]triazol-3-yl)-4,5-dihydro-6-oxa-3-thia-1-aza-benzo[e]azulene (0.18 g, 0.49 mmol), 2,4-difluorobenzaldehyde (64 μL, 0.59 mmol) and 4 Å molecular sieves in chloroform (7 mL) was heated to reflux for 3.5 hours. After cooling sodium triacetoxyborohydride (0.50 g, 2.36 mmol) was added and the mixture was stirred at RT overnight. Aqueous saturated sodium bicarbonate solution was added and the phases were separated. The aqueous phase was extracted with 10% MeOH/DCM (×4) and the combined organic phase was dried (Na$_2$SO$_4$) and concentrated in vacuo. The resultant residue was purified by flash chromatography (SiO$_2$, 50-100% EtOAc in cyclohexane) to give 372 (122 mg, 50%). LCMS: R$_T$=8.65 min, [M+H]$^+$=494. $^1$H NMR δ (ppm) (CDCl$_3$): 8.31

(1H, d, J=2.33 Hz), 7.90 (1H, s), 7.33 (1H, q, J=7.71 Hz), 7.14 (1H, dd, J=8.27, 2.33 Hz), 7.01 (1H, d, J=8.26 Hz), 6.86-6.74 (2H, m), 5.94-5.84 (1H, m), 4.37 (2H, t, J=5.06 Hz), 3.83-3.73 (3H, m), 3.68 (2H, s), 3.39 (2H, t, J=5.07 Hz), 3.29-3.23 (2H, m), 1.61 (6H, d, J=6.65 Hz)

Example 373

9-[1-(2-Chloro-benzyl)-azetidin-3-yl]-2-(2-isopropyl-2H-[1,2,4]triazol-3-yl)-4,5-dihydro-6-oxa-3-thia-1-aza-benzo[e]azulene 373

Following the procedure for 372, a mixture of 9-azetidin-3-yl-2-(2-isopropyl-2H-[1,2,4]triazol-3-yl)-4,5-dihydro-6-oxa-3-thia-1-aza-benzo[e]azulene (0.18 g, 0.49 mmol) and 2-chlorobenzaldehyde gave 373 (123 mg, 51%). LCMS: $R_T$=8.80 min, [M+H]$^+$=492/494. $^1$H NMR δ (ppm) (CDCl$_3$): 8.34 (1H, d, J=2.34 Hz), 7.90 (1H, s), 7.43 (1H, d, J=7.55 Hz), 7.33 (1H, dd, J=7.76, 1.47 Hz), 7.24-7.13 (3H, m), 7.01 (1H, d, J=8.25 Hz), 5.95-5.82 (1H, m), 4.40-4.34 (2H, m), 3.90-3.83 (2H, m), 3.85-3.76 (3H, m), 3.42-3.36 (2H, m), 3.35-3.28 (2H, m), 1.60 (6H, d, J=6.65 Hz)

Example 374

2-(2-Isopropyl-2H-[1,2,4]triazol-3-yl)-8-pyrrolidin-3-yl-4,5-dihydro-6-oxa-3-thia-1-aza-benzo[e]azulene 374

Following the procedure for 375, 3-[2-(2-isopropyl-2H-[1,2,4]triazol-3-yl)-4,5-dihydro-6-oxa-3-thia-1-aza-benzo[e]azulen-8-yl]-pyrrolidine-1-carboxylic acid tert-butyl ester was treated with acid. The crude product was purified by trituration with EtOAc containing a few drops of MeOH to give 374 as a pale brown solid (5.8 mg, 34%). LCMS: $R_T$=7.68 min, [M+H]$^+$=382. $^1$H NMR δ (ppm) (DMSO-d6): 9.11 (2H, s), 8.27 (1H, d, J=8.21 Hz), 8.05 (1H, s), 7.14 (1H, dd, J=8.26, 1.86 Hz), 7.03 (1H, d, J=1.80 Hz), 5.81-5.71 (1H, m), 4.35-4.29 (2H, m), 3.57 (1H, dd, J=11.24, 8.03 Hz), 3.45-3.31 (4H, m), 3.23-3.12 (1H, m), 3.11-2.99 (1H, m), 2.37-2.27 (1H, m), 1.97-1.85 (1H, m), 1.49 (6H, d, J=6.59 Hz)

Example 375

2-(2-Isopropyl-2H-[1,2,4]triazol-3-yl)-8-piperidin-4-yl-4,5-dihydro-6-oxa-3-thia-1-aza-benzo[e]azulene 375

Following the procedure for 235, 4-[2-(2-isopropyl-2H-[1,2,4]triazol-3-yl)-4,5-dihydro-6-oxa-3-thia-1-aza-benzo[e]azulen-8-yl]-piperidine-1-carboxylic acid tert-butyl ester and a 1:3 ratio of TFA:DCM gave 375 isolated as a brown solid (2.18 g, 87%). LCMS: $R_T$=2.90 min, [M+H]$^+$=396

Alternatively, to a suspension of 4-[2-(2-isopropyl-2H-[1,2,4]triazol-3-yl)-4,5-dihydro-6-oxa-3-thia-1-aza-benzo[e]azulen-8-yl]-piperidine-1-carboxylic acid tert-butyl ester (470 mg, 0.95 mmol) in MeOH (10 mL) was added 1M HCl in ether (1.9 mL, 1.90 mmol). The reaction mixture was stirred for 18 hours then the volatiles were removed in vacuo. The resultant residue was stirred in diethyl ether (20 mL) for 20 minutes then the solid was filtered off and further triturated with a mixture of MeOH and ether to give 375 as a white solid (104 mg, 28%). LCMS: $R_T$=7.82 min, [M+H]$^+$=396. $^1$H NMR δ (ppm) (DMSO-d6): 8.86 (2H, s), 8.26 (1H, d, J=8.20 Hz), 8.05 (1H, s), 7.03 (1H, dd, J=8.26, 1.83 Hz), 6.87 (1H, d, J=1.78 Hz), 5.81-5.71 (1H, m), 4.31 (2H, t, J=5.01 Hz), 3.37 (2H, t, J=5.01 Hz), 3.30 (2H, d, J=12.46 Hz), 2.93 (2H, d, J=11.52 Hz), 2.84-2.75 (1H, m), 1.92-1.75 (4H, m), 1.49 (6H, d, J=6.59 Hz)

Example 376

2-{3-[2-(2-Isopropyl-2H-[1,2,4]triazol-3-yl)-4,5-dihydro-6-oxa-3-thia-1-aza-benzo[e]azulen-9-yl]-azetidin-1-yl}-ethanol 376

A solution of 2-(2-isopropyl-2H-[1,2,4]triazol-3-yl)-9-{1-[2-(tetrahydro-pyran-2-yloxy)-ethyl]-azetidin-3-yl}-4,5-dihydro-6-oxa-3-thia-1-aza-benzo[e]azulene (110 mg, 0.22 mmol) in MeOH (3 mL) and DCM (3 mL) was treated with 4N HCl/dioxan (2 mL, 8 mmol) and the mixture left to stand for 3 hours then concentrated in vacuo. The resultant residue was triturated with diethyl ether and dried under vacuum. Further purification by flash chromatography (SiO$_2$, 0-10% 2N NH$_3$/MeOH in DCM) gave 376 (29 mg, 32%). LCMS: $R_T$=6.96 min, [M+H]$^+$=412. $^1$H NMR δ (ppm) (CDCl$_3$): 8.31 (1H, d, J=2.34 Hz), 7.90 (1H, s), 7.15 (1H, dd, J=8.27, 2.35 Hz), 7.01 (1H, d, J=8.26 Hz), 5.94-5.84 (1H, m), 4.40-4.34 (2H, m), 3.89-3.83 (2H, m), 3.84-3.72 (1H, m), 3.59-3.54 (2H, m), 3.41-3.36 (2H, m), 3.28-3.21 (2H, m), 2.71-2.66 (2H, m), 1.62 (6H, d, J=6.65 Hz). 1 Exchangeable proton not seen Example 377

1-{3-[2-(2-Isopropyl-2H-[1,2,4]triazol-3-yl)-4,5-dihydro-6-oxa-3-thia-1-aza-benzo[e]azulen-9-yl]-azetidin-1-yl}-2-methyl-propan-2-ol 377

Lithium perchlorate (52 mg, 0.49 mmol) was added to THF (5 mL) followed by 1,2-epoxy-2-methylpropane (0.43 mL, 4.9 mmol) and the mixture was stirred for 10-15 minutes giving a clear solution. 9-Azetidin-3-yl-2-(2-isopropyl-2H-[1,2,4]triazol-3-yl)-4,5-dihydro-6-oxa-3-thia-1-aza-benzo[e]azulene (0.18 g, 0.49 mmol) was added and the reaction mixture was stirred for 72 hours then concentrated in vacuo. The resultant residue was purified by flash chromatography (SiO$_2$, 0-10% MeOH in EtOAc) and the resulting solid extracted several times with ether. The ether extracts were concentrated in vacuo to give 377 (77 mg, 97%). LCMS: $R_T$=7.45 min, [M+H]$^+$=440. $^1$H NMR δ (ppm) (CDCl$_3$): 8.28 (1H, d, J=2.34 Hz), 7.90 (1H, s), 7.16 (1H, dd, J=8.29, 2.35 Hz), 7.02 (1H, d, J=8.27 Hz), 5.93-5.83 (1H, m), 4.40-4.34 (2H, m), 4.04-3.95 (2H, m), 3.89-3.79 (1H, m), 3.46-3.36 (4H, m), 2.55 (2H, s), 1.63 (6H, d, J=6.64 Hz), 1.15 (6H, s). 1 Exchangeable proton not seen

Example 378

(S)-2-Hydroxy-1-{4-[2-(2-isopropyl-2H-[1,2,4]triazol-3-yl)-4,5-dihydro-6-oxa-3-thia-1-aza-benzo[e]azulen-9-yl]-piperidin-1-yl}-propan-1-one 378

Following the procedure for 358, using L-(+)-lactic acid instead of D-(−)-lactic acid to give 378 isolated as a white solid (126 mg, 63%). LCMS: $R_T$=11.58 min, [M+H]$^+$=468. $^1$H NMR δ (ppm) (DMSO-d6): 8.19 (1H, d, J=2.29 Hz), 8.06 (1H, s), 7.14 (1H, d, J=8.33 Hz), 6.96 (1H, d, J=8.24 Hz), 5.79-5.69 (1H, m), 4.80 (1H, s), 4.51-4.37 (2H, m), 4.33-4.27 (2H, m), 4.16-3.98 (1H, m), 3.41-3.35 (2H, m), 3.16-3.02 (1H, m), 2.84-2.75 (1H, m), 2.71-2.59 (1H, m), 1.84 (2H, d, J=12.53 Hz), 1.57-1.47 (8H, m), 1.20-1.14 (3H, m)

Example 380

2-Methyl-1-(4-{2-[2-(1-methyl-piperidin-4-yl)-2H-[1,2,4]triazol-3-yl]-4,5-dihydro-6-oxa-3-thia-1-aza-benzo[e]azulen-8-yl}-pyrazol-1-yl)-propan-2-ol 380

Following the procedure for 114, 8-Bromo-2-[2-(1-methyl-piperidin-4-yl)-2H-[1,2,4]triazol-3-yl]-4,5-dihydro-6-oxa-3-thia-1-aza-benzo[e]azulene was reacted with 2-Methyl-1-[4-(4,4,5,5-tetramethyl-[1,3,2]dioxaborolan-2-yl)-pyrazol-1-yl]-propan-2-ol to give 380. MS(ESI+) 506.2. $^1$H NMR (400 MHz, DMSO) δ 8.32 (d, J=8.3, 1H), 8.20 (s, 1H), 8.11 (s, 1H), 7.97 (s, 1H), 7.44 (dd, J=8.3, 1.8, 1H), 7.32 (d, J=1.7, 1H), 5.47-5.35 (m, 1H), 4.72 (s, 1H), 4.39 (t, J=4.9, 2H), 4.04 (s, 2H), 3.45 (t, J=5.0, 2H), 3.05-2.95 (m, 2H), 2.28 (s, 3H), 2.22-1.98 (m, 6H), 1.10 (s, 6H)

Example 381

(S)-1-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-propan-2-ol 381

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with (S)-1-[4-(4,4,5,5-Tetramethyl-[1,3,2]dioxaborolan-2-yl)-pyrazol-1-yl]-propan-2-ol to give 381. MS(ESI+) 477.1

Example 382

8-[1-(2-Hydroxy-2-methyl-propyl)-1H-pyrazol-4-yl]-4,5-dihydro-6-oxa-3-thia-1-aza-benzo[e]azulene-2-carboxylic acid cyclohexyl-(2-dimethylamino-ethyl)-amide 382

To a well stirred solution of 8-[2-methyl-1-(1H-pyrazol-1-yl)propan-2-ol)]-4,5-dihydro-6-oxa-3-thia-1-aza-benzo[e]azulene-2-carboxylic acid (0.211 mg, 0.546 mmol) in DMF (1.7 mL) at room temperature was added N1-cyclohexyl-N2,N2-dimethylethane-1,2-diamine (0.19 mmol), followed by the addition of DIPEA (0.46 ml, 2.7 mmol). Finally, HATU (0.230 grams, 0.600 mmol) was added and the reaction mixture was heated as a slurry at room temperature for 90 minutes. The reaction mixture was conc. in vacuo and taken into a large volume of EtOAc and the org. was washed with dilute aqueous bicarbonate, water and then saline and dried (Na2SO4), then concentrated to a residue. The crude material was purified by preparative RP-HPLC to give 382 as a lyophilized solid. MS: (ESI+)=558.3

Example 383

N2-(2-chloro-5-(2-hydroxyethyl)(methyl)carbamoyl)phenyl)-N2,N8-dimethyl-4,5-dihydrobenzo[b]thieno[2,3-d]oxepine-2,8-dicarboxamide 383

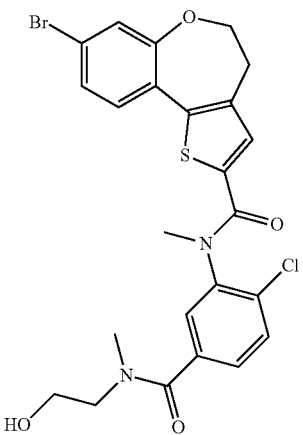 [SMILES: CN(CCO)C(=O)c1ccc(Cl)c(N(C)C(=O)c2cc3c(s2)-c2ccc(Br)cc2OCC3)c1]

To a mixture of 3-(8-bromo-N-methyl-4,5-dihydrobenzo[b]thieno[2,3-d]oxepine-2-carboxamido)-4-chlorobenzoic acid (3 g, 6.09 mmol) in THF (50 mL) was added EDCI (2.34 g, 12.18 mmol), HOBt (1.23 g, 9.13 mmol), DIPEA (5 mL) and 2-(methylamino)ethanol (0.69 g, 9.13 mmol) by sequence under nitrogen atmosphere at room temperature. The reaction mixture was stirred overnight, diluted with water. The resulting precipitate was washed with water and EtOAc to give 8-bromo-N-(2-chloro-5-((2-hydroxyethyl)(methyl)carbamoyl)phenyl)-N-methyl-4,5-dihydrobenzo[b]thieno[2,3-d]oxepine-2-carboxamide (2.8 g, yield: 87%). LC-MS: (ESI, m/z)=549 [M+H]$^+$ A suspension of 8-bromo-N-(2-chloro-5-((2-hydroxyethyl)(methyl)carbamoyl)phenyl)-N-methyl-4,5-dihydrobenzo[b]thieno[2,3-d]oxepine-2-carboxamide (400 mg, 0.76 mmol), Pd(OAc)$_2$ (10 mg, 0.045 mmol), Xantphos (44 mg, 0.076 mmol), MeNH$_2$.HCl (77 mg, 1.14 mmol) and Na$_2$CO$_3$ (242 mg, 2.28 mmol) in toluene (5 mL) was heated at 80° C. under atmosphere of CO from balloon overnight. Then it was filtrated and concentrated, the crude product was purified by column (EtOAc:MeOH=10:1) to afford 383 (87.2 mg, yield: 22%). $^1$HNMR (DMSO-d6, 400 MHz): δ8.45 (d, J=4.4 Hz, 1H), 7.72-7.43 (m, 6H), 6.73 (s, 1H), 4.89-4.76 (m, 1H), 4.20-4.04 (m, 2H), 3.60-2.66 (m, 15H). LC-MS: (ESI, m/z)=528 [M+H]$^+$

Example 384

N2-(2-chloro-5-(3-hydroxyazetidine-1-carbonyl)phenyl)-N2-methyl-N8-(2-(methylsulfonyl)ethyl)-4,5-dihydrobenzo[b]thieno[2,3-d]oxepine-2,8-dicarboxamide 384

A suspension of 8-bromo-N-(2-chloro-5-(3-hydroxyazetidine-1-carbonyl)phenyl)-N-methyl-4,5-dihydrobenzo[b]thieno[2,3-d]oxepine-2-carboxamide (400 mg, 0.73 mmol), Pd(OAc)$_2$ (8 mg, 0.037 mmol), Xantphos (42 mg, 0.073 mmol), MeSO$_2$(CH$_2$)$_2$NH$_2$.HCl (175 mg, 1.095 mmol) and Na₂CO₃ (232 mg, 2.19 mmol) in toluene (5 mL) and DMF (5 mL) was heated at 80° C. under atmosphere of CO from balloon for overnight. Then it was filtrated and concentrated, the crude product was purified by flash column chromatography on silica gel (DCM:MeOH=20:1 as eluted solvent) to give a white solid which was washed with MeOH and dried to give 384 (206.7 mg, yield 46%). ¹H NMR (DMSO, 400 MHz): δ8.74 (t, J=5.6 Hz, 1H, NH), 7.87-6.61 (m, 7H, ArH), 5.75 (d, J=6.0 Hz, 1H, OH), 4.48-2.99 (m, 19H). LC-MS: (ESI, m/z)=618 [M+H]⁺

Example 385

N2-(2-chloro-5-(2-hydroxyethylcarbamoyl)phenyl)-N2-methyl-N8-(2-(methylsulfonyl)ethyl)-4,5-dihydrobenzo[b]thieno[2,3-d]oxepine-2,8-dicarboxamide 385

A suspension of 2-(3-(8-bromo-N-methyl-4,5-dihydrobenzo[b]thieno[2,3-d]oxepine-2-carboxamido)-4-chlorobenzamido)ethyl acetate (400 mg, 0.69 mmol), Pd(OAc)₂ (10 mg, 0.045 mmol), Xantphos (40 mg, 0.069 mmol), MeSO₂CH₂CH₂NH₂·HCl (165 mg, 1.04 mmol) and Na₂CO₃ (219 mg, 2.07 mmol) in toluene (5 mL) was heated at 80° C. under atmosphere of CO from balloon overnight. Then it was filtrated and concentrated, the crude product was purified by column (EtOAc:MeOH=10:1) to afford 385 (76.8 mg, yield: 18%). ¹HNMR (DMSO-d6, 400 MHz): δ8.70 (t, J=5.6 Hz, 1H), 8.61 (d, J=5.6 Hz, 1H), 8.07-7.41 (m, 6H), 6.57 (s, 1H), 4.72 (s, 1H), 4.71 (t, J=5.6 Hz, 1H), 3.63-2.95 (m, 16H). LC-MS: (ESI, m/z)=606 [M+H]⁺

Example 386

N2-(2-chloro-5-(2-hydroxyethyl)(methyl)carbamoyl)phenyl)-N2-methyl-N8-(2-(methylsulfonyl)ethyl)-4,5-dihydrobenzo[b]thieno[2,3-d]oxepine-2,8-dicarboxamide 386

A suspension of 8-bromo-N-(2-chloro-5-((2-hydroxyethyl)(methyl)carbamoyl)phenyl)-N-methyl-4,5-dihydrobenzo[b]thieno[2,3-d]oxepine-2-carboxamide (400 mg, 0.76 mmol), Pd(OAc)₂ (10 mg, 0.045 mmol), Xantphos (44 mg, 0.076 mmol), MeSO₂CH₂CH₂NH₂·HCl (181 mg, 1.14 mmol) and Na₂CO₃ (242 mg, 2.28 mmol) in toluene (5 mL) was heated at 80° C. under atmosphere of CO from balloon overnight. Then it was filtrated and concentrated, the crude product was purified by column (EtOAc:MeOH=10:1) to afford 386 (56.9 mg, yield: 12%). ¹HNMR (DMSO-d6, 400 MHz): δ8.71 (t, J=5.6 Hz, 1H), 7.71-7.41 (m, 6H), 6.70 (s, 1H), 4.83-4.73 (m, 1H), 4.18-4.15 (m, 2H), 3.64-2.88 (m, 19H). LC-MS: (ESI, m/z)=620 [M+H]⁺

Example 387

N2-(2-chloro-5-((R)-2-hydroxypropylcarbamoyl)phenyl)-N2-methyl-N8-(2-(methylsulfonyl)ethyl)-4,5-dihydrobenzo[b]thieno[2,3-d]oxepine-2,8-dicarboxamide 387

A suspension of 8-bromo-N-(2-chloro-5-((R)-2-hydroxypropylcarbamoyl)phenyl)-N-methyl-4,5-dihydrobenzo[b]thieno[2,3-d]oxepine-2-carboxamide (500 mg, 0.91 mmol), Pd(OAc)₂ (10 mg, 0.045 mmol), Xantphos (53 mg, 0.091 mmol), MeSO₂(CH₂)₂NH₂·HCl (218 mg, 1.36 mmol) and Na₂CO₃ (289 mg, 2.73 mmol) in toluene (5 mL) and DMF (5 mL) was heated at 80° C. under atmosphere of CO from balloon overnight. Then it was filtrated and concentrated, the crude product was purified by pre-TLC (DCM:MeOH=10:1 as eluted solvent) to give 387 (101.5 mg, yield 18%). ¹H NMR (DMSO-d6, 400 MHz): δ8.73 (s, 1H, NH), 8.60 (s, 1H, NH), 8.12-7.45 (m, 6H, ArH), 6.61 (s, 1H, =CH), 4.76 (d, J=4.8 Hz, 1H, OH), 4.20 (br s, 2H, CH₂), 3.80-3.77 (m, 1H, CH), 3.67-2.98 (m, 14H, CH₃, CH₂), 1.06 (t, J=5.2 Hz, 3H, CH₃). LC-MS: (ESI, m/z)=542 [M+Na]⁺

Example 388

(S)-1-(4-{2-[2-(2,4-Difluoro-phenyl)-2H-[1,2,4]triazol-3-yl]-4,5-dihydro-6-oxa-1-thia-10-aza-benzo[e]azulen-9-yl}-piperazin-1-yl)-2-hydroxy-propan-1-one 388

2-[2-(2,4-Difluoro-phenyl)-2H-[1,2,4]triazol-3-yl]-9-piperazin-1-yl-4,5-dihydro-6-oxa-1-thia-10-aza-benzo[e]azulene (150 mg, 0.32 mmol), HATU (244 mg, 0.64 mmol) and DIPEA (165 mg, 1.28 mmol) was dissolved in DMF (5 mL). The reaction mixture was stirred at room temperature for 2 hours. LC-MS showed the reaction is completed. To the reaction was added water (15 mL), some solid appeared. It was filtered, and the solid was collected and used to the next step directly (140 mg yield: 60%). The above residue (140 mg, 0.21 mmol) was dissolved in 5 mL of THF, and then NaOH (18 mg, 0.42 mmol) in 5 mL of water was added dropwise at 0° C. The reaction mixture was allowed to warm up to room temperature slowly and stirred at room temperature for 1 hour. Evaporated to remove most of THF, extracted with dichloromethane, dried over anhydrous sodium sulfate, concentrated to dryness to afford 388 (45 mg, yield: 40%). ¹H NMR (CDCl₃, 400 MHz): δ8.08 (s, 1H), 7.54-7.51 (m, 1H), 7.24-7.02 (m, 4H), 6.54-6.53 (d, J=7.2 Hz, 1H), 4.55-4.51 (m, 1H), 4.24-4.22 (m, 2H), 3.82-3.76 (m, 3H), 3.52-3.50 (m, 4H), 3.43-3.41 (m, 2H), 3.11-3.08 (m, 2H), 1.40-1.38 (m, 6H). ESI-MS: m/z=539 [M+H⁺]

Example 389

(S)-1-(3-{2-[2-(2,4-Difluoro-phenyl)-2H-[1,2,4]triazol-3-yl]-4,5-dihydro-6-oxa-1-thia-10-aza-benzo[e]azulen-9-ylamino}-azetidin-1-yl)-2-hydroxy-propan-1-one 389

Compound 435 (150 mg, 0.31 mmol), (S)-2-(benzyloxycarbonyloxy)propanoic acid, EDCI (127 mg, 0.61 mmol), HOBt (83 mg, 0.61 mmol) and DIPEA (240 mg, 1.86 mmol) was dissolved in DMF (10 mL). The reaction mixture was stirred at about −5° C. for 1 hour. LC-MS indicated the reaction was completed. To the reaction mixture was added 20 mL of water, the mixture was extracted with dichloromethane. The organic layer was dried over anhydrous sodium sulfate, concentrated to dryness, and purified by pre-TLC to afford 110 mg of Cbz protected 389.

The above Cbz protected 389 intermediate (110 mg, 0.17 mmol) was dissolved in THF (5 mL), then NaOH (13 mg, 0.34 mmol) in 5 mL of water was added dropwise at 0° C. The reaction mixture was allowed to warm up to room temperature slowly and stirred at room temperature for 1 hour. It was evaporated to remove most of THF, extracted with dichloromethane, dried over anhydrous sodium sulfate, concentrated to dryness and purified by pre-HPLC to afford 44 mg of 389 (yield=50%). ¹H NMR (CDCl₃, 400 MHz): δ8.02 (s, 1H), 7.50-7.45 (m, 1H), 7.09-6.88 (m, 4H), 6.28-6.25 (m, 1H), 4.56-4.41 (m, 5H), 4.19-4.17 (m, 2H), 3.92-3.91 (m, 2H), 3.55-3.48 (m, 1H), 3.06-3.02 (m, 2H), 1.35-1.25 (m, 3H). LC-MS (ESI): m/z=525 [M+H]+

Example 390

9-[(3R,5S)-4-(2,2-Difluoro-ethyl)-3,5-dimethyl-piperazin-1-yl]-2-[2-(2,4-difluoro-phenyl)-2H-[1,2,4]triazol-3-yl]-4,5-dihydro-6-oxa-1-thia-10-aza-benzo[e]azulene 390

Compound 391 (120 mg, 0.21 mmol) was dissolved in tetrahydrofuran (5 mL), borane/dimethylsulfane (10 mol/L, 2 mL) was added dropwise at 0° C., 30 min later the temperature of the mixture was allowed to warm to about 25° C. and stirred for 1 hour. To the reaction mixture was added 15 mL of methanol slowly, then 5 mL of conc. HCl was added followed, the mixture was stirred at room temperature for 2 hours. The mixture was concentrated to remove methanol and dimethylsulfane. The residue was dissolved in dichloromethane, washed with water, the organic layer was concentrated to dryness and the crude was purified by pre-TLC to afford 65 mg of 390. Yield: 56%. $^1$H NMR (CDCl$_3$, 400 MHz): δ8.01 (s, 1H), 7.49-7.48 (m, 1H), 7.09-6.98 (m, 4H), 6.45-6.43 (d, J=8.8 Hz, 1H), 5.92 (t, J=60.0 Hz, 1H), 4.18-4.16 (m, 2H), 3.84-3.81 (m, 2H), 3.07-3.05 (m, 2H), 2.98-2.90 (m, 2H), 2.70-2.67 (m, 2H), 2.53-2.50 (m, 2H), 1.12-1.11 (m, 6H). LC-MS (ESI): m/z=559 [M+H]+

Example 391

1-((2R,6S)-4-{2-[2-(2,4-Difluoro-phenyl)-2H-[1,2,4]triazol-3-yl]-4,5-dihydro-6-oxa-1-thia-10-aza-benzo[e]azulen-9-yl}-2,6-dimethyl-piperazin-1-yl)-2,2-difluoro-ethanone 391

2-[2-(2,4-Difluoro-phenyl)-2H-[1,2,4]triazol-3-yl]-9-((3R,5S)-3,5-dimethyl-piperazin-1-yl)-4,5-dihydro-6-oxa-1-thia-10-aza-benzo[e]azulene (200 mg, 0.4 mmol) was dissolved in 10 mL of THF. Then the mixture was stirred at about −15° C. for 5 min, pyridine (1 mL) was added dropwise followed. 5 min later, difluoro-acetyl chloride (excess) was bubbled in to the reaction mixture for about 2 min. The temperature of the reaction was allowed to warm to ambient temperature slowly and stirred for about 1 hour. To the reaction mixture was added saturated sodium bicarbonate and extracted with DCM, the organic phase was dried over anhydrous sodium sulfate and concentrated to dryness to give 391. HPLC indicated the purity is above 95%. $^1$H NMR (CDCl$_3$, 400 MHz): δ8.04 (s, 1H), 7.52-7.47 (m, 1H), 7.19-7.00 (m, 4H), 6.50-6.48 (m, 1H), 4.62-4.60 (m, 1H), 4.23-4.16 (m, 4H), 3.91-3.88 (m, 1H), 3.07-2.89 (m, 4H), 1.36-1.31 (m, 6H). LC-MS (ESI): m/z=573 [M+H]+

Example 392

N-(2-{2-[2-(2,4-Difluoro-phenyl)-2H-[1,2,4]triazol-3-yl]-4,5-dihydro-6-oxa-1-thia-10-aza-benzo[e]azulen-9-ylamino}-ethyl)-acetamide 392

A mixture of 9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), Pd$_2$(dba)$_3$ (66 mg, 0.072 mmol), N-(2-Amino-ethyl)-acetamide (147 mg, 1.44 mmol), Xphos (69 mg, 0.144 mmol) in dioxane (2 mL) was added to a MW tube. The mixture was bubbled N$_2$ for about 2 min, $^t$BuONa (142 mg, 1.44 mmol), was added followed and bubbled N$_2$ for another 2 min. The mixture was stirred at 120° C. for 45 min under the irradiation of microwave. The mixture was filtered though a ceilite, the filtrate was concentrated to dryness and purified by pre-TLC (pure EtOAc) and pre-HPLC to afford 56 mg of 392. (yield=16%). $^1$H NMR (CDCl$_3$, 400 MHz): δ8.02 (s, 1H), 7.50-7.44 (m, 1H), 7.19-6.99 (m, 4H), 6.25-6.17 (m, 2H), 4.55 (s, 1H), 4.18-4.16 (m, 2H), 3.46-3.40 (m, 2H), 3.06-3.04 (m, 2H), 1.80-1.79 (m, 1H). ESI-MS: m/z=483 [M+H+]

Example 393

1,1-Dimethyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-ethylamine 393

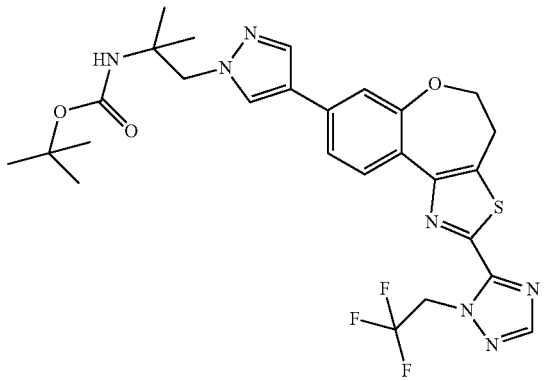 [SMILES: CC(C)(Cn1cc(-c2ccc3c(c2)OCCc2sc(-c4ncnn4CC(F)(F)F)nc2-3)cn1)NC(=O)OC(C)(C)C]

Following the procedure for 114, 8-Bromo-2-[2-(2,2,2-trifluoro-ethyl)-2H-[1,2,4]triazol-3-yl]-4,5-dihydro-6-oxa-3-thia-1-aza-benzo[e]azulene was reacted with {1,1-Dimethyl-2-[4-(4,4,5,5-tetramethyl-[1,3,2]dioxaborolan-2-yl)-pyrazol-1-yl]-ethyl}-carbamic acid tert-butyl ester to give [1,1-Dimethyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-ethyl]-carbamic acid tert-butyl ester. MS(ESI+) 590.2.

To a round bottom flask containing [1,1-Dimethyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-ethyl]-carbamic acid tert-butyl ester (0.175 g, 0.000297 mol) in methylene chloride (1.1 mL, 0.017 mol) was added trifluoroacetic acid (1.3 mL, 0.017 mol). The solution was stirred at room temperature until CO$_2$ evolution stopped (30 minutes). The solvent was removed in vacuo and purified by reverse-phase HPLC to give 393 (21.8 mg) as a white solid. MS(ESI+) 490.1. $^1$H NMR (400 MHz, DMSO) δ 8.37 (d, J=9.7, 1H), 8.29 (s, 1H), 8.26 (d, J=8.3, 1H), 7.98 (s, 1H), 7.49 (dd, J=8.3, 1.7, 1H), 7.37 (d, J=1.7, 1H), 5.86 (q, J=8.7, 2H), 4.39 (t, J=5.0, 2H), 3.47 (t, J=5.0, 2H), 2.86 (s, 2H), 1.50 (s, 6H).

Example 394

2-{3-[2-(2-Isopropyl-2H-[1,2,4]triazol-3-yl)-4,5-dihydro-6-oxa-3-thia-1-aza-benzo[e]azulen-9-yl]-azetidine-1-sulfonyl}-ethanol 394

To a solution of 9-azetidin-3-yl-2-(2-isopropyl-2H-[1,2,4]triazol-3-yl)-4,5-dihydro-6-oxa-3-thia-1-aza-benzo[e]azulene (0.20 g, 0.54 mmol) in dry THF (20 mL) at 0° C. was added 2-chloroethanesulfonyl chloride (65 μL, 0.6 mmol) and the reaction mixture was stirred at RT for 18 hours. The reaction mixture was cooled to 0° C. and a further 2-chloroethanesulfonyl chloride (1304) was added and the reaction mixture was stirred at RT for 18 hours. An aqueous sodium hydroxide solution (8M, 3.38 mL, 27 mmol) was added and the mixture was heated at 40° C. for 18 hours then concentrated in vacuo. The resultant residue was extracted several times with 10% MeOH in DCM and the combined extracts concentrated in vacuo. The residue was purified by flash chromatography ($SiO_2$, 0-20% MeOH in DCM) followed by preparative HPLC (Gemini $C_{18}$ column, gradient 5-95% MeOH in $H_2O$+0.1% $HCO_2H$) to give 394 (58 mg, 23%). LCMS: $R_T$=8.45 min, $[M+H]^+$=476. $^1$H NMR δ (ppm) (DMSO-d6, 80° C.): 8.22 (1H, d, J=2.31 Hz), 8.01 (1H, s), 7.33 (1H, dd, J=8.34, 2.39 Hz), 7.08 (1H, d, J=8.32 Hz), 5.81-5.73 (1H, m), 4.53 (2H, s), 4.37 (2H, t, J=5.09 Hz), 4.22 (3H, s), 3.57 (2H, t, J=6.26 Hz), 3.43 (2H, t, J=5.09 Hz), 2.79 (2H, t, J=6.37 Hz), 1.59 (6H, d, J=6.61 Hz). 1 Exchangeable proton not observed Example 395

2-(2-Isopropyl-2H-[1,2,4]triazol-3-yl)-8-(1-methanesulfonyl-piperidin-4-yl)-4,5-dihydro-6-oxa-3-thia-1-aza-benzo[e]azulene 395

To a suspension of 2-(2-isopropyl-2H-[1,2,4]triazol-3-yl)-8-piperidin-4-yl-4,5-dihydro-6-oxa-3-thia-1-aza-benzo[e]azulene 375 hydrochloride salt (141 mg, 0.33 mmol) in DCM (3.3 mL) was added triethylamine (0.16 mL, 1.14 mmol). The reaction mixture was cooled to 0° C. then methanesulfonyl chloride (30 μL, 0.39 mmol) was added and the reaction mixture was stirred at RT for 18 hours. The reaction mixture was cooled to 0° C. and a further triethylamine (45 μL) and methanesulfonyl chloride (30 μL) were added and the reaction mixture was stirred at 0° C. for 30 minutes. Water was added and the phases were separated. The aqueous layer was extracted with DCM (×2) and the combined organic extracts were washed with an aqueous 10% citric acid solution, followed by an aqueous saturated sodium bicarbonate solution and then brine, dried ($Na_2SO_4$) and concentrated in vacuo. The resultant residue was purified by flash chromatography ($SiO_2$, 0-20% EtOAc in DCM). The resulting solid was suspended in cyclohexane and collected by filtration to give 395 as a white solid (78 mg, 50%). LCMS: $R_T$=11.69 min, $[M+H]^+$=474. $^1$H NMR δ (ppm) ($CDCl_3$): 8.31 (1H, d, J=8.19 Hz), 7.90 (1H, s), 7.01 (1H, dd, J=8.23, 1.88 Hz), 6.90 (1H, d, J=1.84 Hz), 5.93-5.85 (1H, m), 4.39 (2H, t, J=5.03 Hz), 3.93 (2H, d, J=11.84 Hz), 3.39 (2H, t, J=5.04 Hz), 2.81-2.70 (5H, m), 2.60 (1H, tt, J=12.04, 3.68 Hz), 1.97 (2H, d, J=13.31 Hz), 1.89-1.76 (2H, m), 1.61 (6H, d, J=6.63 Hz)

Example 396

2-(2-Isopropyl-2H-[1,2,4]triazol-3-yl)-8-(1-methanesulfonyl-pyrrolidin-3-yl)-4,5-dihydro-6-oxa-3-thia-1-aza-benzo[e]azulene 396

Following the procedure for 395, 2-(2-isopropyl-2H-[1,2,4]triazol-3-yl)-8-pyrrolidin-3-yl-4,5-dihydro-6-oxa-3-thia-1-aza-benzo[e]azulene hydrochloride salt and methanesulfonyl chloride gave 396 isolated as a pale orange solid (28 mg, 48%). LCMS: $R_T$=11.27 min, $[M+H]^+$=460. $^1$H NMR δ (ppm) ($CDCl_3$): 8.33 (1H, d, J=8.21 Hz), 7.90 (1H, s), 7.05 (1H, dd, J=8.24, 1.91 Hz), 6.94 (1H, d, J=1.87 Hz), 5.93-5.83 (1H, m), 4.42-4.36 (2H, m), 3.79 (1H, dd, J=9.53, 7.31 Hz), 3.61 (1H, ddd, J=9.97, 8.27, 3.30 Hz), 3.50-3.31 (5H, m), 2.86 (3H, s), 2.41-2.32 (1H, m), 2.15-2.03 (1H, m), 1.61 (6H, d, J=6.63 Hz)

Example 397

2-Hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-ethanone 397

Following the procedure for 318, 8-azetidin-3-yl-2-(2-isopropyl-2H-[1,2,4]triazol-3-yl)-4,5-dihydro-6-oxa-3-thia-1-aza-benzo[e]azulene TFA salt 31 and glycolic acid were reacted. Purification by reverse phase preparative HPLC (Gemini $C_{18}$ column, gradient 5-98% MeOH in $H_2O$+0.1% $HCO_2H$) gave 397 as a white solid (46 mg, 27%). LCMS: $R_T$=10.33 min, $[M+H]^+$=426. $^1$H NMR δ (ppm) (DMSO-d6): 8.30 (1H, d, J=8.20 Hz), 8.05 (1H, s), 7.20-7.15 (1H, m), 7.01 (1H, d, J=1.82 Hz), 5.82-5.72 (1H, m), 4.88-4.81 (1H, m), 4.55-4.46 (1H, m), 4.34-4.29 (2H, m), 4.30-4.17 (1H, m), 4.16 (1H, dd, J=9.24, 5.41 Hz), 3.90 (2H, d, J=5.77 Hz), 3.89-3.77 (2H, m), 3.41-3.35 (2H, m), 1.49 (6H, d, J=6.59 Hz)

Example 398

(R)-2-Hydroxy-1-{3-[2-(2-isopropyl-2H-[1,2,4]triazol-3-yl)-4,5-dihydro-6-oxa-3-thia-1-aza-benzo[e]azulen-9-yl]-azetidin-1-yl}-propan-1-one 398

Following the procedure for 318, 9-azetidin-3-yl-2-(2-isopropyl-2H-[1,2,4]triazol-3-yl)-4,5-dihydro-6-oxa-3-thia-1-aza-benzo[e]azulene and sodium D-lactate in DMF were reacted. After purification by flash chromatography a lactate-ester by-product of the title compound was present. The mixture (0.11 g, 0.2 mmol) was dissolved in 1,4-dioxan (2 mL) and treated with 1M aqueous sodium hydroxide solution (0.2 mL, 0.2 mmol). The reaction mixture was stirred for 2 hours then diluted with EtOAc and water. The aqueous phase was extracted with EtOAc (×2) and the combined organic extracts were dried ($Na_2SO_4$) and concentrated in vacuo. Further drying under vacuum gave 398 (90 mg, 36%). LCMS: $R_T$=10.71 min, $[M+H]^+$=440. $^1$H NMR δ (ppm) ($CDCl_3$): 8.37 (1H, s), 7.90 (1H, s), 7.20-7.12 (1H, m), 7.06 (1H, dd, J=8.28, 5.28 Hz), 5.85-5.76 (1H, m), 4.64-4.30 (4H, m), 4.25-4.10 (3H, m), 3.98-3.87 (1H, m), 3.45-3.35 (2H, m), 1.62 (6H, d, J=6.65 Hz), 1.33 (3H, dd, J=11.04, 6.67 Hz). 1 Exchangeable not observed Example 399

2-(2-Isopropyl-2H-[1,2,4]triazol-3-yl)-9-(6-pyrrolidin-1-yl-pyridin-3-yl)-4,5-dihydro-6-oxa-3-thia-1-aza-benzo[e]azulene 399

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 2-(pyrrolidin-1-yl)-5-(4,4,5,5-tetramethyl-1,3,2-dioxaborolan-2-yl)pyridine were reacted to give 399 (0.078 g, 62%). $^1$H NMR (400 MHz, DMSO) δ 8.57 (d, J=2.4, 1H), 8.41 (d, J=2.2, 1H), 8.08 (d, J=24.7, 1H), 7.78 (dd, J=8.7, 2.6, 1H), 7.52 (dd, J=8.4, 2.5, 1H), 7.13 (d, J=8.4, 1H), 6.57 (d, J=8.7, 1H), 5.79 (dt, J=13.1, 6.5, 1H), 4.35 (dd, J=39.9, 34.8, 2H), 3.65-3.37 (m, 6H), 2.11-1.80 (m, 4H), 1.58 (d, J=6.6, 6H). MS (ESI(+)): m/z 459.2 (M+H)

Example 400

1-Isopropyl-5-{8-[1-(3-methyl-oxetan-3-ylmethyl)-1H-pyrazol-4-yl]-4,5-dihydro-6-oxa-3-thia-1-aza-benzo[e]azulen-2-yl}-1H-[1,2,4]triazol-3-ylamine 400

Similar to as described in General Procedure C, 5-(8-Bromo-4,5-dihydro-6-oxa-3-thia-1-aza-benzo[e]azulen-2-yl)-1-isopropyl-1H-[1,2,4]triazol-3-ylamine was reacted with 1-((3-methyloxetan-3-yl)methyl)-4-(4,4,5,5-tetramethyl-1,3,2-dioxaborolan-2-yl)-1H-pyrazole. Purification of the crude reaction mixture by reverse phase HPLC gave 400. LCMS: 478.2

Example 401

8-[1-(2-Hydroxy-2-methyl-propyl)-1H-pyrazol-4-yl]-4,5-dihydro-6-oxa-3-thia-1-aza-benzo[e]azulene-2-carboxylic acid (2-hydroxy-ethyl)-isopropyl-amide 401

Following Example 267, 8-Bromo-4,5-dihydro-6-oxa-3-thia-1-aza-benzo[e]azulene-2-carboxylic acid (2-hydroxy-ethyl)-isopropylamide and 2-methyl-1-(4-(4,4,5,5-tetramethyl-1,3,2-dioxaborolan-2-yl)-1H-pyrazol-1-yl)propan-2-ol were reacted to give 401. MS: (ESI+)=471.2

Example 402

9-(2-Fluoro-5-methyl-pyridin-3-yl)-2-(2-isopropyl-2H-[1,2,4]triazol-3-yl)-4,5-dihydro-6-oxa-3-thia-1-aza-benzo[e]azulene 402

Following the procedure for Example 128, 9-Bromo-2-(2-isopropyl-2H-[1,2,4]triazol-3-yl)-4,5-dihydro-6-oxa-3-thia-1-aza-benzo[e]azulene from Example 6, and 2-fluoro-5-methylpyridin-3-ylboronic acid were reacted to give 402 (0.054 g, 37%). $^1$H NMR (400 MHz, DMSO) δ 8.74 (t, J=2.0, 1H), 8.11 (s, 1H), 8.07-7.97 (m, 2H), 7.60 (d, J=8.5, 1H), 7.21 (d, J=8.4, 1H), 5.82 (dt, J=13.2, 6.6, 1H), 4.44 (t, J=4.9, 2H), 3.49 (t, J=4.9, 2H), 2.37 (s, 3H), 1.54 (d, J=6.6, 6H). MS (ESI(+)): m/z 422.1 (M+H)

Example 403

2-{4-[2-(5-Amino-2-isopropyl-2H-[1,2,4]triazol-3-yl)-4,5-dihydro-6-oxa-3-thia-1-aza-benzo[e]azulen-8-yl]-pyrazol-1-yl}-ethanol 403

Similar to as described in General Procedure C, 5-(8-Bromo-4,5-dihydro-6-oxa-3-thia-1-aza-benzo[e]azulen-2-yl)-1-isopropyl-1H-[1,2,4]triazol-3-ylamine was reacted with 1-(2-(tetrahydro-2H-pyran-2-yloxy)ethyl)-4-(4,4,5,5-tetramethyl-1,3,2-dioxaborolan-2-yl)-1H-pyrazole. Subsequent to the Suzuki coupling, deprotection of the tetrahydropyranyl ether was accomplished by adding 2N HCl to the crude reaction mixture. Purification by reverse phase HPLC gave 403 as a colorless solid (16 mg). LCMS: 438.1

Example 404

1-{4-[2-(2-Isopropyl-5-methyl-2H-[1,2,4]triazol-3-yl)-4,5-dihydro-6-oxa-3-thia-1-aza-benzo[e]azulen-8-yl]-pyrazol-1-yl}-3-methoxy-propan-2-ol 404

Similar to as described in General Procedure C, 8-Bromo-2-(2-isopropyl-5-methyl-2H-[1,2,4]triazol-3-yl)-4,5-dihydro-6-oxa-3-thia-1-aza-benzo[e]azulene was reacted with 1-methoxy-3-(4-(4,4,5,5-tetramethyl-1,3,2-dioxaborolan-2-yl)-1H-pyrazol-1-yl)propan-2-ol. Purification of the crude reaction mixture by reverse phase HPLC gave 404. LCMS: 481.2.

Example 405

2-(2-{8-[1-(2-Hydroxy-2-methyl-propyl)-1H-pyrazol-4-yl]-4,5-dihydro-6-oxa-3-thia-1-aza-benzo[e]azulen-2-yl}-imidazol-1-yl)-N-methyl-acetamide 405

Following the procedure for 355, 2-[2-(8-Bromo-4,5-dihydro-6-oxa-3-thia-1-aza-benzo[e]azulen-2-yl)-imidazol-1-yl]-N-methyl-acetamide and 2-methyl-1-(4-(4,4,5,5-tetramethyl-1,3,2-dioxaborolan-2-yl)-1H-pyrazol-1-yl)propan-2-ol were reacted under Suzuki palladium conditions to give 405 MS: (ESI+)=497.2. $^1$H NMR (400 MHz, DMSO) δ 8.32 (d, J=8.3 Hz, 1H), 8.15 (s, 1H), 7.93 (s, OH), 7.38 (d, J=0.8 Hz, 1H), 7.32 (dd, J=8.3, 1.8 Hz, 1H), 7.25 (d, J=1.7 Hz, 1H), 7.05 (d, J=0.8 Hz, 0H), 5.23 (s, 1H), 4.72 (s, 1H), 4.34 (t, J=5.0 Hz, 1H), 4.04 (s, 1H), 2.66 (t, J=4.4 Hz, 2H), 1.08 (s, 6H)

Example 406

8-(1-Azetidin-3-yl-1H-pyrazol-4-yl)-2-(2-isopropyl-5-methyl-2H-[1,2,4]triazol-3-yl)-4,5-dihydro-6-oxa-3-thia-1-aza-benzo[e]azulene 406

Similarly to as described in General Procedure C, 8-Bromo-2-(2-isopropyl-5-methyl-2H-[1,2,4]triazol-3-yl)-4,5-dihydro-6-oxa-3-thia-1-aza-benzo[e]azulene was reacted with tert-butyl 3-(4-(4,4,5,5-tetramethyl-1,3,2-dioxaborolan-2-yl)-1H-pyrazol-1-yl)azetidine-1-carboxylate. Removal of the tertbutoxycarbonyl protecting group was accomplished with trifluoroacetic acid in dichloromethane. Purification of the crude reaction mixture by reverse phase HPLC gave 406. LCMS: 448.2

Example 407

2-(5-Amino-2-isopropyl-2H-[1,2,4]triazol-3-yl)-4,5-dihydro-6-oxa-3-thia-1-aza-benzo[e]azulene-8-carboxylic acid (1-methyl-azetidin-3-yl)-amide 407

Similar to as described in General Procedure F, 5-(8-Bromo-4,5-dihydro-6-oxa-1,3a-diaza-benzo[e]azulen-2-yl)-1-isopropyl-1H-[1,2,4]triazol-3-ylamine was reacted with 1-methyl-3-aminoazetidine hydrochloride to give 407 after purification by reverse phase HPLC (15 mg). LCMS: 440.1

Example 408

2-(2-Isopropyl-2H-[1,2,4]triazol-3-yl)-8-(1-methyl-1H-imidazol-4-yl)-4,5-dihydro-6-oxa-3-thia-1-aza-benzo[e]azulene 408

Following General Procedure G: Stille coupling to aryl bromides, a solution of 8-Bromo-2-(2-isopropyl-2H-[1,2,4]triazol-3-yl)-4,5-dihydro-6-oxa-3-thia-1-aza-benzo[e]azulene 27 in 3 mL of acetonitrile was degassed and treated with 150 mg of 1-methyl-4-(tributylstannyl)-1H-imidazole. Tetrakis(triphenylphosphine)palladium(0) (12 mg) was added and the reaction mixture was heated in a microwave reactor at 140° C. for 25 min. Concentration and purification by reverse phase HPLC gave 408 as a colorless solid (23 mg, 44%). LCMS: 393.1. ¹H NMR (400 MHz, DMSO) δ 8.32 (d, J=8.3 Hz, 1H), 8.10 (s, 1H), 7.66 (d, J=8.2 Hz, 2H), 7.57 (dd, J=8.3, 1.7 Hz, 1H), 7.43 (d, J=1.6 Hz, 1H), 5.84 (dt, J=13.2, 6.6 Hz, 1H), 4.39 (t, J=5.0 Hz, 2H), 3.70 (s, 3H), 3.44 (t, J=5.0 Hz, 2H), 1.56 (d, J=6.6 Hz, 6H).

Example 409

8-[1-(2-Hydroxy-2-methyl-propyl)-1H-pyrazol-4-yl]-4,5-dihydro-6-oxa-3-thia-1-aza-benzo[e]azulene-2-carboxylic acid (2-hydroxy-ethyl)-(tetrahydro-pyran-4-yl)-amide 409

Following the procedures of Example 382, to a well stirred solution of 8-[2-methyl-1-(1H-pyrazol-1-yl)propan-2-ol)]-4,5-dihydro-6-oxa-3-thia-1-aza-benzo[e]azulene-2-carboxylic acid in DMF at room temperature was added 2-(tetrahydro-2H-pyran-4-ylamino)ethanol, followed by the addition of DIPEA and HATU to give 409. MS: (ESI+)=513.2

Example 410

8-[1-(2-Hydroxy-2-methyl-propyl)-1H-pyrazol-4-yl]-4,5-dihydro-6-oxa-3-thia-1-aza-benzo[e]azulene-2-carboxylic acid (1-acetyl-piperidin-4-yl)-(2-hydroxy-ethyl)-amide 410

Following the procedures of Example 382, to a well stirred solution of 8-[2-methyl-1-(1H-pyrazol-1-yl)propan-2-ol)]-4,5-dihydro-6-oxa-3-thia-1-aza-benzo[e]azulene-2-carboxylic acid in DMF at room temperature was added 1-(4-(2-hydroxyethylamino)piperidin-1-yl)ethanol, followed by the addition of DIPEA and HATU to give 410. MS: (ESI+)=554.2

Example 411

1-{4-[2-(1-azetidin-3-yl-1H-imidazol-2-yl)-4,5-dihydro-6-oxa-3-thia-1-aza-benzo[e]azulen-8-yl]-pyrazol-1-yl}-2-methyl-propan-2-ol 411

Following the procedure for 355, 2-(1-Azetidin-3-yl-1H-imidazol-2-yl)-8-bromo-4,5-dihydro-6-oxa-3-thia-1-aza-benzo[e]azulene and 2-methyl-1-(4-(4,4,5,5-tetramethyl-1,3,2-dioxaborolan-2-yl)-1H-pyrazol-1-yl)propan-2-ol were reacted under Suzuki palladium conditions to give 411. MS: (ESI+)=463.2. ¹H NMR (400 MHz, DMSO) δ 8.36 (d, J=8.2 Hz, 1H), 8.15 (s, 1H), 7.94 (s, 1H), 7.84 (s, 1H), 7.45 (dd, J=8.3, 1.7 Hz, 1H), 7.28 (d, J=1.7 Hz, 1H), 7.14 (s, 1H), 6.16-6.06 (m, 1H), 4.72 (s, 1H), 4.36 (t, J=5.0 Hz, 2H), 4.04 (s, 2H), 3.98 (t, J=8.2 Hz, 2H), 3.82-3.76 (m, 2H), 1.10 (s, 6H)

Example 412

2-methyl-2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-propylamine 412

To a solution of 2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-isobutyramide (0.182 g, 0.000361 mol) in tetrahydrofuran (5.864 mL, 0.07229 mol) under N₂ at 0° C. was added lithium tetrahydroaluminate (1M in THF, 1.44 mL, 0.00145 mol) dropwise. The reaction was stirred at room temperature for 6 h. The reaction was quenched with saturated Na₂SO₄ until no more hydrogen evolution was observed. MgSO₄ was added and the solution was filtered and rinsed with copious amounts of methylene chloride. The mixture was concentrated and purified by reverse-phase HPLC to give 412 (12.8 mg) as a colorless solid. MS(ESI+) 490.1. ¹H NMR (400 MHz, DMSO) δ 8.36 (s, 1H), 8.29 (s, 1H), 8.26 (d, J=8.3, 1H), 7.98 (s, 1H), 7.49 (dd, J=8.3, 1.7, 1H), 7.37 (d, J=1.7, 1H), 5.86 (q, J=8.7, 2H), 4.39 (t, J=5.0, 2H), 3.47 (t, J=5.0, 2H), 2.86 (s, 2H), 1.50 (s, 6H)

Example 413

2-hydroxy-1-[3-(2-{8-[1-(2-hydroxy-2-methyl-propyl)-1H-pyrazol-4-yl]-4,5-dihydro-6-oxa-3-thia-1-aza-benzo[e]azulen-2-yl}-imidazol-1-yl)-azetidin-1-yl]-propan-1-one 413

Compound 411 (0.110 g, 0.000238 mol) dissolved in N,N-Dimethylformamide (3.72 mL, 0.0480 mol) and treated sequentially with N,N-Diisopropylethylamine (0.248 mL, 0.00143 mol) Acetic acid (0.0270 mL, 0.000476 mol) then N,N,N',N'-Tetramethyl-O-(7-azabenzotriazol-1-yl)uronium Hexafluorophosphate (0.108 g, 0.000285 mol). Stir at r.t. overnight. Add sat. sodium bicarbonate, extract with ethyl acetate. Dried combined organics over sodium sulfate and concentrated. The crude product was purified by rHPLC to give 413. MS: (ESI+)=535.2. ¹H NMR (400 MHz, DMSO) δ 8.37 (d, J=8.3 Hz, 1H), 8.15 (s, 1H), 7.93 (s, 1H), 7.89 (d, J=5.7 Hz, 1H), 7.42 (dd, J=8.2, 1.7 Hz, 1H), 7.28 (d, J=1.7 Hz, 1H), 7.18 (d, J=1.0 Hz, 1H), 6.17 (s, 1H), 5.15 (s, 1H), 4.91 (dd, J=17.5, 8.2 Hz, 1H), 4.71 (s, 1H), 4.51 (dd, J=16.3, 10.1 Hz, 2H), 4.36 (t, J=5.6 Hz, 2H), 4.20 (d, J=6.5 Hz, 2H), 3.39 (t, J=5.1 Hz, 2H), 1.23 (d, J=6.7 Hz, 3H), 1.09 (s, 6H)

Example 414

2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-ethylamine 414

Methanesulfonyl chloride (0.055 mL, 0.74 mmol) was added to a solution of 2-{4-[2-(2-Isopropyl-5-methyl-2H-[1,2,4]triazol-3-yl)-4,5-dihydro-6-oxa-3-thia-1-aza-benzo[e]azulen-8-yl]-pyrazol-1-yl}-ethanol (201 mg, 0.48 mmol) in cold dichloromethane (3 mL). After 15 min, saturated sodium bicarbonate was added and the mixture extracted with EtOAc. The combined organics were concentrated and the residue dissolved in 2 mL of DMSO. Sodium azide (62 mg) was added and the mixture heated at 70° C. overnight. Aqueous extraction with EtOAc gave the crude azide. The azide was dissolved in THF and water (3 mL, 0.5 mL) and the reaction mixture treated with triphenylphosphine (250 mg, 0.95 mmol). After 8 h at 50° C., the reaction mixture was concentrated and the residue purified by reverse phase HPLC to give 414 as a colorless solid (160 mg, 80%). LCMS: 422.1

Example 415

3-[2-(2-Isopropyl-2H-[1,2,4]triazol-3-yl)-4,5-dihydro-6-oxa-3-thia-1-aza-benzo[e]azulen-9-yl]-5-methyl-1H-pyridin-2-one 415

Following the procedure for Example 330, 9-(2-Fluoro-5-methyl-pyridin-3-yl)-2-(2-isopropyl-2H-[1,2,4]triazol-3-yl)-4,5-dihydro-6-oxa-3-thia-1-aza-benzo[e]azulene 402 was treated with aqueous HCl in DME to give 415 (0.038 g, 93%). ¹H NMR (400 MHz, DMSO) δ 11.58 (s, 1H), 8.94 (d, J=2.3, 1H), 8.10 (s, 1H), 7.75 (dd, J=8.4, 2.3, 1H), 7.58 (d, J=2.5, 1H), 7.17 (s, 1H), 7.10 (s, 1H), 7.07 (d, J=8.5, 1H), 5.90 (dt, J=13.2, 6.6, 1H), 4.40 (t, J=4.9, 2H), 3.46 (t, J=4.9, 2H), 2.09 (s, 3H), 1.56 (d, J=6.6, 6H). MS (ESI(+)): m/z 420.1 (M+H)

Example 416

1-[3-(2-{8-[1-(2-Hydroxy-2-methyl-propyl)-1H-pyrazol-4-yl]-4,5-dihydro-6-oxa-3-thia-1-aza-benzo[e]azulen-2-yl}-imidazol-1-yl)-azetidin-1-yl]-ethanone 416

Compound 411 (0.110 g, 0.000238 mol) dissolved in N,N-Dimethylformamide (3.72 mL, 0.0480 mol) and treated sequentially with N,N-Diisopropylethylamine (0.248 mL, 0.00143 mol) Acetic acid (0.0270 mL, 0.000476 mol) then N,N,N',N'-Tetramethyl-O-(7-azabenzotriazol-1-yl)uronium Hexafluorophosphate (0.108 g, 0.000285 mol). Stir at r.t. overnight. Add sat. sodium bicarbonate, extract with ethyl acetate. Dried combined organics over sodium sulfate and concentrated. The crude product was purified by rHPLC to give 416. MS: (ESI+)=505.2. $^1$H NMR (400 MHz, DMSO) δ 8.37 (d, J=8.3 Hz, 1H), 8.15 (s, 1H), 7.95-7.90 (m, 2H), 7.43 (dd, J=8.3, 1.8 Hz, 1H), 7.28 (d, J=1.8 Hz, 1H), 7.17 (d, J=1.1 Hz, 1H), 6.24-6.13 (m, 1H), 4.78-4.66 (m, 2H), 4.51-4.39 (m, 2H), 4.36 (t, J=5.5 Hz, 2H), 4.04 (s, 2H), 3 (t, J=5.1 Hz, 2H), 1.84 (s, 3H), 1.10 (s, 6H).

Example 417

2-Methyl-1-{4-[2-(2-pyridin-2-ylmethyl-2H-[1,2,4]triazol-3-yl)-4,5-dihydro-6-oxa-3-thia-1-aza-benzo[e]azulen-8-yl]-pyrazol-1-yl}-propan-2-ol 417

Following the procedure for 114, 8-Bromo-2-(2-pyridin-2-ylmethyl-2H-[1,2,4]triazol-3-yl)-4,5-dihydro-6-oxa-3-thia-1-aza-benzo[e]azulene was reacted with 2-Methyl-1-[4-(4,4,5,5-tetramethyl-[1,3,2]dioxaborolan-2-yl)-pyrazol-1-yl]-propan-2-ol to give 417. MS(ESI+) 500.1. $^1$H NMR (400 MHz, CDCl$_3$) δ 8.56-8.52 (d, J=4.2, 1H), 8.19 (s, 1H), 8.14 (s, 1H), 8.03 (d, J=8.3, 1H), 7.92 (s, 1H), 7.78 (td, J=7.7, 1.8, 1H), 7.32-7.26 (m, 2H), 7.24 (d, J=1.7, 1H), 7.16 (d, J=7.9, 1H), 6.17 (s, 2H), 4.71 (s, 1H), 4.34 (t, J=5.0, 2H), 4.03 (s, 2H), 3.41 (t, J=5.0, 2H), 1.09 (s, 6H)

Example 418

{5-[2-(2-Isopropyl-2H-[1,2,4]triazol-3-yl)-4,5-dihydro-6-oxa-3-thia-1-aza-benzo[e]azulen-8-yl]-1-methyl-1H-imidazol-2-yl}-methanol 418

Following the procedure for 114, (5-Bromo-1-methyl-1H-imidazol-2-yl)-methanol was reacted with 2-(2-Isopropyl-5-methyl-2H-[1,2,4]triazol-3-yl)-8-(4,4,5,5-tetramethyl-[1,3,2]dioxaborolan-2-yl)-4,5-dihydro-6-oxa-3-thia-1-aza-benzo[e]azulene to give 418. MS(ESI+) 423.1. $^1$H NMR (400 MHz, DMSO) δ 8.43 (d, J=8.3, 1H), 8.11 (s, 1H), 7.33 (dd, J=8.3, 1.8, 1H), 7.17 (d, J=1.8, 1H), 7.05 (s, 1H), 5.92-5.78 (m, 1H), 5.32 (t, J=5.3, 1H), 4.55 (d, J=5.0, 2H), 4.42 (t, J=5.0, 2H), 3.72 (s, 3H), 3.47 (t, J=5.0, 2H), 1.56 (d, J=6.6, 6H)

Example 419

5-(8-azetidin-3-yl-4,5-dihydro-6-oxa-1-thia-benzo[e]azulen-2-yl)-1-(2,4-difluoro-phenyl)-1H-[1,2,4]triazole 419

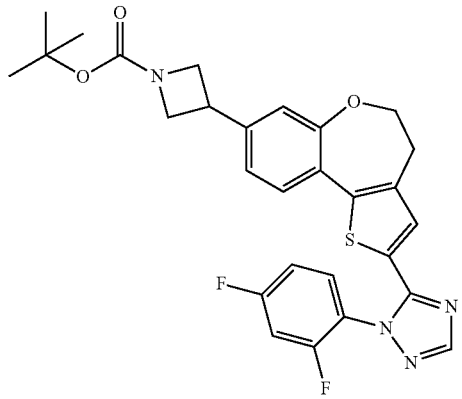 [SMILES: CC(C)(C)OC(=O)N1CC(c2ccc3c(c2)OCCc2cc(-c4ncnn4-c4ccc(F)cc4F)sc2-3)C1]

5-(8-bromo-4,5-dihydrobenzo[b]thieno[2,3-d]oxepin-2-yl)-1-(2,4-difluorophenyl)-1H-1,2,4-triazole (300 mg, 0.6 mmol) was dissolved in N,N-dimethyacetamide and purged with nitrogen. Added [1,1'-Bis(diphenylphosphino)ferrocene]dichloropalladium(II) complex with dichloromethane (1:1) (30 mg, 0.04 mmol) and copper(I)iodide (10 mg, 0.08 mmol). Bubbled in nitrogen for 10 minutes. Added (1-(tert-butoxycarbonyl)azetidin-3-yl)zinc(II) iodide (230 mg, 0.65 mmol) in 2.3 mL DMA. Heated at 80° C. overnight. Complete reaction was confirmed by LCMS. Diluted reaction mixture with 1 M HCl and extracted the t-Boc protected intermediate, tert-butyl 3-(2-(1-(2,4-difluorophenyl)-1H-1,2,4-triazol-5-yl)-4,5-dihydrobenzo[b]thieno[2,3-d]oxepin-8-yl)azetidine-1-carboxylate, with ethyl acetate. Dried over magnesium sulfate and concentrated in vacuo. Purified by flash chromatography (0 to 50% ethyl acetate in hexanes). Concentrated in vacuo and re-dissolved the residue in 10 mL 1,4-dioxane. Added 5 mL 4 N HCl in dioxane and let stir for 2 hours. Complete deprotection was confirmed by LCMS. Concentrated in vacuo purified by HPLC to give 419 (21.1 mg, 7% yield, M=1 437.1).

Example 420

2-Methyl-1-{4-[2-(1-oxetan-3-yl-1H-imidazol-2-yl)-4,5-dihydro-6-oxa-3-thia-1-aza-benzo[e]azulen-8-yl]-pyrazol-1-yl}-propan-2-ol 420

Following the procedure for 355, 8-Bromo-2-(1-oxetan-3-yl-1H-imidazol-2-yl)-4,5-dihydro-6-oxa-3-thia-1-aza-benzo[e]azulene and 2-methyl-1-(4-(4,4,5,5-tetramethyl-1,3,2-dioxaborolan-2-yl)-1H-pyrazol-1-yl)propan-2-ol were reacted under Suzuki palladium conditions to give 420. MS: (ESI+)=464.1. $^1$H NMR (400 MHz, DMSO) δ 8.36 (d, J=8.3 Hz, 1H), 8.15 (s, 1H), 7.94 (d, J=1.4 Hz, 2H), 7.47 (dd, J=8.3, 1.7 Hz, 1H), 7.28 (d, J=1.7 Hz, 1H), 7.19 (d, J=1.0 Hz, 1H), 6.38 (p, J=6.8 Hz, 1H), 5.10 (t, J=7.3 Hz, 2H), 4.86 (t, J=6.6 Hz, 2H), 4.72 (s, 1H), 4.36 (t, J=5.0 Hz, 2H), 4.04 (s, 2H), 3.38 (t, J=5.0 Hz, 2H), 1.10 (s, 6H)

Example 421

1-{3-[2-(2-Isopropyl-2H-[1,2,4]triazol-3-yl)-4,5-dihydro-6-oxa-3-thia-1-aza-benzo[e]azulen-8-yl]-azetidin-1-yl}-2-methyl-propan-2-ol 421

To a mixture of 8-azetidin-3-yl-2-(2-isopropyl-2H-[1,2,4]triazol-3-yl)-4,5-dihydro-6-oxa-3-thia-1-aza-benzo[e]azulene TFA salt 235 (250 mg, 0.52 mmol) in MeOH (3 mL) was added diisopropylethylamine (110 µL, 0.62 mmol) followed by 1,2-epoxy-2-methylpropane (230 µL, 2.6 mmol) and the reaction mixture was stirred at RT for 18 hours. The reaction mixture was concentrated in vacuo and the residue purified by flash chromatography (SiO$_2$, 0-7.5% MeOH in DCM) to give a solid that was recrystallised from heptane to give 421 (87 mg, 38%). LCMS: R$_T$=7.41 min, [M+H]$^+$=440. $^1$H NMR δ (ppm) (DMSO-d6): 8.26 (1H, d, J=8.17 Hz), 8.06 (1H, d, J=0.59 Hz), 7.16 (1H, dd, J=8.23, 1.81 Hz), 7.00 (1H, d, J=1.76 Hz), 5.83-5.75 (1H, m), 4.32 (2H, t, J=5.03 Hz), 4.00 (1H, s), 3.65 (2H, t, J=6.98 Hz), 3.61-3.51 (1H, m), 3.39 (2H, t, J=5.08 Hz), 3.14 (2H, t, J=6.52 Hz), 2.32 (2H, s), 1.51 (6H, d, J=6.59 Hz), 1.03 (6H, s)

Example 422

2-(2-Isopropyl-2H-[1,2,4]triazol-3-yl)-8-[1-(2,2,2-trifluoro-ethyl)-azetidin-3-yl]-4,5-dihydro-6-oxa-3-thia-1-aza-benzo[e]azulene 422

Following the procedure of 319, 8-azetidin-3-yl-2-(2-isopropyl-2H-[1,2,4]triazol-3-yl)-4,5-dihydro-6-oxa-3-thia-1-aza-benzo[e]azulene TFA salt 235, trifluoroethyl triflate and triethylamine were reacted to give 422 isolated as a white solid (105 mg, 52%). LCMS: R$_T$=12.34 min, [M+H]$^+$=450. $^1$H NMR δ (ppm) (CDCl$_3$): 8.32 (1H, d, J=8.18 Hz), 7.90 (1H, s), 7.10 (1H, dd, J=8.21, 1.86 Hz), 6.98 (1H, d, J=1.83 Hz), 5.93-5.84 (1H, m), 4.39 (2H, t, J=5.05 Hz), 3.90 (2H, t, J=7.29 Hz), 3.82-3.73 (1H, m), 3.42-3.33 (4H, m), 3.04 (2H, q, J=9.39 Hz), 1.61 (6H, d, J=6.63 Hz)

Example 423

8-(1-Isopropyl-azetidin-3-yl)-2-(2-isopropyl-2H-[1,2,4]triazol-3-yl)-4,5-dihydro-6-oxa-3-thia-1-aza-benzo[e]azulene 423

A suspension of 8-azetidin-3-yl-2-(2-isopropyl-2H-[1,2,4]triazol-3-yl)-4,5-dihydro-6-oxa-3-thia-1-aza-benzo[e]azulene TFA salt 235 (215 mg, 0.45 mmol) in dry DCE (4.5 mL) under argon was treated with acetone (49 µL, 0.67 mmol) followed by sodium triacetoxyborohydride (190 mg, 0.89 mmol). The reaction mixture was stirred at RT for 18 hours. Aqueous saturated sodium bicarbonate solution and DCM were added and the phases were separated. The aqueous phase was extracted with DCM (×2) and the combined organic phase was washed with water followed by brine, dried (Na$_2$SO$_4$) and concentrated in vacuo. The resultant solid was triturated with ether, to give 423 as an off-white solid (115 mg, 63%). LCMS: R$_T$=7.44 min, [M+H]$^+$=410. $^1$H NMR δ (ppm) (CDCl$_3$): 8.30 (1H, d, J=8.17 Hz), 7.89 (1H, s), 7.07 (1H, dd, J=8.20, 1.83 Hz), 6.96 (1H, d, J=1.81 Hz), 5.93-5.84 (1H, m), 4.38 (2H, t, J=5.05 Hz), 3.79 (2H, t, J=7.00 Hz), 3.74-3.63 (1H, m), 3.39 (2H, t, J=5.06 Hz), 3.12 (2H, m), 2.38 (1H, m), 1.60 (6H, d, J=6.63 Hz), 0.97 (6H, d, J=6.21 Hz)

Example 424

(S)-3-{3-[2-(2-Isopropyl-2H-[1,2,4]triazol-3-yl)-4,5-dihydro-6-oxa-3-thia-1-aza-benzo[e]azulen-8-yl]-azetidin-1-yl}-propane-1,2-diol 424

Following the procedure for 322, 8-[1-((S)-2,2-dimethyl-[1,3]dioxolan-4-ylmethyl)-azetidin-3-yl]-2-(2-isopropyl-2H-[1,2,4]triazol-3-yl)-4,5-dihydro-6-oxa-3-thia-1-aza-benzo[e]azulene was reacted with acid, warming the reaction at 50° C. overnight. The crude product was triturated with diethyl ether to give 424 (72 mg, 60%). LCMS: R$_T$=7.02 min, [M+H]$^+$=442. $^1$H NMR δ (ppm) (DMSO-d6): 10.50 (1H, s), 8.31 (1H, dd, J=8.22, 5.90 Hz), 8.07 (1H, s), 7.30-7.22 (1H, m), 7.17 (1H, dd, J=15.00, 1.80 Hz), 5.81-5.72 (1H, m), 4.42-4.22 (5H, m), 4.22-4.10 (1H, m), 3.76 (1H, d, J=9.24 Hz), 3.47-3.22 (5H, m), 3.20-3.09 (1H, m), 1.51 (6H, d, J=6.59 Hz). 1 Proton obscured by water peak. 2 Exchangeable protons not observed

Example 425

(1-Amino-cyclopropyl)-{3-[2-(2-isopropyl-2H-[1,2,4]triazol-3-yl)-4,5-dihydro-6-oxa-3-thia-1-aza-benzo[e]azulen-8-yl]-azetidin-1-yl}-methanone 425

To a suspension of (1-{3-[2-(2-isopropyl-2H-[1,2,4]triazol-3-yl)-4,5-dihydro-6-oxa-3-thia-1-aza-benzo[e]azulen-8-yl]-azetidine-1-carbonyl}-cyclopropyl)-carbamic acid tert-butyl ester (225 mg, 0.41 mmol) in MeOH (3.1 mL) was added 4N HCl/dioxan (1.0 mL, 4.1 mmol) and the reaction mixture was stirred for 18 hours. The resulting solid was filtered off and washed with diethyl ether before being partitioned between DCM and an aqueous saturated sodium bicarbonate solution. The phases were separated and the aqueous phase was extracted with DCM (×2). The combined organic extracts were washed with brine, dried (Na$_2$SO$_4$) and concentrated in vacuo. The resultant residue was purified by flash chromatography (SiO$_2$, 0-8% 2N NH$_3$/MeOH in DCM). The resulting solid was suspended in ether and collected by filtration to give 425 as a white solid (108 mg, 59%). LCMS: R$_T$=7.96 min, [M+H]$^+$=451. $^1$H NMR δ (ppm) (DMSO-d6): 8.35 (1H, d, J=8.20 Hz), 8.02 (1H, s), 7.20 (1H, dd, J=8.22, 1.81 Hz), 7.05 (1H, s), 5.86-5.78 (1H, m), 4.59 (2H, t, J=9.01 Hz), 4.40 (2H, t, J=5.07 Hz), 4.20 (2H, d, J=7.67 Hz), 3.85 (1H, t, J=7.50 Hz), 3.44 (2H, t, J=5.08 Hz), 2.18 (2H, s), 1.58 (6H, d, J=6.59 Hz), 1.09-1.06 (2H, m), 0.70 (2H, q, J=3.28 Hz)

Example 426

4-{8-[1-(2-Hydroxy-ethyl)-1H-pyrazol-4-yl]-4,5-dihydro-6-oxa-3-thia-1-aza-benzo[e]azulen-2-yl}-5-isopropyl-2-methyl-2,4-dihydro-[1,2,4]triazol-3-one 426

Following the procedure for 322, 5-isopropyl-2-methyl-4-(8-{1-[2-(tetrahydro-pyran-2-yloxy)-ethyl]-1H-pyrazol-4-yl}-4,5-dihydro-6-oxa-3-thia-1-aza-benzo[e]azulen-2-yl)-2,4-dihydro-[1,2,4]triazol-3-one was reacted with acid. The product was precipitated from the reaction mixture by the addition of ether and collected by filtration to give 426 as a white solid (8.5 mg, quant.). LCMS: R$_T$=11.47 min, [M+H]$^+$=453. $^1$H NMR δ (ppm) (DMSO-d6): 8.16 (1H, s), 8.10 (1H, d, J=8.26 Hz), 7.89 (1H, s), 7.36 (1H, dd, J=8.26, 1.84 Hz), 7.23 (1H, d, J=1.81 Hz), 4.32 (2H, t, J=5.01 Hz), 4.11 (2H, t, J=5.65 Hz), 3.90-3.82 (1H, m), 3.72 (2H, t, J=5.66

Hz), 3.38 (3H, s), 1.31 (6H, d, J=6.81 Hz). 2 Protons obscured by water peak. 1 Exchangeable proton not seen.

Example 427

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-2-methyl-propan-1-ol 427

A solution of 2-{3-[2-(2-isopropyl-2H-[1,2,4]triazol-3-yl)-4,5-dihydro-6-oxa-3-thia-1-aza-benzo[e]azulen-8-yl]-azetidin-1-yl}-2-methyl-propionic acid methyl ester (147 mg, 0.31 mmol) in anhydrous THF (5 mL) at 0° C. under nitrogen was treated dropwise with a 1M solution of LiAlH$_4$ in THF (0.47 mL, 0.47 mmol) and the mixture was stirred for 15 minutes then allowed to warm to RT. After 1.5 hours the mixture was cooled to 0° C. and quenched by cautious addition of water. EtOAc was added and the organic layer was washed with brine, dried (Na$_2$SO$_4$) and concentrated in vacuo. The resultant residue was dissolved in DCM (20 mL) and treated with 4N HCl/dioxan (1 mL). The resulting solid was filtered off, washed with ether and dried to give 427 (142 mg, quant.). LCMS: R$_T$=7.54 min, [M+H]$^+$=440. $^1$H NMR δ (ppm) (DMSO-d6): 10.61 (1H, s), 8.32 (1H, d, J=8.21 Hz), 8.07 (1H, s), 7.22-7.16 (1H, m), 7.06 (1H, d, J=1.80 Hz), 5.81-5.72 (1H, m), 4.55 (1H, td, J=10.55, 4.79 Hz), 4.38-4.26 (3H, m), 4.16-3.92 (3H, m), 3.46-3.37 (5H, m), 1.53-1.48 (6H, m), 1.27-1.14 (6H, m)

Example 428

2-{8-[1-(2-Hydroxy-2-methyl-propyl)-1H-pyrazol-4-yl]-4,5-dihydro-6-oxa-3-thia-1-aza-benzo[e]azulen-2-ylamino}-2-methyl-propan-1-ol 428

2-(8-Bromo-4,5-dihydrothiazolo[4,5-d]benzo[b]oxepine-2-ylamino)-2-methylpropan-1-ol from Example 356, was coupled with 2-methyl-1-(4-(4,4,5,5-tetramethyl-1,3,2-dioxaborolan-2-yl)-1H-pyrazol-1-yl)propan-2-ol under Suzuki conditions to give 428. Yield 18%. MS(ESI+): 429.2. 1H NMR (400 MHz, DMSO) δ 8.14-8.04 (m, 2H), 7.87 (s, 1H), 7.29 (dd, J=8.2, 1.8, 1H), 7.17 (d, J=1.8, 1H), 7.07 (s, 1H), 4.97 (t, J=5.6, 1H), 4.70 (s, 1H), 4.26 (t, J=5.0, 2H), 4.02 (s, 2H), 3.58 (d, J=5.6, 2H), 3.05 (t, J=5.0, 2H), 1.34 (s, 6H), 1.09 (s, 6H)

Example 429

1-{8-[1-(2-Hydroxy-2-methyl-propyl)-1H-pyrazol-4-yl]-4,5-dihydro-6-oxa-3-thia-1-aza-benzo[e]azulen-2-yl}-5,5-dimethyl-imidazolidin-2-one 429

Step 1: 1-(2-Methyl-1-(tritylamino)propan-2-yl)thiourea

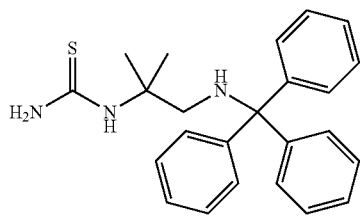 [SMILES: CC(C)(CNC(c1ccccc1)(c1ccccc1)c1ccccc1)NC(N)=S]

2-Methyl-N1-tritylpropane-1,2-diamine, prepared from 2-methylpropane-1,2-diamine and trityl chloride (EP1204654) in yield of 44%, was coupled with benzoylisothiocyanate to give N-(2-methyl-1-(tritylamino)propan-2-ylcarbamothioyl)benzamide (US2008/45579) which was then reacted with lithium hydroxide to give 1-(2-methyl-1-(tritylamino)propan-2-yl)thiourea. Yield 79%. 1H NMR (400 MHz, CDCl3) δ 7.40-7.12 (m, 16H), 6.30 (s, 1H), 2.38 (d, J=8.3, 2H), 2.15 (t, J=8.3, 1H), 1.31 (s, 6H)

Step 2: N2-(8-Bromo-4,5-dihydrothiazolo[4,5-d]benzo[b]oxepin-2-yl)-2-methylpropane-1,2-diamine hydrobromide

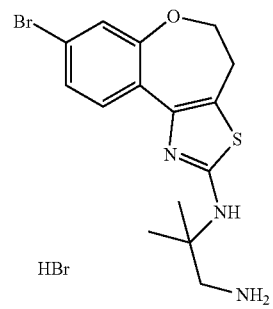 [SMILES: CC(C)(CN)Nc1nc2c(s1)CCOc1cc(Br)ccc1-2 ; Br]

Following the Example 356, 1-(2-methyl-1-(tritylamino)propan-2-yl)thiourea was reacted with 4,8-dibromo-3,4-dihydro-2Hbenzo[b]oxepin-5-one in ethanol under reflux for 18 hours to give N2-(8-bromo-4,5-dihydrothiazolo[4,5-d]benzo[b]oxepin-2-yl)-2-methylpropane-1,2-diamine hydrobromide. Yield 68%. MS(ESI+): 368.0

Step 3: 1-(8-Bromo-4,5-dihydrothiazolo[4,5-d]benzo[b]oxepin-2-yl)-5,5-dimethylimidazolidin-2-one

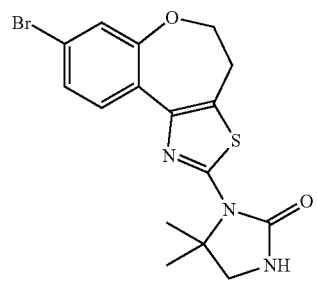 [SMILES: CC1(C)CNC(=O)N1c1nc2c(s1)CCOc1cc(Br)ccc1-2]

Following the Example 356, N2-(8-bromo-4,5-dihydrothiazolo[4,5-d]benzo[b]oxepin-2-yl)-2-methylpropane-1,2-diamine hydrobromide was reacted with triphosgene in tetrahydrofuran and purified on silicagel column eluting with 50% of ethyl acetate in heptane to give 1-(8-bromo-4,5-dihydrothiazolo[4,5-d]benzo[b]oxepin-2-yl)-5,5-dimethylimidazolidin-2-one. Yield 51%. MS(ESI+): 393.9

Step 4

1-(8-Bromo-4,5-dihydrothiazolo[4,5-d]benzo[b]oxepin-2-yl)-5,5-dimethylimidazolidin-2-one was coupled with 2-methyl-1-(4-(4,4,5,5-tetramethyl-1,3,2-dioxaborolan-2-yl)-1H-pyrazol-1-yl)propan-2-ol under Suzuki conditions to give 429. Yield 12%. MS(ESI+): 454.1. 1H NMR (400 MHz, DMSO) δ 8.18 (d, J=8.2, 1H), 8.10 (s, 1H), 7.89 (s, 1H), 7.61 (s, 1H), 7.35 (dd, J=8.2, 1.8, 1H), 7.21 (d, J=1.7, 1H), 4.71 (s, 1H), 4.31 (t, J=5.0, 2H), 4.03 (d, J=5.6, 2H), 3.18 (dd, J=9.3, 5.1, 3H), 1.72 (s, 6H), 1.09 (s, 6H)

Example 430

2-(2-Isopropyl-2H-[1,2,4]triazol-3-yl)-8-(1-methanesulfonylmethyl-1H-pyrazol-4-yl)-4,5-dihydro-6-oxa-3-thia-1-aza-benzo[e]azulene 430

Following the procedure for 114, 8-Bromo-2-(2-isopropyl-2H-[1,2,4]triazol-3-yl)-4,5-dihydro-6-oxa-3-thia-1-aza-benzo[e]azulene 27 was reacted with 1-Methanesulfonylmethyl-4-(4,4,5,5-tetramethyl-[1,3,2]dioxaborolan-2-yl)-1H-pyrazole to give 430. MS(ESI+) 471.1. $^1$H NMR (400 MHz, DMSO) δ 8.36 (m, 2H), 8.19 (s, 1H), 8.10 (s, 1H), 7.49 (dd, J=8.3, 1.8, 1H), 7.36 (d, J=1.7, 1H), 5.84 (m, 1H), 5.75 (s, 2H), 4.40 (t, J=5.0, 2H), 3.46 (t, J=5.0, 2H), 3.06 (s, 3H), 1.56 (d, J=6.6, 6H)

Example 431

N2-(2-chloro-5-(2-hydroxyethylcarbamoyl)phenyl)-N2,N8-dimethyl-4,5-dihydrobenzo[b]thieno[2,3-d]oxepine-2,8-dicarboxamide 431

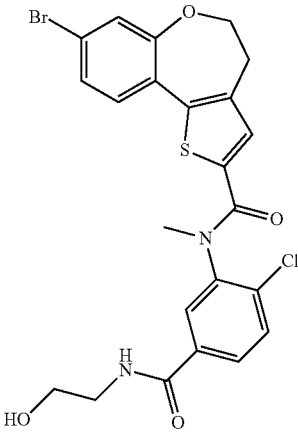 [SMILES: CN(C(=O)c1cc2c(s1)-c1ccc(Br)cc1OCC2)c1cc(C(=O)NCCO)ccc1Cl]

To a mixture of 3-(8-bromo-N-methyl-4,5-dihydrobenzo[b]thieno[2,3-d]oxepine-2-carboxamido)-4-chlorobenzoic acid (3 g, 6.09 mmol) in THF (50 mL) was added EDCI (2.34 g, 12.18 mmol), HOBt (1.23 g, 9.13 mmol), DIPEA (5 mL) and 2-aminoethanol (0.56 g, 9.13 mmol) by sequence under nitrogen atmosphere at room temperature. The reaction mixture was stirred overnight, diluted with water. The resulting precipitate was washed with water and EtOAc to give 8-bromo-N-(2-chloro-5-(2-hydroxyethylcarbamoyl)phenyl)-N-methyl-4,5-dihydrobenzo[b]thieno[2,3-d]oxepine-2-carboxamide (2.52 g, yield 77%). LC-MS: (ESI, m/z)=535 [M+H]$^+$ 8-Bromo-N-(2-chloro-5-(2-hydroxyethylcarbamoyl)phenyl)-N-methyl-4,5-dihydrobenzo[b]thieno[2,3-d]oxepine-2-carboxamide (0.5 g, 0.933 mmol) was dissolved in 5 mL of pyridine. The mixture was stirred at 0° C. and acetic anhydride (0.2 g, 2 eq) was added dropwise. It was stirred at room temperature for overnight. The mixture was poured into ice water and the mixture was extracted by DCM. The combined organics were dried and evaporated in vacuum to afford the acetylated product, 2-(3-(8-bromo-N-methyl-4,5-dihydrobenzo[b]thieno[2,3-d]oxepine-2-carboxamido)-4-chlorobenzamido)ethyl acetate (0.45 g, yield: 83%). LC-MS: (ESI, m/z)=577 [M+H]$^+$ A suspension of 2-(3-(8-bromo-N-methyl-4,5-dihydrobenzo[b]thieno[2,3-d]oxepine-2-carboxamido)-4-chlorobenzamido)ethyl acetate (400 mg, 0.69 mmol), Pd(OAc)$_2$ (10 mg, 0.045 mmol), Xantphos (40 mg, 0.069 mmol), MeNH$_2$.HCl (70 mg, 1.04 mmol) and Na$_2$CO$_3$ (219 mg, 2.07 mmol) in toluene (5 mL) was heated at 80° C. under atmosphere of CO from balloon overnight. Then it was filtrated and concentrated, the crude product was dissolved in 10 mL of THF/H$_2$O=1:1. 0.14 g of NaOH was added. The mixture was stirred at room temperature for overnight. The mixture was extracted by DCM and purified by column (EtOAc: MeOH=10:1) to afford 431 (72.6 mg, yield: 20%)$^1$H NMR (DMSO-d6, 400 MHz): δ8.62 (t, J=5.6 Hz, 1H), 8.41 (d, J=4.8 Hz, 1H), 8.07 (s, 1H), 7.95 (d, J=7.6 Hz, 1H), 7.74 (d, J=8.4 Hz, 1H), 7.46 (s, 2H), 7.39 (s, 1H), 6.58 (s, 1H), 4.73 (t, J=5.6 Hz, 1H), 4.16 (s, 2H), 3.50 (dd, J=6.0, 10.0 Hz, 2H), 3.31-3.27 (m, 5H), 2.94 (s, 2H), 2.72 (d, J=4.4 Hz, 3H). LC-MS: (ESI, m/z)=514 [M+H]$^+$ Example 432

N2-(2-chloro-5-(3,3-difluoroazetidine-1-carbonyl)phenyl)-N2-methyl-N8-(2-(methylsulfonyl)ethyl)-4,5-dihydrobenzo[b]thieno[2,3-d]oxepine-2,8-dicarboxamide 432

A suspension of 8-bromo-N-(2-chloro-5-(3,3-difluoroazetidine-1-carbonyl)phenyl)-N-methyl-4,5-dihydrobenzo[b]thieno[2,3-d]oxepine-2-carboxamide (400 mg, 0.70 mmol), Pd(OAc)$_2$ (8 mg, 0.035 mmol), Xantphos (41 mg, 0.070 mmol), MeSO$_2$(CH$_2$)$_2$NH$_2$.HCl (169 mg, 1.06 mmol) and Na$_2$CO$_3$ (224 mg, 2.11 mmol) in toluene (5 mL) and DMF (5 mL) was heated at 80° C. under atmosphere of CO from balloon for 3 h. Then it was filtrated and concentrated, the crude product was purified by flash column chromatography on silica gel (petroleum ether:EtOAc=2:1~1:5 as eluted solvent) to give a white solid which was washed with DCM and dried to give 432 (121.3 mg, yield: 27%). $^1$H NMR (DMSO-d6, 400 MHz): δ 8.73-6.60 (m, 8H, NH, ArH), 4.75-3.02 (m, 18H). LC-MS: (ESI, m/z)=638 [M+H]$^+$ Example 433

{2-[2-(2,4-Difluoro-phenyl)-2H-[1,2,4]triazol-3-yl]-4,5-dihydro-6-oxa-1-thia-10-aza-benzo[e]azulen-9-yl}-(1-methyl-azetidin-3-yl)-amine 433

3-{2-[2-(2,4-Difluoro-phenyl)-2H-[1,2,4]triazol-3-yl]-4,5-dihydro-6-oxa-1-thia-10-aza-benzo[e]azulen-9-ylamino}-azetidine-1-carboxylic acid tert-butyl ester (300 mg, 0.54 mmol) was dissolved in THF (20 mL), and LiAlH$_4$ was added in the solution. The reaction mixture was stirred at room temperature for 2 hr, filtered to gather the solution, washed by DCM (10 mL), and separated by TLC (DCM/EtOAc=10:1) to give 433 (128.3 mg, yield: 51%). $^1$H NMR (DMSO-d$_6$, 400 MHz): δ8.36 (s, 1H), 8.28-7.95 (m, 2H), 7.75-7.56 (m, 1H), 7.54 (m, 1H), 6.98-6.83 (m, 1H), 6.73-6.55 (m, 1H), 4.10 (m, 6H), 3.55 (s, 1H), 3.48 (s, 1H), 3.02 (t, J=8.0 Hz, 2H). LC-MS (ESI): m/z=467 [M+H]$^+$

Example 434

{2-[2-(2,4-Difluoro-phenyl)-2H-[1,2,4]triazol-3-yl]-4,5-dihydro-6-oxa-1-thia-10-aza-benzo[e]azulen-9-yl}-oxetan-3-yl-amine 434

Compound 134 (200 mg, 0.5 mmol) was dissolved in THF, and oxetan-3-one (252 mg, 0.35 mmol) was added at 0° C. The mixture was warmed to 80° C. and stirred for 0.5 h at this temperature. It was cooled to 0° C., NaBH(CN)$_3$ (67 mg, 0.6 mmol) was added. Then the mixture was warmed to 80° C. and stirred for further 0.5 h at this temperature. The reaction mixture was filtered to gather the solution. Then water was added into the solution. It was extracted by DCM (20 mL×3). The combined organics were dried over Na$_2$SO$_4$, concentrated in vacuo, and separated by prep TLC (EtOAc/hexanes=4:1) to give 434 (115 mg, yield: 50%). $^1$H NMR (DMSO-d6, 400 MHz): δ9.42 (s, 1H), 8.42 (s, 1H), 8.00-7.49 (m, 4H), 7.12 (s, 1H), 7.04 (d, J=9.6 Hz, 1H), 4.85-4.83 (m, 1H), 4.58-4.38 (m, 4H), 3.65 (t, J=6.4 Hz, 2H), 2.93 (t, J=6.4 Hz, 2H). LC-MS (ESI): m/z=454 [M+H]$^+$

Example 435

Azetidin-3-yl-{2-[2-(2,4-difluoro-phenyl)-2H-[1,2,4]triazol-3-yl]-4,5-dihydro-6-oxa-1-thia-10-aza-benzo[e]azulen-9-yl}-amine 435

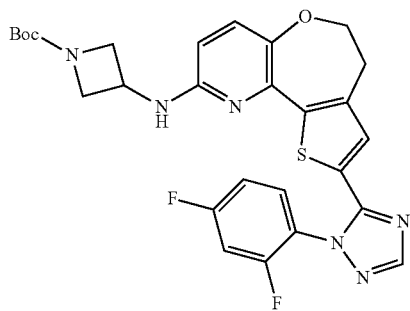 [SMILES: CC(C)(C)OC(=O)N1CC(Nc2ccc3c(n2)-c2sc(-c4ncnn4-c4ccc(F)cc4F)cc2CCO3)C1]

9-Chloro-2-[2-(2,4-difluoro-phenyl)-2H-[1,2,4]triazol-3-yl]-4,5-dihydro-6-oxa-1-thia-10-aza-benzo[e]azulene (812 mg, 2.0 mmol), tert-butyl 3-aminoazetidine-1-carboxylate (412 mg, 2.4 mmol), Pd(OAc)2 (45 mg, 0.20 mmol), Xphos (95 mg, 2.0 mmol), t-BuONa (460 mg, 4.0 mmol) and dioxane (4.0 mL) were added into a 10 mL of sealed tube, and the mixture was heated by microwave at 112° C. for 7 min under N$_2$. The reaction mixture was filtered to gather the solution and water was added. The mixture was extracted by DCM (20 mL×3). The combined organic layers were dried over Na$_2$SO$_4$, concentrated in vacuo, and purified by column (DCM/EtOAc=10:1) to give 3-{2-[2-(2,4-Difluoro-phenyl)-2H-[1,2,4]triazol-3-yl]-4,5-dihydro-6-oxa-1-thia-10-aza-benzo[e]azulen-9-ylamino}-azetidine-1-carboxylic acid tert-butyl ester (703 mg, yield: 64%). $^1$HNMR (Acetone-d$_6$, 400 MHz): δ7.99 (s, 1H), 7.76-7.73 (m, 1H), 7.38-7.27 (m, 2H), 7.14 (s, 1H), 7.00 (d, J=8.8 Hz, 1H), 6.37 (d, J=8.8 Hz, 1H), 6.27 (d, J=5.2 Hz, 1H), 4.29-4.09 (m, 6H), 3.57 (s, 1H), 3.02 (t, J=4.8 Hz, 2H), 1.34 (s, 9H). ESI-MS: m/z=553 [M+H$^+$]
3-{2-[2-(2,4-Difluoro-phenyl)-2H-[1,2,4]triazol-3-yl]-4,5-dihydro-6-oxa-1-thia-10-aza-benzo[e]azulen-9-ylamino}-azetidine-1-carboxylic acid tert-butyl ester (558 mg, 1.0 mmol) was dissolved in EtOAc (10 mL). Hydrogen chloride dissolved in Ethyl acetate (EtOAc—HCl, 10 mL) was added by drop to the solution and the reaction mixture was stirred at room temperature for 2 h. The reaction mixture was filtered to gather the solid which was washed with DCM (10 mL) to give 435 (0.43 g, yield: 87%). $^1$HNMR (DMSO-d$_6$, 400 MHz): δ7.99 (s, 1H), 7.74-7.72 (m, 1H), 7.36-7.27 (m, 2H), 7.14 (s, 1H), 7.00 (d, J=8.8 Hz, 1H), 6.38-6.26 (m, 2H), 4.11-4.09 (m, 6H), 3.56 (s, 1H), 3.02 (t, J=4.8 Hz, 2H). ESI-MS: m/z=453 [M+H$^+$]

Example 436

2-[2-(2,4-Difluoro-phenyl)-2H-[1,2,4]triazol-3-yl]-9-(6-fluoro-5-methyl-pyridin-3-yl)-4,5-dihydro-6-oxa-1-thia-10-aza-benzo[e]azulene 436

9-Chloro-2-[2-(2,4-difluoro-phenyl)-2H-[1,2,4]triazol-3-yl]-4,5-dihydro-6-oxa-1-thia-10-aza-benzo[e]azulene (416 mg, 1.0 mmol) was dissolved in CH$_3$CN/H$_2$O (3 mL), Pd(dppf)$_2$Cl$_2$ (58 mg, 0.10 mmol), Cs$_2$CO$_3$ (658 mg, 2.0 mmol) were added in a 10 mL of sealed tube. The reaction mixture was heated by microwave at 120° C. for 20 min under N$_2$. The reaction mixture was concentrated in vacuo. The residue was dissolved in DCM (20 mL), washed by water, dried by Na$_2$SO$_4$, concentrated in vacuo, and separated by prep. TLC (EtOAc/Hexanes=1:3) to give 436 (300 mg, yield: 61%). $^1$HNMR (DMSO-d6, 400 MHz): δ8.68 (s, 1H), 8.43-8.34 (m, 1H), 8.12-8.01 (m, 1H), 8.00 (d, J=8.4 Hz, 1H), 7.84-7.78 (m, 1H), 7.58-7.50 (m, 1H), 7.26 (s, 1H), 4.39 (m, 2H), 3.39 (s, 2H), 3.00 (s, 2H), 2.41 (s, 3H). LC-MS (ESI): m/z=492 [M+H]$^1$

Example 437

2-[2-(2,4-Difluoro-phenyl)-2H-[1,2,4]triazol-3-yl]-9-[5-methyl-6-(4-methyl-piperazin-1-yl)-pyridin-3-yl]-4,5-dihydro-6-oxa-1-thia-10-aza-benzo[e]azulene 437

Compound 436 (200 mg, 0.41 mmol) was dissolved in NMP (2 mL), N-Methyl-piperazine (82 mg, 0.82 mmol) was added in it. The reaction mixture was heated by mw at 150° C. for 90 min. The reaction mixture was concentrated in vacuo, dissolved in DCM (20 mL). And the organic layer was washed by water, dried by Na$_2$SO$_4$, concentrated in vacuo, and separated by prep. TLC (EtOAc/Hexanes=1:3) to give 437 (72.1 mg, yield: 31%). $^1$H NMR (DMSO-d$_6$, 400 MHz): δ9.759 (s, 1H), 8.58 (s, 1H), 8.47 (t, J=11.8 Hz, 1H), 8.25 (s, 1H), 7.90 (d, J=8.4 Hz, 1H), 7.63-7.53 (m, 2H), 7.29-7.19 (m, 2H), 7.08 (d, J=11.2 Hz, 2H), 4.36 (t, J=4.8 Hz, 2H), 4.20-4.11 (m, 2H), 3.74-3.68 (m, 2H), 3.29 (s, 6H), 2.76 (s, 3H), 2.32 (s, 3H). LC-MS (ESI): m/z=572 [M+H]$^+$

Example 438

N2-(2-chloro-5-((S)-2-hydroxypropylcarbamoyl)phenyl)-N2-methyl-N8-(2-(methylsulfonyl)ethyl)-4,5-dihydrobenzo[b]thieno[2,3-d]oxepine-2,8-dicarboxamide 438

A suspension of 8-bromo-N-(2-chloro-5-((S)-2-hydroxypropylcarbamoyl)phenyl)-N-methyl-4,5-dihydrobenzo[b]thieno[2,3-d]oxepine-2-carboxamide (400 mg, 0.73 mmol), Pd(OAc)$_2$ (8 mg, 0.037 mmol), Xantphos (42 mg, 0.073 mmol), MeSO$_2$(CH$_2$)$_2$NH$_2$.HCl (175 mg, 1.095 mmol) and Na$_2$CO$_3$ (232 mg, 2.19 mmol) in toluene (5 mL) and DMF (5 mL) was heated at 80° C. under atmosphere of CO from balloon overnight. Then it was filtrated and concentrated, the crude product was purified by pre-TLC (eluted by DCM: MeOH=10:1) to give 438 (191.9 mg, yield 42%). $^1$H NMR (DMSO-d6, 400 MHz): δ8.74 (t, J=5.2 Hz, 1H, NH), 8.62 (t, J=5.2 Hz, 1H, NH), 8.12-7.44 (m, 6H, ArH), 6.61 (s, 1H, =CH), 4.77 (d, J=4.8 Hz, 1H, OH), 4.20 (br s, 2H, CH$_2$), 3.80-3.75 (m, 1H, CH), 3.67-2.98 (m, 14H, CH$_3$, CH$_2$), 1.05 (t, J=6.0 Hz, 3H, CH$_3$). LC-MS: (ESI, m/z)=620 [M+H]$^+$ Example 439

2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-isobutyramide 439

Following the procedure for 240, 2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-2-methyl-propionic acid was reacted with ammonium chloride to give 439. MS(ESI+) 464.1. $^1$H NMR (400 MHz, DMSO) δ 8.41 (s, 1H), 8.32 (d, J=8.3, 1H), 8.10 (s, 1H), 8.02 (s, 1H), 7.50 (dd, J=8.3, 1.8, 1H), 7.39 (d, J=1.7, 1H), 7.17 (br, 1H), 6.79 (br, 1H), 5.93-5.74 (m, 1H), 4.39 (t, J=5.0, 2H), 3.45 (t, J=5.0, 2H), 1.75 (s, 6H), 1.56 (d, J=6.6, 6H)

Example 440

2-{4-[2-(2-Isopropyl-5-methyl-2H-[1,2,4]triazol-3-yl)-4,5-dihydro-6-oxa-3-thia-1-aza-benzo[e]azulen-8-yl]-imidazol-1-yl}-ethanol 440

Similar to described in General Procedure G: 8-Bromo-2-(2-isopropyl-5-methyl-2H-[1,2,4]triazol-3-yl)-4,5-dihydro-6-oxa-3-thia-1-aza-benzo[e]azulene was reacted with a mixture of 1-(2-(tetrahydro-2H-pyran-2-yloxy)ethyl)-4-(tributylstannyl)-1H-imidazole and 1-(2-(tetrahydro-2H-pyran-2-yloxy)ethyl)-5-(tributylstannyl)-1H-imidazole to give 440 after THP-removal with aqueous HCl purification by reverse phase HPLC (55 mg). LCMS: 437.1.

Example 441

2-{5-[2-(2-Isopropyl-5-methyl-2H-[1,2,4]triazol-3-yl)-4,5-dihydro-6-oxa-3-thia-1-aza-benzo[e]azulen-8-yl]-imidazol-1-yl}-ethanol 441

Similar to described in General Procedure G: 8-Bromo-2-(2-isopropyl-5-methyl-2H-[1,2,4]triazol-3-yl)-4,5-dihydro-6-oxa-3-thia-1-aza-benzo[e]azulene was reacted with a mixture of 1-(2-(tetrahydro-2H-pyran-2-yloxy)ethyl)-4-(tributylstannyl)-1H-imidazole and 1-(2-(tetrahydro-2H-pyran-2-yloxy)ethyl)-5-(tributylstannyl)-1H-imidazole to give 441 after THP-removal with aqueous HCl purification by reverse phase HPLC (4.8 mg). LCMS: 437.1.

Example 442

1-(4-{2-[2-(2-Hydroxy-ethyl)-2H-[1,2,4]triazol-3-yl]-4,5-dihydro-6-oxa-3-thia-1-aza-benzo[e]azulen-8-yl}-pyrazol-1-yl)-2-methyl-propan-2-ol 442

Following the procedure for 114, 2-[5-(8-Bromo-4,5-dihydro-6-oxa-3-thia-1-aza-benzo[e]azulen-2-yl)-[1,2,4]triazol-1-yl]-ethanol was reacted with 2-Methyl-1-[4-(4,4,5,5-tetramethyl-[1,3,2]dioxaborolan-2-yl)-pyrazol-1-yl]-propan-2-ol to give 442. MS(ESI+) 453.1. $^1$H NMR (400 MHz, DMSO) δ 8.35 (d, J=8.3, 1H), 8.16 (s, 1H), 8.10 (s, 1H), 7.94 (s, 1H), 7.42 (dd, J=8.3, 1.8, 1H), 7.30 (d, J=1.7, 1H), 4.94 (t, J=5.5, 1H), 4.89 (t, J=5.9, 2H), 4.71 (s, 1H), 4.39 (t, J=5.0, 2H), 4.04 (s, 2H), 3.91 (q, J=5.8, 2H), 3.44 (t, J=5.0, 2H), 1.10 (s, 6H)

Example 443

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-ethanesulfonic acid dimethylamide 443

Following the procedure for 320, 8-azetidin-3-yl-2-(2-isopropyl-2H-[1,2,4]triazol-3-yl)-4,5-dihydro-6-oxa-3-thia-1-aza-benzo[e]azulene TFA salt 235 and ethenesulfonic acid dimethylamide were reacted. The reaction mixture was concentrated in vacuo and the residue partitioned between DCM and water. The organic phase was washed with water followed by brine, dried (Na$_2$SO$_4$) and concentrated in vacuo. The residue was purified by flash chromatography (SiO$_2$, 2% MeOH in DCM) to give 443 as a beige solid (117 mg, 75%). LCMS: R$_T$=7.69 min, [M+H]$^+$=503. $^1$H NMR δ (ppm) (CDCl$_3$): 8.31 (1H, d, J=8.17 Hz), 7.89 (1H, s), 7.08 (1H, dd, J=8.21, 1.86 Hz), 6.99-6.96 (1H, m), 5.92-5.83 (1H, m), 4.38 (2H, t, J=5.05 Hz), 3.77 (2H, t, J=6.90 Hz), 3.74-3.64 (1H, m), 3.39 (2H, t, J=5.06 Hz), 3.23 (2H, t, J=6.67 Hz), 3.00-2.92 (4H, m), 2.87 (6H, s), 1.60 (6H, d, J=6.64 Hz)

Example 444

2-Hydroxy-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-2-methyl-propan-1-one 444

Following the procedure for 318, 8-azetidin-3-yl-2-(2-isopropyl-2H-[1,2,4]triazol-3-yl)-4,5-dihydro-6-oxa-3-thia-1-aza-benzo[e]azulene TFA salt 235 and 2-hydroxyisobutyric acid were reacted in DMF. Purification by trituration with ether then reverse phase preparative HPLC (Gemini C$_{18}$ column, gradient 40-98% MeOH in H$_2$O+0.1% HCO$_2$H) gave 444 as a white solid (39 mg, 21%). LCMS: R$_T$=11.04 min, [M+H]$^+$=454. $^1$H NMR δ (ppm) (CDCl$_3$): 8.36 (1H, d, J=8.19 Hz), 7.90 (1H, s), 7.11 (1H, dd, J=8.22, 1.90 Hz), 7.00-6.96 (1H, m), 5.92-5.83 (1H, m), 4.74 (1H, d, J=9.42 Hz), 4.46 (1H, t, J=9.76 Hz), 4.39 (3H, t, J=5.47 Hz), 4.14 (1H, s), 3.87-3.78 (1H, m), 3.65 (1H, s), 3.40 (2H, t, J=5.00 Hz), 1.60 (6H, d, J=6.63 Hz), 1.43 (6H, s)

Example 445

2-{3-[2-(2-Isopropyl-2H-[1,2,4]triazol-3-yl)-4,5-dihydro-6-oxa-3-thia-1-aza-benzo[e]azulen-8-yl]-azetidine-1-sulfonyl}-ethanol 445

Following the procedure for 394, 8-azetidin-3-yl-2-(2-isopropyl-2H-[1,2,4]triazol-3-yl)-4,5-dihydro-6-oxa-3-thia-1-aza-benzo[e]azulene TFA salt 235, 2-chloroethanesulfonyl chloride, and 1.0 equivalents of triethylamine were reacted to give 445. LCMS: $R_T$=8.49 min, [M+H]$^+$=476. $^1$H NMR δ (ppm) (DMSO-d6): 8.29 (1H, d, J=8.20 Hz), 8.06-8.03 (1H, m), 7.22 (1H, dd, J=8.27, 1.86 Hz), 7.13 (1H, d, J=1.82 Hz), 5.82-5.72 (1H, m), 4.36-4.26 (4H, m), 4.10-3.94 (3H, m), 3.45-3.35 (4H, m), 2.72-2.65 (2H, m), 1.50 (6H, d, J=6.59 Hz). 1 Exchangeable proton not seen Example 446

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-isobutyramide 446

A solution of 2-{3-[2-(2-isopropyl-2H-[1,2,4]triazol-3-yl)-4,5-dihydro-6-oxa-3-thia-1-aza-benzo[e]azulen-8-yl]-azetidin-1-yl}-2-methyl-propionitrile (0.26 g, 0.6 mmol) in DMSO (5 mL) was treated with potassium carbonate (16 mg, 0.12 mmol) followed by hydrogen peroxide (30% aq., 0.33 mL) and the mixture was heated at 45° C. for 18 hours then at 50° C. for a few more hours. Further hydrogen peroxide (33 mL, 30% aq.) was added and the mixture heated at 50° C. for 18 hours. After cooling, water was added and the mixture was extracted with EtOAc (×5). The combined organic extracts were dried (Na$_2$SO$_4$), and concentrated in vacuo and the residue purified by flash chromatography (SiO$_2$, first time with 0-10% MeOH in EtOAc then second time with 0-5% MeOH in DCM). Further purification was by reverse-phase preparative HPLC (Gemini C$_{18}$ column, gradient 30-40% MeOH in H$_2$O+0.1% HCO$_2$H). A solution of the product in a mixture of chloroform and DCM was treated with 0.2M HCl in ether (0.32 mL) and then concentrated in vacuo to give 446 (27 mg, 9%). LCMS: $R_T$=7.41 min, [M+H]$^+$=453. $^1$H NMR δ (ppm) (DMSO-d6): 10.79 (1H, s), 8.34-8.28 (1H, m), 8.06 (1H, s), 7.82 (1H, d, J=17.45 Hz), 7.65 (1H, d, J=4.94 Hz), 7.27-7.16 (1H, m), 7.07 (1H, d, J=1.80 Hz), 5.80-5.72 (1H, m), 4.47 (1H, td, J=10.76, 4.67 Hz), 4.37-4.26 (3H, m), 4.20-3.94 (3H, m), 3.41 (2H, q, J=4.96 Hz), 1.55-1.45 (12H, m)

Example 447

5-{8-[1-(2-Hydroxy-2-methyl-propyl)-1H-pyrazol-4-yl]-4,5-dihydro-6-oxa-3-thia-1-aza-benzo[e]azulen-2-yl}-4-isopropyl-2,4-dihydro-[1,2,4]triazol-3-one 447

Similarly to as described in General Procedure C, 5-(8-Bromo-4,5-dihydro-6-oxa-3-thia-1-aza-benzo[e]azulen-2-yl)-4-isopropyl-2,4-dihydro-[1,2,4]triazol-3-one was reacted with 2-methyl-1-(4-(4,4,5,5-tetramethyl-1,3,2-dioxaborolan-2-yl)-1H-pyrazol-1-yl)propan-2-ol. Purification of the crude reaction mixture by reverse phase HPLC gave 447. LCMS: 467.1. $^1$H NMR (400 MHz, DMSO) δ 12.21 (s, 1H), 8.25 (d, J=8.3 Hz, 1H), 8.15 (s, 1H), 7.94 (s, 1H), 7.43 (dd, J=8.3, 1.8 Hz, 1H), 7.29 (d, J=1.8 Hz, 1H), 5.35-5.18 (m, 1H), 4.71 (s, 1H), 4.37 (t, J=5.0 Hz, 2H), 4.03 (s, 2H), 3.39 (dd, J=17.6, 12.4 Hz, 2H), 1.56 (d, J=6.9 Hz, 6H), 1.09 (s, 6H)

Example 448

N2-(2-chloro-5-(3,3-difluoroazetidine-1-carbonyl)phenyl)-N2,N8-dimethyl-4,5-dihydrobenzo[b]thieno[2,3-d]oxepine-2,8-dicarboxamide 448

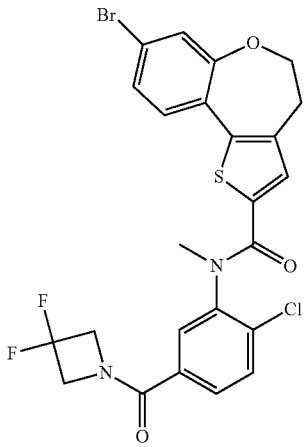 [SMILES: CN(C(=O)c1cc2c(s1)-c1ccc(Br)cc1OCC2)c1cc(C(=O)N2CC(F)(F)C2)ccc1Cl]

To a mixture of 3,3-difluoroazetidine hydrochloride (1.18 g, 9.13 mmol), DIPEA (5 mL), HATU (2.78 g, 7.31 mmol) in THF (60 mL) was added 3-(8-bromo-N-methyl-4,5-dihydrobenzo[b]thieno[2,3-d]oxepine-2-carboxamido)-4-chlorobenzoic acid (3.00 g, 6.09 mmol) under nitrogen atmosphere at room temperature. The reaction mixture was stirred for 5 h, diluted with water, extracted with EtOAc. The organic layer was dried over Na$_2$SO$_4$, concentrated in vacuo to give 8-bromo-N-(2-chloro-5-(3,3-difluoroazetidine-1-carbonyl)phenyl)-N-methyl-4,5-dihydrobenzo[b]thieno[2,3-d]oxepine-2-carboxamide (3.2 g, yield 93%). $^1$H NMR (DMSO, 400 MHz): δ7.56-6.59 (m, 7H, ArH), 4.76-4.48 (m, 4H, 2CH$_2$), 4.31 (t, J=5.2 Hz, 2H, CH$_2$), 3.33 (s, 3H, CH$_3$), 2.96 (t, J=5.2 Hz, 2H, CH$_2$)

A suspension of 8-bromo-N-(2-chloro-5-(3,3-difluoroazetidine-1-carbonyl)phenyl)-N-methyl-4,5-dihydrobenzo[b]thieno[2,3-d]oxepine-2-carboxamide (400 mg, 0.70 mmol), Pd(OAc)$_2$ (8 mg, 0.035 mmol), Xantphos (41 mg, 0.070 mmol), MeNH$_2$.HCl (71 mg, 1.06 mmol) and Na$_2$CO$_3$ (224 mg, 2.11 mmol) in toluene (5 mL) and DMF (5 mL) was heated at 80° C. under atmosphere of CO from balloon for 4 h, and then filtered and concentrated. The crude product was purified by pre-HPLC to give 448 (121.4 mg, yield 32%). $^1$H NMR (DMSO, 400 MHz): δ8.45 (m, 1H, NH), 7.98-7.44 (m, 6H, ArH), 6.60 (s, 1H, =CH), 4.75 (brs, 2H, CH$_2$), 4.48 (br s, 2H, CH$_2$), 4.20 (s, 2H, CH$_2$), 3.30 (s, 3H, CH$_3$), 2.99 (s, 2H, CH$_2$), 2.75 (d, J=4.4 Hz, 3H, CH$_3$). LC-MS: (ESI, m/z)=546 [M+H]$^+$

Example 449

{2-[2-(2,4-Difluoro-phenyl)-2H-[1,2,4]triazol-3-yl]-4,5-dihydro-6-oxa-1-thia-10-aza-benzo[e]azulen-9-ylamino}-acetic acid 449

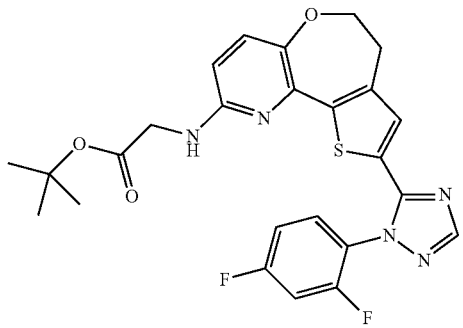 [SMILES: CC(C)(C)OC(=O)CNc1ccc2c(n1)-c1sc(-c3ncnn3-c3ccc(F)cc3F)cc1CCO2]

Compound 134 (800 mg, 2.0 mmol) was dissolved in THF (20 mL). It was stirred at 0° C. and NaH (58 mg, 2.4 mmol) was added. Then the mixture was warmed to r.t. and stirred for further 0.5 h. The mixture was cooled to 0° C. and tert-butyl 3-bromopropanoate (502 mg, 2.4 mmol) was added. Later, it was warmed to 80° C. for 2 h. The reaction mixture was filtered to gather the solution. Then water was added into the solution. It was extracted by DCM (20 mL×3). The combined organics were dried over $Na_2SO_4$, concentrated in vacuo, and separated by prep TLC (DCM) to give {2-[2-(2,4-Difluoro-phenyl)-2H-[1,2,4]triazol-3-yl]-4,5-dihydro-6-oxa-1-thia-10-aza-benzo[e]azulen-9-ylamino}-acetic acid tert-butyl ester (900 mg, yield: 90%) $^1$HNMR ($CDCl_3$, 400 MHz): δ 8.04 (s, 1H), 7.45-7.52 (m, 1H), 7.42 (s, 1H), 7.06-6.93 (m, 4H). 4.25-4.15 (m, 2H), 4.08-3.99 (m, 2H), 3.06 (s, 2H), 1.38 (s, 9H). LC-MS (ESI): m/z=512 [M+H]$^+$ {2-[2-(2,4-Difluoro-phenyl)-2H-[1,2,4]triazol-3-yl]-4,5-dihydro-6-oxa-1-thia-10-aza-benzo[e]azulen-9-ylamino}-acetic acid tert-butyl ester (900 mg, 1.76 mmol) was dissolved in dioxane-HCl (20 mL), and the reaction mixture was stirred at room temperature for 0.5 h. The reaction mixture was filtered to gather the solid. The resulting solid was washed by DCM (10 mL) to give 449 as HCl salt (500 mg, yield: 57%). $^1$H NMR (DMSO-$d_6$, 400 MHz): δ 8.27 (s, 1H), 7.82-7.90 (m, 1H), 7.63-7.69 (m, 1H), 7.61-7.62 (m, 2H), 7.35-7.40 (m, 2H), 7.21 (s, 1H), 6.95 (s, 2H), 6.52 (d, J=8.8 Hz, 1H), 4.15 (t, J=4.0 Hz, 2H), 3.88 (s, 2H), 3.05 (t, J=4.8 Hz, 2H). LC-MS (ESI): m/z=456 [M+H]$^+$

Example 450

3-{2-[2-(2,4-Difluoro-phenyl)-2H-[1,2,4]triazol-3-yl]-4,5-dihydro-6-oxa-1-thia-10-aza-benzo[e]azulen-9-ylamino}-propane-1,2-diol 450

3-Aminopropane-1,2-diol (400 mg, 4.4 mmol) was dissolved in EtOAc—HCl (20 mL). And the reaction mixture was stirred at r.t. for 30 min. The reaction mixture was concentrated in vacuo to get to the white solid. The white solid was added in 2,2-dimethoxy-propane (10 mL) and toluene-4-sulfonic acid (86 mg, 0.5 mmol) was added into the mixture. The reaction mixture was stirred at 60° C. for 12 h. The reaction mixture was concentrated in vacuo, washed by acetone to give (2,2-dimethyl-1,3-dioxolan-4-yl)methanamine (350 mg, yield: 46%). $^1$HNMR (DMSO-d6, 400 MHz): δ8.08 (s, 2H), 4.32 (s, 1H), 4.05 (q, J=4.8 Hz, 1H), 3.73 (t, J=6.4 Hz, 1H), 3.00-2.78 (m, 2H), 1.37 (s, 3H), 1.28 (s, 3H)

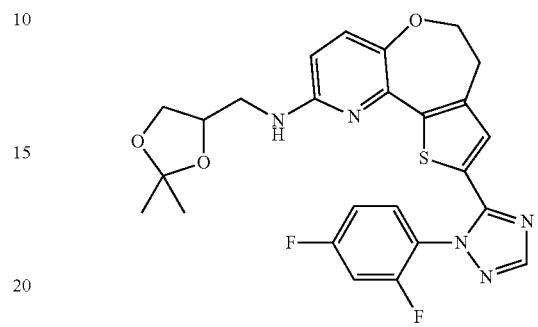

9-Chloro-2-[2-(2,4-difluoro-phenyl)-2H-[1,2,4]triazol-3-yl]-4,5-dihydro-6-oxa-1-thia-10-aza-benzo[e]azulene (300 mg, 0.72 mmol), C-(2,2-Dimethyl-[1,3]dioxolan-4-yl)-methyl-amine (101 mg, 0.86 mmol), $Pd_2(dba)_3$ (66 mg, 0.072 mmol), Xphos (34 mg, 0.072 mmol), t-BuONa (138 mg, 1.44 mmol) and dioxane (2 mL) was added in a 10 mL of sealed tube. The reaction mixture was heated by microwave at 112° C. for 7 min under $N_2$. The reaction mixture was filtered to gather the solution. Then water was added in the solution and extracted by DCM (3×50 mL); The combined organic layer was dried by $Na_2SO_4$, concentrated in vacuo, separated by TLC (DCM) to {2-[2-(2,4-Difluoro-phenyl)-2H-[1,2,4]triazol-3-yl]-4,5-dihydro-6-oxa-1-thia-10-aza-benzo[e]azulen-9-yl}-(2,2-dimethyl-[1,3]dioxolan-4-ylmethyl)-amine (248 mg, yield: 67%). $^1$H NMR (DMSO-$d_6$, 400 MHz): δ8.16 (s, 1H), 7.79 (q, J=2.8, 8.4 Hz, 1H), 7.76-7.55 (m, 1H, 7.31 (t, J=8.4 Hz, 1H), 6.99 (t, J=4.4 Hz, 1H), 6.52 (t, J=6.0 Hz, 1H, 6.33 (d, J=8.4 Hz, 1H), 4.12-3.81 (m, 5H), 3.52-3.49 (m, 2H), 2.96 (t, J=4.8 Hz, 2H), 1.87 (s, 2H), 1.18 (d, 6H) LC-MS (ESI): m/z=512 [M+H]$^+$ {2-[2-(2,4-Difluoro-phenyl)-2H-[1,2,4]triazol-3-yl]-4,5-dihydro-6-oxa-1-thia-10-aza-benzo[e]azulen-9-yl}-(2,2-dimethyl-[1,3]dioxolan-4-ylmethyl)-amine (240 mg, 0.52 mmol) was dissolved in dioxane-HCl (20 mL), and then the reaction mixture was stirred at room temperature for 2 h. Then the reaction mixture was filtered to gather the solid. Then the solid was washed by DCM (10 mL) to give 450 (130 mg, yield: 53%). $^1$HNMR (DMSO-$d_6$, 400 MHz): δ8.26 (s, 1H), 7.91-7.85 (m, 1H), 7.70-7.55 (m, 1H), 7.42-7.37 (m, 1H), 7.09 (d, J=8.8 Hz, 1H), 6.99 (s, 1H), 4.15 (t, J=4.4 Hz, 2H), 3.67-3.03 (m, 8H) LC-MS (ESI): m/z=472 [M+H]$^+$

Example 451

2-{2-[2-(2,4-Difluoro-phenyl)-2H-[1,2,4]triazol-3-yl]-4,5-dihydro-6-oxa-1-thia-10-aza-benzo[e]azulen-9-ylamino}-N,N-dimethyl-acetamide 451

Compound 448 (150 mg, 0.33 mmol) was dissolved in THF (20 mL), DIPEA (85 mg, 0.66 mmol), HATU (250 mg, 0.66 mmol), dimethyl-amine (83 mg, 0.66 mmol) was added in it. The reaction mixture was stirred at room temperature for 2 h. The reaction mixture was concentrated in vacuo, dissolved in DCM (10 mL). The organic layer was washed by water, dried by Na$_2$SO$_4$, concentrated in vacuo, separated by TLC to give 451 (21 mg, yield: 13%). $^1$HNMR (DMSO-d6, 400 MHz): δ 9.46 (s, 1H), 8.35-8.31 (m, 1H), 7.98-7.94 (m, 1H), 7.90-7.74 (m, 1H), 7.49-7.44 (m, 1H), 7.29 (s, 1H), 7.18 (s, 2H), 7.14-7.00 (m, 1H), 6.63 (d, J=8.8 Hz, 2H), 4.22 (s, 2H), 4.07 (s, 2H), 3.02 (m, 2H). LC-MS (ESI): m/z=483 [M+H]$^+$ Example 452

2-{2-[2-(2,4-Difluoro-phenyl)-2H-[1,2,4]triazol-3-yl]-4,5-dihydro-6-oxa-1-thia-10-aza-benzo[e]azulen-9-ylamino}-acetamide 452

Compound 448 (150 mg, 0.33 mmol) was dissolved in THF (10 mL), and DIPEA (85 mg, 0.66 mmol), HATU (250 mg, 0.66 mmol), (NH$_4$)$_2$CO$_3$ (64 mg, 0.66 mmol) were added. The reaction mixture was stirred at room temperature for 2 h. The reaction mixture was concentrated in vacuo, and dissolved in DCM (30 mL). The mixture was washed by water, dried over Na$_2$SO$_4$, concentrated in vacuo, and separated by prep. TLC (EtOAc/MeOH=10:1) to give 452 (15 mg, yield: 10%). $^1$H NMR (DMSO-d$_6$, 400 MHz): δ8.34 (s, 1H), 7.97-7.91 (m, 1H), 7.82-7.73 (m, 1H), 7.49-7.32 (m, 1H), 7.28-7.21 (m, 1H), 7.05 (s, 1H), 7.03 (s, 1H), 6.86 (s, 1H), 6.59 (d, J=8.8 Hz, 1H), 4.21 (m, 2H), 4.16 (m, 2H), 3.10 (t, J=4.4 Hz, 2H). LC-MS (ESI): m/z=455 [M+H]$^+$ Example 453

2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-N-(1-methyl-azetidin-3-yl)-isobutyramide 453

To a solution of 2-{4-[2-(2-Isopropyl-2H-[1,2,4]triazol-3-yl)-4,5-dihydro-6-oxa-3-thia-1-aza-benzo[e]azulen-8-yl]-pyrazol-1-yl}-2-methyl-propionic acid (0.350 g, 0.000753 mol) and oxalyl chloride (2M in methylene chloride, 0.38 mL, 0.0007534 mol) in dry methylene chloride (2.415 mL, 0.03767 mol) was added 1 drop of N,N-dimethylformamide (0.02917 mL, 0.0003767 mol). The solution was stirred for 1 h at room temperature and concentrated in vacuo. The acid chloride was re-dissolved in methylene chloride (1.739 mL, 0.02712 mol) and added dropwise to a solution of 1-methyl-azetidin-3-ylamine (0.1198 g, 0.0007534 mol) and triethylamine (0.3255 mL, 0.002336 mol) in methylene chloride (1.739 mL, 0.02712 mol). The reaction was stirred at room temperature for 3 h. Brine and methylene chloride were added and the aqueous layer was extracted 3× with methylene chloride. The organic layers were combined, dried with MgSO$_4$, and concentrated. The crude was purified by reverse-phase HPLC to give 453 (90.1 mg) as a beige solid. MS(ESI+) 533.2. $^1$H NMR (400 MHz, DMSO) δ 8.40 (s, 1H), 8.32 (d, J=8.3, 1H), 8.10 (s, 1H), 8.02 (s, 1H), 7.76 (d, J=6.9, 1H), 7.51 (dd, J=8.3, 1.8, 1H), 7.40 (d, J=1.7, 1H), 5.84 (sept, J=6.4, 1H), 4.39 (t, J=5.0, 2H), 4.25-4.15 (m, 3H), 3.46 (m, 4H), 2.89 (t, J=7.3, 2H), 2.22 (s, 3H), 1.73 (s, 6H), 1.56 (d, J=6.6, 6H)

Example 454

8-{1-[2-(3,3-Difluoro-azetidine-1-sulfonyl)-ethyl]-azetidin-3-yl}-2-(2-isopropyl-2H-[1,2,4]triazol-3-yl)-4,5-dihydro-6-oxa-3-thia-1-aza-benzo[e]azulene 454

Following the procedure for 320, 8-azetidin-3-yl-2-(2-isopropyl-2H-[1,2,4]triazol-3-yl)-4,5-dihydro-6-oxa-3-thia-1-aza-benzo[e]azulene TFA salt 235 and 1-ethenesulfonyl-3,3-difluoro-azetidine were reacted to give 454 isolated as a white solid (139 mg, 84%). LCMS: R$_T$=8.30 min, [M+H]$^+$=551. $^1$H NMR δ (ppm) (CDCl$_3$): 8.32 (1H, d, J=8.18 Hz), 7.89 (1H, s), 7.08 (1H, dd, J=8.21, 1.87 Hz), 6.97 (1H, d, J=1.84 Hz), 5.93-5.83 (1H, m), 4.38 (2H, t, J=5.05 Hz), 4.31 (4H, t, J=12.10 Hz), 3.76 (2H, t, J=6.86 Hz), 3.75-3.63 (1H, m), 3.43-3.36 (2H, m), 3.23 (2H, t, J=6.61 Hz), 3.11 (2H, t, J=7.01 Hz), 2.92 (2H, t, J=7.00 Hz), 1.60 (6H, d, J=6.63 Hz)

Example 455

(2-{3-[2-(2-Isopropyl-2H-[1,2,4]triazol-3-yl)-4,5-dihydro-6-oxa-3-thia-1-aza-benzo[e]azulen-8-yl]-azetidine-1-sulfonyl}-ethyl)-dimethyl-amine 455

To a suspension of 8-(1-ethenesulfonyl-azetidin-3-yl)-2-(2-isopropyl-2H-[1,2,4]triazol-3-yl)-4,5-dihydro-6-oxa-3-thia-1-aza-benzo[e]azulene (75 mg, 0.17 mmol) in IMS (2 mL) was added dimethylamine (2M in MeOH, 158 µL, 0.32 mmol) and the reaction mixture was stirred for 72 hours. The mixture was concentrated in vacuo to low volume and partitioned between DCM and water. The layers were separated and the organic layer was washed with water followed by brine, dried (Na$_2$SO$_4$) and concentrated in vacuo. The resultant residue was combined with a previous batch of the desired compound and purified by flash chromatography (SiO$_2$, 0-2% MeOH in DCM) to give 455 as a white solid (43 mg, 34%). LCMS: R$_T$=8.51 min, [M+H]$^+$=503. $^1$H NMR δ (ppm) (CDCl$_3$): 8.36 (1H, d, J=8.20 Hz), 7.90 (1H, s), 7.16 (1H, dd, J=8.24, 1.92 Hz), 7.03 (1H, d, J=1.88 Hz), 5.93-5.83 (1H, m), 4.39 (2H, t, J=5.04 Hz), 4.26 (2H, t, J=8.23 Hz), 4.10 (2H, t, J=7.33 Hz), 3.81-3.74 (1H, m), 3.40 (2H, t, J=5.05 Hz), 3.22-3.14 (2H, m), 2.81 (2H, t, J=7.47 Hz), 2.29 (6H, s), 1.61 (6H, d, J=6.63 Hz)

Example 456

4-Isopropyl-5-{8-[1-(3-methyl-oxetan-3-ylmethyl)-1H-pyrazol-4-yl]-4,5-dihydro-6-oxa-3-thia-1-aza-benzo[e]azulen-2-yl}-2,4-dihydro-[1,2,4]triazol-3-one 456

Similarly to as described in General Procedure C, 5-(8-Bromo-4,5-dihydro-6-oxa-3-thia-1-aza-benzo[e]azulen-2-yl)-4-isopropyl-2,4-dihydro-[1,2,4]triazol-3-one was reacted with 1-((3-methyloxetan-3-yl)methyl)-4-(4,4,5,5-tetramethyl-1,3,2-dioxaborolan-2-yl)-1H-pyrazole. Purification of the crude reaction mixture by reverse phase HPLC gave 456. LCMS: 479.1

Example 457

1-[3-(5-Chloro-2-{8-[1-(2-hydroxy-2-methyl-propyl)-1H-pyrazol-4-yl]-4,5-dihydro-6-oxa-3-thia-1-aza-benzo[e]azulen-2-yl}-imidazol-1-yl)-azetidin-1-yl]-ethanone 457

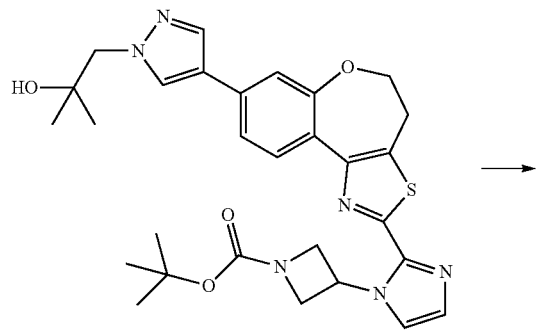

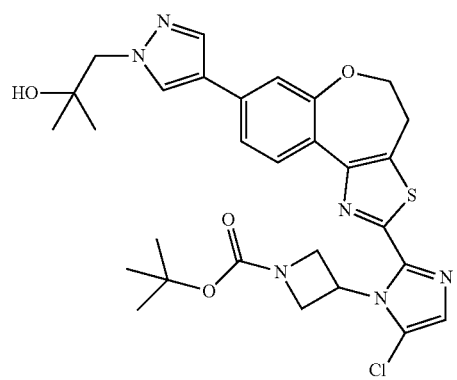

To a solution of 3-(2-{8-[1-(2-Hydroxy-2-methyl-propyl)-1H-pyrazol-4-yl]-4,5-dihydro-6-oxa-3-thia-1-aza-benzo[e]azulen-2-yl}-imidazol-1-yl)-azetidine-1-carboxylic acid tert-butyl ester (90.0 mg, 0.179 mmol) in N,N-Dimethylformamide (3.35 mL, 43.3 mmol) was added N-Chlorosuccinimide (19 mg, 0.14 mmol) and 1.00 M of Hydrogen chloride in Water (0.018 mL). The reaction was stirred at rt 4 h. the reaction was quenched with water then extracted with EtOAc 3×. The organic layer was dried Na2SO4, concentrated. The crude product was purified by isco column to give 3-(5-Chloro-2-{8-[1-(2-hydroxy-2-methyl-propyl)-1H-pyrazol-4-yl]-4,5-dihydro-6-oxa-3-thia-1-aza-benzo[e]azulen-2-yl}-imidazol-1-yl)-azetidine-1-carboxylic acid tert-butyl ester (EtOAc/Hep eluted at 75%). MS: (ESI+)=483.1

3-(5-Chloro-2-{8-[1-(2-hydroxy-2-methyl-propyl)-1H-pyrazol-4-yl]-4,5-dihydro-6-oxa-3-thia-1-aza-benzo[e]azulen-2-yl}-imidazol-1-yl)-azetidine-1-carboxylic acid tert-butyl ester was deprotected and acetylated to give 457 MS: (ESI+)=539.1. $^1$H NMR (400 MHz, DMSO) δ 8.35 (d, J=8.3 Hz, 1H), 8.14 (s, 1H), 7.92 (s, 1H), 7.39 (dd, J=8.3, 1.8 Hz, 1H), 7.31-7.27 (m, 2H), 6.72-6.61 (m, 1H), 4.74-4.69 (m, 3H), 4.44-4.32 (m, 4H), 4.04 (s, 2H), 3.40 (t, J=5.0 Hz, 2H), 1.84 (s, 3H), 1.10 (s, 6H)

Example 459

1-(4-{2-[2-(2-Hydroxy-propyl)-2H-[1,2,4]triazol-3-yl]-4,5-dihydro-6-oxa-3-thia-1-aza-benzo[e]azulen-8-yl}-pyrazol-1-yl)-2-methyl-propan-2-ol 459

Following the procedure for 114, 1-[5-(8-Bromo-4,5-dihydro-6-oxa-3-thia-1-aza-benzo[e]azulen-2-yl)-[1,2,4]triazol-1-yl]-propan-2-ol was reacted with 2-Methyl-1-[4-(4,4,5,5-tetramethyl-[1,3,2]dioxaborolan-2-yl)-pyrazol-1-yl]-propan-2-ol to give 459. MS(ESI+) 467.1. $^1$H NMR (400 MHz, DMSO) δ 8.35 (d, J=8.3, 1H), 8.17 (s, 1H), 8.09 (s, 1H), 7.95 (s, 1H), 7.43 (dd, J=8.3, 1.8, 1H), 7.30 (d, J=1.7, 1H), 4.95 (d, J=5.3, 1H), 4.82 (dd, J=13.3, 7.5, 1H), 4.76-4.66 (m, 2H), 4.46-4.32 (m, 2H), 4.28-4.14 (m, 1H), 4.03 (s, 2H), 3.44 (t, J=5.0, 2H), 1.16 (d, J=6.3, 3H), 1.10 (s, 6H)

Example 460

2-Methyl-1-(4-{2-[2-(2-morpholin-4-yl-ethyl)-2H-[1,2,4]triazol-3-yl]-4,5-dihydro-6-oxa-3-thia-1-aza-benzo[e]azulen-8-yl}-pyrazol-1-yl)-propan-2-ol 460

Following the procedure for 114, 8-bromo-2-[2-(2-morpholin-4-yl-ethyl)-2H-[1,2,4]triazol-3-yl]-4,5-dihydro-6-oxa-3-thia-1-aza-benzo[e]azulene was reacted with 2-methyl-1-[4-(4,4,5,5-tetramethyl-[1,3,2]dioxaborolan-2-yl)-pyrazol-1-yl]-propan-2-ol to give 460. MS(ESI+) 522.2. $^1$H NMR (400 MHz, DMSO) δ 8.34 (d, J=8.3, 1H), 8.17 (s, 1H), 8.11 (s, 1H), 7.95 (s, 1H), 7.38 (dd, J=8.3, 1.7, 1H), 7.30 (d, J=1.6, 1H), 4.95 (t, J=6.5, 2H), 4.72 (s, 1H), 4.39 (t, J=5.0, 2H), 4.04 (s, 2H), 3.45 (t, J=5.0, 2H), 3.43-3.38 (m, 4H), 2.82 (t, J=6.5, 2H), 2.46-2.35 (m, 4H), 1.10 (s, 6H).

Example 461

Oxetan-3-yl-[2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-ethyl]-amine 461

Step 1: 1-(2-chloroethyl)-4-(4,4,5,5-tetramethyl-1,3,2-dioxaborolan-2-yl)-1H-pyrazole

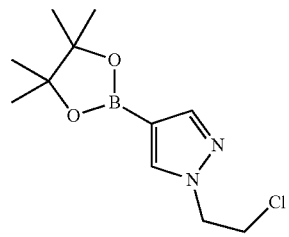 [SMILES: CC1(C)OB(c2cnn(CCCl)c2)OC1(C)C]

To a solution of 4-(4,4,5,5-tetramethyl-1,3,2-dioxaborolan-2-yl)-1H-pyrazole (1.0 G, 5.2 mmol) in 30 mL of DMSO was added cesium carbonate (6.73 G, 20.6 mmol) and 2-chloroethylbromide (0.854 mL, 10.3 mmol). This reaction mixture was stirred at room temperature for 4 hours. The reaction mixture was then diluted with a large volume of EtOAc. The organic was washed with water×1, saline×1, then dried over Na2SO4 and conc. to give 1-(2-chloroethyl)-4-(4,4,5,5-tetramethyl-1,3,2-dioxaborolan-2-yl)-1H-pyrazole as a solid.

427

Step 2: 8-[1-(2-chloro-ethyl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene

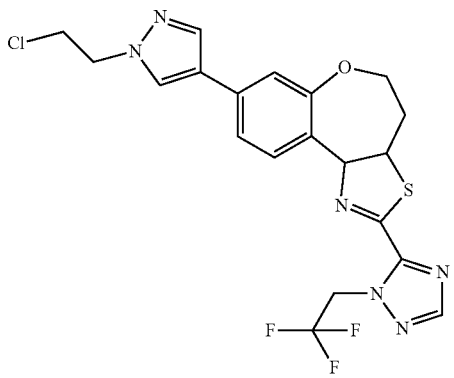 [SMILES: FC(F)(F)Cn1ncnc1C1=NC2c3ccc(-c4cnn(CCCl)c4)cc3OCCC2S1]

To a solution of the 8-Bromo-2-[2-(2,2,2-trifluoro-ethyl)-2H-[1,2,4]triazol-3-yl]-4,5-dihydro-6-oxa-3-thia-1-aza-benzo[e]azulene from Example 51 (2.00 g, 34.75 mmol) and 1-(2-chloroethyl)-4-(4,4,5,5-tetramethyl-1,3,2-dioxaborolan-2-yl)-1H-pyrazole in 8 mL of acetonitrile was added 7 mL of 2M of potassium carbonate in water followed by the addition of tetrakis(triphenylphosphine)palladium(0) (0.55 G, 0.476 mmol). This reaction mixture was heated on a Biotage microwave at 140 C for 10 minutes. The cooled reaction mixture was diluted with EtOAc, filtered to remove a black ppt, then washed with water×1, saline×1, then dried over Na2SO4, concentrated and purified by MPLC on a 12 gram silica column, eluting with 10-80% EtOAc/heptanes to give 8-[1-(2-chloro-ethyl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene (1.6 g) as a yellow powder.

Step 3

To a solution of 8-[1-(2-chloro-ethyl)-1H-pyrazol-4-yl]-2-[2-(2,2,2-trifluoro-ethyl)-2H-[1,2,4]triazol-3-yl]-4,5-dihydro-6-oxa-3-thia-1-aza-benzo[e]azulene (0.200 g, 0.416 mmol) and 3-oxetanamine (0.608 g, 2.08 mmol) in 5 mL of DMF was added potassium carbonate (0.287 g, 2.08 mmol) and potassium iodide (0.069 g, 0.416 mmol). The reaction mixture was heated at 50° C. for approximately 4 hours. The heated was increased to 70 C and the reaction was continued another 15 hours to give the desired product as determined by LCMS. The crude material was purified by RP-HPLC to cleanly give 461. MS: (ESI+)=518.3

Example 462

1-[4-(2-{2-[1-(2-Hydroxy-ethyl)-piperidin-4-yl]-2H-[1,2,4]triazol-3-yl}-4,5-dihydro-6-oxa-3-thia-1-aza-benzo[e]azulen-8-yl)-pyrazol-1-yl]-2-methyl-propan-2-ol 462

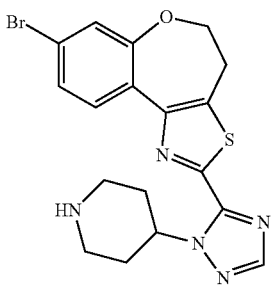 [SMILES: Brc1ccc2c(c1)OCCc1sc(-c3ncnn3C3CCNCC3)nc1-2]

428

8-Bromo-4,5-dihydro-6-oxa-3-thia-1-aza-benzo[e]azulene-2-carboxylic acid 1-dimethylamino-meth-(Z)-ylideneamide was reacted with 4-Hydrazino-piperidine-1-carboxylic acid benzyl ester to give 8-bromo-2-(2-piperidin-4-yl-2H-[1,2,4]triazol-3-yl)-4,5-dihydro-6-oxa-3-thia-1-aza-benzo[e]azulene. MS(ESI+) 432.0/434.0.

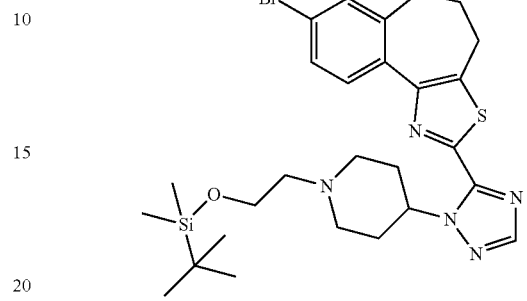

To a solution of 8-bromo-2-(2-piperidin-4-yl-2H-[1,2,4]triazol-3-yl)-4,5-dihydro-6-oxa-3-thia-1-aza-benzo[e]azulene (0.216 g, 0.000500 mol) in methylene chloride (6.227 mL, 0.09715 mol) was added (tert-butyl-dimethyl-silanyloxy)-acetaldehyde (0.2855 mL, 0.001499 mol) and acetic acid (0.002841 mL, 4.996E-5 mol) followed by sodium triacetoxyborohydride (0.3177 g, 0.001499 mol). The reaction was stirred at room temperature for 5 hours.

The reaction was quenched with 1N NaOH. Methylene chloride was added and the mixture was extracted 3 times with methylene chloride. The organic phases were combined, dried with MgSO4 and concentrated. The mixture was purified by flash chromatography (0-10% MeOH in DCM) to afford 8-Bromo-2-(2-{1-[2-(tert-butyl-dimethyl-silanyloxy)-ethyl]-piperidin-4-yl}-2H-[1,2,4]triazol-3-yl)-4,5-dihydro-6-oxa-3-thia-1-aza-benzo[e]azulene (117 mg) as a white solid. MS(ESI+) 590.2/592.2.

Following the procedure for 114, 8-Bromo-2-(2-{1-[2-(tert-butyl-dimethyl-silanyloxy)-ethyl]-piperidin-4-yl}-2H-[1,2,4]triazol-3-yl)-4,5-dihydro-6-oxa-3-thia-1-aza-benzo[e]azulene was reacted with 2-methyl-1-[4-(4,4,5,5-tetramethyl-[1,3,2]dioxaborolan-2-yl)-pyrazol-1-yl]-propan-2-ol to give 1-{4-[2-(2-{1-[2-(tert-Butyl-dimethyl-silanyloxy)-ethyl]-piperidin-4-yl}-2H-[1,2,4]triazol-3-yl)-4,5-dihydro-6-oxa-3-thia-1-aza-benzo[e]azulen-8-yl]-pyrazol-1-yl}-2-methyl-propan-2-ol. MS(ESI+) 650.3

To a solution of 1-{4-[2-(2-{1-[2-(tert-Butyl-dimethyl-silanyloxy)-ethyl]-piperidin-4-yl}-2H-[1,2,4]triazol-3-yl)-4,5-dihydro-6-oxa-3-thia-1-aza-benzo[e]azulen-8-yl]-pyrazol-1-yl}-2-methyl-propan-2-ol (0.150 g, 0.000231 mol) in methanol (2.0 mL, 0.049 mol) was added hydrogen chloride (4N in dioxane, 1 mL, 0.00025 mol). The reaction was stirred at room temperature overnight. The solvent was removed in vacuo and the crude was purified by reverse-phase HPLC to give 462 (31.1 mg) as a white solid. MS(ESI+) 536.2

Example 463

1-Isopropyl-5-{8-[1-(2-methanesulfonyl-ethyl)-azetidin-3-yl]-4,5-dihydro-6-oxa-3-thia-1-aza-benzo[e]azulen-2-yl}-1H-[1,2,4]triazol-3-ylamine 463

A suspension of (1-isopropyl-5-{8-[1-(2-methanesulfonyl-ethyl)-azetidin-3-yl]-4,5-dihydro-6-oxa-3-thia-1-aza-benzo[e]azulen-2-yl}-1H-[1,2,4]triazol-3-yl)-carbamic acid benzyl ester (157 mg, 0.25 mmol) in IMS (25 mL) was treated with a slurry of palladium on carbon (50 mg, 50% in water) and the mixture was stirred under an atmosphere of hydrogen for 3 days. More palladium on carbon was added and the mixture stirred for another 18 hours before being filtered through celite. The filtrate was concentrated in vacuo and the residue purified by reverse-phase preparative HPLC (Gemini $C_{18}$ column, gradient 10-90% MeOH in $H_2O$+0.1% $HCO_2H$) to give 463 as a white solid after freeze drying (43 mg, 35%). LCMS: $R_T$=6.30 min, [M+H]$^+$=489. $^1H$ NMR δ (ppm) (DMSO-d6): 8.22 (1H, d, J=8.18 Hz), 7.14 (1H, dd, J=8.25, 1.81 Hz), 6.99 (1H, d, J=1.77 Hz), 5.67-5.59 (1H, m), 5.54 (2H, s), 4.30 (2H, t, J=5.02 Hz), 3.63-3.50 (3H, m), 3.10 (4H, t, J=6.28 Hz), 3.01 (3H, s), 2.78 (2H, t, J=6.83 Hz), 1.42 (6H, d, J=6.58 Hz). 2 Protons obscured by water peak Example 464

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-N-methyl-isobutyramide 464

Following the procedure of Example 319, a suspension of 8-azetidin-3-yl-2-(2-isopropyl-2H-[1,2,4]triazol-3-yl)-4,5-dihydro-6-oxa-3-thia-1-aza-benzo[e]azulene TFA salt 235 (200 mg, 0.42 mmol) and 2-bromo-2,N-dimethyl-propionamide in cesium carbonate and DMF were reacted at 80° C. to give 464 isolated as a white solid (33 mg, 17%). LCMS: $R_T$=7.62 min, [M+H]$^+$=467. $^1H$ NMR δ (ppm) (DMSO-d6): 8.27 (1H, d, J=8.17 Hz), 8.06 (1H, s), 7.63 (1H, s), 7.16 (1H, dd, J=8.20, 1.82 Hz), 6.96 (1H, s), 5.83-5.73 (1H, m), 4.32 (2H, t, J=5.01 Hz), 3.53 (2H, s), 3.39 (2H, t, J=5.02 Hz), 2.58 (3H, d, J=4.63 Hz), 1.50 (6H, d, J=6.59 Hz), 1.06 (6H, s). 3 Protons obscured by water peak Example 465

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-ethanesulfonic acid methylamide 465

Following the procedure for 320, 8-azetidin-3-yl-2-(2-isopropyl-2H-[1,2,4]triazol-3-yl)-4,5-dihydro-6-oxa-3-thia-1-aza-benzo[e]azulene TFA salt 235 and N-methyl ethene sulfonamide were reacted to give 465. LCMS: $R_T$=7.25 min, [M+H]$^+$=489. $^1H$ NMR δ (ppm) (CDCl$_3$): 8.31 (1H, t, J=8.17 Hz), 7.89 (1H, s), 7.06 (1H, dd, J=8.21, 1.88 Hz), 6.97 (1H, d, J=1.83 Hz), 5.93-5.83 (1H, m), 4.91 (1H, s), 4.38 (2H, t, J=5.03 Hz), 3.76 (2H, t, J=7.01 Hz), 3.72-3.62 (1H, m), 3.41-3.34 (2H, m), 3.25 (2H, t, J=6.71 Hz), 3.08-3.02 (2H, m), 2.99-2.91 (2H, m), 2.80 (3H, s), 1.60 (6H, d, J=6.78 Hz)

Example 466

2-(5-{8-[1-(2-Hydroxy-2-methyl-propyl)-1H-pyrazol-4-yl]-4,5-dihydro-6-oxa-3-thia-1-aza-benzo[e]azulen-2-yl}-[1,2,4]triazol-1-yl)-propan-1-ol 466

Following the procedure for 114, 2-[5-(8-bromo-4,5-dihydro-6-oxa-3-thia-1-aza-benzo[e]azulen-2-yl)-[1,2,4]triazol-1-yl]-propyl ester was reacted with 2-Methyl-1-[4-(4,4,5,5-tetramethyl-[1,3,2]dioxaborolan-2-yl)-pyrazol-1-yl]-propan-2-ol to give 466. MS(ESI+) 467.1. $^1H$ NMR (400 MHz, DMSO) δ 8.34 (d, J=8.3, 1H), 8.16 (s, 1H), 8.11 (s, 1H), 7.95 (s, 1H), 7.44 (dd, J=8.3, 1.8, 1H), 7.30 (d, J=1.7, 1H), 5.86-5.74 (m, 1H), 4.95 (t, J=5.4, 1H), 4.72 (s, 1H), 4.39 (t, J=5.2, 2H), 4.04 (s, 2H), 3.86 (ddd, J=10.9, 7.9, 5.7, 1H), 3.78-3.71 (m, 1H), 3.44 (t, J=5.0, 2H), 1.50 (d, J=6.7, 3H), 1.10 (s, 6H)

Example 467

2-(4-{2-[2-(2-Morpholin-4-yl-ethyl)-2H-[1,2,4]triazol-3-yl]-4,5-dihydro-6-oxa-3-thia-1-aza-benzo[e]azulen-8-yl}-pyrazol-1-yl)-ethanol 467

Following the procedure for 258, 8-bromo-2-[2-(2-morpholin-4-yl-ethyl)-2H-[1,2,4]triazol-3-yl]-4,5-dihydro-6-oxa-3-thia-1-aza-benzo[e]azulene was reacted with 1-[2-(Tetrahydro-pyran-2-yloxy)-ethyl]-4-(4,4,5,5-tetramethyl-[1,3,2]dioxaborolan-2-yl)-1H-pyrazole to give 467. MS(ESI+) 494.1. $^1H$ NMR (400 MHz, DMSO) δ 8.34 (d, J=8.3, 1H), 8.23 (s, 1H), 8.11 (s, 1H), 7.95 (s, 1H), 7.38 (dd, J=8.3, 1.7, 1H), 7.30 (d, J=1.7, 1H), 4.95 (t, J=6.5, 2H), 4.91 (t, J=5.3, 1H), 4.39 (t, J=5.0, 2H), 4.16 (t, J=5.7, 2H), 3.77 (q, J=5.6, 2H), 3.51-3.38 (m, 6H), 2.82 (t, J=6.5, 2H), 2.46-2.36 (m, 4H)

Example 468

1-(4-(2-(3-amino-1-isopropyl-1H-1,2,4-triazol-5-yl)-4,5-dihydrobenzo[b]thieno[2,3-d]oxepin-8-yl)-1H-pyrazol-1-yl)-2-methylpropan-2-ol 468

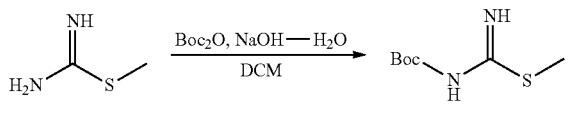

To a rapid stirred suspension of 2-Methyl-isothiourea (13.0 g, 144.1 mmol) in DCM (200 mL) was added NaOH aqueous solution (100 mL, 2 N) The mixture was cooled to 0° C. in ice-water bath and then was added a solution of Boc$_2$O (8.6 g, 65 mmol) in DCM (50 mL) dropwise over 1 hour. After stirred for over night, the mixture was added water (100 mL). The aqueous was separated and the organic was washed with water (50 mL×2). The organic layer was dried over anhydrous sodium sulfate, concentrated to afford 7.1 g of N-Boc-2-Methyl-isothiourea. Yield: 26%. $^1H$ NMR (CDCl$_3$, 400 MHz) δ: 2.44 (s, 3H), 1.49 (s, 9H). LC-MS: m/z=191 [M+H$^+$]

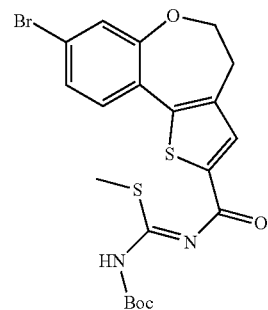 [SMILES: CS/C(=N\C(=O)c1cc2c(s1)-c1ccc(Br)cc1OCC2)NC(=O)OC(C)(C)C]

A mixture 8-bromo-4,5-dihydrobenzo[b]thieno[2,3-d]oxepine-2-carboxylic acid (10.0 g, 30.3 mmol), EDCI (7.5 g, 36.4 mmol) in DCM (200 mL) was stirred at room temperature for 10 min, then DMAP (7.39 g, 60.6 mmol) was added by one portion. 10 minutes later, N-Boc-2-Methyl-isothiourea (6.9 g, 36.4 mmol) was added. The reaction mixture was stirred at room temperature overnight. After removal of the solvent, the residue was treated with methanol/water (20 mL, 1:1) to afford 10.2 g of methyl N'-8-bromo-4,5-dihydrobenzo[b]thieno[2,3-d]oxepine-2-carbonyl-N-Boc-carbamimidothioate. Yield: 67%. $^1$H NMR (CDCl$_3$, 400 MHz): δ12.33 (s, 1H), 7.95-7.51 (m, 2H), 7.35-6.94 (m, 2H), 4.28-4.25 (m, 2H), 3.15-3.30 (m, 2H), 2.52 (s, 3H), 1.51-1.45 (s, 9H). LC-MS: m/z=497 [M+H$^+$]

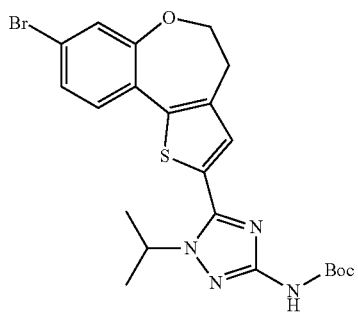 [SMILES: CC(C)n1nc(NC(=O)OC(C)(C)C)nc1-c1cc2c(s1)-c1ccc(Br)cc1OCC2]

A mixture of N'-8-bromo-4,5-dihydrobenzo[b]thieno[2,3-d]oxepine-2-carbonyl-N-Boc-carbamimidothioate (100 mg, 0.2 mmol), DIPEA (260 mg, 2 mmol), isopropyl-hydrazine HCl salt (30 mg, 0.4 mmol) in DMF (5 mL) was stirred at 90° C. for 4 hours. The reaction mixture was concentrated to dryness, and then purified by pre-TLC to afford 65 mg of 5-(8-bromo-4,5-dihydrobenzo[b]thieno[2,3-d]oxepin-2-yl)-1-isopropyl-1H-1,2,4-triazol-3-N-Boc-amine. Yield: 64%. $^1$H NMR (CDCl$_3$, 400 MHz): δ7.48-7.46 (m, 1H), 7.20-7.16 (m, 1H), 7.16-7.09 (m, 3H), 4.82-4.79 (m, 1H), 4.29-4.26 (m, 2H), 3.18-3.19 (m, 2H), 1.52-1.50 (s, 6H), 1.45-1.40 (m, 9H). LC-MS: m/z=505 [M+H$^+$]

A mixture of 5-(8-bromo-4,5-dihydrobenzo[b]thieno[2,3-d]oxepin-2-yl)-1-isopropyl-1H-1,2,4-triazol-3-N-Boc-amine (500 mg, 0.99 mmol), Pd(dppf)Cl$_2$ (72 mg, 0.099 mmol), cesium carbonate (644 mg, 2.0 mmol), 2-Methyl-1-[4-(4,4,5,5-tetramethyl-[1,3,2]dioxaborolan-2-yl)-pyrazol-1-yl]-propan-2-ol (318 mg, 1.19 mmol) in DME-H$_2$O (15 mL, 3:1) was stirred at 80° C. under N$_2$ atmosphere overnight. After cooled down, the reaction mixture was filtered though a ceilite, concentrated and purified by column (eluted with Hexanes:EtOAc=2:1) to give 110 mg (yield=20%) of Boc-protected 468 and about 20 mg of 468. Boc-protected 468 (110 mg, 0.2 mmol) was dissolved in methanol, and HCl-methanol (4 mol/L, 20 mL) was added dropwise. The mixture was stirred for over night, concentrated and purified by pre-TLC to afford 70 mg of 468, yield: 76%. $^1$H NMR (CDCl$_3$, 400 MHz): δ7.77 (s, 1H), 7.64-7.70 (m, 2H), 7.26 (s, 1H), 7.13-7.11 (m, 2H), 4.81-4.74 (m, 1H), 4.32-4.30 (m, 2H), 4.04 (s, 2H), 3.23-3.20 (m, 2H), 1.51-1.48 (m, 6H), 1.52-1.50 (s, 6H), 1.18-1.14 (m, 6H). LC-MS: m/z=464 [M+H$^+$]

Example 469

2-Amino-1-{3-[2-(2-isopropyl-2H-[1,2,4]triazol-3-yl)-4,5-dihydro-6-oxa-3-thia-1-aza-benzo[e]azulen-8-yl]-azetidin-1-yl}-2-methyl-propan-1-one 469

To a solution of (2-{3-[2-(2-isopropyl-2H-[1,2,4]triazol-3-yl)-4,5-dihydro-6-oxa-3-thia-1-aza-benzo[e]azulen-8-yl]-azetidin-1-yl}-1,1-dimethyl-2-oxo-ethyl)-carbamic acid tert-butyl ester (203 mg, 0.36 mmol) in DCM (2 mL) was added TFA (2 mL) and the reaction mixture was stirred for 1 hour then concentrated in vacuo. The residual solid was triturated with ether, filtered off and air-dried before being dissolved in DCM. The organic solution was washed (aqueous saturated sodium bicarbonate solution, followed by water and then brine), dried (MgSO$_4$) and concentrated in vacuo. The residue was freeze-dried from MeOH/H$_2$O to give 469 as a white solid (116 mg, 71%). LCMS: R$_T$=8.13 min, [M+H]$^+$=453. $^1$H NMR δ (ppm) (DMSO-d6): 8.30 (1H, d, J=8.19 Hz), 8.06 (1H, s), 7.18 (1H, dd, J=8.24, 1.86 Hz), 7.00 (1H, d, J=1.82 Hz), 5.82-5.74 (1H, m), 4.79 (1H, s), 4.42 (1H, s), 4.33 (2H, t, J=5.13 Hz), 4.19 (1H, s), 3.77-3.70 (2H, m), 3.39 (2H, t, J=5.02 Hz), 1.74 (2H, s), 1.50 (6H, d, J=6.59 Hz), 1.17 (6H, s)

Example 470

N-Isopropyl-2-{3-[2-(2-isopropyl-2H-[1,2,4]triazol-3-yl)-4,5-dihydro-6-oxa-3-thia-1-aza-benzo[e]azulen-8-yl]-azetidin-1-yl}-acetamide 470

Following the procedure of 319, a suspension of 8-azetidin-3-yl-2-(2-isopropyl-2H-[1,2,4]triazol-3-yl)-4,5-dihydro-6-oxa-3-thia-1-aza-benzo[e]azulene TFA salt 235 (200 mg, 0.42 mmol) and N-isopropyl-2-chloroacetamide gave 470 isolated as a yellow solid (91 mg, 26%). LCMS: R$_T$=3.31 min, [M+H]$^+$=467. $^1$H NMR δ (ppm) (DMSO-d6): 8.26 (1H, d, J=8.18 Hz), 8.05 (1H, s), 7.40 (1H, d, J=8.06 Hz), 7.17 (1H, dd, J=8.24, 1.83 Hz), 6.99 (1H, d, J=1.78 Hz), 5.83-5.73 (1H, m), 4.35-4.29 (2H, m), 3.86-3.80 (1H, m), 3.69-3.58 (3H, m), 3.41-3.35 (2H, m), 3.18 (2H, d, J=6.73 Hz), 3.00 (2H, s), 1.50 (6H, d, J=6.59 Hz), 1.03 (6H, d, J=6.59 Hz)

Example 471

2-{3-[2-(2-Isopropyl-2H-[1,2,4]triazol-3-yl)-4,5-dihydro-6-oxa-3-thia-1-aza-benzo[e]azulen-8-yl]-azetidin-1-yl}-1-morpholin-4-yl-ethanone 471

Following the procedure of 319, a suspension of 8-azetidin-3-yl-2-(2-isopropyl-2H-[1,2,4]triazol-3-yl)-4,5-dihydro-6-oxa-3-thia-1-aza-benzo[e]azulene TFA salt 235 (200 mg, 0.42 mmol) and 4-(2-chloroacetyl)morpholine gave 471 isolated as a yellow solid (79 mg, 22%). LCMS: R$_T$=3.17 min, [M+H]$^+$=495. $^1$H NMR δ (ppm) (DMSO-d6): 8.25 (1H, d, J=8.17 Hz), 8.05 (1H, s), 7.17 (1H, dd, J=8.24, 1.82 Hz), 7.03 (1H, d, J=1.77 Hz), 5.82-5.73 (1H, m), 4.35-4.29 (2H, m), 3.67-3.56 (2H, m), 3.58-3.45 (5H, m), 3.44-3.34 (6H, m), 3.31 (2H, s), 3.16 (2H, t, J=6.11 Hz), 1.50 (6H, d, J=6.59 Hz)

Example 472

N-(2-Hydroxy-2-methyl-propyl)-2-{3-[2-(2-isopropyl-2H-[1,2,4]triazol-3-yl)-4,5-dihydro-6-oxa-3-thia-1-aza-benzo[e]azulen-8-yl]-azetidin-1-yl}-acetamide 472

A solution of {3-[2-(2-isopropyl-2H-[1,2,4]triazol-3-yl)-4,5-dihydro-6-oxa-3-thia-1-aza-benzo[e]azulen-8-yl]-azetidin-1-yl}-acetic acid TFA salt (228 mg, 0.42 mmol), EDCI (97 mg, 0.50 mmol) and HOBT (68 mg, 0.50 mmol) in THF (3 mL) was stirred for 20 minutes. 1-Amino-2-methyl-propan-2-ol (42 mg, 0.47 mmol) and diisopropylethylamine (0.18 mL, 1.05 mmol) in THF (2 mL) were added and the reaction mixture was stirred at RT for 18 hours. Another portion of 1-amino-2-methyl-propan-2-ol, EDCI, HOBT, DIPEA and THF (1.5 mL) was added and the reaction mixture was warmed at 45° C. for 3 hours. Aqueous saturated sodium bicarbonate solution was added and the mixture was extracted with DCM (×2). The combined organic extracts were dried (MgSO$_4$), concentrated in vacuo and the residue purified by flash chromatography (SiO$_2$, 0-10% MeOH in DCM) to give 472 as a white solid (92 mg, 44%). LCMS: R$_T$=3.14 min, [M+H]$^+$=497. $^1$H NMR δ (ppm) (DMSO-d6): 8.26 (1H, d, J=8.18 Hz), 8.06 (1H, s), 7.44 (1H, t, J=6.04 Hz), 7.19 (1H, dd, J=8.24, 1.80 Hz), 7.01 (1H, d, J=1.75 Hz), 5.82-5.74 (1H, m), 4.51 (1H, s), 4.32 (2H, t, J=5.03 Hz), 3.73-3.60 (3H, m), 3.39 (2H, t, J=5.06 Hz), 3.26-3.16 (2H, m), 3.10 (2H, s), 3.02 (2H, d, J=6.03 Hz), 1.50 (6H, d, J=6.59 Hz), 1.01 (6H, s)

Example 473

4-{8-[1-(2-Hydroxy-2-methyl-propyl)-1H-pyrazol-4-yl]-4,5-dihydro-6-oxa-3-thia-1-aza-benzo[e]azulen-2-yl}-2,5-dimethyl-2,4-dihydro-[1,2,4]triazol-3-one 473

A microwave vial was charged with an approximately 1:1 mixture of 4-(8-bromo-4,5-dihydro-6-oxa-3-thia-1-aza-benzo[e]azulen-2-yl)-2,5-dimethyl-2,4-dihydro-[1,2,4]triazol-3-one and 4-(8-iodo-4,5-dihydro-6-oxa-3-thia-1-aza-benzo[e]azulen-2-yl)-2,5-dimethyl-2,4-dihydro-[1,2,4]triazol-3-one (41 mg), 2-methyl-1-[4-(4,4,5,5-tetramethyl-[1,3,2]dioxaborolan-2-yl)-pyrazol-1-yl]-propan-2-ol (33 mg, 0.13 mmol), PdCl$_2$(dppf)$_2$.DCM (3.5 mg, 0.004 mmol), cesium carbonate (68 mg, 0.21 mmol), THF (1 mL) and water (0.2 mL). The vial was sealed and the mixture evacuated and purged with argon (×3). The reaction mixture was heated at 80° C. for 17 hours then a further 2-methyl-1-[4-(4,4,5,5-tetramethyl-[1,3,2]dioxaborolan-2-yl)-pyrazol-1-yl]-propan-2-ol (15 mg) and PdCl$_2$(dppf)$_2$.DCM (4 mg) were added, the vial was re-filled with argon as before and stirring at 80° C. was continued for a further 20 hours. After cooling the reaction mixture was concentrated in vacuo. The resultant residue was purified by flash chromatography (SiO$_2$, 0-4% MeOH in DCM) to give 473 as a white solid (12 mg, 27%). LCMS: R$_T$=4.14 min, [M+H]$^+$=453. $^1$H NMR δ (ppm) (DMSO-d6): 8.14 (1H, d, J=8.26 Hz), 8.08 (1H, s), 7.87 (1H, s), 7.33 (1H, dd, J=8.26, 1.84 Hz), 7.22 (1H, d, J=1.82 Hz), 4.68 (1H, s), 4.31 (2H, t, J=5.01 Hz), 3.98 (2H, s), 3.35 (3H, s), 3.28 (2H, m), 2.65 (3H, s), 1.04 (6H, s)

Example 474

4-{8-[1-(2-Hydroxy-2-methyl-propyl)-1H-pyrazol-4-yl]-4,5-dihydro-6-oxa-3-thia-1-aza-benzo[e]azulen-2-yl}-2-isopropyl-5-methyl-2,4-dihydro-[1,2,4]triazol-3-one 474

Following the procedure for 473, a mixture of 4-(8-bromo-4,5-dihydro-6-oxa-3-thia-1-aza-benzo[e]azulen-2-yl)-2-isopropyl-5-methyl-2,4-dihydro-[1,2,4]triazol-3-one and 4-(8-iodo-4,5-dihydro-6-oxa-3-thia-1-aza-benzo[e]azulen-2-yl)-2-isopropyl-5-methyl-2,4-dihydro-[1,2,4]triazol-3-one and 2-methyl-1-[4-(4,4,5,5-tetramethyl-[1,3,2]dioxaborolan-2-yl)-pyrazol-1-yl]-propan-2-ol were reacted to give 474 isolated as a white solid (34 mg, 59%). LCMS: R$_T$=4.79 min, [M+H]$^+$=481. $^1$H NMR δ (ppm) (DMSO-d6): 8.15 (1H, d, J=8.26 Hz), 8.08 (1H, s), 7.87 (1H, d, J=0.74 Hz), 7.33 (1H, dd, J=8.26, 1.84 Hz), 7.22 (1H, d, J=1.82 Hz), 4.68 (1H, s), 4.38-4.28 (3H, m), 3.99 (2H, s), 3.28 (2H, m), 2.67 (3H, s), 1.29 (6H, t, J=6.68 Hz), 1.05 (6H, s)

Example 475

2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-acetamide 475

To a solution of 2-(2-isopropyl-2H-[1,2,4]triazol-3-yl)-8-piperidin-4-yl-4,5-dihydro-6-oxa-3-thia-1-aza-benzo[e]azulene TFA salt 375 (250 mg, 0.49 mmol) in DCM (2.5 mL) was added triethylamine (157 μL, 1.13 mmol) followed by 2-bromoacetamide (81 mg, 0.59 mmol). The reaction mixture was stirred for 42 hours before being diluted with MeOH and water. The DCM was removed in vacuo to give a suspension. The solid was filtered off and washed with MeOH then ether to give 475 as an off-white solid (160 mg, 72%). LCMS: R$_T$=3.17 min, [M+H]$^+$=453. $^1$H NMR δ (ppm) (DMSO-d6): 8.23 (1H, d, J=8.20 Hz), 8.05 (1H, s), 7.17 (1H, s), 7.08 (1H, s), 7.07-7.02 (1H, m), 6.90 (1H, d, J=1.75 Hz), 5.81-5.71 (1H, m), 4.35-4.28 (2H, m), 3.37 (2H, s), 2.90-2.79 (4H, m), 2.13 (2H, dd, J=8.92, 8.51 Hz), 1.77-1.67 (4H, m), 1.50 (6H, d, J=6.58 Hz). 1 Proton obscured by solvent peaks Example 476

2-(2-Isopropyl-2H-[1,2,4]triazol-3-yl)-8-[1-(2-methanesulfonyl-ethyl)-piperidin-4-yl]-4,5-dihydro-6-oxa-3-thia-1-aza-benzo[e]azulene 476

Following the procedure for 320, 2-(2-isopropyl-2H-[1,2,4]triazol-3-yl)-8-piperidin-4-yl-4,5-dihydro-6-oxa-3-thia-1-aza-benzo[e]azulene TFA salt 375 and methyl vinyl sulfone were reacted, with added DCM to aid dissolution. Addition of a mixture of methanol, ethanol and water followed by removal in vacuo of the DCM precipitated the product from the reaction mixture. The resulting solid was collected by filtration to give 476 as an off-white solid (175 mg, 71%). LCMS: R$_T$=3.30 min, [M+H]$^+$=502. $^1$H NMR δ (ppm) (DMSO-d6): 8.23 (1H, d, J=8.20 Hz), 8.05 (1H, s), 7.05 (1H, dd, J=8.25, 1.78 Hz), 6.89 (1H, d, J=1.74 Hz), 5.82-5.72 (1H, m), 4.33-4.27 (2H, m), 3.37 (2H, t, J=5.06 Hz), 3.02 (3H, s), 2.97 (2H, s), 2.70 (2H, s), 2.03 (2H, s), 1.75 (2H, d, J=12.38 Hz), 1.67-1.55 (2H, m), 1.50 (6H, d, J=6.59 Hz). 3 Protons obscured by solvent peaks Example 477

3-[2-(2-Isopropyl-2H-[1,2,4]triazol-3-yl)-4,5-dihydro-6-oxa-3-thia-1-aza-benzo[e]azulen-9-yl]-1-(2-methoxy-ethyl)-1H-pyridin-2-one 477

To 330 (0.075 g, 0.18 mmol) in DMF (2 mL) was added 1-bromo-2-methoxyethane (0.1 mL, 0.55 mmol) and cesium fluoride (0.084 g, 0.55 mmol). The reaction mixture was allowed to stir and heat at 80° C. for 2 days while monitoring by LCMS. To the reaction mixture was added bromo-2-methoxyethane (1 mL, 7.2 mmol) and cesium fluoride (1.0 g, 6.6 mmol). The reaction mixture was allowed to stir and heat at 80° C. for 2 days before cooling, concentrating under reduced pressure, and diluting with EtOAc. The solution was washed sequentially with water, and brine, before drying over MgSO$_4$ and concentrating under reduced pressure. The crude material was dissolved in DMF and purified by reverse phase HPLC to provide 477 (21 mg, 24%). $^1$H NMR (400 MHz, DMSO) δ 9.08 (d, J=2.3, 1H), 8.10 (s, 1H), 7.73-7.55 (m, 3H), 7.08 (d, J=8.4, 1H), 6.34 (t, J=6.9, 1H), 5.95 (dt, J=13.1, 6.5, 1H), 4.40 (t, J=4.9, 2H), 4.16 (t, J=5.3, 2H), 3.66 (t, J=5.3, 2H), 3.46 (t, J=5.0, 2H), 3.27 (s, 3H), 1.55 (d, J=6.6, 6H). MS (ESI(+)): m/z 464.1 (M+H)

Example 478

2-(2-isopropyl-2H-[1,2,4]triazol-3-yl)-9-[2-(2-methoxy-ethoxy)-pyridin-3-yl]-4,5-dihydro-6-oxa-3-thia-1-aza-benzo[e]azulene 478

To 330 (0.075 g, 0.18 mmol) in DMF (2 mL) was added 1-bromo-2-methoxyethane (0.1 mL, 0.55 mmol) and cesium fluoride (0.084 g, 0.55 mmol). The reaction mixture was allowed to stir and heat at 80° C. for 2 days while monitoring by LCMS. To the reaction mixture was added bromo-2-methoxyethane (1 mL, 7.2 mmol) and cesium fluoride (1.0 g, 6.6 mmol). The reaction mixture was allowed to stir and heat at 80° C. for 2 days before cooling, concentrating under reduced pressure, and diluting with EtOAc. The solution was washed sequentially with water, and brine, before drying over MgSO₄ and concentrating under reduced pressure. The crude material was dissolved in DMF and purified by reverse phase HPLC to provide 478 (5 mg, 6%). ¹H NMR (400 MHz, DMSO) δ 8.60 (d, J=2.3, 1H), 8.16 (dd, J=4.9, 1.8, 1H), 8.10 (s, 1H), 7.80 (dd, J=7.4, 1.8, 1H), 7.59 (dd, J=8.4, 2.3, 1H), 7.13 (dd, J=7.7, 5.0, 2H), 5.73 (dt, J=13.1, 6.6, 1H), 4.51-4.38 (m, 4H), 3.70-3.58 (m, 2H), 3.48 (t, J=5.0, 2H), 3.18 (d, J=14.6, 3H), 1.55-1.46 (m, 6H). MS (ESI(+)): m/z 464.1 (M+H)

Example 479

3-{8-[1-(2-hydroxy-2-methyl-propyl)-1H-pyrazol-4-yl]-4,5-dihydro-6-oxa-3-thia-1-aza-benzo[e]azulen-2-yl}-1,4,4-trimethyl-imidazolidin-2-one 479

Step 1: 1-(8-Bromo-4,5-dihydrothiazolo[4,5-d]benzo[b]oxepin-2-yl)-3,5,5-trimethylimidazolidin-2-one

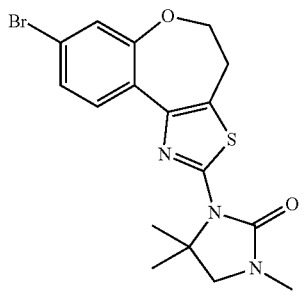 [SMILES: CN1CC(C)(C)N(c2nc3c(s2)CCOc2cc(Br)ccc2-3)C1=O]

A mixture of 0.254 g (0.65 mmol) of 1-(8-bromo-4,5-dihydrothiazolo[4,5-d]benzo[b]oxepin-2-yl)-5,5-dimethylimidazolidin-2-one from Example 429, and 50.0 mg (1.25 mmol) of 60% sodium hydride dispersion in mineral oil in 2 ml of tetrahydrofuran and 2 ml of dimethylformamide was stirred for 20 min. 0.062 ml (1.00 mmol) of methyl iodide was added in one portion to the above mixture. The mixture was stirred for 30 min and poured into 10 ml of 1 N aq hydrochloric acid. The mixture was extracted with ethyl acetate. The organic extracts were washed with water, brine, dried over magnesium sulfate and concentrated in vacuum. The residue was triturated with hexane and the resulting precipitate was filtered and washed with hexane. Yield 260 mg (98%). MS(ESI+): 408.1

Step 2

1-(8-Bromo-4,5-dihydrothiazolo[4,5-d]benzo[b]oxepin-2-yl)-3,5,5-trimethylimidazolidin-2-one was coupled with 2-methyl-1-(4-(4,4,5,5-tetramethyl-1,3,2-dioxaborolan-2-yl)-1H-pyrazol-1-yl)propan-2-ol to give 479. Yield 33%. MS(ESI):468.2. 1H NMR (400 MHz, DMSO) δ 8.17 (d, J=8.2, 1H), 8.10 (s, 1H), 7.90 (s, 1H), 7.36 (dd, J=8.2, 1.8, 1H), 7.22 (d, J=1.7, 1H), 4.73 (s, 1H), 4.31 (t, J=4.9, 2H), 4.03 (s, 2H), 3.35 (d, J=5.6, 2H), 3.19 (t, J=5.0, 2H), 2.83 (s, 3H), 1.72 (s, 6H), 1.09 (s, 6H)

Example 480

1-(3-{4-[2-(2-isopropyl-5-methyl-2H-[1,2,4]triazol-3-yl)-4,5-dihydro-6-oxa-3-thia-1-aza-benzo[e]azulen-8-yl]-pyrazol-1-yl}-azetidin-1-yl)-2-methyl-propan-2-ol 480

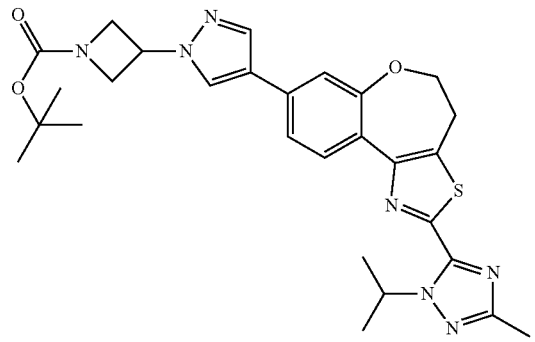 [SMILES: Cc1nc(-c2nc3c(s2)CCOc2cc(-c4cnn(C5CN(C(=O)OC(C)(C)C)C5)c4)ccc2-3)n(C(C)C)n1]

Following the procedure for 114, 8-Bromo-2-(2-isopropyl-5-methyl-2H-[1,2,4]triazol-3-yl)-4,5-dihydro-6-oxa-3-thia-1-aza-benzo[e]azulene was reacted with 3-[4-(4,4,5,5-Tetramethyl-[1,3,2]dioxaborolan-2-yl)-pyrazol-1-yl]-azetidine-1-carboxylic acid tert-butyl ester to give 3-{4-[2-(2-Isopropyl-5-methyl-2H-[1,2,4]triazol-3-yl)-4,5-dihydro-6-oxa-3-thia-1-aza-benzo[e]azulen-8-yl]-pyrazol-1-yl}-azetidine-1-carboxylic acid tert-butyl ester which was treated with acid via General Procedure F to give 8-(1-Azetidin-3-yl-1H-pyrazol-4-yl)-2-(2-isopropyl-5-methyl-2H-[1,2,4]triazol-3-yl)-4,5-dihydro-6-oxa-3-thia-1-aza-benzo[e]azulene.

To a slurry of 8-(1-Azetidin-3-yl-1H-pyrazol-4-yl)-2-(2-isopropyl-5-methyl-2H-[1,2,4]triazol-3-yl)-4,5-dihydro-6-oxa-3-thia-1-aza-benzo[e]azulene (0.232 g, 0.000519 mol) in methanol (3.0 mL, 0.074 mol) was added N,N-Diisopropylethylamine (0.108 mL, 0.000623 mol) then isobutylene oxide (0.330 mL, 0.0037 mol). The reaction was stirred at room temperature overnight. The solvent was removed in vacuo and purified by reverse-phase HPLC to give 480 (24.3 mg) as a colorless solid. MS(ESI+) 520.2. ¹H NMR (400 MHz, DMSO) δ 8.45 (s, 1H), 8.31 (d, J=8.3, 1H), 8.01 (s, 1H), 7.47 (dd, J=8.3, 1.8, 1H), 7.35 (d, J=1.8, 1H), 5.86-5.68 (m, 1H), 4.97 (p, J=6.9, 1H), 4.39 (t, J=5.0, 2H), 4.11 (s, 1H), 3.79 (dd, J=8.0, 7.3, 2H), 3.49 (dd, J=8.0, 6.8, 2H), 3.44 (t, J=5.0, 2H), 2.44 (s, 2H), 2.32 (s, 3H), 1.53 (d, J=6.6, 6H), 1.08 (s, 6H).

Example 481

2-(2-isopropyl-2H-[1,2,4]triazol-3-yl)-8-(1-oxazol-2-ylmethyl-azetidin-3-yl)-4,5-dihydro-6-oxa-3-thia-1-aza-benzo[e]azulene 481

Following the procedure for 423, a suspension of 8-azetidin-3-yl-2-(2-isopropyl-2H-[1,2,4]triazol-3-yl)-4,5-dihydro-6-oxa-3-thia-1-aza-benzo[e]azulene TFA salt 235 and oxazole-2-carbaldehyde were reacted. The crude product was purified by flash chromatography (SiO₂, 0-6% 2N NH₃/MeOH in DCM) to give an oil. The oil was triturated with ether, the resulting solid filtered off and washed with ether to give 481 as a cream solid (81 mg, 44%). LCMS: $R_T$=3.21 min, [M+H]$^+$=449. $^1$H NMR δ (ppm) (CDCl$_3$): 8.30 (1H, d, J=8.18 Hz), 7.89 (1H, s), 7.62 (1H, d, J=0.84 Hz), 7.08 (1H, dd, J=8.21, 1.86 Hz), 7.06 (1H, d, J=0.83 Hz), 6.96 (1H, d, J=1.83 Hz), 5.93-5.84 (1H, m), 4.38 (2H, t, J=5.06 Hz), 3.87 (2H, t, J=7.32 Hz), 3.80 (2H, s), 3.78-3.69 (1H, m), 3.41-3.34 (4H, m), 1.60 (6H, d, J=6.63 Hz)

Example 482 phosphoric acid mono-(2-{4-[2-(2-isopropyl-2H-[1,2,4]triazol-3-yl)-4,5-dihydro-6-oxa-3-thia-1-aza-benzo[e]azulen-8-yl]-pyrazol-1-yl}-ethyl) ester 482

Phosphoric acid dibenzyl ester 2-{4-[2-(2-isopropyl-2H-[1,2,4]triazol-3-yl)-4,5-dihydro-6-oxa-3-thia-1-aza-benzo[e]azulen-8-yl]-pyrazol-1-yl}-ethyl ester (180 mg, 0.26 mmol) was dissolved in methanol:EtOAc (1:1, 6 mL) and the solution was flushed with bubbling nitrogen. Palladium hydroxide (5% on carbon, 40 mg) was added and the reaction mixture was placed under hydrogen atmosphere (1 atm, balloon) overnight while rapidly stirred. Filtration over celite and concentration of the filtrate gave 482. Lyophilization of a solution in acetonitrile and 1% NH$_4$OH in water gave 482 as the bis-ammonium salt.

Example 483

2-{4-[2-(2-isopropyl-2H-[1,2,4]triazol-3-yl)-4,5-dihydro-6-oxa-3-thia-1-aza-benzo[e]azulen-8-yl]-piperidin-1-yl}-isobutyramide 483

2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-2-methyl-propionitrile (346 mg, ~50% pure, ~0.40 mmol) was treated with concentrated sulphuric acid (5 mL) and the mixture was stirred for 5.5 hours then diluted with ice chips (~50 mL) and made basic with solid sodium carbonate. The mixture was extracted with 10% MeOH in DCM (×4) and the combined organic extracts were dried (Na$_2$SO$_4$) and concentrated in vacuo. The resultant residue was purified by flash chromatography (SiO$_2$, 0-5% MeOH in DCM first time then 0-100% EtOAc in DCM) to give 483 as a white solid (36 mg, 19%). LCMS: $R_T$=3.28 min, [M+H]$^+$=481. $^1$H NMR δ (ppm) (DMSO-d6): 9.54 (1H, s), 8.27 (1H, d, J=8.13 Hz), 8.05 (1H, s), 7.98 (1H, s), 7.86 (1H, s), 7.05 (1H, d, J=8.29 Hz), 6.90 (1H, s), 5.81-5.73 (1H, m), 4.32 (2H, s), 3.41-3.30 (4H, m), 3.12 (1H, m), 2.83 (1H, m), 2.13 (2H, d, J=13.80 Hz), 1.99 (1H, d, J=13.56 Hz), 1.72 (1H, s), 1.50 (12H, d, J=6.50 Hz). 1 Proton obscured by water peak Example 484 diethyl-[2-(4-{2-[2-(2,2,2-trifluoro-ethyl)-2H-[1,2,4]triazol-3-yl]-4,5-dihydro-6-oxa-3-thia-1-aza-benzo[e]azulen-8-yl}-pyrazol-1-yl)-ethyl]-amine 484

To a reaction vial charged with 2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-ethanol 150 (0.250 g, 0.540 mmol) was added 4 mL DCM to give a slurry. Next, Dess-Martin periodinane (1,1,1-triacetoxy-1,1-dihydro-1,2-benziodoxol-3(1H)-one, 0.2522 g, 0.594 mmol) was added portion-wise and the reaction mixture was stirred at room temperature with LCMS monitor. Full conversion was seen after 30 minutes reaction time. The reaction mixture was diluted with water to give a white precipitate. This solid was collected by vacuum filtration, washed with EtOAc and dried on high vacuum to give the intermediate aldehyde, 2-(4-{2-[2-(2,2,2-Trifluoro-ethyl)-2H-[1,2,4]triazol-3-yl]-4,5-dihydro-6-oxa-3-thia-1-aza-benzo[e]azulen-8-yl}-pyrazol-1-yl)-ethanal. To a suspension of the aldehyde (0.160 g, 0.347 mmol) and diethylamine (0.127 g, 1.74 mmol) in 1.0 ml of DCM was added acetic acid (0.0198 mL, 0.347 mmol) and the reaction mixture was heated at 40 C for 1 hour. Finally sodium cyanoborohydride (0.0350 g, 0.556 mmol) was added in portions. The reaction mixture was heated at 40° C. for 45 minutes with complete conversion to product as determined by LCMS. The cooled reaction mixture was diluted with DCM, washed with water and saline, and concentrated to a solid which was purified by RP-HPLC to give 484. MS: (ESI+)=518.2

Example 485

1-{8-[1-(2-Hydroxy-2-methyl-propyl)-1H-pyrazol-4-yl]-4,5-dihydro-6-oxa-3-thia-1-aza-benzo[e]azulen-2-yl}-5,5-dimethyl-imidazolidine-2,4-dione 485

Step 1: 2-Bromo-2-methylpropanoyl isocyanate

Oxalyl chloride (0.61 ml, 7.2 mmol) was added to a mixture of 0.996 g (6.00 mmol)2-bromo-2-propionamide in 35 ml of dichloroethane. The mixture was stirred at room temperature for 1 hr. The mixture was stirred at room temperature for 1 h hour and then heated at 85° C. for 4 hours. The mixture was concentrated in vacuum 6.5 kPa at 37° C. giving 1.25 g of 2-Bromo-2-methylpropanoyl isocyanate which was then used without further purification.

Step 2: 2-Bromo-2-methyl-N-(8-bromo-4,5-dihydrothiazolo[4,5-d]benzo[b]oxepin-2-yl)carbamoylpropanamide

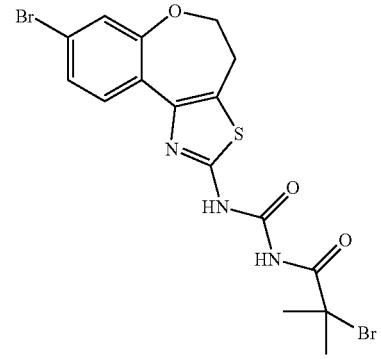 [SMILES: CC(C)(Br)C(=O)NC(=O)Nc1nc2c(s1)CCOc1cc(Br)ccc1-2]

A mixture of 1250 mg (4.20 mmol) of 2-amino-8-bromo-4,5-dihydrothiazolo[4,5-d]benzo[b]oxepine in tetrahydrofuran (6.75 mL, 83.2 mmol) was mixed with 1.25 g (6.00 mmol, 1.42 eq.) of crude 2-bromo-2-methylpropanoyl isocyanate and stirred for 20 hours. The precipitate was filtered off, washed with ethyl ether and dried on air to give 2-Bromo-2-methyl-N-(8-bromo-4,5-dihydrothiazolo[4,5-d]benzo[b]oxepin-2-yl)carbamoylpropanamide. Weight 2.21 g (75%). MS(ESI+): 488.0

439

Step 3: 1-(8-Bromo-4,5-dihydrothiazolo[4,5-d]benzo[b]oxepin-2-yl)-5,5-dimethylimidazolidin-2,4-dione

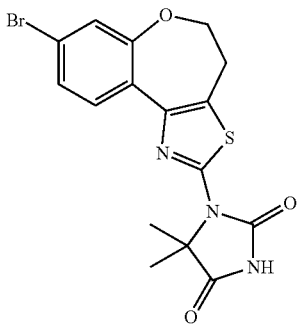 [SMILES: CC1(C)C(=O)NC(=O)N1c1nc2c(s1)CCOc1cc(Br)ccc1-2]

A mixture of 1.002 g (2.048 mmol) of 2-bromo-2-methyl-N-(8-bromo-4,5-dihydrothiazolo[4,5-d]benzo[b]oxepin-2-yl)carbamoylpropanamide and 1.660 g (5.11 mmol) of cesium carbonate in 100 ml of N,N-Dimethylformamide was stirred at 60° C. for 2 hours. The mixture was filtered, the filtrate concentrated in high vacuum, the residue partitioned between ethyl acetate and water. pH was adjusted to 5 by addition of 5% aq citric acid. The organic extracts were washed with water, brine, dried over MgSO4 and concentrated in vacuum to give 1-(8-Bromo-4,5-dihydrothiazolo[4,5-d]benzo[b]oxepin-2-yl)-5,5-dimethylimidazolidin-2,4-dione as an off-white powder which was used in the next steps without further purification. Yield 0.812 g (97%). MS(ESI+): 408.1

Step 4

1-(8-Bromo-4,5-dihydrothiazolo[4,5-d]benzo[b]oxepin-2-yl)-5,5-dimethylimidazolidin-2,4-dione was coupled with 2-methyl-1-(4-(4,4,5,5-tetramethyl-1,3,2-dioxaborolan-2-yl)-1H-pyrazol-1-yl)propan-2-ol under Suzuki conditions to give 485. Yield 12% MS (ESI+): 468.2. 1H NMR (400 MHz, DMSO) δ 11.86 (s, 1H), 8.16 (t, J=8.8, 1H), 8.12 (s, 1H), 7.91 (s, 1H), 7.38 (dd, J=8.2, 1.8, 1H), 7.24 (d, J=1.8, 1H), 4.73 (s, 1H), 4.33 (t, J=4.9, 2H), 4.03 (s, 2H), 3.25 (t, J=5.0, 2H), 1.78 (s, 6H), 1.09 (s, 6H)

Example 486

2-{4-[2-(2-Isopropyl-2H-[1,2,4]triazol-3-yl)-4,5-dihydro-6-oxa-3-thia-1-aza-benzo[e]azulen-8-yl]-imidazol-1-yl}-ethanol 486

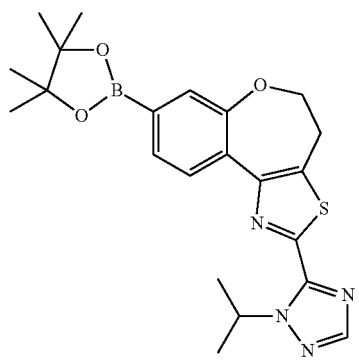 [SMILES: CC(C)n1ncnc1-c1nc2c(s1)CCOc1cc(B3OC(C)(C)C(C)(C)O3)ccc1-2]

A solution of 8-Bromo-2-(2-isopropyl-2H-[1,2,4]triazol-3-yl)-4,5-dihydro-6-oxa-3-thia-1-aza-benzo[e]azulene 27 (0.100 g, 0.000256 mol) and potassium acetate (0.07524 g, 0.0007667 mol) in dimethyl sulfoxide (0.8343 mL, 0.01176 mol) in a round bottom flask equipped with a magnetic stir bar was thoroughly purged with nitrogen. Bispinacol ester boronate (0.07139 g, 0.0002811 mol) and [1,1'-Bis(diphenylphosphino)ferrocene]dichloropalladium(II), complex with dichloromethane (1:1) (0.02087 g, 2.556E-5 mol) were added and the reaction was heated to 85° C. under inert atmosphere overnight. The mixture was partitioned between water and methylene chloride and the mixture was extracted 3× with methylene chloride. The organic phases were combined, dried with MgSO4 and concentrated. The whole was loaded onto silica and purified by flash chromatography (0-10% MeOH in DCM) to give 2-(2-Isopropyl-2H-[1,2,4]triazol-3-yl)-8-(4,4,5,5-tetramethyl-[1,3,2]dioxaborolan-2-yl)-4,5-dihydro-6-oxa-3-thia-1-aza-benzo[e]azulene (89 mg) as a yellow solid. MS(ESI+) 439.2.

Following the procedure for 258, 4-Bromo-1-[2-(tetrahydro-pyran-2-yloxy)-ethyl]-1H-imidazole was reacted with 2-(2-Isopropyl-2H-[1,2,4]triazol-3-yl)-8-(4,4,5,5-tetramethyl-[1,3,2]dioxaborolan-2-yl)-4,5-dihydro-6-oxa-3-thia-1-aza-benzo[e]azulene to give 486. MS(ESI+) 423.1. 1H NMR (400 MHz, DMSO) δ 8.32 (d, J=8.3, 1H), 8.11 (s, 1H), 7.73 (d, J=1.0, 1H), 7.68 (d, J=0.9, 1H), 7.58 (dd, J=8.3, 1.7, 1H), 7.44 (d, J=1.7, 1H), 5.95-5.74 (m, 1H), 5.00 (t, J=5.2, 1H), 4.39 (t, J=5.0, 2H), 4.03 (t, J=5.4, 2H), 3.70 (q, J=5.3, 2H), 3.44 (t, J=5.0, 2H), 1.56 (d, J=6.6, 6H)

Example 487

8-(2-Fluoro-pyridin-3-yl)-2-(2-isopropyl-2H-[1,2,4]triazol-3-yl)-4,5-dihydro-6-oxa-3-thia-1-aza-benzo[e]azulene 487

Following the procedure for 128, 2-(2-Isopropyl-2H-[1,2,4]triazol-3-yl)-8-bromo-4,5-dihydro-6-oxa-3-thia-1-aza-benzo[e]azulene and 2-fluoropyridin-3-ylboronic acid were reacted to give 487 (0.226 g, 20%). 1H NMR (400 MHz, DMSO) δ 8.48 (d, J=8.3, 1H), 8.33-8.18 (m, 2H), 8.12 (s, 1H), 7.54-7.45 (m, 2H), 7.37 (d, J=1.5, 1H), 5.96-5.75 (m, 1H), 4.44 (t, J=5.0, 2H), 3.49 (t, J=5.0, 2H), 1.90-1.28 (m, 6H). MS (ESI(+)): m/z 408.12 (M+H)

Example 488

3-[2-(2-Isopropyl-2H-[1,2,4]triazol-3-yl)-4,5-dihydro-6-oxa-3-thia-1-aza-benzo[e]azulen-8-yl]-1H-pyridin-2-one 488

Following the procedures for 330, 487 was treated with HCl to give 488 0.086 g, 37%. 1H NMR (400 MHz, DMSO) δ 11.87 (s, 1H), 8.35 (d, J=8.3, 1H), 8.12 (d, J=4.0, 1H), 7.79 (dd, J=7.0, 2.0, 1H), 7.67-7.58 (m, 2H), 7.42 (d, J=5.9, 1H), 6.32 (t, J=6.7, 1H), 5.85 (dt, J=13.1, 6.5, 1H), 4.41 (dd, J=13.4, 8.4, 2H), 3.46 (t, J=5.0, 2H), 1.56 (d, J=6.6, 6H). MS (ESI(+)): m/z 406.1 (M+H)

Example 489

1-Isopropyl-3-[2-(2-isopropyl-2H-[1,2,4]triazol-3-yl)-4,5-dihydro-6-oxa-3-thia-1-aza-benzo[e]azulen-9-yl]-1H-pyridin-2-one 489

Following the procedure for 477, compound 330 and 2-iodopropane were reacted to give 489 (0.018 g, 12%). 1H NMR (400 MHz, DMSO) δ 9.06 (d, J=2.3, 1H), 8.20-8.01 (m, 1H), 7.77 (dd, J=6.9, 1.9, 1H), 7.62 (ddd, J=10.8, 7.7, 2.2, 2H), 7.08 (d, J=8.4, 1H), 6.41 (t, J=6.9, 1H), 6.11-5.79 (m, 1H), 5.20 (dt, J=13.8, 6.9, 1H), 4.55-4.22 (m, 2H), 3.46 (t, J=5.0, 2H), 1.56 (t, J=7.5, 6H), 1.36 (d, J=6.8, 6H). MS (ESI(+)): m/z 448.2 (M+H)

Example 490

(S)-2-Hydroxy-1-{3-[2-(2-isopropyl-5-methyl-2H-[1,2,4]triazol-3-yl)-4,5-dihydro-6-oxa-3-thia-1-aza-benzo[e]azulen-8-yl]-azetidin-1-yl}-propan-1-one 490

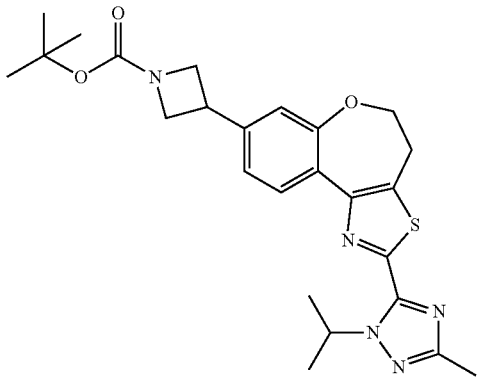 [SMILES: Cc1nc(-c2nc3c(s2)CCOc2cc(C4CN(C(=O)OC(C)(C)C)C4)ccc2-3)n(C(C)C)n1]

Zinc (0.9862 g, 0.01508 mol) was stirred in 5 mL of degassed N,N-dimethylacetamide under N₂ atmosphere. Chlorotrimethylsilane (0.164 mL, 0.00129 mol) and 1,2-dibromoethane (0.0928 mL, 0.00108 mol) were added and the mixture was stirred for 15 minutes. 3-Iodo-azetidine-1-carboxylic acid tert-butyl ester (3.05 g, 0.0108 mol) in degassed N,N-dimethylacetamide (24.00 mL, 0.2581 mol) was added slowly and the cloudy reaction was stirred at room temperature for 1.5 h.

A solution of 8-Bromo-2-(2-isopropyl-5-methyl-2H-[1,2,4]triazol-3-yl)-4,5-dihydro-6-oxa-3-thia-1-aza-benzo[e]azulene (2.704 g, 0.006671 mol) in N,N-dimethylacetamide (20 mL, 0.2 mol) was degassed with N₂ for 5 minutes. [1,1'-Bis(diphenylphosphino)ferrocene]dichloropalladium(II), complex with dichloromethane (1:1) (0.2729 g, 0.0003342 mol) and copper(I) iodide (0.1270 g, 0.0006671 mol) were added followed by the zinc solution prepared above (0.37M in DMA, 21.6 mL, 0.008006 mol). The reaction was heated to 80° C. overnight. Saturated ammonium chloride and methylene chloride were added and the mixture was filtered through celite and extracted 3× with methylene chloride. The organic phases were combined, dried with MgSO₄ and concentrated. The crude product was purified by flash chromatography (0-10% MeOH in methylene chloride) to give 3-[2-(2-Isopropyl-5-methyl-2H-[1,2,4]triazol-3-yl)-4,5-dihydro-6-oxa-3-thia-1-aza-benzo[e]azulen-8-yl]-azetidine-1-carboxylic acid tert-butyl ester. MS(ESI+) 482.2

3-[2-(2-Isopropyl-5-methyl-2H-[1,2,4]triazol-3-yl)-4,5-dihydro-6-oxa-3-thia-1-aza-benzo[e]azulen-8-yl]-azetidine-1-carboxylic acid tert-butyl ester was treated with acid to give 8-Azetidin-3-yl-2-(2-isopropyl-5-methyl-2H-[1,2,4]triazol-3-yl)-4,5-dihydro-6-oxa-3-thia-1-aza-benzo[e]azulene. MS(ESI+) 382.2.

To a solution of 8-Azetidin-3-yl-2-(2-isopropyl-5-methyl-2H-[1,2,4]triazol-3-yl)-4,5-dihydro-6-oxa-3-thia-1-aza-benzo[e]azulene (0.811 g, 0.000786 mol) and N,N-diisopropylethylamine (0.274 mL, 0.00157 mol) in tetrahydrofuran (5.0 mL, 0.062 mol) was added simultaneously L-lactic acid (0.0708 g, 0.000786 mol) and N,N,N',N'-tetramethyl-O-(7-azabenzotriazol-1-yl)uronium hexafluorophosphate (0.329 g, 0.000865 mol). The reaction was stirred at room temperature overnight. The mixture was partitioned between saturated sodium bicarbonate and methylene chloride and extracted 3 times with methylene chloride. The organic phases were combined, dried with MgSO₄, and concentrated. The crude was purified by reverse-phase HPLC to give 490 (191.2 mg) as a colorless solid. MS(ESI+) 454.2. ¹H NMR (400 MHz, DMSO) δ 8.34 (d, J=8.2, 1H), 7.22 (m, 1H), 7.06 (s, 1H), 5.84-5.66 (m, 1H), 5.09 (dd, J=11.1, 5.8, 1H), 4.65 (m, 1H), 4.37 (t, J=5.0, 2H), 4.28 (m, 2H), 4.16 (quin, J=6.5, 1H), 3.94-3.78 (m, 2H), 3.43 (t, J=5.0, 2H), 2.32 (s, 3H), 1.52 (d, J=6.6, 6H), 1.21 (d, J=6.7, 3H)

Example 491

2-(2-Isopropyl-5-methyl-2H-[1,2,4]triazol-3-yl)-8-[1-(2-methanesulfonyl-ethyl)-azetidin-3-yl]-4,5-dihydro-6-oxa-3-thia-1-aza-benzo[e]azulene 491

To a solution of 8-Azetidin-3-yl-2-(2-isopropyl-5-methyl-2H-[1,2,4]triazol-3-yl)-4,5-dihydro-6-oxa-3-thia-1-aza-benzo[e]azulene (0.811 g, 0.000786 mol) in ethanol (4.0 mL, 0.068 mol) was added methyl vinyl sulfone (0.0703 mL, 0.000786 mol) via syringe. The reaction was stirred at room temperature overnight. The mixture was partitioned between saturated sodium bicarbonate and methylene chloride and extracted 3 times with methylene chloride. The organic phases were combined, dried with MgSO₄, and concentrated. The crude was purified by reverse-phase HPLC to give 491 (213.4 mg) as a colorless solid. MS(ESI+) 488.2. ¹H NMR (400 MHz, DMSO) δ 8.29 (d, J=8.2, 1H), 7.20 (dd, J=8.3, 1.7, 1H), 7.05 (d, J=1.6, 1H), 5.85-5.64 (m, 1H), 4.36 (t, J=5.0, 2H), 3.62 (m, 3H), 3.42 (t, J=5.0, 2H), 3.15 (m, 4H), 3.06 (s, 3H), 2.85 (m, 2H), 2.32 (s, 3H), 1.52 (d, J=6.6, 6H)

Example 492

1-{8-[1-(2-Hydroxy-2-methyl-propyl)-1H-pyrazol-4-yl]-4,5-dihydro-6-oxa-3-thia-1-aza-benzo[e]azulen-2-yl}-3,5,5-trimethyl-imidazolidine-2,4-dione 492

Step 1: 1-(8-Bromo-4,5-dihydrothiazolo[4,5-d]benzo[b]oxepin-2-yl)-3,5,5-trimethylimidazolidin-2,4-dione

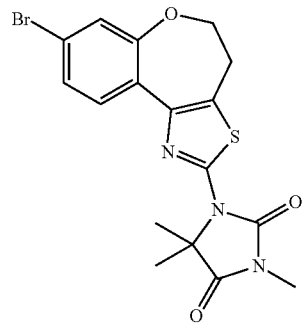 [SMILES: CN1C(=O)N(c2nc3c(s2)CCOc2cc(Br)ccc2-3)C(C)(C)C1=O]

A mixture of 204 mg (0.50 mmol) of 1-(8-bromo-4,5-dihydrothiazolo[4,5-d]benzo[b]oxepin-2-yl)-5,5-dimethylimidazolidin-2,4-dione, 0.0411 ml (0.66 mmol) of methyl iodide and 244 mg (0.750 mmol) of Cesium Carbonate in 5.0 ml of N,N-Dimethylformamide was heated at 80° C. for 2 hours. The mixture was filtered, the filtrate concentrated in high vacuum, the residue partitioned between ethyl acetate and water. The organic extracts were washed with water, brine, dried over MgSO4 and concentrated to give 1-(8-Bromo-4,5-dihydrothiazolo[4,5-d]benzo[b]oxepin-2-yl)-3,5,5-trimethylimidazolidin-2,4-dione. Weight 0.205 (97%). MS(ESI+): 421.9

Step 2

1-(8-Bromo-4,5-dihydrothiazolo[4,5-d]benzo[b]oxepin-2-yl)-3,5,5-trimethylimidazolidin-2,4-dione was coupled with 2-methyl-1-(4-(4,4,5,5-tetramethyl-1,3,2-dioxaborolan-2-yl)-1H-pyrazol-1-yl)propan-2-ol under Suzuki palladium conditions to give 492. Yield 12%. MS(ESI+):482.2. 1H NMR (400 MHz, DMSO) δ 8.18 (d, J=8.3, 1H), 8.12 (s, 1H), 7.91 (s, 1H), 7.39 (dd, J=8.3, 1.8, 1H), 7.24 (t, J=4.4, 1H), 4.73 (s, 1H), 4.34 (t, J=4.9, 2H), 4.03 (s, 2H), 3.26 (t, J=5.0, 2H), 3.02 (s, 3H), 1.81 (s, 6H), 1.09 (s, 6H)

Example 493

1-(4,5-Dihydro-6-oxa-3-thia-1-aza-benzo[e]azulen-2-yl)-5,5-dimethyl-imidazolidine-2,4-dione 493

A mixture of 49 mg (0.12 mmol) of 1-(8-Bromo-4,5-dihydrothiazolo[4,5-d]benzo[b]oxepin-2-yl)-5,5-dimethylimidazolidin-2,4-dione from Example 485, and 0.0334 ml (0.24 mmol) of triethylamine in 5 ml of ethanol was hydrogenated over 120 mg of 10% palladium on charcoal at 1 atm for 3 hours. The mixture was filtered through celite and concentrated in vacuum. The residue was purified on 4 g siligal column eluting the product with ethyl acetate gradient in heptane to give 493. Yield 20 mg (51%). MS(ESI+): 330.1

Example 494

(S)-3-{3-[2-(2-Isopropyl-5-methyl-2H-[1,2,4]triazol-3-yl)-4,5-dihydro-6-oxa-3-thia-1-aza-benzo[e]azulen-8-yl]-azetidin-1-yl}-propane-1,2-diol 494

To a solution of 8-Azetidin-3-yl-2-(2-isopropyl-5-methyl-2H-[1,2,4]triazol-3-yl)-4,5-dihydro-6-oxa-3-thia-1-aza-benzo[e]azulene (0.311 g, 0.000816 mol) in methylene chloride (4.5 mL, 0.070 mol) was added acetone D-glyceraldehyde (0.319 g, 0.00245 mol) and acetic acid (2.5 mL, 0.044 mol) followed by sodium triacetoxyborohydride (0.519 g, 0.00245 mol). The reaction was stirred at room temperature overnight, then quenched with 1N NaOH until basic. Methylene chloride was added and the mixture was extracted 3 times with methylene chloride. The organic layers were combined, dried with MgSO₄ and concentrated.

The crude was redissolved in methanol (4 mL, 0.1 mol). Hydrogen chloride (4N in dioxanes, 0.82 mL, 0.00326 mol), was added slowly and the mixture was stirred at room temperature for 2 h. The solvent was removed in vacuo and the crude was partitioned between 1N NaOH and methylene chloride and extracted 3 times with methylene chloride. The organic layers were combined, dried with MgSO₄ and concentrated. The crude was purified by reverse-phase HPLC to give 494 (204.2 mg) as a white solid. MS(ESI+) 456.2

Example 495

9-(6-Fluoro-pyridin-3-yl)-2-(2-isopropyl-2H-[1,2,4]triazol-3-yl)-4,5-dihydro-6-oxa-3-thia-1-aza-benzo[e]azulene 495

Following the procedure for 128, 9-Bromo-2-(2-isopropyl-2H-[1,2,4]triazol-3-yl)-4,5-dihydro-6-oxa-3-thia-1-aza-benzo[e]azulene from Example 6 and 6-fluoropyridin-3-yl-boronic acid were reacted to give 495 (0.346 g, 30%). ¹H NMR (500 MHz, DMSO) δ 8.68 (d, J=2.3, 1H), 8.55 (s, 1H), 8.28 (td, J=8.3, 2.5, 1H), 8.13 (s, 1H), 7.68 (dd, J=8.4, 2.3, 1H), 7.35 (dd, J=8.6, 2.7, 1H), 7.22 (d, J=8.4, 1H), 5.77 (dt, J=13.1, 6.6, 1H), 4.43 (t, J=4.9, 2H), 3.49 (t, J=4.9, 2H), 1.51 (dd, J=54.9, 6.6, 6H). MS (ESI(+)): m/z 408.1 (M+H)

Example 496

5-[2-(2-Isopropyl-2H-[1,2,4]triazol-3-yl)-4,5-dihydro-6-oxa-3-thia-1-aza-benzo[e]azulen-9-yl]-1H-pyridin-2-one 496

Following the procedures for Example 330, 495 was treated with HCl to give 496 (0.271 g, 81%). ¹H NMR (500 MHz, DMSO) δ 11.88 (s, 1H), 8.50 (d, J=2.2, 1H), 8.12 (s, 1H), 7.82 (dd, J=9.5, 2.6, 1H), 7.65 (s, 1H), 7.50 (dd, J=8.4, 2.2, 1H), 7.12 (d, J=8.4, 1H), 6.49 (d, J=9.5, 1H), 5.79 (dt, J=13.1, 6.5, 1H), 4.39 (t, J=4.8, 2H), 3.46 (t, J=4.8, 2H), 1.58 (d, J=6.6, 6H). MS (ESI(+): m/z 406.2 (M+H)

Example 498

3-[2-(2-Isopropyl-2H-[1,2,4]triazol-3-yl)-4,5-dihydro-6-oxa-3-thia-1-aza-benzo[e]azulen-9-yl]-1-(2-morpholin-4-yl-ethyl)-1H-pyridin-2-one 498

Following the procedure for 477, compound 330 and 4-(2-chloroethyl)morpholine hydrochloride were reacted to give 498 (0.005 g, 2%). ¹H NMR (500 MHz, DMSO) δ 9.09 (d, J=2.3, 1H), 8.09 (s, 1H), 7.72-7.66 (m, 2H), 7.61 (dd, J=8.4, 2.3, 1H), 7.08 (d, J=8.4, 1H), 6.35 (t, J=6.9, 1H), 5.95 (dt, J=13.1, 6.5, 1H), 4.40 (t, J=5.0, 2H), 4.10 (t, J=6.5, 2H), 3.60-3.53 (m, 4H), 3.46 (t, J=5.0, 2H), 2.64 (t, J=6.5, 2H), 2.46 (d, J=4.4, 4H), 1.55 (d, J=6.6, 6H). MS (ESI(+)): m/z 519.2 (M+H)

Example 499

2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-ethanesulfonic acid dimethylamide 499

To a solution of 2-(2-isopropyl-2H-[1,2,4]triazol-3-yl)-8-piperidin-4-yl-4,5-dihydro-6-oxa-3-thia-1-aza-benzo[e]azulene TFA salt 375 (188 mg, 0.37 mmol) and triethylamine (0.18 mL, 1.3 mmol) in IMS (3 mL) was added ethenesulfonic acid dimethylamide and the reaction mixture stirred at RT for 18 h before being concentrated in vacuo. The resultant residue was subjected to flash chromatography (SiO₂, gradient 0 to 5% MeOH in DCM) to give 499 as a beige solid (145 mg, 74%). LCMS: R$_f$=3.47 min, [M+H]⁺=531. ¹H NMR δ (ppm) (DMSO-d6): 8.23 (1H, d, J=8.19 Hz), 8.05 (1H, s), 7.04 (1H, dd, J=8.26, 1.80 Hz), 6.88 (1H, d, J=1.76 Hz), 5.82-5.72 (1H, m), 4.30 (2H, t, J=5.02 Hz), 3.37 (2H, t, J=5.04 Hz), 3.19 (2H, t, J=7.23 Hz), 2.95 (2H, d, J=10.97 Hz), 2.75 (6H, s), 2.65 (2H, t, J=7.25 Hz), 2.04 (2H, t, J=11.43 Hz), 1.75 (2H, d, J=12.62 Hz), 1.67-1.53 (2H, m), 1.50 (6H, d, J=6.58 Hz). 1H obscured by solvent

Example 500

8-(1H-Pyrazol-4-yl)-4,5-dihydro-6-oxa-3-thia-1-aza-benzo[e]azulene-2-carboxylic acid dimethylamide 500

Following the procedure for 103, 8-(1H-Pyrazol-4-yl)-4,5-dihydro-6-oxa-3-thia-1-aza-benzo[e]azulene-2-carboxylic acid (50.0 mg, 0.2 mmol) was reacted with dimethylamine (1.2 equiv) to give 500 (11.7 mg, M+1 341.0)

Example 501

{3-[2-(2-Isopropyl-2H-[1,2,4]triazol-3-yl)-4,5-dihydro-6-oxa-3-thia-1-aza-benzo[e]azulen-9-yl]-2-oxo-2H-pyridin-1-yl}-acetic acid 501

Following the procedure for 477, compound 330 and methyl 2-bromoacetate gave the methyl ester of 501 (0.734 mg, 62%). $^1$H NMR (500 MHz, DMSO) δ 9.17 (d, J=2.4, 1H), 8.09 (s, 1H), 7.78 (dd, J=7.1, 2.0, 1H), 7.73 (dd, J=6.7, 1.9, 1H), 7.59 (dd, J=8.4, 2.4, 1H), 7.08 (d, J=8.4, 1H), 6.42 (t, J=6.9, 1H), 5.97 (dt, J=13.4, 6.7, 1H), 4.79 (s, 2H), 4.40 (t, J=4.9, 2H), 3.71 (s, 3H), 3.46 (t, J=4.9, 2H), 1.53 (d, J=6.6, 6H). MS (ESI(+)): m/z 478.2 (M+H)

To the methyl ester of 501 (0.100 g, 0.209 mmol) in acetonitrile (2 mL), THF (2 mL), and water (2 mL) was added lithium hydroxide monohydrate (0.043 g, 1.05 mmol). The mixture was stirred at room temperature for 24 hours before concentrating under reduced pressure. EtOAc was added to the residue that was then washed with 1N HCl. The aqueous layer was extracted with additional EtOAc and the combined organic layers were washed with brine, dried over MgSO$_4$, and concentrated under reduced pressure to provide 501 (0.77 g, 79%). $^1$H NMR (500 MHz, DMSO) δ 12.95 (s, 1H), 9.16 (s, 1H), 8.09 (s, 1H), 7.73 (dd, J=17.8, 7.0, 2H), 7.60 (d, J=8.3, 1H), 7.08 (d, J=8.4, 1H), 6.38 (t, J=6.9, 1H), 6.01-5.93 (m, 1H), 4.69 (s, 2H), 4.40 (s, 2H), 3.46 (s, 2H), 1.54 (d, J=6.5, 6H). MS (ESI(+)): m/z 464.2 (M+H)

Example 502

3-[2-(2-Isopropyl-2H-[1,2,4]triazol-3-yl)-4,5-dihydro-6-oxa-3-thia-1-aza-benzo[e]azulen-9-yl]-1-methyl-1H-pyridin-2-one 502

Following the procedure for 477, compound 330 and iodomethane were reacted to give 502 (0.039 g, 20%). $^1$H NMR (500 MHz, DMSO) δ 9.05 (d, J=2.3, 1H), 8.09 (s, 1H), 7.73 (dd, J=6.7, 1.9, 1H), 7.66 (ddd, J=10.7, 7.7, 2.1, 2H), 7.07 (d, J=8.4, 1H), 6.34 (t, J=6.8, 1H), 5.94 (dt, J=13.2, 6.6, 1H), 4.40 (t, J=4.9, 2H), 3.53 (s, 3H), 3.46 (t, J=5.0, 2H), 1.55 (d, J=6.6, 6H). MS (ESI(+)): m/z 420.2 (M+H).

Example 503

2-{3-[2-(2-Isopropyl-2H-[1,2,4]triazol-3-yl)-4,5-dihydro-6-oxa-3-thia-1-aza-benzo[e]azulen-9-yl]-2-oxo-2H-pyridin-1-yl}-N,N-dimethyl-acetamide 503

Following the procedure for 504, to 501 in THF was added diisopropylethylamine, 2M dimethylamine in MeOH, and HATU to give 503 (0.030 g, 19%). $^1$H NMR (500 MHz, DMSO) δ 9.14 (d, J=2.3, 1H), 8.08 (s, 1H), 7.72 (dd, J=7.0, 2.0, 1H), 7.63-7.55 (m, 2H), 7.07 (d, J=8.4, 1H), 6.36 (t, J=6.9, 1H), 5.96 (dd, J=13.1, 6.7, 1H), 4.87 (s, 2H), 4.40 (t, J=4.9, 2H), 3.45 (t, J=5.0, 2H), 3.10 (s, 3H), 2.89 (s, 3H), 1.52 (d, J=6.6, 6H). MS (ESI(+)): m/z 491.1 (M+H)

Example 504

2-{3-[2-(2-Isopropyl-2H-[1,2,4]triazol-3-yl)-4,5-dihydro-6-oxa-3-thia-1-aza-benzo[e]azulen-9-yl]-2-oxo-2H-pyridin-1-yl}-acetamide 504

To 501 (0.150 g, 0.324 mmol) in THF (4 mL) was added diisopropylethylamine (0.33 mL, 1.94 mmol), ammonium chloride (0.069 g, 1.29 mmol), and HATU (0.184 g, 0.485 mmol). The resulting mixture was stirred 24 h at room temperature. The reaction mixture was diluted with EtOAc. The solution was washed sequentially with saturated sodium bicarbonate, water, and brine, before drying over MgSO$_4$ and concentrating under reduced pressure to 50 mL of EtOAc. The solids were collected by filtration to give 504 (0.101 g, 68%). $^1$H NMR (500 MHz, DMSO) δ 9.10 (d, J=2.3, 1H), 8.08 (s, 1H), 7.70 (dd, J=7.0, 1.9, 1H), 7.61 (ddd, J=10.8, 7.6, 2.1, 2H), 7.07 (d, J=8.4, 1H), 6.34 (t, J=6.9, 1H), 5.94 (dt, J=13.1, 6.6, 1H), 4.60 (s, 2H), 4.40 (t, J=4.9, 2H), 3.45 (t, J=4.9, 2H), 1.55 (d, J=6.6, 6H). MS (ESI(+)): m/z 463.1 (M+H)

Example 505

4-[2-(2-Isopropyl-2H-[1,2,4]triazol-3-yl)-4,5-dihydro-6-oxa-3-thia-1-aza-benzo[e]azulen-9-yl]-1H-pyridin-2-one 505

Step 1: 9-(2-fluoro-pyridin-4-yl)-2-(2-isopropyl-2H-[1,2,4]triazol-3-yl)-4,5-dihydro-6-oxa-3-thia-1-aza-benzo[e]azulene

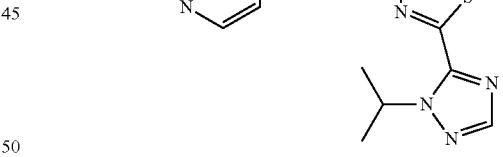

Following the procedure for 128, 2-(2-Isopropyl-2H-[1,2,4]triazol-3-yl)-9-bromo-4,5-dihydro-6-oxa-3-thia-1-aza-benzo[e]azulene from Example 6, and fluoropyridin-4-ylboronic acid were reacted to give 9-(2-fluoro-pyridin-4-yl)-2-(2-isopropyl-2H-[1,2,4]triazol-3-yl)-4,5-dihydro-6-oxa-3-thia-1-aza-benzo[e]azulene (230 mg, 20%). $^1$H NMR (500 MHz, DMSO) δ 8.84 (d, J=2.5, 1H), 8.34 (d, J=5.3, 1H), 8.12 (s, 1H), 7.82 (dd, J=8.4, 2.5, 1H), 7.67 (d, J=5.3, 1H), 7.48 (s, 1H), 7.24 (d, J=8.4, 1H), 5.82 (dt, J=13.2, 6.6, 1H), 4.45 (t, J=4.9, 2H), 3.49 (t, J=4.9, 2H), 1.59 (d, J=6.6, 6H). MS (ESI(+)): m/z 408.1 (M+H)

Step 2

Following the procedure for 330, 9-(2-fluoro-pyridin-4-yl)-2-(2-isopropyl-2H-[1,2,4]triazol-3-yl)-4,5-dihydro-6- oxa-3-thia-1-aza-benzo[e]azulene and HCl were reacted to give 505 (64 mg, 31%). ¹H NMR (500 MHz, DMSO) δ 11.57 (s, 1H), 8.73 (d, J=2.4, 1H), 8.11 (s, 1H), 7.66 (dd, J=8.4, 2.4, 1H), 7.49 (d, J=7.1, 1H), 7.17 (d, J=8.4, 1H), 6.58 (s, 1H), 6.50 (d, J=5.8, 1H), 5.81 (dt, J=13.2, 6.6, 1H), 4.43 (t, J=4.8, 2H), 3.48 (t, J=4.9, 2H), 1.59 (d, J=6.6, 6H). MS (ESI(+)): m/z 406.1 (M+H)

Example 506

5-[2-(2-Isopropyl-2H-[1,2,4]triazol-3-yl)-4,5-dihydro-6-oxa-3-thia-1-aza-benzo[e]azulen-9-yl]-1H-pyrimidine-2,4-dione 506

9-Bromo-2-(2-isopropyl-2H-[1,2,4]triazol-3-yl)-4,5-dihydro-6-oxa-3-thia-1-aza-benzo[e]azulene from Example 6 (500 mg, 1.3 mmol) and potassium acetate (380 mg, 3.8 mmol) were suspended in N,N-dimethylformamide (5 mL) and water (5 mL) and degassed by bubbling N₂ for 5 min. Charged with 2,4-dioxo-1,2,3,4-tetrahydropyrimidin-5-ylboronic acid (250 mg, 1.6 mmol) and then tetrakis(triphenylphosphine)palladium(0) (150 mg, 0.13 mmol). The reaction was microwaved at 300 watts, 140° C. for 20 minutes. Subsequently after cooling to r.t. and diluting with water (20 mL), the mixture was extracted with ethyl acetate. The combined organics portions were concentrated and purified by reverse phase HPLC to provide 506 as a white crystalline compound (70 mg, 10% yield). LC/MS (ESI+): m/z 423.1 (M+H). ¹H NMR (500 MHz, DMSO) δ 1.22 (s, 2H), 8.71 (s, 1H), 8.11 (s, 1H), 7.65 (s, 1H), 7.48 (d, J=8.2 Hz, 1H), 7.06 (d, J=8.4 Hz, 1H), 5.92-5.81 (m, 1H), 4.38 (s, 2H), 3.45 (s, 2H), 1.55 (d, J=6.5 Hz, 4H)

Example 507

2-{3-[2-(2-Isopropyl-2H-[1,2,4]triazol-3-yl)-4,5-dihydro-6-oxa-3-thia-1-aza-benzo[e]azulen-9-yl]-2-oxo-2H-pyridin-1-yl}-N-methyl-acetamide 507

Following the procedure for 504, to 501 in THF was added diisopropylethylamine, 2M methylamine in MeOH, and HATU to give 507 (0.014 g, 9%). ¹H NMR (500 MHz, DMSO) δ 9.11 (d, J=2.3, 1H), 8.08 (s, 1H), 7.71 (dd, J=7.0, 2.0, 1H), 7.64 (dd, J=6.7, 1.9, 1H), 7.58 (dd, J=8.4, 2.3, 1H), 7.07 (d, J=8.4, 1H), 6.35 (t, J=6.9, 1H), 5.94 (dt, J=13.0, 6.5, 1H), 4.60 (s, 2H), 4.40 (t, J=4.9, 2H), 3.45 (t, J=4.9, 2H), 2.65 (d, J=4.6, 3H), 1.53 (d, J=6.6, 6H). MS (ESI(+)): m/z 477.2 (M+H)

Example 508

2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-N-methyl-acetamide 508

To a solution of 2-(2-isopropyl-2H-[1,2,4]triazol-3-yl)-8-piperidin-4-yl-4,5-dihydro-6-oxa-3-thia-1-aza-benzo[e]azulene 375 TFA salt (300 mg, 0.59 mmol) in THF (5 mL) was added potassium carbonate (285 mg, 2.10 mmol) followed by 2-bromo-N-methylacetamide (99 mg, 0.65 mmol). The reaction mixture was stirred for 3 hours before being diluted with DCM and water. The organic layer was dried over anhydrous magnesium sulfate and concentrated in vacuo. The resulting residue was triturated with diethyl ether to give 508 as a brown solid (226 mg, 82%). LCMS: R$_T$=3.21 min, [M+H]⁺=467. ¹H NMR δ (ppm) (DMSO-d₆): 8.28 (1H, d, J=8.19 Hz), 8.10 (1H, s), 7.75-7.68 (1H, m), 7.10 (1H, dd, J=8.24, 1.81 Hz), 6.96 (1H, d, J=1.76 Hz), 5.86-5.77 (1H, m), 4.36 (2H, t, J=5.02 Hz), 3.42 (2H, t, J=5.03 Hz), 2.91-2.87 (4H, m), 2.64 (3H, d, J=4.74 Hz), 2.55-2.45 (1H, m), 2.19-2.17 (2H, m), 1.76-1.75 (4H, m), 1.55 (6H, d, J=6.59 Hz)

Example 509

2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-N,N-dimethyl-acetamide 509

To a solution of 2-(2-isopropyl-2H-[1,2,4]triazol-3-yl)-8-piperidin-4-yl-4,5-dihydro-6-oxa-3-thia-1-aza-benzo[e]azulene 375 TFA salt (386 mg, 0.76 mmol) in THF (5 mL) was added potassium carbonate (210 mg, 1.52 mmol) followed by 2-chloro-N,N-dimethylacetamide (102 mg, 0.84 mmol). The reaction mixture was stirred for 65 hours before being diluted with DCM and water. The organic layer was dried over anhydrous magnesium sulfate and concentrated in vacuo. The resulting residue was purified by silica gel flash chromatography (SiO₂, gradient 0-3% methanol in DCM) then freeze-dried from methanol and water to give 509 as a white solid (158 mg, 43%). LCMS: R$_T$=3.33 min, [M+H]⁺=481. ¹H NMR δ (ppm) (DMSO-d₆): 8.27 (1H, d, J=8.20 Hz), 8.09 (1H, d, J=0.59 Hz), 7.09 (1H, dd, J=8.25, 1.83 Hz), 6.93 (1H, d, J=1.77 Hz), 5.83-5.81 (1H, m), 4.35 (2H, t, J=5.02 Hz), 3.41 (2H, t, J=5.05 Hz), 3.15 (2H, s), 3.05 (3H, s), 2.93 (2H, d, J=10.95 Hz), 2.82 (3H, s), 2.48-2.44 (1H, m), 2.16-2.13 (2H, m), 1.81-1.70 (2H, m), 1.66-1.64 (2H, m), 1.54 (6H, d, J=6.59 Hz)

Example 510

N-tert-Butyl-2-{4-[2-(2-isopropyl-2H-[1,2,4]triazol-3-yl)-4,5-dihydro-6-oxa-3-thia-1-aza-benzo[e]azulen-8-yl]-piperidin-1-yl}-acetamide 510

To a solution of 2-(2-isopropyl-2H-[1,2,4]triazol-3-yl)-8-piperidin-4-yl-4,5-dihydro-6-oxa-3-thia-1-aza-benzo[e]azulene 375 TFA salt (250 mg, 0.49 mmol) in THF (5 mL) was added potassium carbonate (136 mg, 0.98 mmol) followed by N-tert-butyl-2-chloroacetamide (81 mg, 0.54 mmol). The reaction mixture was stirred for 65 hours before being diluted with DCM and water. The organic layer was dried over anhydrous magnesium sulfate and concentrated in vacuo. The resulting residue was purified by silica gel flash chromatography (SiO₂, gradient 0-3% methanol in DCM) then freeze-dried from methanol and water to give 510 as a beige solid (158 mg, 63%). LCMS: R$_T$=3.67 min, [M+H]⁺=509. ¹H NMR δ (ppm) (CDCl₃): 8.34 (1H, d, J=8.18 Hz), 7.93 (1H, s), 7.10-7.06 (2H, m), 6.96 (1H, d, J=1.81 Hz), 5.92-5.91 (1H, m), 4.42 (2H, t, J=5.03 Hz), 3.42 (2H, t, J=5.05 Hz), 3.00-2.91 (4H, m), 2.61-2.48 (1H, m), 2.35-2.24 (2H, m), 1.96-1.87 (3H, m), 1.83-1.71 (1H, m), 1.64 (6H, d, J=6.63 Hz), 1.39 (9H, s)

Example 511

2-(2-Isopropyl-2H-[1,2,4]triazol-3-yl)-8-[1-(2-methoxy-ethyl)-piperidin-4-yl]-4,5-dihydro-6-oxa-3-thia-1-aza-benzo[e]azulene 511

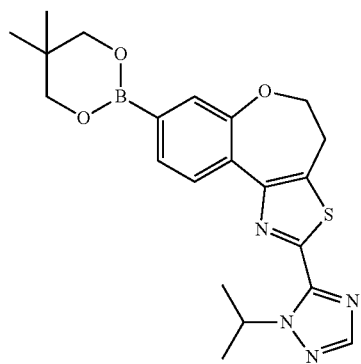 [SMILES: CC(C)n1ncnc1-c1nc2c(s1)CCOc1cc(B3OCC(C)(C)CO3)ccc1-2]

A mixture of 8-bromo-2-(2-isopropyl-2H-[1,2,4]triazol-3-yl)-4,5-dihydro-6-oxa-3-thia-1-aza-benzo[e]azulene 27 (2.00 g, 5.11 mmol), bis(neopentylglycolato)diboron (1.73 g, 7.67 mmol) and potassium acetate (1.76 g, 17.89 mmol) in 1,4-dioxan (20 mL) was stirred while nitrogen was bubbled through for 10 min before addition $PdCl_2$dppf.DCM (0.209 g, 0.256 mmol). The reaction mixture was heated at 90° C. for 6.5 h before the cooled mixture was diluted with DCM (200 mL) and stirred for 15 min with activated charcoal. The mixture was filtered and the filtrate was concentrated in vacuo. The resultant residue was sonicated with cyclohexane and the solid was filtered off and dried (vacuum, 40° C.) to give 8-(5,5-dimethyl-[1,3,2]dioxaborinan-2-yl)-2-(2-isopropyl-2H-[1,2,4]triazol-3-yl)-4,5-dihydro-6-oxa-3-thia-1-aza-benzo[e]azulene (1.97 g, 91%). LCMS $R_T$=3.78, $[M+H]^+$=357 (hydrolysis product). $^1H$ NMR 400 MHz ($CDCl_3$) δ: 8.36 (1H, d, J=7.87 Hz), 7.92 (1H, s), 7.60 (1H, dd, J=7.86, 1.25 Hz), 7.51 (1H, d, J=1.20 Hz), 5.93 (1H, t, J=6.62 Hz), 4.40 (2H, t, J=5.10 Hz), 3.79 (4H, s), 3.43 (2H, t, J=5.12 Hz), 1.63 (6H, d, J=6.63 Hz), 1.04 (6H, s).

To a solution of 2-(2-isopropyl-2H-[1,2,4]triazol-3-yl)-8-piperidin-4-yl-4,5-dihydro-6-oxa-3-thia-1-aza-benzo[e]azulene 375 (300 mg, 0.59 mmol) in DMF (3.5 mL) was added 2-bromoethyl methyl ether (60 μl, 0.65 mmol) and potassium carbonate (285 mg, 2.07 mmol) and the reaction mixture stirred at 60° C. for 2 h. The reaction mixture was diluted with DCM and washed with saturated aqueous sodium bicarbonate, then water followed by brine, dried ($MgSO_4$) and concentrated in vacuo. The resultant residue was subjected to flash chromatography ($SiO_2$, gradient 0-10% MeOH in DCM) followed by trituration in cyclohexane to give 511 (187 mg, 70%). LCMS $R_T$=3.42 min, $[M+H]^+$=454. $^1H$ NMR 400 MHz (DMSO-d6) δ: 8.23 (1H, d, J=8.19 Hz), 8.05 (1H, s), 7.04 (1H, dd, J=8.22, 1.79 Hz), 6.88 (1H, d, J=1.74 Hz), 5.77-5.76 (1H, m), 4.31 (2H, t, J=5.00 Hz), 3.44-3.34 (5H, m), 3.20 (3H, s), 2.93 (3H, d, J=10.98 Hz), 2.02 (2H, t, J=11.43 Hz), 1.71 (3H, m), 1.64-1.53 (2H, m), 1.50 (6H, d, J=6.58 Hz)

Example 512

2-{4-[2-(2-Isopropyl-2H-[1,2,4]triazol-3-yl)-4,5-dihydro-6-oxa-3-thia-1-aza-benzo[e]azulen-8-yl]-piperidin-1-yl}-ethanol 512

Step 1: 2-(2-Isopropyl-2H-[1,2,4]triazol-3-yl)-8-{1-[2-(tetrahydro-pyran-2-yloxy)-ethyl]-piperidin-4-yl}-4,5-dihydro-6-oxa-3-thia-1-aza-benzo[e]azulene To a solution of 2-(2-isopropyl-2H-[1,2,4]triazol-3-yl)-8-piperidin-4-yl-4,5-dihydro-6-oxa-3-thia-1-aza-benzo[e]azulene 375 (310 mg, 0.61 mmol) in DMF (3.5 mL) was added 2(2-bromoethoxy)tetrahydro-2H-pyran (0.1 mL, 0.67 mmol) and potassium carbonate (290 mg, 2.10 mmol) and the reaction mixture stirred at 60° C. for 16 h. The reaction mixture was diluted with DCM and washed with sodium bicarbonate (sat aq.) then water followed by brine, dried ($MgSO_4$) and concentrated in vacuo. The resultant residue was subjected to flash chromatography ($SiO_2$, gradient 0-10% MeOH in DCM) to give 2-(2-Isopropyl-2H-[1,2,4]triazol-3-yl)-8-{1-[2-(tetrahydro-pyran-2-yloxy)-ethyl]-piperidin-4-yl}-4,5-dihydro-6-oxa-3-thia-1-aza-benzo[e]azulene (106 mg, 33%). LCMS: $R_T$=3.71 min, $[M+H]^+$=524 $^1H$ NMR 400 MHz (DMSO-d6) δ: 8.27 (1H, d, J=8.19 Hz), 8.09 (1H, d, J=0.58 Hz), 7.09 (1H, dd, J=8.26, 1.82 Hz), 6.92 (1H, d, J=1.78 Hz), 5.82-5.82 (1H, m), 4.58 (1H, t, J=3.52 Hz), 4.35 (2H, t, J=5.02 Hz), 3.75-3.74 (2H, m), 3.44-3.42 (4H, m), 2.99 (2H, t, J=10.97 Hz), 2.54 (2H, t, J=6.17 Hz), 2.47 (1H, s), 2.09 (2H, t, J=11.61 Hz), 1.79-1.55 (6H, m), 1.55 (6H, d, J=6.59 Hz), 1.52-1.43 (4H, m).

Step 2

To a solution of 2-(2-isopropyl-2H-[1,2,4]triazol-3-yl)-8-{1-[2-(tetrahydro-pyran-2-yloxy)-ethyl]-piperidin-4-yl}-4,5-dihydro-6-oxa-3-thia-1-aza-benzo[e]azulene (103 mg, 0.20 mmol) in MeOH (2 mL) was added HCl (1 mL, 4N in dioxan) and the reaction mixture stirred at RT for 30 min. The reaction mixture was concentrated in vacuo and the residue freeze dried from MeOH/$H_2O$ to give 512 as a solid (136 mg). LCMS: $R_T$=3.16 min, $[M+H]^+$=440 [ad823338] $^1H$ NMR 400 MHz ($d_6$-DMSO) δ: 8.27 (1H, d, J=8.19 Hz), 8.03 (1H, s), 7.04 (1H, dd, J=8.13, 1.84 Hz), 6.89 (1H, d, J=1.75 Hz), 5.79-5.71 (1H, m), 4.31 (2H, t, J=5.0 Hz), 3.74 (2H, t, J=5.0 Hz), 3.57 (2H, d, J=12.01 Hz), 3.37 (2H, t, J=4.96 Hz), 3.08-3.07 (4H, m), 2.79 (1H, t, J=7.80 Hz), 1.98-1.97 (4H, m), 1.49 (6H, d, J=6.59 Hz)

Example 513

2-(2-Isopropyl-2H-5-amino[1,2,4]triazol-3-yl)-8-fluoro-4,5-dihydro-6-oxa-3-thia-1-aza-benzo[e]azulene 513

Following the procedures of Example 516, 1-(5-fluoro-2-hydroxyphenyl)ethanone was converted to 513.

Example 514

1-(8-Piperidin-4-yl-4,5-dihydrothiazolo[4,5-d]benzo[b]oxepin-2-yl)-5,5-dimethylimidazolidin-2,4-dione 514

Step 1: tert-Butyl 4-(2-(5,5-dimethyl-2,4-dioxoimidazolidin-1-yl)4,5-dihydrothiazolo[4,5-d]benzo[b]oxepin-8-yl)-5,6-dihydropyridine-1(2H)-carboxylate

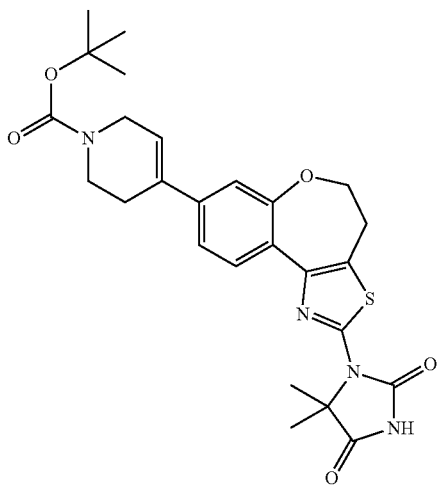 [SMILES: CC(C)(C)OC(=O)N1CC=C(c2ccc3c(c2)OCCc2sc(N4C(=O)NC(=O)C4(C)C)nc2-3)CC1]

1-(8-Bromo-4,5-dihydrothiazolo[4,5-d]benzo[b]oxepin-2-yl)-5,5-dimethylimidazolidin-2,4-dione was coupled with tert-butyl 4-(4,4,5,5-tetramethyl-1,3,2-dioxaborolan-2-yl)-5,6-dihydropyridine-1(2H)-carboxylate to give tert-butyl 4-(2-(5,5-dimethyl-2,4-dioxoimidazolidin-1-yl)4,5-dihydrothiazolo[4,5-d]benzo[b]oxepin-8-yl)-5,6-dihydropyridine-1(2H)-carboxylate. Yield 19%. MS(ESI+):511.3

Step 2: tert-Butyl 4-(2-(5,5-dimethyl-2,4-dioxoimidazolidin-1-yl)4,5-dihydrothiazolo[4,5-d]benzo[b]oxepin-8-yl)-tetrahydropyridine-1(2H)-carboxylate

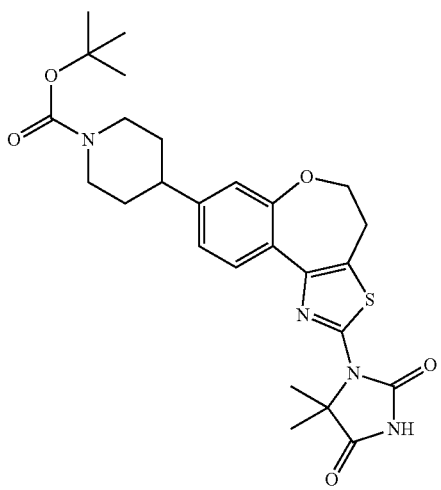 [SMILES: CC(C)(C)OC(=O)N1CCC(c2ccc3c(c2)OCCc2sc(N4C(=O)NC(=O)C4(C)C)nc2-3)CC1]

Tert-butyl 4-(2-(5,5-dimethyl-2,4-dioxoimidazolidin-1-yl)4,5-dihydrothiazolo[4,5-d]benzo[b]oxepin-8-yl)-5,6-dihydropyridine-1(2H)-carboxylate (48 mg, 0.094 mmol) in 6 ml of ethanol was hydrogenated at 1 atm over 50 mg of 10% palladium on charcoal for 18 hours. The mixture was filtered through celite and concentrated in vacuum giving 49 mg (100%) of tert-butyl 4-(2-(5,5-dimethyl-2,4-dioxoimidazolidin-1-yl)4,5-dihydrothiazolo[4,5-d]benzo[b]oxepin-8-yl)-tetrahydropyridine-1(2H)-carboxylate. MS(ESI+): 513.3

Step 3 tert-Butyl 4-(2-(5,5-dimethyl-2,4-dioxoimidazolidin-1-yl)4,5-dihydrothiazolo[4,5-d]benzo[b]oxepin-8-yl)-tetrahydropyridine-1(2H)-carboxylate was stirred in 50% trifluoroacetic acid in dichloromethane to give 514. Yield 30%. MS(ESI+):413.2. 1H NMR (500 MHz, DMSO) δ 8.23 (s, 1H), 8.17 (d, J=8.2, 1H), 7.02 (d, J=8.2, 1H), 6.85 (d, J=1.6, 1H), 4.30 (t, J=4.9, 2H), 3.22-3.20 (m, 3H), 2.88 (t, J=11.2, 2H), 2.75 (t, J=12.0, 1H), 1.89 (d, J=12.5, 2H), 1.67 (d, J=12.9, 7H)

Example 515

5-[2-(2-Isopropyl-2H-[1,2,4]triazol-3-yl)-4,5-dihydro-6-oxa-3-thia-1-aza-benzo[e]azulen-9-yl]-1H—N-methylpyridin-2-one 515

Following the procedure for 477, to 496 in DMF was added iodomethane and cesium fluoride to give 515 (0.014 g, 7%). ¹H NMR (500 MHz, DMSO) δ 8.52 (d, J=2.4, 1H), 8.11 (s, 1H), 8.08 (d, J=2.6, 1H), 7.78 (dd, J=9.5, 2.7, 1H), 7.50 (dd, J=8.4, 2.4, 1H), 7.14 (d, J=8.4, 1H), 6.53 (d, J=9.4, 1H), 5.80 (dt, J=13.2, 6.5, 1H), 4.40 (t, J=5.0, 2H), 3.52 (s, 3H), 3.47 (t, J=5.0, 2H), 1.58 (d, J=6.6, 6H). MS (ESI(+)): m/z 420.1 (M+H)

Example 516

2-(2-Isopropyl-2H-5-amino[1,2,4]triazol-3-yl)-9-fluoro-4,5-dihydro-6-oxa-3-thia-1-aza-benzo[e]azulene 516

Step 1:
1-(2-(2-bromoethoxy)-5-fluorophenyl)ethanone

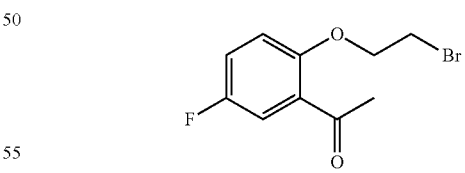

Dissolved 1-(5-fluoro-2-hydroxyphenyl)ethanone (10.0 g, 64.9 mmol) in 18 mL 1,2-Dibromoethane and added Potassium carbonate (18.8 g, 136 mmol) and 100 mL 2-Butanone. Heated the reaction mixture to reflux and allowed to stir overnight under nitrogen. Reaction was complete by LCMS. Diluted reaction mixture with water and extracted the product with ethyl acetate. Concentrated in vacuo and purified by flash chromatography (0 to 30% ethyl acetate/heptanes) to give 3.71 g (21.9% yield) of 1-(2-(2-bromoethoxy)-5-fluorophenyl)ethanone.

Step 2: 7-fluoro-3,4-dihydrobenzo[b]oxepin-5(2H)-one

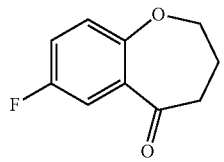 [SMILES: O=C1CCCOc2ccc(F)cc21]

Weighed out Sodium Hydride (561 mg, 23.4 mmol) into a nitrogen purged round bottom flask and added 10 mL THF. Placed the solution under nitrogen and added 1-(2-(2-bromoethoxy)-5-fluorophenyl)ethanone (4.07 g, 15.6 mmol) in 15 mL THF. Let stir at room temperature overnight. Concentrated in vacuo and flashed 0 to 50% ethyl acetate/hexanes. NMR confirmed product as 7-fluoro-3,4-dihydrobenzo[b]oxepin-5(2H)-one (1.58 g, 56.2% yield).

Step 3: 4-bromo-7-fluoro-3,4-dihydrobenzo[b]oxepin-5(2H)-one

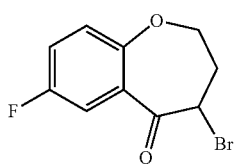 [SMILES: O=C1c2cc(F)ccc2OCCC1Br]

Dissolved 7-fluoro-3,4-dihydrobenzo[b]oxepin-5(2H)-one (1.58 g, 8.77 mmol) in 80 mL ether and added bromine (0.497 mL, 9.65 mmol) and allowed the reaction mixture to stir at room temperature 20 hours. Reaction was complete by LCMS. Concentrated the reaction in vacuo and purified by flash chromatography (0 to 30% ethyl acetate/heptanes). Concentrated in vacuo and NMR indicated 4-bromo-7-fluoro-3,4-dihydrobenzo[b]oxepin-5(2H)-one.

Step 4: 9-fluoro-4,5-dihydro-6-oxa-3-thia-1-aza-benzo[e]azulene-2-carboxylic acid ethyl ester

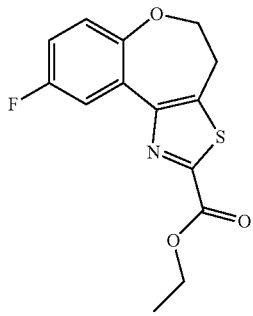 [SMILES: CCOC(=O)c1nc2c(s1)CCOc1ccc(F)cc1-2]

Dissolved 4-bromo-7-fluoro-3,4-dihydrobenzo[b]oxepin-5(2H)-one (1.06 g, 4.09 mmol) in ethanol (100 mL) and added Ethyl Thioamidooxalate (1.09 g, 8.18 mmol). Heated to reflux with a vigreux condensation column attached. Allowed to stir a reflux overnight and confirmed complete reaction by LCMS. Concentrated in vacuo and purified by flash chromatography using ethyl acetate/heptanes (0 to 10% over 60 minutes) to give 0.75 g (62% yield) of 9-fluoro-4,5-dihydro-6-oxa-3-thia-1-aza-benzo[e]azulene-2-carboxylic acid ethyl ester

Step 5: 9-fluoro-4,5-dihydro-6-oxa-3-thia-1-aza-benzo[e]azulene-2-carboxylic acid

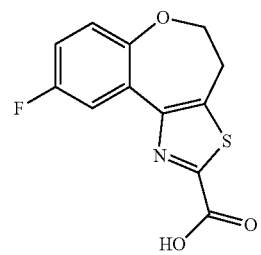 [SMILES: O=C(O)c1nc2c(s1)CCOc1ccc(F)cc1-2]

Dissolved 9-fluoro-4,5-dihydro-6-oxa-3-thia-1-aza-benzo[e]azulene-2-carboxylic acid ethyl ester (0.75 g, 2.6 mmol) in 30 mL THF and added 1 M Lithium Hydroxide (10 mL, 10 mmol). Allowed reaction mixture to stir for 2 hours at room temperature. Reaction was complete by LCMS. THF was removed by rotovap and the aqueous layer was acidified with 1 M HCl. The product was extracted by DCM and concentrated in vacuo to give 0.68 g (100% yield unpurified) of 9-fluoro-4,5-dihydro-6-oxa-3-thia-1-aza-benzo[e]azulene-2-carboxylic acid.

Step 5: tert-butyl amino(methylthio)methylenecarbamate

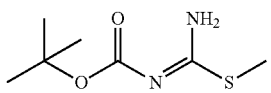

2-Methyl-2-thiopseudourea sulfate (20.0 g, 71.8 mmol) was dissolved in methylene chloride (100 mL) and sodium hydroxide (9.22 g, 0.230 mol) in 110 mL of water was added. The solution was cooled to −10° C. in an ice and brine bath. Di-tert-Butyldicarbonate (11.6 g, 53.2 mmol) was added in 40 mL of DCM dropwise over 2 hours by syringe pump. The solution was allowed to warm up to room temperature and stir over the week-end. The solution was diluted with water and extracted with methylene chloride, washed with brine and concentrated in vacuo to give 13.7 g (68.9% yield) of tert-butyl amino(methylthio)methylenecarbamate

Step 6: 9-fluoro-4,5-dihydro-6-oxa-3-thia-1-aza-benzo[e]azulene-2-carboxylic acid

Example 517

4-[2-(2-Isopropyl-2H-[1,2,4]triazol-3-yl)-4,5-dihydro-6-oxa-3-thia-1-aza-benzo[e]azulen-8-yl]-piperidin-4-ol hydrochloride 517

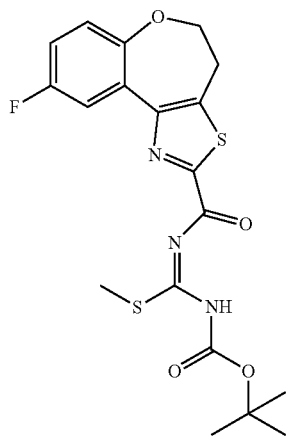 [SMILES: CS/C(=N/C(=O)c1nc2c(s1)CCOc1ccc(F)cc1-2)NC(=O)OC(C)(C)C]

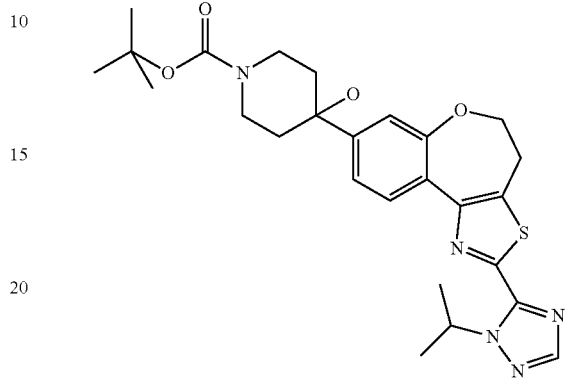

Suspended 9-fluoro-4,5-dihydro-6-oxa-3-thia-1-aza-benzo[e]azulene-2-carboxylic acid (0.68 g, 2.6 mmol) in 30 mL methylene chloride and 30 mL acetonitrile and added oxalyl chloride (0.434 mL, 5.13 mmol) and N,N-Dimethylformamide (19.8 uL, 0.256 mmol) and let the reaction mixture stir for 30 minutes. Complete formation of the acid chloride was confirmed by TLC after quenching an aliquot with triethylamine. Reaction was concentrated in vacuo and dissolved in methylene chloride again (20 mL). tert-Butyl amino(methylthio)methylenecarbamate was added (536 mg, 2.82 mmol) followed by triethylamine (0.52 ml, 3.7 mmol). The reaction was heated to 90° C. and allowed to stir for 3.5 hours. Reaction was complete by TLC and was diluted with water and the product extracted with methylene chloride, concentrated in vacuo, and purified by flash chromatography using ethyl acetate/hexanes (0 to 40%) and concentrated in vacuo to give 0.69 g (62% yield) of the tert-butyl carbamate intermediate

Step 7

The tert-butyl carbamate intermediate from Step 6 (0.69 g, 1.6 mmol) was dissolved in 30 mL N,N-dimethylformamide (DMF). Isopropyl hydrazine hydrochloride (0.52 g, 4.7 mmol) followed by N,N-Diisopropylethylamine (1.65 mL, 9.46 mmol) were added and let stir at 70° for 3.5 hours. Complete reaction was confirmed by LCMS and the reaction mixture was concentrated in vacuo and purified by flash chromatography in ethyl acetate/heptanes (0 to 40%) to give the tert-butyloxycarbonyl intermediate which was immediately dissolved in 1,2-dichloroethane and 1.5 mL (19 mmol) of trifluoroacetic acid was added. The reaction mixture was heated to 40° C. for 4.5 hours and complete deprotection was confirmed by LCMS. Reaction was concentrated in vacuo and the final product purified by HPLC to give 220 mg (40% yield) of 516.

8-(5,5-Dimethyl-[1,3,2]dioxaborinan-2-yl)-2-(2-isopropyl-2H-[1,2,4]triazol-3-yl)-4,5-dihydro-6-oxa-3-thia-1-aza-benzo[e]azulene (200 mg, 0.47 mmol), 4-oxo-piperidine-1-carboxylic acid tert-butyl ester (63 mg, 0.31 mmol), bis(1,5-cyclooctadiene)nickel(0) (17 mg, 0.063 mmol), 1,3-bis(2,6-diisopropylphenyl)imidazolium chloride (27 mg, 0.063 mmol) and cesium fluoride (81 mg, 0.53 mmol) were loaded into a reaction vial, which was then flushed with nitrogen. Dry toluene (3 mL) was then added and nitrogen was bubbled through the mixture for 15 min. before heating at 80° C. for 30 min. The reaction mixture was combined with a mixture from a similar reaction (same quantities of boronate ester and oxo-piperidine, half-quantities of nickel and imidazolium catalysts, heated for 19.5 h) and extracted with ethyl acetate. The organic extract was washed with saturated aqueous sodium bicarbonate followed by brine, then dried ($Na_2SO_4$) and concentrated in vacuo. The resultant residue was subjected to flash chromatography ($SiO_2$, gradient 20-70% ethyl acetate in cyclohexane) to give 4-hydroxy-4-[2-(2-isopropyl-2H-[1,2,4]triazol-3-yl)-4,5-dihydro-6-oxa-3-thia-1-aza-benzo[e]azulen-8-yl]-piperidine-1-carboxylic acid tert-butyl ester (100 mg). LCMS $R_T$=4.73, $[M+H]^+$=512.

To a solution of 4-hydroxy-4-[2-(2-isopropyl-2H-[1,2,4]triazol-3-yl)-4,5-dihydro-6-oxa-3-thia-1-aza-benzo[e]azulen-8-yl]-piperidine-1-carboxylic acid tert-butyl ester (20 mg, 39 μmol) in DCM (2 mL) was added TFA (0.5 mL) and the reaction mixture stirred at RT for 3 h. The reaction mixture was concentrated in vacuo and the resultant residue subjected to flash chromatography (Si—$NH_2$, gradient 1-4% MeOH in DCM). The purified product was dissolved in MeOH (5 mL) and HCl (0.5 mL, 3N in MeOH) added. The reaction mixture was concentrated in vacuo and the residue triturated with MeCN to give 517 as a colourless solid (9 mg, 51%). LCMS: $R_T$=2.94 min, $[M+H]^+$=412 [ad823591] $^1$H NMR 400 MHz ($d_6$-DMSO) δ: 8.38 (1H, d, J=8.2 Hz), 7.97 (1H, s), 7.28 (1H, dd, J=8.2, 1.9 Hz), 7.20 (1H, d, J=1.9 Hz), 5.93 (1H, sept, J=6.6 Hz), 4.37 (2H, t, J=5.0 Hz), 3.49-3.29 (6H, m), 2.29-2.17 (2H, m), 1.98-1.90 (2H, m), 1.59 (6H, d, J=6.6 Hz)

Example 518

2-(2-Isopropyl-5-methyl-2H-[1,2,4]triazol-3-yl)-8-[1-(2-methoxy-ethyl)-azetidin-3-yl]-4,5-dihydro-6-oxa-3-thia-1-aza-benzo[e]azulene 518

To a solution of 8-azetidin-3-yl-2-(2-isopropyl-5-methyl-2H-[1,2,4]triazol-3-yl)-4,5-dihydro-6-oxa-3-thia-1-aza-benzo[e]azulene, from Example 519, (0.300 g, 0.786 mmol) and Cesium Carbonate (0.384 g, 0.00118 mol) in N,N-Dimethylformamide (7.9 mL) was added 1-bromo-2-methoxy-ethane, (0.0739 mL, 0.786 mmol) dropwise. The reaction was stirred at room temperature overnight. The mixture was diluted with water and methylene chloride and extracted 3 times with methylene chloride. The crude was purified by column chromatography followed by reverse-phase HPLC to obtain 518 as a white solid (66.3 mg). MS(ESI+) 440.2. $^1$H NMR (400 MHz, DMSO) δ 8.28 (d, J=8.2 Hz, 1H), 7.19 (dd, J=8.2, 1.5 Hz, 1H), 7.02 (d, J=1.5 Hz, 1H), 5.76 (hept, J=6.6 Hz, 1H), 4.38-4.32 (m, 2H), 3.66-3.52 (m, 3H), 3.41 (t, J=5.0 Hz, 2H), 3.34-3.29 (m, 2H), 3.23 (s, 3H), 3.15-3.07 (m, 2H), 2.58 (t, J=5.9 Hz, 2H), 2.32 (s, 3H), 1.52 (d, J=6.6 Hz, 6H)

Example 519

2-{3-[2-(2-Isopropyl-5-methyl-2H-[1,2,4]triazol-3-yl)-4,5-dihydro-6-oxa-3-thia-1-aza-benzo[e]azulen-8-yl]-azetidin-1-yl}-ethanol 519

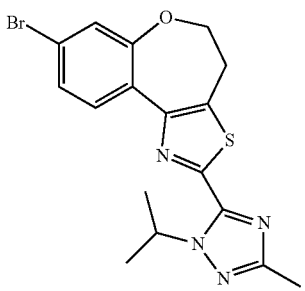 [SMILES: Cc1nc(-c2nc3c(s2)CCOc2cc(Br)ccc2-3)n(C(C)C)n1]

To a solution of 8-Bromo-4,5-dihydro-6-oxa-3-thia-1-aza-benzo[e]azulene-2-carboxylic acid amide (9.040 g, 0.02780 mol) in Toluene (150 mL) was added dimethylacetamide-dimethylacetal (12.38 mL, 0.08340 mol). The reaction was stirred at 95° C. for 4 hours. The toluene was then removed in vacuo and the crude was carried forward without further purification. The crude material was redissolved in acetic acid (90 mL). Isopropylhydrazine hydrochloride (3.689 g, 0.03336 mol) was added and the reaction was stirred at room temperature overnight. The acetic acid was then removed in vacuo. The crude material was triturated in isopropyl alcohol, and filtered to give 8-Bromo-2-(2-isopropyl-5-methyl-2H-[1,2,4]triazol-3-yl)-4,5-dihydro-6-oxa-3-thia-1-aza-benzo[e]azulene as a light yellow solid (10.422 g). MS(ESI+) 405.0/407.0

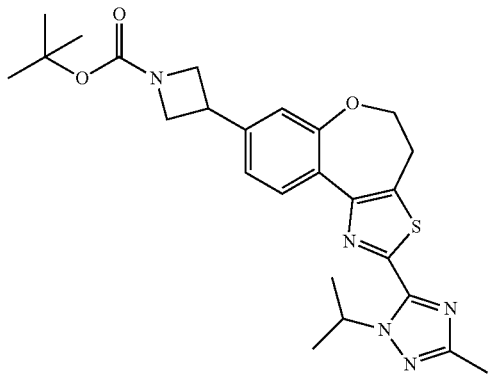 [SMILES: Cc1nc(-c2nc3c(s2)CCOc2cc(C4CN(C(=O)OC(C)(C)C)C4)ccc2-3)n(C(C)C)n1]

Zinc (2.472 g, 0.03780 mol) was stirred in 10 mL of degassed N,N-dimethylacetamide under N$_2$ atmosphere. Chlorotrimethylsilane (0.411 mL, 0.00324 mol) and 1,2-Dibromoethane (0.233 mL, 0.00270 mol) were added and the mixture was stirred for 20 minutes. Tert-butyl 3-iodoazetidine-1-carboxylate (7.644 g, 0.02700 mol) in degassed N,N-dimethylacetamide (60.0 mL) was added slowly and the cloudy reaction was stirred at room temperature for 1.5 hours to give (1-(tert-butoxycarbonyl)azetidin-3-yl)zinc(II) iodide.

8-Bromo-2-(2-isopropyl-5-methyl-2H-[1,2,4]triazol-3-yl)-4,5-dihydro-6-oxa-3-thia-1-aza-benzo[e]azulene (5.000 g, 0.01234 mol) was dissolved in N,N-dimethylacetamide (35 mL) and the solution was degassed for 5 minutes. [1,1'-Bis(diphenylphosphino)ferrocene]dichloropalladium(II), complex with dichloromethane (1:1) (0.5037 g, 0.0006168 mol) and copper(I) iodide (0.2349 g, 0.001234 mol) were added and the reaction was further purged with N$_2$. (1-(Tert-butoxycarbonyl)azetidin-3-yl)zinc(II) iodide (0.01480 mol, 0.38M in DMA, 40 mL), was added and the reaction was heated to 80° C. overnight. Saturated NH$_4$Cl and methylene chloride were added. The mixture was extracted 3 times with methylene chloride. The organic phases were combined, dried with MgSO$_4$ and concentrated. The crude was purified by flash chromatography (10-80% ethyl acetate in hexanes) to afford 3-[2-(2-Isopropyl-5-methyl-2H-[1,2,4]triazol-3-yl)-4,5-dihydro-6-oxa-3-thia-1-aza-benzo[e]azulen-8-yl]-azetidine-1-carboxylic acid tert-butyl ester as a white solid (4.11 g). MS(ESI+) 482.2

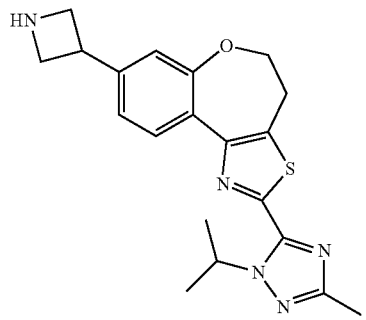 [SMILES: Cc1nc(-c2nc3c(s2)CCOc2cc(C4CNC4)ccc2-3)n(C(C)C)n1]

To a solution of 3-[2-(2-Isopropyl-5-methyl-2H-[1,2,4]triazol-3-yl)-4,5-dihydro-6-oxa-3-thia-1-aza-benzo[e]azulen-8-yl]-azetidine-1-carboxylic acid tert-butyl ester (4.11 g, 0.01234 mol) in methylene chloride (42 mL) was added trifluoroacetic acid (20 mL) dropwise. The reaction was stirred at room temperature for 1 hour. Water and ethyl acetate were added and the mixture was extracted with 1N HCl. The aqueous phase was basified to pH 13 with 1N NaOH. The aqueous phase was filtered and rinsed with cold water to afford 8-azetidin-3-yl-2-(2-isopropyl-5-methyl-2H-[1,2,4]triazol-3-yl)-4,5-dihydro-6-oxa-3-thia-1-aza-benzo[e]azulene as an off-white solid (3.2 g). MS(ESI+) 382.2

To a solution of 8-azetidin-3-yl-2-(2-isopropyl-5-methyl-2H-[1,2,4]triazol-3-yl)-4,5-dihydro-6-oxa-3-thia-1-aza-benzo[e]azulene (0.300 g, 0.000786 mol) in methylene chloride (4.33 mL) was added 2-(tert-butyldimethylsilyloxy)acetaldehyde (0.449 mL, 0.00236 mol) and acetic acid (2.68 mL, 0.0472 mol) followed by sodium triacetoxyborohydride (1.000 g, 0.004718 mol). The reaction was stirred at room temperature for 3 hours. The reaction was quenched with 1N NaOH. Methylene chloride was added and the mixture was extracted 3 times with methylene chloride. The organic phases were combined, dried with MgSO$_4$ and concentrated. The crude material was redissolved in methanol (6.69 mL). Hydrogen chloride (0.000786 mol, 4N in dioxanes, 0.2 mL) was added dropwise and the reaction was stirred at room temperature for 2 hours. 1N NaOH was added until the solution was basic. The mixture was extracted 3 times with methylene chloride. The organic phases were combined, dried with MgSO$_4$ and concentrated. The crude was purified by reverse-phase HPLC to give 519 as a white solid (89.6 mg). m+1 426.2 MS(ESI+) 426.2. $^1$H NMR (400 MHz, DMSO) δ 8.28 (d, J=8.2 Hz, 1H), 7.19 (dd, J=8.2, 1.5 Hz, 1H), 7.03 (d, J=1.4 Hz, 1H), 5.85-5.66 (m, 1H), 4.39-4.32 (m, 3H), 3.67-3.53 (m, 3H), 3.41 (t, J=5.1 Hz, 2H), 3.39-3.34 (m, 2H), 3.15-3.08 (m, 2H), 2.54-2.50 (m, 2H), 2.32 (s, 3H), 1.52 (d, J=6.6 Hz, 6H)

Example 520

1-{3-[2-(2-Isopropyl-5-methyl-2H-[1,2,4]triazol-3-yl)-4,5-dihydro-6-oxa-3-thia-1-aza-benzo[e]azulen-8-yl]-azetidin-1-yl}-3-methoxy-propan-2-ol 520

To a solution of 8-azetidin-3-yl-2-(2-isopropyl-5-methyl-2H-[1,2,4]triazol-3-yl)-4,5-dihydro-6-oxa-3-thia-1-aza-benzo[e]azulene, from Example 519, (0.300 g, 0.000786 mol) and cesium carbonate (0.384 g, 0.00118 mol) in N,N-dimethylformamide (7.9 mL) was added 1-chloro-3-methoxy-2-propanol (0.0844 mL, 0.786 mmol) dropwise. The reaction was heated to 50° C. overnight. Sodium iodide (0.236 g, 0.00157 mol) was added and stirring was continued at 50° C. The mixture was diluted with water and methylene chloride and extracted 3 times with methylene chloride. Purify by flash chromatography then reverse-phase HPLC to obtain 520 as a white solid (22.5 mg). MS(ESI+) 470.2

Example 521

8-[1-(2-Fluoro-ethyl)-azetidin-3-yl]-2-(2-isopropyl-5-methyl-2H-[1,2,4]triazol-3-yl)-4,5-dihydro-6-oxa-3-thia-1-aza-benzo[e]azulene 521

To a solution of 8-azetidin-3-yl-2-(2-isopropyl-5-methyl-2H-[1,2,4]triazol-3-yl)-4,5-dihydro-6-oxa-3-thia-1-aza-benzo[e]azulene, from Example 519, (0.300 g, 0.000786 mol) and cesium carbonate (0.384 g, 0.00118 mol) in N,N-dimethylformamide (7.9 mL) was added 2-fluoro-1-iodoethane (0.137 g, 0.000786 mol) dropwise. The reaction was stirred at room temperature overnight. The mixture was diluted with water and methylene chloride and extracted 3 times with methylene chloride. The crude was purified by column chromatography then reverse-phase HPLC to obtain 521 as a white solid (84.0 mg). m+1 428.1 MS(ESI+) 428.1.

$^1$H NMR (400 MHz, DMSO) δ 8.29 (d, J=8.2 Hz, 1H), 7.20 (dd, J=8.2, 1.3 Hz, 1H), 7.04 (d, J=1.1 Hz, 1H), 5.84-5.66 (m, 1H), 4.48 (t, J=4.9 Hz, 1H), 4.40-4.32 (m, 3H), 3.70-3.56 (m, 3H), 3.42 (t, J=5.0 Hz, 2H), 3.20-3.14 (m, 2H), 2.73 (dt, J=28.8, 4.9 Hz, 2H), 2.32 (s, 3H), 1.52 (d, J=6.6 Hz, 6H)

Example 522

2-{3-[2-(2-Isopropyl-2H-[1,2,4]triazol-3-yl)-4,5-dihydro-6-oxa-3-thia-1-aza-benzo[e]azulen-8-yl]-phenyl}-acetamide 522

A solution of crude {3-[2-(2-isopropyl-2H-[1,2,4]triazol-3-yl)-4,5-dihydro-6-oxa-3-thia-1-aza-benzo[e]azulen-8-yl]-phenyl}-acetic acid (0.38 mmol) in 5 mL DMF was treated sequentially with DIPEA (0.33 mL, 1.92 mmol), ammonium chloride (164 mg, 3.1 mmol) and HATU (292 mg, 0.77 mmol). The reaction was monitored by LCMS. After complete conversion, the mixture was diluted with water and extracted with ethylacetate. The combined organics were washed with brine, dried over sodium sulfate and concentrated. The crude residue was purified by reverse phase HPLC to give 522 as a colorless solid (93 mg, 56%). LCMS: 446.1. $^1$H NMR (400 MHz, DMSO) δ 8.45 (d, J=8.3 Hz, 1H), 8.11 (s, 1H), 7.66 (s, 1H), 7.60 (d, J=7.8 Hz, 1H), 7.54 (dd, J=8.3, 1.8 Hz, 1H), 7.49 (s, 1H), 7.44-7.35 (m, 2H), 7.27 (d, J=7.6 Hz, 1H), 6.88 (s, 1H), 5.92-5.78 (m, 1H), 4.43 (t, J=4.9 Hz, 2H), 3.47 (overlapping m, 4H), 1.57 (d, J=6.6 Hz, 6H)

Example 523

2-{4-Fluoro-4-[2-(2-isopropyl-2H-[1,2,4]triazol-3-yl)-4,5-dihydro-6-oxa-3-thia-1-aza-benzo[e]azulen-8-yl]-piperidin-1-yl}-N,N-dimethyl-acetamide 523

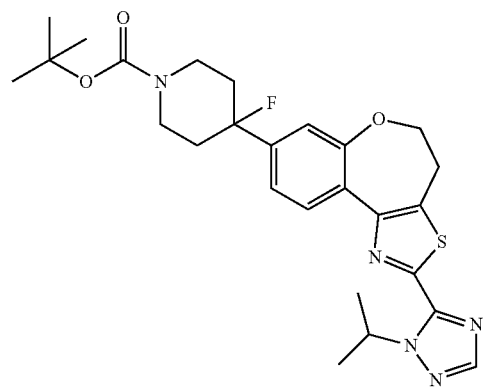 [SMILES: CC(C)n1ncnc1-c1nc2c(s1)CCOc1cc(C3(F)CCN(C(=O)OC(C)(C)C)CC3)ccc1-2]

To a solution of 4-hydroxy-4-[2-(2-isopropyl-2H-[1,2,4]triazol-3-yl)-4,5-dihydro-6-oxa-3-thia-1-aza-benzo[e]azulen-8-yl]-piperidine-1-carboxylic acid tert-butyl ester, from Example 511, (80 mg, 0.16 mmol) in DCM (8 mL) at −78° C. was added DAST (200 μL, 1.52 mmol). The reaction mixture was stirred at −78° C. for 30 min then allowed to warm to RT and stirred for 16 h. The reaction mixture was stirred at RT for 16 h then diluted with DCM (20 mL) and washed with saturated aqueous sodium bicarbonate solution. The aqueous layer was extracted with DCM (3×5 mL) and the combined organic extracts were dried (MgSO$_4$), filtered and concentrated in vacuo. The resultant residue was subjected to flash chromatography (SiO$_2$, 20% ethyl acetate in DCM) to give 4-Fluoro-4-[2-(2-isopropyl-2H-[1,2,4]triazol-3-yl)-4,5-dihydro-6-oxa-3-thia-1-aza-benzo[e]azulen-8-yl]-piperidine-1-carboxylic acid tert-butyl ester (45 mg, 56%). LCMS: R$_T$=5.05 min, [M+H]$^+$=514

To a solution of 4-fluoro-4-[2-(2-isopropyl-2H-[1,2,4]triazol-3-yl)-4,5-dihydro-6-oxa-3-thia-1-aza-benzo[e]azulen-8-yl]-piperidine-1-carboxylic acid tert-butyl ester (45 mg, 88 μmol) in DCM (2.5 mL) was added TFA (0.8 mL) and the reaction mixture stirred at RT for 1 h before being concentrated in vacuo. The residue was dissolved in DCM (2 mL) and triethylamine (88 μL, 0.61 mmol), tetrabutylammonium iodide (8 mg, 21 μmol) and 2-chloro-N,N-dimethylacetamide (14 μL, 0.1 mmol) added. The reaction mixture was stirred at RT for 16 h then diluted with DCM (20 mL) and washed with saturated aqueous sodium bicarbonate solution. The aqueous layer was extracted with DCM (3×5 mL) and the combined organic extracts were dried (MgSO$_4$), filtered and concentrated in vacuo. The resultant residue was subjected to flash chromatography (SiO$_2$ 20% ethyl acetate in DCM then 2% MeOH in DCM) producing impure material. The material was subjected to flash chromatography (Si—NH$_2$ eluting with DCM) to yield 523. LCMS: R$_T$=3.43 min, [M+H]$^+$=499 [ad823805] $^1$H NMR 400 MHz (d$_6$-DMSO) δ: 8.37 (1H, d, J=8.4 Hz), 7.96 (1H, s), 7.18 (1H, dd, J=1.8, 8.4 Hz), 7.09 (1H, d, J=1.8 Hz), 5.93 (1H, sept, J=6.6 Hz), 4.37 (2H, t, J=5.1 Hz), 3.42 (2H, t, J=5.1 Hz), 3.30 (2H, s), 3.09 (3H, s), 2.93 (3H, s), 2.92-2.85 (2H, m), 2.55-2.46 (2H, m), 2.31-2.11 (2H, m), 1.97-1.87 (2H, m), 1.59 (6H, d, J=6.6 Hz)

Example 524

{1-[2-(2-Isopropyl-5-methyl-2H-[1,2,4]triazol-3-yl)-4,5-dihydro-6-oxa-3-thia-1-aza-benzo[e]azulen-8-yl]-methyl}-urea 524

Following the procedures for 542, C-[2-(2-Isopropyl-5-methyl-2H-[1,2,4]triazol-3-yl)-4,5-dihydro-6-oxa-3-thia-1-aza-benzo[e]azulen-8-yl]-methylamine 532 was reacted with potassium cyanate in acetic acid and water to give 524. MS(ESI+) 399.1. $^1$H NMR (400 MHz, DMSO) δ 8.27 (d, J=8.2 Hz, 1H), 7.07 (dd, J=8.2, 1.3 Hz, 1H), 6.95 (br, 1H), 6.44 (t, J=6.1 Hz, 1H), 5.83-5.68 (m, 1H), 5.54 (s, 2H), 4.35 (t, J=5.0 Hz, 2H), 4.18 (d, J=6.1 Hz, 2H), 3.42 (t, J=5.0 Hz, 2H), 2.32 (s, 3H), 1.52 (d, J=6.6 Hz, 6H).

Example 525

1-ethyl-3-[2-(2-isopropyl-5-methyl-2H-[1,2,4]triazol-3-yl)-4,5-dihydro-6-oxa-3-thia-1-aza-benzo[e]azulen-8-ylmethyl]-urea 525

To a solution of C-[2-(2-Isopropyl-5-methyl-2H-[1,2,4]triazol-3-yl)-4,5-dihydro-6-oxa-3-thia-1-aza-benzo[e]azulen-8-yl]-methylamine 532 (0.050 g, 0.00014 mol) in tetrahydrofuran (1.0 mL) was added triethylamine (0.0588 mL, 0.000422 mol) then isocyanatoethane (0.110 mL, 0.00141 mol). The reaction was stirred at room temperature overnight, quenched with a small amount of methanol and concentrated in vacuo. The crude was precipitated from MeOH/H$_2$O to give 525. MS(ESI+) 427.1

Example 526

3-{3-[2-(2-Isopropyl-5-methyl-2H-[1,2,4]triazol-3-yl)-4,5-dihydro-6-oxa-3-thia-1-aza-benzo[e]azulen-8-yl]-azetidin-1-yl}-propan-1-ol 526

Following the procedures for 519, 8-azetidin-3-yl-2-(2-isopropyl-5-methyl-2H-[1,2,4]triazol-3-yl)-4,5-dihydro-6-oxa-3-thia-1-aza-benzo[e]azulene was reacted with 3-(tert-butyldimethylsilyloxy)propanal to give 526. MS(ESI+) 440.2

Example 527

N-Isopropyl-2-{3-[2-(2-isopropyl-5-methyl-2H-[1,2,4]triazol-3-yl)-4,5-dihydro-6-oxa-3-thia-1-aza-benzo[e]azulen-8-yl]-azetidin-1-yl}-acetamide 527

2-Chloro-N-isopropylacetamide (0.124 g, 0.917 mmol) and tetra-n-butylammonium iodide (0.678 g, 0.00183 mol) were premixed in methylene chloride (3 mL). This solution was added dropwise to a solution of 8-azetidin-3-yl-2-(2-isopropyl-5-methyl-2H-[1,2,4]triazol-3-yl)-4,5-dihydro-6-oxa-3-thia-1-aza-benzo[e]azulene from Example 519 (0.350 g, 0.917 mmol) and triethylamine (0.256 mL, 0.00183 mol) in methylene chloride (7 mL). The reaction was stirred at room temperature for 24 hours. Water was added and the mixture was extracted 3 times with methylene chloride. The organic layers were combined, dried with MgSO$_4$ and concentrated. The crude was purified by reverse-phase HPLC to obtain 527 as a white solid (51 mg). MS(ESI+) 481.2. $^1$H NMR (400 MHz, DMSO) δ 8.29 (d, J=8.2 Hz, 1H), 7.42 (d, J=7.9 Hz, 1H), 7.20 (dd, J=8.3, 1.6 Hz, 1H), 7.03 (d, J=1.5 Hz, 1H), 5.87-5.65 (m, 1H), 4.36 (t, J=5.0 Hz, 2H), 3.87 (dq, J=13.2, 6.6 Hz, 1H), 3.76-3.59 (m, 3H), 3.42 (t, J=5.0 Hz, 2H), 3.22 (t, J=6.0 Hz, 2H), 3.04 (s, 2H), 2.32 (s, 3H), 1.52 (d, J=6.6 Hz, 6H), 1.07 (d, J=6.6 Hz, 6H)

Example 528

4-[2-(2-Isopropyl-2H-[1,2,4]triazol-3-yl)-4,5-dihydro-6-oxa-3-thia-1-aza-benzo[e]azulen-9-yl]-1H—N-methylpyridin-2-one 528

Following the procedure for 477, to 505 in DMF was added iodomethane and cesium fluoride to give 528 (0.077 g, 10%). $^1$H NMR (400 MHz, DMSO) δ 8.74 (d, J=2.4, 1H), 8.12 (s, 1H), 7.82 (d, J=7.1, 1H), 7.68 (dd, J=8.4, 2.4, 1H), 7.18 (d, J=8.4, 1H), 6.67 (d, J=1.9, 1H), 6.55 (dd, J=7.1, 2.0, 1H), 5.81 (dt, J=13.1, 6.4, 1H), 4.43 (t, J=4.9, 2H), 3.46 (s, 5H), 1.59 (d, J=6.6, 6H). MS (ESI(+)): m/z 420.1 (M+H)

Example 529

2-(2-Isopropyl-5-methyl-2H-[1,2,4]triazol-3-yl)-8-oxetan-3-yl-4,5-dihydro-6-oxa-3-thia-1-aza-benzo[e]azulene 529

2-(2-Isopropyl-5-methyl-2H-[1,2,4]triazol-3-yl)-8-(4,4,5,5-tetramethyl-[1,3,2]dioxaborolan-2-yl)-4,5-dihydro-6-oxa-3-thia-1-aza-benzo[e]azulene was reacted with 3-iodooxetane in a CEM microwave vial with nickel(II)iodide, trans-2-aminocyclohexanol hydrochloride and sodium hexamethyldisilazane to give 529. MS(ESI+) 383.1. $^1$H NMR (400 MHz, DMSO) δ 8.34 (d, J=8.2 Hz, 1H), 7.27 (dd, J=8.2, 1.4 Hz, 1H), 7.08 (d, J=1.3 Hz, 1H), 5.76 (hept, J=6.8 Hz, 1H), 4.94 (dd, J=8.3, 5.9 Hz, 2H), 4.63 (t, J=6.3 Hz, 2H), 4.37

(t, J=5.0 Hz, 2H), 4.31-4.20 (m, 1H), 3.43 (t, J=5.0 Hz, 2H), 2.32 (s, 3H), 1.52 (d, J=6.6 Hz, 6H)

Example 530

4-[2-(2-Isopropyl-2H-[1,2,4]triazol-3-yl)-4,5-dihydro-6-oxa-3-thia-1-aza-benzo[e]azulen-8-yl]-1H-pyridin-2-one 530

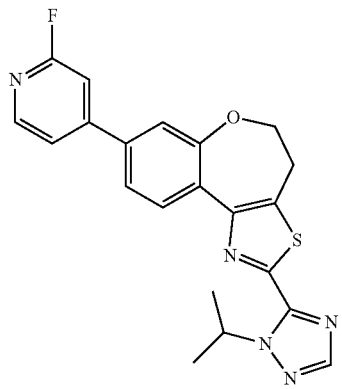 [SMILES: CC(C)n1ncnc1-c1nc2c(s1)CCOc1cc(-c3ccnc(F)c3)ccc1-2]

Following the procedures for 128, 2-(2-Isopropyl-2H-[1,2,4]triazol-3-yl)-8-bromo-4,5-dihydro-6-oxa-3-thia-1-aza-benzo[e]azulene was reacted with 2-fluoropyridin-4-ylboronic acid to give 2-(2-isopropyl-2H-[1,2,4]triazol-3-yl)-8-(2-fluoropyrid-4-yl)-4,5-dihydro-6-oxa-3-thia-1-aza-benzo[e]azulene (0.60 g, 30%). MS (ESI(+): m/z 408.0 (M+H)

Following the procedures for 330, 2-(2-isopropyl-2H-[1,2,4]triazol-3-yl)-8-(2-fluoropyrid-4-yl)-4,5-dihydro-6-oxa-3-thia-1-aza-benzo[e]azulene and HCl were reacted to give 530 (0.352 g, 60%). $^1$H NMR (400 MHz, DMSO) δ 11.62 (s, 1H), 8.45 (d, J=8.3, 1H), 8.12 (s, 1H), 7.56 (d, J=8.2, 1H), 7.45 (d, J=6.8, 1H), 7.40 (s, 1H), 6.64 (s, 1H), 6.57 (d, J=6.8, 1H), 5.84 (dt, J=13.1, 6.5, 1H), 4.42 (t, J=4.8, 2H), 3.48 (t, J=4.8, 2H), 1.56 (d, J=6.6, 6H). MS (ESI(+)): m/z 406.1 (M+H)

Example 531

2-(2-Isopropyl-2H-5-methoxymethyl[1,2,4]triazol-3-yl)-4,5-dihydro-6-oxa-3-thia-1-aza-benzo[e]azulene 531

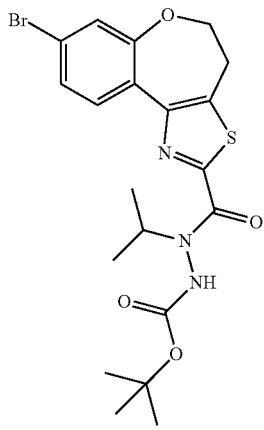 [SMILES: CC(C)N(NC(=O)OC(C)(C)C)C(=O)c1nc2c(s1)CCOc1cc(Br)ccc1-2]

Step 1: N'-(8-Bromo-4,5-dihydro-6-oxa-3-thia-1-aza-benzo[e]azulene-2-carbonyl)-N'-isopropyl-hydrazinecarboxylic acid tert-butyl ester To a mixture of 8-bromo-4,5-dihydro-6-oxa-3-thia-1-aza-benzo[e]azulene-2-carboxylic acid (5.20 g, 16.0 mmol) and N'-isopropyl-hydrazinecarboxylic acid tert-butyl ester (3.33 g, 19.1 mmol) in DMF (100 mL) at 0° C. was added DIPEA (6.93 mL, 39.9 mmol) followed by HATU (9.09 g, 23.9 mmol). The reaction mixture was stirred at RT for 72 h before being concentrated in vacuo. The resultant residue was treated with water then extracted with DCM (×3) before the combined organic extracts were washed with 10% citric acid, then saturated sodium bicarbonate solution followed by brine. The organic layer was dried (Na$_2$SO$_4$), filtered and concentrated in vacuo to give a brown oil. The oil was extracted with diethyl ether (×5) and the diethyl ether extracts concentrated in vacuo before being triturated with pentane to give the title compound as a light brown solid (6.14 g, 12.7 mmol, 80%). LCMS: R$_T$=5.02 min, [M+H]$^+$=482/484.

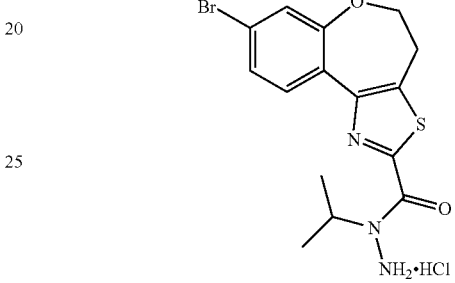

Step 2: 8-Bromo-4,5-dihydro-6-oxa-3-thia-1-aza-benzo[e]azulene-2-carboxylic acid N-isopropyl-hydrazide hydrochloride A suspension of N'-(8-bromo-4,5-dihydro-6-oxa-3-thia-1-aza-benzo[e]azulene-2-carbonyl)-N'-isopropyl-hydrazinecarboxylic acid tert-butyl ester (6.14 g, 12.7 mmol) in methanol (49 mL) was treated with 4N HCl in dioxan (12.7 mL, 51.0 mmol) and stirred at RT for 0.75 h before being warmed to 50° C. and stirred for 3 h. The reaction mixture was concentrated in vacuo and the resultant solid was triturated with diethyl ether to give the title compound as a yellow brown solid (5.14 g, 12.3 mmol, 96%). LCMS: R$_T$=4.79 min, [M+H]$^+$=382/384.

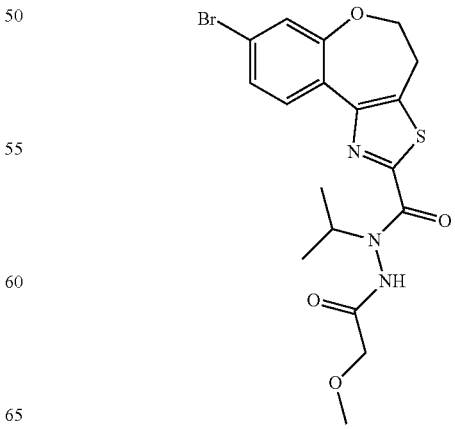

Step 3: 8-Bromo-4,5-dihydro-6-oxa-3-thia-1-aza-benzo[e]azulene-2-carboxylic acid N-isopropyl-N'-(2-methoxy-acetyl)-hydrazide To a mixture of 8-bromo-4,5-dihydro-6-oxa-3-thia-1-aza-benzo[e]azulene-2-carboxylic acid N-isopropyl-hydrazide hydrochloride (3.5 g, 8.4 mmol) and TEA (4.07 mL, 29.3 mmol) in DCM (35 mL) at 0° C. was added methoxy-acetyl chloride (1.53 mL, 16.7 mmol) dropwise and the reaction mixture was stirred at 0° C. for 0.75 h then 18 h at RT. The reaction was quenched by the addition of saturated aqueous sodium bicarbonate solution and the phases separated. The aqueous phase was extracted with DCM (×2) before the combined organic extracts were washed with 10% citric acid solution, followed by brine then dried ($Na_2SO_4$) and concentrated in vacuo to give a yellow brown solid. The solid was triturated with diethyl ether to give the title compound as an off white solid (2.66 g, 5.86 mmol, 70%). LCMS $R_T$=4.64 min, $[M+H]^+$=454/456.

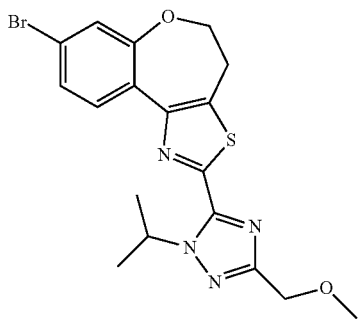 [SMILES: COCc1nc(-c2nc3c(s2)CCOc2cc(Br)ccc2-3)n(C(C)C)n1]

Step 4: 8-Bromo-2-(2-isopropyl-5-methoxymethyl-2H-[1,2,4]triazol-3-yl)-4,5-dihydro-6-oxa-3-thia-1-aza-benzo[e]azulene A suspension of 8-bromo-4,5-dihydro-6-oxa-3-thia-1-aza-benzo[e]azulene-2-carboxylic acid N-isopropyl-N'-(2-methoxy-acetyl)-hydrazide (2.66 g, 5.86 mmol) in phosphorus (V) oxychloride (26 mL) was stirred at 100° C. for 18 h. The reaction mixture was concentrated in vacuo and the resultant residue azeotroped with toluene (×4) affording a brown solid. The solid was treated with acetic acid (26 mL) and ammonium acetate (4.51 g, 58.6 mmol) before the mixture was stirred at 125° C. for 1 h. A further addition of ammonium acetate (2.31 g, 30.0 mmol) was made and the reaction stirred at 125° C. for 2 h before being concentrated in vacuo. The resultant residue was diluted with water and extracted with DCM (×2) before the combined organic extracts were washed with saturated sodium bicarbonate solution followed by brine, then dried ($Na_2SO_4$) and concentrated in vacuo to give a pale brown solid. The solid was treated with phosphorus (V) oxychloride (26 mL) and stirred at 100° C. for 24 h before being concentrated in vacuo then treated with acetic acid (23 mL) and ammonium acetate (4.23 g, 55.0 mmol). The mixture was stirred at 125° C. for 1.5 h then concentrated in vacuo and azeotroped with toluene (×4). The resultant residue was diluted with water and extracted with DCM (×2) and the combined organic extracts were washed with saturated sodium bicarbonate solution followed by brine, then dried ($Na_2SO_4$) and concentrated in vacuo to give a brown solid. The solid was recrystallised from methanol/chloroform to give the title compound as a dark brown solid (1.17 g, 2.69 mmol, 46%). LCMS $R_T$=4.97 min, $[M+H]^+$=435/437. $^1$H NMR 400 MHz (DMSO-d6) δ: 8.23 (1H, d, J=8.58 Hz), 7.36 (1H, dd, J=8.58, 2.10 Hz), 7.26 (1H, d, J=2.07 Hz), 5.72-5.71 (1H, m), 4.39 (2H, s), 4.35 (2H, t, J=5.02 Hz), 3.39 (2H, t, J=5.02 Hz), 3.29 (3H, s), 1.49 (6H, d, J=6.59 Hz).

Step 5

To a solution of 8-bromo-2-(2-isopropyl-5-methoxymethyl-2H-[1,2,4]triazol-3-yl)-4,5-dihydro-6-oxa-3-thia-1-aza-benzo[e]azulene (1.17 g, 2.7 mmol) in IMS (15 mL) and chloroform (10 mL) was added water (3 mL), ammonium formate (1.69 g, 27 mmol) and palladium on carbon (10% by wt, 350 mg). The reaction mixture was heated at 50° C. for 1 hour. Palladium on carbon (10% by wt, 350 mg) was added and heating continued for 4.5 h. More palladium on carbon (10% by wt, 350 mg) was added and the reaction mixture heated at 50° C. for 16 h. The reaction mixture was filtered and the solids washed with chloroform. The filtrate was washed with water extracting with DCM (2×20 mL). The combined organic extracts were washed with citric acid (10% aqueous) then brine, dried ($MgSO_4$) and concentrated in vacuo. The resultant residue was subjected to flash chromatography ($SiO_2$ eluting with 0-50% ethyl acetate in cyclohexane) to give the title compound (456 mg). A portion of this material was further purified by RPHPLC (C18 column, gradient 50-95% MeOH in water, +0.1% formic acid) to give 531. LCMS: $R_T$=5.41 min, $[M+H]^+$=357 [ad823933] [NMR 72713] $^1$H NMR 400 MHz (d$_6$-DMSO) δ: 8.31 (1H, dd, J=7.9, 1.8 Hz), 7.29-7.23 (1H, m), 7.19-7.13 (1H, m), 7.03 (1H, dd, J=7.9, 1.2 Hz), 5.76 (1H, sept, J=6.6 Hz), 4.40 (2H, s), 4.32 (2H, t, J=5.0 Hz), 3.40 (2H, t, J=5.0 Hz), 3.30 (3H, s), 1.50 (6H, d, J=6.6 Hz)

Example 532

C-[2-(2-Isopropyl-5-methyl-2H-[1,2,4]triazol-3-yl)-4,5-dihydro-6-oxa-3-thia-1-aza-benzo[e]azulen-8-yl]-methylamine 532

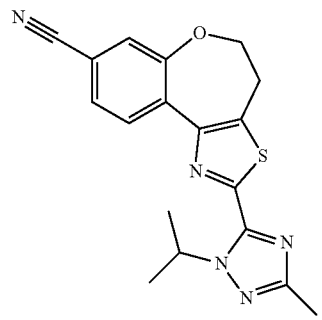 [SMILES: Cc1nc(-c2nc3c(s2)CCOc2cc(C#N)ccc2-3)n(C(C)C)n1]

To a CEM microwave vial was added 8-bromo-2-(2-isopropyl-5-methyl-2H-[1,2,4]triazol-3-yl)-4,5-dihydro-6-oxa-3-thia-1-aza-benzo[e]azulene (1.000 g, 0.002467 mol) and degassed N,N-Dimethylformamide (12.00 mL). The mixture was thoroughly purged with $N_2$. Zinc cyanide (0.2897 g, 0.002467 mol) and tetrakis(triphenylphosphine)palladium (0) (0.1426 g, 0.0001234 mol) were added in one portion and the vial was immediately sealed. The reaction was submitted to microwave irradiation at 60 W for 30 minutes ($T_{max}$=175° C.). The mixture was diluted with methylene chloride and washed with saturated $NH_4Cl$. The organic layers were combined, dried with $MgSO_4$ and concentrated. The crude was loaded as a solid onto silica gel and purified by flash chromatography (10-100% EtOAc in hexanes) to give 2-(2-Isopropyl-5-methyl-2H-[1,2,4]triazol-3-yl)-4,5-dihydro-6-oxa-3-thia-1-aza-benzo[e]azulene-8-carbonitrile as a light yellow solid (593 mg). MS(ESI+) 352.1

To a solution of 2-(2-Isopropyl-5-methyl-2H-[1,2,4]triazol-3-yl)-4,5-dihydro-6-oxa-3-thia-1-aza-benzo[e]azulene-8-carbonitrile (0.500 g, 0.00142 mol) in Tetrahydrofuran (14 mL) was added Lithium tetrahydroaluminate (0.00569 mol, 1M in THF, 5.7 mL), dropwise at 0° C. The reaction was stirred for 2 hours and quenched with saturated $Na_2SO_4$ until $H_2$ evolution ceased. $MgSO_4$ was added and the whole was diluted with copious amounts of methylene chloride, filtered over celite, and concentrated in vacuo. The crude was purified by flash chromatography (1-15% MeOH in DCM spiked with $Et_3N$) to afford 532 as a yellow solid (238 mg). MS(ESI+) 356.1

Example 533

N-[2-(2-isopropyl-5-methyl-2H-[1,2,4]triazol-3-yl)-4,5-dihydro-6-oxa-3-thia-1-aza-benzo[e]azulen-8-ylmethyl]-methanesulfonamide 533

To a solution of C-[2-(2-Isopropyl-5-methyl-2H-[1,2,4]triazol-3-yl)-4,5-dihydro-6-oxa-3-thia-1-aza-benzo[e]azulen-8-yl]-methylamine 532 (0.050 g, 0.14 mmol) and triethylamine (0.0235 mL, 0.169 mmol) in methylene chloride (0.902 mL) was added methanesulfonyl chloride (13.1 uL, 0.169 mmol) dropwise. The reaction was stirred at room temperature for 1 hour. Water was added and the mixture was extracted 3 times with methylene chloride. The organic layers were combined, dried with $MgSO_4$, and concentrated. The crude was purified by reverse-phase HPLC to give 533 as a white solid (24 mg). MS(ESI+) 434.1. $^1$H NMR (400 MHz, DMSO) δ 8.31 (d, J=8.2 Hz, 1H), 7.61 (t, J=6.3 Hz, 1H), 7.17 (d, J=8.2 Hz, 1H), 7.06 (br, 1H), 5.76 (hept, J=6.1 Hz, 1H), 4.36 (t, J=5.0 Hz, 2H), 4.17 (d, J=6.2 Hz, 2H), 3.43 (t, J=4.9 Hz, 2H), 2.89 (s, 3H), 2.32 (s, 3H), 1.52 (d, J=6.6 Hz, 6H)

Example 534

2-(2-Isopropyl-2H-5-hydroxymethyl[1,2,4]triazol-3-yl)-4,5-dihydro-6-oxa-3-thia-1-aza-benzo[e]azulene 534

2-(2-Isopropyl-2H-5-methoxymethyl[1,2,4]triazol-3-yl)-4,5-dihydro-6-oxa-3-thia-1-aza-benzo[e]azulene 531 (456 mg, 1.28 mmol) and HBr (8 mL, 48% solution) were heated at 100° C. for 4 h. The reaction mixture was diluted with water and the pH adjusted to ~pH 8 by the addition of sodium carbonate solution (1M). The mixture was extracted with DCM (5×30 mL) and the combined organic extracts washed with water, then brine, dried ($MgSO_4$) and concentrated in vacuo. The resultant residue was subjected to flash chromatography ($SiO_2$ eluting with 0-3% MeOH in DCM) to give the title product (246 mg, 56%). A portion of this material was further purified on reverse phase preparative HPLC (C18 column, gradient 55-98% MeOH in water, 0.1% formic acid) to yield 534. LCMS: $R_T$=4.57 min, [M+H]$^+$=343 [ad824015] [73244] $^1$H NMR 400 MHz ($d_6$-DMSO) δ: 8.31 (1H, dd, J=7.9, 1.8 Hz), 7.29-7.23 (1H, m), 7.19-7.13 (1H, m), 7.04 (1H, dd, J=7.9, 1.2 Hz), 5.76 (1H, sept, J=6.6 Hz), 5.35 (1H, t, OH J=6.1 Hz), 4.43 (2H, d, J=6.1 Hz), 4.32 (2H, t, J=5.0 Hz), 3.40 (2H, t, J=5.0 Hz), 1.50 (6H, d, J=6.6 Hz)

Examples 535 and 536

2-(2-Isopropyl-5-methyl-2H-[1,2,4]triazol-3-yl)-8-piperidin-3S-yl-4,5-dihydro-6-oxa-3-thia-1-aza-benzo[e]azulene 535 and 2-(2-Isopropyl-5-methyl-2H-[1,2,4]triazol-3-yl)-8-piperidin-3R-yl-4,5-dihydro-6-oxa-3-thia-1-aza-benzo[e]azulene 536

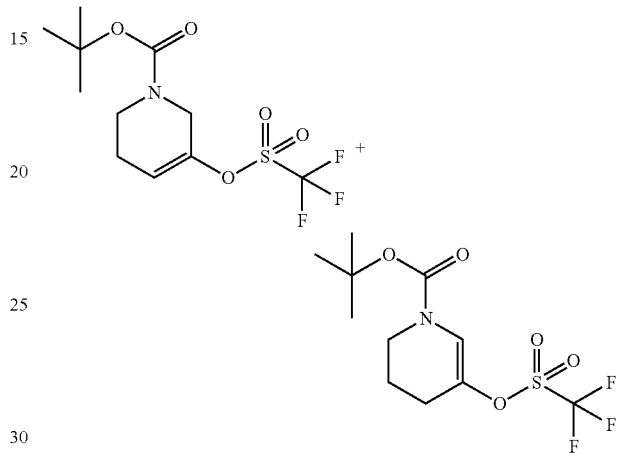

To a solution of lithium diisopropylamide (0.0144 mol, 2M in heptane/THF/EtPh, 7.2 mL) in tetrahydrofuran (25 mL) at −78° C. was added a solution of 3-Oxo-piperidine-1-carboxylic acid tert-butyl ester (2.00 g, 0.0100 mol) in tetrahydrofuran (5 mL) dropwise. After 15 minutes, N-phenylbis(trifluoromethanesulphonimide) (4.303 g, 0.01204 mol) in tetrahydrofuran (10 mL) was added. The reaction was slowly warmed to room temperature and stirred overnight. The reaction was cooled to 0° C. and quenched with saturated $NH_4Cl$, diluted with water, and extracted 3 times with dichloromethane. The organic layers were combined, dried with $MgSO_4$, and concentrated. The mixture was purified by flash chromatography (EtOAc/hexanes) to give 0.933 g of 5-Trifluoromethanesulfonyloxy-3,6-dihydro-2H-pyridine-1-carboxylic acid tert-butyl ester and 1.1234 g of 5-Trifluoromethanesulfonyloxy-3,4-dihydro-2H-pyridine-1-carboxylic acid tert-butyl ester.

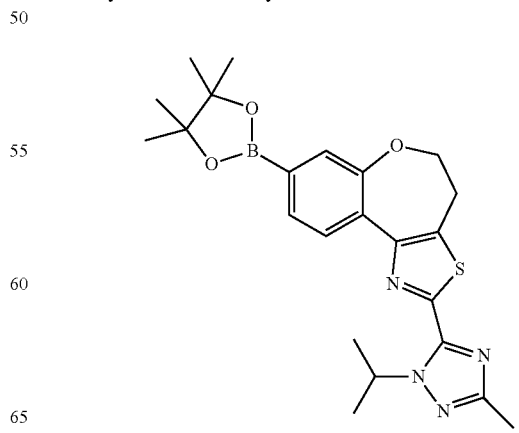

A solution of 8-bromo-2-(2-isopropyl-5-methyl-2H-[1,2,4]triazol-3-yl)-4,5-dihydro-6-oxa-3-thia-1-aza-benzo[e]azulene (2.50 g, 0.00617 mol) and potassium acetate (1.816 g, 0.01850 mol) in Dimethyl sulfoxide (20.0 mL) was thoroughly purged with $N_2$. Bispinacol ester boronate (1.723 g, 0.006785 mol) and [1,1'-Bis(diphenylphosphino)ferrocene]dichloropalladium(II), complex with dichloromethane (1:1) (0.504 g, 0.617 mmol) were added and the flask was sealed and heated to 85° C. overnight. The reaction was diluted with dichloromethane and filtered through celite. Water was added and the solution was extracted 3 times with dichloromethane. The organic phases were combined, dried with $MgSO_4$ and concentrated. The crude was purified by flash chromatography (10-100% EtOAc in hexanes) to obtain 2-(2-Isopropyl-5-methyl-2H-[1,2,4]triazol-3-yl)-8-(4,4,5,5-tetramethyl-[1,3,2]dioxaborolan-2-yl)-4,5-dihydro-6-oxa-3-thia-1-aza-benzo[e]azulene as a light yellow solid (1.564 g). MS(ESI+) 453.2

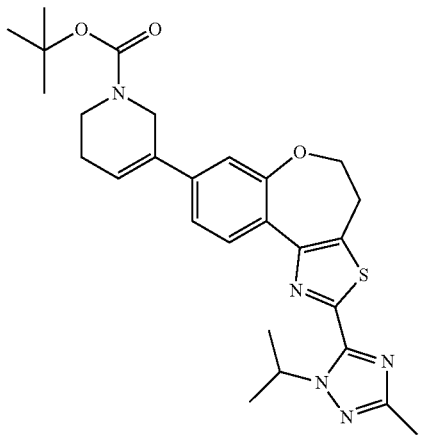 [SMILES: Cc1nc(-c2nc3c(s2)CCOc2cc(C4=CCCN(C(=O)OC(C)(C)C)C4)ccc2-3)n(C(C)C)n1]

2-(2-Isopropyl-5-methyl-2H-[1,2,4]triazol-3-yl)-8-(4,4,5,5-tetramethyl-[1,3,2]dioxaborolan-2-yl)-4,5-dihydro-6-oxa-3-thia-1-aza-benzo[e]azulene (0.496 g, 0.00110 mol), 5-trifluoromethanesulfonyloxy-3,6-dihydro-2H-pyridine-1-carboxylic acid tert-butyl ester (0.550 g, 0.996 mmol) and sodium carbonate (0.317 g, 0.00299 mol) were dissolved in 1,2-dimethoxyethane (5.6 mL) and water (3.1 mL). The reaction was thoroughly degassed with $N_2$. Tetrakis(triphenylphosphine)palladium(0) (0.115 g, 0.0000996 mol) was added and the reaction was heated to 80° C. for 3 hours. Water and dichloromethane were added and the mixture was extracted 3 times with dichloromethane. The organic layers were combined, dried with $MgSO_4$ and concentrated. The crude was purified by flash chromatography to afford 5-[2-(2-Isopropyl-5-methyl-2H-[1,2,4]triazol-3-yl)-4,5-dihydro-6-oxa-3-thia-1-aza-benzo[e]azulen-8-yl]-3,6-dihydro-2H-pyridine-1-carboxylic acid tert-butyl ester as a yellow solid (396 mg). MS(ESI+) 508.2

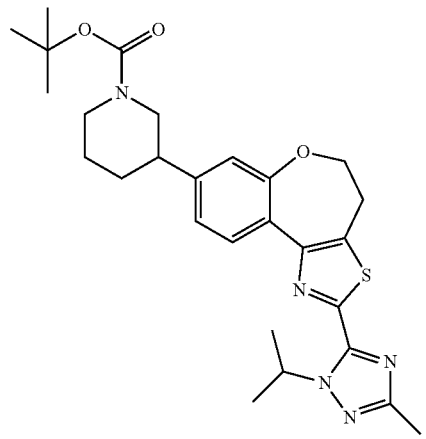 [SMILES: Cc1nc(-c2nc3c(s2)CCOc2cc(C4CCCN(C(=O)OC(C)(C)C)C4)ccc2-3)n(C(C)C)n1]

5-[2-(2-Isopropyl-5-methyl-2H-[1,2,4]triazol-3-yl)-4,5-dihydro-6-oxa-3-thia-1-aza-benzo[e]azulen-8-yl]-3,6-dihydro-2H-pyridine-1-carboxylic acid tert-butyl ester (0.390 g, 0.768 mmol), was dissolved in Methanol (15 mL). The reaction was run on the H-cube with a Pd/C cartridge and complete by LC/MS after the first run. The crude 3-[2-(2-Isopropyl-5-methyl-2H-[1,2,4]triazol-3-yl)-4,5-dihydro-6-oxa-3-thia-1-aza-benzo[e]azulen-8-yl]-piperidine-1-carboxylic acid tert-butyl ester (MS(ESI+) 510.3) was dissolved (0.768 mmol) in methylene chloride (1.0 mL) and trifluoroacetic acid (1.0 mL) and stirred at room temperature for 30 minutes. The solvents were removed in vacuo. The crude was purified by reverse-phase HPLC and resolved by chiral SFC to give 14.2+16.8 mg (each enantiomer) 535 and 536 as pure white solids. MS(ESI+) 410.2.

Example 537

2-(2-Isopropyl-2H-[1,2,4]triazol-3-yl)-8-pyrrolidin-2-yl-4,5-dihydro-6-oxa-3-thia-1-aza-benzo[e]azulene 537

(1-(tert-Butoxycarbonyl)pyrrolidin-2-yl)zinc(II) chloride (2.75 mL, 1.02 mmol, 0.37M) was added to a 10 mL microwave vial under nitrogen, 8-Bromo-2-(2-isopropyl-2H-[1,2,4]triazol-3-yl)-4,5-dihydro-6-oxa-3-thia-1-aza-benzo[e]azulene 27 from FIG. 4 (200 mg, 0.51 mmol), $Pd(OAc)_2$ (12 mg) and tri-tert-butylphosphonium tetrafluoroborate (18 mg) were added. The reaction vessel was sealed and the mixture heated at 100° C. overnight. Aqueous work-up and concentration gave a crude residue which was treated with TFA in DCM (1:1 mix). After 1 h at room temperature, the solvent was removed and the residue purified by reverse phase HPLC to give 537 (10 mg, 5%). LCMS: 382.1

Example 538

4-[2-(2-Isopropyl-2H-[1,2,4]triazol-3-yl)-4,5-dihydro-6-oxa-3-thia-1-aza-benzo[e]azulen-9-yl]-1H—N-2-methoxyethylpyridin-2-one 538

Following the procedures in Example 477, to 505 in DMF was added 1-bromo-2-methoxyethane and cesium fluoride to give 538 (0.005 g, 3%). $^1$H NMR (400 MHz, DMSO) δ 8.75 (s, 1H), 8.13 (s, 1H), 7.74 (d, J=7.2, 1H), 7.69 (d, J=8.2, 1H), 7.18 (d, J=8.4, 1H), 6.67 (s, 1H), 6.56 (d, J=7.0, 1H), 5.92-

5.75 (m, 1H), 4.44 (s, 2H), 4.08 (t, J=4.8, 2H), 3.61 (t, J=4.9, 2H), 3.48 (s, 2H), 3.26 (s, 3H), 1.59 (d, J=6.5, 6H). MS (ESI(+)): m/z 464.2 (M+H)

Example 539

4-[2-(2-Isopropyl-2H-[1,2,4]triazol-3-yl)-4,5-dihydro-6-oxa-3-thia-1-aza-benzo[e]azulen-9-yl]-1H—N-isopropylpyridin-2-one 539

Following the procedures in Example 477, to 505 in DMF was added 2-iodopropane and cesium fluoride to give 539 (0.011 g, 5%). $^1$H NMR (400 MHz, DMSO) δ 8.75 (s, 1H), 8.13 (s, 1H), 7.87 (d, J=7.3, 1H), 7.69 (d, J=8.4, 1H), 7.18 (d, J=8.5, 1H), 6.66 (s, 1H), 6.61 (d, J=7.1, 1H), 5.93-5.72 (m, 1H), 5.19-4.97 (m, 1H), 4.43 (s, 2H), 3.48 (s, 2H), 1.61 (d, J=6.5, 6H), 1.33 (d, J=6.8, 6H). MS (ESI(+)): m/z 448.1 (M+H)

Example 540

4-[2-(2-Isopropyl-2H-[1,2,4]triazol-3-yl)-4,5-dihydro-6-oxa-3-thia-1-aza-benzo[e]azulen-9-yl]-(2-isopropoxyl)pyridine 540

Following the procedure for Example 478, 4-[2-(2-Isopropyl-2H-[1,2,4]triazol-3-yl)-4,5-dihydro-6-oxa-3-thia-1-aza-benzo[e]azulen-9-yl]-1H-pyridin-2-one 505 and 2-iodopropane were reacted to give 540. $^1$H NMR (400 MHz, DMSO) δ 8.81 (s, 1H), 8.24 (d, J=5.4 Hz, 1H), 8.13 (s, 1H), 7.74 (d, J=8.4 Hz, 1H), 7.25 (d, J=5.3 Hz, 1H), 7.19 (d, J=8.7 Hz, 1H), 5.85 (dt, J=13.3, 6.7 Hz, 1H), 5.38-5.22 (m, 1H), 4.44 (s, 2H), 3.48 (s, 2H), 1.59 (d, J=6.5 Hz, 6H), 1.32 (d, J=6.0 Hz, 6H). MS (ESI(+)): m/z 448.1 (M+H)

Example 541

5-[2-(2-Isopropyl-2H-[1,2,4]triazol-3-yl)-4,5-dihydro-6-oxa-3-thia-1-aza-benzo[e]azulen-8-yl]-1H-pyridin-2-one 541

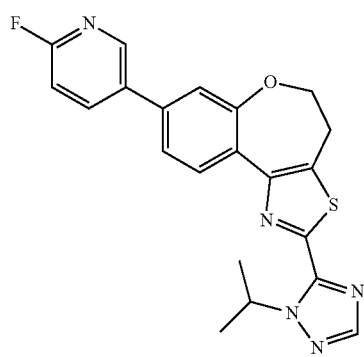 [SMILES: CC(C)n1ncnc1-c1nc2c(s1)CCOc1cc(-c3ccc(F)nc3)ccc1-2]

Following the procedures for 128, 2-(2-Isopropyl-2H-[1,2,4]triazol-3-yl)-8-bromo-4,5-dihydro-6-oxa-3-thia-1-aza-benzo[e]azulene was reacted with 6-fluoropyridin-3-ylboronic acid to give 2-(2-sopropyl-2H-[1,2,4]triazol-3-yl)-8-(2-fluoropyrid-5-yl)-4,5-dihydro-6-oxa-3-thia-1-aza-benzo[e]azulene (1.11 g, 50%). $^1$H NMR (400 MHz, DMSO) δ 8.64 (s, 1H), 8.47 (d, J=8.1, 1H), 8.38 (t, J=7.8, 1H), 8.12 (s, 1H), 7.61 (d, J=8.4, 1H), 7.49 (s, 1H), 7.30 (d, J=8.6, 1H), 5.84 (dd, J=13.2, 6.4, 1H), 4.43 (s, 2H), 3.49 (s, 2H), 1.57 (d, J=6.5, 6H). MS (ESI(+)): m/z 408.2 (M+H)

Following the procedures for 330, 2-(2-Isopropyl-2H-[1,2,4]triazol-3-yl)-8-(2-fluoropyrid-5-yl)-4,5-dihydro-6-oxa-3-thia-1-aza-benzo[e]azulene and HCl were reacted to give 541 (1.04 g, 100%. $^1$H NMR (400 MHz, DMSO) δ 11.91 (s, 1H), 8.37 (d, J=8.3, 1H), 8.12 (s, 1H), 7.92 (d, J=9.8, 1H), 7.84 (s, 1H), 7.45 (d, J=8.5, 1H), 7.31 (s, 1H), 6.43 (d, J=9.6, 1H), 5.85 (dd, J=12.6, 6.2, 1H), 4.40 (s, 2H), 3.46 (s, 2H), 1.56 (d, J=6.5, 6H). MS (ESI(+)): m/z 406.1 (M+H)

Example 542

{1-[2-(2-Isopropyl-5-methyl-2H-[1,2,4]triazol-3-yl)-4,5-dihydro-6-oxa-3-thia-1-aza-benzo[e]azulen-8-yl]-ethyl}-urea 542

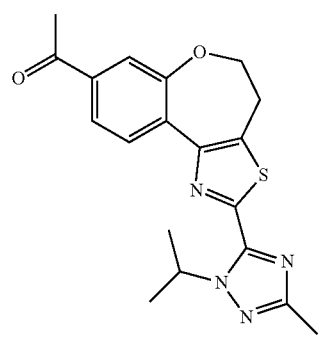 [SMILES: CC(=O)c1ccc2c(c1)OCCc1sc(-c3nc(C)nn3C(C)C)nc1-2]

A mixture of 8-bromo-2-(2-isopropyl-5-methyl-2H-[1,2,4]triazol-3-yl)-4,5-dihydro-6-oxa-3-thia-1-aza-benzo[e]azulene (0.220 g, 0.000543 mol), tributyl-ethoxyvinyl-tin (0.202 mL, 0.000597 mol), and bis(triphenylphosphine)palladium(II) chloride (0.0190 g, 0.0271 mmol) was degassed with N$_2$. The reaction was heated to 100° C. overnight. The crude was hydrolyzed with 10% HCl and extracted 3 times with ethyl acetate. The organic layers were combined, dried with MgSO$_4$ and concentrated. The crude was loaded as a solid onto silica and purified by flash chromatography (45-100% ethyl acetate in hexanes) to give 1-[2-(2-Isopropyl-5-methyl-2H-[1,2,4]triazol-3-yl)-4,5-dihydro-6-oxa-3-thia-1-aza-benzo[e]azulen-8-yl]-ethanone as a white solid (126 mg). MS(ESI+) 369.2

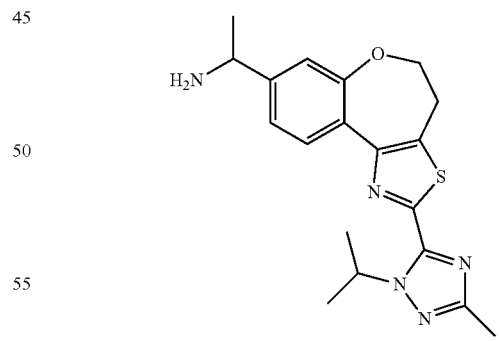

To a solution of 1-[2-(2-isopropyl-5-methyl-2H-[1,2,4]triazol-3-yl)-4,5-dihydro-6-oxa-3-thia-1-aza-benzo[e]azulen-8-yl]-ethanone (0.126 g, 0.000342 mol) in methanol (5.0 mL) was added ammonium acetate (0.140 g, 0.00182 mol) then sodium cyanoborohydride (0.172 g, 0.00274 mol). The reaction was stirred at 50° C. overnight. The mixture was basified with 1N NaOH and extracted 3 times with methylene chloride. The organic phases were combined, dried with Na$_2$SO$_4$ and concentrated to give 1-[2-(2-Isopropyl-5-methyl-2H-[1,2,4]triazol-3-yl)-4,5-dihydro-6-oxa-3-thia-1-aza-benzo[e]azulen-8-yl]-ethylamine. MS(ESI+) 370.2.

To a solution of 1-[2-(2-isopropyl-5-methyl-2H-[1,2,4]triazol-3-yl)-4,5-dihydro-6-oxa-3-thia-1-aza-benzo[e]azulen-8-yl]-ethylamine (0.120 g, 0.325 mmol) in acetic acid (0.0923 mL) and water (3.45 mL) was added a solution of potassium cyanate (0.132 g, 0.00162 mol) in Water (1.0 mL, 0.056 mol) dropwise. The reaction was stirred at 50° C. overnight, cooled down, filtered, and rinsed with cold water. The crude was precipitated in methanol/water and repurified by reverse-phase HPLC to give 542 as a beige solid (5.5 mg). MS(ESI+) 413.1. $^1$H NMR (400 MHz, DMSO) δ 8.27 (d, J=8.2 Hz, 1H), 7.12 (dd, J=8.3, 1.5 Hz, 1H), 6.98 (d, J=1.4 Hz, 1H), 6.47 (d, J=8.2 Hz, 1H), 5.83-5.68 (m, 1H), 5.47 (s, 2H), 4.70 (p, J=7.1 Hz, 1H), 4.44-4.25 (m, 2H), 3.42 (t, J=4.9 Hz, 2H), 2.32 (s, 3H), 1.52 (dd, J=6.5, 1.6 Hz, 6H), 1.32 (d, J=7.0 Hz, 3H)

Example 543

4-[2-(2-Isopropyl-2H-[1,2,4]triazol-3-yl)-4,5-dihydro-6-oxa-3-thia-1-aza-benzo[e]azulen-8-yl]-1-ethyl-pyridin-2-one 543

Following the procedures in Example 477, to 530 in DMF was added iodoethane and cesium fluoride to give 543 (0.734 g, 62%. $^1$H NMR (400 MHz, DMSO) δ 8.45 (d, J=8.3, 1H), 8.13 (s, 1H), 7.80 (d, J=7.1, 1H), 7.58 (dd, J=8.4, 1.9, 1H), 7.43 (d, J=1.8, 1H), 6.72 (s, 1H), 6.66 (dd, J=7.1, 2.0, 1H), 5.84 (dt, J=13.2, 6.5, 1H), 4.42 (s, 2H), 3.94 (d, J=7.1, 2H), 3.48 (s, 2H), 1.56 (d, J=6.6, 6H), 1.24 (t, J=7.1, 3H). MS (ESI(+)): m/z 434.1 (M+H)

Example 544

5-[2-(2-Isopropyl-2H-[1,2,4]triazol-3-yl)-4,5-dihydro-6-oxa-3-thia-1-aza-benzo[e]azulen-8-yl]-1-(2-methoxyethyl)-pyridin-2-one 544

Following the procedures in Example 477, 541 and 1-bromo-2-methoxyethane were reacted to give 544 (0.21 g, 23%). $^1$H NMR (400 MHz, DMSO) δ 8.39 (d, J=8.3, 1H), 8.15 (d, J=2.5, 1H), 8.11 (s, 1H), 7.90 (dd, J=9.5, 2.7, 1H), 7.45 (dd, J=8.4, 1.9, 1H), 7.32 (d, J=1.9, 1H), 6.49 (d, J=9.5, 1H), 5.84 (dt, J=13.1, 6.5, 1H), 4.41 (t, J=4.9, 2H), 4.16 (t, J=5.4, 2H), 3.63 (t, J=5.4, 2H), 3.46 (t, J=4.9, 2H), 3.27 (s, 3H), 1.56 (d, J=6.6, 6H). MS (ESI(+)): m/z 464.2 (M+H)

Example 545

2-[2-(2-Isopropyl-5-methyl-2H-[1,2,4]triazol-3-yl)-4,5-dihydro-6-oxa-3-thia-1-aza-benzo[e]azulen-8-yl]-benzenesulfonamide 545

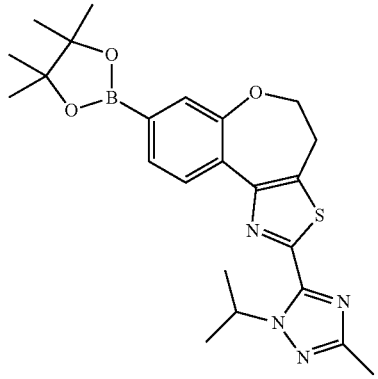

To a microwave vial was added benzenesulfonamide (0.0992 g, 0.420 mmol) and potassium acetate (0.124 g, 0.00126 mol) in acetonitrile (2.0 mL) and water (2.0 mL). The mixture was thoroughly purged with $N_2$. 2-(2-Isopropyl-5-methyl-2H-[1,2,4]triazol-3-yl)-8-(4,4,5,5-tetramethyl-[1,3,2]dioxaborolan-2-yl)-4,5-dihydro-6-oxa-3-thia-1-aza-benzo[e]azulene (0.200 g, 0.442 mmol) and tetrakis(triphenylphosphine)palladium(0) (0.0485 g, 0.0420 mmol) were added and the vial was sealed immediately. The reaction was heated to 140° C. for 20 minutes in the microwave. Methylene chloride and saturated $NH_4Cl$ were added and the mixture was extracted 3 times with methylene chloride. The organic layers were combined, dried with $MgSO_4$ and concentrated. The crude was purified by reverse-phase HPLC to give 545 as a white solid. MS(ESI+) 482.1. $^1$H NMR (400 MHz, DMSO) δ 8.35 (d, J=8.2 Hz, 1H), 8.05 (dd, J=7.7, 1.3 Hz, 1H), 7.67-7.55 (m, 2H), 7.37 (dd, J=7.4, 1.4 Hz, 1H), 7.23 (m, 3H), 7.10 (d, J=1.7 Hz, 1H), 5.79 (hept, J=6.6 Hz, 1H), 4.41 (t, J=4.9 Hz, 2H), 3.46 (t, J=4.9 Hz, 2H), 2.33 (s, 3H), 1.54 (d, J=6.6 Hz, 6H)

Example 546

(S)-1-[2-(2-Isopropyl-2H-[1,2,4]triazol-3-yl)-4,5-dihydro-6-oxa-3-thia-1-aza-benzo[e]azulen-8-ylm-ethyl]-pyrrolidine-2-carboxylic acid amide 546

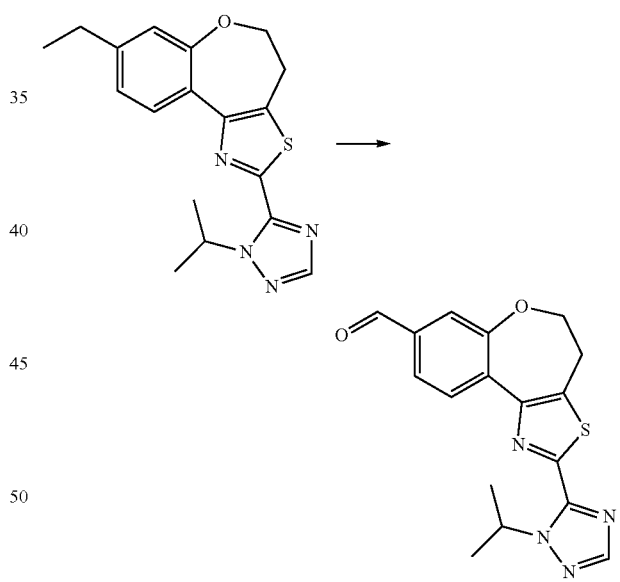

To a solution of 2-(2-Isopropyl-2H-[1,2,4]triazol-3-yl)-8-vinyl-4,5-dihydro-6-oxa-3-thia-1-aza-benzo[e]azulene (0.200 g, 0.591 mmol) in tetrahydrofuran (20 mL) and water (10 mL) was added osmium tetraoxide (0.0473 mmol, 4% wt in water, 0.3 ml) followed by sodium metaperiodate (0.253 g, 0.00118 mol) slowly. The mixture was stirred at room temperature for 6 hours. The reaction was quenched with saturated sodium thiosulfate, then diluted with ethyl acetate and extracted 3 times with ethyl acetate. The organic phases were combined, dried with $Na_2SO_4$ and concentrated to give 2-(2-Isopropyl-2H-[1,2,4]triazol-3-yl)-4,5-dihydro-6-oxa-3-thia-1-aza-benzo[e]azulene-8-carbaldehyde. MS(ESI+) 341.1

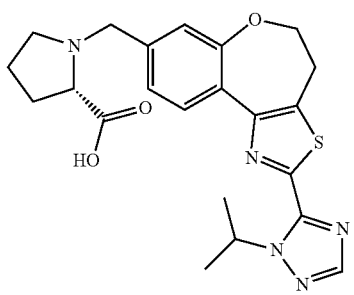 [SMILES: CC(C)n1ncnc1-c1nc2c(s1)CCOc1cc(CN3CCC[C@H]3C(=O)O)ccc1-2]

To a solution of 2-(2-isopropyl-2H-[1,2,4]triazol-3-yl)-4,5-dihydro-6-oxa-3-thia-1-aza-benzo[e]azulene-8-carbaldehyde (0.100 g, 0.294 mmol) in 1,2-dichloroethane (3.0 mL) was added L-proline (0.0372 g, 0.323 mmol) and 4 Å molecular sieves. After 2 hours, Sodium triacetoxyborohydride (0.124 g, 0.588 mmol) was added. The reaction was stirred at room temperature overnight, diluted with dichloromethane, filtered and concentrated. The crude was redissolved in tetrahydrofuran (1.5 mL). N,N-diisopropylethylamine (0.409 mL, 0.00235 mol), ammonium chloride (0.0628 g, 0.00118 mol) and N,N,N',N'-tetramethyl-O-(7-azabenzotriazol-1-yl) uronium hexafluorophosphate (0.128 g, 0.000338 mol) were added and the reaction was stirred at room temperature for 5 hours. Saturated NaHCO$_3$ was added and the mixture was extracted with 3 times with ethyl acetate. The organic phases were combined, dried with MgSO$_4$ and concentrated. The crude was purified by reverse-phase HPLC to give 546 as a white solid (15.2 mg). MS(ESI+) 439.2. $^1$H NMR (400 MHz, DMSO) δ 8.30 (d, J=8.1 Hz, 1H), 8.10 (s, 1H), 7.24 (d, J=2.7 Hz, 1H), 7.22 (dd, J=8.2, 1.5 Hz, 1H), 7.07 (d, J=1.3 Hz, 1H), 7.04 (d, J=1.7 Hz, 1H), 5.88-5.77 (m, 1H), 4.36 (t, J=5.0 Hz, 2H), 3.85 (d, J=13.4 Hz, 1H), 3.43 (t, J=5.1 Hz, 2H), 3.40 (d, J=13.5 Hz, 1H), 3.01-2.87 (m, 2H), 2.24 (dd, J=16.3, 8.1 Hz, 1H), 2.13-1.99 (m, 1H), 1.77-1.65 (m, 3H), 1.55 (d, J=6.6 Hz, 6H)

Examples 547 and 548

(R)-2-(2-Isopropyl-2H-[1,2,4]triazol-3-yl)-8-(1-amino-1-oxopropan-2-yloxy)-4,5-dihydro-6-oxa-3-thia-1-aza-benzo[e]azulene 547, and (S)-2-(2-Isopropyl-2H-[1,2,4]triazol-3-yl)-8-(1-amino-1-oxopropan-2-yloxy)-4,5-dihydro-6-oxa-3-thia-1-aza-benzo[e]azulene 548

Step 1: 2-(2-Isopropyl-2H-[1,2,4]triazol-3-yl)-8-hydroxyl-4,5-dihydro-6-oxa-3-thia-1-aza-benzo[e]azulene

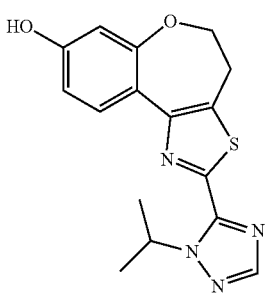 [SMILES: CC(C)n1ncnc1-c1nc2c(s1)CCOc1cc(O)ccc1-2]

A mixture of 8-bromo-2-(2-isopropyl-2H-[1,2,4]triazol-3-yl)-4,5-dihydro-6-oxa-3-thia-1-aza-benzo[e]azulene 27, see FIG. 4 (1.06 g, 2.70 mmol), pulverized potassium hydroxide (303 mg, 5.4 mmol), tris(dibenzylideneacetone)di palladium (0) (24.8 mg, 0.027 mmol), 2-di-t-butylphosphino-3,4,5,6-tetramethyl-2',4',6'-tri-i-propylbiphenyl (26.0 mg, 0.054 mmol) were combined in a sealed tube. The mixture was then taken up in 1,4-dioxane (2.4 mL), water (2.4 mL), and sealed. The reaction mixture was placed in a pre-heated bath and stirred at 100° C. overnight. Added an additional 2.0 eq of pulverized potassium hydroxide, 1 mol % tris(dibenzylideneacetone)di palladium(0), 2 mol % 2-di-t-butylphosphino-3,4,5,6-tetramethyl-2',4',6'-tri-i-propylbiphenyl, and 0.2 mL of water and 1,4-dioxane and heated at 100° C. for 2 h. The reaction mixture was filtered through a plug of celite and concentrated in vacuo and the residue purified by flash chromatography (silica, 80 g column, ISCO, 0-100% ethyl acetate in heptane) to afford 2-(2-Isopropyl-2H-[1,2,4]triazol-3-yl)-8-hydroxyl-4,5-dihydro-6-oxa-3-thia-1-aza-benzo[e]azulene as a yellow solid (480 mg, 54%). $^1$H NMR (400 MHz, DMSO) δ 9.87 (s, 1H), 8.22 (d, J=8.8 Hz, 1H), 7.81 (s, 1H), 6.61 (dd, J=8.8, 2.4 Hz, 1H), 6.41 (d, J=2.4 Hz, 1H), 5.90 (hept, J=6.6 Hz, 1H), 4.51-4.38 (m, 4H), 1.47 (d, J=6.6 Hz, 6H).

Step 2: 2-(2-Isopropyl-2H-[1,2,4]triazol-3-yl)-8-(methyl propionate-2-oxy)-4,5-dihydro-6-oxa-3-thia-1-aza-benzo[e]azulene

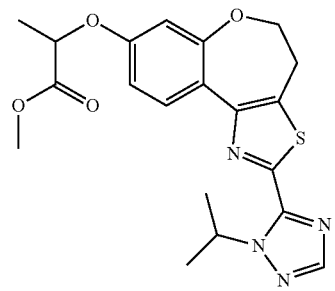 [SMILES: COC(=O)C(C)Oc1ccc2c(c1)OCCc1sc(-c3ncnn3C(C)C)nc1-2]

(81 mg, 0.246 mmol) and dicesium carbonate (240 mg, 0.74 mmol) were suspended in N, N-dimethylformamide (0.95 mL) and treated with propanoic acid, 2-bromo, methyl ester (55 µL, 0.49 mmol). The resultant reaction mixture was stirred at ambient temperature for 1.5 h, then diluted with water (25 mL) and extracted into 20% MeOH in DCM (3×25 mL). The combined organic phase was dried over sodium sulfate, filtered, and the solvent removed in vacuo to afford racemic 2-(2-Isopropyl-2H-[1,2,4]triazol-3-yl)-8-(methyl propionate-2-oxy)-4,5-dihydro-6-oxa-3-thia-1-aza-benzo[e]azulene as a colorless liquid-solid.

Step 3: 2-(2-Isopropyl-2H-[1,2,4]triazol-3-yl)-8-(1-hydroxy-1-oxopropan-2-yloxy)-4,5-dihydro-6-oxa-3-thia-1-aza-benzo[e]azulene

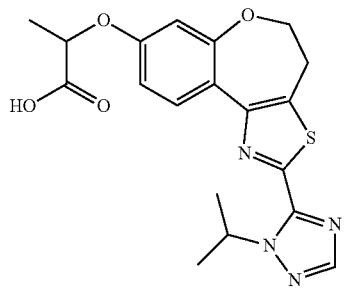 [SMILES: CC(Oc1ccc2c(c1)OCCc1sc(-c3ncnn3C(C)C)nc1-2)C(=O)O]

2-(2-Isopropyl-2H-[1,2,4]triazol-3-yl)-8-(methyl propionate-2-oxy)-4,5-dihydro-6-oxa-3-thia-1-aza-benzo[e]azulene (102 mg, 0.246 mmol) was dissolved in tetrahydrofuran (0.97 mL) and water (0.97 mL) and treated with as 1.0 M aqueous solution of LiOH (1.23 mL). The mixture was heated at 35° C. overnight. An additional 0.55 mL of the 1.0 M aqueous solution of LiOH was added and the mixture continued to heat at 35° C. for 4 h. The resultant solution was partitioned between ethyl acetate and aqueous 1N HCl, and the layers separated. The aqueous phase was extracted into ethyl acetate, dried over sodium sulfate, filtered, and concentrated in vacuo to afford the racemic carboxylic acid, 2-(2-Isopropyl-2H-[1,2,4]triazol-3-yl)-8-(1-hydroxy-1-oxopropan-2-yloxy)-4,5-dihydro-6-oxa-3-thia-1-aza-benzo[e]azulene, as a light yellow solid.

Step 4

Ammonium chloride (52.6 mg, 0.98 mmol) and N, N-diisopropylamine (85 mL, 0.49 mmol) were added to a solution of the carboxylic acid (98 mg, 0.246 mmol) in tetrahydrofuran (0.80 mL). After 5 min N,N,N',N'-tetratmethyl-O-(7-azabenzotriazol-1-yl)uranium hexafluorophosphate (103 mg, 0.27 mmol) was added at ambient temperature and stirred for 2 h. The resultant solution was partitioned between ethyl acetate and sat. sodium bicarbonate, and the layers separated. The aqueous phase was extracted into ethyl acetate, dried over sodium sulfate, filtered, and concentrated in vacuo. The crude residue was purified via HPLC to afford 2-(2-Isopropyl-2H-[1,2,4]triazol-3-yl)-8-(1-amino-1-oxopropan-2-yloxy)-4,5-dihydro-6-oxa-3-thia-1-aza-benzo[e]azulene as a racemic mixture of 547 and 548 as a white solid. LC/MS (ESI+): m/z 400 (M+H). $^1$H NMR (400 MHz, DMSO) δ 8.25 (d, J=8.8 Hz, 1H), 8.08 (s, 1H), 7.51 (s, 1H), 7.24 (s, 1H), 6.77 (dd, J=8.9, 2.6 Hz, 1H), 6.60 (d, J=2.5 Hz, 1H), 5.81 (m, 1H), 4.66 (q, J=6.7 Hz, 1H), 4.36 (t, J=4.9 Hz, 2H), 3.40 (t, J=4.9 Hz, 2H), 1.54 (d, J=6.6 Hz, 6H), 1.45 (d, J=6.6 Hz, 3H). The enantiomers were separated by chiral HPLC and analyzed by SFC/MS.

Instrument: Berger Analytical SFC/MS, Column: ChiralPak AS from Chiral Technologies, 4.6×100 mm, Sum particle size, Flowrate: 5.0 mL/min, Detection: UV 254 nm, Backpressure setting: 120 Bar, Temperature setting: 40 C, Mobile Phase A: CO2, Mobile Phase B: MeOH, Sample was run under isocratic conditions at 40% mobile phase B, Runtime: 3 minutes, 547 Retention Time: 0.70 minutes, 548 retention time 0.48 minutes Example 601 p110α (alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110 alpha PI3K (Upstate Cell Signaling Solutions, Charlottesville, Va.) starting at a final concentration of 20 ug/mL in polarization buffer (10 mM tris pH 7.5, 50 mM NaCl, 4 mM MgCl$_2$, 0.05% Chaps, and 1 mM DTT) to 10 mM PIP$_2$ (Echelon-Inc., Salt Lake City, Utah) final concentration. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume Proxiplates (PerkinElmer, Wellesley, Mass.) Fluorescence polarization values were plotted as a function of the protein concentration, and the EC$_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor IC$_{50}$ values were determined by addition of the 0.04 mg/mL p110 alpha PI3K (final concentration) combined with PIP$_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume proxi plates (PerkinElmer, Wellesley, Mass.) Fluorescence polarization values were plotted as a function of the antagonist concentration, and the IC$_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 hr at room temperature, and the reaction was terminated by the addition of PBS. IC$_{50}$ values were subsequently determined using sigmoidal dose-response curve fit (variable slope).

Example 602

In Vitro Cell Proliferation Assay

Efficacy of Formula I compounds were measured by a cell proliferation assay employing the following protocol (Promega Corp. Technical Bulletin TB288; Mendoza et al (2002) Cancer Res. 62:5485-5488):

1. An aliquot of 100 μl of cell culture containing about 10$^4$ cells (PC3, Detroit562, or MDAMB361.1) in medium was deposited in each well of a 384-well, opaque-walled plate.

2. Control wells were prepared containing medium and without cells.

3. The compound was added to the experimental wells and incubated for 3-5 days.

4. The plates were equilibrated to room temperature for approximately 30 minutes.

5. A volume of CellTiter-Glo Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 hr before reading at 544 nm excitation, 590 nm emission. EC$_{50}$ values were calculated using a sigmoidal dose response curve fit. The term EC$_{50}$ refers to the half maximal effective concentration and is the concentration at which a drug induces a response halfway between the baseline and maximum after some specified exposure time. It is commonly used as a measure of drug potency.

The anti-proliferative effects of Formula I exemplary compounds were measured by the CellTiterGlo® Assay against various tumor cell lines, including the following:

| Cell line | Tissue Type | Mutation Status | EC50 (µmole) 127 | EC50 (µmole) 193 | EC50 (µmole) 375 | EC50 (µmole) 440 | EC50 (µmole) 463 |
|---|---|---|---|---|---|---|---|
| AU565 | Breast | WT | 0.037 | 0.493 | 0.241 | 1.235 | 0.225 |
| BT474 | Breast | PI3K(amped | | | 0.428 | 1.634 | 0.638 |
| CAL120 | Breast | WT | | | | | |
| CAL51 | Breast | PI3K/PTEN | | | | | |
| EFM19-2A | Breast | WT | | | | | |
| EVSA-T | Breast | PTEN | 0.147 | 2.741 | 0.225 | 4.932 | 0.746 |
| HCC1954 | Breast | PI3K | | | 0.348 | 1.616 | 0.340 |
| KPL4 | Breast | PI3K | | | 0.151 | 0.338 | 0.103 |
| MCF7 | Breast | PI3K | | | | | |
| MDA-MB-231 | Breast | K-RAS | | | | | |
| MDA-MB-361.1 | Breast | PI3K | 0.060 | 0.943 | 1.088 | 2.606 | 0.855 |
| MFM223 | Breast | PI3K | | | 0.739 | 4.414 | 0.559 |
| SKBR3 | Breast | WT | | | | 1.728 | |
| T47D | Breast | PI3K | | | 0.145 | 0.569 | 0.185 |
| Colo205 | Colon | B-Raf | | | | | |
| HCT116 | Colon | PI3K/KRAS | | | | | |
| KM12 | Colon | PTEN | | | 1.749 | | 0.321 |
| MDST8 | Colon | PTEN | | | 1.738 | | 1.721 |
| RKO | Colon | PI3K | | | | | |
| LN229 | Glioma | PI3K | | | | | |
| U87MG | Glioma | PTEN | | | 0.858 | | 2.093 |
| H1703 | Lung(NSCLC) | WT | | | | | |
| H2122 | Lung(NSCLC) | K-RAS | | | 1.174 | 10 | 0.542 |
| H520 | Lung(NSCLC) | PTEN | | | 0.226 | | 0.972 |
| 537MEL | Melanoma | PTEN | | | | | |
| A2058 | Melanoma | PTEN | | | | | |
| A375 | Melanoma | B-Raf | | | | | |
| IGROV1 | Ovarian | PI3K | | | | | |
| TOV21GX1 | Ovarian | PI3K/PTEN | | | | | |
| PC3 | Prostate | PTEN | | | 0.145 | 3.029 | 0.185 |

Example 603

Caco-2 Permeability

Caco-2 cells are seeded onto Millipore Multiscreen plates at $1 \times 10^5$ cells/cm$^2$, and cultured for 20 days. Assessment of compound permeability is subsequently conducted. The compounds are applied to the apical surface (A) of cell monolayers and compound permeation into the basolateral (B) compartment was measured. This is performed in the reverse direction (B-A) to investigate active transport. A permeability coefficient value, $P_{app}$, for each compound, a measure of the rate of permeation of the compound across the membrane, is calculated. Compounds are grouped into low ($P_{app}</=1.0 \times 10^6$ cm/s) or high ($P_{app}>/=1.0 \times 10^6$ cm/s) absorption potential based on comparison with control compounds with established human absorption.

For assessment of a compound's ability to undergo active efflux, the ratio of basolateral (B) to apical (A) transport compared with A to B was determined. Values of B–A/A–B>/=1.0 indicate the occurrence of active cellular efflux.

Example 604

Hepatocyte Clearance

Suspensions of cryopreserved human hepatocytes are used. Incubations are performed at compound concentration of 1 mM or 3 µM at a cell density of $0.5 \times 10^6$ viable cells/mL. The final DMSO concentration in the incubation is about 0.25%. Control incubations are also performed in the absence of cells to reveal any non-enzymatic degradation. Duplicate samples (50 µL) are removed from the incubation mixture at 0, 5, 10, 20, 40 and 60 minutes (control sample at 60 minutes only) and added to methanol containing internal standard (100 µL)—to terminate the reaction. Tolbutamide, 7-hydroxycoumarin, and testosterone may be used as control compounds. Samples are centrifuged and the supernatants at each time point pooled for analysis by LC-MSMS. From a plot of ln peak area ratio (parent compound peak area/internal standard peak area) against time, intrinsic clearance ($CL_{int}$) is calculated as follows: $CL_{int}$ (µl/min/million cells)=V×k, where k is the elimination rate constant, obtained from the gradient of ln concentration plotted against time; V is a volume term derived from the incubation volume and is expressed as uL $10^6$ cells$^{-1}$.

Example 605

Cytochrome P450 Inhibition

Formula I compounds may be screened against CYP450 targets (1A2, 2C9, 2C19, 2D6, 3A4) at about 10 concentrations in duplicate, with a top concentration of about 100 uM. Standard inhibitors (furafylline, sulfaphenazole, tranylcypromine, quinidine, ketoconazole) may be used as controls. Plates may be read using a BMG LabTechnologies PolarStar in fluorescence mode.

Example 606

Cytochrome P450 Induction

Freshly isolated human hepatocytes from a single donor may be cultured for about 48 hr prior to addition of Formula I compound at three concentrations and incubated for 72 hr. Probe substrates for CYP3A4 and CYP1A2 are added for 30 minutes and 1 hr before the end of the incubation. At 72 hr, cells and media are removed and the extent of metabolism of each probe substrate quantified by LC-MS/MS. The experiment is controlled by using inducers of the individual P450s incubated at one concentration in triplicate.

Example 607

Plasma Protein Binding

Solutions of Formula I compound (Sum, 0.5% final DMSO concentration) are prepared in buffer and 10% plasma (v/v in buffer). A 96 well HT dialysis plate is assembled so that each well is divided in two by a semi-permeable cellulose membrane. The buffer solution is added to one side of the membrane and the plasma solution to the other side; incubations are then conducted at 37° C. over 2 hr in triplicate. The cells are subsequently emptied, and the solutions for each batch of compounds are combined into two groups (plasma-free and plasma-containing) then analyzed by LC-MSMS using two sets of calibration standards for plasma-free (6 points) and plasma-containing solutions (7 points). The fraction unbound value for the compound is calculated.

Example 608 hERG Channel Blockage

Formula I compounds are evaluated for ability to modulate rubidium efflux from HEK-294 cells stably expressing hERG potassium channels using established flux methodology. Cells are prepared in medium containing RbCl, plated into 96-well plates and grown overnight to form monolayers. The efflux experiment is initiated by aspirating the media and washing each well with 3×100 µL of pre-incubation buffer (containing low [K$^+$]) at room temperature. Following the final aspiration, 50 µL of working stock (2×) compound is added to each well and incubated at room temperature for 10 minutes. Stimulation buffer 50 µL (containing high [K+]) is then added to each well giving the final test compound concentrations. Cell plates are then incubated at room temperature for a further 10 minutes. Supernatant 80 µL from each well is then transferred to equivalent wells of a 96-well plate and analyzed via atomic emission spectroscopy. The compound is screened as 10 pt duplicate IC$_{50}$ curves, n=2, from a top concentration of 100 µM.

Example 609

In Vivo Tumor Xenograft

Animals suitable for transgenic experiments can be obtained from standard commercial sources. Groups of Taconic nude mice (were implanted subcutaneously in the hind flank with MDA-MB-361.1 (PI3K mutant) breast cancer cells. Mouse xenografts were dosed daily for 21 days with drug or vehicle. Tumor sizes were recorded twice weekly over the course of the study. Mouse body weights were also recorded twice weekly, and the mice were observed regularly. Tumor volume was measured in two dimensions (length and width) using Ultra Cal-IV calipers (Model 54-10-111; Fred V. Fowler Co., Inc.; Newton, Mass.) and analyzed using Excel v.11.2 (Microsoft Corporation; Redmond, Wash.). Tumor inhibition graphs were plotted using KaleidaGraph, Version 3.6 (Synergy Software; Reading, Pa.). The tumor volume was calculated with formula: Tumor size (mm$^3$)=(longer measurement×shorter measurement)×0.5

Animal body weights were measured using an Adventurera Pro AV812 scale (Ohaus Corporation; Pine Brook, N.J.). Graphs were generated using KaleidaGraph Version 3.6. Percent weight change was calculated using formula: Group percent weight change=(1−(initial weight/new weight))×100.

Mice whose tumor volume exceeded 2000 mm$^3$ or whose body weight loss was >20% of their starting weight were promptly euthanized according to regulatory guidance.

The percent tumor growth inhibition (% INH) at the end of study (EOS) was calculated using formula: % INH=100× (EOS mean volume of tumors in animals given vehicle−EOS mean volume of tumors in animals given the drug)/EOS mean volume of tumors in animals given vehicle.

Tumor incidence (TI) was determined based on the number of measurable tumors remaining in each group at the end of the study. A partial response (PR) was defined as a >50% but <100% reduction in tumor volume, compared with the starting tumor volume, observed on any day of the study. A complete response (CR) was defined as a 100% reduction in tumor volume, compared with the initial tumor volume, observed on any day of the study. Data were analyzed and p-values were determined using the Dunnett's test with JMP statistical software, version 5.1.2 (SAS Institute; Cary, N.C.). Individual tumor volumes at end of study and mean tumor volume±SEM values were calculated using JMP statistical software, version 5.1.2. Body weight data were graphed based on the mean percentage of change from initial body weights±SEM.

Example 610

Phospho AKT Induction Assay

In a 6-well tissue culture plate cells were seeded at 5×10$^5$ cells per well overnight. Cells were treated with an EC$_{80}$ of the Formula I compound. Following treatment, cells were washed once with cold PBS and lysed in 1× Cell Extraction Buffer from Biosource (Carlsbad, Calif.) supplemented with protease inhibitors (Roche, Mannheim, Germany), 1 mM PMSF, and Phosphatase Inhibitor Cocktails 1 and 2 from Sigma (St. Louis, Mo.). Determination of protein concentration was performed using the Pierce BCA Protein Assay Kit (Rockford, Ill.). Levels of pAkt (Ser$^{473}$) and total Akt were assessed using bead kits from Biosource (Carlsbad, Calif.) and the Luminex Bio-Plex system (Bio-Rad, Hercules, Calif.).

The foregoing description is considered as illustrative only of the principles of the invention. Further, since numerous modifications and changes will be readily apparent to those skilled in the art, the invention is not limited to the exact examples shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A method of treating a hyperproliferative disease comprising administering a pharmaceutical composition comprised of a therapeutically effective amount of 2-(3-amino-1-(2,4-difluorophenyl)-1H-1,2,4-triazol-5-yl)-N-methyl-4,5- dihydrobenzo[b]thieno[2,3-d]oxepine-8-carboxamide and a pharmaceutically acceptable carrier, glidant, diluent, or excipient to a patient having said hyperproliferative disease, wherein the hyperproliferative disease is cancer selected from breast, colon, glioma, lung, melanoma, ovarian and prostate cancer.

2. The method of claim 1 wherein the pharmaceutical composition is administered to the patient by injection.

3. The method of claim 1 wherein the patient is further treated with ranibizumab or bevacizumab.

4. A method of inhibiting PI3K and/or mTOR in a patient, the method comprising administering a therapeutically effective amount of 2-(3-amino-1-(2,4-difluorophenyl)-1H-1,2,4-triazol-5-yl)-N-methyl-4,5-dihydrobenzo[b]thieno[2,3-d]oxepine-8-carboxamide together with a pharmaceutically acceptable carrier, glidant, diluent, or excipient to the patient.

5. A process for making 2-(3-amino-1-(2,4-difluorophenyl)-1H-1,2,4-triazol-5-yl)-N-methyl-4,5-dihydrobenzo[b]thieno[2,3-d]oxepine-8-carboxamide comprising reacting 2-[5-amino-2-(2,4-difluoro-phenyl)-2H-[1,2,4]triazol-3-yl]-4,5-dihydro-6-oxa-1-thia-benzo[e]azulene-8-carboxylic acid and methylamine hydrochloride.

* * * * *